(12) United States Patent
Charifson et al.

(10) Patent No.: US 9,296,701 B2
(45) Date of Patent: Mar. 29, 2016

(54) DNA-PK INHIBITORS

(71) Applicant: Vertex Pharmaceuticals Incorporated, Cambridge, MA (US)

(72) Inventors: Paul S Charifson, Farmingham, MA (US); Kevin Michael Cottrell, Cambridge, MA (US); Hongbo Deng, Southborough, MA (US); John P. Duffy, Northborough, MA (US); Huai Gao, Arlington, MA (US); Simon Giroux, Cambridge, MA (US); Jeremy Green, Waltham, MA (US); Katrina Lee Jackson, Cambridge, MA (US); Joseph M Kennedy, Charlestown, MA (US); David J. Lauffer, Stow, MA (US); Mark Willem Ledeboer, Acton, MA (US); Pan Li, Lexington, MA (US); John Patrick Maxwell, Hingham, MA (US); Mark A. Morris, Somerville, MA (US); Albert Charles Pierce, Cambridge, MA (US); Nathan D. Waal, Cambridge, MA (US); Jinwang Xu, Framingham, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 13/868,703

(22) Filed: Apr. 23, 2013

(65) Prior Publication Data

US 2013/0281431 A1    Oct. 24, 2013

Related U.S. Application Data

(60) Provisional application No. 61/637,512, filed on Apr. 24, 2012, provisional application No. 61/725,652, filed on Nov. 13, 2012, provisional application No. 61/777,806, filed on Mar. 12, 2013.

(51) Int. Cl.

| | |
|---|---|
| C07D 417/04 | (2006.01) |
| C07D 417/14 | (2006.01) |
| C07D 471/04 | (2006.01) |
| C07D 491/048 | (2006.01) |
| C07D 405/14 | (2006.01) |
| C07D 401/04 | (2006.01) |
| C07D 401/14 | (2006.01) |
| C07D 413/04 | (2006.01) |
| C07D 403/04 | (2006.01) |
| C07D 239/02 | (2006.01) |
| C07D 239/42 | (2006.01) |
| A61K 47/48 | (2006.01) |
| C07D 413/14 | (2006.01) |
| C07D 403/10 | (2006.01) |
| C07D 409/04 | (2006.01) |
| C07D 409/14 | (2006.01) |
| C07D 413/10 | (2006.01) |

(Continued)

(52) U.S. Cl.
CPC .......... *C07D 239/42* (2013.01); *A61K 41/0038* (2013.01); *A61K 47/481* (2013.01); *C07D 401/04* (2013.01); *C07D 401/14* (2013.01); *C07D 403/04* (2013.01); *C07D 403/10* (2013.01); *C07D 405/14* (2013.01); *C07D 409/04* (2013.01); *C07D 409/14* (2013.01); *C07D 413/04* (2013.01); *C07D 413/10* (2013.01); *C07D 413/14* (2013.01); *C07D 417/04* (2013.01); *C07D 417/10* (2013.01); *C07D 417/14* (2013.01); *C07D 471/04* (2013.01); *C07D 491/048* (2013.01); *C07D 491/056* (2013.01); *C07D 495/04* (2013.01); *C07D 521/00* (2013.01)

(58) Field of Classification Search
CPC ............. A61K 47/481; A61K 47/0038; C07D 417/04; C07D 417/14; C07D 471/04; C07D 491/048; C07D 491/056; C07D 405/14; C07D 401/04; C07D 401/14; C07D 413/04; C07D 413/10; C07D 413/14; C07D 403/04; C07D 403/10; C07D 239/42
USPC ............ 514/210.18, 252.18, 235.8, 256, 245, 514/230.5; 544/328, 295, 212, 105
See application file for complete search history.

(56) References Cited

U.S. PATENT DOCUMENTS

| 5,478,938 A | 12/1995 | Clemence et al. |
| 5,571,506 A | 11/1996 | Regan et al. |

(Continued)

FOREIGN PATENT DOCUMENTS

| CA | 2716898 | 9/2009 |
| DE | 102006050512 A1 | 4/2008 |

(Continued)

OTHER PUBLICATIONS

Veuger et al. Radiosensitization and DNA repair inhibition by combined use of novel inhibitors of DNA-dependent protein kinase and poly(ADP-ribose) polymerase-1; Cancer Res. 63, 6008-6015, (2003).*
International Search Report Received in the corresponding PCT Application No. PCT/US2013/037811 (Aug. 29, 2013).
Davis, A.J., et al., "Dynamics of the PI3K-like protein kinase members ATM and DNA-PKcs at DNA double strand breaks", Cell Cycle. Jul. 1, 2010;9(13):2529-36.
Edelman, M.J. et al., "Targeted radiopharmaceutical therapy for advanced lung cancer: phase I trial of rhenium Re188 P2045, a somatostatin analog", J Thorac Oncol 4(12): 1550-4 2009.

(Continued)

*Primary Examiner* — James O Wilson
*Assistant Examiner* — Ebenezer O Sackey
(74) *Attorney, Agent, or Firm* — Wolf, Greenfield & Sacks, P.C.

(57) ABSTRACT

The present invention relates to compounds useful as inhibitors of DNA-PK. The invention also provides pharmaceutically acceptable compositions comprising said compounds and methods of using the compositions in the treatment of various disease, conditions, or disorders.

17 Claims, No Drawings

(51) Int. Cl.
  *C07D 491/056* (2006.01)
  *C07D 495/04* (2006.01)
  *C07D 521/00* (2006.01)
  *A61K 41/00* (2006.01)
  *C07D 417/10* (2006.01)

(56) References Cited

U.S. PATENT DOCUMENTS

| | | |
|---|---|---|
| 5,571,815 A | 11/1996 | Schaper et al. |
| 5,668,140 A | 9/1997 | Schaper et al. |
| 5,723,461 A | 3/1998 | Rosner et al. |
| 5,977,117 A | 11/1999 | Chan et al. |
| 6,004,979 A | 12/1999 | Clemence et al. |
| 6,057,371 A | 5/2000 | Glennon |
| 6,222,073 B1 | 4/2001 | Herwig et al. |
| 6,265,428 B1 | 7/2001 | Chan et al. |
| 6,610,677 B2 | 8/2003 | Davies et al. |
| 6,613,776 B2 | 9/2003 | Knegtel et al. |
| 6,638,926 B2 | 10/2003 | Davies et al. |
| 6,642,227 B2 | 11/2003 | Cao et al. |
| 6,653,300 B2 | 11/2003 | Bebbington et al. |
| 6,653,301 B2 | 11/2003 | Bebbington et al. |
| 6,656,939 B2 | 12/2003 | Bebbington et al. |
| 6,660,731 B2 | 12/2003 | Bebbington et al. |
| 6,664,247 B2 | 12/2003 | Bebbington et al. |
| 6,689,778 B2 | 2/2004 | Bemis et al. |
| 6,696,452 B2 | 2/2004 | Davies et al. |
| 6,727,251 B2 | 4/2004 | Bebbington et al. |
| 6,743,791 B2 | 6/2004 | Cao et al. |
| 6,762,179 B2 | 7/2004 | Cochran et al. |
| 6,777,413 B2 | 8/2004 | Zhu et al. |
| 6,825,190 B2 | 11/2004 | Moon et al. |
| 6,844,347 B1 | 1/2005 | Schnidler et al. |
| 6,875,781 B2 | 4/2005 | Hong et al. |
| 6,884,804 B2 | 4/2005 | Choon-Moon |
| 6,949,544 B2 | 9/2005 | Bethiel et al. |
| 6,989,385 B2 | 1/2006 | Bebbington et al. |
| 7,008,948 B2 | 3/2006 | Bebbington et al. |
| 7,084,159 B2 | 8/2006 | Cao et al. |
| 7,087,603 B2 | 8/2006 | Bebbington et al. |
| 7,098,330 B2 | 8/2006 | Bebbington et al. |
| 7,115,739 B2 | 10/2006 | Bebbington et al. |
| 7,122,552 B2 | 10/2006 | Ledford et al. |
| 7,144,911 B2 | 12/2006 | Flynn et al. |
| 7,179,912 B2 | 2/2007 | Halbrook et al. |
| 7,189,724 B2 | 3/2007 | An et al. |
| 7,208,507 B2 | 4/2007 | Hong et al. |
| 7,226,919 B2 | 6/2007 | Ledeboer et al. |
| 7,244,735 B2 | 7/2007 | Straub et al. |
| 7,253,187 B2 | 8/2007 | Cao et al. |
| 7,256,190 B2 | 8/2007 | Cochran et al. |
| 7,259,161 B2 | 8/2007 | Bethiel et al. |
| 7,271,179 B2 | 9/2007 | Bemis et al. |
| 7,300,929 B2 | 11/2007 | Baxter et al. |
| 7,304,061 B2 | 12/2007 | Hale et al. |
| 7,304,071 B2 | 12/2007 | Cochran |
| 7,312,227 B2 | 12/2007 | Ledeboer et al. |
| 7,329,652 B2 | 2/2008 | Salituro et al. |
| 7,345,054 B2 | 3/2008 | Hale et al. |
| 7,358,258 B2 | 4/2008 | Hale et al. |
| 7,361,665 B2 | 4/2008 | Ledeboer et al. |
| 7,390,815 B2 | 6/2008 | Davies et al. |
| 7,407,962 B2 | 8/2008 | Aronov et al. |
| 7,419,984 B2 | 9/2008 | Bhatt et al. |
| 7,427,681 B2 | 9/2008 | Bebbington et al. |
| 7,456,190 B2 | 11/2008 | Maltais et al. |
| 7,473,691 B2 | 1/2009 | Davies et al. |
| 7,488,727 B2 | 2/2009 | Cochran et al. |
| 7,501,415 B2 | 3/2009 | Aronov et al. |
| 7,517,870 B2 | 4/2009 | Auricchio et al. |
| 7,528,142 B2 | 5/2009 | Binch et al. |
| 7,531,536 B2 | 5/2009 | Bebbington et al. |
| 7,557,106 B2 | 7/2009 | Charrier et al. |
| 7,592,340 B2 | 9/2009 | Bemis et al. |
| 7,625,913 B2 | 12/2009 | Bebbington et al. |
| 7,635,683 B2 | 12/2009 | Gai et al. |
| 7,666,895 B2 | 2/2010 | Flynn et al. |
| 7,691,853 B2 | 4/2010 | Bebbington et al. |
| 7,696,204 B2 | 4/2010 | McDonald et al. |
| 7,732,444 B2 | 6/2010 | Fleming et al. |
| 7,767,672 B2 | 8/2010 | Binch et al. |
| 7,820,685 B2 | 10/2010 | Binch et al. |
| 7,951,820 B2 | 5/2011 | Bebbington et al. |
| 7,968,565 B2 | 6/2011 | Arkin et al. |
| 7,982,037 B2 | 7/2011 | Bebbington et al. |
| 8,026,359 B2 | 9/2011 | Chen |
| 8,084,457 B2 | 12/2011 | Choidas et al. |
| 8,129,399 B2 | 3/2012 | Binch et al. |
| 8,268,811 B2 | 9/2012 | Mortimore et al. |
| 8,268,829 B2 | 9/2012 | Charrier et al. |
| 8,304,414 B2 | 11/2012 | Bebbington et al. |
| 8,372,850 B2 | 2/2013 | Jimenez et al. |
| 8,383,633 B2 | 2/2013 | Mortimore et al. |
| 8,410,133 B2 | 4/2013 | Jimenez et al. |
| 8,426,425 B2 | 4/2013 | Jimenez et al. |
| 8,455,500 B2 | 6/2013 | Okano et al. |
| 8,455,507 B2 | 6/2013 | Studley et al. |
| 8,476,287 B2 | 7/2013 | Okano et al. |
| 8,518,953 B2 | 8/2013 | Pierce et al. |
| 8,524,720 B2 | 9/2013 | Bebbington et al. |
| 8,541,428 B2 | 9/2013 | Gavish et al. |
| 8,546,392 B2 | 10/2013 | Hartmann et al. |
| 8,557,833 B2 | 10/2013 | Binch et al. |
| 8,563,549 B2 | 10/2013 | Burger et al. |
| 8,633,210 B2 | 1/2014 | Bebbington et al. |
| 8,637,511 B2 | 1/2014 | Binch et al. |
| 8,664,219 B2 | 3/2014 | Jimenez et al. |
| 8,691,847 B2 | 4/2014 | Zhu et al. |
| 8,697,685 B2 | 4/2014 | Axten et al. |
| 8,697,698 B2 | 4/2014 | Bebbington et al. |
| 8,735,593 B2 | 5/2014 | Jimenez et al. |
| 8,779,127 B2 | 7/2014 | Charrier et al. |
| 8,784,782 B2 | 7/2014 | Tachdjian et al. |
| 8,785,444 B2 | 7/2014 | Mortimore et al. |
| 8,841,308 B2 | 9/2014 | Charrier et al. |
| 9,062,076 B2 | 6/2015 | Williams et al. |
| 2002/0111353 A1 | 8/2002 | Ledeboer et al. |
| 2003/0096813 A1 | 5/2003 | Cao et al. |
| 2003/0199525 A1 | 10/2003 | Hirst et al. |
| 2003/0199526 A1 | 10/2003 | Choquette et al. |
| 2003/0207873 A1 | 11/2003 | Harrington et al. |
| 2003/0207886 A1 | 11/2003 | Plucker et al. |
| 2004/0097502 A1 | 5/2004 | Gellibert et al. |
| 2004/0235834 A1 | 11/2004 | Farmer et al. |
| 2005/0054568 A1 | 3/2005 | Ling et al. |
| 2006/0142572 A1 | 6/2006 | Martinez-Botella et al. |
| 2006/0166936 A1 | 7/2006 | Binch et al. |
| 2007/0179125 A1 | 8/2007 | Fraysse et al. |
| 2007/0265263 A1 | 11/2007 | Cao et al. |
| 2007/0270420 A1 | 11/2007 | Harbeson et al. |
| 2008/0139585 A1 | 6/2008 | Rathinavelu et al. |
| 2008/0207616 A1 | 8/2008 | Aquila et al. |
| 2008/0267918 A1 | 10/2008 | Gai et al. |
| 2008/0280891 A1 | 11/2008 | Kelly et al. |
| 2009/0023729 A1 | 1/2009 | Nakamura et al. |
| 2009/0053192 A1 | 2/2009 | Millan et al. |
| 2009/0221581 A1 | 9/2009 | Wabnitz et al. |
| 2009/0298844 A1 | 12/2009 | Pollard et al. |
| 2010/0137305 A1 | 6/2010 | Binch et al. |
| 2011/0046104 A1 | 2/2011 | Mortimore et al. |
| 2011/0060013 A1 | 3/2011 | Mortimore et al. |
| 2011/0065739 A1 | 3/2011 | Ishikawa et al. |
| 2011/0275643 A1 | 11/2011 | Liou et al. |
| 2011/0319618 A1 | 12/2011 | Nishio |
| 2012/0009151 A1 | 1/2012 | Han et al. |
| 2012/0202806 A1 | 8/2012 | Dürrenberger et al. |
| 2013/0209400 A1 | 8/2013 | Bach Taña et al. |
| 2014/0045869 A1* | 2/2014 | Charifson et al. ........ 514/266.21 |
| 2014/0113012 A1 | 4/2014 | Schultz et al. |
| 2014/0148434 A1 | 5/2014 | Boyall et al. |
| 2014/0187772 A1 | 7/2014 | Bebbington et al. |
| 2014/0194444 A1 | 7/2014 | Jimenez et al. |
| 2014/0256703 A1 | 9/2014 | Jimenez et al. |

(56) References Cited

U.S. PATENT DOCUMENTS

| | | |
|---|---|---|
| 2014/0275024 A1 | 9/2014 | Maxwell et al. |
| 2014/0275059 A1 | 9/2014 | Maxwell et al. |
| 2015/0111871 A1 | 4/2015 | Charifson et al. |

FOREIGN PATENT DOCUMENTS

| | | |
|---|---|---|
| DE | 102007044032 A1 | 3/2009 |
| EP | 1678147 | 7/2006 |
| EP | 1701944 | 9/2006 |
| JP | 10251255 | 9/1998 |
| JP | 2005336138 A | 12/2005 |
| JP | 2007/008045 A | 1/2007 |
| WO | 9322291 | 11/1993 |
| WO | 0009496 | 8/1998 |
| WO | 9837079 | 8/1998 |
| WO | 9854158 | 12/1998 |
| WO | 0127089 | 4/2000 |
| WO | WO 00/42026 A1 | 7/2000 |
| WO | WO 01/64646 A2 | 9/2001 |
| WO | 2005026129 | 3/2005 |
| WO | 2005066139 | 7/2005 |
| WO | 2005089730 A2 | 9/2005 |
| WO | 2005121121 | 12/2005 |
| WO | 2006044503 | 4/2006 |
| WO | 2006044732 A2 | 4/2006 |
| WO | WO 2006/108107 A1 | 10/2006 |
| WO | WO 2006/138418 A2 | 12/2006 |
| WO | 2007056143 | 5/2007 |
| WO | 2007082899 | 7/2007 |
| WO | 2007109783 | 9/2007 |
| WO | 2008042639 | 9/2007 |
| WO | 2008006583 | 1/2008 |
| WO | 2008008747 | 1/2008 |
| WO | 2008008852 | 1/2008 |
| WO | 2008028691 A1 | 3/2008 |
| WO | 2008042639 | 4/2008 |
| WO | 2008070661 | 6/2008 |
| WO | WO 2008/083346 A1 | 7/2008 |
| WO | 2008092199 | 8/2008 |
| WO | 2008106202 | 9/2008 |
| WO | 2008115973 | 9/2008 |
| WO | 2008144253 | 11/2008 |
| WO | WO 2008/141065 A1 | 11/2008 |
| WO | 2008145616 | 12/2008 |
| WO | 2009008991 | 1/2009 |
| WO | WO 2009/004621 A1 | 1/2009 |
| WO | WO 2009/016841 A1 | 2/2009 |
| WO | 2009047359 | 4/2009 |
| WO | 2009105220 | 8/2009 |
| WO | 2009107391 | 9/2009 |
| WO | 2009115517 | 9/2009 |
| WO | WO 2009/109258 A1 | 9/2009 |
| WO | WO 2009/152909 A1 | 12/2009 |
| WO | 2010048149 | 4/2010 |
| WO | 2010064737 | 6/2010 |
| WO | 2010065899 | 6/2010 |
| WO | WO 2010/093808 A1 | 8/2010 |
| WO | 2011022348 | 2/2011 |
| WO | 2011051535 | 5/2011 |
| WO | 2011113512 A1 | 9/2011 |
| WO | 2012000632 A1 | 1/2012 |
| WO | 2012028233 A1 | 3/2012 |
| WO | 2013024282 | 2/2013 |
| WO | 2013072015 A1 | 3/2013 |
| WO | WO 2013/032951 A1 | 3/2013 |
| WO | WO 2013/040515 A1 | 3/2013 |
| WO | WO 2013/043935 A1 | 3/2013 |
| WO | WO 2013/049701 A1 | 4/2013 |
| WO | 2013083991 | 6/2013 |
| WO | WO 2013/112950 A2 | 8/2013 |
| WO | 2013163190 A1 | 10/2013 |
| WO | WO 2014/075077 A1 | 5/2014 |

OTHER PUBLICATIONS

International Search Report for PCT/US2014/061033.
Kashishian, A., et al., "DNA-dependent protein kinase inhibitors as drug candidates for the treatment of cancer", Mol Cancer Ther 2(12): 1257-64 2003.
Kuntzinger, T., et al., "Protein phosphatase 1 regulators in DNA damage signaling", Cell Cycle 10:9, 1-7; May 1, 2011.

* cited by examiner

DNA-PK INHIBITORS

CROSS-REFERENCE TO RELATED APPLICATIONS

This application claims the benefit, under 35 U.S.C. §119, of U.S. Provisional Application No. 61/637,512, filed on Apr. 24, 2012; U.S. Provisional Application No. 61/725,652, filed on Nov. 13, 2012; and U.S. Provisional Application No. 61/777,806, filed on Mar. 12, 2013, the entire disclosures of which are incorporated herein by reference.

TECHNICAL FIELD OF THE INVENTION

The present invention relates to compounds useful as inhibitors of DNA-dependent protein kinase (DNA-PK). The invention also provides pharmaceutically acceptable compositions comprising the compounds of the invention and methods of using the compositions in the treatment of cancer.

BACKGROUND OF THE INVENTION

Ionizing radiation (IR) induces a variety of DNA damage of which double strand breaks (DSBs) are the most cytotoxic. These DSBs can lead to cell death via apoptosis and/or mitotic catastrophe if not rapidly and completely repaired. In addition to IR, certain chemotherapeutic agents including topoisomerase II inhibitors, bleomycin, and doxorubicin also cause DSBs. These DNA lesions trigger a complex set of signals through the DNA damage response network that function to repair the damaged DNA and maintain cell viability and genomic stability. In mammalian cells, the predominant repair pathway for DSBs is the Non-Homologous End Joining Pathway (NHEJ). This pathway functions regardless of the phase of the cell cycle and does not require a template to re-ligate the broken DNA ends. NHEJ requires coordination of many proteins and signaling pathways. The core NHEJ machinery consists of the Ku70/80 heterodimer and the catalytic subunit of DNA-dependent protein kinase (DNA-PKcs), which together comprise the active DNA-PK enzyme complex. DNA-PKcs is a member of the phosphatidylinositol 3-kinase-related kinase (PIKK) family of serine/threonine protein kinases that also includes ataxia telangiectasia mutated (ATM), ataxia telangiectasia and Rad3-related (ATR), mTOR, and four PI3K isoforms. However, while DNA-PKcs is in the same protein kinase family as ATM and ATR, these latter kinases function to repair DNA damage through the Homologous Recombination (HR) pathway and are restricted to the S and $G_2$ phases of the cell cycle. While ATM is also recruited to sites of DSBs, ATR is recruited to sites of single stranded DNA breaks.

NHEJ is thought to proceed through three key steps: recognition of the DSBs, DNA processing to remove non-ligatable ends or other forms of damage at the termini, and finally ligation of the DNA ends. Recognition of the DSB is carried out by binding of the Ku heterodimer to the ragged DNA ends followed by recruitment of two molecules of DNA-PKcs to adjacent sides of the DSB; this serves to protect the broken termini until additional processing enzymes are recruited. Recent data supports the hypothesis that DNA-PKcs phosphorylates the processing enzyme, Artemis, as well as itself to prepare the DNA ends for additional processing. In some cases DNA polymerase may be required to synthesize new ends prior to the ligation step. The auto-phosphorylation of DNA-PKcs is believed to induce a conformational change that opens the central DNA binding cavity, releases DNA-PKcs from DNA, and facilitates the ultimate religation of the DNA ends.

It has been known for some time that DNA-PK$^{-/-}$ mice are hypersensitive to the effects of IR and that some non-selective small molecule inhibitors of DNA-PKcs can radiosensitize a variety of tumor cell types across a broad set of genetic backgrounds. While it is expected that inhibition of DNA-PK will radiosensitize normal cells to some extent, this has been observed to a lesser degree than with tumor cells likely due to the fact that tumor cells possess higher basal levels of endogenous replication stress and DNA damage (oncogene-induced replication stress) and DNA repair mechanisms are less efficient in tumor cells. Most importantly, an improved therapeutic window with greater sparing of normal tissue will be imparted from the combination of a DNA-PK inhibitor with recent advances in precision delivery of focused IR, including image-guide RT (IGRT) and intensity-modulated RT (IMRT).

Inhibition of DNA-PK activity induces effects in both cycling and non-cycling cells. This is highly significant since the majority of cells in a solid tumor are not actively replicating at any given moment, which limits the efficacy of many agents targeting the cell cycle. Equally intriguing are recent reports that suggest a strong connection between inhibition of the NHEJ pathway and the ability to kill traditionally radioresistant cancer stem cells (CSCs). It has been shown in some tumor cells that DSBs in dormant CSCs predominantly activate DNA repair through the NHEJ pathway; it is believed that CSCs are usually in the quiescent phase of the cell cycle. This may explain why half of cancer patients may experience local or distant tumor relapse despite treatment as current strategies are not able to effectively target CSCs. A DNA-PK inhibitor may have the ability to sensitize these potential metastatic progenitor cells to the effects of IR and select DSB-inducing chemotherapeutic agents.

Given the involvement of DNA-PK in DNA repair processes, an application of specific DNA-PK inhibitory drugs would be to act as agents that will enhance the efficacy of both cancer chemotherapy and radiotherapy. Accordingly, it would be desirable to develop compounds useful as inhibitors of DNA-PK.

SUMMARY OF THE INVENTION

It has been found that compounds of this invention, and pharmaceutically acceptable compositions thereof, are effective as inhibitors of DNA-PK. Accordingly, the invention features compounds having the general formula:

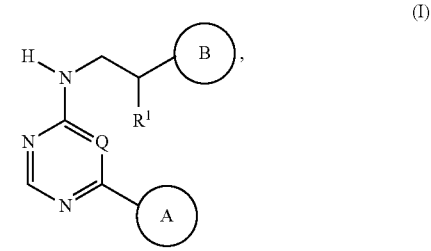

or a pharmaceutically acceptable salt thereof, where each of $R^1$, Q, Ring A, and Ring B is as defined herein.

The invention also provides pharmaceutical compositions that include a compound of formula I and a pharmaceutically acceptable carrier, adjuvant, or vehicle. These compounds and pharmaceutical compositions are useful for treating or lessening the severity of cancer.

The compounds and compositions provided by this invention are also useful for the study of DNA-PK in biological and pathological phenomena; the study of intracellular signal transduction pathways mediated by such kinases; and the comparative evaluation of new kinase inhibitors.

DETAILED DESCRIPTION OF THE INVENTION

Definitions and General Terminology

As used herein, the following definitions shall apply unless otherwise indicated. For purposes of this invention, the chemical elements are identified in accordance with the Periodic Table of the Elements, CAS version, and the Handbook of Chemistry and Physics, 75$^{th}$ Ed. 1994. Additionally, general principles of organic chemistry are described in "Organic Chemistry," Thomas Sorrell, University Science Books, Sausalito: 1999, and "March's Advanced Organic Chemistry," 5$^{th}$ Ed., Smith, M. B. and March, J., eds. John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted," whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position.

As described herein, when the term "optionally substituted" precedes a list, said term refers to all of the subsequent substitutable groups in that list. For example, if X is halogen; optionally substituted $C_{1-3}$ alkyl or phenyl; X may be either optionally substituted alkyl or optionally substituted phenyl. Likewise, if the term "optionally substituted" follows a list, said term also refers to all of the substitutable groups in the prior list unless otherwise indicated. For example: if X is halogen, $C_{1-3}$ alkyl, or phenyl, wherein X is optionally substituted by $J^X$, then both $C_{1-3}$ alkyl and phenyl may be optionally substituted by $J^X$. As is apparent to one having ordinary skill in the art, groups such as H, halogen, $NO_2$, CN, $NH_2$, OH, or $OCF_3$ would not be included because they are not substitutable groups. As is also apparent to a skilled person, a heteroaryl or heterocyclic ring containing an NH group can be optionally substituted by replacing the hydrogen atom with the substituent. If a substituent radical or structure is not identified or defined as "optionally substituted," the substituent radical or structure is unsubstituted.

Combinations of substituents envisioned by this invention are preferably those that result in the formation of stable or chemically feasible compounds. The term "stable," as used herein, refers to compounds that are not substantially altered when subjected to conditions to allow for their production, detection, and, preferably, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "alkyl" or "alkyl group," as used herein, means a straight-chain (i.e., unbranched) or branched, substituted or unsubstituted hydrocarbon chain that is completely saturated. Unless otherwise specified, alkyl groups contain 1-8 carbon atoms. In some embodiments, alkyl groups contain 1-6 carbon atoms, and in yet other embodiments, alkyl groups contain 1-4 carbon atoms (represented as "$C_{1-4}$ alkyl"). In other embodiments, alkyl groups are characterized as "$C_{0-4}$ alkyl" representing either a covalent bond or a $C_{1-4}$ alkyl chain. Examples of alkyl groups include methyl, ethyl, propyl, butyl, isopropyl, isobutyl, sec-butyl, and tert-butyl. The term "alkylene," as used herein, represents a saturated divalent straight or branched chain hydrocarbon group and is exemplified by methylene, ethylene, isopropylene and the like. The term "alkylidene," as used herein, represents a divalent straight chain alkyl linking group. The term "alkenyl," as used herein, represents monovalent straight or branched chain hydrocarbon group containing one or more carbon-carbon double bonds. The term "alkynyl," as used herein, represents a monovalent straight or branched chain hydrocarbon group containing one or more carbon-carbon triple bonds.

The term "cycloalkyl" (or "carbocycle") refers to a monocyclic $C_3$-$C_8$ hydrocarbon or bicyclic $C_8$-$C_{12}$ hydrocarbon that is completely saturated and has a single point of attachment to the rest of the molecule, and wherein any individual ring in said bicyclic ring system has 3-7 members. Suitable cycloalkyl groups include, but are not limited to, cyclopropyl, cyclobutyl, cyclopentyl, cyclohexyl, and cycloheptyl.

The term "heterocycle," "heterocyclyl," "heterocycloalkyl," or "heterocyclic" as used herein refers to a monocyclic, bicyclic, or tricyclic ring system in which at least one ring in the system contains one or more heteroatoms, which is the same or different, and that is completely saturated or that contains one or more units of unsaturation, but which is not aromatic, and that has a single point of attachment to the rest of the molecule. In some embodiments, the "heterocycle," "heterocyclyl," "heterocycloalkyl," or "heterocyclic" group has three to fourteen ring members in which one or more ring members is a heteroatom independently selected from oxygen, sulfur, nitrogen, or phosphorus, and each ring in the system contains 3 to 8 ring members.

Examples of heterocyclic rings include, but are not limited to, the following monocycles: 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl; and the following bicycles: 3-1H-benzimidazol-2-one, 3-(1-alkyl)-benzimidazol-2-one, indolinyl, tetrahydroquinolinyl, tetrahydroisoquinolinyl, benzothiolane, benzodithiane, and 1,3-dihydroimidazol-2-one.

The term "heteroatom" means one or more of oxygen, sulfur, nitrogen, or phosphorus, including any oxidized form of nitrogen, sulfur, or phosphorus; the quaternized form of any basic nitrogen; or a substitutable nitrogen of a heterocyclic ring, for example N (as in 3,4-dihydro-2H-pyrrolyl), NH (as in pyrrolidinyl) or NR$^+$ (as in N-substituted pyrrolidinyl).

The term "unsaturated," as used herein, means that a moiety has one or more units of unsaturation.

The term "alkoxy," or "thioalkyl," as used herein, refers to an alkyl group, as previously defined, attached to the principal carbon chain through an oxygen ("alkoxy") or sulfur ("thioalkyl") atom.

The terms "haloalkyl," "haloalkenyl," and "haloalkoxy" mean alkyl, alkenyl, or alkoxy, as the case may be, substituted with one or more halogen atoms. The term "halogen" means F, Cl, Br, or I.

The term "aryl" used alone or as part of a larger moiety as in "aralkyl," "aralkoxy," or "aryloxyalkyl," refers to a monocyclic, bicyclic, or tricyclic carbocyclic ring system having a total of six to fourteen ring members, wherein said ring system has a single point of attachment to the rest of the molecule, at least one ring in the system is aromatic and wherein each ring in the system contains 4 to 7 ring members. The term "aryl" may be used interchangeably with the term "aryl ring." Examples of aryl rings include phenyl, naphthyl, and anthracene.

The term "heteroaryl," used alone or as part of a larger moiety as in "heteroaralkyl," or "heteroarylalkoxy," refers to a monocyclic, bicyclic, and tricyclic ring system having a total of five to fourteen ring members, wherein said ring system has a single point of attachment to the rest of the molecule, at least one ring in the system is aromatic, at least one ring in the system contains one or more heteroatoms independently selected from nitrogen, oxygen, sulfur or phosphorus, and wherein each ring in the system contains 4 to 7 ring members. The term "heteroaryl" may be used interchangeably with the term "heteroaryl ring" or the term "heteroaromatic."

Further examples of heteroaryl rings include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

As described herein, a bond drawn from a substituent to the center of one ring within a multiple-ring system (as shown below) represents substitution of the substituent at any substitutable position in any of the rings within the multiple ring system. For example, Structure a represents possible substitution in any of the positions shown in Structure b.

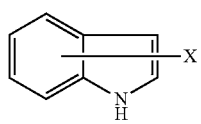

Structure a

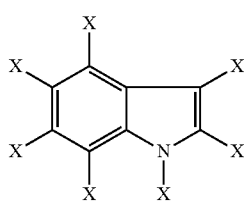

Structure b

This also applies to multiple ring systems fused to optional ring systems (which would be represented by dotted lines). For example, in Structure c, X is an optional substituent both for ring A and ring B.

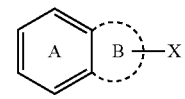

Structure c

If, however, two rings in a multiple ring system each have different substituents drawn from the center of each ring, then, unless otherwise specified, each substituent only represents substitution on the ring to which it is attached. For example, in Structure d, Y is an optionally substituent for ring A only, and X is an optional substituent for ring B only.

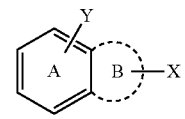

Structure d

The term "protecting group," as used herein, represent those groups intended to protect a functional group, such as, for example, an alcohol, amine, carboxyl, carbonyl, etc., against undesirable reactions during synthetic procedures. Commonly used protecting groups are disclosed in Greene and Wuts, *Protective Groups In Organic Synthesis*, 3$^{rd}$ Edition (John Wiley & Sons, New York, 1999), which is incorporated herein by reference. Examples of nitrogen protecting groups include acyl, aroyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl and chiral auxiliaries such as protected or unprotected D, L or D, L-amino acids such as alanine, leucine, phenylalanine and the like; sulfonyl groups such as benzenesulfonyl, p-toluenesulfonyl and the like; carbamate groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl and the like, arylalkyl groups such as benzyl, triphenylmethyl, benzyloxymethyl and the like and silyl groups such as trimethylsilyl and the like. Preferred N-protecting groups are formyl, acetyl, benzoyl, pivaloyl, t-butylacetyl, alanyl, phenylsulfonyl, benzyl, t-butyloxycarbonyl (Boc) and benzyloxycarbonyl (Cbz).

Unless otherwise depicted or stated, structures recited herein are meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Compounds that have been drawn with stereochemical centers defined, usually through the use of a hatched (⋯) or bolded (—) bond, are stereochemically pure, but with the absolute stereochemistry still undefined. Such compounds can have either the R or S configuration. In those cases where the absolute configuration has been determined, the chiral center(s) are labeled (R) or (S) in the drawing.

Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools, probes in biological assays, or as DNA-PK inhibitors with an improved therapeutic profile.

Description of Compounds of the Invention

In one aspect, the invention features compounds having the formula:

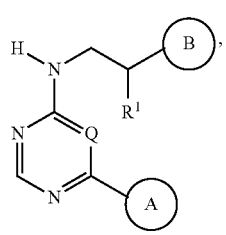

(I)

or a pharmaceutically acceptable salt thereof, wherein
Q is N or CH;
$R^1$ is hydrogen, $CH_3$, $CH_2CH_3$, or $R^1$ and the carbon to which it is bound form a $C=CH_2$ group;
Ring A is a ring system selected from

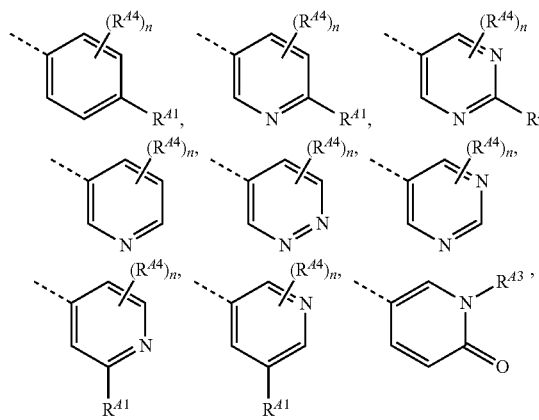

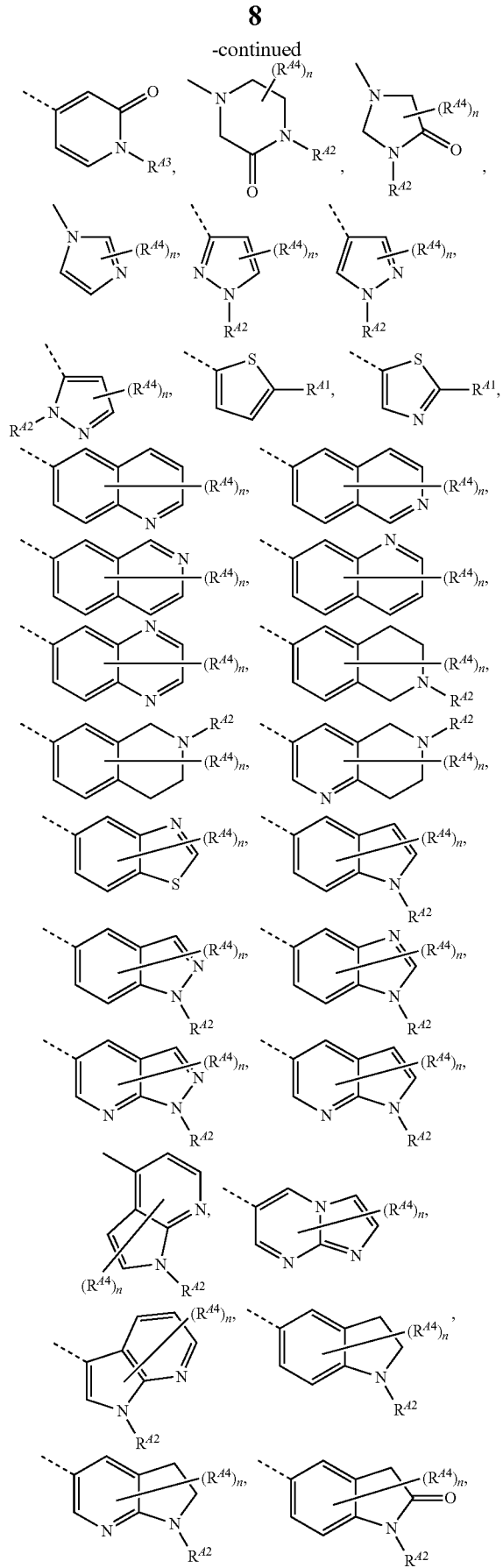

$R^{A1}$ is hydrogen, halogen, $C_{1-4}$alkyl, $C_{0-4}$alkyl-$C_{3-6}$cycloalkyl, $C_{0-4}$alkyl-$OR^{A1a}$, $C_{0-4}$alkyl-$SR^{A1a}$, $C_{0-4}$alkyl-C(O)N($R^{A1a}$)$_2$, $C_{0-4}$alkyl-CN, $C_{0-4}$alkyl-S(O)—$C_{1-4}$alkyl, $C_{0-4}$alkyl-S(O)$_2$—$C_{1-4}$alkyl, $C_{0-4}$alkyl-C(O)$OR^{A1b}$, $C_{0-4}$alkyl-C(O)$C_{1-4}$alkyl, $C_{0-4}$alkyl-N($R^{A1b}$)C(O)$R^{A1a}$, $C_{0-4}$alkyl-N($R^{A1b}$)S(O)$_2R^{A1a}$, $C_{0-4}$alkyl-N($R^{A1a}$)$_2$, $C_{0-4}$alkyl-N($R^{A1b}$)(3-6 membered-cycloalkyl), $C_{0-4}$alkyl-N($R^{A1b}$)(4-6 membered-heterocyclyl), N($R^{A1b}$)$C_{2-4}$alkyl-N($R^{A1a}$)$_2$, N($R^{A1b}$)$C_{2-4}$alkyl-$OR^{A1a}$, N($R^{A1b}$)$C_{1-4}$alkyl-(5-10 membered heteroaryl), N($R^{A1b}$)$C_{1-4}$alkyl-(4-6 membered heterocyclyl), N($R^{A1b}$)$C_{2-4}$alkyl-N($R^{A1b}$)C(O)$R^{A1a}$, $C_{0-4}$alkyl-N($R^{A1b}$)C(O)$C_{1-4}$alkyl, $C_{0-4}$alkyl-N($R^{A1b}$)C(O)$OC_{1-4}$alkyl, $C_{0-4}$alkyl-(phenyl), $C_{0-4}$alkyl-(3-10 membered-heterocyclyl), $C_{0-4}$alkyl-C(O)-(4-6 membered-heterocyclyl), $C_{0-4}$alkyl-O—$C_{0-4}$alkyl-(4-6 membered-heterocyclyl), $C_{0-4}$alkyl-(5-6 membered-heteroaryl), $C_{0-4}$alkyl-C(O)-(5-6 membered-heteroaryl), $C_{0-4}$alkyl-O—$C_{0-4}$alkyl-(5-6 membered-heteroaryl), $C_{0-4}$alkyl-N($R^{A1a}$)(4-6 membered-heterocyclyl), or $C_{0-4}$alkyl-N($R^{A1b}$)(5-6 membered-heteroaryl), wherein each of said $R^{A1}$ heterocyclyl is a ring system selected from aziridinyl, oxetanyl, tetrahydropyran, tetrahydrofuranyl, dioxanyl, dioxolanyl, azetidinyl, pyrrolidinyl, pyrrolidinonyl, pyrrolidinedionyl, morpholinyl, piperidinyl, piperazinyl, piperazinonyl, tetrahydrothiophenedioxidyl, 1,1-dioxothietanyl, 2-oxa-6-azaspiro[3.4]octanyl, or isoindolinonyl wherein each of said $R^{A1}$ heteroaryl is a ring system selected from furanyl, thiophenyl, imidazolyl, benzoimidazolyl, oxazolyl, oxadiazolyl, thiazolyl, pyrazolyl, thiadiazolyl, pyridinyl, pyrimidinyl, pyrazinyl, triazolyl, or tetrazolyl, and wherein each of said $R^{A1}$ alkyl, cycloalkyl, phenyl, heterocyclyl, or heteroaryl groups is optionally substituted with up to three F atoms, up to two $C_{1-2}$alkyl groups, a $C_{3-6}$cycloalkyl group, a phenyl group, a benzyl group, an alkenyl-$C_{0-2}$alkyl group, an alkynyl-$C_{0-2}$alkyl group, up to two $C_{0-2}$alkyl-$OR^{A1b}$ groups, a $C_{0-2}$alkyl-N($R^{A1b}$)$_2$ group, a $SC_{1-4}$alkyl group, a $S(O)_2C_{1-4}$alkyl group, a C(O)$R^{A1b}$ group, a C(O)$OR^{A1b}$ group, a C(O)N($R^{A1b}$)$_2$ group, a —CN group, or a $C_{4-6}$heterocyclic ring system selected from oxetanyl, tetrahydrofuranyl, tetrahydropyran, piperidinyl, or morpholinyl;

each $R^{A1a}$ is, independently, hydrogen, $C_{1-4}$alkyl, $C_{3-6}$cycloalkyl, $C_{4-6}$heterocyclyl selected from oxetanyl, tetrahydrofuranyl, tetrahydropyran, pyrrolidinyl, or piperidinyl, $C_{5-6}$heteroaryl selected from imidazolyl, triazolyl, tetrazolyl, pyrazolyl, thiophenyl, thiazolyl, pyridinyl, pyrimidinyl, or pyrazinyl, or two $R^{A1a}$ and an intervening nitrogen atom form a 3-6 membered heterocyclic ring selected from aziridinyl, azetidinyl, pyrrolidinyl, pyrrolidinonyl, piperidinyl, piperidinonyl, tetrahydropyridinyl, piperazinyl, or morpholinyl, wherein each of said $R^{A1a}$ alkyl, cycloalkyl, heterocyclyl, or heteroaryl groups is optionally substituted with up to three F atoms, up to two $C_{1-2}$alkyl groups, a $C_{3-6}$cycloalkyl group, up to two $C_{0-2}$alkyl-$OR^{A1b}$ groups, a $C_{0-2}$alkyl-N($R^{A1b}$)$_2$ group, a $SC_{1-4}$alkyl group, a C(O)$R^{A1b}$ group, a C(O)$OR^{A1b}$ group, a C(O)N($R^{A1b}$)$_2$ group, or a —CN group;

each $R^{A1b}$ is, independently, hydrogen, $C_{1-2}$alkyl, or $C_{3-4}$cycloalkyl;

$R^{A2}$ is hydrogen, $C_{1-4}$alkyl, $C_{0-4}$alkyl-$C_{3-6}$cycloalkyl, $C_{0-2}$alkyl-(4-6 membered)heterocyclyl, $C_{2-4}$alkyl-$OR^{A2a}$, $C_{0-2}$alkyl-C(O)N($R^{A2a}$)$_2$, $C_{0-2}$alkyl-S(O)$_2$—$C_{1-4}$alkyl, $C_{0-2}$alkyl-C(O)$OC_{1-4}$alkyl, $C_{0-2}$alkyl-C(O)-(4-6 membered)heterocyclyl, wherein each of said heterocyclyl is selected from oxetanyl, tetrahydropyran, tetrahydrofuranyl, dioxanyl, dioxolanyl, azetidinyl, pyrrolidinyl, pyrrolidinonyl, pyrrolidinedionyl, morpholinyl, piperidinyl, piperazinyl, piperazinonyl, or 1,1-dioxothietanyl, and each of said $R^{A2}$ groups except hydrogen is optionally substituted with up to three F atoms, up to two $C_{1-2}$alkyl groups, a $C_{3-6}$cycloalkyl group, an alkenyl-$C_{0-2}$alkyl group, an alkynyl-$C_{0-2}$alkyl group, up to two $OR^{A2b}$ groups, a $C_{0-2}$alkyl-N($R^{A2b}$)$_2$ group, a $SC_{1-4}$alkyl group, a $S(O)_2C_{1-4}$alkyl group, a C(O)$R^{A2b}$ group, a C(O)$OR^{A2b}$ group, a C(O)N($R^{A2b}$)$_2$ group, or a —CN group;

each $R^{A2a}$ is, independently, hydrogen, $C_{1-4}$alkyl, a $C_{5-6}$heteroaryl selected from imidazolyl, triazolyl, tetrazolyl, pyrazolyl, thiophenyl, thiazolyl, pyridinyl, pyrimidinyl, or pyrazinyl, or two $R^{A2a}$ and an intervening nitrogen atom form a 3-6 membered heterocyclic ring selected from aziridinyl, azetidinyl, pyrrolidinyl, pyrrolidinonyl, piperidinyl, piperidinonyl, tetrahydropyridinyl, piperazinyl, or morpholinyl;

each $R^{A2b}$ is, independently, hydrogen, $C_{1-4}$alkyl, or $C_{3-4}$cycloalkyl;

$R^{A3}$ is hydrogen or $C_{1-2}$alkyl;

each $R^{A4}$ is, independently, deuterium, halogen, CN, $C_{1-4}$alkyl, or $OC_{1-4}$alkyl, wherein each $R^{A4}$ alkyl is optionally substituted with up to 3 F atoms, two non-geminal OH groups, or one OC$_{1-2}$alkyl, or two R$^{A4}$ together with an intervening saturated carbon atom form a spiral cyclopropyl or cyclobutyl ring;
n is 0-3;
Ring B is a ring system selected from
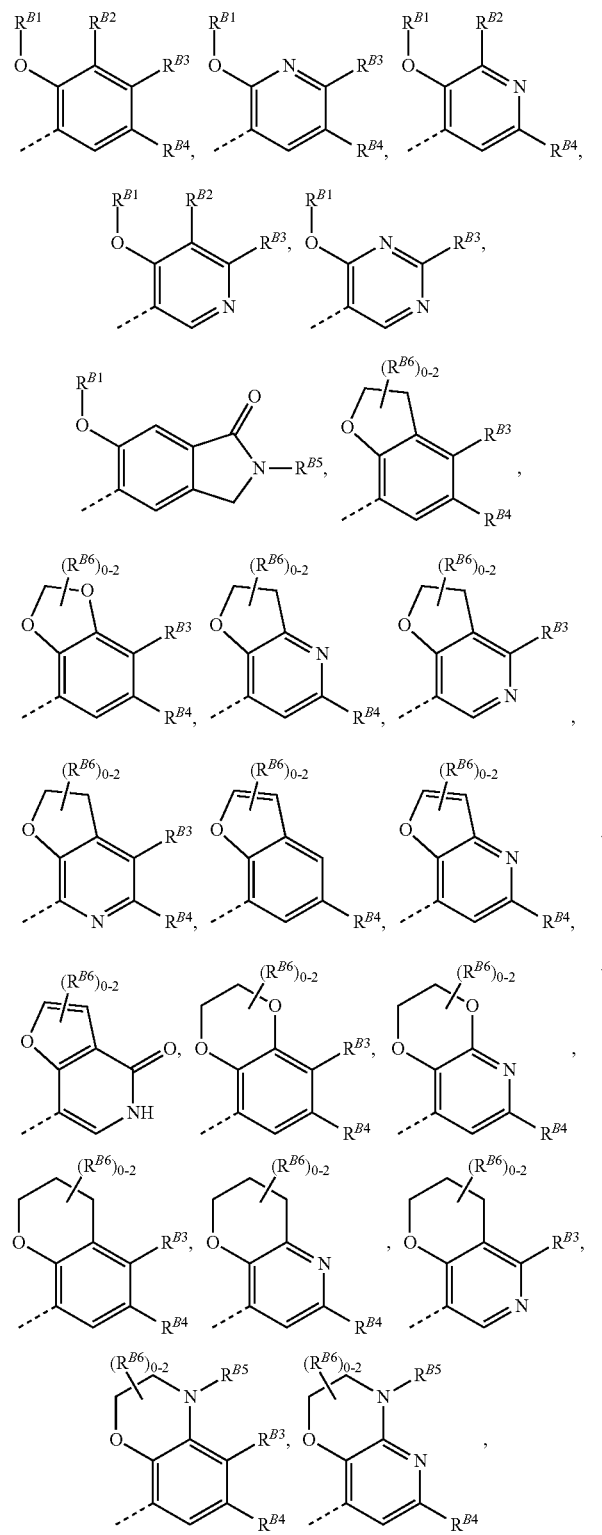
-continued
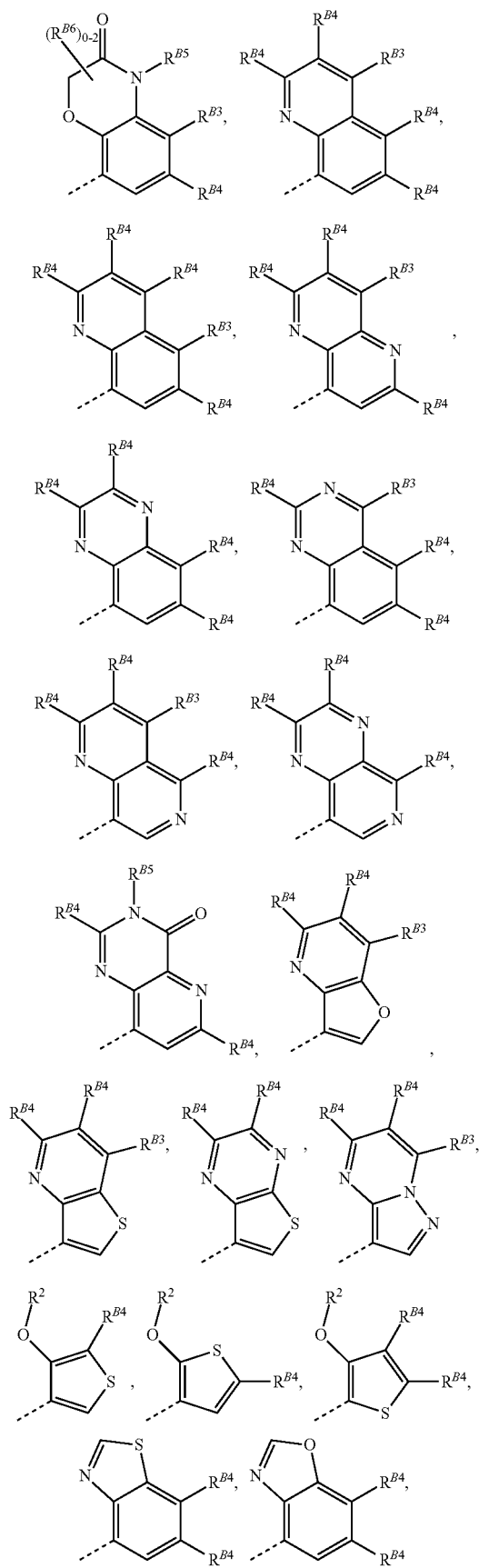

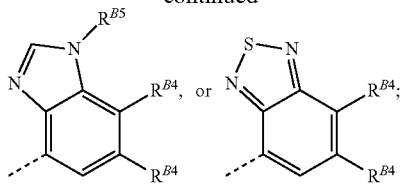

$R^{B1}$ is hydrogen, $C_{1-4}$ alkyl, $(CH_2)_{0-1}C_{3-6}$cycloalkyl, $C(O)$ $C_{1-2}$alkyl, $(CH_2)_{0-1}$-(4-6 membered)heterocyclyl ring wherein said heterocyclic ring is selected from selected from oxetanyl, tetrahydrofuranyl, tetrahydropyran, dioxanyl, dioxolanyl, or pyrrolidinonyl, phenyl, benzyl, or $(CH_2)_{1-2}$(5-6 membered)heteroaryl ring wherein said heteroaryl ring is selected from pyridinyl, imidazolyl, or pyrazolyl, and wherein each of said $R^{B1}$ alkyl, cycloalkyl, phenyl, benzyl, heterocyclyl or heteroaryl groups is optionally substituted with up to 3 F atoms, up to two $C_{1-2}$alkyl groups, two non-geminal OH groups, or one $OC_{1-2}$alkyl;

$R^{B2}$ is hydrogen, $C_{1-4}$alkyl, $OC_{1-4}$alkyl;

each $R^{B3}$ is, independently, hydrogen, halogen, $C_{1-4}$alkyl, $C_{2-4}$alkenyl, $C_{2-4}$alkynyl, CN, C(O)H, $C(O)C_{1-4}$alkyl, $C(O)OC_{1-4}$alkyl, $C(O)C_{1-4}$alkyl, $C(O)NH_2$, $C(O)NHC_{1-4}$alkyl, $C(O)NH(CH_2)_{0-1}C_{3-6}$cycloalkyl, $C(O)$ $NHCH_2$oxetanyl, $C(O)NHCH_2$tetrahydrofuranyl, $C(O)$ $NHCH_2$tetrahydropyranyl, C(O)NHphenyl, C(O)NHbenzyl, C(O)NHOH, $C(O)NHOC_{1-4}$alkyl, $C(O)NHO(CH_2)_{0-1}$ $C_{3-6}$cycloalkyl, $C(O)NHO(CH_2)_{0-1}$oxetanyl, $C(O)NHO$ $(CH_2)_{0-1}$tetrahydrofuranyl, $C(O)NHO(CH_2)_{0-1}$tetrahydropyranyl, C(O)NHOphenyl, C(O)NHObenzyl, $NH_2$, NHC $(O)C_{1-4}$ alkyl, $OC_{1-4}$alkyl, $SC_{1-4}$alkyl, $S(O)C_{1-4}$alkyl, or a 5-membered-heteroaryl ring system selected from furanyl, thiophenyl, imidazolyl, pyrrole, pyrazolyl, and oxadiazolyl, wherein each $R^{B3}$ group except hydrogen or halogen is optionally substituted with Cl, up to three F atoms, up to two non-geminal OH groups, up to two $OC_{1-2}$alkyl, one $NH_2$, one $NHC_{1-2}$alkyl, one $NHC(O)C_{1-2}$alkyl, or one $N(C_{1-2}$ alkyl)$_2$;

each $R^{B4}$ is, independently, hydrogen, halogen, $C_{1-4}$alkyl, $OC_{1-4}$alkyl, $SC_{1-4}$alkyl, $NH_2$, $NH(C_{1-4}$alkyl), $N(C_{1-4}$ alkyl)$_2$, $NHC(O)C_{1-4}$alkyl, C(O)OH, $C(O)OC_{1-4}$alkyl, $C(O)NH_2$, $C(O)NHC_{1-4}$alkyl, $C(O)N(C_{1-4}$alkyl)$_2$, CN, a morpholinyl ring, or an imidazolyl ring, wherein each $R^{B4}$ alkyl is optionally substituted with up to 3 F atoms, two non-geminal OH groups, or one $OC_{1-2}$alkyl;

$R^{B5}$ is hydrogen, $C_{1-4}$alkyl, $C(O)C_{1-4}$alkyl, $C(O)OC_{1-4}$alkyl, $C(O)NH_2$, $C(O)NHC_{1-4}$alkyl, or $C(O)N(C_{1-4}$alkyl)$_2$, wherein said $R^{B5}$ alkyl is optionally substituted with up to 3 F atoms, two non-geminal OH groups, or one $OC_{1-2}$alkyl and $R^{B6}$ is F or $C_{1-2}$alkyl, or two $R^{B6}$ and an intervening carbon atom from a spirocyclopropyl or spirocyclobutyl ring.

In one embodiment, the compound has the following formula:

(I-A-1)

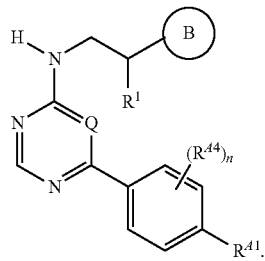

In one embodiment, the compound has one of the following formulae:

(I-A-2)

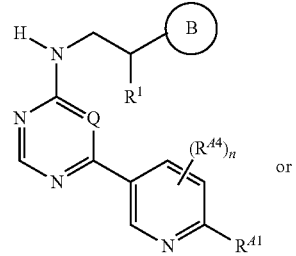

or (I-A-3)

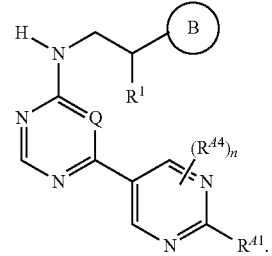

In one embodiment, the compound has one of the following formulae:

(I-A-4)

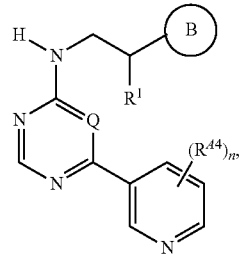

(I-A-5)

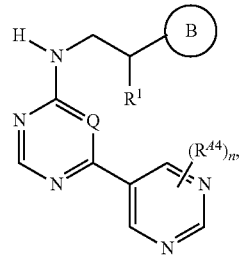

(I-A-6)

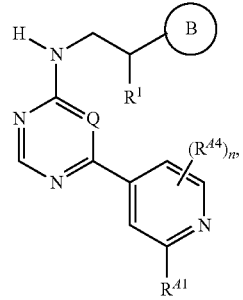

-continued (I-A-7)
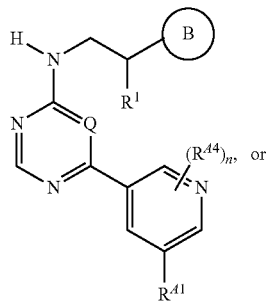

(I-A-8)
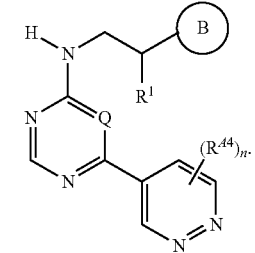

In one embodiment, the compound has one of the following formulae:

(I-A-9)
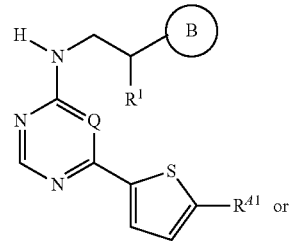

(I-A-10)
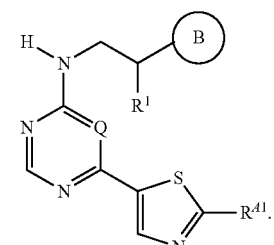

In a further embodiment for any compound of formulae I-A-1 to I-A-3, I-A-6 to I-A-7, or I-A-9 to I-A-10, $R^{41}$ is $C_{1-4}$alkyl, $OC_{1-4}$alkyl, or $N(R^{41a})_2$, wherein each $R^{41a}$ is, independently, hydrogen or $C_{1-4}$alkyl, or two $R^{41a}$ and an intervening nitrogen atom form a 3-6 membered heterocyclic ring selected from aziridinyl, azetidinyl, pyrrolidinyl, pyrrolidinonyl, piperidinyl, piperidinonyl, tetrahydropyridinyl, piperazinyl, or morpholinyl, wherein each of said $R^{41}$ alkyl or heterocyclyl groups is optionally substituted with up to three F atoms, up to three $^2H$ atoms, up to two $C_{1-2}$alkyl groups, a $C_{3-6}$cycloalkyl group, up to two $C_{0-2}$alkyl-$OR^{41b}$ groups, a $C_{0-2}$alkyl-$N(R^{41b})_2$ group, a $SC_{1-4}$alkyl group, a $C(O)R^{41b}$ group, a $C(O)OR^{41b}$ group, a $C(O)N(R^{41b})_2$ group, or a —CN group, wherein each $R^{41b}$ is, independently, hydrogen, $C_{1-2}$alkyl, or $C_{3-4}$cycloalkyl.

In one embodiment, the compound has one of the following formulae:

(I-A-11)
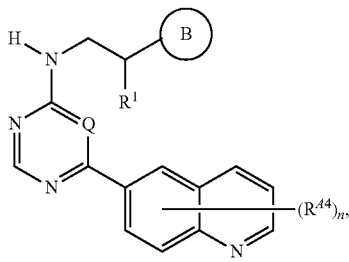

(I-A-12)
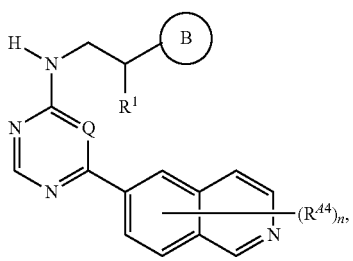

(I-A-13)
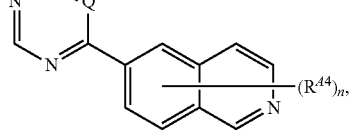

(I-A-14)
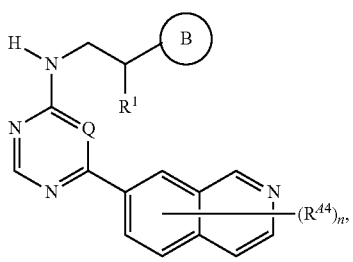

(I-A-15)
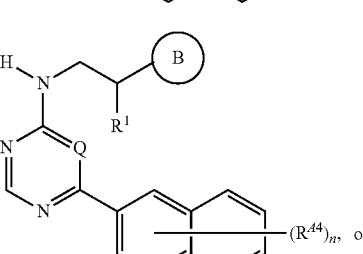

(I-A-16)
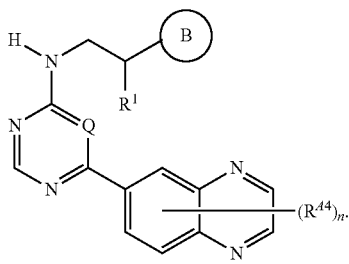

In one embodiment, the compound has the following formula:
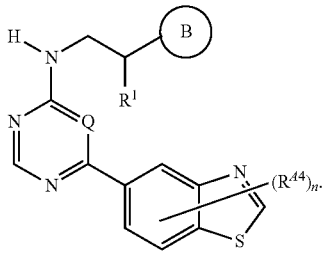
(I-A-17)
In one embodiment, the compound has one of the following formulae:
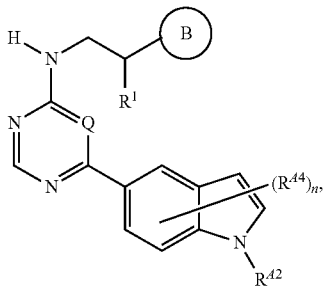
(I-A-18)
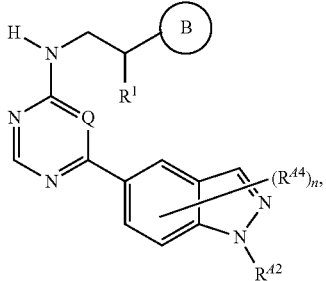
(I-A-19)
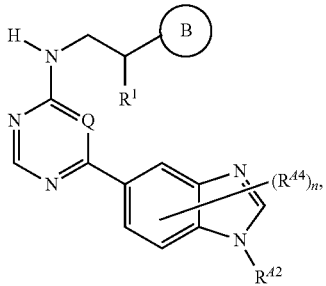
(I-A-20)
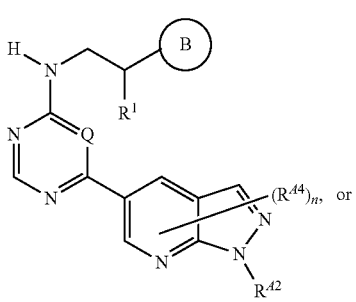
(I-A-21) or
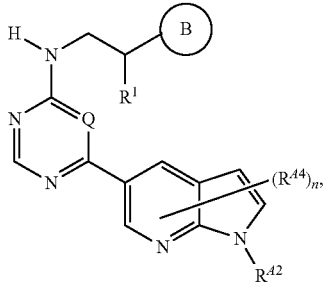
(I-A-22)
In one embodiment, the compound has one of the following formulae:
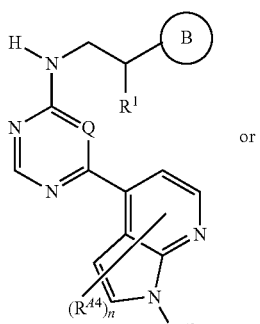
(I-A-23) or
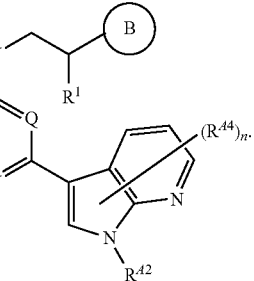
(I-A-24)
In one embodiment, the compound has the following formula:
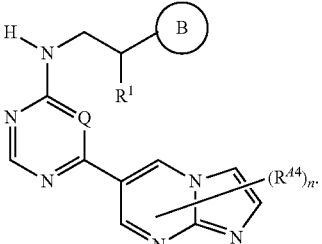
(I-A-25)
In one embodiment, the compound has one of the following formulae:

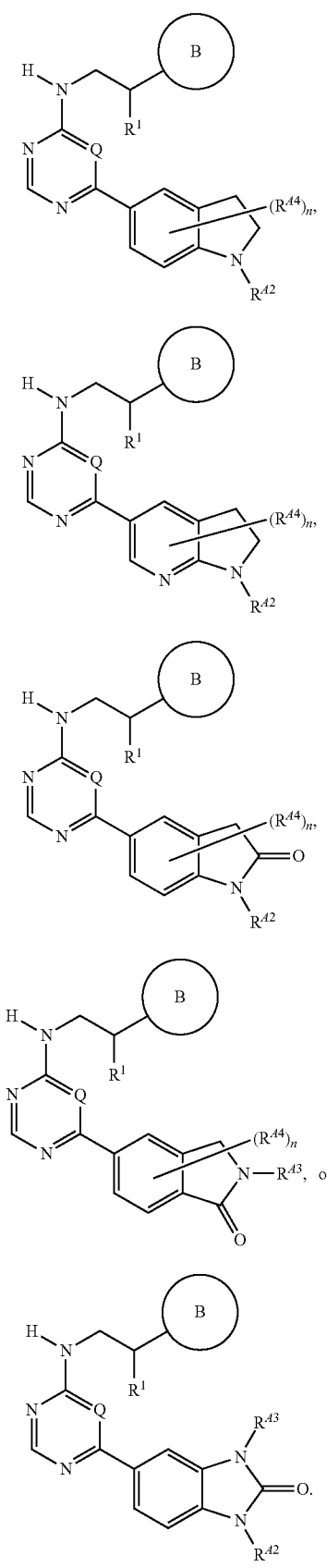
In one embodiment, the compound has one of the following formulae:
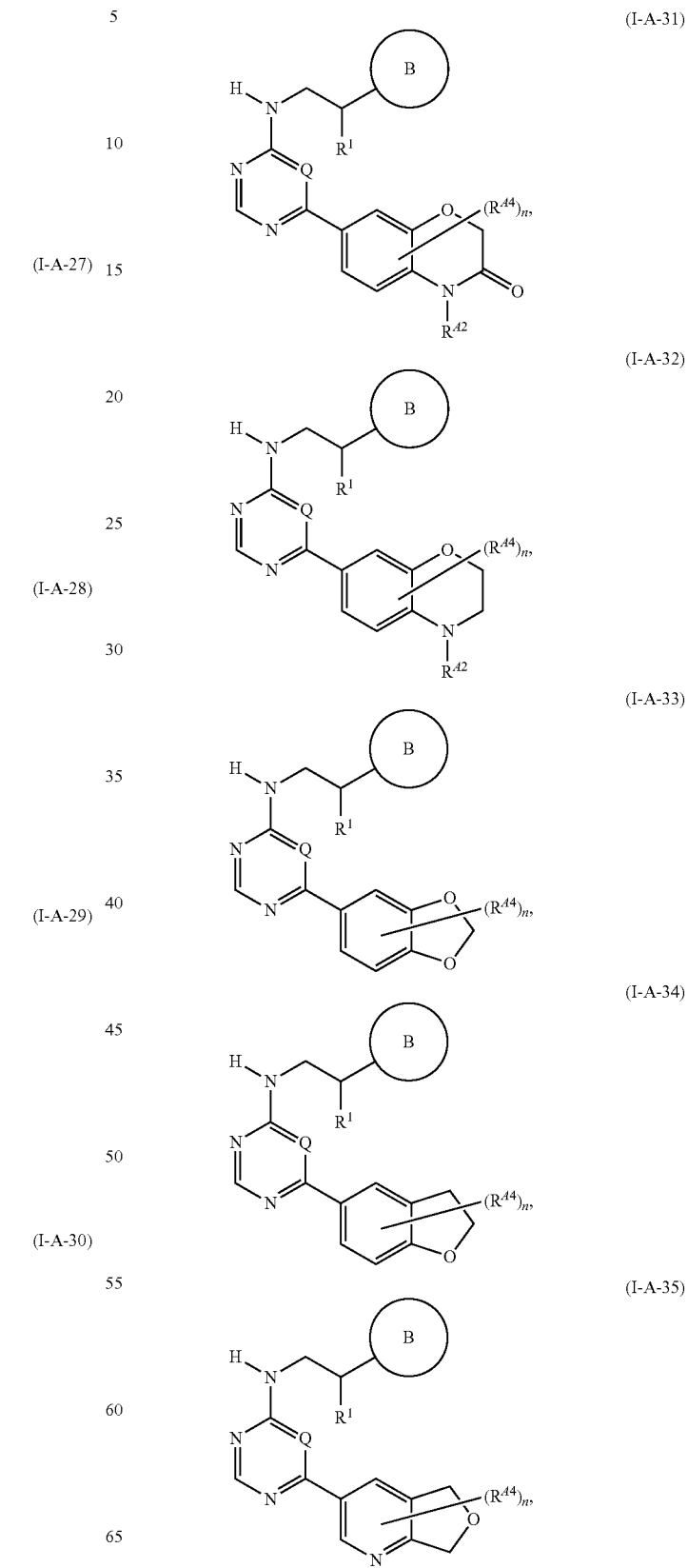

-continued
(I-A-36)
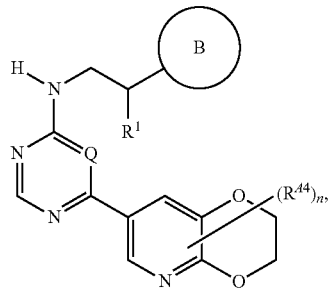
(I-A-37)
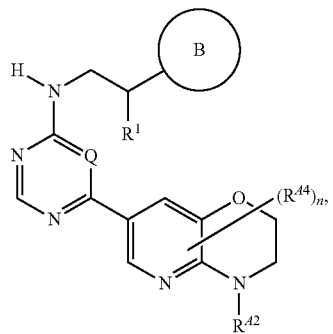
(I-A-38)
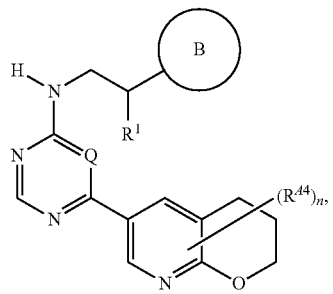
(I-A-39)
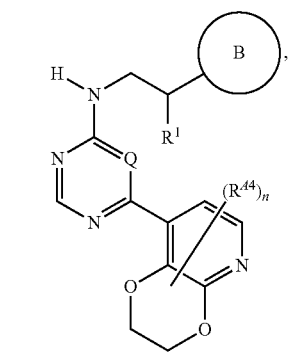
(I-A-40)
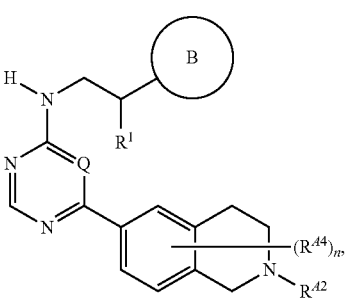
-continued
(I-A-41)
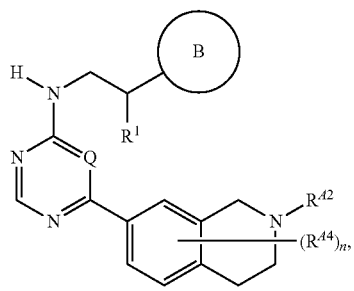
(I-A-42)
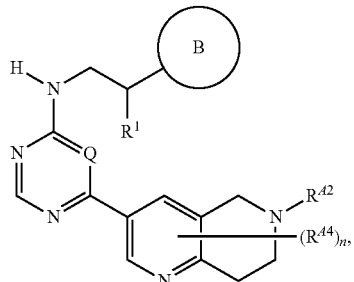
(I-A-43)
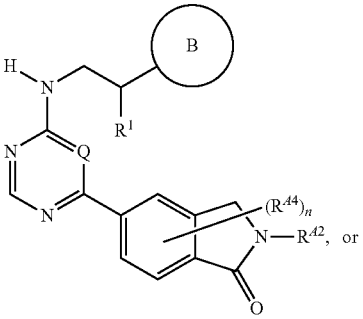
(I-A-44)
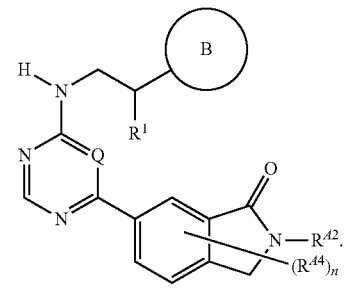
In one embodiment, the compound has one of the following formulae:
(I-A-45)

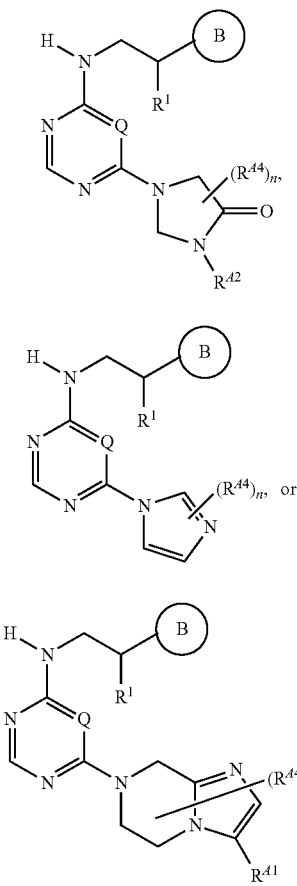
(I-A-46)
(I-A-47)
(I-A-48)
In one embodiment, the compound has one of the following formulae
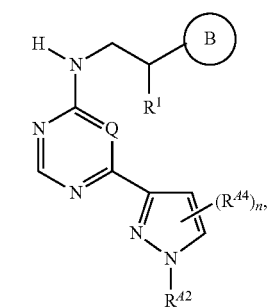
(I-A-49)
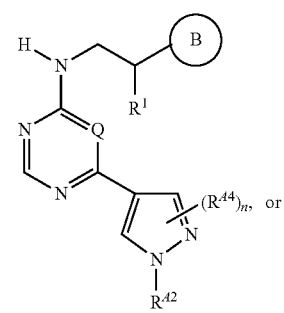
(I-A-50)
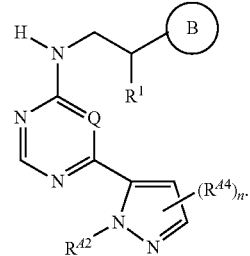
(I-A-51)
In one embodiment, the compound has the following formula
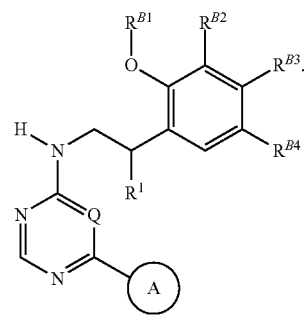
(I-B-1)
In one embodiment, the compound has one of the following formulae:
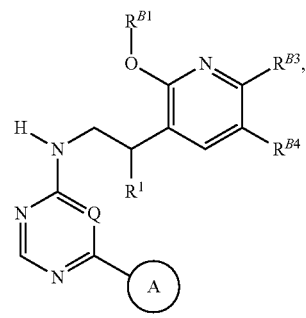
(I-B-2)
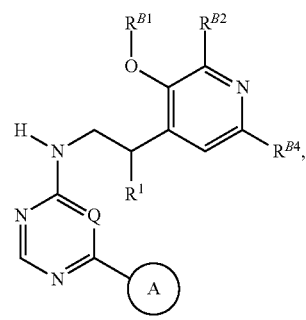
(I-B-3)

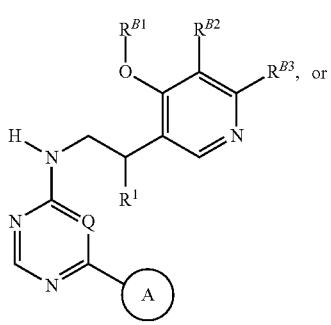
(I-B-4)
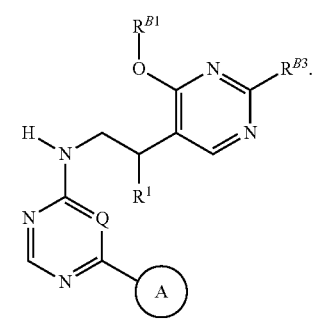
(I-B-5)
In one embodiment, the compound has the following formula:
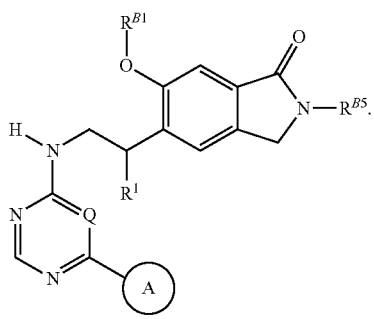
(I-B-6)
In one embodiment, the compound has the following formula:
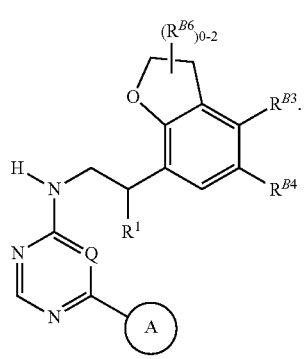
(I-B-7)
In one embodiment, the compound has the following formula:
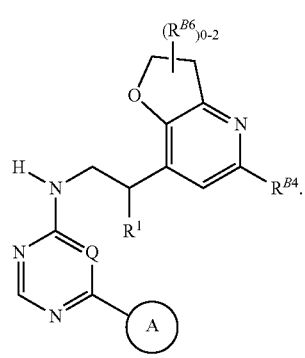
(I-B-8)
In one embodiment, the compound has one of the following formulae:
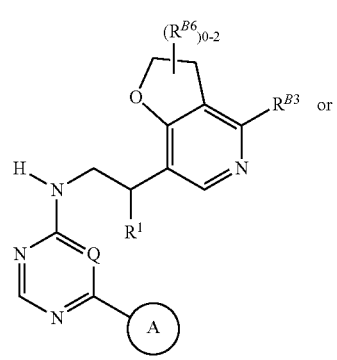
(I-B-9)
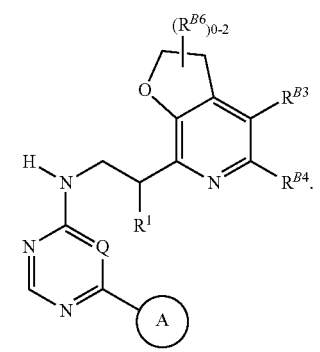
(I-B-10)
In one embodiment, the compound has one of the following formulae:
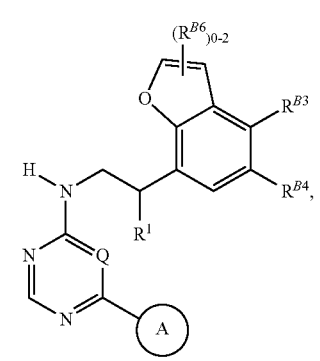
(I-B-11)

-continued
(I-B-12)
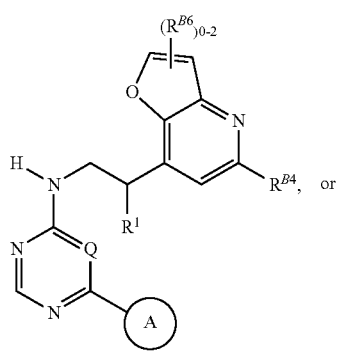
or
(I-B-13)
In one embodiment, the compound has the following formula:
(I-B-14)
In one embodiment, the compound has the following formula:
(I-B-15)
In one embodiment, the compound has the following formula:
(I-B-16)
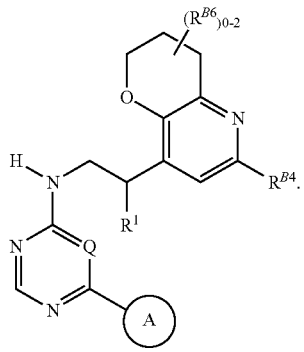
In one embodiment, the compound has one of the following formulae:
(I-B-17)
(I-B-18)
or
(I-B-19)

In one embodiment, the compound has one of the following formulae:
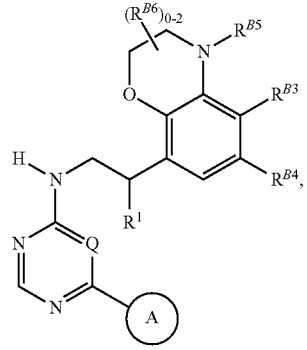
(I-B-20)
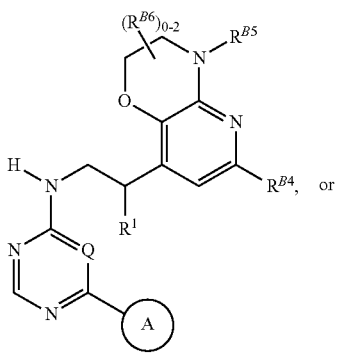
(I-B-21)
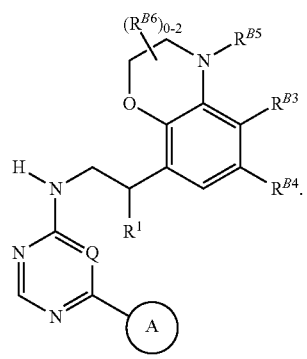
(I-B-22)
In one embodiment, the compound has the following formula:
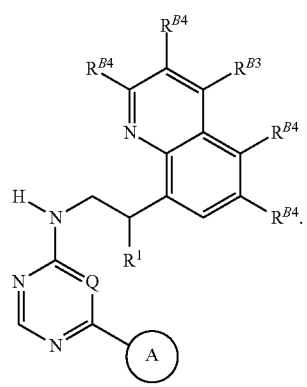
(I-B-23)
In one embodiment, the compound has one of the following formulae:
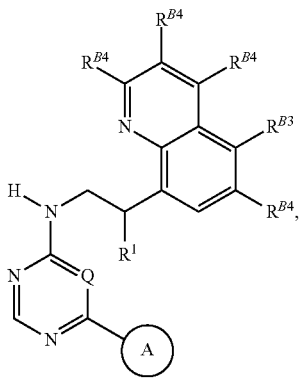
(I-B-24)
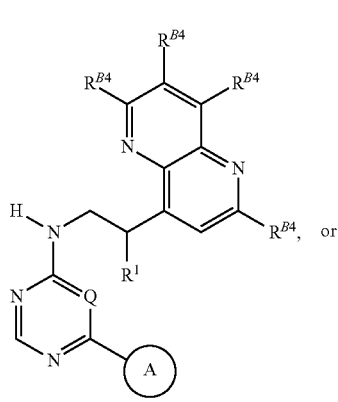
(I-B-25)
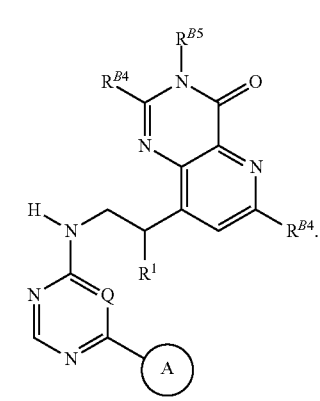
(I-B-26)
In one embodiment, the compound has one of the following formulae:
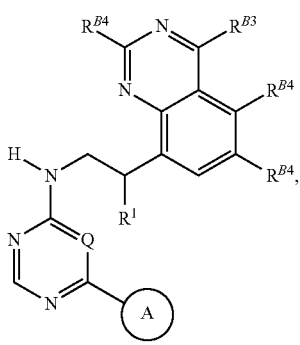
(I-B-27)

(I-B-28)
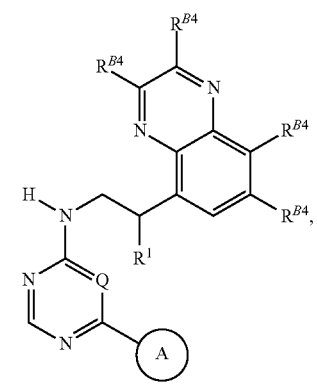
(I-B-29)
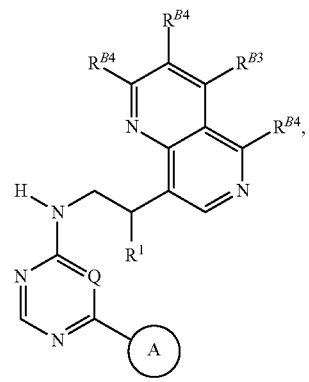
(I-B-30)
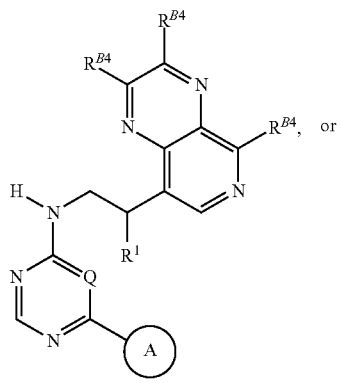
or
(I-B-31)
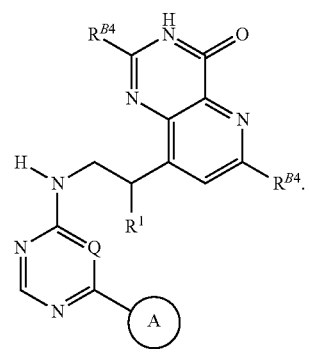
In one embodiment, the compound has one of the following formulae:
(I-B-32)
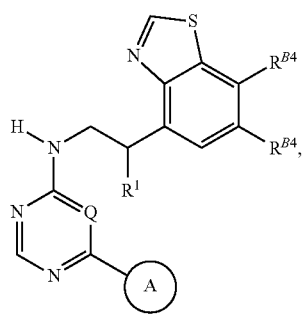
(I-B-33)
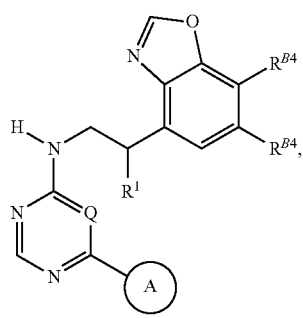
In one embodiment, the compound has one of the following formulae:
(I-B-34)
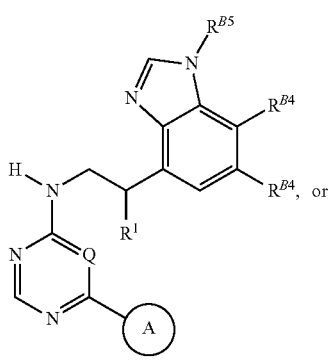
or
(I-B-35)
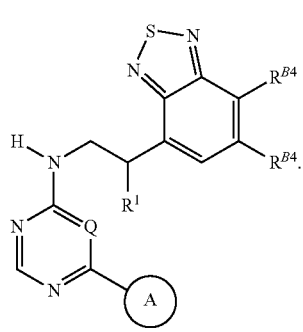
In one embodiment, the compound has one of the following formulae:

(I-B-36)
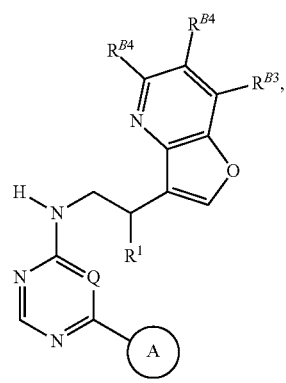
(I-B-37)
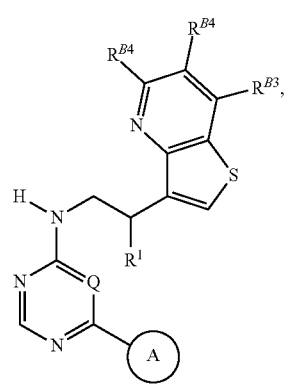
(I-B-38)
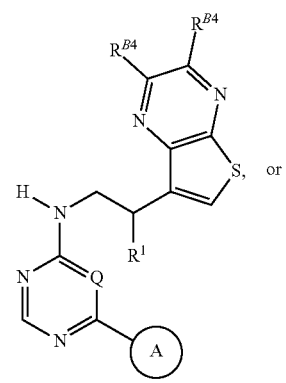
(I-B-39)
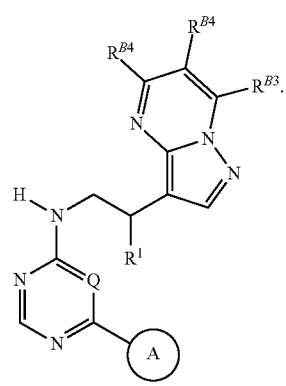
In one embodiment, the compound has one of the following formulae:
(I-B-40)
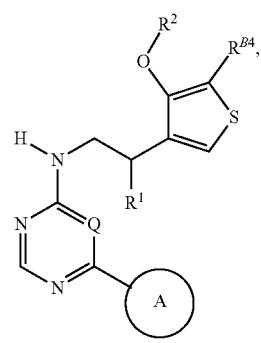
(I-B-41)
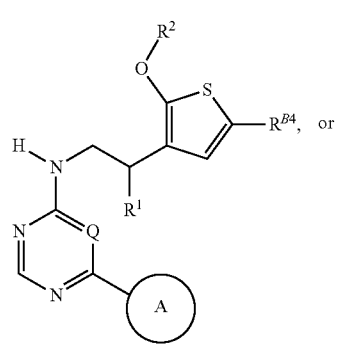
(I-B-42)
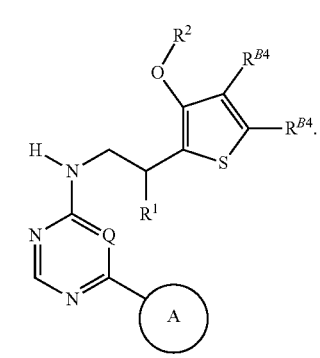
In another embodiment, the B Ring of a compound of the invention is linked to the remainder of the molecule wherein
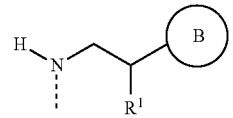
is
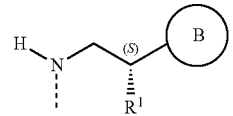

and $R^1$ is $CH_3$; except when Ring B is

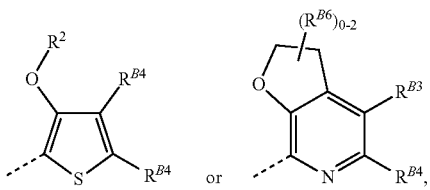

wherein

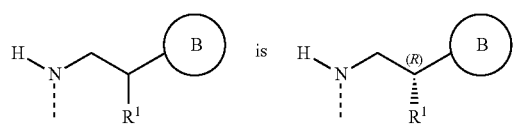

and $R^1$ is $CH_3$.

In another embodiment, Q is CH for a compound of the invention.

In another embodiment, Ring A of compounds of the invention comprises a heterocyclyl or heteroaryl ring.

In a further embodiment, Ring A is selected from

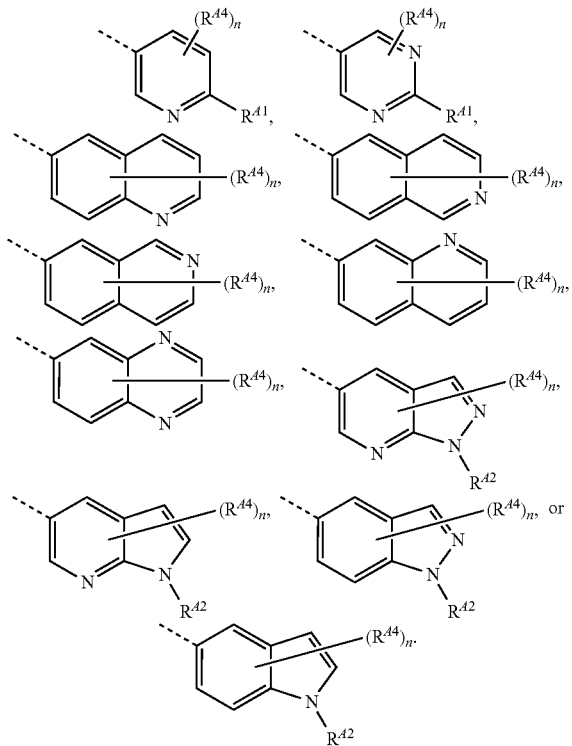

In another further embodiment, Ring A is selected from

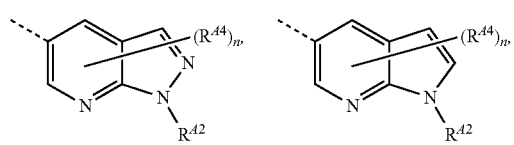

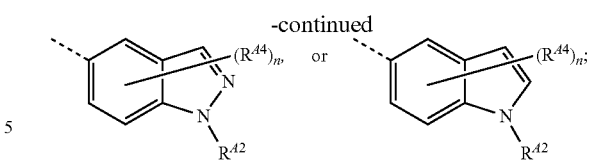

wherein $R^{A2}$ is hydrogen, $C_{1-4}$alkyl, $C_{0-2}$alkyl-$C_{3-6}$cycloalkyl, $C_{0-2}$alkyl-(4-6 membered)heterocyclyl, $C_{2-4}$alkyl-$OR^{A2a}$, $C_{0-2}$alkyl-$C(O)N(R^{A2a})_2$, $C_{0-2}$alkyl-$S(O)_2$—$C_{1-4}$alkyl, or $C_{0-2}$alkyl-$C(O)OC_{1-4}$alkyl, wherein each of said heterocyclyl is selected from oxetan-2-yl, azetidin-2-yl, piperidin-4-yl, or 1,1-dioxothietan-2-yl, and each of said $R^{A2}$ groups is optionally substituted with up to three F atoms, up to two $C_{1-2}$alkyl groups, up to two $OR^{A2b}$ groups, a $C_{0-2}$alkyl-$N(R^{A2b})_2$ group, a $C(O)R^{A2b}$ group, a $C(O)OR^{A2b}$ group, a $C(O)N(R^{A2b})_2$ group, or a —CN group; each $R^{A2a}$ is, independently, H, $C_{1-4}$alkyl, or two $R^{A2a}$ and an intervening nitrogen atom form a 3-6 membered heterocyclic ring selected from aziridinyl, azetidinyl, pyrrolidinyl, pyrrolidinonyl, piperidinyl, piperidinonyl, tetrahydropyridinyl, piperazinyl, or morpholinyl; each $R^{A2b}$ is, independently, H or $C_{1-4}$alkyl; and n is 0.

In yet another further embodiment, Ring A is selected from

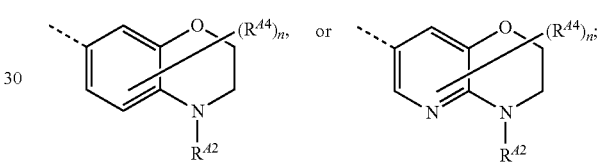

wherein
$R^{A2}$ is a hydrogen, $C_{1-4}$alkyl, $C_{0-2}$alkyl-$C_{3-6}$cycloalkyl, $C_{0-2}$alkyl-(4-6 membered)heterocyclyl, $C_{2-4}$alkyl-$OR^{A2a}$, $C_{0-2}$alkyl-$C(O)N(R^{A2a})_2$, $C_{0-2}$alkyl-$S(O)_2$—$C_{1-4}$alkyl, or $C_{0-2}$alkyl-$C(O)OC_{1-4}$alkyl, wherein each of said heterocyclyl is selected from oxetan-2-yl, azetidin-2-yl, piperidin-4-yl, or 1,1-dioxothietan-2-yl, and each of said $R^{A2}$ groups is optionally substituted with up to three F atoms, up to two $C_{1-2}$alkyl groups, up to two $OR^{A2b}$ groups, a $C_{0-2}$alkyl-$N(R^{A2})_2$ group, a $C(O)R^{A2b}$ group, a $C(O)OR^{A2b}$ group, a $C(O)N(R^{A2b})_2$ group, or a —CN group; each $R^{A2a}$ is, independently, H, $C_{1-4}$alkyl, or two $R^{A2a}$ and an intervening nitrogen atom form a 3-6 membered heterocyclic ring selected from aziridinyl, azetidinyl, pyrrolidinyl, pyrrolidinonyl, piperidinyl, piperidinonyl, tetrahydropyridinyl, piperazinyl, or morpholinyl; each $R^{A2b}$ is, independently, H or $C_{1-4}$alkyl; and n is 0.

In yet another further embodiment, Ring A is selected from

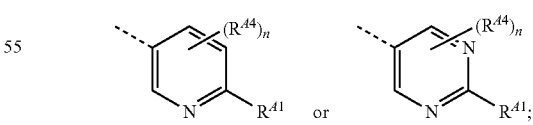

wherein
$R^{A1}$ is $C_{1-4}$alkyl, $C_{0-4}$alkyl-$C_{3-6}$cycloalkyl, $C_{0-4}$alkyl-$OR^{A1a}$, $C_{0-4}$alkyl-$C_{3-6}$cycloalkyl, $C_{0-4}$alkyl-$N(R^{A1a})_2$, $N(R^{A1a})C_{2-4}$alkyl-$N(R^{A1a})_2$, wherein each of said $R^{A1}$ alkyl or cycloalkyl is optionally substituted with up to three F atoms, up to three $^2$H atoms, or up to two $C_{0-2}$alkyl-$OR^{A1b}$ groups; each $R^{A1a}$ is, independently, hydrogen, $C_{1-4}$alkyl, a $C(O)R^{A1b}$ group, or two $R^{A1a}$ and an intervening nitrogen atom form a 3-6 membered heterocyclic ring selected from aziridinyl, azetidinyl, pyrrolidinyl, pyrrolidinonyl, piperidinyl, piperidinonyl, tetrahydropyridinyl, piperazinyl, or morpholinyl, wherein each of said alkyl or heterocyclyl group of $R^{A1a}$ is optionally substituted with up to three F atoms, up to two $C_{1-2}$alkyl groups, up to two $OR^{A1b}$ groups, or a —CN group; each $R^{A1b}$ is, independently, hydrogen or $C_{1-2}$alkyl; each $R^{A4}$ is, independently, halogen, $^2H$, $C_{1-4}$alkyl, $N(R^{1a})_2$, or $OC_{1-4}$alkyl, wherein each $R^{A4}$ alkyl is optionally substituted with up to 3 F atoms, up to two non-geminal OH groups, or up to two $OC_{1-2}$alkyl, and wherein n is 0-3.

In yet another further embodiment, Ring A is selected from

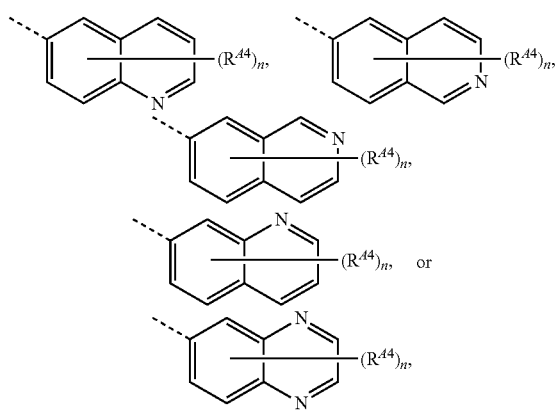

wherein
each $R^{A4}$ is, independently, halogen, $C_{1-4}$alkyl, or $OC_{1-4}$alkyl, wherein each $R^{A4}$ alkyl is optionally substituted with up to 3 F atoms, up to two non-geminal OH groups, or up to two $OC_{1-2}$alkyl, and wherein n is 0-2.

In another embodiment, Ring B of compounds of the invention comprises a heterocyclyl or heteroaryl ring.

In one embodiment, Ring B is selected from

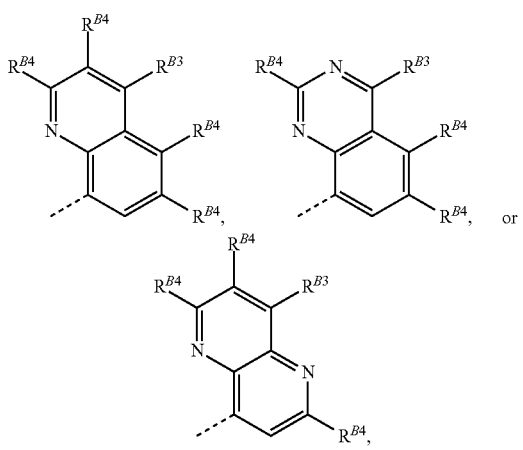

wherein
$R^{B3}$ is $C(O)NHC_{1-4}$ alkyl, wherein said alkyl is optionally substituted with up to three F atoms, two non-geminal OH groups, or one $OC_{1-2}$alkyl; and
each $R^{B4}$ is, independently, hydrogen, $^2H$, F, $C_{1-4}$alkyl, or $OC_{1-4}$alkyl, wherein each $R^{B4}$ alkyl is optionally substituted with up to 3 F atoms, two non-geminal OH groups, or one $OC_{1-2}$alkyl.

In a further embodiment, Ring A is

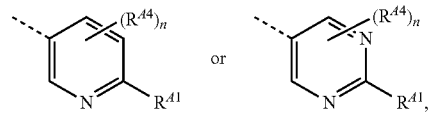

wherein
$R^{A1}$ is F, $C_{1-4}$alkyl, $OC_{1-4}$alkyl, $OC_{0-4}$alkyl-$C_{3-5}$cycloalkyl, $NH_2$, $NHC_{1-4}$alkyl, $NHC_{0-4}$alkyl-$C_{3-5}$cycloalkyl, or $C_{0-4}$alkyl-heterocyclyl, wherein said heterocyclic ring system is selected from oxetanyl, tetrahydrofuranyl, tetrahydropyranyl, or morpholinyl, and each of said alkyl, cycloalkyl, or heterocyclyl is optionally substituted with up to three F atoms, up to three $^2H$ atoms, up to two non-geminal OH groups, or up to two $OC_{1-2}$alkyl;

each $R^{A4}$ is, independently, F, $^2H$, $OC_{1-4}$alkyl, or $NH_2$; and n is 0-2.

In another embodiment, Ring B is

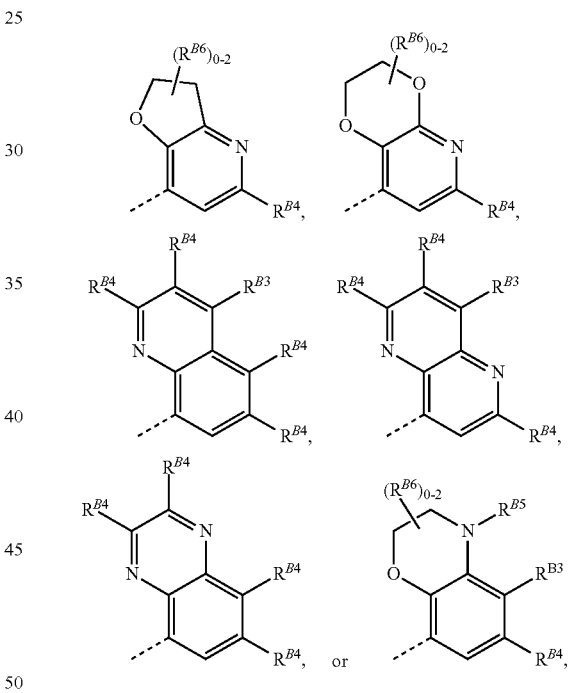

wherein
each of $R^{B3}$ and $R^{B4}$ is, independently, hydrogen, halogen, or $C_{1-4}$alkyl, wherein each of said $R^{B3}$ or $R^{B4}$ alkyl is optionally substituted with up to 3 F atoms, two non-geminal OH groups, or one $OC_{1-2}$alkyl;
$R^{B5}$ is hydrogen, $C_{1-4}$alkyl, $C(O)C_{1-4}$alkyl, $C(O)OC_{1-4}$alkyl, $C(O)NH_2$, $C(O)NHC_{1-4}$alkyl, or $C(O)N(C_{1-4}$alkyl$)_2$, wherein said $R^{B5}$ alkyl is optionally substituted with up to 3 F atoms, up to two non-geminal OH groups, or up to two $OC_{1-2}$alkyl; and
$R^{B6}$ is F or $C_{1-2}$alkyl, or two $R^{B6}$ and an intervening carbon atom from a spirocyclopropyl or spirocyclobutyl ring.

In another aspect, the invention features a compound having formula (II)

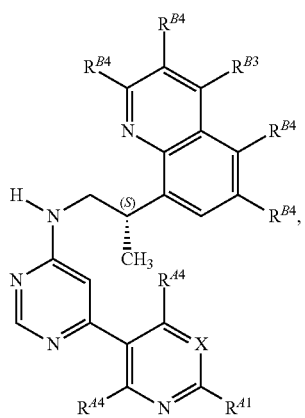

or a pharmaceutically acceptable salt thereof, wherein
X is N, $CR^{A5}$;
$R^{A1}$ is F, $C_{1-4}$alkyl, $C_{3-5}$cycloalkyl, $OC_{1-4}$alkyl, $OC_{1-4}$alkyl-$C_{3-5}$cycloalkyl, $NH_2$, $NHC_{1-4}$alkyl, $NHC_{1-4}$alkyl-$C_{3-5}$cycloalkyl, or $C_{0-4}$alkyl-heterocyclyl, wherein said heterocyclic ring system is selected from oxetanyl, tetrahydrofuranyl, tetrahydropyran, or morpholinyl, and each of said alkyl, cycloalkyl, or heterocyclyl is optionally substituted with up to three F atoms, up to three $^2H$ atoms, up to two non-geminal OH groups, or up to two $OC_{1-2}$ alkyl;
each $R^{A4}$ is, independently, H or $^2H$;
$R^{A5}$ is hydrogen, F, $C_{1-4}$alkyl, or $OC_{1-4}$alkyl, wherein each of said alkyl is optionally substituted with up to three F atoms or up to three $^2H$ atoms;
$R^{B3}$ is $C(O)NHC_{1-4}$ alkyl, wherein said alkyl is optionally substituted with up to three F atoms, up to three $^2H$ atoms, up to two non-geminal OH groups, or up to two $OC_{1-2}$ alkyl; and
each $R^{B4}$ is, independently, hydrogen, deuterium, F, or $C_{1-4}$alkyl.

In another aspect, the invention features a compound having formula (III)

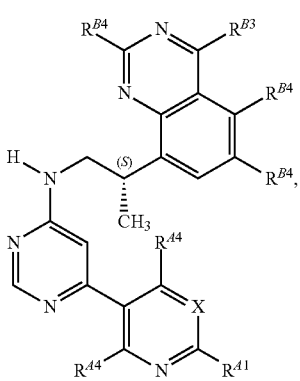

wherein
X is N, $CR^{A5}$;
$R^{A1}$ is F, $C_{1-4}$alkyl, $C_{3-5}$cycloalkyl, $OC_{1-4}$alkyl, $OC_{1-4}$alkyl-$C_{3-5}$cycloalkyl, $NH_2$, $NHC_{1-4}$alkyl, $NHC_{0-4}$alkyl-$C_{3-5}$cycloalkyl, or $C_{0-4}$alkyl-heterocyclyl, wherein said heterocyclic ring system is selected from oxetanyl, tetrahydrofuranyl, tetrahydropyran, or morpholinyl, and each of said alkyl, cycloalkyl, or heterocyclyl is optionally substituted with up to three F atoms, up to three $^2H$ atoms, up to two non-geminal OH groups, or up to two $OC_{1-2}$ alkyl;
each $R^{A4}$ is, independently, H or $^2H$;
$R^{A5}$ is hydrogen, F, $C_{1-4}$alkyl, or $OC_{1-4}$alkyl, wherein each of said alkyl is optionally substituted with up to three F atoms or up to three $^2H$ atoms;
$R^{B3}$ is $C(O)NHC_{1-4}$ alkyl, wherein said alkyl is optionally substituted with up to three F atoms, up to three $^2H$ atoms, up to two non-geminal OH groups, or up to two $OC_{1-2}$ alkyl; and
each $R^{B4}$ is, independently, hydrogen, deuterium, F, or $C_{1-4}$alkyl In another aspect, the invention features a compound selected from the group of compounds listed in Table 1 or Table 2.

Compositions, Formulations, and Administration of Compounds of the Invention

In another embodiment, the invention provides a pharmaceutical composition comprising a compound of any of the formulae described herein and a pharmaceutically acceptable excipient. In a further embodiment, the invention provides a pharmaceutical composition comprising a compound of Table 1 or Table 2. In a further embodiment, the composition additionally comprises an additional therapeutic agent.

According to another embodiment, the invention provides a composition comprising a compound of this invention or a pharmaceutically acceptable derivative thereof and a pharmaceutically acceptable carrier, adjuvant, or vehicle. In one embodiment, the amount of compound in a composition of this invention is such that is effective to measurably inhibit a DNA-PK in a biological sample or in a patient. In another embodiment, the amount of compound in the compositions of this invention is such that is effective to measurably inhibit DNA-PK. In one embodiment, the composition of this invention is formulated for administration to a patient in need of such composition. In a further embodiment, the composition of this invention is formulated for oral administration to a patient.

The term "patient," as used herein, means an animal, preferably a mammal, and most preferably a human.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof. As used herein, the term "inhibitory active metabolite or residue thereof" means that a metabolite or residue thereof is also an inhibitor of DNA-PK.

As used herein, the term "pharmaceutically acceptable salt" refers to those salts which are, within the scope of sound medical judgment, suitable for use in contact with the tissues of humans and lower animals without undue toxicity, irritation, allergic response and the like.

Pharmaceutically acceptable salts are well known in the art. For example, S. M. Berge et al., describe pharmaceutically acceptable salts in detail in J. Pharmaceutical Sciences, 66:1-19, 1977, which is incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. In Remington: *The Science and Practice of Pharmacy,* 21st edition, 2005, ed. D. B. Troy, Lippincott Williams & Wilkins, Philadelphia, and *Encyclopedia of Pharmaceutical Technology,* eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraocular, intrahepatic, intralesional, epidural, intraspinal, and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated, e.g., as micronized suspensions in isotonic, pH adjusted sterile saline or other aqueous solution, or, preferably, as solutions in isotonic, pH adjusted sterile saline or other aqueous solution, either with or without a preservative such as benzylalkonium chloride. Alternatively, for ophthalmic uses, the pharmaceutically acceptable compositions may be formulated in an ointment such as petrolatum. The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, dissolving or suspending the compound in an oil vehicle accomplishes delayed absorption of a parenterally administered compound form. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

Depending upon the particular proliferative condition or cancer to be treated, additional therapeutic agents, which are normally administered to treat or prevent that condition, may also be present in the compositions of this invention. As used herein, additional therapeutic agents which are normally administered to treat or prevent a particular proliferative condition or cancer are known as "appropriate for the disease, or condition, being treated." Examples of additional therapeutic agents are provided infra.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Uses of the Compounds and Compositions of the Invention

In one embodiment, the invention provides a method of sensitizing a cell to an agent that induces a DNA lesion comprising the step of contacting the cell with one or more DNA-PK inhibitors of formula I or subformula thereof (e.g., formulae I-A-1, I-A-2, . . . to I-A-51, I-B-1, I-B-2, . . . to I-B-42) or a DNA-PK inhibitor of formula II or formula III.

The invention further provides methods of potentiating a therapeutic regimen for treatment of cancer comprising the step of administering to an individual in need thereof an effective amount of a DNA-PK inhibitor of formula I, formula II, formula III, or subformulae thereof. In one embodiment, the therapeutic regimen for treatment of cancer includes radiation therapy. Compounds of the invention are useful in instances where radiation therapy is indicated to enhance the therapeutic benefit of such treatment. In addition, radiation therapy frequently is indicated as an adjuvent to surgery in the treatment of cancer. The goal of radiation therapy in the adjuvant setting is to reduce the risk of recurrence and enhance disease-free survival when the primary tumor has been controlled. For example, adjuvant radiation therapy is indicated in cancers, including but not limited to, breast cancer, colorectal cancer, gastric-esophageal cancer, fibrosarcoma, glioblastoma, hepatocellular carcinoma, head and neck squamous cell carcinoma, melanoma, lung cancer, pancreatic cancer, and prostate cancer as described below.

The invention also can be practiced by including another anti-cancer chemotherapeutic agent with a compound of the invention in a therapeutic regimen for the treatment of cancer, with or without radiation therapy. The combination of a DNA-PK inhibitor compound of the invention with such other agents can potentiate the chemotherapeutic protocol. For example, the inhibitor compound of the invention can be administered with etoposide or bleomycin, agents known to cause DNA strand breakage.

The invention further relates to radiosensitizing tumor cells utilizing a compound of formula I, formula II, formula III, or subformulae thereof. The preferred compounds are those as described for the pharmaceutical compositions of the invention. A compound that can "radiosensitize" a cell, as used herein, is defined as a molecule, preferably a low molecular weight molecule, administered to animals in therapeutically effective amount to increase the sensitivity of cells to electromagnetic radiation and/or to promote the treatment of diseases that are treatable with electromagnetic radiation (e.g., X-rays). Diseases that are treatable with electromagnetic radiation include neoplastic diseases, benign and malignant tumors, and cancerous cells.

The present invention also provides methods of treating cancer in an animal that includes administering to the animal an effective amount of a DNA-PK inhibitor such as, for example, a compound of the invention. The invention further is directed to methods of inhibiting cancer cell growth, including processes of cellular proliferation, invasiveness, and metastasis in biological systems. Methods include use of a compound of the invention as an inhibitor of cancer cell growth. Preferably, the methods are employed to inhibit or reduce cancer cell growth, invasiveness, metastasis, or tumor incidence in living animals, such as mammals. Methods of the invention also are readily adaptable for use in assay systems, e.g., assaying cancer cell growth and properties thereof, as well as identifying compounds that affect cancer cell growth.

Tumors or neoplasms include growths of tissue cells in which the multiplication of the cells is uncontrolled and progressive. Some such growths are benign, but others are termed "malignant" and can lead to death of the organism. Malignant neoplasms or "cancers" are distinguished from benign growths in that, in addition to exhibiting aggressive cellular proliferation, they can invade surrounding tissues and metastasize. Moreover, malignant neoplasms are characterized in that they show a greater loss of differentiation (greater "dedifferentiation") and their organization relative to one another and their surrounding tissues. This property is also called "anaplasia."

Neoplasms treatable by the present invention also include solid tumors, i.e., carcinomas and sarcomas. Carcinomas include those malignant neoplasms derived from epithelial cells which infiltrate (invade) the surrounding tissues and give rise to metastases. Adenocarcinomas are carcinomas derived from glandular tissue, or from tissues which form recognizable glandular structures. Another broad category of cancers includes sarcomas, which are tumors whose cells are embedded in a fibrillar or homogeneous substance like embryonic connective tissue. The invention also enables treatment of cancers of the myeloid or lymphoid systems, including leukemias, lymphomas, and other cancers that typically do not present as a tumor mass, but are distributed in the vascular or lymphoreticular systems.

DNA-PK activity can be associated with various forms of cancer in, for example, adult and pediatric oncology, growth of solid tumors/malignancies, myxoid and round cell carcinoma, locally advanced tumors, metastatic cancer, human soft tissue sarcomas, including Ewing's sarcoma, cancer metastases, including lymphatic metastases, squamous cell carcinoma, particularly of the head and neck, esophageal squamous cell carcinoma, oral carcinoma, blood cell malignancies, including multiple myeloma, leukemias, including acute lymphocytic leukemia, acute nonlymphocytic leukemia, chronic lymphocytic leukemia, chronic myelocytic leukemia, and hairy cell leukemia, effusion lymphomas (body cavity based lymphomas), thymic lymphoma lung cancer, including small cell carcinoma, cutaneous T cell lymphoma, Hodgkin's lymphoma, non-Hodgkin's lymphoma, cancer of the adrenal cortex, ACTH-producing tumors, nonsmall cell cancers, breast cancer, including small cell carcinoma and ductal carcinoma, gastrointestinal cancers, including stomach cancer, colon cancer, colorectal cancer, polyps associated with colorectal neoplasia, pancreatic cancer, liver cancer, urological cancers, including bladder cancer, including primary superficial bladder tumors, invasive transitional cell carcinoma of the bladder, and muscle-invasive bladder cancer, prostate cancer, malignancies of the female genital tract, including ovarian carcinoma, primary peritoneal epithelial neoplasms, cervical carcinoma, uterine endometrial cancers, vaginal cancer, cancer of the vulva, uterine cancer and solid tumors in the ovarian follicle, malignancies of the male genital tract, including testicular cancer and penile cancer, kidney cancer, including renal cell carcinoma, brain cancer, including intrinsic brain tumors, neuroblastoma, astrocytic brain tumors, gliomas, metastatic tumor cell invasion in the central nervous system, bone cancers, including osteomas and osteosarcomas, skin cancers, including malignant melanoma, tumor progression of human skin keratinocytes, squamous cell cancer, thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma. Methods to potentiate treatment of these and other forms of cancer are embraced by the invention.

The invention provides a method of inhibiting DNA-PK activity in a biological sample that includes contacting the biological sample with a compound or composition of the invention. The term "biological sample," as used herein, means a sample outside a living organism and includes, without limitation, cell cultures or extracts thereof biopsied material obtained from a mammal or extracts thereof and blood, saliva, urine, feces, semen, tears, or other body fluids or extracts thereof. Inhibition of kinase activity, particularly DNA-PK activity, in a biological sample is useful for a variety of purposes known to one of skill in the art. An example includes, but is not limited to, the inhibition of DNA-PK in a biological assay. In one embodiment, the method of inhibiting DNA-PK activity in a biological sample is limited to non-therapeutic methods.

Preparation of Compounds of the Invention

As used herein, all abbreviations, symbols and conventions are consistent with those used in the contemporary scientific literature. See, e.g., Janet S. Dodd, ed., *The ACS Style Guide: A Manual for Authors and Editors,* 2nd Ed., Washington, D.C.: American Chemical Society, 1997. The following definitions describe terms and abbreviations used herein:

BPin pinacol boronate ester
Brine a saturated NaCl solution in water
DCM dichloromethane
DIEA diisopropylethylamine
DMA dimethylacetamide
DME dimethoxyethane
DMF dimethylformamide
DMSO methylsulfoxide
DTT dithiothreitol
EtDuPhos (2R,5R)-1-[2-[(2R,5R)-2,5-diethylphospholan-1-yl]phenyl]-2,5-diethylphospholane
ESMS electrospray mass spectrometry
Et$_2$O ethyl ether
EtOAc ethyl acetate
EtOH ethyl alcohol HATU O-(7-azabenzotriazol-1-yl)-N,N,N',N'-tetramethyluronium hexafluorophosphate
HEPES 4-(2-hydroxyethyl)-1-piperazineethanesulfonic acid
HPLC high performance liquid chromatography
IPA isopropanol
LAH lithium aluminum hydride
LC-MS liquid chromatography-mass spectrometry
LDA lithium diisoproylethylamide
Me methyl
MeOH methanol
MTBE methyl t-butyl ether
NMP N-methylpyrrolidine
Pd(dppf)Cl$_2$ 1,1'bis(diphenylphosphino)-ferrocene dichloro-palladium
Ph phenyl
RT or rt room temperature
SFC supercritical fluid chromatography
SPhos 2-dicyclohexylphosphino-2',6'-dimethoxybiphenyl
TBAI tetrabutylammonium iodide
TBME tert-butylmethyl ether
tBu tertiary butyl
THF tetrahydrofuran
TEA triethylamine
TMEDA tetramethylethylenediamine
VPhos [3-(2-dicyclohexylphosphanylphenyl)-2,4-dimethoxy-phenyl]sulfonyloxysodium General Synthetic Procedures In general, the compounds of this invention may be prepared by methods described herein or by other methods known to those skilled in the art.

Example 1

General Preparation of the Compounds of Formula I

Compounds of formula I can be prepared as outlined below in Scheme 1—Method A. Accordingly, as shown in step 1-i of Scheme 1, 4,6-dichloropyrimidine is reacted with an amine of formula A in the presence of a tertiary amine base at elevated temperatures to produce a compound of formula B. As shown in step 1-ii of Scheme 1, reaction of a compound of formula B with a suitable boronic acid or boronate of formula C in the presence of an appropriate palladium catalyst produces compounds of formula I. Procedures for preparing a boronate or boronic acid from aryl or heteroaryl halides are described in *Boronic Acids*, ISBN: 3-527-30991-8, Wiley-VCH, 2005 (Dennis G. Hall, editor). In one example, the halogen is bromine and the boronate is prepared by reacting the aryl or heteroaryl bromide with 4,4,5,5-tetramethyl-2-(4,4,5,5-tetramethyl-1,3,2-dioxaborolan-2-yl)-1,3,2-dioxaborolane. In subsequent coupling reactions, boronates or boronic acids so formed can be reacted with halopyrimidines in the presence of a palladium catalyst such as 1,1'bis(diphenylphosphino)-ferrocene dichloro-palladium.dichloromethane [Pd(dppf)Cl$_2$].

Scheme 1 - Method A

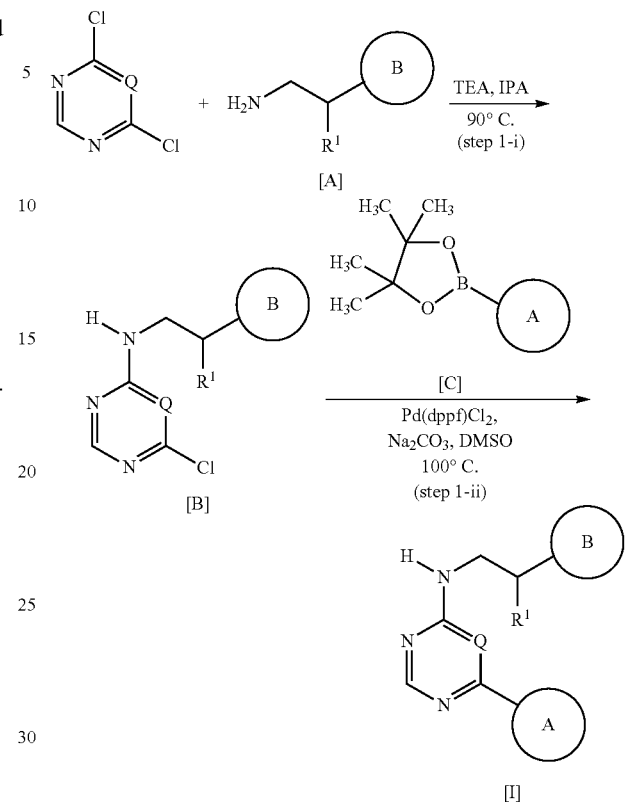

Alternatively, as shown in Scheme 1—Method B, the order of coupling compounds of formula A and compounds of formula C to 4,6-dichloropyrimidine can be reversed to produce the formula I compounds of the invention.

Scheme 1-Method B

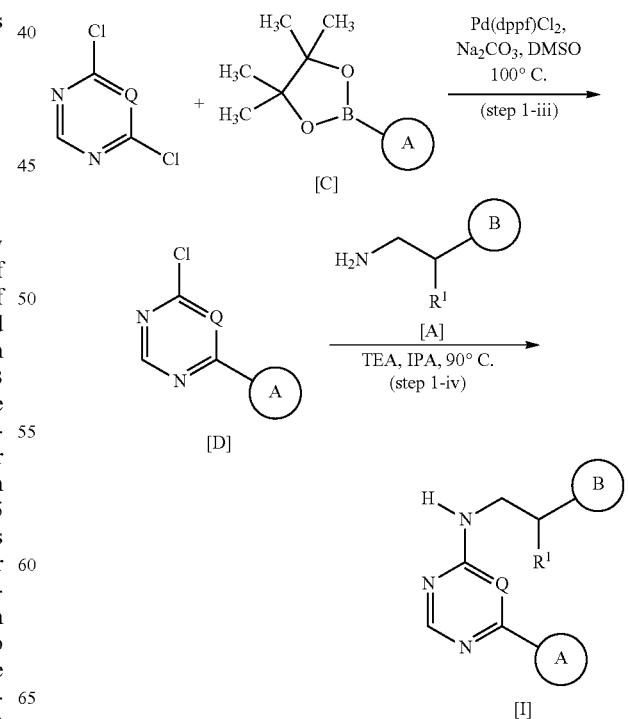

Compounds of formula I can also be prepared by employing Suzuki boronate-type couplings to form the carbon-carbon bond between a carbon atom of aromatic or heteroaromatic B Ring moieties and the unsaturation 2-carbon of N-allylpyrimidin-4-amines. In one example, as shown in Scheme 1—Method C, compounds of formula D are reacted with allylamine boronates of formula E to produce compounds of formula F. Subsequent reaction of the boronate with an aromatic or heteroaromatic B Ring halide of formula G results in compounds of formula H, the double bond of which can be reduced to form compounds of formula I.

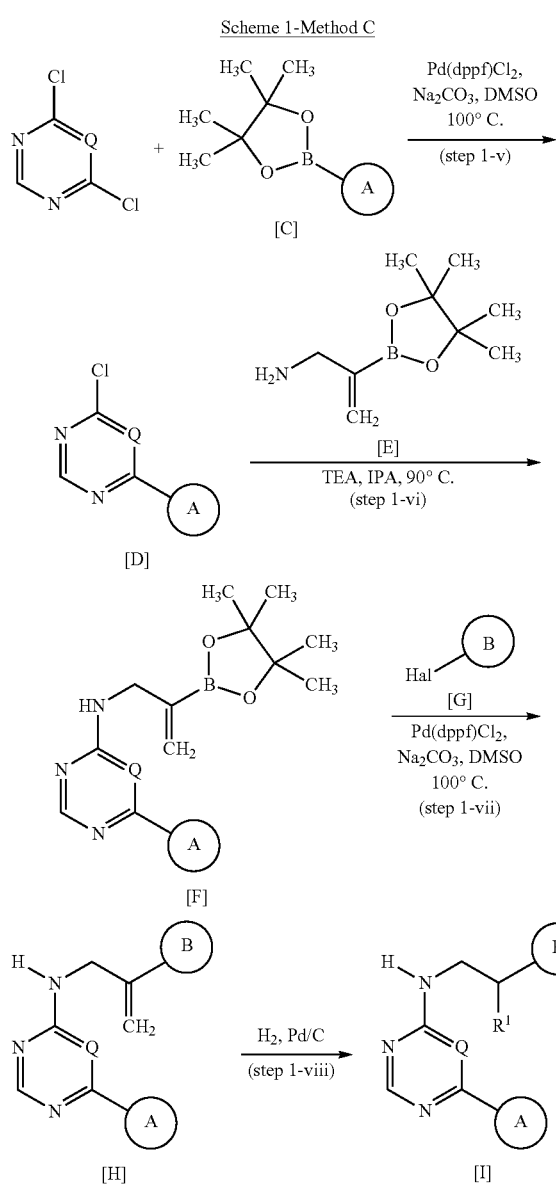

Alternatively, as shown in Scheme 1—Method D, the carbon-carbon bond between aromatic or heteroaromatic B Ring and the remainder of the molecule in compounds of formula I is formed by reacting vinyl halides of formula K and B-ring boronates of formula L. As before, the double bond of resulting compound of formula H can be reduced to form compounds of formula I.

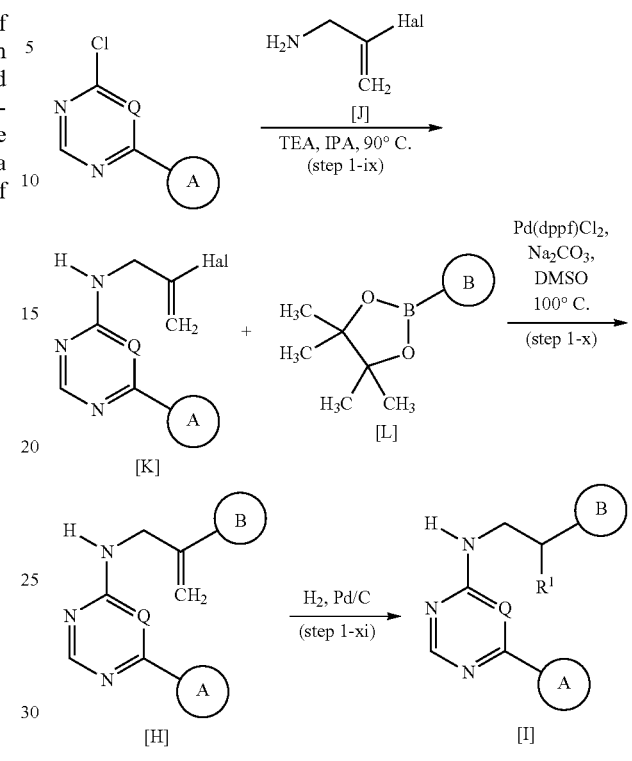

As previously mentioned, boronate or boronic acid intermediates can be prepared by reacting an aryl or heteroaryl, or vinyl halide with 4,4,5,5-tetramethyl-2-(4,4,5,5-tetramethyl-1,3,2-dioxaborolan-2-yl)-1,3,2-dioxaborolane in the presence of a palladium catalyst such as 1,1'bis(diphenylphosphino)-ferrocene dichloro-palladium.dichloromethane [Pd(dppf)Cl$_2$]. For example, in order to prepare Ring A boronate intermediates of Formula O, the procedures outlined in Example 2 can be followed.

Example 2

General Preparation of the Ring A Intermediates of Formula O

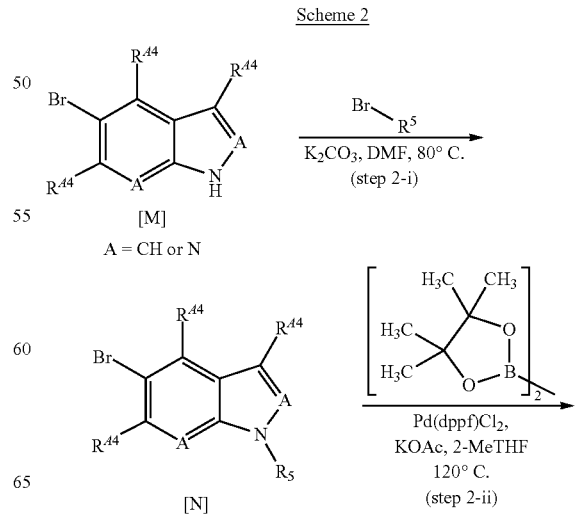

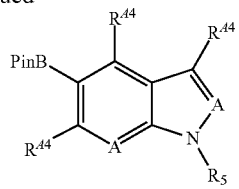

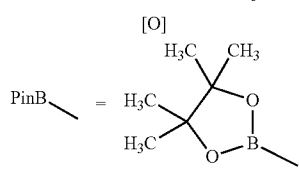

As shown in step 2-i of Scheme 2, to a solution of a compound of formula M (1 equiv.) and $K_2CO_3$ (3 equiv.) in DMF (0.3 M) was added an alkyl bromide (2 equiv.) at room temperature. The reaction mixture was then stirred at 80° C. for 5 hours. The reaction was cooled down to room temperature and filtered over a pad of diatomaceous earth. The resulting cake was washed with EtOAc. To the filtrate was added $H_2O$ and the two phases were separated. The aqueous phase was extracted with EtOAc and the organic phase was washed with brine. The combined organic phases were dried over $Na_2SO_4$ and evaporated. The residue was purified by medium pressure silica gel chromatography (0→100% EtOAc in hexanes) to provide intermediate N.

As shown in step 2-ii of Scheme 2, A solution of the 5-bromo-pyrazolo[3,4-b]pyridine of formula N (1 equiv.), bis-pinacol borane (1.15 equiv.), KOAc (3 equiv.) in 2-methyl-THF (0.3 M) was degassed with a stream of $N_2$ for 20 min. Then, Pd(dppf)$Cl_2$ (0.05 equiv.) was added to the reaction mixture. The resulting solution was heated in a sealed tube at 120° C. for 3 h in an oil bath. The solution was cooled down to room temperature and filtered over a pad of Florisil®. The filtrate was evaporated and the resulting compound of formula O was produced. In many cases, these compounds could be subsequently used without any further purification.

The procedure of Example 2 can be followed to prepare the following compounds.

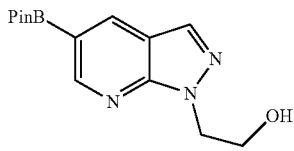

2-(5-(4,4,5,5-tetramethyl-1,3,2-dioxaborolan-2-yl)-1H-pyrazolo[3,4-b]pyridin-1-yl)ethanol: ESMS (M+H)=289.43; $^1$H NMR (400 MHz, CDCl$_3$) δ 8.79 (d, J=0.7 Hz, 1H), 8.48 (d, J=0.4 Hz, 1H), 7.97 (s, 1H), 4.63 (t, J=4.6 Hz, 2H), 4.45 (s, 1H), 4.05 (t, J=4.6 Hz, 2H) and 1.30 (s, 12H)

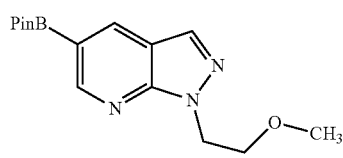

1-(2-methoxyethyl)-5-(4,4,5,5-tetramethyl-1,3,2-dioxaborolan-2-yl)-1H-pyrazolo[3,4-b]pyridine: ESMS (M+H)= 303.16; $^1$H NMR (400 MHz, CDCl$_3$) δ 8.81 (d, J=1.2 Hz, 1H), 8.44 (d, J=1.2 Hz, 1H), 7.97 (s, 1H), 4.67 (t, J=5.6 Hz, 2H), 3.82 (t, J=5.6 Hz, 2H), 3.25 (s, 3H) and 1.30 (s, 12H)

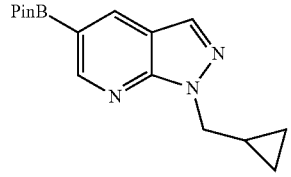

1-(cyclopropylmethyl)-5-(4,4,5,5-tetramethyl-1,3,2-dioxaborolan-2-yl)-1H-pyrazolo[3,4-b]pyridine: ESMS (M+H)= 301.14; $^1$H NMR (400 MHz, CDCl$_3$) δ 8.79 (d, J=1.0 Hz, 1H), 8.44 (d, J=1.0 Hz, 1H), 7.96 (s, 1H), 4.35 (d, J=7.1 Hz, 2H), 1.35 (s, 12H) and 0.49-0.39 (m, 5H)

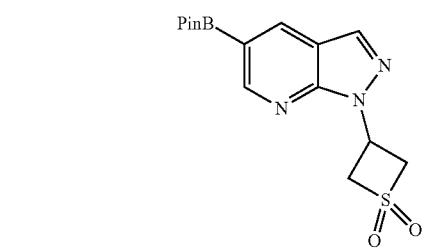

1-(thietane-1,1-dioxide)-5-(4,4,5,5-tetramethyl-1,3,2-dioxaborolan-2-yl)-1H-pyrazolo[3,4-b]pyridine: ESMS (M+H)=350.37

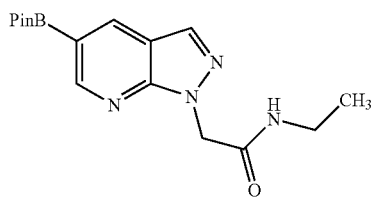

N-ethyl-2-(5-(4,4,5,5-tetramethyl-1,3,2-dioxaborolan-2-yl)-1H-pyrazolo[3,4-b]pyridin-1-yl)ethanamide: ESMS (M+H)=331.66

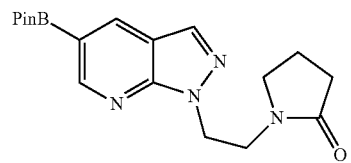

1-(2-(5-(4,4,5,5-tetramethyl-1,3,2-dioxaborolan-2-yl)-1H-pyrazolo[3,4-b]pyridin-1-yl)ethyl)pyrrolidin-2-one: ESMS (M+H)=358.12

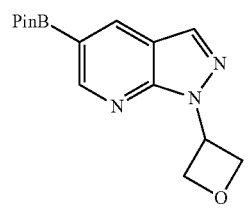

1-(oxetan-3-yl)-5-(4,4,5,5-tetramethyl-1,3,2-dioxaborolan-2-yl)-1H-pyrazolo[3,4-b]pyridine: ESMS (M+H)=

302.16; ¹H NMR (400 MHz, CDCl₃) δ 8.80 (d, J=10.8 Hz, 1H), 8.45 (s, 1H), 8.06 (s, 1H), 6.19 (p, J=7.2 Hz, 1H), 5.25 (t, J=6.5 Hz, 2H), 5.08-5.03 (m, 2H), 1.30 (s, 12H)

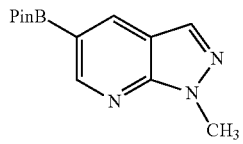

1-methyl-5-(4,4,5,5-tetramethyl-1,3,2-dioxaborolan-2-yl)-1H-pyrazolo[3,4-b]pyridine: ESMS (boronic acid, M+H)=178.23; ¹H NMR (400 MHz, CDCl₃) δ d 8.93 (d, J=1.2 Hz, 1H), 8.45 (d, J=1.1 Hz, 1H), 7.87 (s, 1H), 4.18 (s, 3H) and 1.29 (s, 12H)

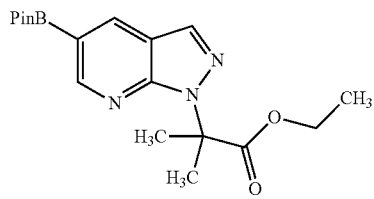

ethyl 2-methyl-2-(5-(4,4,5,5-tetramethyl-1,3,2-dioxaborolan-2-yl)-1H-pyrazolo[3,4-b]pyridin-1-yl)propanoate: ESMS (M+H)=360.29; ¹H NMR (400 MHz, CDCl₃) δ 8.94 (s, 1H), 8.47 (s, 1H), 8.04 (s, 1H), 4.16-4.05 (m, 2H), 1.95 (s, 6H), 1.30 (s, 12H), 1.13-1.05 (m, 3H)

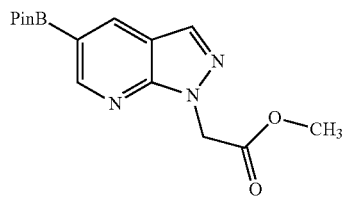

methyl 2-(5-(4,4,5,5-tetramethyl-1,3,2-dioxaborolan-2-yl)-1H-pyrazolo[3,4-b]pyridin-1-yl)ethanoate: ESMS (M+H)=317.2; ¹H NMR (400 MHz, CDCl₃) δ 8.90 (d, J=1.1 Hz, 1H), 8.56 (t, J=3.9 Hz, 1H), 8.11 (d, J=7.7 Hz, 1H), 5.36 (s, 2H), 3.76 (s, 3H), 1.38 (s, 12H)

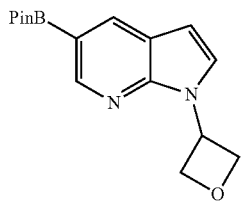

1-(oxetan-3-yl)-5-(4,4,5,5-tetramethyl-1,3,2-dioxaborolan-2-yl)-1H-pyrrolo[2,3-b]pyridine: ESMS (M+H)=301.4; ¹H NMR (400 MHz, CDCl₃) δ 8.72-8.52 (m, 1H), 8.41-8.28 (m, 1H), 7.71 (d, J=3.4 Hz, 1H), 6.64 (dd, J=24.9, 3.5 Hz, 1H), 6.18 (dd, J=13.6, 6.6 Hz, 1H), 5.30-5.02 (m, 4H), 1.28 (s, 12H)

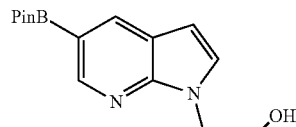

2-(5-(4,4,5,5-tetramethyl-1,3,2-dioxaborolan-2-yl)-1H-pyrrolo[2,3-b]pyridin-1-yl)ethanol: ESMS (M+H)=289.32

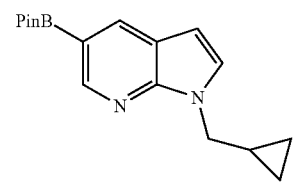

1-(cyclopropylmethyl)-5-(4,4,5,5-tetramethyl-1,3,2-dioxaborolan-2-yl)-1H-pyrrolo[2,3-b]pyridine: ESMS (M+H)=299.38

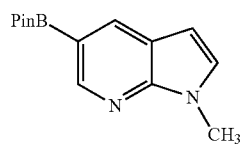

1-methyl-5-(4,4,5,5-tetramethyl-1,3,2-dioxaborolan-2-yl)-1H-pyrrolo[2,3-b]pyridine: ESMS (M+H)=260.14; ¹H NMR (400 MHz, CDCl₃) d 8.63 (d, J=1.0 Hz, 1H), 8.28 (d, J=1.0 Hz, 1H), 7.08 (d, J=3.4 Hz, 1H), 6.38 (d, J=3.4 Hz, 1H), 3.83 (s, 3H) and 1.30 (s, 12H)

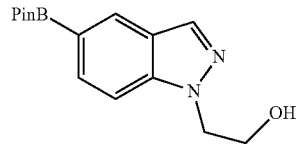

2-(5-(4,4,5,5-tetramethyl-1,3,2-dioxaborolan-2-yl)-1H-indazol-1-yl)ethanol: ESMS (M+H)=289.33

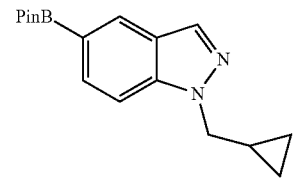

1-(cyclopropylmethyl)-5-(4,4,5,5-tetramethyl-1,3,2-dioxaborolan-2-yl)-1H-indazole: ESMS (M+H)=298.02

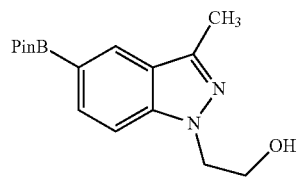

2-(3-methyl-5-(4,4,5,5-tetramethyl-1,3,2-dioxaborolan-2-yl)-1H-indazol-1-yl)ethanol: ESMS (M+H)=302.22; ¹H NMR (400 MHz, CDCl₃) δ 8.18-8.04 (m, 1H), 7.70 (dd, J=18.8, 8.1 Hz, 1H), 7.30 (dd, J=20.1, 8.5 Hz, 1H), 4.36 (dt, J=9.4, 5.1 Hz, 2H), 4.22-3.96 (m, 2H), 2.58-2.47 (m, 3H), 1.20 (t, J=2.0 Hz, 12H)

J=8.5 Hz, 1H), 7.32-7.20 (m, 1H), 5.76-5.63 (m, 1H), 5.24 (dd, J=12.3, 5.7 Hz, 2H), 5.05 (t, J=7.3 Hz, 2H), 2.76 (s, 3H), 1.30 (s, 12H)

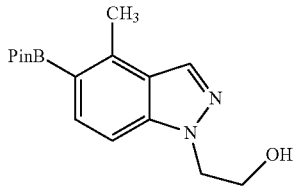

2-(4-methyl-5-(4,4,5,5-tetramethyl-1,3,2-dioxaborolan-2-yl)-1H-indazol-1-yl)ethanol: ESMS (M+H)=302.22; ¹H NMR (400 MHz, CDCl₃) δ 8.07-7.93 (m, 1H), 7.71 (t, J=9.9 Hz, 1H), 7.15 (d, J=8.6 Hz, 1H), 4.50-4.34 (m, 2H), 4.16-3.98 (m, 2H), 2.80-2.67 (m, 3H), 1.20 (s, 12H)

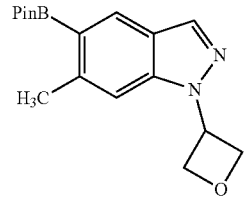

6-methyl-1-(oxetan-3-yl)-5-(4,4,5,5-tetramethyl-1,3,2-dioxaborolan-2-yl)-1H-indazole: ESMS (M+H)=315.57; ¹H NMR (400 MHz, CDCl₃) δ 8.17 (s, 1H), 7.94 (s, 1H), 7.19 (s, 1H), 5.76-5.59 (m, 1H), 5.29-5.18 (m, 2H), 5.12-4.99 (m, 2H), 2.61 (s, 3H), 1.29 (s, 12H)

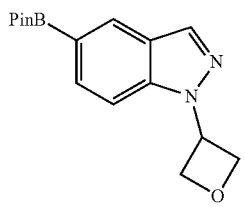

1-(oxetan-3-yl)-5-(4,4,5,5-tetramethyl-1,3,2-dioxaborolan-2-yl)-1H-indazole: ESMS (M+H)=301.34

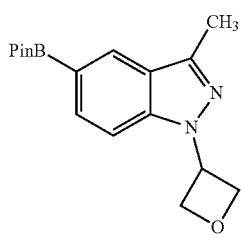

3-methyl-1-(oxetan-3-yl)-5-(4,4,5,5-tetramethyl-1,3,2-dioxaborolan-2-yl)-1H-indazole: ESMS (M+H)=315.57; ¹H NMR (400 MHz, CDCl₃) δ 8.23 (d, J=8.2 Hz, 1H), 7.82 (d, J=8.5 Hz, 1H), 7.49-7.41 (m, 1H), 5.74 (p, J=7.1 Hz, 1H), 5.31 (t, J=6.5 Hz, 2H), 5.12 (t, J=7.2 Hz, 2H), 2.63 (d, J=5.1 Hz, 3H), 1.40 (s, 12H)

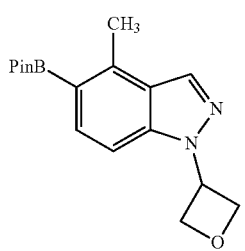

4-methyl-1-(oxetan-3-yl)-5-(4,4,5,5-tetramethyl-1,3,2-dioxaborolan-2-yl)-1H-indazole: ESMS (M+H)=315.57; ¹H NMR (400 MHz, CDCl₃) δ 8.06 (d, J=21.0 Hz, 1H), 7.72 (d,

Example 3

Preparation of N-(2-(3,3-dimethyl-2,3-dihydrobenzofuran-7-yl)ethyl)-6-(6-(4-methylpiperazin-1-yl)pyridin-3-yl)pyrimidin-4-amine (Compound 68)

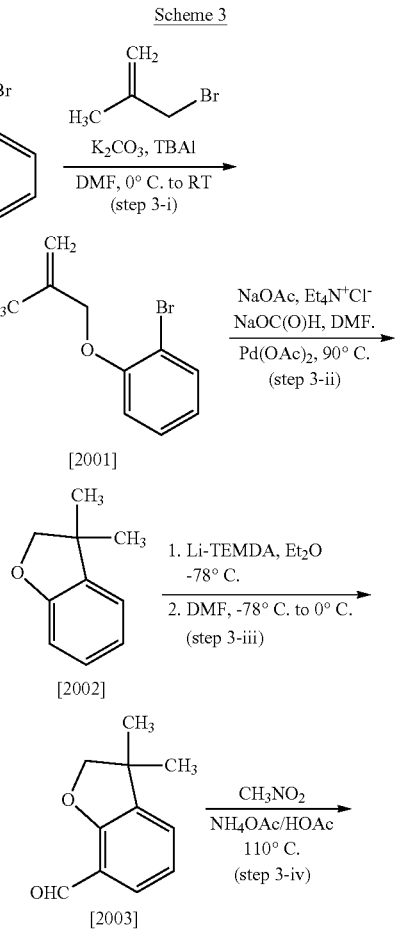

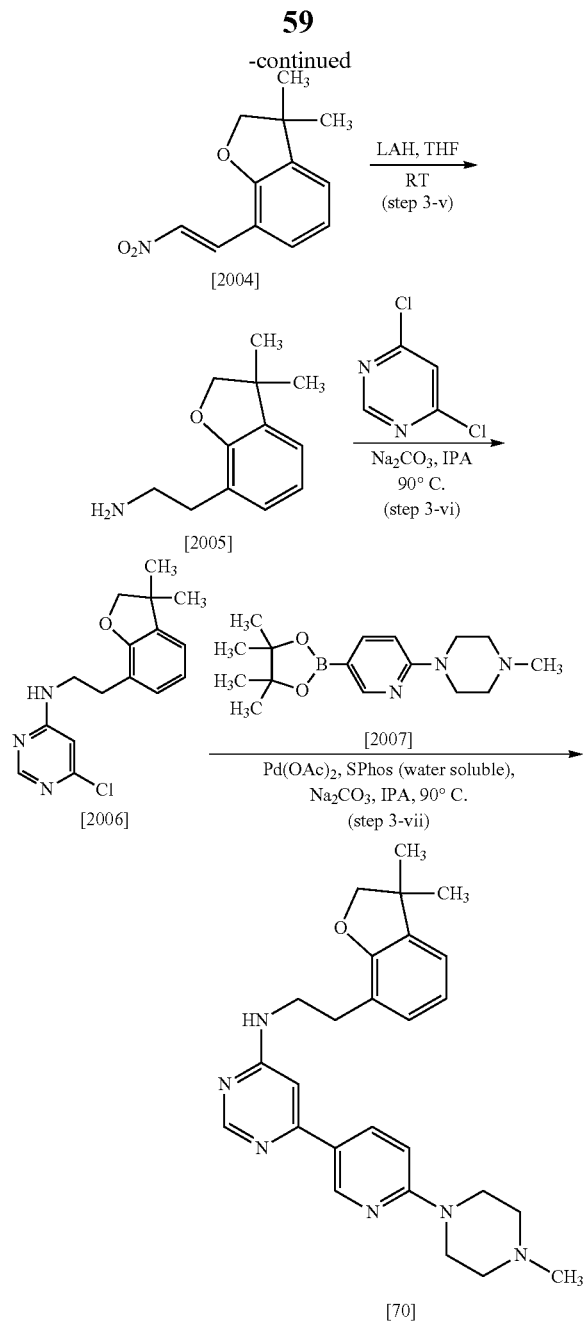

As shown in step 3-i of Scheme 3, to a solution of 2-bromophenol (15 g, 86.7 mmol) in DMF (180 mL) at 0° C. was added 3-bromo-2-methyl-prop-1-ene (12.8 g, 9.61 mL, 95.37 mmol) followed by $K_2CO_3$ (23.96 g, 173.4 mmol) and TBAI (384 mg, 1.04 mmol). The reaction mixture was then stirred at RT for 24 hours and quenched with $H_2O$ (90 mL). The aqueous phase was extracted with EtOAc and the organic phase was dried over $Na_2SO_4$. Removal of the volatiles under reduced pressure gave 1-bromo-2-((2-methylallyl)oxy)benzene (Compound 2001, 19.12 g, 97% yield, colorless liquid): $^1$H NMR (400 MHz, $CDCl_3$) δ 7.46 (dd, J=1.5, 7.8 Hz, 1H), 7.18-7.13 (m, 1H), 6.81-6.73 (m, 2H), 5.09 (s, 1H), 4.93 (t, J=1.1 Hz, 1H), 4.42 (s, 2H) and 1.78 (s, 3H) ppm. This material was used as is in subsequent reactions.

As shown in step 3-ii of Scheme 3, a solution of Compound 2001 (13.8 g, 60.7 mmol), NaOAc (12.46 g, 151.9 mmol), tetraethylammonium chloride hydrate (13.4 g, 72.9 mmol), and sodium formate (4.95 g, 72.9 mmol) in DMF (140 mL) was degassed for 30 min using a $N_2$ stream. $Pd(OAc)_2$ (682.1 mg, 3.04 mmol) was added and the mixture was heated to 90° C. for 4 hours. The reaction mixture was cooled down to RT and diluted with $Et_2O$ (50 mL). The resulting solution was filtered though diatomaceous earth and the filtrate was washed with $H_2O$ and brine. The organic phase was dried over $Na_2SO_4$, concentrated under reduced pressure, and purified by medium pressure chromatography on silica gel (0 to 20% EtOAc in hexanes) to give 3,3-dimethyl-2,3-dihydrobenzofuran (Compound 2002, 3.86 g, 43% yield) as a colorless oil: $^1$H NMR (400 MHz, $CDCl_3$) δ 7.03 (d, J=7.6 Hz, 2H), 6.81 (t, J=7.4 Hz, 1H), 6.72 (d, J=7.8 Hz, 1H), 4.15 (d, J=0.7 Hz, 2H) and 1.27 (s, 6H) ppm.

As shown in step 3-iii of Scheme 3, to a solution of TMEDA (3.93 g, 5.11 mL, 33.8 mmol) in $Et_2O$ (60 mL) was added sec-butyllithium (22.3 mL of 1.4 M, 31.2 mmol) at −78° C. After 10 minutes at −78° C., 3,3-dimethyl-2H-benzofuran (Compound 2002, 3.86 g, 26.0 mmol) in $Et_2O$ (60 mL) was added dropwise over 15 min. After 10 min, the mixture was stirred at 0° C. for 30 min. Then, the solution was cooled to −78° C. and DMF (4.76 g, 5.04 mL, 65.1 mmol) was added dropwise. The reaction mixture was stirred at −78° C. for 10 minutes and was then warmed to 0° C. over 2 hours. The reaction was quenched with 1N HCl (20 mL) and diluted with hexane/$Et_2O$ (1:1, 50 mL). The organics were dried over $Na_2SO_4$ and the volatiles were removed under reduced pressure to give 3,3-dimethyl-2,3-dihydrobenzofuran-7-carbaldehyde (Compound 2003, 4.1 g, 89% yield): $^1$H NMR (400 MHz, $CDCl_3$) δ 10.14 (s, 1H), 7.53 (dd, J=1.3, 7.8 Hz, 1H), 7.25 (dd, J=1.3, 7.2 Hz, 1H), 6.90 (t, J=7.5 Hz, 1H), 4.34 (s, 2H) and 1.30 (s, 6H) ppm; ESMS (M+H)=177.25.

As shown in step 3-iv of Scheme 3, to a solution of 3,3-dimethyl-2H-benzofuran-7-carbaldehyde (0.5 g, 2.837 mmol) in AcOH (11.1 mL) was added nitromethane (519.5 mg, 461.0 μL, 8.511 mmol) and ammonium acetate (546.7 mg, 7.092 mmol) at RT. The reaction mixture was then heated at 110° C. for 2 hours. The reaction mixture was then cooled and the volatiles removed under reduced pressure. The residue was dissolved in DCM, the organic phase was washed with $H_2O$ and brine, dried over $Na_2SO_4$, concentrated under reduced pressure, and purified by medium pressure chromatography on silica gel (0 to 75% EtOAc in hexanes) to give (E)-3,3-dimethyl-7-(2-nitrovinyl)-2,3-dihydrobenzofuran (Compound 2004, 160 mg, 34% yield) as a yellow solid: $^1$H NMR (400 MHz, $CDCl_3$) δ 7.91 (q, J=13.4 Hz, 2H), 7.14 (t, J=7.1 Hz, 2H), 6.88 (t, J=7.5 Hz, 1H), 4.34 (s, 2H) and 1.30 (s, 6H) ppm; ESMS (M+H)=220.02.

As shown in step 3-v of Scheme 3, to a solution of $LiAlH_4$ (4.01 mL of 1M/THF, 4.01 mmol) was added (E)-3,3-dimethyl-7-(2-nitrovinyl)-2,3-dihydrobenzofuran (160 mg, 0.72 mmol) in THF (14.0 mL) at RT. The yellow solution was stirred at RT for 15 hours. The reaction was quenched very slowly with water (15 mL) and extracted with $Et_2O$ and EtOAc. The organics were dried over $Na_2SO_4$ and concentrated under reduced pressure to give 2-(3,3-dimethyl-2,3-dihydrobenzofuran-7-yl)ethanamine (Compound 2005, 139 mg, 99% yield): $^1$H NMR (400 MHz, $CDCl_3$) δ 6.90 (dd, J=6.2, 6.9 Hz, 2H), 6.79-6.71 (m, 1H), 4.15 (s, 2H), 2.88 (t, J=6.9 Hz, 2H), 2.65 (t, J=6.9 Hz, 2H) and 1.26 (s, 6H) ppm; ESMS (M+H)=192.07.

As shown in step 3-vi of Scheme 3, a solution of 4,6-dichloropyrimidine (111.6 mg, 0.726 mmol), 2-(3,3-dimethyl-2H-benzofuran-7-yl)ethanamine (139 mg, 0.726 mmol), $Na_2CO_3$ (231.1 mg, 2.180 mmol) in i-PrOH (5.56 mL) was sealed in a microwave-type tube and heated at 90° C. in an oil bath for 18 hours. The reaction mixture was filtered through a pad of diatomaceous earth, the volatiles removed under reduced pressure, and the residue purified by medium pressure chromatography on silica gel (0 to 100% EtOAc in hexanes) to give 6-chloro-N-(2-(3,3-dimethyl-2,3-dihydrobenzofuran-7-yl)ethyl)pyrimidin-4-amine (Compound 2006) as a colorless oil: $^1$H NMR (400 MHz, CDCl$_3$) δ 8.24 (s, 1H), 6.94 (d, J=7.3 Hz, 1H), 6.88 (d, J=7.4 Hz, 1H), 6.78 (t, J=7.4 Hz, 1H), 4.20 (d, J=5.9 Hz, 2H), 4.05 (d, J=7.1 Hz, H), 3.47 (s, 2H), 2.83 (t, J=6.6 Hz, 2H), 1.50 (s, 2H) and 1.27 (s, 6H) ppm; ESMS (M+H)=304.06.

As shown in step 3-vii of Scheme 3, a solution of -chloro-N-(2-(3,3-dimethyl-2,3-dihydrobenzofuran-7-yl)ethyl)pyrimidin-4-amine (60 mg, 0.197 mmol), 1-methyl-4-[5-(4,4,5,5-tetramethyl-1,3,2-dioxaborolan-2-yl)-2-pyridyl]piperazine (71.86 mg, 0.237 mmol), Na$_2$CO$_3$ (296.2 μL of 2M, 0.592 mmol), and [3-(2-dicyclohexylphosphanylphenyl)-2,4-dimethoxy-phenyl]sulfonyloxysodium (VPhos, 8.1 mg, 0.0158 mmol) in i-PrOH (1.6 mL) was degassed using a stream of N$_2$ for 30 minutes. Pd(OAc)$_2$ (0.88 mg, 0.0039 mmol) was added and the solution was heated to 90° C. for 2 hours. The solution was concentrated under reduced pressure and purified by medium pressure chromatography on silica gel (0 to 100% (10% MeOH/EtOAc) in hexanes) to give N-(2-(3,3-dimethyl-2,3-dihydrobenzofuran-7-yl)ethyl)-6-(6-(4-methylpiperazin-1-yl)pyridin-3-yl)pyrimidin-4-amine (Compound 68, 32.4 mg, 36%) as a white solid: $^1$H NMR (400 MHz, CDCl$_3$) δ 8.69 (s, 1H), 8.49 (s, 1H), 8.07 (d, J=8.1 Hz, 1H), 6.94-6.90 (m, 2H), 6.77 (t, J=7.3 Hz, 1H), 6.62 (d, J=8.9 Hz, 1H), 6.55 (s, 1H), 5.30 (s, 1H), 4.20 (s, 2H), 3.60 (s, 6H), 2.86 (t, J=6.4 Hz, 2H), 2.45 (s, 4H), 2.28 (s, 3H) and 1.27 (s, 6H) ppm; ESMS (M+H)=445.09.

Example 4

Preparation (S)—N-(2-(2-Methoxyphenyl)propyl)-6-(6-(4-methylpiperazin-1-yl)pyridin-3-yl)pyrimidin-4-amine (Compound 32)

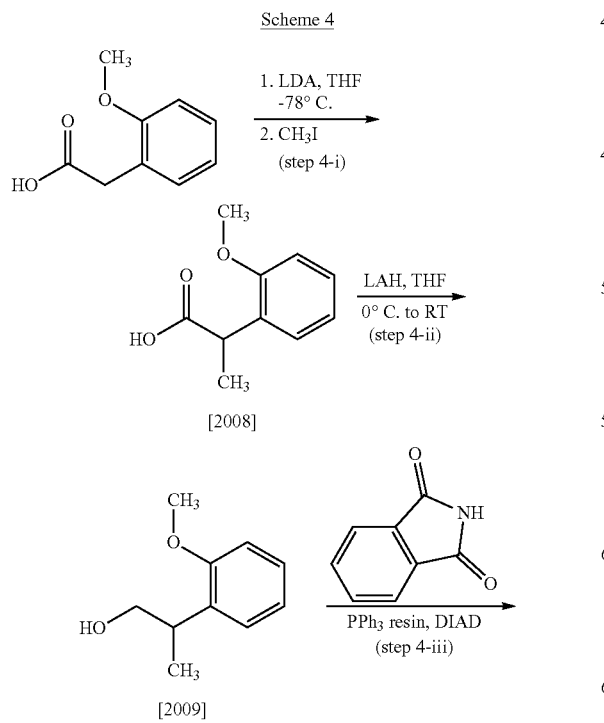

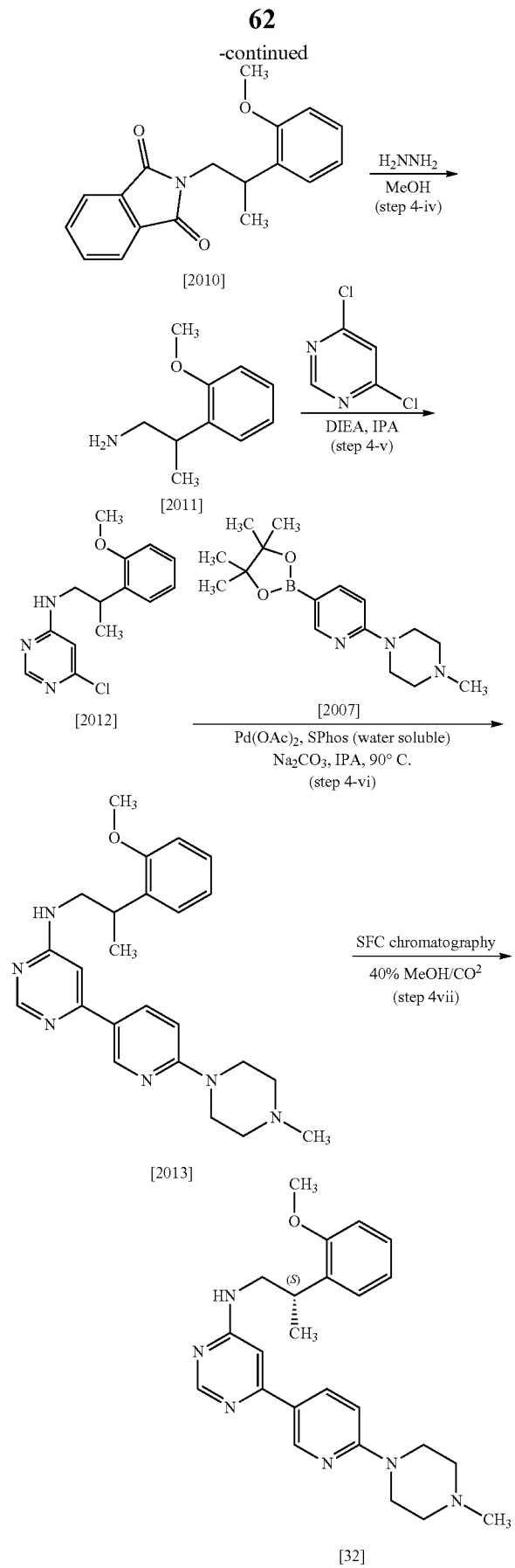

As shown in step 4-i of Scheme 4, to a solution of diisopropylamine (6.70 g, 9.28 mL, 66.2 mmol) in THF (60 mL) at −78° C. under $N_2$ was added n-butyllithium (33.1 mL of 2.0 M in cyclohexane, 66.2 mmol) and the solution was stirred for 40 minutes. A solution of 2-(2-methoxyphenyl)acetic acid (5.00 g, 30.1 mmol) in THF (30 mL) was added dropwise, then the reaction was allowed to warm to room temperature over one hour. The reaction was then cooled to −78° C. and iodomethane (4.27 g, 1.87 mL, 30.1 mmol) was added to the reaction in one portion. The reaction was warmed to room temperature 18 hours, 15 mL of water was added, and the organics were collected and the volatiles removed under reduced pressure. The residue was acidified with 1N HCl and the crude product extracted with $Et_2O$ (3×). The combined organics were dried over $MgSO_4$, filtered, concentrated under reduced pressure, and the residue purified by medium pressure chromatography on silica gel (25 to 50% EtOAc in hexanes) to give 2-(2-methoxyphenyl)propanoic acid as a white solid (Compound 2008, 4.86 g, 85% yield): $^1H$ NMR ($CDCl_3$) δ 7.31-7.21 (m, 2H), 7.01-6.84 (m, 2H), 4.09 (q, J=7.2 Hz, 1H), 3.84 (s, 3H), 1.49 (d, J=7.2 Hz, 3H).

As shown in step 4-ii of Scheme 4, to a solution of 2-(2-methoxyphenyl)propanoic acid (1.50 g, 7.91 mmol) in THF (20 mL) at 0° C. was added lithium aluminum hydride (31.6 mL of 0.5 M solution, 15.8 mmol) and the reaction was warmed to room temperature and stirred for 3.5 hours. After the sequential addition of 0.7 mL water, 0.7 mL 1M NaOH, 1.9 mL water, and $MgSO_4$ to sequester the water, the reaction mixture was filtered through diatomaceous earth and concentrated under reduced pressure to give 2-(2-methoxyphenyl)-1-propanol as a clear, colorless liquid (Compound 2009, 1.41 g, 96% yield): $^1H$ NMR ($CDCl_3$) δ 7.27-7.20 (m, 2H), 7.03-6.87 (m, 2H), 3.85 (s, 3H), 3.67 (m, 2H), 3.54-3.42 (m, 1H), 1.54 (t, J=6.1 Hz, 1H), 1.29 (d, J=7.1 Hz, 3H).

As shown in step 4-iii of Scheme 4, a mixture of 2-(2-methoxyphenyl)-1-propanol (1.31 g, 7.08 mmol), phthalimide (1.09 g, 7.44 mmol), and $PPh_3$ resin (3.43 g, 10.6 mmol) was stirred at room temperature for 15 minutes to allow the resin to swell. Diisopropylazodicarboxylate (2.29 g, 2.24 mL, 10.6 mmol) was added and the reaction was stirred for 18 hours. The reaction mixture was filtered through diatomaceous earth, which was subsequently washed with EtOAc and DCM. The filtrate was concentrated under reduced pressure and purified by medium pressure chromatography on silica gel (10 to 20% EtOAc in hexanes) to give 2-(2-(2-methoxyphenyl)propyl)isoindoline-1,3-dione as a clear, colorless oil (Compound 2010, 2.15 g, quantitative yield): $^1H$ NMR ($CDCl_3$) δ 7.81 (dd, J=5.5, 3.0 Hz, 2H), 7.69 (dd, J=5.5, 3.0 Hz, 2H), 7.34-7.24 (m, 1H), 7.19 (ddd, J=8.1, 7.5, 1.7 Hz, 1H), 6.94 (td, J=7.5, 1.1 Hz, 1H), 6.76 (dd, J=8.2, 0.9 Hz, 1H), 4.03-3.69 (m, 3H), 3.66 (s, 3H), 1.32 (d, J=6.8 Hz, 3H).

As shown in step 4-iv of Scheme 4, to a stirred solution of 2-(2-(2-methoxyphenyl)propyl)isoindoline-1,3-dione (363 mg, 1.23 mmol) in MeOH (4.0 mL) was added hydrazine (39.4 mg, 38.6 μL, 1.23 mmol) and the reaction was stirred for 18 hours. The precipitate that had formed was filtered, washed with MeOH, and the filtrate concentrated under reduced pressure to give 2-(methoxyphenyl)-1-propanamine as a light yellow oil (Compound 2011, 144 mg, 71% yield): $^1H$ NMR ($CDCl_3$) δ 7.27-7.13 (m, 2H), 6.95 (ddd, J=18.2, 12.3, 4.6 Hz, 2H), 3.84 (s, 3H), 3.39-3.18 (m, 1H), 2.86 (qd, J=12.7, 6.8 Hz, 2H), 1.44 (s, 2H), 1.24 (d, J=7.0 Hz, 3H).

As shown in step 4-v of Scheme 4, a mixture of 4,6-dichloropyrimidine (817 mg, 5.49 mmol), 2-(2-methoxyphenyl)-1-propanamine (0.997 g, 6.03 mmol), and DIEA (2.13 g, 2.87 mL, 16.5 mmol) in isopropanol (5.0 mL) was stirred for 18 hours. The reaction mixture was concentrated under reduced pressure and the residue purified by medium pressure chromatography on silica gel (25% EtOAc in hexanes) to give 6-chloro-N-(2-(2-methoxyphenyl)propyl)pyrimidin-4-amine as a colorless solid (Compound 2012, 1.18 g, 77% yield): $^1H$ NMR ($CDCl_3$) δ 8.31 (s, 1H), 7.23 (dd, J=12.0, 4.5 Hz, 2H), 7.03-6.87 (m, 2H), 6.41 (s, 1H), 5.42 (s, 1H), 3.89 (s, 3H), 3.67-3.18 (m, 3H), 1.35 (d, J=6.8 Hz, 3H).

As shown in step 4-vi of Scheme 4, a mixture of 6-chloro-N-(2-(2-methoxyphenyl)propyl)pyrimidin-4-amine (75.0 mg, 0.270 mmol), 1-methyl-4-[5-(4,4,5,5-tetramethyl-1,3,2-dioxaborolan-2-yl)-2-pyridyl]piperazine (Compound 2007, 90.1 mg, 0.297 mmol), $Pd(OAc)_2$ (1.21 mg, 0.00540 mmol), [3-(2-dicyclohexylphosphanylphenyl)-2,4-dimethoxy-phenyl]sulfonyloxysodium (VPhos, 11.1 mg, 0.0216 mmol), and $Na_2CO_3$ (405 μL of 2 M, 0.810 mmol) in IPA (2 mL) was degassed and back-filled with $N_2$ (repeated 2×), then heated to 90° C. for 4 hours. The reaction mixture was filtered through diatomaceous earth and concentrated under reduced pressure. The residue was purified by medium pressure chromatography on silica gel (90-100% EtOAc in hexanes) to give N-(2-(2-methoxyphenyl)propyl)-6-(6-(4-methylpiperazin-1-yl)pyridin-3-yl)pyrimidin-4-amine as a clear, yellow oil (Compound 2013, 48.0 mg, 42% yield): $^1H$ NMR ($CDCl_3$) δ 8.77 (d, J=2.2 Hz, 1H), 8.56 (s, 1H), 8.15 (dd, J=9.0, 2.5 Hz, 1H), 7.28-7.21 (m, 2H), 7.01-6.89 (m, 2H), 6.72 (d, J=9.0 Hz, 1H), 6.60 (s, 1H), 5.09 (bs, 1H), 3.87 (s, 3H), 3.76-3.65 (m, 4H), 3.65-3.46 (m, 3H), 2.62-2.48 (m, 4H), 2.38 (s, 3H), 1.36 (d, J=6.7 Hz, 3H).

As shown in step 4-vii of Scheme 4, N-(2-(2-methoxyphenyl)propyl)-6-(6-(4-methylpiperazin-1-yl)pyridin-3-yl)pyrimidin-4-amine (30.0 mg, 0.0710 mmol) was purified by supercritical fluid chromatorgraphy using a chiral OJ column and eluting with 40% MeOH (0.2% DEA) in $CO_2$ to give (S)—N-(2-(2-Methoxyphenyl)propyl)-6-(6-(4-methylpiperazin-1-yl)pyridin-3-yl)pyrimidin-4-amine as an off-white residue (Compound 32, 13.5 mg): $^1H$ NMR ($CDCl_3$) δ 8.77 (d, J=2.3 Hz, 1H), 8.56 (s, 1H), 8.14 (dd, J=9.0, 2.5 Hz, 1H), 7.28-7.18 (m, 2H), 7.04-6.86 (m, 2H), 6.71 (d, J=9.0 Hz, 1H), 6.59 (s, 1H), 5.24 (d, J=47.4 Hz, 1H), 3.86 (s, 3H), 3.75-3.64 (m, 4H), 3.64-3.43 (m, 3H), 2.65-2.47 (m, 4H), 2.37 (s, 3H), 1.36 (d, J=6.7 Hz, 3H).

Example 5

Preparation (S)—N-(2-(2-Methoxyphenyl)propyl)-6-(6-(4-methylpiperazin-1-yl)pyridin-3-yl)pyrimidin-4-amine (Compound 2016)

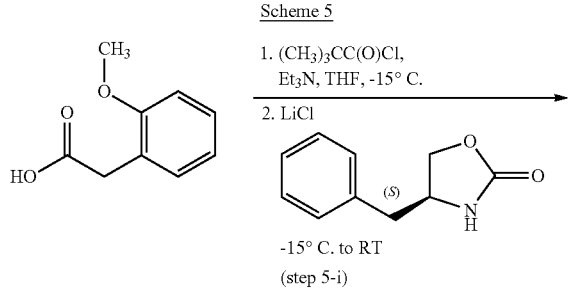

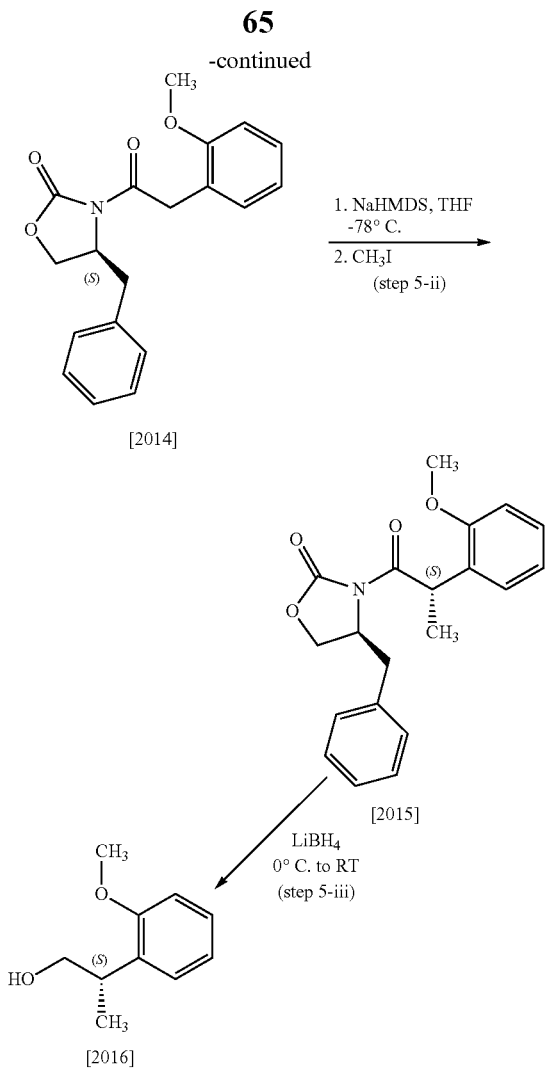

The chirality of asymmetric 1-carbon center of 2-aminoethyl-B-Ring moieties can be ascertained by preparing intermediates analogous to Compound 2016 and using such intermediates in the preparation of the compounds of the invention. Accordingly, the chirality of Compound 34 was ascertained by preparing Compound 2009 as a mixture of racemates having an enantiomeric excess greatly in favor the (S)-configuration. See Evans D. A. et al., in *J. Am. Chem. Soc.*, Vol 104, 1737-1739 (1982). Accordingly, as shown in step 5-i of Scheme 5, to a solution of 2-(2-methoxyphenyl)acetic acid (5.00 g, 30.1 mmol) and Et₃N (6.70 g, 9.23 mL, 66.2 mmol) in THF (150 mL) at −15° C. was added pivaloyl chloride (3.70 g, 3.78 mL, 30.7 mmol) and the resulting solution was stirred for 15 minutes. Lithium chloride (1.53 g, 36.1 mmol) and (4S)-4-benzyloxazolidin-2-one (6.29 g, 35.5 mmol) were added to the solution and the reaction was warmed to room temperature over 18 hours. Saturated ammonium chloride was added and the reaction was extracted with EtOAc (2×). The organic extracts were combined and washed with NaHCO₃ (sat), brine, dried over MgSO₄, filtered, and then concentrated under reduced pressure. The residue was purified by medium pressure silica gel chromatography (15 to 30% EtOAc in hexanes) to give (4S)-4-benzyl-3-[2-(2-methoxyphenyl)acetyl]-oxazolidin-2-one (Compound 2014, 7.11 g, 72.6% yield) as a white solid: $^1$H NMR (300 MHz, CDCl₃) δ 7.42-7.15 (m, 7H), 6.96 (dd, J=15.6, 7.8 Hz, 2H), 4.79-4.65 (m, 1H), 4.44-4.09 (m, 4H), 3.85 (s, 3H), 3.33 (dd, J=13.3, 2.9 Hz, 1H), 2.84 (dd, J=13.3, 9.5 Hz, 1H).

As shown in step 5-ii of Scheme 5, to a solution of sodium hexamethyldisilazide (NaHMDS, 5.06 g, 26.2 mmol) in THF (100 mL) under an atmosphere of nitrogen at −78° C. was added (4S)-4-benzyl-3-[2-(2-methoxyphenyl)acetyl]oxazolidin-2-one (7.11 g, 21.9 mmol) and the reaction was stirred for 1.5 hours. Methyl iodide (3.08 g, 1.35 mL, 21.7 mmol) was then added dropwise and stirring continued at −78° C. for 4 hours, then the reaction was warmed to room temperature over 18 hours. The reaction was cooled to −20° C. and quenched with NH₄Cl (sat). The organics were removed under reduced pressure and the aqueous layer was extracted with DCM (3×). The organic extracts were combined and washed with brine, dried over MgSO₄, filtered, and concentrated under reduced pressure. The residue was purified by medium pressure silica gel chromatography (5 to 25% EtOAc in hexanes) to give (4S)-4-benzyl-3-[(2S)-2-(2-methoxyphenyl)propanoyl]oxazolidin-2-one as a white solid with a de of 9:1 (S/R). The solid was then purified via supercritical fluid chromatography (SFC) on an IC column (10% MeOH/CO₂ isocratic gradient) to give (4S)-4-benzyl-3-[(2S)-2-(2-methoxyphenyl)propanoyl]oxazolidin-2-one (Compound 2015, 3.14 g, 41.8% yield) with an enantiomeric excess of 99.9% by analytical SFC: $^1$H NMR (300 MHz, CDCl₃) δ 7.41-7.20 (m, 7H), 6.96 (dd, J=13.8, 6.6 Hz, 1H), 6.93-6.84 (m, 1H), 5.30 (q, J=7.1 Hz, 1H), 4.68 (qd, J=6.7, 3.5 Hz, 1H), 4.22-4.11 (m, 2H), 3.84 (s, 3H), 3.35 (dd, J=13.3, 3.2 Hz, 1H), 2.82 (dd, J=13.3, 9.7 Hz, 1H), 1.64-1.46 (m, 3H).

As shown in step 5-iii of Scheme 5, to an ice-cooled solution of (4S)-4-benzyl-3-[(2S)-2-(2-methoxyphenyl)-propanoyl]oxazolidin-2-one (3.10 g, 9.13 mmol) in THF (183 mL) and MeOH (1.24 mL) was added LiBH₄ (9.13 mL of 2.0 M solution, 18.3 mmol) and the reaction was stirred at 0° C. for 2 hours, then warmed to room temperature over 18 hours. A solution of NaOH (18.6 mL of 2.0 M solution) was added and the reaction stirred until both layers were clear. The layers were separated and the aqueous layer was extracted with Et₂O (2×). The organic extracts were combined and washed with H₂O, brine, dried over MgSO₄, filtered, and concentrated. The residue was purified by flash chromatography on silica gel (0 to 20% EtOAc in hexanes) to give (2S)-2-(2-methoxyphenyl)propan-1-ol (Compound 2016, 1.49 g, 95.4% yield) as a clear, colorless liquid: $^1$H NMR (300 MHz, CDCl₃) δ 7.30-7.19 (m, 2H), 6.98 (td, J=7.5, 1.0 Hz, 1H), 6.95-6.86 (m, 1H), 3.85 (s, 3H), 3.83-3.63 (m, 2H), 3.56-3.38 (m, 1H), 1.84 (s, 1H), 1.30 (d, J=7.1 Hz, 3H); [α]$_D^{25.7}$+4.18 (c 1.11, CHCl₃). This optical rotation compares with the rotation for Compound 2016 as described by Denmark S E et al. in *J. Am. Chem. Soc.* Vol. 132, pages 3612-3620 (2010) and by Matsumoto T et al., in *Bull. Chem. Soc. Jpn.* Vol. 58, 340-345 (1985).

Compound 34 produced as described in Scheme 4 and resolved by preparative SFC separation at the end of the synthesis was compared the same compound prepared using the chiral intermediate Compound 1016 in order to determine its absolute stereochemical configuration.

Example 6

Preparation (S)—N-(2-(2,3-dihydrofuro[3,2-b]pyridin-7-yl)propyl)-6-(6-(methylamino)pyridin-3-yl)pyrimidin-4-amine (Compound 430)

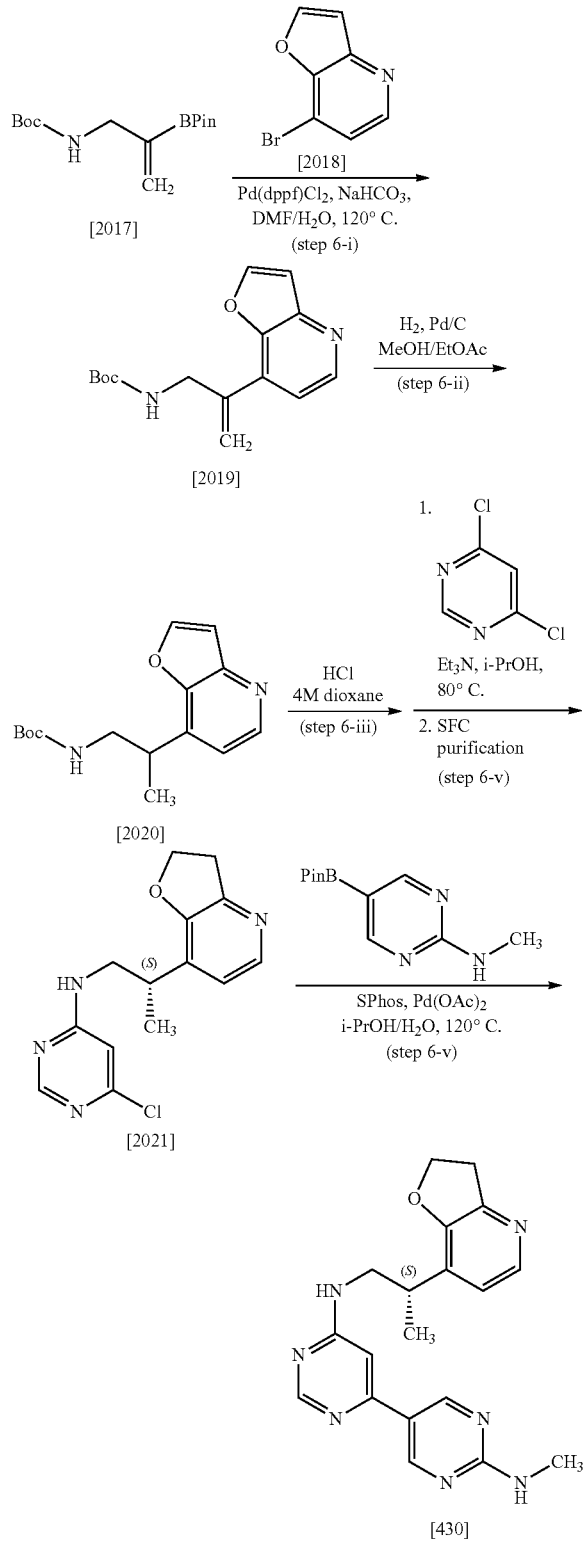

As shown in step 6-i of Scheme 6, tert-butyl (2-(4,4,5,5-tetramethyl-1,3,2-dioxaborolan-2-yl)allyl)carbamate (Compound 1017, 1.455 g, 5.138 mmol), 7-chlorofuro[3,2-b]pyridine (0.789 g, 5.138 mmol), NaHCO$_3$ (8.56 mL of 1.2 M, 10.276 mmol), DMF (14.3 mL), and H$_2$O (4.8 mL) were combined. The resultant mixture was flushed with nitrogen gas for 10 minutes. Pd(dppf)Cl$_2$ (419.6 mg, 0.514 mmol) was added and the reaction was heated to 120° C. in the microwave for 30 minutes. The crude reaction mixture was filtered over diatomaceous earth and the filter pad washed with ethyl acetate. The combined organics were dried (Na$_2$SO$_4$) and concentrated under reduced pressure. The residue was purified by silica gel chromatography (0-20% EtOAc/hexanes) to furnish tert-butyl (2-(furo[3,2-b]pyridin-7-yl)allyl)carbamate (Compound 1019, 0.94 g, 67% yield): LCMS=275.26 (M+H); $^1$H NMR (400 MHz, CDCl$_3$) δ 8.51 (d, J=5.0 Hz, 1H), 7.86 (d, J=2.2 Hz, 1H), 7.23 (d, J=4.8 Hz, 1H), 7.01 (d, J=2.2 Hz, 1H), 6.02 (d, J=15.6 Hz, 1H), 5.69 (s, 1H), 4.79 (s, 1H), 4.34 (d, J=5.6 Hz, 2H), 1.42 (s, 9H).

As shown in step 6-ii of Scheme 6, a mixture of tert-butyl (2-(furo[3,2-b]pyridin-7-yl)allyl)carbamate (0.940 g, 3.427 mmol), Pd/C (10%, 364.7 mg, 3.427 mmol), EtOAc (34.3 mL) and MeOH (34.3 mL) was stirred under H$_2$ at 1 atm for 16 hours. The reaction mixture was filtered through diatomaceous earth and the filter pad was rinsed with 1:1 EtOAc/MeOH. The combined filtrate was concentrated under reduced pressure. The crude residue was purified by silica gel chromatography (0-100% EtOAc/hexanes) to furnish tert-butyl (2-(2,3-dihydrofuro[3,2-b]pyridin-7-yl)propyl)carbamate (Compound 1020, 0.711 g, 75% yield): LCMS=279.47 (M+H); $^1$H NMR (400 MHz, CDCl$_3$) δ 7.98 (d, J=4.8 Hz, 1H), 6.86 (d, J=4.8 Hz, 1H), 4.64 (t, J=8.8 Hz, 2H), 4.54 (s, 1H), 3.44-3.20 (m, 4H), 3.13-3.00 (m, 1H), 1.40 (s, 9H), 1.24 (d, J=6.9 Hz, 3H).

As shown in step 6-iii of Scheme 6, tert-butyl (2-(2,3-dihydrofuro[3,2-b]pyridin-7-yl)propyl)carbamate (710 mg, 2.551 mmol) was dissolved in HCl (19.13 mL of 4 M dioxane solution, 76.53 mmol) and the reaction mixture stirred for 10 minutes. The solvent was removed under reduced pressure and the resulting 2-(2,3-dihydrofuro[3,2-b]pyridin-7-yl)propan-1-amine.2HCl (LCMS=179.22 [M+H]) was used in the following reaction as is.

As shown in step 6-iv of Scheme 6, to a suspension of 2-(2,3-dihydrofuro[3,2-b]pyridin-7-yl)propan-1-amine.2HCl and 4,6-dichloropyrimidine (456.0 mg, 3.061 mmol) in i-PrOH (17.01 mL) was added Et$_3$N (1.291 g, 1.778 mL, 12.76 mmol). The reaction mixture was heated at 80° C. for 2 h, cooled to room temperature, and partitioned between saturated aqueous NaHCO$_3$ and EtOAc. The aqueous layer was further extracted with EtOAc (2×50 mL) and the combined organics were washed with H$_2$O (50 mL) and brine (50 mL), dried (Na$_2$SO$_4$), filtered, and concentrated under reduced pressure. The residue was purified by silica gel chromatography (0-100% EtOAc/hexanes, then isocratic EtOAc) to afford 6-chloro-N-(2-(2,3-dihydrofuro[3,2-b]pyridin-7-yl)propyl)pyrimidin-4-amine (600.3 mg, 81% yield over two steps). Chiral SFC purification (20% MeOH at 5 mL/min on a ChiralPak® AD-H (4.6 mm×100 mm) column, 100 bar, 35° C., 220 nm) provided (S)-6-chloro-N-(2-(2,3-dihydrofuro[3,2-b]pyridin-7-yl)propyl)pyrimidin-4-amine (Compound 2021, 300 mg, SFC retention time 1.05 minutes): LCMS=291.04 (M+H); $^1$H NMR (400 MHz, CDCl$_3$) δ 8.32 (s, 1H), 8.00 (d, J=4.5 Hz, 1H), 6.92 (d, J=4.4 Hz, 1H), 6.36 (s, 1H), 5.24 (s, 1H), 4.71 (t, J=8.9 Hz, 2H), 3.61-3.35 (m, 4H), 3.23 (dd, J=14.0, 6.9 Hz, 1H), 1.35 (d, J=6.9 Hz, 3H). The corresponding (R)-enantiomer had a retention time of 1.25 minutes).

As shown in step 6-v of Scheme 6, (S)-6-chloro-N-(2-(2,3-dihydrofuro[3,2-b]pyridin-7-yl)propyl)pyrimidin-4-amine (29.2 mg, 0.1003 mmol), N-methyl-5-(4,4,5,5-tetramethyl-1,3,2-dioxaborolan-2-yl)pyridin-2-amine (30.7 mg, 0.2006 mmol), Na$_2$CO$_3$ (150.4 µL of 2 M aqueous solution, 0.3009 mmol), and i-PrOH (2.0 mL) were combined and flushed with nitrogen gas for 10 minutes. SPhos (water soluble, 10.28 mg, 0.0201 mmol) and Pd(OAc)$_2$ (1.13 mg, 0.0050 mmol) were added and the reaction vessel sealed and heated to 120° C. in a microwave for 30 minutes. The reaction mixture was filtered over diatomaceous earth and the filtrate was concentrated under reduced pressure. The residue was purified by reversed-phase HPLC (0-30% CH$_3$CN/H$_2$O, 0.1% TFA). The TFA salt obtained was neutralized using a StratoShperes™ PL-HCO$_3$ MP-Resin cartridge to provide (S)—N-(2-(2,3-dihydrofuro[3,2-b]pyridin-7-yl)propyl)-6-(6-(methylamino)pyridin-3-yl)pyrimidin-4-amine (Compound 430, 23.8 mg, 65% yield): LCMS=364.12 (M+H); $^1$H NMR (400 MHz, DMSO-d$_6$) δ 8.83 (s, 2H), 8.41 (s, 1H), 7.90 (d, J=5.1 Hz, 1H), 7.55 (s, 1H), 7.39 (s, 1H), 7.01 (s, 1H), 6.77 (s, 1H), 4.61 (t, J=8.4 Hz, 2H), 3.66-3.40 (m, 2H), 3.26-3.12 (m, 3H), 2.86 (d, J=4.5 Hz, 3H), 1.21 (d, J=6.6 Hz, 3H).

Example 7

Preparation of (S)—N$^6$-(2-(2,3-dihydro-[1,4]dioxino[2,3-b]pyridin-8-yl)propyl)-N$^{2'}$-methyl-[4,5'-bipyrimidine]-2',6-diamine (Compound 462)

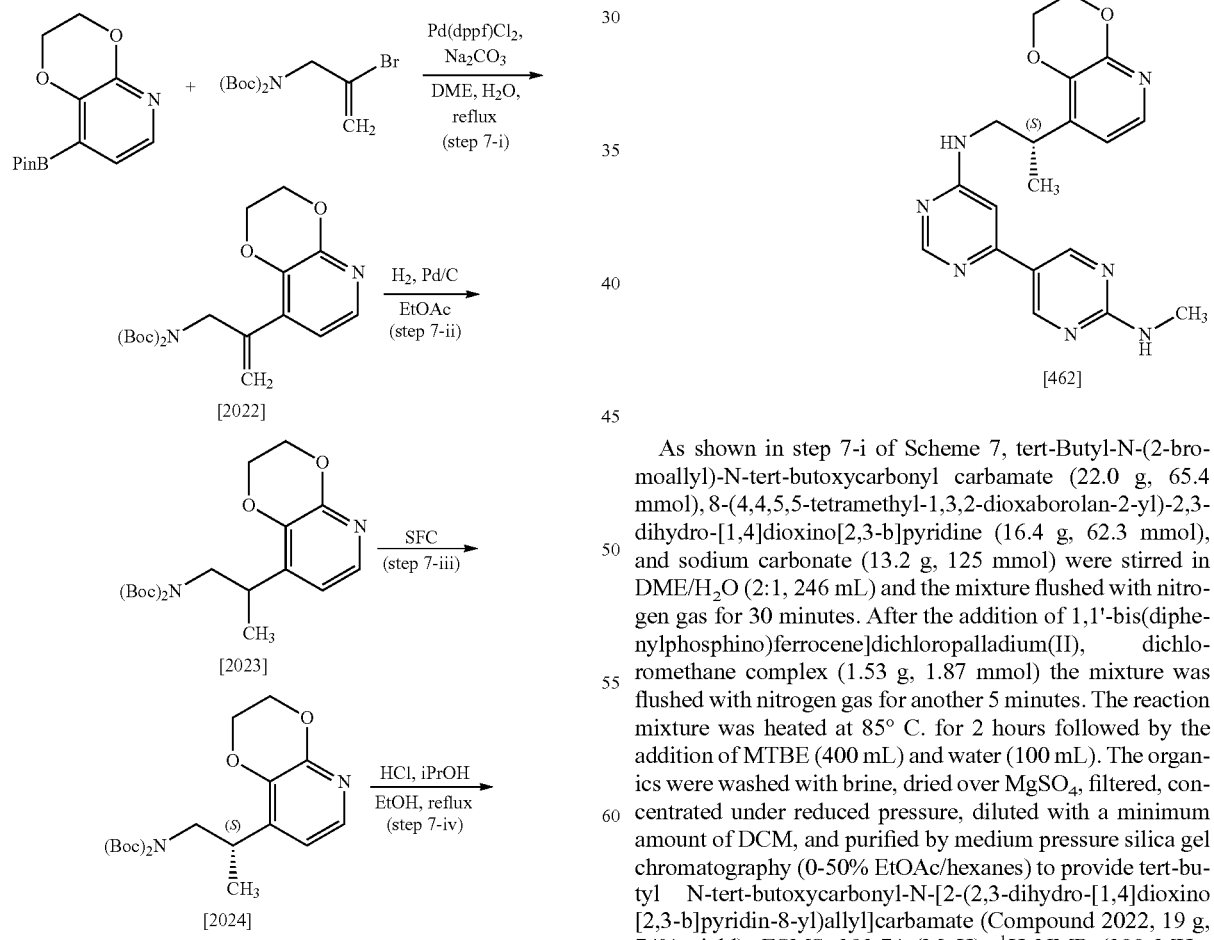

As shown in step 7-i of Scheme 7, tert-Butyl-N-(2-bromoallyl)-N-tert-butoxycarbonyl carbamate (22.0 g, 65.4 mmol), 8-(4,4,5,5-tetramethyl-1,3,2-dioxaborolan-2-yl)-2,3-dihydro-[1,4]dioxino[2,3-b]pyridine (16.4 g, 62.3 mmol), and sodium carbonate (13.2 g, 125 mmol) were stirred in DME/H$_2$O (2:1, 246 mL) and the mixture flushed with nitrogen gas for 30 minutes. After the addition of 1,1'-bis(diphenylphosphino)ferrocene]dichloropalladium(II), dichloromethane complex (1.53 g, 1.87 mmol) the mixture was flushed with nitrogen gas for another 5 minutes. The reaction mixture was heated at 85° C. for 2 hours followed by the addition of MTBE (400 mL) and water (100 mL). The organics were washed with brine, dried over MgSO$_4$, filtered, concentrated under reduced pressure, diluted with a minimum amount of DCM, and purified by medium pressure silica gel chromatography (0-50% EtOAc/hexanes) to provide tert-butyl N-tert-butoxycarbonyl-N-[2-(2,3-dihydro-[1,4]dioxino[2,3-b]pyridin-8-yl)allyl]carbamate (Compound 2022, 19 g, 74% yield): ESMS=393.74 (M+H); $^1$H NMR (300 MHz, CDCl$_3$) δ 7.75 (d, 1H), 6.75 (d, 1H), 5.30 (s, 1H), 5.25 (s, 1H), 4.55 (s, 2H), 4.40 (m, 2H), 4.25 (m, 2H), 1.45 (s, 18H).

As shown in step 7-ii of Scheme 7, tert-butyl N-tert-butoxycarbonyl-N-[2-(2,3-dihydro-[1,4]dioxino[2,3-b]pyridin-8-yl)allyl]carbamate (18.9 g, 48.2 mmol) was stirred in EtOAc (200 mL) with 10% palladium/carbon (550 mg, 5.14 mmol). The reaction mixture was purged of atmosphere which was replaced with hydrogen gas (3×) and stirred under an atmosphere of hydrogen for 5 hours. The atmosphere was replaced with nitrogen gas and the mixture filtered, concentrated to a minimum volume under reduced pressure, and purified by medium pressure silica gel chromatography (0-100% EtOAc/hexanes) to provide tert-butyl N-tert-butoxycarbonyl-N-[2-(2,3-dihydro-[1,4]dioxino[2,3-b]pyridin-8-yl)propyl]carbamate (Compound 2023, 18.06 g, 95% yield): ESMS=395.75 (M+H); $^1$H NMR (300 MHz, CDCl$_3$) δ 7.75 (d, 1H), 6.75 (d, 1H), 4.45 (s, 2H), 4.25 (m, 2H), 3.65-3.80 (m, 3H), 1.45 (s, 18H), 1.25 (3H).

As shown in step 7-iii of Scheme 7, tert-butyl N-tert-butoxycarbonyl-N-[2-(2,3-dihydro-[1,4]dioxino[2,3-b]pyridin-8-yl)propyl]carbamate (18.0 g, 45.6 mmol) was diluted with EtOH and aliquots were purified by supercritical fluid chromatography on a Chiralpak® IC preparative column (10 mm×250 mm) eluting with 40% CO$_2$/EtOH at 35° C. and a pressure of 100 atm. with a flow rate of 12 mL/min. The first peak to elute (retention time=6.61 min) was collected. All first peak fractions were combined and the volatiles removed under reduced pressure to provide (S)-tert-butyl N-tert-butoxycarbonyl-N-[2-(2,3-dihydro-[1,4]dioxino[2,3-b]pyridin-8-yl)propyl]carbamate (Compound 2024, 7.74 g, 43% yield, enantiomeric excess=97.9%)

As shown in step 7-iv of Scheme 7, (S)-tert-butyl N-tert-butoxycarbonyl-N-[2-(2,3-dihydro-[1,4]dioxino[2,3-b]pyridin-8-yl)propyl]carbamate (7.74 g, 39.8 mmol) was dissolved in EtOH, HCl in IPA (60 mL of 4 M solution, 240 mmol) was added and the reaction mixture was refluxed for 1 hour. The reaction mixture was concentrated under reduced pressure to a minimum volume, Et$_2$O was added, and the resulting suspension stirred for 16 hours. The solid was collected by filtration and dried under high vacuum to provide (S)-2-(2,3-dihydro-[1,4]dioxino[2,3-b]pyridin-8-yl)propan-1-amine, dihydrochloride as a yellowish solid (Compound 2025, 10.55 g, 100% yield): $^1$H NMR (300 MHz, CDCl$_3$) δ 7.80 (d, 1H), 7.10 (d, 1H), 4.50 (m, 2H), 4.40 (m, 2H), 3.40 (m, 1H), 3.00 (m, 2H), 1.25 (d, 3H).

As shown in step 7-v of Scheme 7, (S)-2-(2,3-dihydro-[1,4]dioxino[2,3-b]pyridin-8-yl)propan-1-amine, dihydrochloride (10.0 g, 49.5 mmol), 4,6-dichloropyrimidine (8.11 g, 54.5 mmol), and TEA (15.03 g, 20.7 mL, 148.6 mmol) stirred in NMP (125 mL) at 50° C. for 3.5 hours. The reaction mixture was cooled, 300 mL of EtOAc was added, the organics washed with water, dried over Na$_2$SO$_4$, filtered, concentrated under reduced pressure, diluted with a minimum amount of DCM, and purified by medium pressure silica gel chromatography (0-100% EtOAc/hexanes). Fractions containing product were concentrated under reduced pressure of yield an oil which was dissolved in hot MTBE. Cooling of the MTBE solution resulted in a precipitate which was collected by filtration and suspended in 4:1 hexane/MTBE. Once again the solid was collected by filtration to provide 6-chloro-N-[2-(2,3-dihydro-[1,4]dioxino[2,3-b]pyridin-8-yl)propyl]pyrimidin-4-amine (Compound 2026, 10.78 g, 71% yield): ESMS=307.21 (M+H); $^1$H NMR (300 MHz, CDCl$_3$) δ 8.33 (s, 1H), 7.78 (d, J=7.1 Hz, 1H), 6.80 (d, J=7.1 Hz, 1H), 6.40 (s, 1H), 4.44 (m, 2H), 4.34-4.21 (m, 2H), 3.50 (m, 3H), 1.31 (d, J=6.8 Hz, 3H).

A portion of 6-chloro-N-[2-(2,3-dihydro-[1,4]dioxino[2,3-b]pyridin-8-yl)propyl]pyrimidin-4-amine was recrystallized from toluene and the resulting crystals analyzed by X-ray crystallography, confirming the (S)-configuration. X-ray powder diffraction (XRPD) showed peaks at 8.75, 10.30, 14.15, 17.50, 18.30, 18.80, 20.75, 20.95, 23.10, 23.95, 24.60, 26.20, 26.90, 29.20, 29.95, 30.45, and 31.95 (2-theta scale).

As shown in step 7-vi of Scheme 7,6-chloro-N-[2-(2,3-dihydro-[1,4]dioxino[2,3-b]pyridin-8-yl)propyl]pyrimidin-4-amine (410 mg) was dissolved in IPA (0.75 mL). N-methyl-5-(4,4,5,5-tetramethyl-1,3,2-dioxaborolan-2-yl)pyrimidin-2-amine (23 mg) was added, followed by the addition of 2M Na$_2$CO$_3$ (122 μL) and 1,1'-bis(diphenylphosphino)ferrocene] dichloropalladium(II), dichloromethane complex (7 mg). The reaction vessel was sealed and heated at 80° C. overnight. The mixture was cooled, diluted with ethyl acetate, washed with water, dried over Na$_2$SO$_4$, filtered, concentrated under reduced pressure and purified by reversed-phase HPLC, 5-50%ACN/H$_2$O/0.1% TFA. Fractions containing pure product were collected, dissolved in MeOH, passed through a carbonate cartridge, and concentrated under reduced pressure to provide (S)—N$^6$-(2-(2,3-dihydro-[1,4]dioxino[2,3-b]pyridin-8-yl)propyl)-N$^{2'}$-methyl-[4,5'-bipyrimidine]-2',6-diamine (Compound 462): ESMS=380.39 (M+H); $^1$H NMR (300 MHz, methanol-d$_4$) δ 8.75 (s, 2H), 8.47 (s, 1H), 7.65 (d, J=5.3 Hz, 1H), 6.94 (d, J=5.2 Hz, 1H), 6.76 (s, 1H), 4.46-4.34 (m, 2H), 4.32-4.19 (m, 2H), 3.59 (ddd, J=12.0, 11.5, 7.3 Hz, 3H), 2.99 (s, 3H), 1.32 (d, J=6.7 Hz, 3H).

Example 8

Preparation of (S)—N-(2-(2,3-dihydro-[1,4]dioxino [2,3-]pyridin-8-yl)propyl)-6-(6-methylpyridin-3-yl)pyrimidin-4-amine (Compound 443)

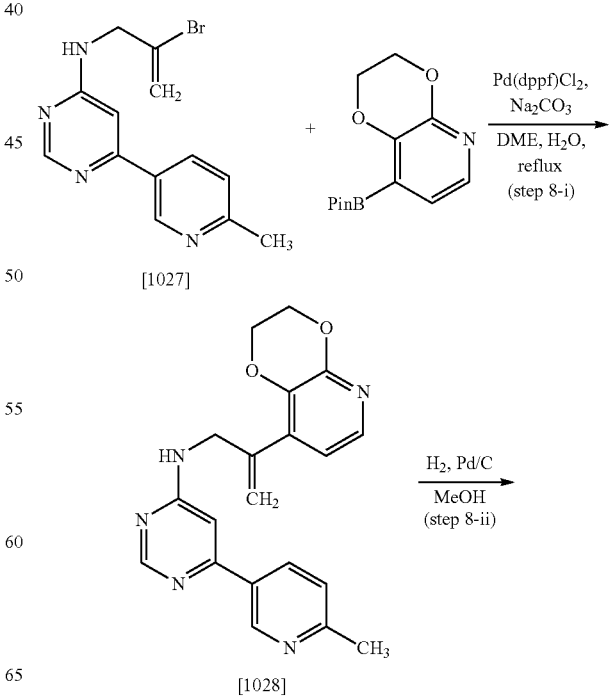

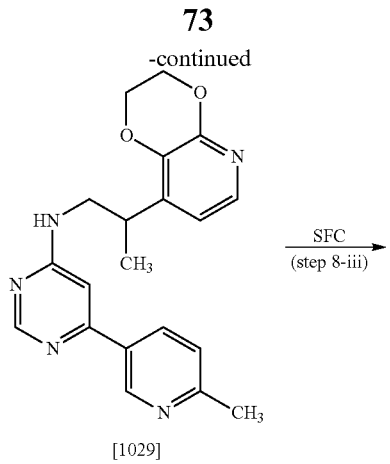

[1029]

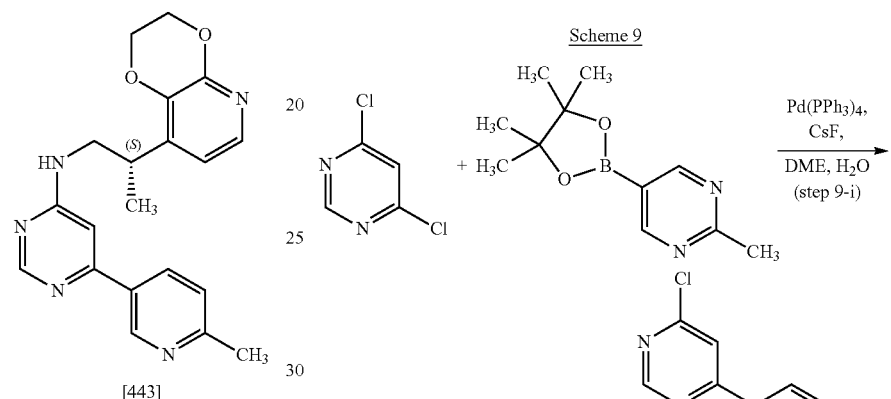

[443]

As shown in step 8-i of Scheme 8, N-(2-bromoallyl)-6-(6-methyl-3-pyridyl)pyrimidin-4-amine (240 mg, 0.7792 mmol, Compound 2027; which was prepared by reacting 4-chloro-6-(6-methylpyridin-3-yl)pyrimidine with 2-bromoprop-2-en-1-amine under basic conditions), 8-(4,4,5,5-tetramethyl-1,3,2-dioxaborolan-2-yl)-2,3-dihydro-[1,4]dioxino[2,3-b]pyridine (287.0 mg, 1.091 mmol), and $Na_2CO_3$ (1.169 mL of 2 M, 2.338 mmol) were stirred in DMSO (5.945 mL). Pd(dppf)Cl$_2$ (63.63 mg, 0.07792 mmol) was added and the reaction mixture stirred at 100° C. for 1 hour, then at RT for 16 hours. After this time the reaction mixture was partitioned between EtOAc and water, the organics dried over $Na_2SO_4$, filtered, and the volatiles removed under reduced pressure. The residue was dissolved in DCM and purified by medium pressure silica gel chromatography (20-100% EtOAc/hexanes, then 0-10% MeOH/DCM) to produce N-(2-(2,3-dihydro-[1,4]dioxino[2,3-b]pyridin-8-yl)allyl)-6-(6-methylpyridin-3-yl)pyrimidin-4-amine (Compound 2028) as yellow oil: LCMS=362.37 (M+H). This material was used as is in subsequent reactions.

As shown in step 8-ii of Scheme 8, N-[2-(2,3-dihydro-[1,4]dioxino[2,3-b]pyridin-8-yl)allyl]-6-(6-methyl-3-pyridyl)pyrimidin-4-amine (150 mg, 0.4151 mmol) was dissolved in MeOH and the reaction mixture was placed under an atmosphere of $H_2$. After stirring for 2 hours, the mixture was filtered, concentrated under reduced pressure, and purified by medium pressure silica gel chromatography (0-5% MeOH/DCM) to produce N-(2-(2,3-dihydro-[1,4]dioxino[2,3-b]pyridin-8-yl)propyl)-6-(6-methylpyridin-3-yl)pyrimidin-4-amine (Compound 2029): LCMS=364.39 (M+H); $^1$H NMR (300 MHz, CDCl$_3$) δ 9.00 (d, J=2.0 Hz, 1H), 8.63 (s, 1H), 8.20 (dd, J=8.1, 2.3 Hz, 1H), 7.81 (d, J=5.0 Hz, 1H), 7.27 (d, J=4.2 Hz, 1H), 6.82 (d, J=5.1 Hz, 1H), 6.71 (s, 1H), 4.43 (dd, J=5.1, 3.0 Hz, 2H), 4.27 (dd, J=5.1, 3.0 Hz, 2H), 3.56 (m, 3H), 2.62 (s, 3H), 1.32 (d, 3H).

As shown in step 8-ii of Scheme 8, N-(2-(2,3-dihydro-[1,4]dioxino[2,3-b]pyridin-8-yl)propyl)-6-(6-methylpyridin-3-yl)pyrimidin-4-amine was purified by supercritical fluid chromatography using a ChiralPak® IC™ column (10 mm×250 mm, 1/1 CO$_2$/EtOH, 35° C., 12 mL/min, 100 atm.) Fractions of the first eluting product with a retention time of 11.08 min were combined to produce (S)—N-(2-(2,3-dihydro-[1,4]dioxino[2,3-]pyridin-8-yl)propyl)-6-(6-methylpyridin-3-yl)pyrimidin-4-amine (Compound 443).

Example 9

Preparation of (S)—N-methyl-8-(1-((2'-methyl-[4,5'-bipyrimidin]-6-yl)amino)propan-2-yl)quinoline-4-carboxamide (Compound 578)

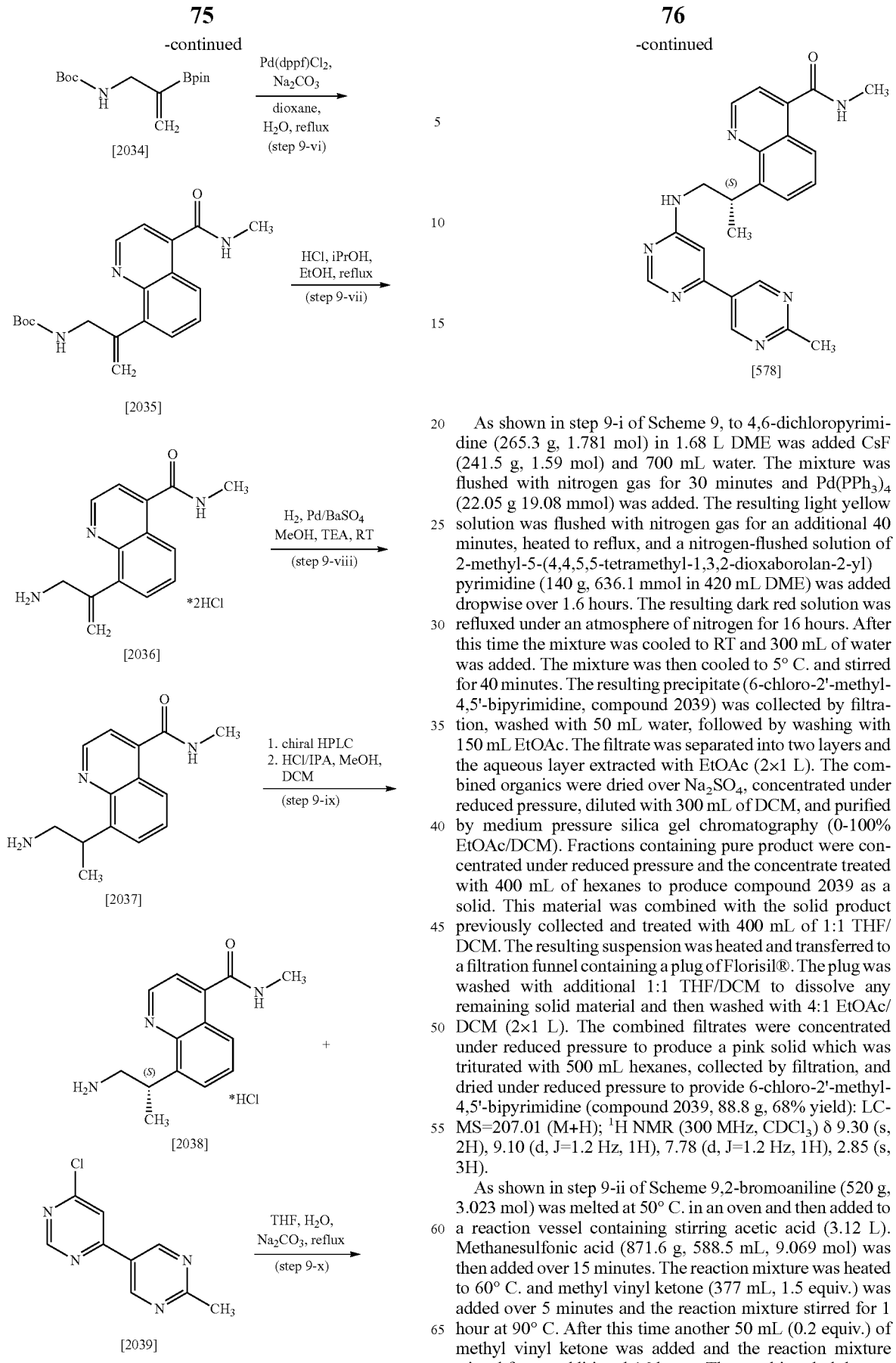

As shown in step 9-i of Scheme 9, to 4,6-dichloropyrimidine (265.3 g, 1.781 mol) in 1.68 L DME was added CsF (241.5 g, 1.59 mol) and 700 mL water. The mixture was flushed with nitrogen gas for 30 minutes and Pd(PPh$_3$)$_4$ (22.05 g 19.08 mmol) was added. The resulting light yellow solution was flushed with nitrogen gas for an additional 40 minutes, heated to reflux, and a nitrogen-flushed solution of 2-methyl-5-(4,4,5,5-tetramethyl-1,3,2-dioxaborolan-2-yl) pyrimidine (140 g, 636.1 mmol in 420 mL DME) was added dropwise over 1.6 hours. The resulting dark red solution was refluxed under an atmosphere of nitrogen for 16 hours. After this time the mixture was cooled to RT and 300 mL of water was added. The mixture was then cooled to 5° C. and stirred for 40 minutes. The resulting precipitate (6-chloro-2'-methyl-4,5'-bipyrimidine, compound 2039) was collected by filtration, washed with 50 mL water, followed by washing with 150 mL EtOAc. The filtrate was separated into two layers and the aqueous layer extracted with EtOAc (2×1 L). The combined organics were dried over Na$_2$SO$_4$, concentrated under reduced pressure, diluted with 300 mL of DCM, and purified by medium pressure silica gel chromatography (0-100% EtOAc/DCM). Fractions containing pure product were concentrated under reduced pressure and the concentrate treated with 400 mL of hexanes to produce compound 2039 as a solid. This material was combined with the solid product previously collected and treated with 400 mL of 1:1 THF/DCM. The resulting suspension was heated and transferred to a filtration funnel containing a plug of Florisil®. The plug was washed with additional 1:1 THF/DCM to dissolve any remaining solid material and then washed with 4:1 EtOAc/DCM (2×1 L). The combined filtrates were concentrated under reduced pressure to produce a pink solid which was triturated with 500 mL hexanes, collected by filtration, and dried under reduced pressure to provide 6-chloro-2'-methyl-4,5'-bipyrimidine (compound 2039, 88.8 g, 68% yield): LC-MS=207.01 (M+H); $^1$H NMR (300 MHz, CDCl$_3$) δ 9.30 (s, 2H), 9.10 (d, J=1.2 Hz, 1H), 7.78 (d, J=1.2 Hz, 1H), 2.85 (s, 3H).

As shown in step 9-ii of Scheme 9, 2-bromoaniline (520 g, 3.023 mol) was melted at 50° C. in an oven and then added to a reaction vessel containing stirring acetic acid (3.12 L). Methanesulfonic acid (871.6 g, 588.5 mL, 9.069 mol) was then added over 15 minutes. The reaction mixture was heated to 60° C. and methyl vinyl ketone (377 mL, 1.5 equiv.) was added over 5 minutes and the reaction mixture stirred for 1 hour at 90° C. After this time another 50 mL (0.2 equiv.) of methyl vinyl ketone was added and the reaction mixture stirred for an additional 16 hours. The resulting dark brown solution was cooled with an ice-water bath and poured portion-wise into a stirring solution of 50% w/w aq NaOH (3.894 L, 73.76 mol) and ice (1 kg) also cooled with an ice-water bath. Additional ice was added as required during addition to maintain the reaction temperature below 25° C. After addition was complete the reaction mixture (pH>10) was stirred for 30 minutes whilst cooling in an ice/water bath. A precipitate formed which was collected by filtration, washed with water (2 L×3), and dissolved in DCM (4 L). The organics were washed with water (2 L) and the aqueous phase back-extracted with DCM (1 L). The combined organics were dried over $Na_2SO_4$, filtered through a pad silica gel (about 2 L), eluted with DCM and then 3% EtOAc/DCM until all of the product came through the plug. The volatiles of the filtrate were removed at reduced pressure and the residue was triturated with hexanes (about 500 mL). The resulting solid was collected by filtration, washed with hexanes (4×500 mL), and dried under vacuum to yield 8-bromo-4-methylquinoline (compound 2030, 363 g, 54% yield) as a light tan solid: LC-MS=222.17 (M+H); $^1$H NMR (300 MHz, $CDCl_3$) δ 8.91 (d, J=4.3 Hz, 1H), 8.06 (d, J=7.4 Hz, 1H), 7.99 (d, J=8.4 Hz, 1H), 7.42 (t, J=7.9 Hz, 1H), 7.30 (d, J=4.2 Hz, 1H), 2.73 (s, 3H).

As shown in step 9-iii of Scheme 9, selenium dioxide (764.7 g, 6.754 mol) was taken up in 3.25 L of dioxane and 500 mL of water. The stirred solution was heated to 77° C. and 8-bromo-4-methylquinoline (compound 2030, 500 g, 2.251 mol) was added in one portion. The reaction mixture was stirred at reflux for 30 minutes and then cooled with a water bath to about 45° C., at which temperature a precipitate was observed. The suspension was filtered through diatomaceous earth which was subsequently washed with the hot THF to dissolve any residual solids. The filtrate was concentrated to a minimum volume under reduced pressure and 2M NaOH (2.81 L, 5.63 mol) was added to achieve a pH of 8 to 9. The reaction mixture was stirred at this pH for 30 minutes. A precipitate resulted which was collected by filtration and air-dried overnight to produce 8-bromoquinoline-4-carbaldehyde (compound 2031) as an yellowish solid: MS=236.16 (M+H); $^1$H NMR (300 MHz, $CDCl_3$) δ 10.52 (s, 1H), 9.34 (d, J=4.2 Hz, 1H), 9.05 (dd, J=8.5, 1.2 Hz, 1H), 8.18 (dd, J=7.5, 1.3 Hz, 1H), 7.88 (d, J=4.2 Hz, 1H), 7.60 (dd, J=8.5, 7.5 Hz, 1H). This material was used as is in subsequent reactions.

As shown in step 9-iv of Scheme 9, to a stirred suspension of 8-bromoquinoline-4-carbaldehyde (531.4 g, 2.25 mol) in THF (4.8 L) was added water (4.8 L) and monosodium phosphate (491.1 g, 4.05 mol). The mixture was cooled to 5° C. and, keeping the reaction temperature below 15° C., sodium chlorite (534.4 g, 4.727 mol) was slowly added portionwise as a solid over about 1 hour. After addition was complete the reaction mixture was stirred at 10° C. for 1 hour followed by the portionwise addition of 1N $Na_2S_2O_3$ (1.18 L) whilst keeping the temperature below 20° C. The reaction mixture was stirred at RT followed by the removal of the THF under reduced pressure. The resulting aqueous solution containing a precipitate was treated with sat'd $NaHCO_3$ (about 1 L) until a pH of 3 to 4 was achieved. This mixture was stirred an additional 15 minutes and the solid was collected by filtration, washed with water (2×1 L), washed with tert butyl methyl ether (2×500 mL), and dried in a convection oven at 60° C. for 48 hours. Additional drying under high vacuum provided 8-bromoquinoline-4-carboxylic acid (compound 2032, 530.7 g, 94% yield from compound 1030) as a yellowish tan solid: LC-MS=252.34 (M+H); $^1$H NMR (300 MHz, DMSO-$d_6$) δ 14.09 (s, 1H), 9.16 (d, J=4.4 Hz, 1H), 8.71 (dd, J=8.6, 1.2 Hz, 1H), 8.25 (dd, J=7.5, 1.2 Hz, 1H), 8.03 (d, J=4.4 Hz, 1H), 7.64 (dd, J=8.6, 7.5 Hz, 1H).

As shown in step 9-v of Scheme 9, to a suspension of 8-bromoquinoline-4-carboxylic acid (compound 2032, 779.4 g, 3.092 mol) in DCM (11.7 L) was added anhydrous DMF (7.182 mL, 92.76 mmol). The reaction mixture was cooled to 10° C. and oxalyl chloride (413 mL, 4.638 mol) was added dropwise over 30 minutes. The reaction mixture was stirred an additional 30 minutes after addition was complete, transferred to an evaporation flask, and the volatiles removed under reduced pressure Anhydrous THF (2 L) was added and the volatiles were once more removed under reduced pressure in order to remove any residual oxalyl chloride. Anhydrous THF was added to the residue under an atmosphere of nitrogen and the resulting suspension of intermediate 8-bromoquinoline-4-carboxylic acid chloride was stored for later use. Separately, the original reaction flask was thoroughly flushed with nitrogen gas to remove any residual oxalyl chloride and the flask charged with dry THF (1.16 L). After cooling to 5° C., aqueous methyl amine (2.14 L of 40% w/w $MeNH_2$/water, 24.74 mol) was added followed by the addition of additional THF (1.16 L). To this solution was added portionwise over 1 hour the intermediate acid chloride suspension, keeping the reaction mixture temperature below 20° C. during addition. The evaporation vessel used to store the acid chloride was rinsed with anhydrous THF and aqueous $MeNH_2$ (500 mL) and this added to the reaction mixture, which was allowed to come to room temperature over 16 hours. The organic volatiles were removed under reduced pressure and the remaining mostly aqueous suspension diluted with water (1.5 L). The solids were collected by filtration, washed with water until the filtrate had a pH of less than 11, washed with MTBE (2×800 mL), and dried in a convection oven at 60° C. to provide 8-bromo-N-methyl-quinoline-4-carboxamide (compound 2033, 740.4 g, 90% yield) as a light brown solid: LC-MS=265.04 (M+H); $^1$H NMR (300 MHz, DMSO-$d_6$) δ 9.08 (d, J=4.3 Hz, 1H), 8.78 (d, J=4.7 Hz, 1H), 8.21 (dd, J=7.5, 1.2 Hz, 1H), 8.16 (dd, J=8.5, 1.3 Hz, 1H), 7.65 (d, J=4.3 Hz, 1H), 7.58 (dd, J=8.5, 7.5 Hz, 1H), 2.88 (d, J=4.6 Hz, 3H).

As shown in step 9-vi of Scheme 9, 8-bromo-N-methyl-quinoline-4-carboxamide (compound 2033, 722 g, 2.723 mol) and tert-butyl-N-[2-(4,4,5,5-tetramethyl-1,3,2-dioxaborolan-2-yl)allyl]carbamate (compound 2034, 925.4 g, 3.268 mol) were combined in a reaction flask. $Na_2CO_3$ (577.2 g, 5.446 mol) was added followed by the addition of water (2.17 L). The mixture was stirred for 5 minutes, 1,4-dioxane (5.78 L) was added, and the mixture was deoxygenated by bubbling in a stream of nitrogen gas for 30 minutes. Pd(dppf) $Cl_2$/DCM (44.47 g, 54.46 mmol) was added and deoxygenation was continued as before for an additional 30 minutes. The reaction mixture was stirred at reflux for 16 hours, allowed to cool to 70° C., and water (5.42 L) was added. The mixture was cooled further with an ice-water bath and stirring continued at <10° C. for 2 hours. A precipitate resulted which was collected by filtration, washed with water (3×1 L), and washed with TBME (2×1 L). The resulting precipitate cake was split into two equal portions. Each portion was dissolved in THF/DCM (4 L) and poured onto a plug of Florisil® (3 L filtration funnel with about 1.5 L of florisil, using DCM to wet plug). The plug was subsequently washed with MeTHF until it was determined by thin layer chromatography analysis that no product remained in the filtrate. The filtrates from both cake portions were combined and concentrated under reduced pressure to give an orange solid. TBME (1 L) was added and the resulting suspension was filtered. The collected solid was washed with 800 mL of TBME and dried under high vacuum overnight to provide tert-butyl (2-(4-(methylcarbamoyl)quinolin-8-yl)allyl)carbamate (compound 2035, 653 g, 70% yield) as an off-white solid: LC-MS=342.31 (M+H); $^1$H NMR (300 MHz, CDCl$_3$) δ 8.93 (d, J=4.3 Hz, 1H), 8.17 (dd, J=8.4, 1.6 Hz, 1H), 7.68-7.53 (m, 2H), 7.41 (d, J=4.3 Hz, 1H), 6.09 (br. s, 1H), 5.54 (s, 1H), 5.28 (s, 1H), 5.10 (br. s, 1H), 4.33 (d, J=6.0 Hz, 2H), 3.11 (d, J=4.8 Hz, 3H), 1.38 (s, 9H). Additional product (34.9 g, 74% total yield) was obtained by concentrating the filtrate under reduced pressure, dissolving the residue in THF, filtering the solution through a plug of Florisil® as before, washing the plug with MeTHF, concentrating the filtrate under reduced pressure, adding 250 mL of TBME, stirring for 0.5 hours, collecting the resulting precipitate by filtration, washing the solid with EtOAc (40 mL), acetonitrile (50 mL), and drying the solid under high vacuum overnight.

As shown in step 9-vii of Scheme 9, to a stirring suspension of tert-butyl (2-(4-(methylcarbamoyl)quinolin-8-yl)allyl) carbamate (compound 2035, 425 g, 1.245 mol) in EtOH (4.25 L) was added 5.5M HCl in iPrOH (1.132 L, 6.225 mol). The reaction mixture was stirred at reflux (76° C. internal temp) for 30 minutes and then over 90 minutes while it was allowed to cool to 40° C. EtOAc (2.1 L) was added and the mixture was stirred for an additional 2 hours. The solid was collected by filtration, washed with EtOAc, and dried under high vacuum to provide 8-[1-(aminomethyl)vinyl]-N-methyl-quinoline-4-carboxamide, dihydrochloride (compound 2036, 357.9 g, 91% yield) as a tan solid: LC-MS=242.12 (M+H); $^1$H NMR (300 MHz, methanol-d$_4$) δ 9.07 (d, J=4.6 Hz, 1H), 8.27 (dd, J=8.5, 1.5 Hz, 1H), 7.89 (dd, J=7.2, 1.5 Hz, 1H), 7.81-7.72 (m, 2H), 5.85 (s, 1H), 5.75 (s, 1H), 4.05 (s, 2H), 3.04 (s, 3H).

As shown in step 9-viii of Scheme 9, 8-[1-(aminomethyl) vinyl]-N-methyl-quinoline-4-carboxamide, dihydrochloride (compound 2036, 168.8 g, 537 mmol) was stirred in MeOH (1.688 L) and TEA (114.2 g, 157.3 mL, 1.129 mol) was added, followed by the addition of 5% Pd on BaSO$_4$ (22.88 g, 10.75 mmol). The atmosphere of the reaction mixture was replaced with hydrogen gas and the reaction stirred at under 1 atmosphere of hydrogen atmosphere for 16 hours. After this time, the hydrogen atmosphere was removed and the mixture filtered through diatomaceous earth, concentrated under reduced pressure, and treated with 800 mL water and 250 mL DCM. The resulting biphasic mixture was stirred vigorously until most of the solids had dissolved, resulting in a thick mixture that separates on standing. The pH of the aqueous layer was checked and found to be pH=8. This layer was washed with 3×500 mL DCM, the pH adjusted to 14 with 500 mL 6N NaOH, and extracted with an additional 500 mL DCM. The aqueous solution was then treated with 500 g NaCl and it was extracted with an additional 500 mL DCM. The combined organics were dried over Na$_2$SO$_4$, filtered, and concentrated under reduced pressure to provide 8-(1-aminopropan-2-yl)-N-methylquinoline-4-carboxamide [compound 2037 (racemic mixture) 104.2 g, 80% yield]: LC-MS=244.43 (M+H); $^1$H NMR (300 MHz, methanol-d$_4$) δ 8.94 (d, J=4.3 Hz, 1H), 8.02 (dd, J=8.3, 1.6 Hz, 1H), 7.72-7.59 (m, 2H), 7.50 (d, J=4.3 Hz, 1H), 4.30 (h, J=7.0 Hz, 1H), 3.04 (dd, J=12.7, 7.0 Hz, 1H), 3.01 (s, 3H), 2.90 (dd, J=12.7, 6.9 Hz, 1H), 1.40 (d, J=7.1 Hz, 3H).

As shown in step 9-ix of Scheme 9, the two racemates of 8-(1-aminopropan-2-yl)-N-methylquinoline-4-carboxamide (compound 137, 1380.5 g) were separated by chiral HPLC. Accordingly, 260 mL aliquots of racemic mixture (6 mg/mL) were loaded onto a Chiralpak AY™ column (11 cm×25 cm) and eluted with acetonitrile (0.2% TEA) at a flow rate of 400 mL/minute. Two major peaks eluted. Peak 1 had a retention time of 7.7 min. and peak 2 had a retention time of 12.2 min. when analyzed by HPLC (Chiralpak AY-H™ column (4.6 mm×250 mm) eluted with acetonitrile (0.1% isopropylamine) at a flow rate of 1 mL/min). The combined peak 2 fractions were collected and the volatiles removed under reduced pressure to produce 8-[(1S)-2-amino-1-methylethyl]-N-methyl-quinoline-4-carboxamide (578.3 g, 97.4% enantiomeric excess): specific rotation (10 mg/mL in MeOH, 100 mm cell)=+24.20; LC-MS=244.19 (M+H); $^1$H NMR (300 MHz, methanol-d$_4$) δ 8.94 (d, J=4.3 Hz, 1H), 8.02 (dd, J=8.3, 1.6 Hz, 1H), 7.72-7.59 (m, 2H), 7.50 (d, J=4.3 Hz, 1H), 4.30 (h, J=7.0 Hz, 1H), 3.05 (dd, J=12.8, 7.1 Hz, 1H), 3.01 (s, 3H), 2.90 (dd, J=12.7, 6.9 Hz, 1H), 1.40 (d, J=7.0 Hz, 3H). The HCl salt was formed by adding 5N HCl/IPA (220 mL, 1.100 mol) to an ice-bath cooled stirring solution of 8-[(1S)-2-amino-1-methyl-ethyl]-N-methyl-quinoline-4-carboxamide (244.5 g, 1.005 mmol) in 980 mL of 1:1 MeOH/DCM. The ice bath was removed and 1470 mL of Et$_2$O was added portionwise. The precipitate was collected by filtration, washed with Et$_2$O and dried under high vacuum to produce 8-[(1S)-2-amino-1-methyl-ethyl]-N-methyl-quinoline-4-carboxamide, hydrochloride (compound 2038, 275.8 g 98.1% yield).

As shown in step 9-x of Scheme 9, to a stirring solution of 4-chloro-6-(2-methylpyrimidin-5-yl)pyrimidine (compound 2039, 60 g, 290.4 mmol) and 8-[(1S)-2-amino-1-methylethyl]-N-methyl-quinoline-4-carboxamide, hydrochloride (compound 2038, 82.87 g, 296.2 mmol) in THF (600 mL) was added water (168.0 mL) and then 2M Na$_2$CO$_3$ (aq.) (363 mL, 726.3 mmol). The reaction mixture was stirred at reflux for 16 hours. A precipitate resulted which was solubilized by the addition of 2M HCl. The solution was washed with DCM (3×500 mL) followed by slow addition of 6M NaOH to achieve a pH of 7. The reaction mixture was stirred for 1 hour at RT. The resulting precipitate was collected by filtration and washed with water (4×250 mL) and IPA (4×125 mL). The solid was then dried under high vacuum at 50° C. for 16 hours to produce (S)—N-methyl-8-(1-((2'-methyl-[4,5'-bipyrimidin]-6-yl)amino)propan-2-yl)quinoline-4-carboxamide (compound 578, 102 g, 85% yield) as a light tan solid: LC-MS=414.40 (M+H); $^1$H NMR (300 MHz, DMSO-d$_6$, 70° C.) δ 9.14 (s, 2H), 8.95 (d, J=4.3 Hz, 1H), 8.47 (s, 1H), 8.34 (br. s, 1H), 8.02 (d, J=8.4 Hz, 1H), 7.74 (d, J=7.3 Hz, 1H), 7.59 (t, J=7.8 Hz, 1H), 7.50 (d, J=4.3 Hz, 1H), 7.28 (br. s, 1H), 7.04 (s, 1H), 4.52 (h, J=7.0 Hz, 1H), 3.83-3.66 (m, 2H), 2.88 (d, J=4.4 Hz, 3H), 2.68 (s, 3H), 1.42 (d, J=6.9 Hz, 3H).

Example 10

Preparation of (S)—N-methyl-8-(1-((2'-methyl-4',6'-dideutero-[4,5'-bipyrimidin]-6-yl)amino)propan-2-yl)quinoline-4-carboxamide (Compound 844)

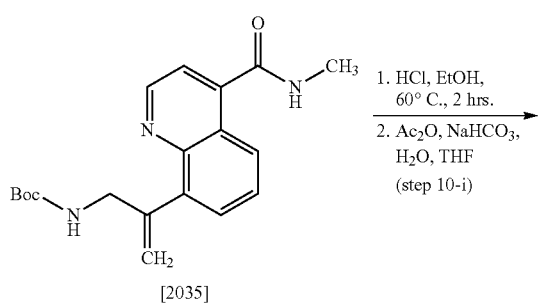

Scheme 10

1. HCl, EtOH, 60° C., 2 hrs.
2. Ac$_2$O, NaHCO$_3$, H$_2$O, THF (step 10-i)

[2035]

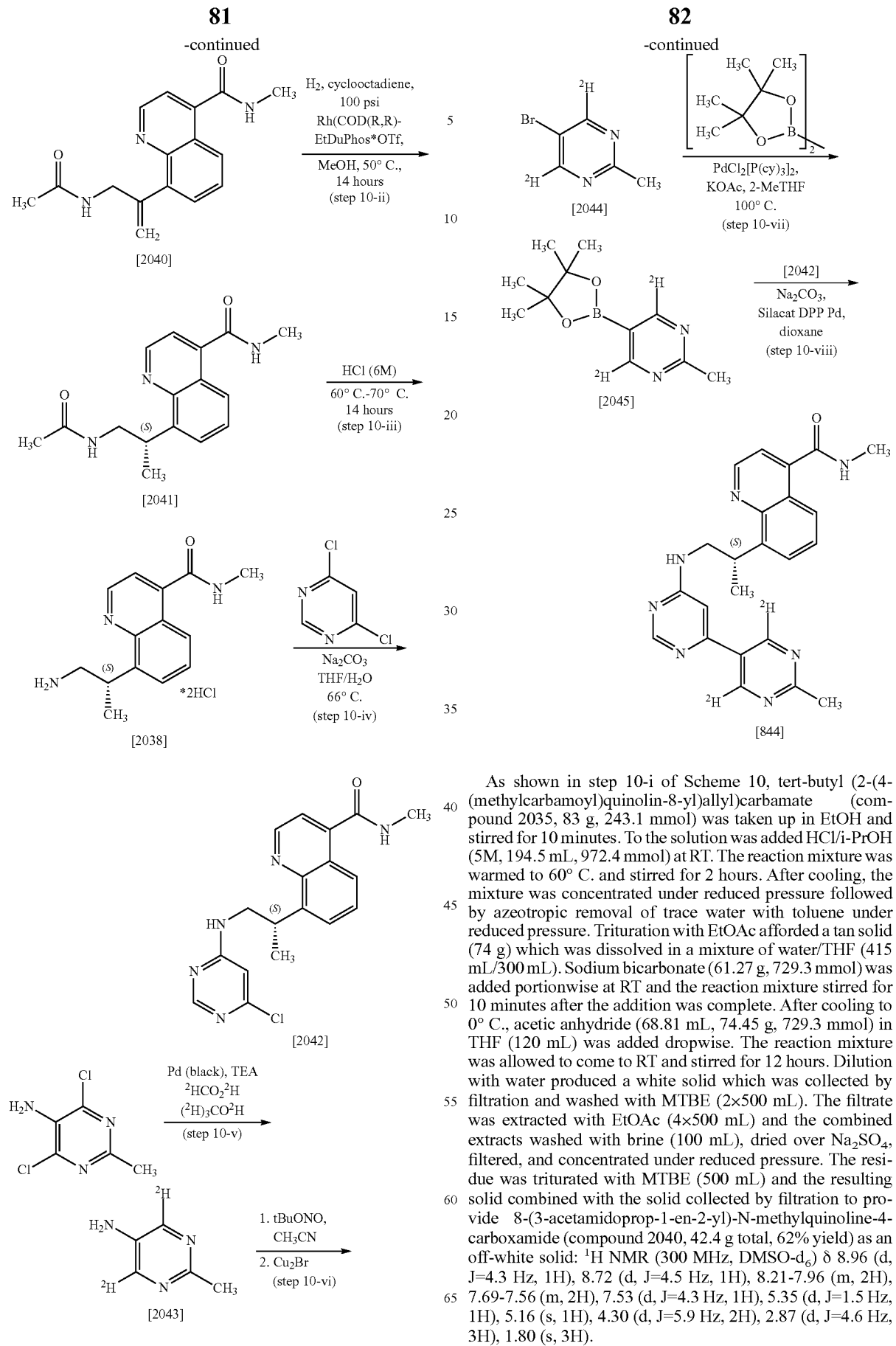

As shown in step 10-i of Scheme 10, tert-butyl (2-(4-(methylcarbamoyl)quinolin-8-yl)allyl)carbamate (compound 2035, 83 g, 243.1 mmol) was taken up in EtOH and stirred for 10 minutes. To the solution was added HCl/i-PrOH (5M, 194.5 mL, 972.4 mmol) at RT. The reaction mixture was warmed to 60° C. and stirred for 2 hours. After cooling, the mixture was concentrated under reduced pressure followed by azeotropic removal of trace water with toluene under reduced pressure. Trituration with EtOAc afforded a tan solid (74 g) which was dissolved in a mixture of water/THF (415 mL/300 mL). Sodium bicarbonate (61.27 g, 729.3 mmol) was added portionwise at RT and the reaction mixture stirred for 10 minutes after the addition was complete. After cooling to 0° C., acetic anhydride (68.81 mL, 74.45 g, 729.3 mmol) in THF (120 mL) was added dropwise. The reaction mixture was allowed to come to RT and stirred for 12 hours. Dilution with water produced a white solid which was collected by filtration and washed with MTBE (2×500 mL). The filtrate was extracted with EtOAc (4×500 mL) and the combined extracts washed with brine (100 mL), dried over Na$_2$SO$_4$, filtered, and concentrated under reduced pressure. The residue was triturated with MTBE (500 mL) and the resulting solid combined with the solid collected by filtration to provide 8-(3-acetamidoprop-1-en-2-yl)-N-methylquinoline-4-carboxamide (compound 2040, 42.4 g total, 62% yield) as an off-white solid: $^1$H NMR (300 MHz, DMSO-d$_6$) δ 8.96 (d, J=4.3 Hz, 1H), 8.72 (d, J=4.5 Hz, 1H), 8.21-7.96 (m, 2H), 7.69-7.56 (m, 2H), 7.53 (d, J=4.3 Hz, 1H), 5.35 (d, J=1.5 Hz, 1H), 5.16 (s, 1H), 4.30 (d, J=5.9 Hz, 2H), 2.87 (d, J=4.6 Hz, 3H), 1.80 (s, 3H).

As shown in step 10-ii of Scheme 10, under an atmosphere of nitrogen 8-(3-acetamidoprop-1-en-2-yl)-N-methylquinoline-4-carboxamide (12.4 g, 43.77 mmol) and cycloocta-1,5-diene/(2R,5R)-1-[2-[(2R,5R)-2,5-diethylphospholan-1-yl]phenyl]-2,5-diethylphospholane: rhodium(+1) cation-trifluoromethanesulfonate (Rh(COD)(R,R)-Et-DuPhos-OTf, 316.3 mg, 0.4377 mmol) in methanol (372.0 mL) were combined and warmed to 35-40° C. until the solids were solubilized. The reaction mixture was placed in a hydrogenation apparatus, the atmosphere replaced with hydrogen, and the mixture agitated under 100 p.s.i. of hydrogen at 50° C. for 14 hours. After cooling to RT, the mixture was filtered through a bed of Florisil®, which was subsequently washed with MeOH (2×50 mL). The filtrate was concentrated under reduced pressure and any trace water removed via a DCM azeotrope under reduced pressure. The residue was triturated with 20% DCM in MTBE (2×100 mL) to afford (S)-8-(1-acetamidopropan-2-yl)-N-methylquinoline-4-carboxamide (compound 2041, 11.0 g, 88% yield, 96% e.e.) as an off-white solid: $^1$H-NMR (300 MHz, DMSO-d$_6$) δ 8.97 (d, J=4.3 Hz, 1H), 8.67 (d, J=4.7 Hz, 1H), 7.97 (dd, J=8.1, 1.5 Hz, 1H), 7.88 (t, J=5.6 Hz, 1H), 7.73-7.54 (m, 2H), 7.52 (d, J=4.3 Hz, 1H), 4.31 (dd, J=14.3, 7.1 Hz, 1H), 3.55-3.32 (m, 3H), 2.86 (d, J=4.6 Hz, 3H), 1.76 (s, 3H), 1.28 (d, J=7.0 Hz, 3H). The enantiomeric excess (e.e.) was determined by chiral HPLC (ChiralPac IC, 0.46 cm×25 cm], flow rate 1.0 mL/min for 20 min at 30° C. (20:30:50 methanol/ethanol/hexanes and 0.1% diethylamine) with a retention time for the (R)-enantiomer of 5.0 min, and for the (S)-enantiomer of 6.7 min.

As shown in step 10-iii of Scheme 10, (S)-8-(1-acetamidopropan-2-yl)-N-methylquinoline-4-carboxamide (11.0 g, 38.55 mmol) in 6M aqueous HCl (192.7 mL, 1.156 mol) was warmed to 60° C. After stirring for 2 days at this temperature, the reaction mixture was cooled and an additional 20 mL of 6M HCl was added. Stirring was continued for an additional 2 days at 70° C. The reaction mixture was cooled with an ice bath and the pH adjusted to about 11 with 6M NaOH (aq). The aqueous mixture was extracted with 5% MeOH/DCM and the combined organic extracts washed with water (60 mL), brine (100 mL), dried over sodium sulfate, filtered, and concentrated under reduced pressure to afford crude product as a tan solid. This solid was suspended in EtOAc (200 mL), cooled to 3° C. with an ice bath, and 6M HCl/i-PrOH (30 mL) was added portionwise to produce a white precipitate which was collected by filtration. The solid was washed with EtOAc (100 mL) and dried under high vacuum to provide (S)-8-(1-aminopropan-2-yl)-N-methylquinoline-4-carboxamide, dihydrochloride [compound 2038, 7.8 g, 61% yield, 95% purity (5% compound 2041)] as a white solid. This material was used as is in subsequent reactions.

As shown in step 10-iv of Scheme 10, 8-[(1S)-2-amino-1-methyl-ethyl]-N-methyl-quinoline-4-carboxamide, hydrochloride (compound 2038, 24.0 g, 72.86 mmol) was taken up in THF (230 mL) and water (40 mL) and stirred for 5 minutes. Sodium carbonate (15.44 g, 145.7 mmol) in 100 mL of water was added and the reaction mixture stirred for 10 minutes. 4,6-Dichloropyrimidine (12.18 g, 80.15 mmol) was added and the reaction mixture heated at reflux at 66° C. for 2 hours. The reaction mixture was cooled to RT, diluted with 200 mL of EtOAc, the organic layer separated, and the aqueous layer extracted with 100 mL EtOAc. The combined organics were washed with water (60 mL), brine (100 mL), dried over Na2SO4, filtered through a bed of silica gel (100 g), and concentrated under reduced pressure. The resulting crude product was triturated with 20% DCM in MBTE (200 mL) then MBTE (200 mL) to produce (S)-8-(1-((6-chloropyrimidin-4-yl)amino)propan-2-yl)-N-methylquinoline-4-carboxamide (compound 2042, 23.15 g, 88% yield) as a white solid: $^1$H NMR (300 MHz, DMSO-d$_6$, 70° C.) δ 8.97 (d, J=4.3 Hz, 1H), 8.38 (s, 1H), 8.20 (s, 1H), 8.03 (d, J=8.5 Hz, 1H), 7.71 (d, J=6.8 Hz, 1H), 7.66-7.55 (m, 1H), 7.52 (d, J=4.2 Hz, 2H), 6.63 (s, 1H), 4.46 (dd, J=14.1, 7.1 Hz, 1H), 3.67 (s, 2H), 2.90 (d, J=4.6 Hz, 3H), 1.40 (d, J=7.0 Hz, 3H); $[α]_D^{24}$=44.77 (c=1.14, MeOH).

As shown in step 10-v of Scheme 10, to a solution of 4,6-dichloro-2-methyl-pyrimidin-5-amine (14.04 g, 78.88 mmol) stirred in methanol-d$_4$ (140.4 mL) was added formic acid-d$_2$ (7.77 g, 161.7 mmol) and Pd black (765 mg, 7.19 mmol, wetted in methanol-d$_4$), followed by triethylamine (16.36 g, 22.53 mL, 161.7 mmol). The reaction mixture was sealed in a tube and stirred at RT overnight. The mixture was then filtered and concentrated under reduced pressure. Et$_2$O (250 mL) was added and the mixture stirred for 1 hour at RT. The resulting solids were filtered and washed with Et$_2$O (×2). The filtrate was concentrated under reduced pressure to yield 4,6-dideutero-2-methyl-pyrimidin-5-amine (compound 2043, 5.65 g, 65% yield) as a light yellow solid: $^1$H NMR (300 MHz, DMSO-d$_6$) δ 5.25 (s, 2H), 2.40 (s, 3H). This compound was used in subsequent steps without further purification.

As shown in step 10-vi of Scheme 10, to 4,6-dideutero-2-methyl-pyrimidin-5-amine (5.35 g, 48.14 mmol) in CH$_3$CN (192.5 mL) was added dibromocopper (16.13 g, 3.38 mL, 72.21 mmol) followed by t-butylnitrite (8.274 g, 9.54 mL, 72.21 mmol). After 1 hour, the reaction was filtered through diatomaceous earth with dichloromethane. The filtrate was washed with water/brine (1:1), the organic layer separated, the aqueous layer extracted with dichloromethane (2×), and the combined organic layers filtered through diatomaceous earth and concentrated under reduced pressure. The crude product was purified by medium pressure silica gel column chromatography (0-10% EtOAc/hexanes) to yield 5-bromo-4,6-dideutero-2-methyl-pyrimidine (compound 2044, 4.1 g, 49% yield): $^1$H NMR (300 MHz, methanol-d$_4$) δ 2.64 (s, 3H).

As shown in step 10-vii of Scheme 10, a mixture of 5-bromo-4,6-dideutero-2-methyl-pyrimidine (8.5 g, 48.57 mmol), bis(pinacolato)diboron (13.57 g, 53.43 mmol), and KOAc (14.30 g, 145.7 mmol) in 2-methyltetrahydrofuran (102.0 mL) was degassed by flushing with nitrogen. To this was added dichloro-bis(tricyclohexylphosphoranyl)-palladium (PdCl$_2$-[P(cy)$_3$]$_2$, 1.01 g, 1.364 mmol) and the reaction mixture stirred in a sealed tube overnight at 100° C. The mixture was filtered and the filtrate stirred with Silabond® DMT silica (SiliCycle, Inc., 0.58 mmol/g, 3.53 g) for 1 hour. The mixture was filtered and concentrated under reduced pressure to yield 2-methyl-4,6-dideutero-5-(4,4,5,5-tetramethyl-1,3,2-dioxaborolan-2-yl)pyrimidine (compound 2045, 13.6 g, 72% purity, the major contaminant being pinacol) as a light yellow oil: $^1$H NMR (300 MHz, CDCl$_3$) δ 2.75 (s, 3H), 1.30 (s, 12H). This compound was used in subsequent steps without further purification.

As shown in step 10-viii of Scheme 10, (S)-8-(1-((6-chloropyrimidin-4-yl)amino)propan-2-yl)-N-methylquinoline-4-carboxamide (2.542 g, 7.146 mmol), 2-methyl-4,6-dideutero-5-(4,4,5,5-tetramethyl-1,3,2-dioxaborolan-2-yl)pyrimidine (2.204 g, 7.146 mmol, 72% by weight), Na$_2$CO$_3$ (10.72 mL of 2 M (aq.), 21.44 mmol), and Silacat® DPP Pd (SiliCycle, Inc., 1.429 g, 0.3573 mmol) were taken up in dioxane (30.00 mL), the solution flushed with nitrogen gas for 5 min, and the reaction mixture stirred at 90° C. for 16 hours. The mixture was filtered through diatomaceous earth, concentrated under reduced pressure, dissolved in DMSO, and purified by reversed-phase chromatography (10-40% CH$_3$CN/H$_2$O, 0.1% TFA). The product fractions were combined and DCM and MeOH were added, followed by the addition of 1N NaOH until a pH of greater than 7 was obtained. The product solution was extracted DCM (2×) and the combined extracts dried over Na$_2$SO$_4$, filtered, and concentrated under reduced pressure to yield (S)—N-methyl-8-

(1-((2'-methyl-4',6'-dideutero-[4,5'-bipyrimidin]-6-yl) amino)propan-2-yl)quinoline-4-carboxamide (Compound 844, 181 mg, 28% yield) as an off-white solid: $^1$H NMR (300 MHz, DMSO-$d_6$, 70° C.) δ 8.95 (d, J=4.2 Hz, 1H), 8.47 (s, 1H), 8.35 (s, 1H), 8.01 (d, J=8.4 Hz, 1H), 7.74 (d, J=7.1 Hz, 1H), 7.59 (t, J=7.8 Hz, 1H), 7.50 (d, J=4.3 Hz, 1H), 7.30 (s, 1H), 7.03 (s, 1H), 4.51 (h, J=7.2 Hz, 1H), 3.78 (m, 2H), 2.88 (d, J=4.6 Hz, 3H), 2.68 (s, 3H), 1.41 (d, J=7.0 Hz, 3H).

Example 11

Preparation of (S)—N-methyl-8-(1-((6-(6-methylpyridin-3-yl)pyrimidin-4-yl)amino)propan-2-yl) quinazoline-4-carboxamide (Compound 971)

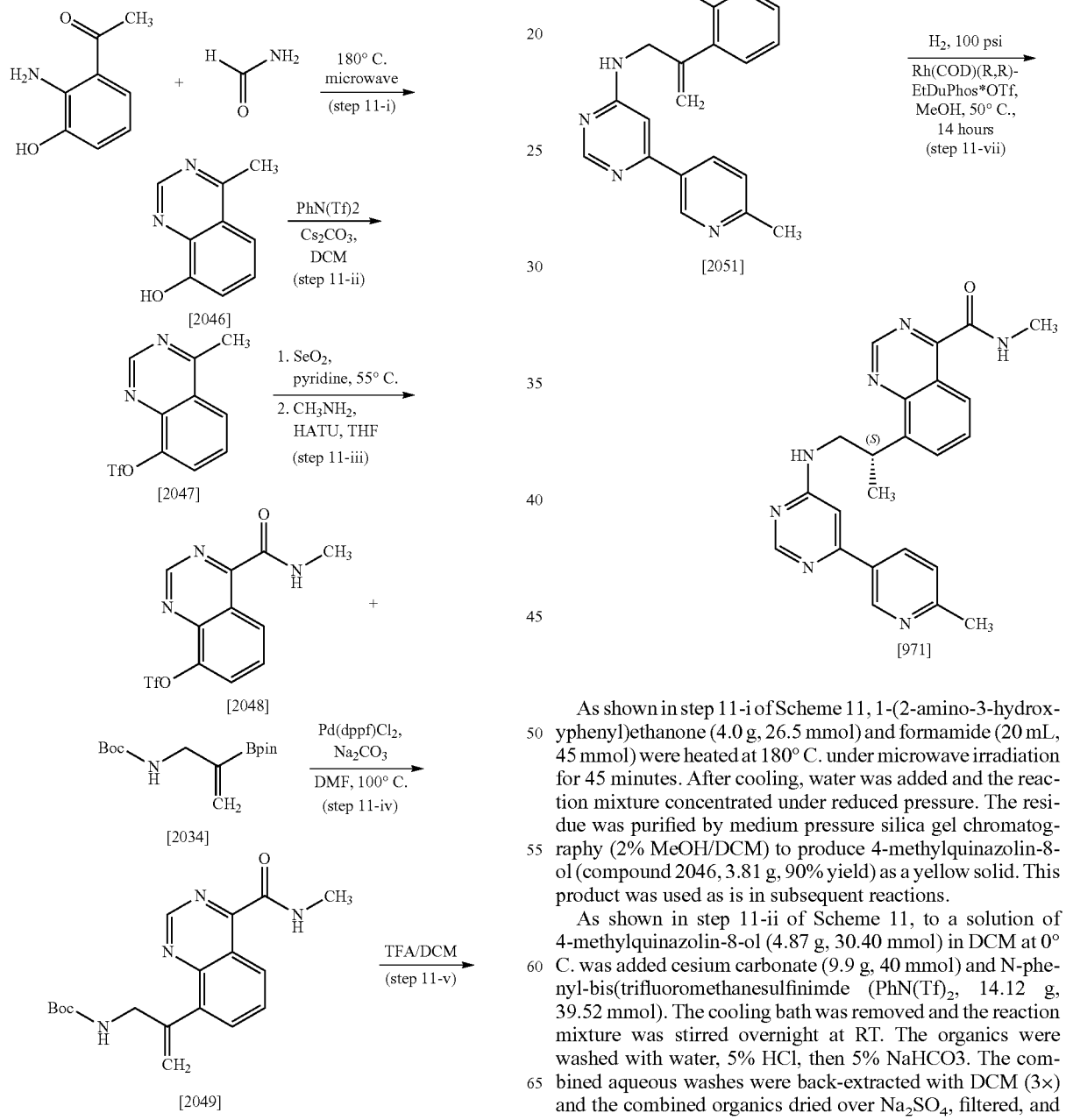

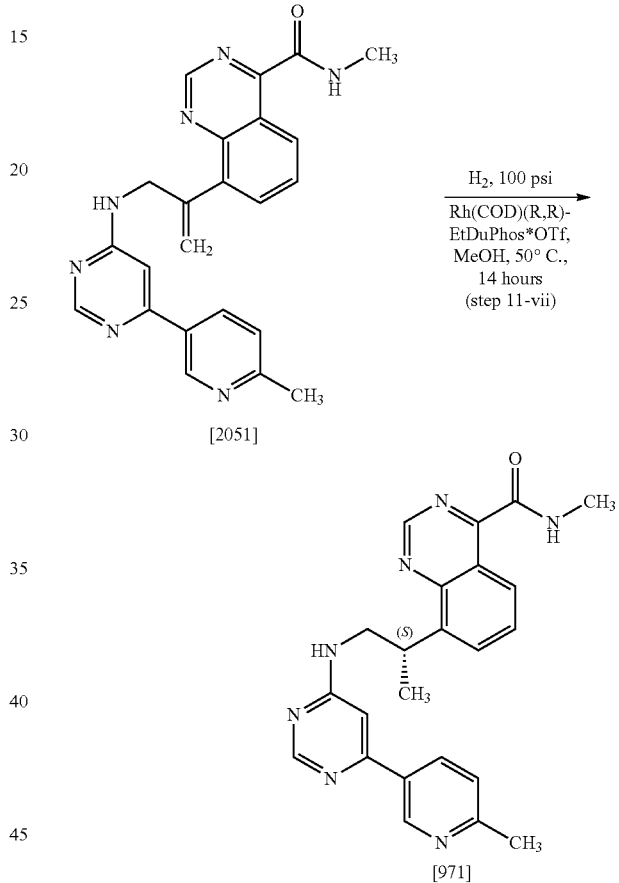

As shown in step 11-i of Scheme 11, 1-(2-amino-3-hydroxyphenyl)ethanone (4.0 g, 26.5 mmol) and formamide (20 mL, 45 mmol) were heated at 180° C. under microwave irradiation for 45 minutes. After cooling, water was added and the reaction mixture concentrated under reduced pressure. The residue was purified by medium pressure silica gel chromatography (2% MeOH/DCM) to produce 4-methylquinazolin-8-ol (compound 2046, 3.81 g, 90% yield) as a yellow solid. This product was used as is in subsequent reactions.

As shown in step 11-ii of Scheme 11, to a solution of 4-methylquinazolin-8-ol (4.87 g, 30.40 mmol) in DCM at 0° C. was added cesium carbonate (9.9 g, 40 mmol) and N-phenyl-bis(trifluoromethanesulfinimde (PhN(Tf)$_2$, 14.12 g, 39.52 mmol). The cooling bath was removed and the reaction mixture was stirred overnight at RT. The organics were washed with water, 5% HCl, then 5% NaHCO3. The combined aqueous washes were back-extracted with DCM (3×) and the combined organics dried over Na$_2$SO$_4$, filtered, and purified by medium pressure silica gel chromatography (0-50% EtOAc/hexanes) to provide 4-methylquinazolin-8-yl trifluoromethanesulfonate (compound 2047, 8.60 g, 93% yield) as a brown solid: $^1$H-NMR (300 MHz, CDCl$_3$) δ 9.33 (s, 1H), 8.17 (dd, J=8.4, 1.3 Hz, 1H), 7.82 (dd, J=7.9, 1.3 Hz), 7.70 (t, J=8.1 Hz), 3.02 (s, 3H); $^{19}$F-NMR (282 MHz, CDCl$_3$) δ −73.5.

As shown in step 11-iii of Scheme 11, 4-methylquinazolin-8-yl trifluoromethanesulfonate (1.19 g, 4.07 mmol) and selenium dioxide (1.0 g, 9.0 mmol) were taken up in 15 mL pyridine and the reaction mixture stirred at 60° C. for 4 hours. The reaction mixture was diluted with 100 mL of THF and 0-(7-azabenzotriazol-1-yl)-N,N,N',N'-tetramethyluronium hexafluorophosphate (HATU, 3.1 g, 8.14 mmol) was added. After stirring at RT for 30 minutes, a 2M methylamine/THF solution (5.0 mL, 10.0 mmol) was added. The reaction mixture was stirred at RT for 1 hour and the volatiles removed under reduced pressure. The residue was taken up in DCM and washed with saturated NH$_4$Cl. The aqueous wash was back-extracted with DCM (2×) and the combined organics dried over Na$_2$SO$_4$, filtered, and concentrated under reduced pressure. The residue was purified by medium pressure silica gel chromatography (0-100% DCM/hexane) to provide 4-(methylcarbamoyl)quinazolin-8-yl trifluoromethanesulfonate (compound 2048, 982 g, 72% yield) as a yellowish solid: LC-MS=335.88 (M+H); $^1$H NMR (300 MHz, CDCl$_3$) δ 9.65 (dd, J=8.6, 1.4 Hz, 1H), 9.47 (s, 1H), 8.27 (s, 1H), 7.89 (dd, J=7.7, 1.3 Hz, 1H), 7.79 (dd, J=8.6, 7.8 Hz, 1H), 3.13 (d, J=5.1 Hz, 3H); $^{19}$F-NMR (282 MHz, CDCl$_3$) δ −73.5.

As shown in step 11-iv of Scheme 11, A nitrogen-flushed solution of tert-butyl N-[2-(4,4,5,5-tetramethyl-1,3,2-dioxaborolan-2-yl)allyl]carbamate (compound 2034, 990 mg, 3.5 mmol), 4-(methylcarbamoyl)quinazolin-8-yl trifluoromethanesulfonate (980 mg, 2.9 mmol) Na$_2$CO$_3$ (3 mL of 2 M (aq), 5.9 mmol) and Pd(dppf)Cl$_2$ (119 mg, 0.14 mmol) in DMF (35 ml) was heated at 100° C. for 3 h. After cooling to RT, the reaction mixture was poured into water and extracted with EtOAc (3×). The extracts were washed with brine (2×). The aqueous phase was re-extracted with EtOAc, and the organic extract washed with brine (2×). The combined organics were dried over Na$_2$SO$_4$, filtered, and concentrated under reduced pressure. The residue was purified by medium pressure silica gel chromatography (EtOAc/hexane 0-50%) to provide tert-butyl (2-(4-(methylcarbamoyl)quinazolin-8-yl)allyl)carbamate (compound 2049, 392 mg, 39% yield) as a yellowish solid. LC-MS=343.13 (M+H); $^1$H NMR (300 MHz, Chloroform-d) δ 9.47 (dd, J=8.6, 1.4 Hz, 1H), 9.30 (s, 1H), 8.31-8.12 (m, 1H), 7.91 ? 7.81 (m, 1H), 7.69 (dd, J=8.7, 7.1 Hz, 1H), 5.57 (s, 1H), 5.31 (s, 1H), 5.02 (d, J=8.1 Hz, 1H), 4.36 (dd, J=5.3, 2.0 Hz, 2H), 3.10 (d, J=5.1 Hz, 3H), 1.37 (s, 9H).

As shown in step 11-v of Scheme 11, a solution of tert-butyl N-[2-[4-(methylcarbamoyl)quinazolin-8-yl]allyl]carbamate (200 mg, 0.58 mmol) in DCM (10 mL) was treated with TFA (2 mL). After stirring for 2 hours at RT, the reaction mixture was concentrated under reduced pressure and dried under high vacuum to provide 8-[1-(aminomethyl)vinyl]-N-methyl-quinazoline-4-carboxamide, trifluoroacetate (compound 2050, 207 mg, 100% yield): LC-MS=243.07 (M+H). This product was used in subsequent reactions as is.

As shown in step 11-vi of Scheme 11, to a suspension of 4-chloro-6-(6-methyl-3-pyridyl)pyrimidine (70 mg, 0.289 mmol), 8-[1-(aminomethyl)vinyl]-N-methyl-quinazoline-4-carboxamide, trifluoroacetate (70 mg, 0.20 mmol) and Na$_2$CO$_3$ (92 mg, 0.86 mmol) was heated at 100° C. for 60 hours. After cooling, the volatiles were removed under reduced pressure, the residue dissolved in DCM, and the organics washed with water. The aqueous phase was back-extracted with DCM (2×) and the combined organics dried over Na$_2$SO$_4$, filtered, and concentrated, and concentrated under reduced pressure. The residue was purified by medium pressure silica gel flash chromatography (0-6% MeOH/DCM) to give to provide N-methyl-8-(3-((6-(6-methylpyridin-3-yl)pyrimidin-4-yl)amino)prop-1-en-2-yl)quinazoline-4-carboxamide (compound 2051, 48 mg, 58% yield): LC-MS=412.09 (M+H); $^1$H NMR (300 MHz, CDCl$_3$) δ 9.46 (dd, J=8.7, 1.5 Hz, 1H), 9.35 (s, 1H), 9.03 (d, J=2.4 Hz, 1H), 8.61 (d, J=1.1 Hz, 1H), 8.39-8.14 (m, 2H), 7.84 (dd, J=7.1, 1.5 Hz, 1H), 7.68 (dd, J=8.7, 7.1 Hz, 1H), 7.27 (d, J=8.1 Hz, 1H), 7.13 (s, 1H), 6.24-5.93 (m, 1H), 5.59 (d, J=1.6 Hz, 1H), 4.64 (d, J=6.3 Hz, 2H), 3.09 (d, J=5.1 Hz, 3H), 2.63 (s, 3H).

As shown in step 11-vii of Scheme 11, N-methyl-8-(3-((6-(6-methylpyridin-3-yl)pyrimidin-4-yl)amino)prop-1-en-2-yl)quinazoline-4-carboxamide (48 mg, 0.12 mmol) in MeOH (2 mL) and Rh(COD)(R,R)-Et-DuPhos-OTf (3 mg) were combined in a glass tube. The reaction mixture was flushed with hydrogen gas then stirred under an atmosphere of 100 psi hydrogen for 24 hours at 60° C. in a stainless steel Parr high pressure reactor. After cooling and replacing the reaction atmosphere with nitrogen, the reaction mixture was filtered through Fluorisil®, the filtrate concentrated under reduced pressure, and the residue purified by medium pressure silica gel chromatography (0-5% MeOH/DCM) to provide (S)—N-methyl-8-(1-((6-(6-methylpyridin-3-yl)pyrimidin-4-yl)amino)propan-2-yl)quinazoline-4-carboxamide (compound 971, 25 mg, 49% yield): LC-MS=414.07 (M+H); $^1$H NMR (400 MHz, methanol-d$_4$) δ 9.29 (s, 1H), 8.86 (br. s, 1H), δ 8.80 (dd, J=8.6, 1.3 Hz, 1H), 8.37 (d, J=1.1 Hz, 1H), 8.14 (s, 1H), 8.04-7.87 (m, 1H), 7.71 (dd, J=8.6, 7.2 Hz, 1H), 7.39 (d, J=8.2 Hz, 1H), 6.71 (br. s, 1H), 4.51 (q, J=7.1 Hz, 1H), 4.10-3.60 (m, 2H), 3.01 (s, 3H), 2.58 (s, 3H), 1.48 (d, J=7.0 Hz, 3H).

Example 12

Preparation of (S)—N-methyl-8-(1-((2'-methyl-4',6'-dideutero-[4,5'-bipyrimidin]-6-yl)amino)propan-2-yl)quinazoline-4-carboxamide (Compound 984)

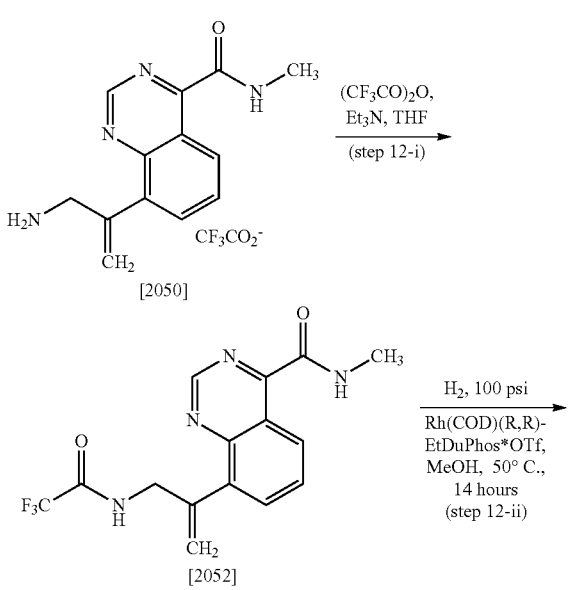

Scheme 12

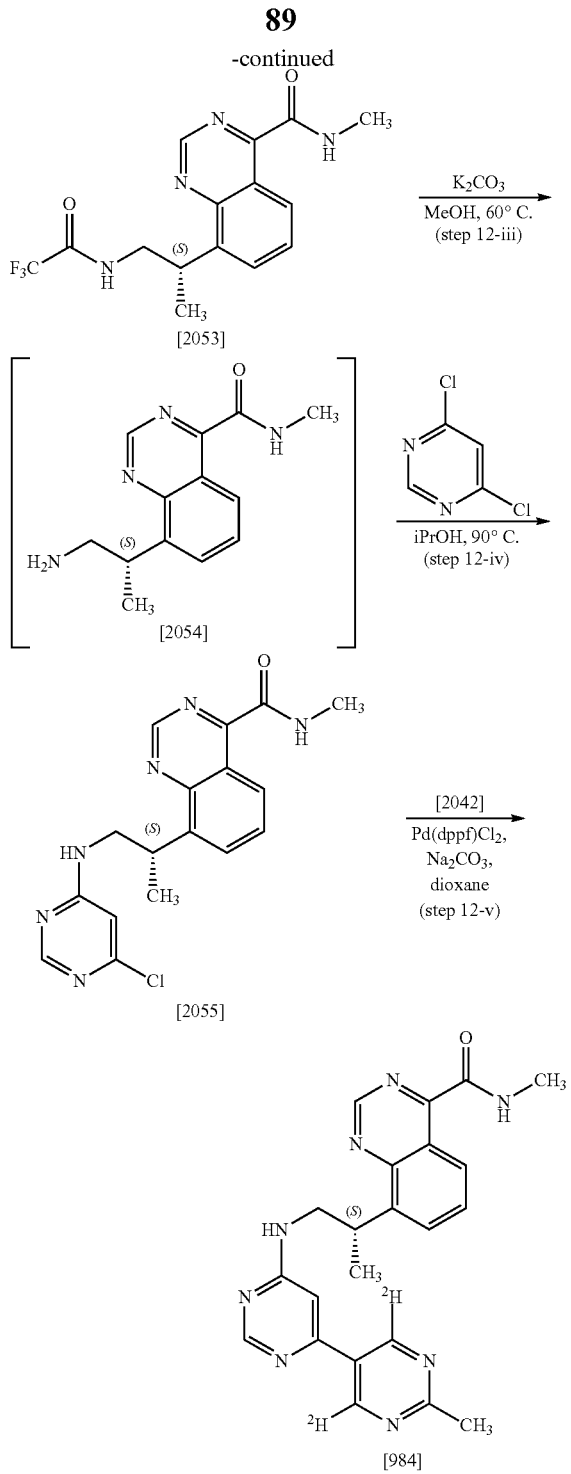

As shown in step 12-i of Scheme 12, 8-[1-(aminomethyl)vinyl]-N-methyl-quinazoline-4-carboxamide, trifluoroacetate (850 mg, 2.39 mmol) was dissolved in THF (30 mL). The solution was treated with Et$_3$N (2.4 mL, 17.5 mmol) and trifluoroacetic anhydride (0.5 mL, 3.8 mmol). The reaction mixture was stirred for 15 hours at RT. The volatiles were removed under reduced pressure and the residue suspended in water, extracted with EtOAc (3×), and the combined organics dried over Na$_2$SO$_4$, filtered, and concentrated under reduced pressure. The residue was purified by medium pressure silica gel chromatography (0-100% EtOAc/hexanes) to provide N-methyl-8-(3-(2,2,2-trifluoroacetamido)prop-1-en-2-yl)quinazoline-4-carboxamide (compound 2052, 783 mg, 97% yield): LC-MS=338.99 (M+H). This material was used in subsequent reactions as is.

As shown in step 12-ii of Scheme 12, N-methyl-8-(3-(2,2,2-trifluoroacetamido)prop-1-en-2-yl)quinazoline-4-carboxamide (700 mg, 2.07 mmol) in MeOH (35 mL) and Rh(COD)(R,R)-Et-DuPhos-OTf (50 mg) were placed in a glass tube. The reaction mixture was flushed with hydrogen gas and stirred under an atmosphere of 100 psi hydrogen for 24 hours at 60° C. in a stainless steel Parr high pressure reactor. After cooling, the reaction atmosphere was flushed with nitrogen. The reaction mixture was filtered through Fluorisil®, the filtrate concentrated under reduced pressure, and the residue purified by medium pressure silica gel chromatography (0-100% EtOAc/hexanes) to provide (S)—N-methyl-8-(1-(2,2,2-trifluoroacetamido)propan-2-yl)quinazoline-4-carboxamide (compound 2053, 317 mg, 45% yield): LC-MS=338.99 (M+H).

As shown in step 12-iii of Scheme 12, a solution of (S)—N-methyl-8-(1-(2,2,2-trifluoroacetamido)propan-2-yl)quinazoline-4-carboxamide (200 mg, 0.588 mmol), K$_2$CO$_3$ (406 mg, 2.94 mmol) in MeOH (10 mL) and water (0.5 mL) was heated at 60° C. for 1 hour. The reaction mixture concentrated under reduced pressure and dried under high vacuum to provide (S)-8-(1-aminopropan-2-yl)-N-methylquinazoline-4-carboxamide (compound 2054). LC-MS: 245.09 (M+), which was used in the following reaction as is.

As shown in step 12-iv of Scheme 12, compound 2054 was suspended in iPrOH (10 mL) and 4,6-dichloropyrimidine (130 mg, 0.80 mmol) was added. The suspension was heated at 90° C. for 1 hour. After cooling, the volatiles were removed under reduced pressure. The residue was dissolved in EtOAc, washed with water, and the aqueous phase back-extracted with EtOAc (2×). The combined organics were dried over Na$_2$SO$_4$, filtered, concentrated under reduced pressure, and purified by medium pressure silica gel chromatography (0-50% EtOAc/hexanes) to provide (S)-8-(1-((6-chloropyrimidin-4-yl)amino)propan-2-yl)-N-methylquinazoline-4-carboxamide (compound 2055, 153 mg, 73% yield): LC-MS=354.97, 357.00 (M+H); $^1$H NMR (300 MHz, CDCl$_3$) δ 9.55-9.16 (m, 2H), 8.27-8.07 (m, 2H), 7.87-7.70 (m, 1H), 7.61 (ddd, J=8.7, 7.2, 3.8 Hz, 1H), 4.35 (q, J=7.0 Hz, 1H), 3.49 (m, 1H), 3.02 (dd, J=5.1, 1.7 Hz, 3H), 1.42 (d, J=7.0 Hz, 3H).

As shown in step 12-v of Scheme 12, a mixture of (S)-8-(1-((6-chloropyrimidin-4-yl)amino)propan-2-yl)-N-methylquinazoline-4-carboxamide (60 mg, 0.27 mmol), 2-methyl-4,6-dideuterium-5-(4,4,5,5-tetramethyl-1,3,2-dioxaborolan-2-yl)pyrimidine (compound 2042, 96 mg, 0.27 mmol), 2M Na$_2$CO$_3$ (aq) (0.3 mL), and Pd(dppf)Cl$_2$ (8 mg) in dioxane (5 mL) were heated under microwave irradiation at 110° C. for 1 hour. The volatiles were removed under reduced pressure and the residue suspended in water and extracted with EtOAc (3×). The combined organics were dried over Na$_2$SO$_4$, filtered, concentrated under reduced pressure, and the residue purified by medium pressure silica gel chromatography (0-100% EtOAc/hexanes) to provide (S)—N-methyl-8-(1-((2'-methyl-4',6'-dideutero-[4,5'-bipyrimidin]-6-yl)amino)propan-2-yl)quinazoline-4-carboxamide (Compound 984, 85 mg, 71%): LC-MS=417.13 (M+H); $^1$H NMR (300 MHz, methanol-d$_4$) δ 9.30 (s, 1H), 8.80 (dd, J=8.5, 1.3 Hz, 1H), 8.40 (d, J=1.2 Hz, 1H), 7.98 (d, J=7.2 Hz, 1H), 7.71 (dd, J=8.6, 7.3 Hz, 1H), 6.77 (s, 1H), 4.52 (q, J=7.1 Hz, 1H), 3.95-3.76 (m, 2H), 3.01 (s, 3H), 2.74 (s, 3H), 1.49 (d, J=7.0 Hz, 3H).

Tables 1 and 2 provide structures and analytical characterization data for compounds of the invention (blank cells indicate that the test was not performed).

TABLE 1

| Cmpnd No. | Structure | ESMS (M + H) | ¹H NMR (300 MHz, unless indicated otherwise) NMR peaks given as δ values |
|---|---|---|---|
| 1 | 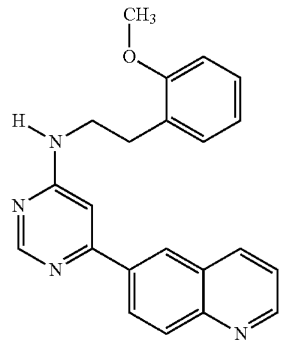 [SMILES: COc1ccccc1CCNc1cc(-c2ccc3ncccc3c2)ncn1] | 357.53 | (DMSO-d₆) δ 8.95 (dd, J = 1.6, 4.2 Hz, 1H), 8.67 (s, 1H), 8.56-8.50 (m, 2H), 8.34 (s, 1H), 8.12 (d, J = 8.9 Hz, 1H), 7.59 (m, 2H), 7.21 (t, J = 7.5 Hz, 2H), 7.09 (s, 1H), 6.98 (d, J = 8.0 Hz, 1H), 6.91-6.86 (m, 1H), 3.80 (s, 3H), 3.56 (s, 2H) and 2.90-2.85 (m, 2H) |
| 2 | 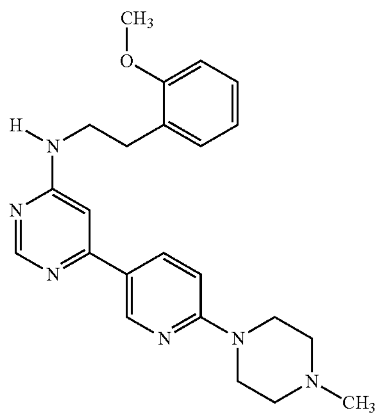 | 405.64 | (CDCl₃) δ 8.75 (d, J = 2.3 Hz, 1H), 8.56 (s, 1H), 8.13 (dd, J = 9.0, 2.5 Hz, 1H), 7.26-7.11 (m, 2H), 6.90 (m, 2H), 6.69 (d, J = 9.0 Hz, 1H), 6.59 (s, 1H), 3.87 (s, 3H), 3.66 (dd, J = 11.7, 6.5 Hz, 4H), 3.58 (dd, J = 12.4, 6.3 Hz, 2H), 2.97 (t, J = 6.9 Hz, 2H), 2.53 (dd, J = 12.1, 6.9 Hz, 4H), 2.35 (s, 3H) |
| 3 | 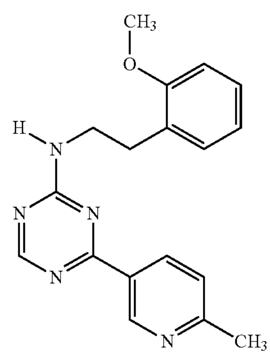 [SMILES: COc1ccccc1CCNc1ncnc(-c2ccc(C)nc2)n1] | 322.1 | (400 MHz, DMSO-d₆) δ 9.31 (s, 1H), 8.52-8.44 (m, 2H), 7.85 (s, 1H), 7.36 (d, J = 7.6 Hz; 1H), 7.16-7.14 (m, 2H), 6.93 (d, J = 8 Hz; 1H), 6.84 (t, J = 7.6 Hz; 1H), 3.80 (s, 3H), 3.62-3.61 (m, 2H), 2.90 (t, J = 6 Hz; 2H), 2.55 (s, 3H) |
| 4 | 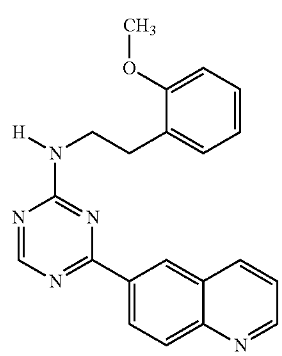 [SMILES: COc1ccccc1CCNc1ncnc(-c2ccc3ncccc3c2)n1] | 358.1 | (400 MHz, DMSO-d₆) δ 8.96-8.95 (m, 2H), 8.63-8.62 (m, 2H), 8.48 (d, J = 8.4 Hz; 1H), 8.11 (d, J = 9.2 Hz; 1H), 7.87 (bs, 1H), 7.58-7.55 (m, 1H), 7.20-7.14 (m, 2H), 6.94 (d, J = 8.4 Hz, 1H), 6.86 (t, J = 7.2 Hz; 1H), 3.81 (s, 3H), 3.68-3.67 (m, 2H), 2.95-2.94 (m, 2H) |

TABLE 1-continued

| Cmpnd No. | Structure | ESMS (M + H) | ¹H NMR (300 MHz, unless indicated otherwise) NMR peaks given as δ values |
|---|---|---|---|
| 5 | 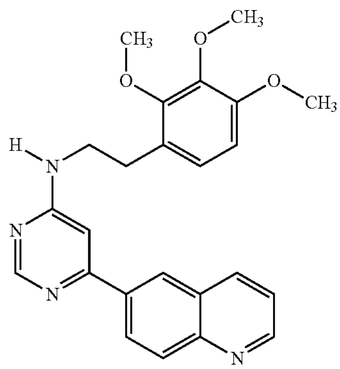 [SMILES: COc1ccc(CCNc2cc(-c3ccc4ncccc4c3)ncn2)c(OC)c1OC] | 417.1 | (CDCl₃, 400 MHz) δ 8.96 (dd, J = 4.4, 1.6 Hz; 1H), 8.68 (s, 1H), 8.54 (s, 1H), 8.28-8.17 (m, 3H), 7.47-7.44 (m, 1H), 6.89-6.84 (m, 2H), 6.65-6.63 (m, 1H), 5.48 (bs, exchanged with D2O, 1H), 3.95 (s, 3H), 3.89 (s, 3H), 3.84 (s, 3H), 3.61 (bs, 2H), 2.93 (t, 2H) |
| 6 | 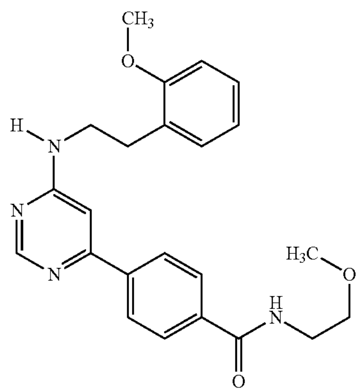 [SMILES: COCCNC(=O)c1ccc(-c2cc(NCCc3ccccc3OC)ncn2)cc1] | | |
| 7 | 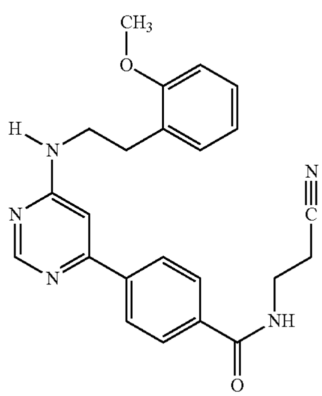 [SMILES: COc1ccccc1CCNc1cc(-c2ccc(C(=O)NCCC#N)cc2)ncn1] | | |
| 8 | 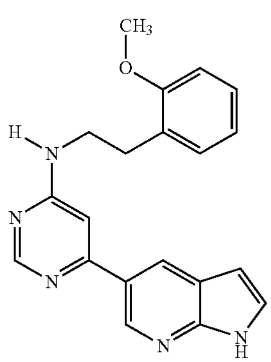 [SMILES: COc1ccccc1CCNc1cc(-c2cnc3[nH]ccc3c2)ncn1] | | |

TABLE 1-continued

| Cmpnd No. | Structure | ESMS (M + H) | ¹H NMR (300 MHz, unless indicated otherwise) NMR peaks given as δ values |
|---|---|---|---|
| 9 | 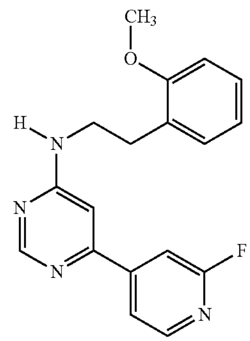 [SMILES: COc1ccccc1CCNc1cc(-c2ccnc(F)c2)ncn1] | | |
| 10 | 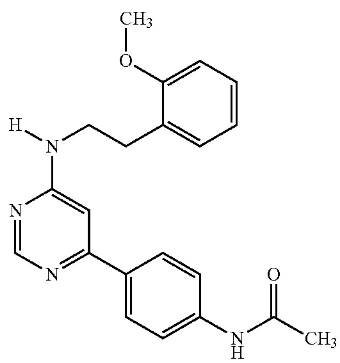 [SMILES: COc1ccccc1CCNc1cc(-c2ccc(NC(C)=O)cc2)ncn1] | | |
| 11 | 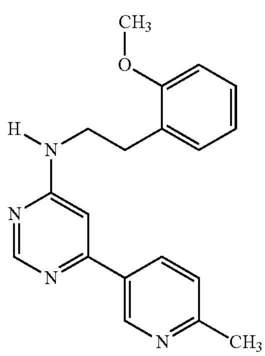 [SMILES: COc1ccccc1CCNc1cc(-c2ccc(C)nc2)ncn1] | | |
| 12 | 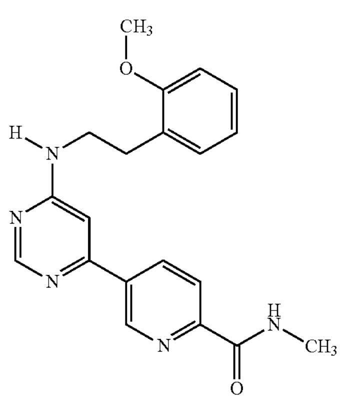 [SMILES: CNC(=O)c1ccc(-c2cc(NCCc3ccccc3OC)ncn2)cn1] | | |

TABLE 1-continued
| Cmpnd No. | Structure | ESMS (M + H) | $^1$H NMR (300 MHz, unless indicated otherwise) NMR peaks given as δ values |
|---|---|---|---|
| 13 | 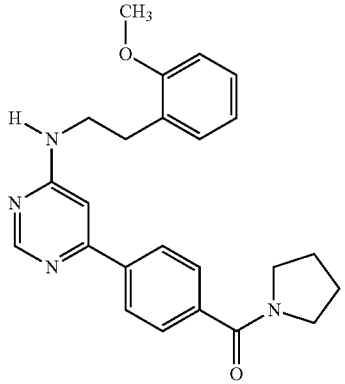 [SMILES: COc1ccccc1CCNc1cc(-c2ccc(C(=O)N3CCCC3)cc2)ncn1] | | |
| 14 | 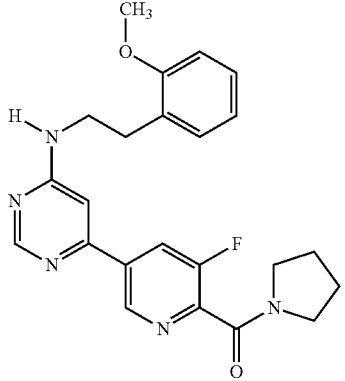 [SMILES: COc1ccccc1CCNc1cc(-c2cnc(C(=O)N3CCCC3)c(F)c2)ncn1] | | |
| 15 | 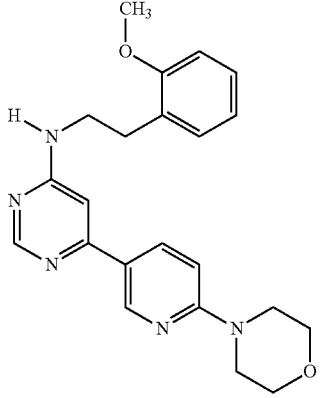 [SMILES: COc1ccccc1CCNc1cc(-c2ccc(N3CCOCC3)nc2)ncn1] | | |

TABLE 1-continued

| Cmpnd No. | Structure | ESMS (M + H) | ¹H NMR (300 MHz, unless indicated otherwise) NMR peaks given as δ values |
|---|---|---|---|
| 16 | 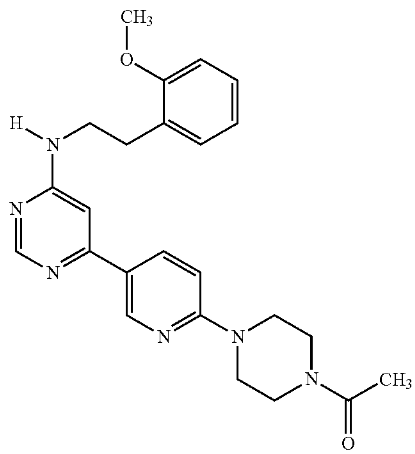 [SMILES: COc1ccccc1CCNc1cc(-c2ccc(N3CCN(C(C)=O)CC3)nc2)ncn1] | | |
| 17 | 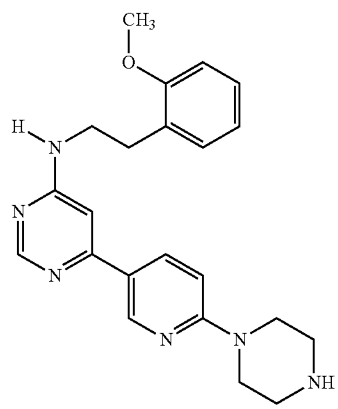 [SMILES: COc1ccccc1CCNc1cc(-c2ccc(N3CCNCC3)nc2)ncn1] | | |
| 18 | 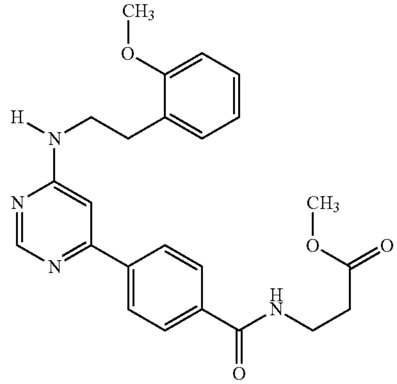 [SMILES: COC(=O)CCNC(=O)c1ccc(-c2cc(NCCc3ccccc3OC)ncn2)cc1] | | |

TABLE 1-continued
| Cmpnd No. | Structure | ESMS (M + H) | ¹H NMR (300 MHz, unless indicated otherwise) NMR peaks given as δ values |
|---|---|---|---|
| 19 | 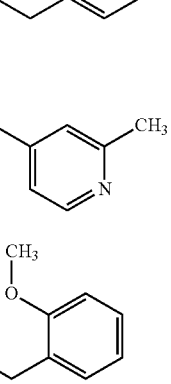 | | |
| 20 | 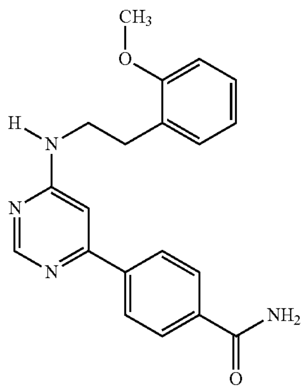 [SMILES: COc1ccccc1CCNc1cc(-c2ccc(C(N)=O)cc2)ncn1] | | |
| 21 | 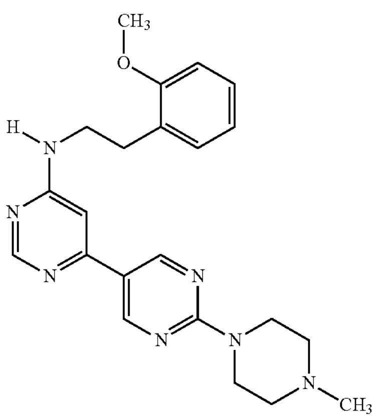 [SMILES: COc1ccccc1CCNc1cc(-c2cnc(N3CCN(C)CC3)nc2)ncn1] | | |
| 22 | 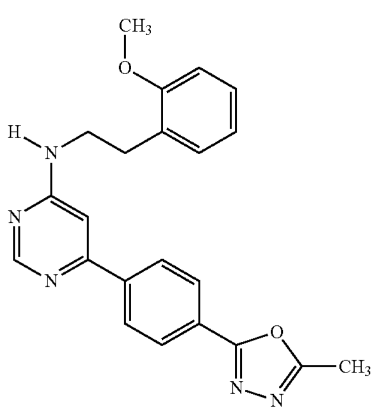 [SMILES: COc1ccccc1CCNc1cc(-c2ccc(-c3nnc(C)o3)cc2)ncn1] | | |

TABLE 1-continued
| Cmpnd No. | Structure | ESMS (M + H) | ¹H NMR (300 MHz, unless indicated otherwise) NMR peaks given as δ values |
|---|---|---|---|
| 23 | 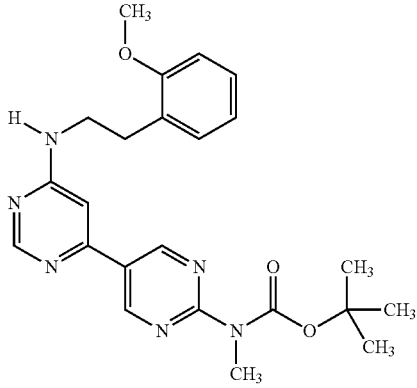 [SMILES: COc1ccccc1CCNc1cc(-c2cnc(N(C)C(=O)OC(C)(C)C)nc2)ncn1] | | |
| 24 | 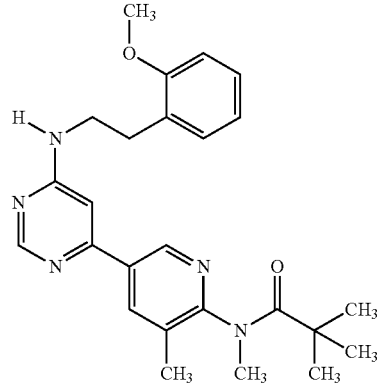 [SMILES: COc1ccccc1CCNc1cc(-c2cnc(N(C)C(=O)C(C)(C)C)c(C)c2)ncn1] | | |
| 25 | 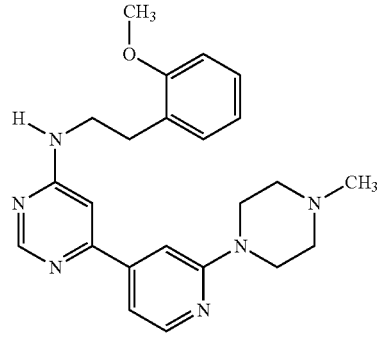 [SMILES: COc1ccccc1CCNc1cc(-c2ccnc(N3CCN(C)CC3)c2)ncn1] | | |
| 26 | 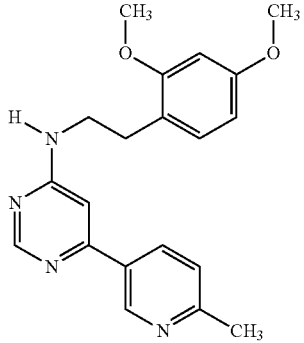 [SMILES: COc1ccc(CCNc2cc(-c3ccc(C)nc3)ncn2)c(OC)c1] | | |

| Cmpnd No. | Structure | ESMS (M + H) | ¹H NMR (300 MHz, unless indicated otherwise) NMR peaks given as δ values |
|---|---|---|---|
| 27 | 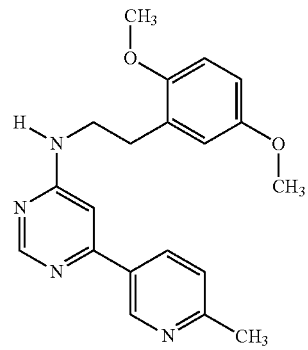 [SMILES: COc1ccc(OC)c(CCNc2cc(-c3ccc(C)nc3)ncn2)c1] | | |
| 28 | 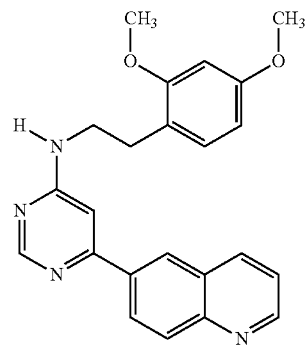 [SMILES: COc1ccc(CCNc2cc(-c3ccc4ncccc4c3)ncn2)c(OC)c1] | | |
| 29 | 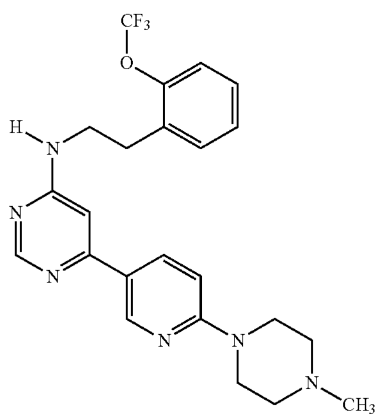 [SMILES: CN1CCN(c2ccc(-c3cc(NCCc4ccccc4OC(F)(F)F)ncn3)cn2)CC1] | 459.31 | (CDCl₃) δ 8.75 (d, J = 2.3 Hz, 1H), 8.58 (s, 1H), 8.12 (dd, J = 9.0, 2.5 Hz, 1H), 7.34-7.19 (m, 4H), 6.69 (d, J = 9.0 Hz, 1H), 6.57 (d, J = 0.9 Hz, 1H), 3.66 (m, 6H), 3.09-2.95 (t, 2H), 2.53 (m, 4H), 2.35 (s, 3H) |
| 30 | 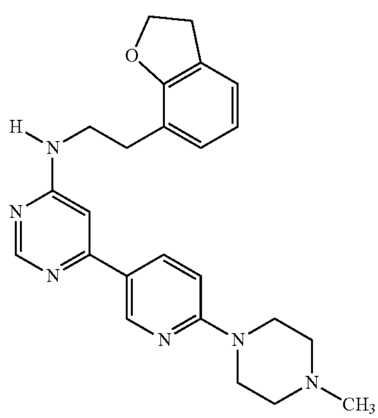 [SMILES: CN1CCN(c2ccc(-c3cc(NCCc4cccc5c4OCC5)ncn3)cn2)CC1] | 417.35 | (CDCl₃) δ 8.77 (d, J = 2.3 Hz, 1H), 8.56 (s, 1H), 8.15 (dd, J = 9.0, 2.5 Hz, 1H), 7.09 (d, J = 6.5 Hz, 1H), 6.96 (d, J = 7.4 Hz, 1H), 6.80 (t, J = 7.4 Hz, 1H), 6.74-6.60 (m, 2H), 4.61 (t, J = 8.7 Hz, 2H), 3.76-3.51 (m, 6H), 3.23 (t, J = 8.7 Hz, 2H), 2.92 (t, J = 6.9 Hz, 2H), 2.59-2.46 (m, 4H), 2.35 (s, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 31 | 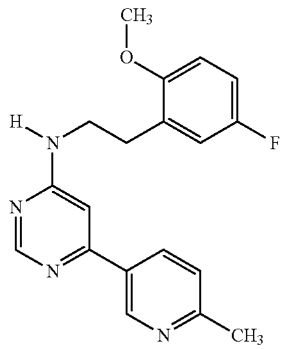 [SMILES: COc1ccc(F)cc1CCNc1cc(-c2ccc(C)nc2)ncn1] | 339.46 | (DMSO-$d_6$) δ 9.00 (s, 1H), 8.77 (m, 2H), 8.35 (d, 1H), 7.65 (d, J = 8.2 Hz, 1H), 7.24-6.93 (m, 4H), 3.77 (s, 3H), 3.68 (m, 2H), 2.90 (t, 2H), 2.63 (s, 3H) |
| 32 | 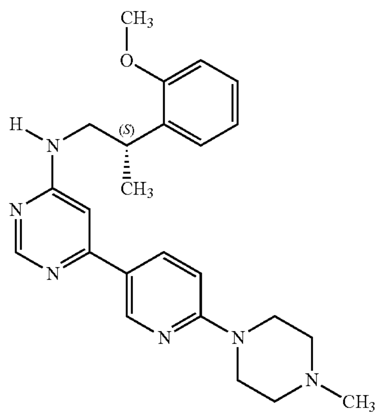 | 419.34 | (CDCl$_3$) δ 8.75 (d, J = 2.2 Hz, 1H), 8.53 (s, 1H), 8.12 (dd, J = 9.0, 2.5 Hz, 1H), 7.25-7.15 (m, 2H), 6.95 (td, J = 7.5, 1.0 Hz, 1H), 6.91-6.83 (m, 1H), 6.67 (d, 1H), 6.58 (s, 1H), 5.28 (s, 1H), 3.84 (s, 3H), 3.71-3.62 (m, 4H), 3.62-3.43 (m, 3H), 2.53 (m, 4H), 2.34 (s, 3H), 1.33 (d, J = 6.6 Hz, 3H) |
| 33 | 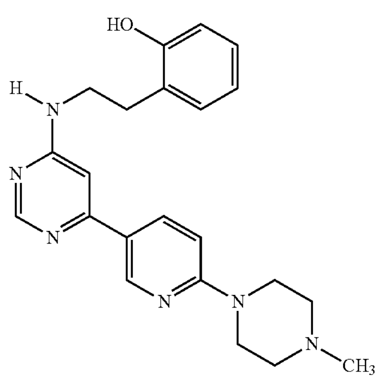 [SMILES: CN1CCN(c2ccc(-c3cc(NCCc4ccccc4O)ncn3)cn2)CC1] | 391.34 | (methanol-$d_4$) δ 8.64 (dd, J = 9.8, 2.5 Hz, 1H), 8.58 (s, 2/3H), 8.45 (s, 1/3H), 8.04-7.94 (m, 1H), 7.14-6.97 (m, 3H), 6.96 (s, 1/3H), 6.83 (s, 2/3H), 6.75 (m, 2H), 4.56 (m, 2H), 3.97 (m, 2H), 3.91-3.50 (m, 6H), 3.01-2.94 (m, 2H), 2.03 (s, 3H). |
| 34 | 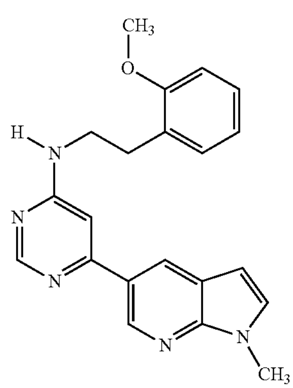 [SMILES: COc1ccccc1CCNc1cc(-c2cnc3c(ccn3C)c2)ncn1] | 360.46 | |

TABLE 1-continued

| Cmpnd No. | Structure | ESMS (M + H) | ¹H NMR (300 MHz, unless indicated otherwise) NMR peaks given as δ values |
|---|---|---|---|
| 35 | 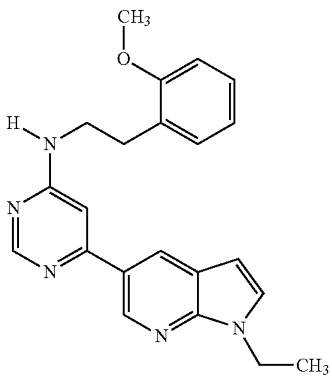 [SMILES: CCn1ccc2cc(-c3cc(NCCc4ccccc4OC)ncn3)cnc21] | 374.49 | |
| 36 | 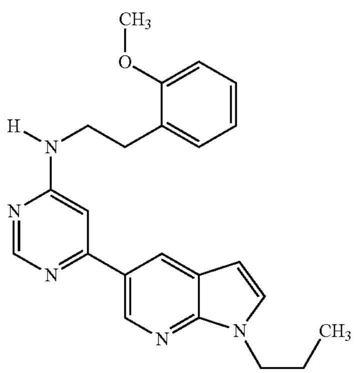 [SMILES: CCCn1ccc2cc(-c3cc(NCCc4ccccc4OC)ncn3)cnc21] | 388.53 | |
| 37 | 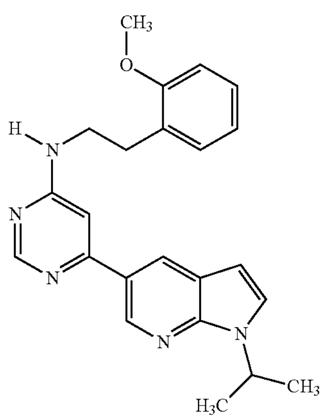 [SMILES: COc1ccccc1CCNc1cc(-c2cnc3c(ccn3C(C)C)c2)ncn1] | 388.49 | |
| 38 | 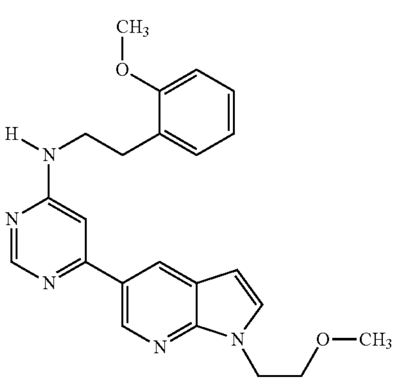 [SMILES: COCCn1ccc2cc(-c3cc(NCCc4ccccc4OC)ncn3)cnc21] | 404.55 | |

TABLE 1-continued
| Cmpnd No. | Structure | ESMS (M + H) | ¹H NMR (300 MHz, unless indicated otherwise) NMR peaks given as δ values |
|---|---|---|---|
| 39 | 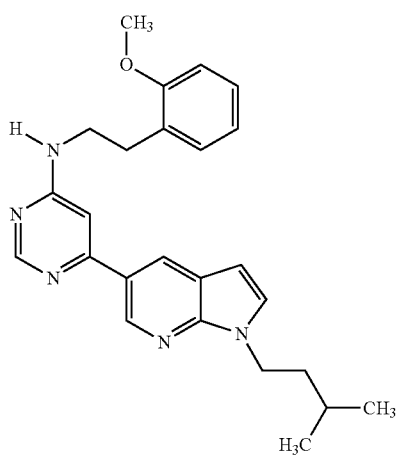 [SMILES: COc1ccccc1CCNc1cc(-c2cnc3c(ccn3CCC(C)C)c2)ncn1] | 416.61 | (CDCl₃) δ 8.89 (s, 1H), 8.57 (d, 1H), 8.48 (s, 1H), 7.32 (d, 1H), 7.18 (s, 2H), 7.00 ¿ 6.86 (m, 3H), 6.60 (d, 1H), 4.36 (s, 2H), 3.91 (s, 3H), 3.65 (s, 2H), 3.04 (d, 2H), 1.78 (dd, 6.9 Hz, 2H), 1.66 ¿ 1.51 (m, 1H), 0.99 (s, 3H), 0.97 (s, 3H) |
| 40 | 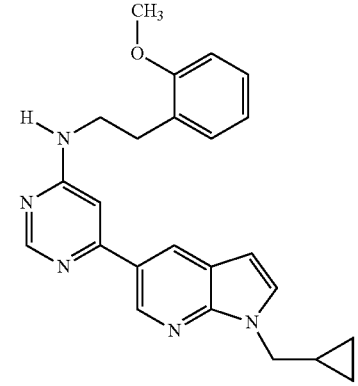 [SMILES: COc1ccccc1CCNc1cc(-c2cnc3c(ccn3CC3CC3)c2)ncn1] | 400.56 | |
| 41 | 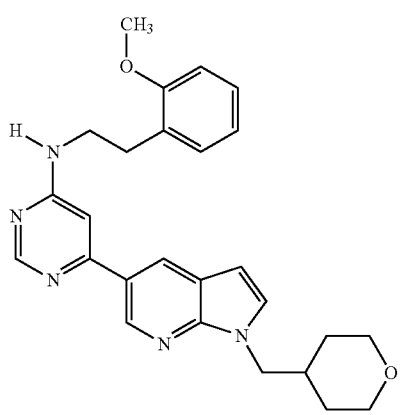 [SMILES: COc1ccccc1CCNc1cc(-c2cnc3c(ccn3CC3CCOCC3)c2)ncn1] | 444.69 | |

TABLE 1-continued

| Cmpnd No. | Structure | ESMS (M + H) | ¹H NMR (300 MHz, unless indicated otherwise) NMR peaks given as δ values |
|---|---|---|---|
| 42 | 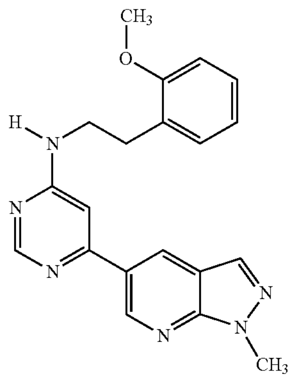 [SMILES: COc1ccccc1CCNc1cc(-c2cnc3c(cnn3C)c2)ncn1] | 361.46 | |
| 43 | 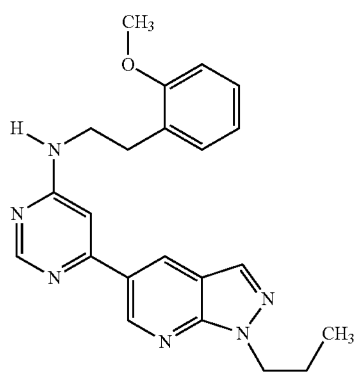 [SMILES: CCCn1ncc2cc(-c3cc(NCCc4ccccc4OC)ncn3)cnc21] | 390.04 | |
| 44 | 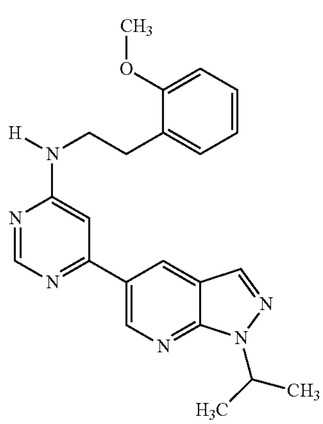 [SMILES: COc1ccccc1CCNc1cc(-c2cnc3c(cnn3C(C)C)c2)ncn1] | 389.74 | |

TABLE 1-continued
| Cmpnd No. | Structure | ESMS (M + H) | ¹H NMR (300 MHz, unless indicated otherwise) NMR peaks given as δ values |
|---|---|---|---|
| 45 | 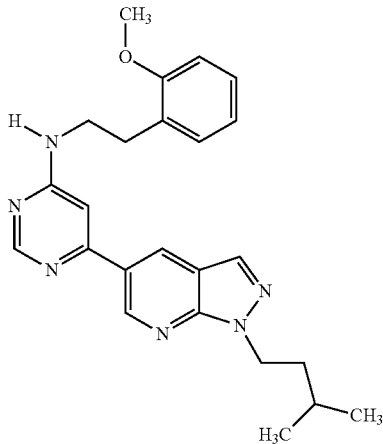 [SMILES: COc1ccccc1CCNc1cc(-c2cnc3c(cnn3CCC(C)C)c2)ncn1] | 417.58 | (CDCl₃) δ 9.05 (s, 1H), 8.76 (s, 1H), 8.48 (s, 1H), 8.15 (s, 1H), 7.20 (d, 2H), 6.99 ¿ 6.86 (m, 3H), 4.60 (t, 2H), 3.92 (s, 3H), 3.67 (s, 2H), 3.06 (s, 2H), 1.89 (d, 2H), 1.58 (s, 1H), 0.99 (d, 6H) |
| 46 | 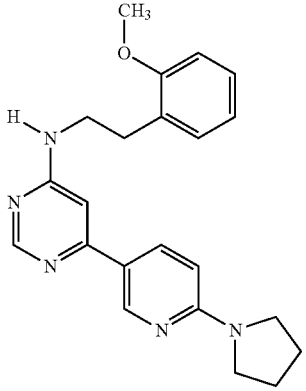 [SMILES: COc1ccccc1CCNc1cc(-c2ccc(N3CCCC3)nc2)ncn1] | 375.75 | (DMSO-d₆) δ 8.74 (s, 1H), 8.40 (s, 1H), 8.06 (d, J = 8.3 Hz, 1H), 7.33-7.12 (m, 3H), 6.97 (d, J = 8.1 Hz, 1H), 6.88 (t, J = 7.4 Hz, 1H), 6.76 (s, 1H), 6.52 (d, J = 8.9 Hz, 1H), 3.80 (s, 3H), 3.44 (m, 6H), 2.83 (t, J = 7.4 Hz, 2H), 1.96 (m, 4H) |
| 47 | 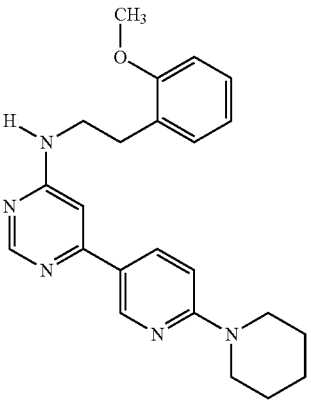 [SMILES: COc1ccccc1CCNc1cc(-c2ccc(N3CCCCC3)nc2)ncn1] | 390.52 | (DMSO-d₆) δ 8.74 (s, 1H), 8.41 (s, 1H), 8.06 (d, J = 8.2 Hz, 1H), 7.35-7.11 (m, 3H), 6.97 (d, J = 7.8 Hz, 1H), 6.93-6.82 (m, 2H), 6.77 (s, 1H), 3.80 (s, 3H), 3.70-3.36 (m, 6H), 2.90-2.76 (m, 2H), 1.59 (dd, J = 23.2, 4.3 Hz, 6H) |

TABLE 1-continued

| Cmpnd No. | Structure | ESMS (M + H) | ¹H NMR (300 MHz, unless indicated otherwise) NMR peaks given as δ values |
|---|---|---|---|
| 48 | 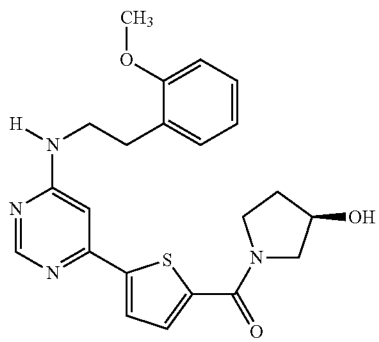 [SMILES: COc1ccccc1CCNc1cc(-c2ccc(C(=O)N3CC[C@@H](O)C3)s2)ncn1] | 426.02 | |
| 49 | 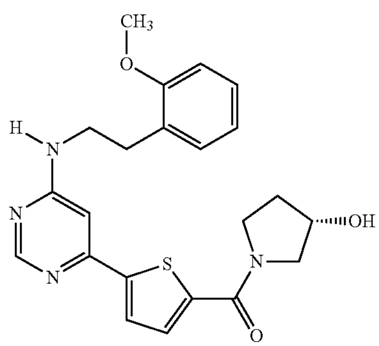 [SMILES: COc1ccccc1CCNc1cc(-c2ccc(C(=O)N3CC[C@H](O)C3)s2)ncn1] | 426.25 | |
| 50 | 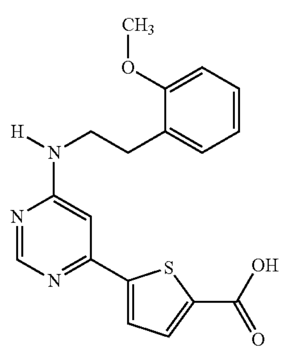 [SMILES: COc1ccccc1CCNc1cc(-c2ccc(C(=O)O)s2)ncn1] | | |
| 51 | 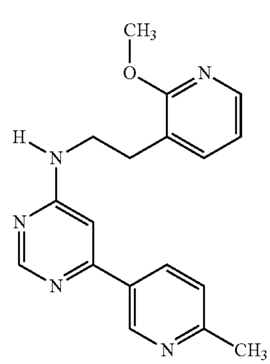 | 322.1 | (CDCl₃) δ 9.02 (d, J = 2.0 Hz, 1H), 8.64 (s, 1H), 8.20 (dd, J = 8.0, 2.3 Hz, 1H), 8.08 (dd, J = 5.0, 1.6 Hz, 1H), 7.50-7.38 (m, 2H), 6.85 (dd, J = 7.0, 5.1 Hz, 1H), 6.70 (s, 1H), 4.01 (s, 3H), 3.66 (m, 2H), 2.94 (t, J = 6.9 Hz, 2H), 2.60 (s, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 52 | 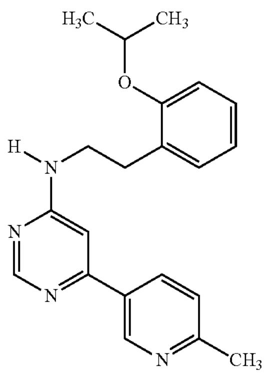 [SMILES: Cc1ccc(-c2cc(NCCc3ccccc3OC(C)C)ncn2)cn1] | 349.06 | (CDCl₃) δ 10.25 (s, 1H), 9.09 (s, 1H), 8.80-8.65 (m, 1H), 8.47 (s, 1H), 7.70 (d, J = 8.2 Hz, 1H), 7.23-7.04 (m, 2H), 6.81 (m, 3H), 4.61 (m, 1H), 3.94-3.70 (m, 2H), 3.04 (m, 2H), 2.90 (s, 3H), 1.35 (d, J = 5.9 Hz, 6H) |
| 53 | 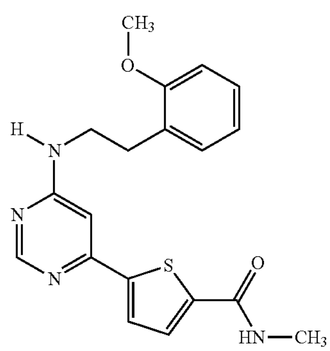 [SMILES: CNC(=O)c1ccc(-c2cc(NCCc3ccccc3OC)ncn2)s1] | 370.22 | |
| 54 | 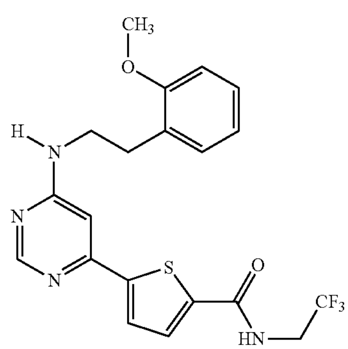 [SMILES: COc1ccccc1CCNc1cc(-c2ccc(C(=O)NCC(F)(F)F)s2)ncn1] | 437.73 | |
| 55 | 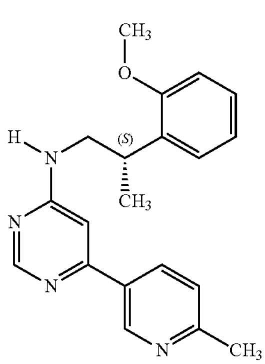 | 335.12 | |

TABLE 1-continued

| Cmpnd No. | Structure | ESMS (M + H) | ¹H NMR (300 MHz, unless indicated otherwise) NMR peaks given as δ values |
|---|---|---|---|
| 56 | 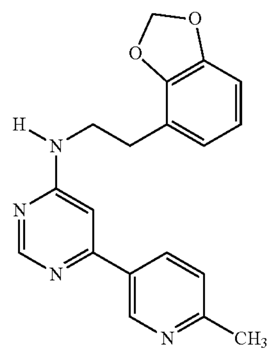 [SMILES: Cc1ccc(-c2cc(NCCc3cccc4c3OCO4)ncn2)cn1] | 335.09 | |
| 57 | 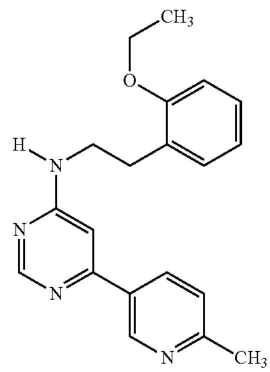 [SMILES: CCOc1ccccc1CCNc1cc(-c2ccc(C)nc2)ncn1] | 335.48 | (CDCl₃) δ 9.00 (d, J = 1.8 Hz, 1H), 8.62 (s, 1H), 8.18 (dd, J = 8.1, 2.2 Hz, 1H), 7.35-7.07 (m, 3H), 6.90 (dd, J = 11.9, 7.8 Hz, 2H), 6.65 (s, 1H), 5.58 (s, 1H), 4.09 (q, J = 7.0 Hz, 2H), 3.78-3.51 (m, 2H), 3.00 (t, J = 6.7 Hz, 2H), 2.63 (s, 3H), 1.45 (t, J = 7.0 Hz, 3H) |
| 58 | 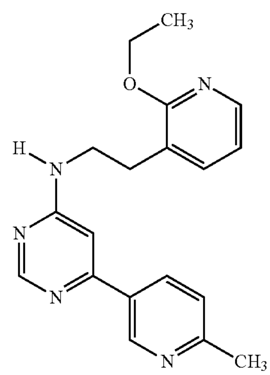 [SMILES: CCOc1ncccc1CCNc1cc(-c2ccc(C)nc2)ncn1] | 336.13 | (CDCl₃) δ 9.01 (d, J = 2.1 Hz, 1H), 8.63 (d, J = 6.0 Hz, 1H), 8.18 (dd, J = 8.1, 2.3 Hz, 1H), 8.05 (dd, J = 5.0, 1.9 Hz, 1H), 7.40 (m, 1H), 7.30-7.22 (m, 2H), 6.82 (m, 1H), 6.66 (s, 1H), 4.43 (q, J = 7.1 Hz, 2H), 3.67 (m, 2H), 2.95 (t, J = 6.7 Hz, 2H), 2.62 (s, 3H), 1.49-1.35 (t, 3H) |
| 59 | 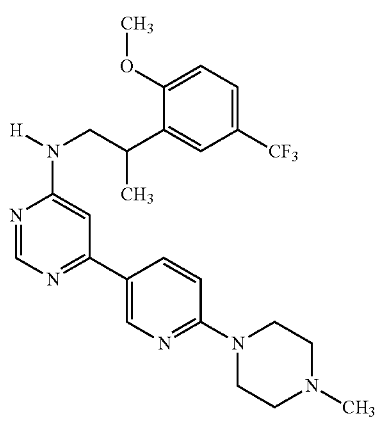 [SMILES: COc1ccc(C(F)(F)F)cc1C(C)CNc1cc(-c2ccc(N3CCN(C)CC3)nc2)ncn1] | 487.18 | (CDCl₃) δ 8.76 (d, 1H), 8.55 (s, 1H), 8.13 (dd, J = 8.9, 2.3 Hz, 1H), 7.56-7.41 (m, 2H), 6.94 (d, J = 8.5 Hz, 1H), 6.70 (d, J = 9.0 Hz, 1H), 6.58 (s, 1H), 5.02 (s, 1H), 3.89 (s, 3H), 3.73-3.44 (m, 7H), 2.61-2.43 (m, 4H), 2.36 (s, 3H), 1.34 (d, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 60 | 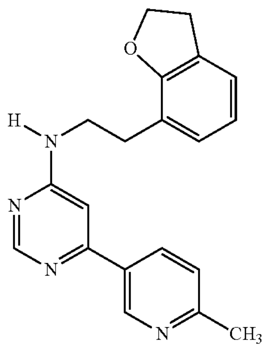 [SMILES: Cc1ccc(-c2cc(NCCc3cccc4c3OCC4)ncn2)cn1] | 332.87 | (CDCl₃) δ 9.05 (s, 1H), 8.59 (s, 1H), 8.26 (dd, J = 8.1, 2.2 Hz, 1H), 8.17 (s, 1H), 7.30 (d, J = 8.1 Hz, 1H), 7.10 (d, J = 7.2 Hz, 1H), 6.97 (d, J = 7.3 Hz, 1H), 6.81 (t, J = 7.4 Hz, 2H), 4.63 (t, J = 8.7 Hz, 2H), 3.61 (m, 2H), 3.24 (t, J = 8.7 Hz, 2H), 2.93 (t, J = 7.0 Hz, 2H), 2.65 (s, 3H) |
| 61 | 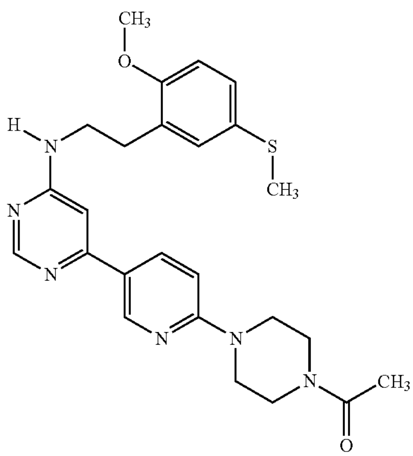 [SMILES: COc1ccc(SC)cc1CCNc1cc(-c2ccc(N3CCN(C(C)=O)CC3)nc2)ncn1] | 479.04 | (DMSO-d₆) δ 9.27 (br. s, 1H), 8.76 (s, 1H), 8.63 (d, J = 11.1 Hz, 1H), 8.04 (dd, J = 56.8, 8.3 Hz, 1H), 7.17 (m, 2H), 7.06 (d, J = 9.2 Hz, 1H), 6.96 (m, 2H), 3.77 (s, 3H), 3.76-3.48 (m, 10H), 2.87 (s, 2H), 2.39 (s, 3H), 2.06 (s, 3H) |
| 62 | 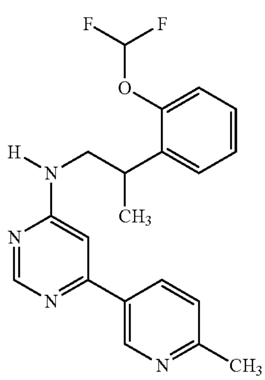 [SMILES: Cc1ccc(-c2cc(NCC(C)c3ccccc3OC(F)F)ncn2)cn1] | 371.24 | |

TABLE 1-continued

| Cmpnd No. | Structure | ESMS (M + H) | ¹H NMR (300 MHz, unless indicated otherwise) NMR peaks given as δ values |
|---|---|---|---|
| 63 | 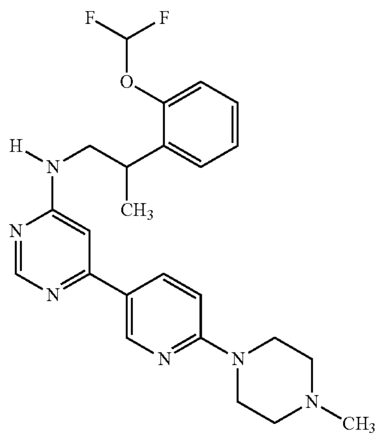 [SMILES: CC(CNc1cc(-c2ccc(N3CCN(C)CC3)nc2)ncn1)c1ccccc1OC(F)F] | 455.27 | (CDCl₃) δ 8.74 (d, J = 1.9 Hz, 1H), 8.55 (s, 1H), 8.12 (dd, J = 9.0, 2.4 Hz, 1H), 7.34 (dd, J = 6.7, 2.6 Hz, 1H), 7.21 (m, 2H), 7.11 (d, J = 8.2 Hz, 1H), 6.69 (d, J = 9.1 Hz, 1H), 6.53 (d, J = 4.8 Hz, 1H), 4.88 (s, 1H), 3.75-3.61 (m, 4H), 3.57 (m, 3H), 2.63-2.43 (m, 4H), 2.35 (s, 3H), 1.34 (d, 3H), 1.25 (s, 1H) |
| 64 | 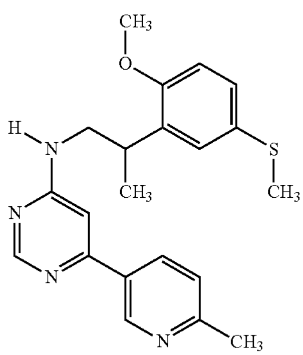 [SMILES: COc1ccc(SC)cc1C(C)CNc1cc(-c2ccc(C)nc2)ncn1] | 381.45 | |
| 65 | 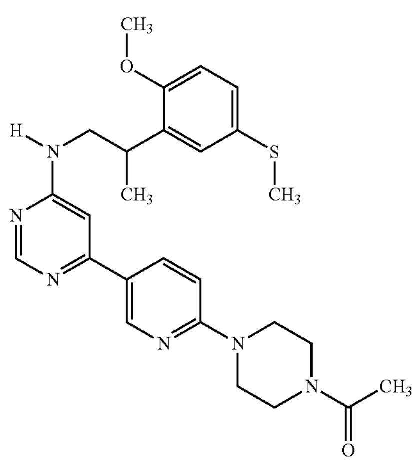 [SMILES: COc1ccc(SC)cc1C(C)CNc1cc(-c2ccc(N3CCN(C(C)=O)CC3)nc2)ncn1] | 492.74 | |

| Cmpnd No. | Structure | ESMS (M + H) | ¹H NMR (300 MHz, unless indicated otherwise) NMR peaks given as δ values |
|---|---|---|---|
| 66 | 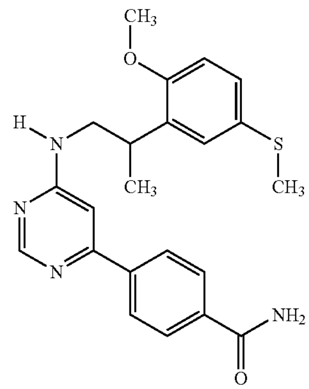 [SMILES: COc1ccc(SC)cc1C(C)CNc1cc(-c2ccc(C(N)=O)cc2)ncn1] | 409.41 | |
| 67 | 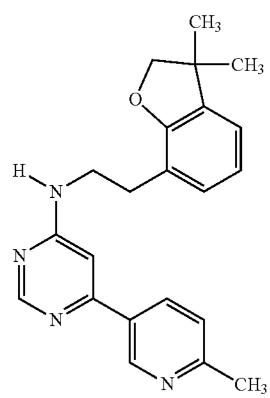 [SMILES: Cc1ccc(-c2cc(NCCc3cccc4c3OCC4(C)C)ncn2)cn1] | 361.45 | (400 MHz, DMSO-d₆) δ 9.02 (s, 1H), 8.50 (s, 1H), 8.21 (s, 1H), 7.55 (s, 1H), 7.38 (d, J = 7.9 Hz, 1H), 7.06-6.95 (m, 3H), 6.80 (t, J = 7.2 Hz, 1H), 4.21 (s, 2H), 3.56 (s, 2H), 2.80 (t, J = 7.0 Hz, 2H), 2.53 (s, 3H) and 1.27 (s, 6H) |
| 68 | 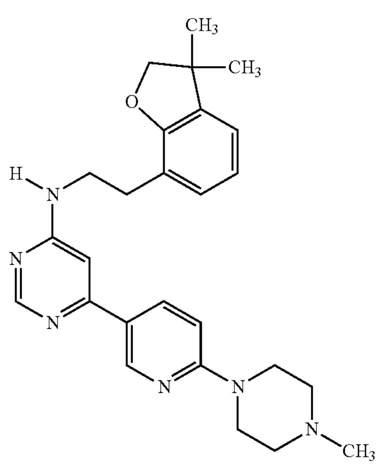 [SMILES: CN1CCN(c2ccc(-c3cc(NCCc4cccc5c4OCC5(C)C)ncn3)cn2)CC1] | 445.09 | (400 MHz, CDCl₃) δ 8.69 (s, 1H), 8.49 (s, 1H), 8.07 (d, J = 8.1 Hz, 1H), 6.94-6.90 (m, 2H), 6.77 (t, J = 7.3 Hz, 1H), 6.62 (d, J = 8.9 Hz, 1H), 6.55 (s, 1H), 5.30 (s, 1H), 4.20 (s, 2H), 3.60 (s, 6H), 2.86 (t, J = 6.4 Hz, 2H), 2.45 (s, 4H), 2.28 (s, 3H) and 1.27 (s, 6H) |

TABLE 1-continued

| Cmpnd No. | Structure | ESMS (M + H) | ¹H NMR (300 MHz, unless indicated otherwise) NMR peaks given as δ values |
|---|---|---|---|
| 69 | 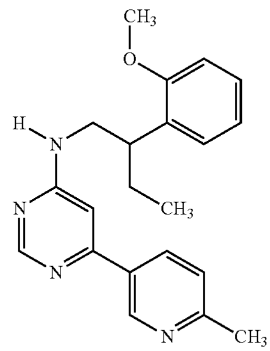 [SMILES: CCC(CNc1cc(-c2ccc(C)nc2)ncn1)c1ccccc1OC] | 349.09 | (400 MHz, CDCl₃) δ 9.01 (s, 1H), 8.61 (s, 1H), 8.19 (d, J = 8.0 Hz, 1H), 7.30-7.17 (m, 3H), 6.98 (t, J = 7.4 Hz, 1H), 6.92 (d, J = 8.2 Hz, 1H), 6.63 (s, 1H), 5.12 (s, 1H), 3.85 (s, 3H), 3.67 (s, 1H), 3.52 (s, 1H), 3.38 (dd, J = 13.1, 7.3 Hz, 1H), 2.64 (s, 3H), 1.91-1.69 (m, 2H), 0.90 (t, J = 7.3 Hz, 3H) |
| 70 | 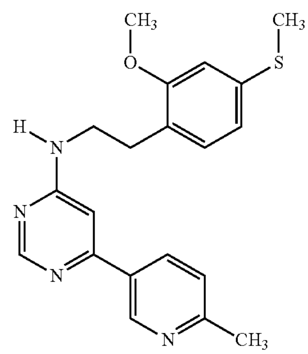 | 367.02 | (400 MHz, methanol-d₄) δ 8.90 (s, 1H), 8.66, 8.52 (2s, 1H), 8.26 (d, J = 7.8 Hz, 1H), 7.65 (d, J = 8.3 Hz, 1H), 7.07 (d, J = 7.8 Hz, 1H), 6.96-6.65 (m, 3H), 3.83 (s, m, 5H), 2.94 (t, J = 6.7 Hz, 2H), 2.70, 2.66 (2s, 3H), 2.45, 2.35 (2s, 3H) |
| 71 | 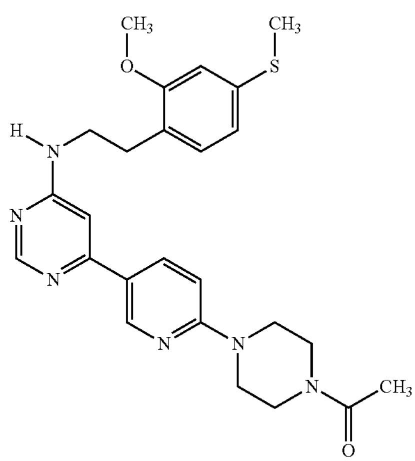 [SMILES: COc1cc(SC)ccc1CCNc1cc(-c2ccc(N3CCN(C(C)=O)CC3)nc2)ncn1] | 479.04 | (400 MHz, methanol-d₄) δ 8.56, 8.42 (m, s, 2H), 7.92 (t, J = 8.6 Hz, 1H), 7.07 (t, J = 7.4 Hz, 1H), 7.03-6.96 (m, 1H), 6.84, 6.60 (2s, 1H), 6.78 (s, 1H), 6.77-6.67 (m, 1H), 3.90-3.64 (m, 13H), 2.92 (q, J = 6.7 Hz, 2H), 2.45, 2.35 (2s, 3H), 2.16 (s, 3H) |
| 72 | 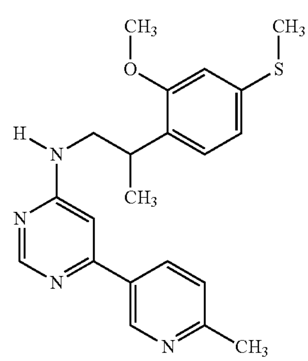 [SMILES: COc1cc(SC)ccc1C(C)CNc1cc(-c2ccc(C)nc2)ncn1] | 381.42 | (400 MHz, methanol-d₄) δ 8.89 (s, 1H), 8.66, 8.51 (2s, 1H), 8.25 (d, J = 8.1 Hz, 1H), 7.64 (d, J = 8.0 Hz, 1H), 7.15 (d, J = 7.5 Hz, 1H), 6.97-6.62 (m, 3H), 3.91-3.73 (m, 4H), 3.69-3.50 (m, 2H), 2.69 (m, 3H), 2.45, 2.34 (2s, 3H), 1.37-1.28 (m, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 73 | 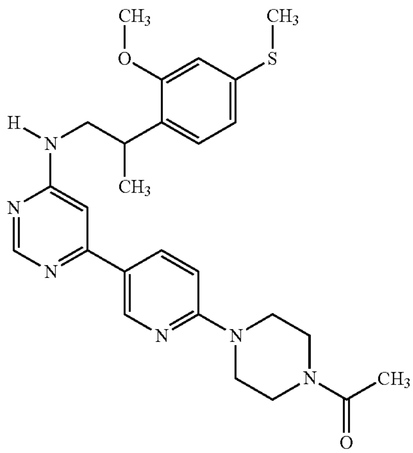 [SMILES: COc1cc(SC)ccc1C(C)CNc1cc(-c2ccc(N3CCN(C(C)=O)CC3)nc2)ncn1] | 493.06 | |
| 74 | 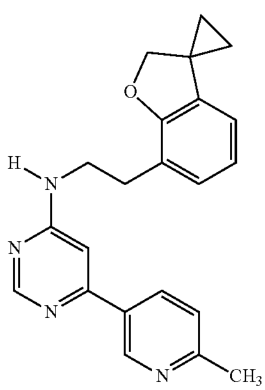 [SMILES: Cc1ccc(-c2cc(NCCc3cccc4c3OCC43CC3)ncn2)cn1] | 359.4 | |
| 75 | 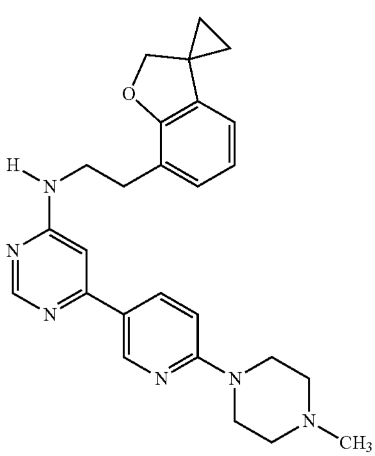 [SMILES: CN1CCN(c2ccc(-c3cc(NCCc4cccc5c4OCC54CC4)ncn3)cn2)CC1] | 443.11 | |

TABLE 1-continued

| Cmpnd No. | Structure | ESMS (M + H) | ¹H NMR (300 MHz, unless indicated otherwise) NMR peaks given as δ values |
|---|---|---|---|
| 76 | 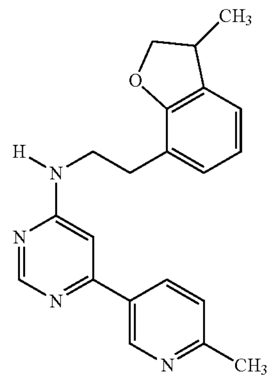 [SMILES: Cc1ccc(-c2cc(NCCc3cccc4c3OCC4C)ncn2)cn1] | 348.08 | |
| 77 | 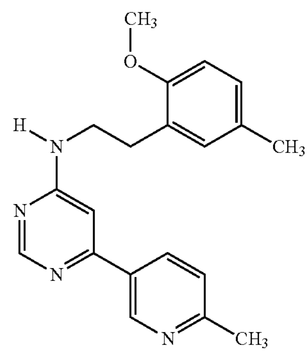 [SMILES: COc1ccc(C)cc1CCNc1cc(-c2ccc(C)nc2)ncn1] | 335.48 | |
| 78 | 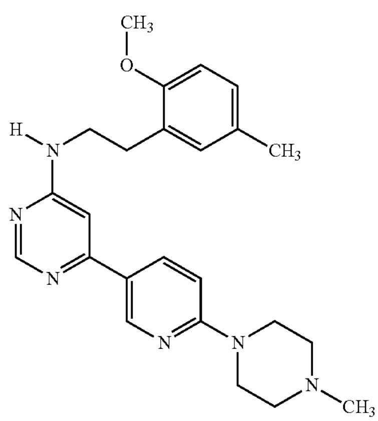 [SMILES: COc1ccc(C)cc1CCNc1cc(-c2ccc(N3CCN(C)CC3)nc2)ncn1] | 419.27 | |
| 79 | 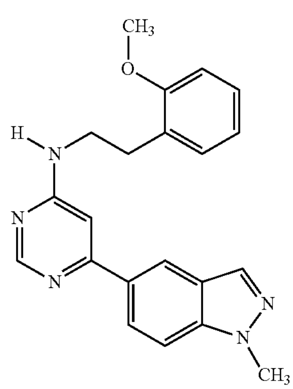 | 360.38 | (CDCl₃) δ 8.63 (s, 1H), 8.39 (dd, J = 1.5, 0.7 Hz, 1H), 8.11-7.98 (m, 2H), 7.46 (d, J = 8.9 Hz, 1H), 7.23 (m, 1H), 7.18 (dd, J = 7.3, 1.6 Hz, 1H), 6.92 (m, 2H), 6.75 (s, 1H), 5.27 (s, 1H), 4.11 (s, 3H), 3.88 (s, 3H), 3.62 (dd, J = 12.7, 6.5 Hz, 2H), 3.00 (t, J = 6.9 Hz, 2H) |

| Cmpnd No. | Structure | ESMS (M + H) | ¹H NMR (300 MHz, unless indicated otherwise) NMR peaks given as δ values |
|---|---|---|---|
| 80 | (structure: 6-[(S)-2-(2-methoxyphenyl)propylamino]-4-(quinolin-6-yl)pyrimidine) | 371.27 | (CDCl₃) δ 8.95 (dd, J = 4.2, 1.7 Hz, 1H), 8.66 (s, 1H), 8.53 (d, J = 1.7 Hz, 1H), 8.30-8.21 (m, 2H), 8.18 (d, J = 8.8 Hz, 1H), 7.44 (dd, J = 8.3, 4.2 Hz, 1H), 7.31-7.21 (m, 2H), 6.97 (dt, J = 11.3, 2.4 Hz, 1H), 6.91 (d, J = 7.9 Hz, 1H), 6.83 (s, 1H), 3.85 (s, 3H), 3.65 (m, 3H), 1.37 (d, J = 6.5 Hz, 3H) |
| 81 | (structure: pyrimidine with 3-methyl-2,3-dihydrobenzofuran-7-ylethylamino and 6-(4-methylpiperazin-1-yl)pyridin-3-yl substituents) | 429.06 | |
| 82 | (structure: pyrimidine with 2-(2-methoxyphenyl)ethylamino and 1-(1-methylpiperidin-4-yl)-1H-pyrazolo[3,4-b]pyridin-5-yl substituents) | 444.13 | (CDCl₃) δ 9.11 (d, J = 1.9 Hz, 1H), 8.70 (s, 1H), 8.10 (s, 1H), 7.27-7.18 (m, 2H), 7.12-6.83 (m, 3H), 6.75 (s, 1H), 5.39 (s, 1H), 4.96 (s, 1H), 4.28-4.20 (m, 1H), 3.65 (d, J = 6.4 Hz, 2H), 3.13 (d, J = 8.8 Hz, 2H), 3.02 (t, J = 6.8 Hz, 2H), 2.57-2.44 (m, 4H), 2.11 (m, 2H), 1.42-1.18 (m, 4H) and 0.87 (d, J = 6.5 Hz, 1H) |

TABLE 1-continued

| Cmpnd No. | Structure | ESMS (M + H) | $^1$H NMR (300 MHz, unless indicated otherwise) NMR peaks given as δ values |
|---|---|---|---|
| 83 | 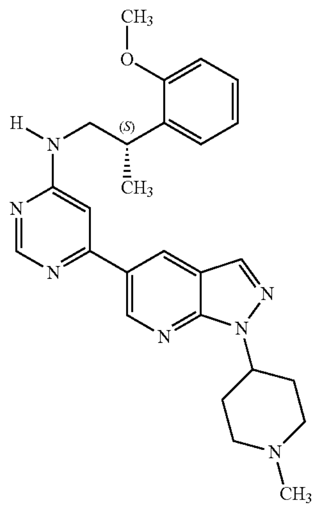 | 458.12 | (CDCl$_3$) δ 9.01 (d, J = 1.8 Hz, 1H), 8.59 (d, J = 1.9 Hz, 1H), 8.55 (s, 1H), 7.97 (d, J = 19.5 Hz, 1H), 7.16-7.14 (m, 2H), 6.93-6.83 (m, 2H), 6.64 (s, 1H), 5.17 (m, 1H), 4.84 (s, 1H), 3.80 (d, J = 8.0 Hz, 2H), 3.57 (s, 2H), 2.99 (d, J = 9.0 Hz, 2H), 2.45-2.32 (m, 4H), 2.20 (s, 2H), 1.99 (d, J = 11.1 Hz, 2H), 1.51 (s, 3H) and 1.29 (d, J = 6.4 Hz, 3H) |
| 84 | 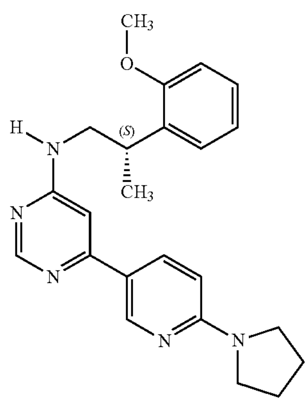 | 390.31 | (CDCl$_3$) δ 8.74 (d, J = 2.2 Hz, 1H), 8.53 (s, 1H), 8.10 (dd, J = 8.9, 2.4 Hz, 1H), 7.22 (m, 2H), 6.95 (dd, J = 13.5, 7.0 Hz, 1H), 6.89 (d, J = 8.4 Hz, 1H), 6.56 (s, 1H), 6.41 (d, J = 8.9 Hz, 1H), 5.03 (s, 3.84 (s, 3H), 3.56 (m, 7H), 2.11-1.94 (m, 4H), 1.34 (d, J = 6.7 Hz, 3H) |
| 85 | 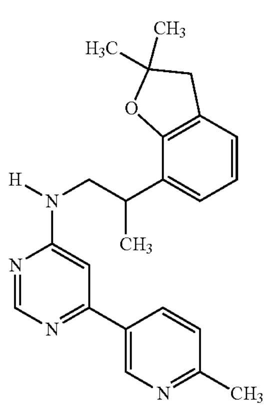 [SMILES: Cc1ccc(-c2cc(NCC(C)c3cccc4c3OC(C)(C)C4)ncn2)cn1] | 375.56 | |

TABLE 1-continued
| Cmpnd No. | Structure | ESMS (M + H) | ¹H NMR (300 MHz, unless indicated otherwise) NMR peaks given as δ values |
|---|---|---|---|
| 86 | 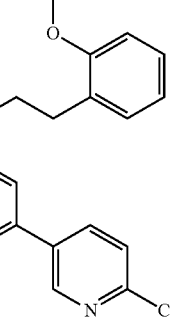 | | (400 MHz, CDCl₃) δ 9.01 (s, 1H), 8.62 (s, 1H), 8.19 (dd, J = 8.1, 2.3 Hz, 1H), 7.31-7.20 (m, 3H), 7.15 (d, J = 6.9 Hz, 1H), 6.98-6.87 (m, 1H), 6.65 (s, 1H), 5.27 (s, 1H), 3.84-3.73 (m, 1H), 3.58 (s, 2H), 2.93 (t, J = 6.7 Hz, 2H), 2.62 (s, 3H), 0.89-0.67 (m, 4H) |
| 87 | 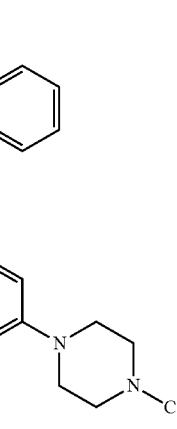 | 431.14 | (400 MHz, CDCl₃) δ 8.77 (s, 1H), 8.58 (s, 1H), 8.16 (dd, J = 8.9, 2.4 Hz, 1H), 7.32-7.21 (m, 2H), 7.16 (d, J = 6.9 Hz, 1H), 6.95 (td, J = 7.4, 2.2 Hz, 1H), 6.72 (d, J = 9.0 Hz, 1H), 6.58 (s, 1H), 5.19 (s, 1H), 3.79 (dq, J = 8.9, 3.1 Hz, 1H), 3.73-3.64 (m, 4H), 3.60-3.54 (m, 2H), 2.93 (t, J = 6.8 Hz, 2H), 2.56-2.52 (m, 4H), 2.37 (s, 3H), 0.87-0.73 (m, 4H) |
| 88 | 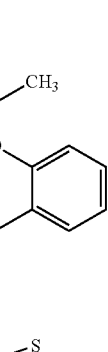 | 369.03 | (400 MHz, CDCl₃) δ 8.47 (s, 1H), 7.62 (d, J = 4.0 Hz, 1H), 7.57 (d, J = 3.9 Hz, 1H), 7.14 (m, 1H), 7.09 (d, J = 6.2 Hz, 1H), 6.85-6.80 (m, 2H), 6.51 (s, 1H), 5.35 (s, 1H), 4.03 (q, J = 6.9 Hz, 2H), 3.55 (s, 2H), 2.92 (t, J = 6.6 Hz, 2H), 2.56-2.46 (m, 3H) and 1.39 (t, J = 7.0 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 89 | 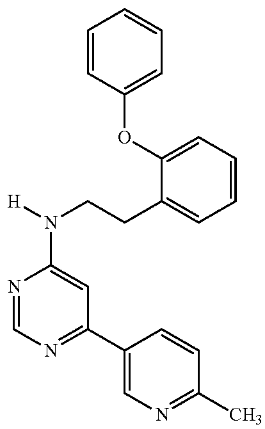 [SMILES: Cc1ccc(-c2cc(NCCc3ccccc3Oc3ccccc3)ncn2)cn1] | 382.86 | (400 MHz, DMSO-$d_6$) δ 9.07-8.95 (m, 2H), 8.73 (br. s, 1H), 8.34 (br. s, 1H), 7.65 (d, J = 7.9 Hz, 1H), 7.41 (br. s, 1H), 7.33 (t, J = 7.7 Hz, 2H), 7.26 (t, J = 7.4 Hz, 1H), 7.15 (t, J = 7.4 Hz, 1H), 7.07-6.87 (m, 4H), 3.72 (br. s, 2H), 2.93 (t, J = 7.0 Hz, 2H), 2.64 (s, 3H) |
| 90 | 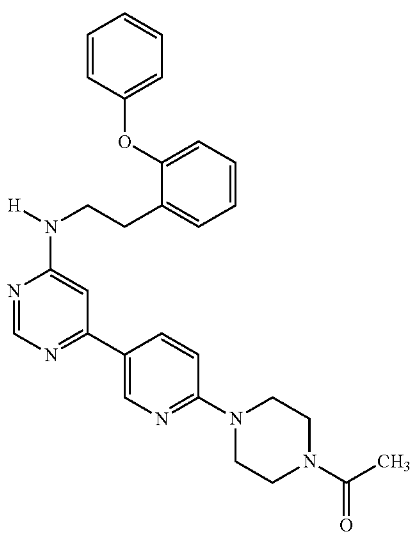 [SMILES: CC(=O)N1CCN(c2ccc(-c3cc(NCCc4ccccc4Oc4ccccc4)ncn3)cn2)CC1] | 495.11 | (400 MHz, DMSO-$d_6$) δ 9.31 (s, 1H), 8.72 (s, 1H), 8.62 (2s, 1H), 8.11-7.88 (m, 1H), 7.51-7.20 (m, 4H), 7.20-6.76 (m, 6H), 3.71 (m, 6H), 3.57 (br. s, 4H), 2.94 (t, J = 6.5 Hz, 2H), 2.06 (s, 3H) |
| 91 | 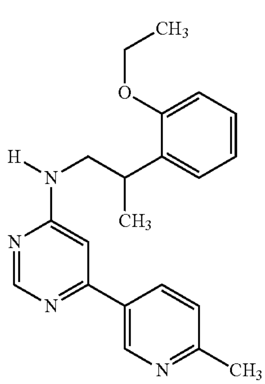 [SMILES: CCOc1ccccc1C(C)CNc1cc(-c2ccc(C)nc2)ncn1] | 349.19 | |

TABLE 1-continued

| Cmpnd No. | Structure | ESMS (M + H) | ¹H NMR (300 MHz, unless indicated otherwise) NMR peaks given as δ values |
|---|---|---|---|
| 92 | 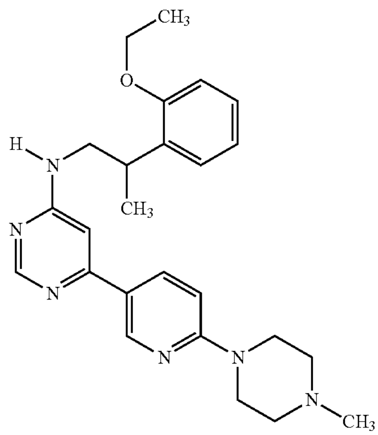 [SMILES: CCOc1ccccc1C(C)CNc1cc(-c2ccc(N3CCN(C)CC3)nc2)ncn1] | 433.32 | |
| 93 | 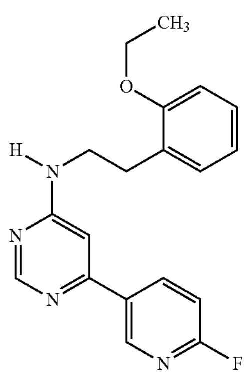 [SMILES: CCOc1ccccc1CCNc1cc(-c2ccc(F)nc2)ncn1] | 340.31 | (400 MHz, CDCl₃) δ 8.74 (s, 1H), 8.62 (s, 1H), 8.44-8.39 (m, 1H), 7.24-7.17 (m, 2H), 7.04 (dd, J = 2.7, 8.5 Hz, 1H), 6.93-6.85 (m, 2H), 6.62 (s, 1H), 5.53 (s, 1H), 4.11 (q, J = 7.0 Hz, 2H), 3.64 (s, 2H), 3.01 (t, J = 6.6 Hz, 2H) and 1.46 (t, J = 7.0 Hz, 3H) |
| 94 | 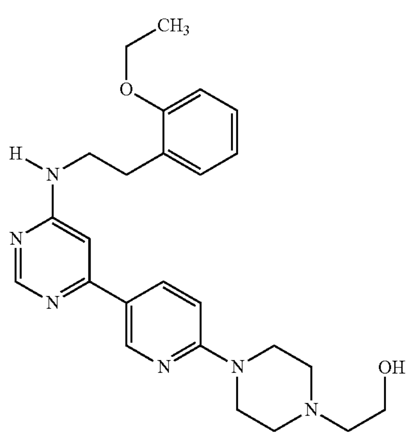 [SMILES: CCOc1ccccc1CCNc1cc(-c2ccc(N3CCN(CCO)CC3)nc2)ncn1] | 449.35 | |

TABLE 1-continued

| Cmpnd No. | Structure | ESMS (M + H) | ¹H NMR (300 MHz, unless indicated otherwise) NMR peaks given as δ values |
|---|---|---|---|
| 95 | 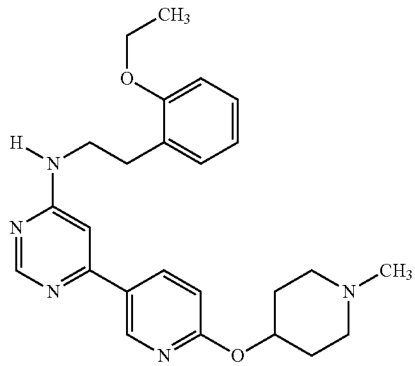 [SMILES: CCOc1ccccc1CCNc1cc(-c2ccc(OC3CCN(C)CC3)nc2)ncn1] | 433.89 | (CDCl$_3$) δ 8.62 (d, J = 2.2 Hz, 1H), 8.51 (s, 1H), 8.09 (dd, J = 2.5, 8.7 Hz, 1H), 7.17-7.07 (m, 2H), 6.85-6.79 (m, 2H), 6.71 (d, J = 8.6 Hz, 1H), 6.50 (s, 1H), 5.25 (s, 1H), 5.09 (td, J = 7.9, 4.0 Hz, 1H), 4.02 (q, J = 7.0 Hz, 2H), 3.54 (d, J = 5.6 Hz, 2H), 2.92 (t, J = 6.6 Hz, 2H), 2.67 (d, J = 4.9 Hz, 2H), 2.27 (s, 5H), 2.02 (dd, J = 2.6, 12.5 Hz, 2H), 1.86-1.75 (m, 2H) and 1.37 (t, J = 7.0 Hz, 3H) |
| 96 | 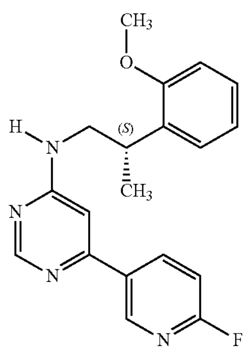 | 339.46 | |
| 97 | 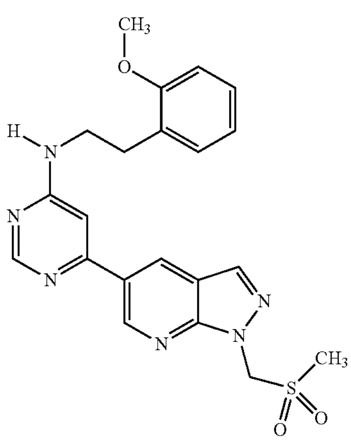 [SMILES: COc1ccccc1CCNc1cc(-c2cnc3c(cnn3CS(C)(=O)=O)c2)ncn1] | | (400 MHz, DMSO-d$_6$) δ 9.21 (d, J = 5.3 Hz, 1H), 8.88 (s, 1H), 8.55 (s, 1H), 8.48 (s, 1H), 7.61 (s, 1H), 7.21 (t, J = 7.5 Hz, 2H), 7.05 (s, 1H), 6.98 (d, J = 8.1 Hz, 1H), 6.88 (t, J = 7.3 Hz, 1H), 6.03 (d, J = 7.6 Hz, 2H), 3.78 (d, J = 18.7 Hz, 3H), 3.55 (s, 2H), 3.16 (d, J = 7.0 Hz, 3H) and 2.89-2.85 (m, 2H) |
| 98 | 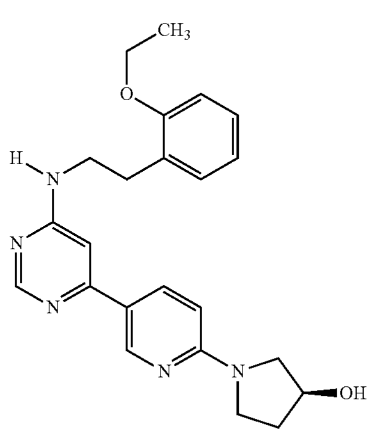 [SMILES: CCOc1ccccc1CCNc1cc(-c2ccc(N3CC[C@H](O)C3)nc2)ncn1] | 406.09 | (400 MHz, CDCl$_3$) δ 8.69 (s, 1H), 8.53 (s, 1H), 8.06 (d, J = 8.4 Hz, 1H), 7.19 (dd, J = 7.2, 20.3 Hz, 2H), 6.88 (t, J = 8.6 Hz, 2H), 6.51 (s, 1H), 6.37 (d, J = 8.7 Hz, 1H), 5.39 (s, 1H), 4.61 (s, 1H), 4.14-3.99 (m, 2H), 3.65-3.59 (m, 6H), 2.98 (d, J = 6.3 Hz, 2H), 2.15-2.05 (m, 2H), 1.45 (t, J = 6.7 Hz, 3H) and 1.25 (s, 1H) |

TABLE 1-continued

| Cmpnd No. | Structure | ESMS (M + H) | ¹H NMR (300 MHz, unless indicated otherwise) NMR peaks given as δ values |
|---|---|---|---|
| 99 | 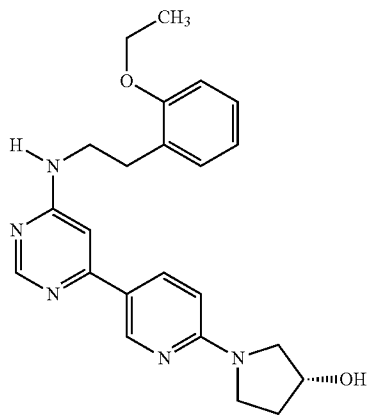 [SMILES: CCOc1ccccc1CCNc1cc(-c2ccc(N3CC[C@@H](O)C3)nc2)ncn1] | 406.9 | (400 MHz, CDCl₃) δ 8.69 (s, 1H), 8.53 (s, 1H), 8.06 (d, J = 8.4 Hz, 1H), 7.19 (dd, J = 7.2, 20.3 Hz, 2H), 6.88 (t, J = 8.6 Hz, 2H), 6.51 (s, 1H), 6.37 (d, J = 8.7 Hz, 1H), 5.39 (s, 1H), 4.61 (s, 1H), 4.14-3.99 (m, 2H), 3.65-3.59 (m, 6H), 2.98 (d, J = 6.3 Hz, 2H), 2.15-2.05 (m, 2H), 1.45 (t, J = 6.7 Hz, 3H) and 1.25 (s, 1H) |
| 100 | 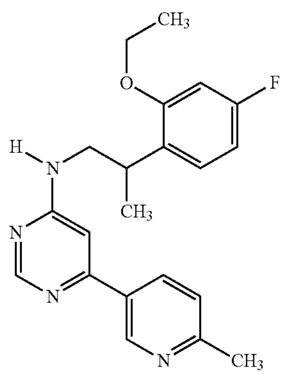 [SMILES: CCOc1cc(F)ccc1C(C)CNc1cc(-c2ccc(C)nc2)ncn1] | 367.24 | |
| 101 | 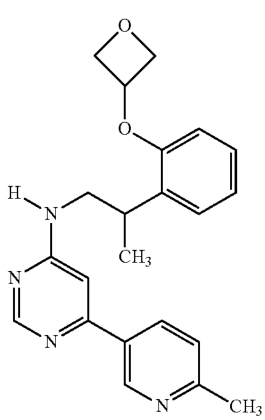 [SMILES: Cc1ccc(-c2cc(NCC(C)c3ccccc3OC3COC3)ncn2)cn1] | 377.1 | (400 MHz, CDCl₃) δ 9.00 (s, 1H), 8.63 (s, 1H), 8.19 (d, J = 8.1 Hz, 1H), 7.33-7.23 (m, 2H), 7.17 (t, J = 7.8 Hz, 1H), 7.01 (t, J = 7.5 Hz, 1H), 6.66 (s, 1H), 6.39 (d, J = 8.1 Hz, 1H), 5.36-5.03 (m, 2H), 4.97 (dt, J = 13.3, 6.7 Hz, 2H), 4.76-4.62 (m, 2H), 3.81-3.60 (m, 2H), 3.60-3.49 (m, 1H), 2.63 (s, 3H), 1.39 (d, J = 6.4 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 102 | 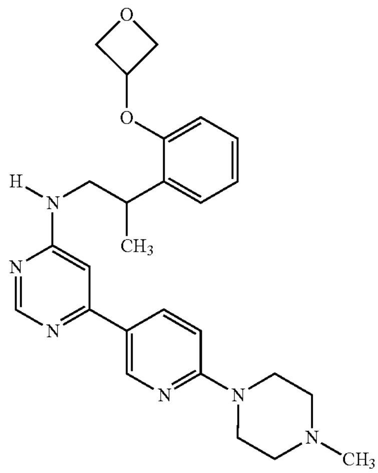 [SMILES: CC(CNc1cc(-c2ccc(N3CCN(C)CC3)nc2)ncn1)c1ccccc1OC1COC1] | 461.12 | (400 MHz, CDCl₃) δ 8.65 (s, 1H), 8.45 (s, 1H), 8.04 (d, J = 9.0 Hz, 1H), 7.25-7.14 (m, 1H), 7.08 (t, J = 7.8 Hz, 1H), 6.92 (t, J = 7.5 Hz, 1H), 6.62 (d, J = 9.0 Hz, 1H), 6.48 (s, 1H), 6.29 (d, J = 8.1 Hz, 1H), 5.16-5.04 (m, 1H), 4.94-4.78 (m, 2H), 4.61 (t, J = 6.0 Hz, 2H), 3.70-3.33 (m, 7H), 2.60-2.40 (m, 4H), 2.30 (s, 3H), 1.30 (d, J = 6.7 Hz, 3H) |
| 103 | 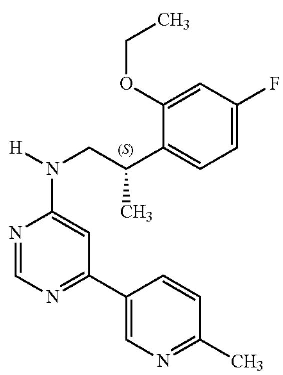 | 367.27 | (CDCl₃) δ 9.06 (s, 1H), 8.56 (s, 1H), 8.34 (d, 1H), 7.38 (d, J = 8.1 Hz, 1H), 7.14 (dd, J = 8.4, 6.7 Hz, 1H), 6.70-6.52 (m, 3H), 4.12-3.95 (m, 2H), 3.55 (s, 3H), 2.70 (s, 3H), 1.47-1.29 (m, 6H) |
| 104 | 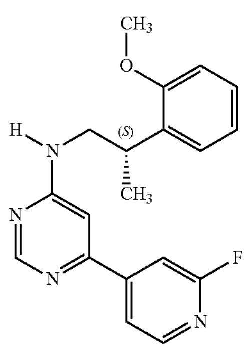 | 416.55 | |
| 105 | 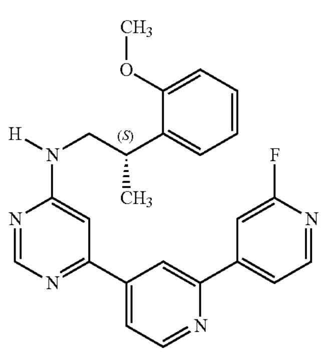 | | |

TABLE 1-continued

| Cmpnd No. | Structure | ESMS (M + H) | ¹H NMR (300 MHz, unless indicated otherwise) NMR peaks given as δ values |
|---|---|---|---|
| 106 | 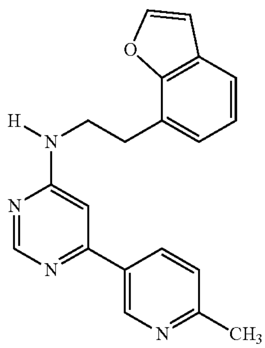 [SMILES: Cc1ccc(-c2cc(NCCc3cccc4ccoc34)ncn2)cn1] | 331.34 | (CDCl$_3$, 400 MHz) δ 9.03 (s, 1H), 8.66 (s, 1H), 8.20 (dd, J = 8.1, 2.3 Hz, 1H), 7.68 (d, J = 2.0 Hz, 1H), 7.52 (dd, J = 7.6, 1.2 Hz, 1H), 7.26 (s, 1H), 7.21 (t, J = 7.5 Hz, 1H), 7.16 (d, J = 7.1 Hz, 1H), 6.82 (d, J = 2.2 Hz, 1H), 6.71 (s, 1H), 5.18 (s, 1H), 3.85 (s, 2H), 3.29 (t, J = 6.9 Hz, 2H), 2.64 (s, 3H). |
| 107 | 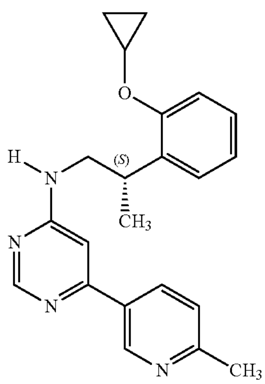 | 361.06 | (400 MHz, CDCl$_3$) δ 8.93 (s, 1H), 8.52 (s, 1H), 8.11 (d, J = 8.1 Hz, 1H), 7.28-7.04 (m, 4H), 6.90 (t, J = 7.2 Hz, 1H), 6.55 (s, 1H), 5.13 (s, 1H), 3.73-3.64 (m, 1H), 3.57-3.22 (m, 3H), 2.55 (s, 3H), 1.25 (d, J = 6.3 Hz, 3H), 0.77-0.53 (m, 4H) |
| 108 | 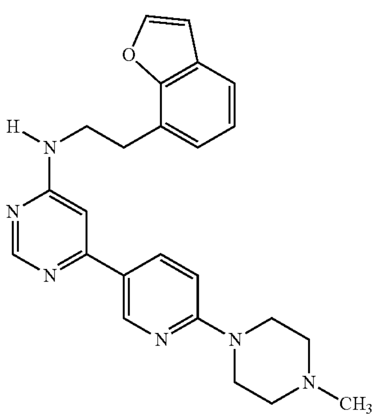 [SMILES: CN1CCN(c2ccc(-c3cc(NCCc4cccc5ccoc45)ncn3)cn2)CC1] | 415.08 | (DMSO-d$_6$, 400 MHz) δ 9.88 (s, 1H), 8.67 (s, 2H), 8.11 (s, 1H), 8.00 (s, 1H), 7.53 (d, J = 7.6 Hz, 1H), 7.20 (d, J = 6.3 Hz, 2H), 7.12 (d, J = 8.8 Hz, 1H), 6.96 (s, 1H), 6.89 (s, 1H), 4.57 (d, J = 13.6 Hz, 2H), 3.81 (s, 2H), 3.54 (d, J = 11.1 Hz, 2H), 3.34-3.14 (m, 4H), 3.09 (s, 2H), 2.86 (s, 3H). |
| 109 | 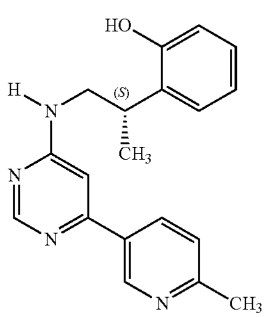 | 321.35 | |

TABLE 1-continued

| Cmpnd No. | Structure | ESMS (M + H) | ¹H NMR (300 MHz, unless indicated otherwise) NMR peaks given as δ values |
|---|---|---|---|
| 110 | 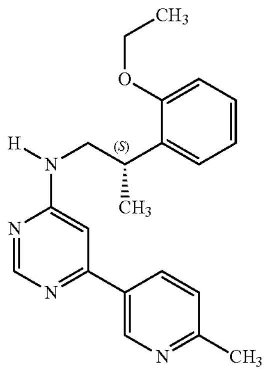 | 349.48 | (CDCl₃) δ 9.00 (dd, J = 10.9, 1.9 Hz, 1H), 8.60 (s, 1H), 8.17 (dd, J = 8.1, 2.3 Hz, 1H), 7.26-7.14 (m, 3H), 6.94 (ddd, J = 7.4, 6.9, 2.4 Hz, 1H), 6.88 (d, J = 8.1 Hz, 1H), 6.60 (s, 1H), 4.16-3.96 (m, 2H), 3.70-3.41 (m, 3H), 2.62 (s, 3H), 1.37 (m, 6H) |
| 111 | 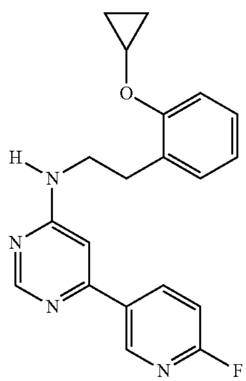 [SMILES: Fc1ccc(-c2cc(NCCc3ccccc3OC3CC3)ncn2)cn1] | 351.37 | (400 MHz, CDCl₃) δ 8.77 (s, 1H), 8.63 (s, 1H), 8.44 (t, J = 8.1 Hz, 1H), 7.26 (dd, J = 11.5, 3.6 Hz, 3H), 7.17 (d, J = 7.4 Hz, 1H), 7.05 (dd, J = 8.6, 2.6 Hz, 1H), 6.95 (t, J = 6.8 Hz, 1H), 6.65 (s, 1H), 5.37 (s, 1H), 3.80 (t, J = 4.4 Hz, 1H), 3.60 (s, 2H), 2.95 (t, J = 6.7 Hz, 2H), 0.89-0.72 (m, 4H) |
| 112 | 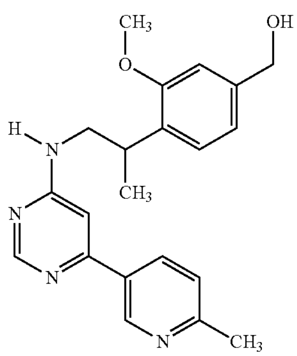 [SMILES: COc1cc(CO)ccc1C(C)CNc1cc(-c2ccc(C)nc2)ncn1] | 365.42 | (400 MHz, DMSO-d₆) δ 9.03 (m, 1H), 8.79-8.11 (m, 3H), 7.53 (d, J = 6.7 Hz, 1H), 7.37-6.71 (m, 4H), 4.46 (s, 2H), 3.74 (s, 3H), 3.50 (m, 1H), 2.59 (s, 3H), 1.21 (s, 3H) |
| 113 | 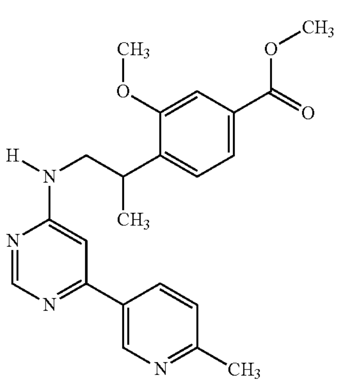 [SMILES: COC(=O)c1ccc(C(C)CNc2cc(-c3ccc(C)nc3)ncn2)c(OC)c1] | 393.38 | (400 MHz, DMSO-d₆) δ 9.03-8.97 (m, 1H), 8.74-65 (m, 2H), 8.38-8.28 (m, 1H), 7.78-7.50 (m, 2H), 7.44 (m, 2H), 7.06 (m, 1H), 3.84, 3.83 (2s, 6H), 3.77-3.42 (m, 4H), 2.59 (s, 3H), 1.25 (s, 2H) |

TABLE 1-continued

| Cmpnd No. | Structure | ESMS (M + H) | ¹H NMR (300 MHz, unless indicated otherwise) NMR peaks given as δ values |
|---|---|---|---|
| 114 | 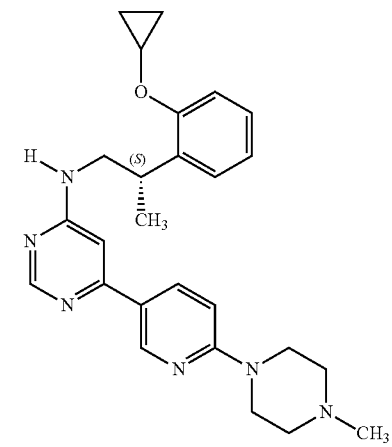 | 445.12 | (400 MHz, CDCl₃) δ 8.67 (s, 1H), 8.47 (s, 1H), 8.05 (dd, J = 8.9, 2.3 Hz, 1H), 7.15 (dd, J = 14.7, 5.4 Hz, 3H), 6.90 (dd, J = 10.3, 4.1 Hz, 1H), 6.62 (d, J = 9.0 Hz, 1H), 6.47 (s, 1H), 5.02 (s, 1H), 3.73-3.64 (m, 1H), 3.60 (dd, J = 12.9, 8.2 Hz, 4H), 3.43 (dd, J = 17.3, 10.9 Hz, 3H), 2.48-2.43 (m, 4H), 2.28 (s, 3H), 1.22 (d, J = 8.7 Hz, 3H), 0.79-0.53 (m, 4H) |
| 115 | 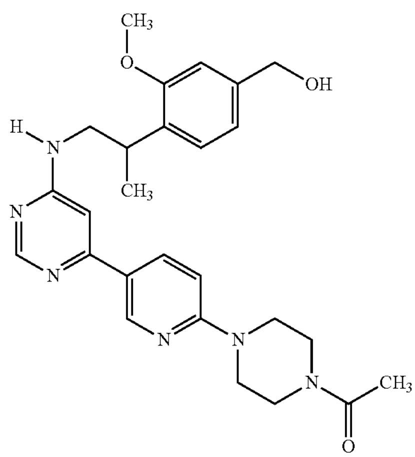 [SMILES: COc1cc(CO)ccc1C(C)CNc1cc(-c2ccc(N3CCN(C(C)=O)CC3)nc2)ncn1] | 477.47 | (400 MHz, DMSO-d₆) δ 8.70 (m, 3H), 8.06 (m, 1H), 7.31-6.77 (m, 5H), 4.46 (s, 2H), 3.88-3.34 (m, 14H), 2.08 (s, 3H), 1.21 (s, 3H) |
| 116 | 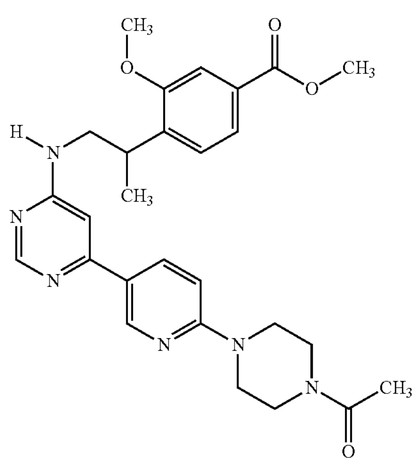 [SMILES: COC(=O)c1ccc(C(C)CNc2cc(-c3ccc(N4CCN(C(C)=O)CC4)nc3)ncn2)c(OC)c1] | 505.12 | (400 MHz, DMSO-d₆) δ 9.15-8.60 (m, 3H), 8.12-7.96 (m, 1H), 7.57-7.38 (m, 3H), 7.15-6.80 (m, 2H), 3.83 (s, 6H), 3.78-3.45 (m, 11H), 2.06 (s, 3H), 1.25 (s, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 117 | 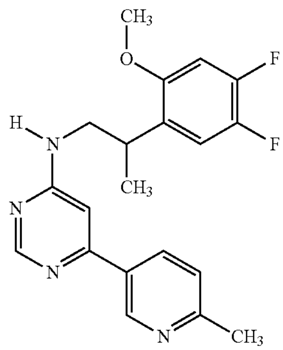 [SMILES: COc1cc(F)c(F)cc1C(C)CNc1cc(-c2ccc(C)nc2)ncn1] | 371.48 | (CDCl$_3$) δ 9.01 (d, J = 2.0 Hz, 1H), 8.62 (s, 1H), 8.19 (dd, J = 8.1, 2.3 Hz, 1H), 7.25 (s, 1H), 7.03 (dd, J = 11.2, 8.9 Hz, 1H), 6.71 (m, 2H), 5.11 (s, 1H), 3.81 (s, 3H), 3.61-3.35 (m, 3H), 2.60 (d, J = 16.3 Hz, 3H), 1.36-1.26 (d, 3H) |
| 118 | 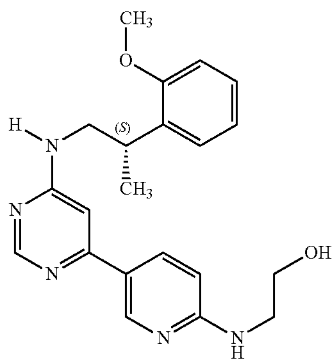 | 380.44 | |
| 119 | 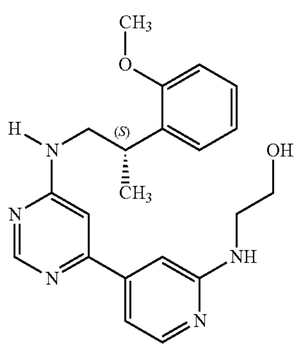 | 380.5 | |
| 120 | 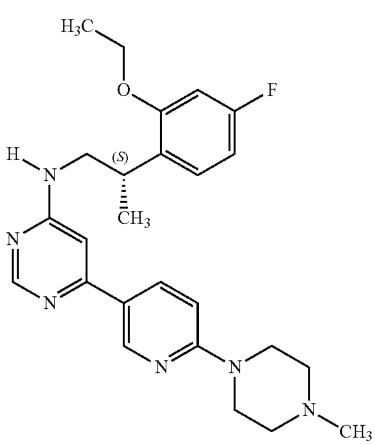 | 451.52 | (CDCl$_3$) δ 8.73 (d, J = 2.2 Hz, 1H), 8.54 (s, 1H), 8.12 (dd, J = 9.0, 2.5 Hz, 1H), 7.18-7.06 (m, 1H), 6.74-6.48 (m, 4H), 5.03 (s, 1H), 4.07-3.93 (q, 2H), 3.74-3.37 (m, 7H), 2.54 (m, 4H), 1.45-1.28 (m, 6H). |

TABLE 1-continued

| Cmpnd No. | Structure | ESMS (M + H) | ¹H NMR (300 MHz, unless indicated otherwise) NMR peaks given as δ values |
|---|---|---|---|
| 121 | 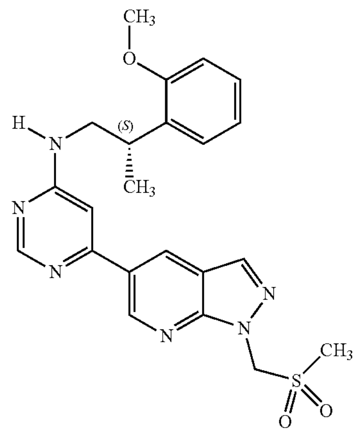 | 454.02 | (CDCl₃) δ 9.08 (s, 1H), 8.68 (s, 1H), 8.55 (s, 1H), 8.16 (s, 1H), 6.83 (s, 2H), 6.65 (s, 1H), 5.71 (s, 2H), 3.79 (s, 3H), 3.55-3.37 (m, 2H), 2.97 (s, 3H), 1.57 (s, 1H), 1.30 (d, J = 6.1 Hz, 3H), 1.18 (s, 2H) and 0.79 (t, J = 7.1 Hz, 1H) |
| 122 | 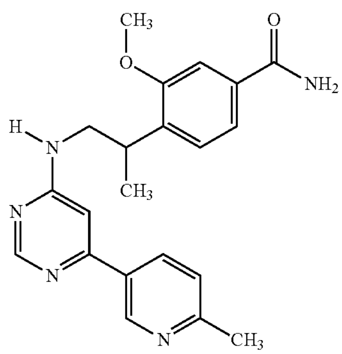 [SMILES: COc1cc(C(N)=O)ccc1C(C)CNc1cc(-c2ccc(C)nc2)ncn1] | 378.06 | (400 MHz, DMSO-d₆) δ 9.16-8.56 (m, 3H), 8.43-8.28 (m, 1H), 7.94 (s, 1H), 7.74-6.84 (m, 6H), 3.81 (s, 3H), 3.79-3.40 (m, 3H), 2.61 (s,3H), 1.24 (s, 3H) |
| 123 | 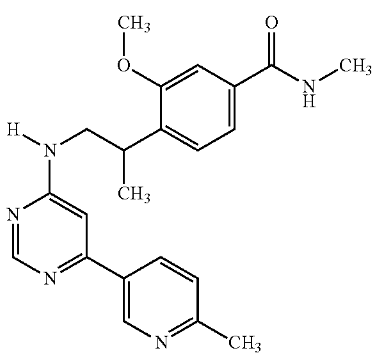 | 392.39 | (400 MHz, DMSO-d₆) δ 9.18-8.59 (m, 3H), 8.48-8.21 (m, 2H), 7.66 (d, J = 7.5 Hz, 1H), 7.48-6.93 (m, 4H), 3.82 (s, 3H), 3.75-3.38 (m, 3H), 2.77 (s, 3H), 2.63 (s, 3H), 1.23 (d, J = 6.3 Hz, 3H) |
| 124 | 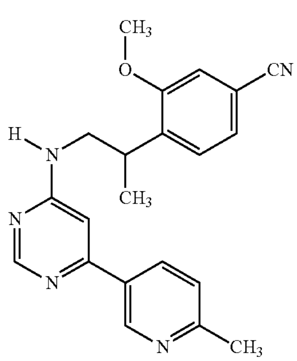 [SMILES: COc1cc(C#N)ccc1C(C)CNc1cc(-c2ccc(C)nc2)ncn1] | 360.46 | (400 MHz, DMSO-d₆) δ 9.23-6.92 (m, 9H), 3.82 (s, 3H), 3.73-3.54 (m, 3H), 2.64 (s, 3H), 1.24 (d, J = 6.3 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 125 | 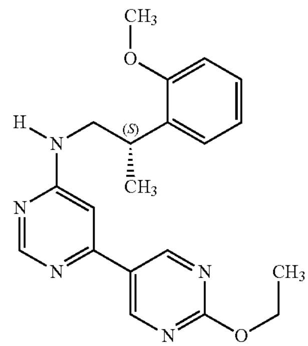 | 366.42 | (CDCl₃) δ 9.05 (s, 2H), 8.56 (s, 1H), 7.26-7.15 (m, 2H), 7.02-6.85 (m, 2H), 6.60 (s, 1H), 4.50 (q, J = 7.1 Hz, 2H), 3.86 (s, 3H), 3.66-3.46 (m, 3H), 1.54-1.40 (t, 3H), 1.32 (d, 3H) |
| 126 | 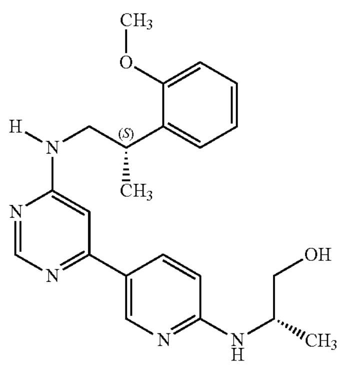 | 394.31 | |
| 127 | 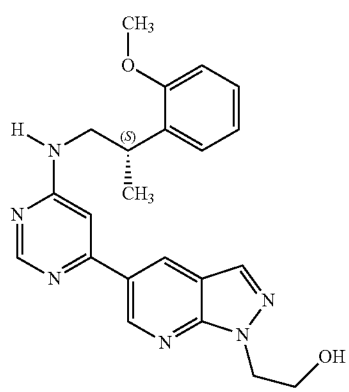 | 406.12 | (400 MHz, DMSO-d₆) δ 9.12 (s, 1H), 8.78 (s, 1H), 8.53 (s, 1H), 8.28 (s, 1H), 7.48 (s, 1H), 7.26 (s, 2H), 7.03-6.91 (m, 3H), 4.90 (s, 1H), 4.55 (s, 2H), 3.89 (d, J = 5.3 Hz, 2H), 3.78 (s, 3H), 3.56-3.41 (m, 3H) and 1.22 (s, 3H) |
| 128 | 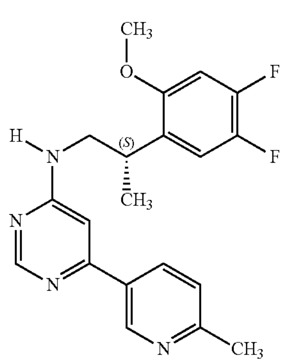 | 371.56 | (CDCl₃) δ 9.01 (d, J = 2.0 Hz, 1H), 8.62 (s, 1H), 8.19 (dd, J = 8.1, 2.3 Hz, 1H), 7.28 (d, 1H), 7.03 (dd, J = 11.2, 8.9 Hz, 1H), 6.71 (m, 2H), 5.15 (s, 1H), 3.81 (s, 3H), 3.54 (d, J = 15.5 Hz, 3H), 2.62 (s, 3H), 1.29 (d, J = 9.6 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 129 | 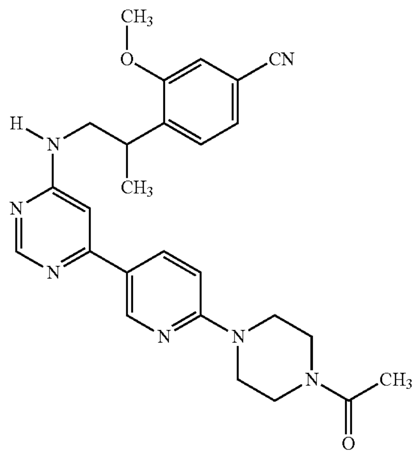 [SMILES: COc1cc(C#N)ccc1C(C)CNc1cc(-c2ccc(N3CCN(C(C)=O)CC3)nc2)ncn1] | 472.16 | (400 MHz, DMSO-d$_6$) δ 9.34-6.73 (m, 9H), 3.82 (s, 3H), 3.74-3.58 (m, 11H), 2.06 (s, 3H), 1.23 (d, J = 6.0 Hz, 3H) |
| 130 | 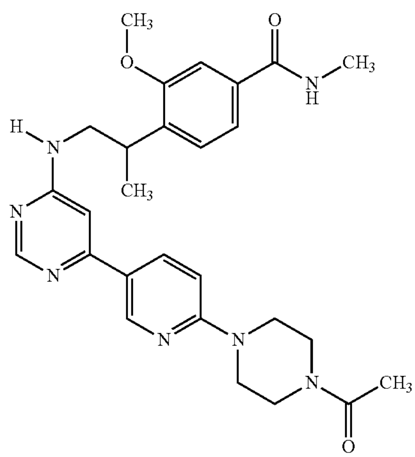 [SMILES: CNC(=O)c1ccc(C(C)CNc2cc(-c3ccc(N4CCN(C(C)=O)CC4)nc3)ncn2)c(OC)c1] | 504.19 | (400 MHz, DMSO-d$_6$) δ 9.54-8.30 (m, 4H), 8.03 (m,1H), 7.54-6.81 (m, 4H), 3.82 (s, 3H), 3.80-3.34 (m, 11H), 2.78 (s, 3H), 2.10 (3, 3H), 1.22 (br.s, 3H) |
| 131 | 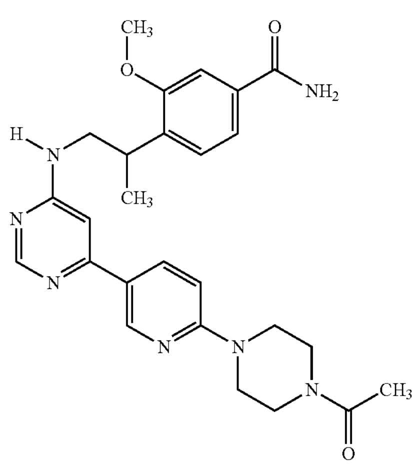 [SMILES: COc1cc(C(N)=O)ccc1C(C)CNc1cc(-c2ccc(N3CCN(C(C)=O)CC3)nc2)ncn1] | 490.18 | (400 MHz, DMSO-d$_6$) δ 9.28-9.16 (m, 1H), 8.76 (br.s, 1H), 8.61 (br.s, 1H), 8.14-7.95 (m, 2H), 7.49-7.28 (m, 4H), 7.09-6.87 (m, 2H), 3.81 (s, 3H), 3.79-3.43 (m, 11H), 2.06 (s, 3H), 1.23 (d, J = 6.7 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 132 | 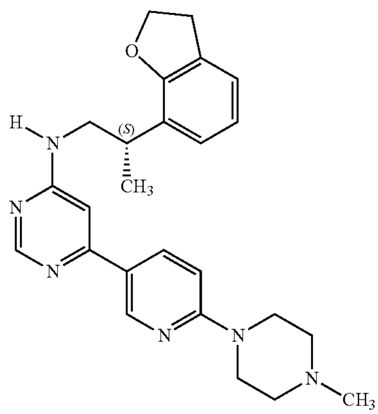 | 431.31 | |
| 133 | 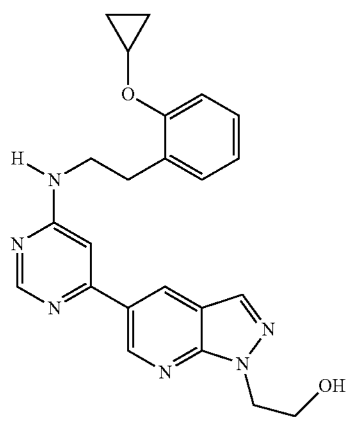 [SMILES: OCCn1ncc2cc(-c3cc(NCCc4ccccc4OC4CC4)ncn3)cnc21] | 418.09 | (CDCl$_3$) δ 9.03 (s, 1H), 8.67 (s, 1H), 8.56 (s, 1H), 8.04 (s, 1H), 7.19 (s, 1H), 7.10 (d, J = 7.0 Hz, 1H), 6.88 (d, J = 5.2 Hz, 1H), 6.64 (s, 1H), 5.28 (s, 1H), 4.66 (s, 2H), 4.10 (s, 2H), 3.73 (s, 1H), 3.52 (s, 1H), 3.41 (q, J = 6.9 Hz, 1H), 2.88 (t, J = 6.4 Hz, 2H), 1.56 (s, 2H), 1.14 (t, J = 6.9 Hz, 1H) and 0.72 (d, J = 11.4 Hz, 3H) |
| 134 | 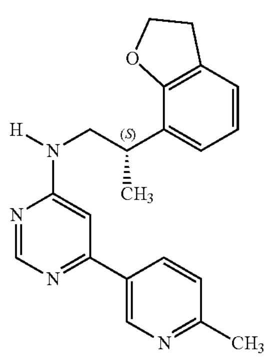 | 347.53 | |

| Cmpnd No. | Structure | ESMS (M + H) | ¹H NMR (300 MHz, unless indicated otherwise) NMR peaks given as δ values |
|---|---|---|---|
| 135 | 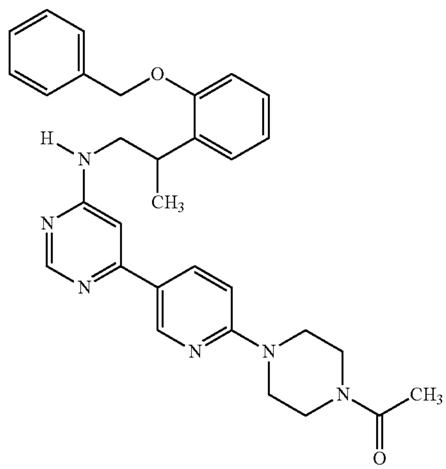 [SMILES: CC(=O)N1CCN(c2ccc(-c3cc(NCC(C)c4ccccc4OCc4ccccc4)ncn3)cn2)CC1] | 523.2 | (methanol-d₄) δ 9.27-9.17 (m, 1H), 8.74-8.57 (m, 2H), 8.16-7.83 (m, 1H), 7.51-6.76 (m, 11H), 5.09 (d, 2H), 3.74-3.57 (m, 11H), 2.07 (s, 3H), 1.25 (d, J = 4.2 Hz, 3H) |
| 136 | 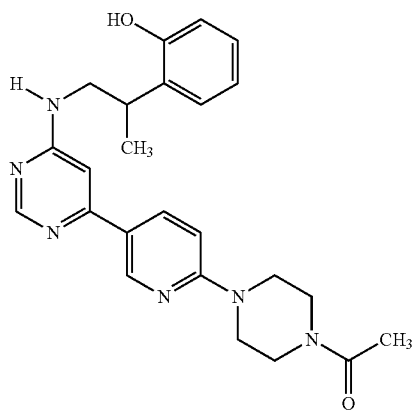 [SMILES: CC(=O)N1CCN(c2ccc(-c3cc(NCC(C)c4ccccc4O)ncn3)cn2)CC1] | 433.16 | (400 MHz, DMSO-d₆) δ 9.88-9.04 (m, 2H), 8.77 (br. s, 1H), 8.68-8.54 (m, 1H), 8.09, 7.96 (2d, J = 7.9 Hz, 1H), 7.29-6.64 (m, 6H), 3.85-3.26 (m, 11H), 2.07 (s, 3H), 1.23 (t, J = 7.5 Hz, 3H) |
| 137 | 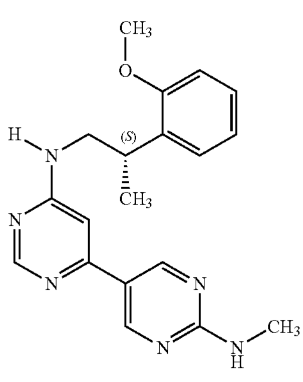 | 351 | |

TABLE 1-continued

| Cmpnd No. | Structure | ESMS (M + H) | ¹H NMR (300 MHz, unless indicated otherwise) NMR peaks given as δ values |
|---|---|---|---|
| 138 | 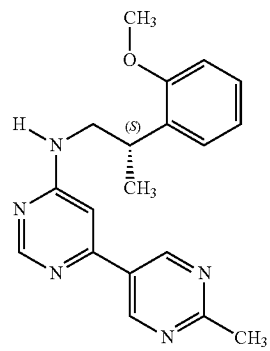 | 336 | (400 MHz, DMSO-d₆) δ 9.15 (d, J = 10.9 Hz, 2H), 8.53 (s, 1H), 7.57 (d, J = 5.4 Hz, 1H), 7.20 (dt, J = 9.1, 5.0 Hz, 2H), 6.93 (ddd, J = 8.9, 8.5, 4.7 Hz, 2H), 6.55 (s, 1H), 3.76 (s, 3H), 3.63-3.37 (m, 3H), 2.69 (s, 3H), 1.26-1.16 (m, 3H) |
| 139 | 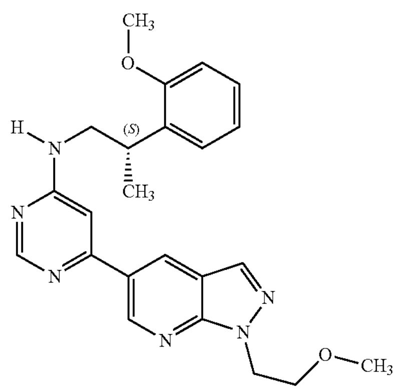 | 420.11 | (CDCl₃) δ 9.12 (s, 1H), 8.69 (d, J = 1.8 Hz, 1H), 8.63 (s, 1H), 8.12 (s, 1H), 7.28-7.23 (m, 2H), 7.01-6.91 (m, 2H), 6.74 (s, H), 5.31 (s, 1H), 4.77 (t, J = 5.5 Hz, 2H), 3.94 (t, J = 5.5 Hz, 2H), 3.87 (s, 3H), 3.66-3.46 (m, 3H), 3.35 (s, 3H) and 1.38 (d, J = 6.3 Hz, 3H) |
| 140 | 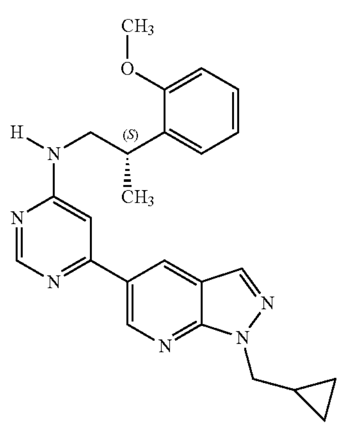 | 416.36 | (CDCl₃) δ 9.01 (s, 1H), 8.60 (s, 1H), 8.54 (s, 1H), 8.02 (s, 1H), 7.19-7.16 (m, 2H), 6.92-6.82 (m, 2H), 6.66 (s, 1H), 5.28 (s, 1H), 4.36 (d, J = 6.8 Hz, 2H), 3.78 (s, 3H), 3.55-3.51 (m, 1H), 3.39 (t, J = 7.0 Hz, 1H), 2.00 (s, 1H), 1.76 (s, 1H), 1.29 (d, J = 5.7 Hz, 3H) and 0.50-0.43 (m, 4H) |

TABLE 1-continued

| Cmpnd No. | Structure | ESMS (M + H) | ¹H NMR (300 MHz, unless indicated otherwise) NMR peaks given as δ values |
|---|---|---|---|
| 141 | 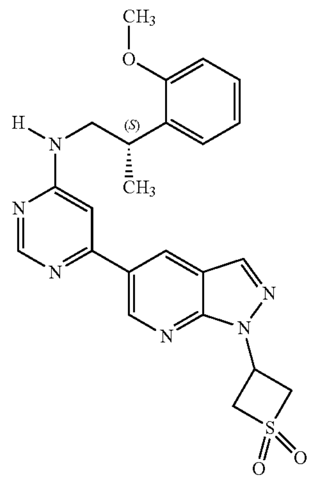 | 466.02 | |
| 142 | 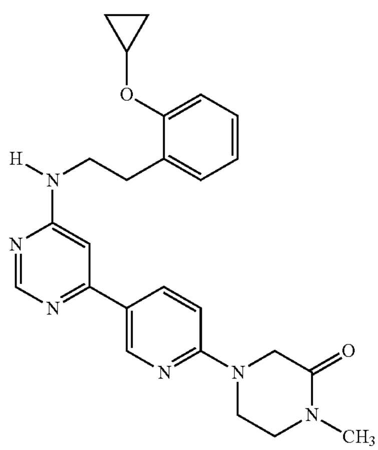 [SMILES: CN1CCN(c2ccc(-c3cc(NCCc4ccccc4OC4CC4)ncn3)cn2)CC1=O] | | (CDCl$_3$) δ 8.80 (d, J = 1.7 Hz, 1H), 8.58 (s, 1H), 8.19 (dd, J = 8.9, 2.3 Hz, 1H), 7.38-7.21 (m, 3H), 7.17 (d, J = 7.0 Hz, 1H), 7.05-6.87 (m, 1H), 6.65 (d, J = 8.9 Hz, 1H), 6.59 (s, 1H), 5.28 (s, 1H), 4.19 (s, 2H), 4.14-3.93 (m, 2H), 3.80 (ddd, J = 8.8, 6.0, 3.1 Hz, 1H), 3.57 (d, J = 5.0 Hz, 2H), 3.54-3.40 (m, 2H), 3.08 (s, 3H), 2.94 (t, J = 6.8 Hz, 2H), 0.95-0.64 (m, 4H) |
| 143 | 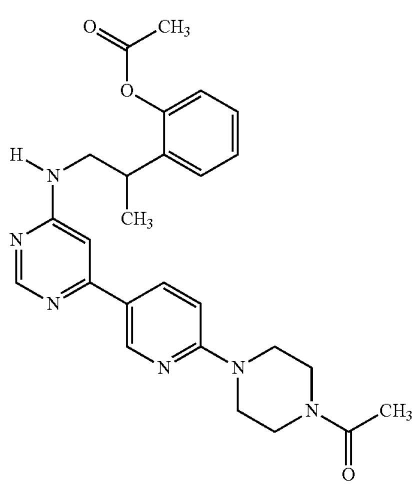 [SMILES: CC(=O)Oc1ccccc1C(C)CNc1cc(-c2ccc(N3CCN(C(C)=O)CC3)nc2)ncn1] | 475.14 | (400 MHz, DMSO-d$_6$) δ 9.25 (s, 1H), 8.78 (s, 1H), 8.62 (s, 1H), 8.10, 7.98 (2d, 1H), 7.52, 7.47 (2s, 1H), 7.27 (d, J = 3.3 Hz, 2H), 7.06 (d, J = 8.8 Hz, 2H), 6.91 (s, 1H), 3.74-3.58 (m, 10H), 3.39-3.19 (m, 1H), 2.25, 2.21 (2s, 3H), 2.06 (s, 3H), 1.21 (d, J = 6.7 Hz, 3H) |

TABLE 1-continued

| Cmpnd No. | Structure | ESMS (M + H) | $^1$H NMR (300 MHz, unless indicated otherwise) NMR peaks given as δ values |
|---|---|---|---|
| 144 | 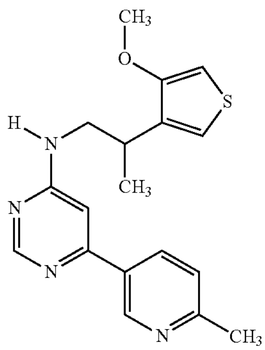 [SMILES: COc1cscc1C(C)CNc1cc(-c2ccc(C)nc2)ncn1] | 341.1 | (400 MHz, CDCl$_3$) δ 8.94 (s, 1H), 8.54 (s, 1H), 8.13 (dd, J = 8.1, 2.1 Hz, 1H), 7.28-7.12 (m, 1H), 6.89 (d, J = 3.2 Hz, 1H), 6.63 (s, 1H), 6.19 (d, J = 3.2 Hz, 1H), 5.22 (s, 1H), 3.80 (s, 3H), 3.64-3.22 (m, 2H), 3.22-3.06 (m, 1H), 2.55 (s, 3H), 1.29 (d, J = 7.0 Hz, 3H). |
| 145 | 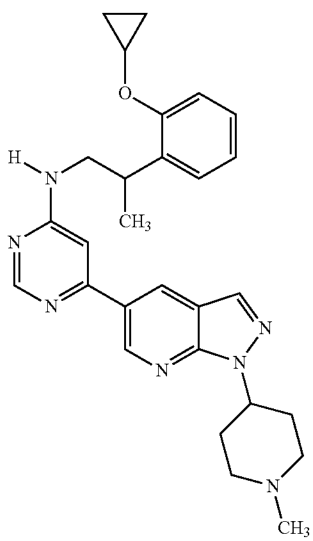 [SMILES: CC(CNc1cc(-c2cnc3c(cnn3C3CCN(C)CC3)c2)ncn1)c1ccccc1OC1CC1] | 484.16 | (400 MHz, CDCl$_3$) δ 9.01 (s, 1H), 8.59 (d, J = 1.9 Hz, 1H), 8.54 (s, 1H), 8.01 (s, 1H), 7.22- 7.11 (m, 3H), 6.98-6.85 (m, 1H), 6.61 (s, 1H), 5.12 (s, 1H), 4.92-4.76 (m, 1H), 3.78-3.64 (m, 1H), 3.64-3.22 (m, 3H), 2.98 (d, J = 11.7 Hz, 2H), 2.39 (qd, J = 12.4, 3.7 Hz, 2H), 2.31 (s, 3H), 2.19 (t, J = 11.5 Hz, 2H), 1.98 (d, J = 7.5 Hz, 2H), 1.26 (d, J = 6.1 Hz, 3H), 0.78-0.53 (m, 4H) |
| 146 | 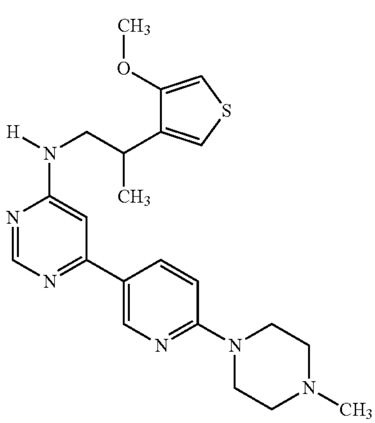 [SMILES: COc1cscc1C(C)CNc1cc(-c2ccc(N3CCN(C)CC3)nc2)ncn1] | 425.13 | (400 MHz, CDCl$_3$) δ 8.68 (d, J = 1.8 Hz, 1H), 8.48 (s, 1H), 8.07 (dd, J = 9.0, 2.4 Hz, 1H), 6.88 (d, J = 3.1 Hz, 1H), 6.63 (d, J = 9.0 Hz, 1H), 6.55 (s, 1H), 6.18 (d, J = 3.2 Hz, 1H), 5.11 (s, 1H), 3.79 (s, 3H), 3.68-3.55 (m, 4H), 3.54-3.23 (m, 2H), 3.22-3.05 (m, 1H), 2.53-2.41 (m, 4H), 2.29 (s, 3H), 1.28 (d, J = 7.0 Hz, 3H). |

| Cmpnd No. | Structure | ESMS (M + H) | ¹H NMR (300 MHz, unless indicated otherwise) NMR peaks given as δ values |
|---|---|---|---|
| 147 | 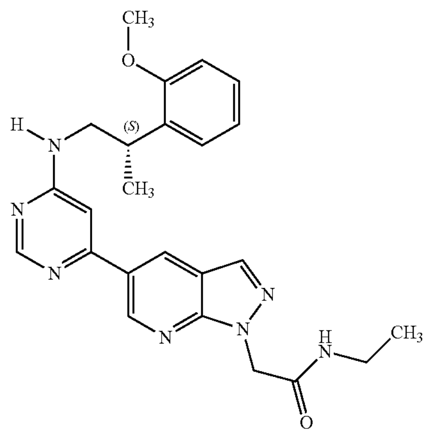 | 447.11 | (400 MHz, CDCl₃) δ 9.04 (s, 1H), 8.67 (s, 1H), 8.55 (s, 1H), 8.12 (s, 1H), 7.16 (d, J = 6.4 Hz, 1H), 6.91 (t, J = 7.4 Hz, 1H), 6.85 (d, J = 8.4 Hz, 1H), 6.66 (s, 1H), 5.94 (s, 1H), 5.17 (s, 2H), 3.79 (s, 3H), 3.53 (t, J = 6.8 Hz, 2H), 3.21 (t, J = 7.0 Hz, 2H), 1.63 (s, 2H), 1.30 (d, J = 6.4 Hz, 3H), 1.14 (t, J = 7.0 Hz, 1H) and 1.01 (t, J = 7.2 Hz, 3H) |
| 148 | 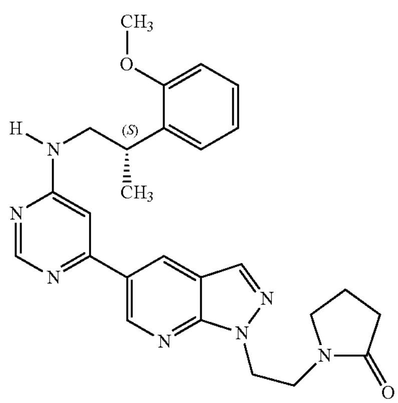 | 474.84 | (400 MHz, CDCl₃) δ 9.02 (s, 1H), 8.59 (s, 1H), 8.54 (s, 1H), 8.02 (s, 1H), 7.20-7.14 (m, 2H), 6.90 (t, J = 7.3 Hz, 1H), 6.84 (d, J = 8.0 Hz, 1H), 6.65 (s, 1H), 5.27 (s, 1H), 4.67 (s, 2H), 3.78 (d, J = 8.5 Hz, 4H), 3.53 (t, J = 6.7 Hz, 2H), 3.07 (t, J = 6.7 Hz, 2H), 2.11 (t, J = 7.8 Hz, 2H), 1.75 (t, J = 7.2 Hz, 2H), 1.29 (d, J = 5.9 Hz, 3H) and 1.14 (t, J = 6.9 Hz, 2H) |
| 149 | 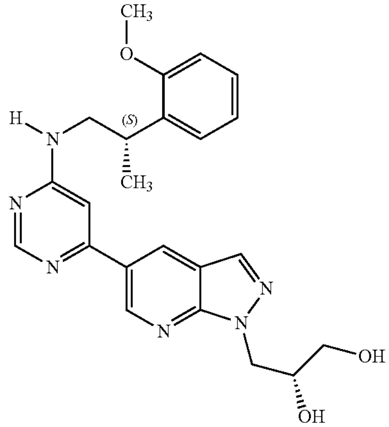 | 436.1 | (400 MHz, CDCl₃) δ 9.06 (s, 1H), 8.71 (s, 1H), 8.59 (s, 1H), 8.10 (s, 1H), 7.28-7.24 (m, 2H), 6.97 (t, J = 7.0 Hz, 1H), 6.71 (s, 1H), 4.74 (d, J = 3.5 Hz, 2H), 4.24 (s, 1H), 4.14 (t, J = 6.8 Hz, 1H), 3.86 (s, 3H), 3.60 (s, 3H), 3.51-3.48 (m, 2H), 2.05 (s, 1H), 1.37 (d, J = 5.2 Hz, 3H) and 1.22 (t, J = 6.5 Hz, 2H) |

TABLE 1-continued

| Cmpnd No. | Structure | ESMS (M + H) | ¹H NMR (300 MHz, unless indicated otherwise) NMR peaks given as δ values |
|---|---|---|---|
| 150 | 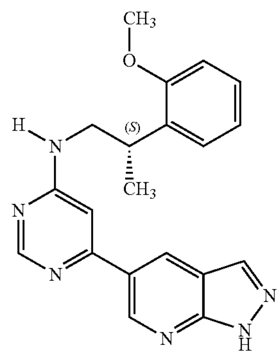 | 362.12 | (400 MHz, CDCl₃) δ 12.69 (s, 1H), 9.13 (s, 1H), 8.73 (s, 1H), 8.58 (s, 1H), 8.14 (d, J = 9.4 Hz, 1H), 7.19-7.14 (m, 2H), 6.90 (t, J = 7.4 Hz, 1 H), 6.85 (d, J = 8.1 Hz, 1H), 6.71 (s, 1H), 5.51 (s, 1H), 3.80 (s, 3H), 3.58-3.50 (m, 3H) and 1.31 (d, J = 6.2 Hz, 3H) |
| 151 | 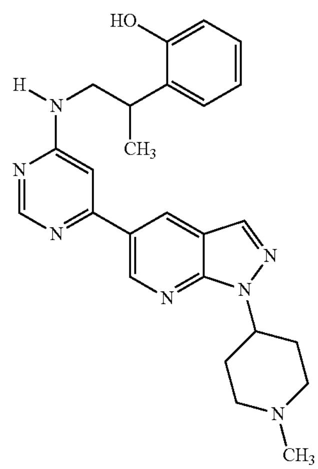 [SMILES: CC(CNc1cc(-c2cnc3c(cnn3C3CCN(C)CC3)c2)ncn1)c1ccccc1O] | 444.32 | |
| 152 | 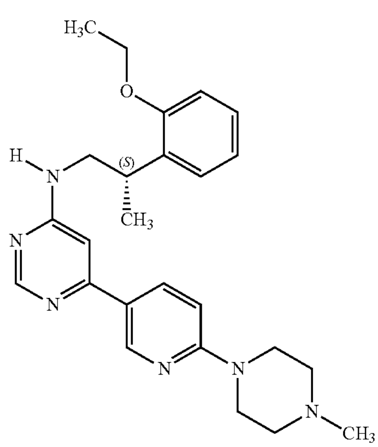 | 433.32 | (CDCl₃) δ 8.73 (d, J = 2.1 Hz, 1H), 8.54 (s, 1H), 8.12 (dd, J = 9.0, 2.4 Hz, 1H), 7.19 (dd, J = 13.0, 4.7 Hz, 2H), 6.93 (dd, J = 14.7, 7.4 Hz, 1H), 6.87 (d, J = 8.1 Hz, 1H), 6.70 (d, J = 9.0 Hz, 1H), 6.52 (s, 1H), 5.11 (s, 1H), 4.06 (m, 2H), 3.72-3.39 (m, 7H), 2.57-2.44 (m, 4H), 2.35 (s, 3H), 1.45-1.29 (m, 6H) |

TABLE 1-continued

| Cmpnd No. | Structure | ESMS (M + H) | ¹H NMR (300 MHz, unless indicated otherwise) NMR peaks given as δ values |
|---|---|---|---|
| 153 | 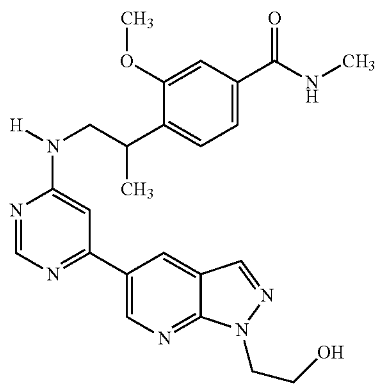 | 462.15 | (CDCl₃) δ 8.95 (s, 1H), 8.61 (s, 1H), 8.51 (s, 1H), 8.01 (s, 1H), 7.32 (s, 1H), 7.16 (s, 2H), 6.60 (s, 1H), 6.24 (s, 1H), 5.37 (s, 1H), 5.23 (s, 1H), 4.64 (s, 2H), 4.09 (d, J = 4.2 Hz, 2H), 3.81 (s, 3H), 3.58-3.52 (m, 3H), 2.90 (d, J = 4.6 Hz, 3H) and 1.28 (d, J = 5.4 Hz, 3H) |
| 154 | 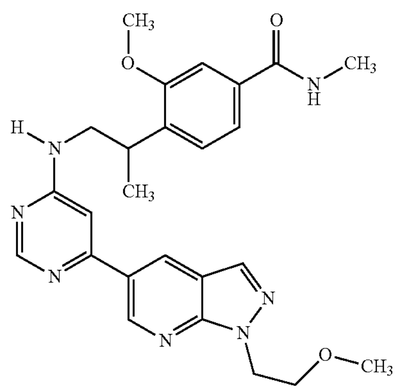 [SMILES: CNC(=O)c1ccc(C(C)CNc2cc(-c3cnc4c(cnn4CCOC)c3)ncn2)c(OC)c1] | 476.16 | (CDCl₃) δ 9.08 (d, J = 1.1 Hz, 1H), 8.67 (d, J = 1.5 Hz, 1H), 8.61 (s, 1H), 8.11 (s, 1H), 7.41 (s, 1H), 7.24 (s, 2H), 6.71 (s, 1H), 6.30 (s, 1H), 5.31 (s, 1H), 4.76 (t, J = 5.5 Hz, 2H), 3.93 (t, J = 5.5 Hz, 2H), 3.89 (s, 3H), 3.62 (s, 3H), 3.34 (s, 3H), 2.99 (d, J = 4.7 Hz, 3H) and 1.36 (d, J = 6.0 Hz, 3H) |
| 155 | 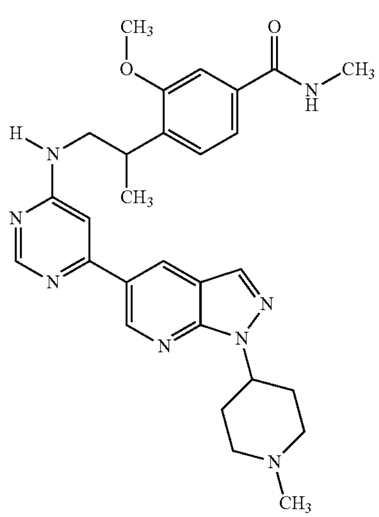 | 515.2 | (CDCl₃) δ 9.05 (d, J = 1.6 Hz, 1H), 8.65-8.61 (m, 2H), 8.08 (s, 1H), 7.41 (s, 1H), 7.24-7.21 (m, 1H), 6.69 (s, 1H), 6.24 (d, J = 3.8 Hz, 1H), 5.30 (s, 1H), 4.94-4.85 (m, 1H), 3.89 (s, 3H), 3.64-3.59 (m, 2H), 3.07-2.99 (m, 5H), 2.52-2.44 (m, 2H), 2.38 (s, 3H), 2.26 (t, J = 11.6 Hz, 2H), 2.05 (d, J = 10.2 Hz, 4H) and 1.36 (d, J = 6.1 Hz, 3H) |

TABLE 1-continued

| Cmpnd No. | Structure | ESMS (M + H) | $^1$H NMR (300 MHz, unless indicated otherwise) NMR peaks given as δ values |
|---|---|---|---|
| 156 | 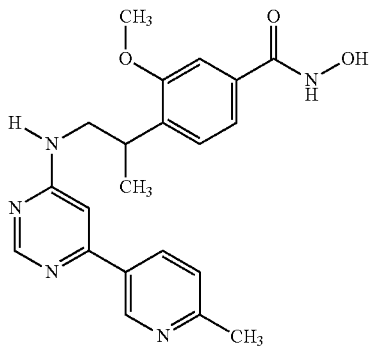 [SMILES: COc1cc(C(=O)NO)ccc1C(C)CNc1cc(-c2ccc(C)nc2)ncn1] | 394.34 | (400 MHz, DMSO-d$_6$) δ 11.21 (br. s, 1H), 9.22-8.15 (m, 4H), 7.63 (d, J = 7.9 Hz, 1H), 7.34 (br. s, 3H), 7.20, 7.01 (2s, 1H), 3.81 (s, 3H), 3.76-3.35 (m, 3H), 2.62 (s, 3H), 1.22 (d, J = 6.5 Hz, 3H) |
| 157 | 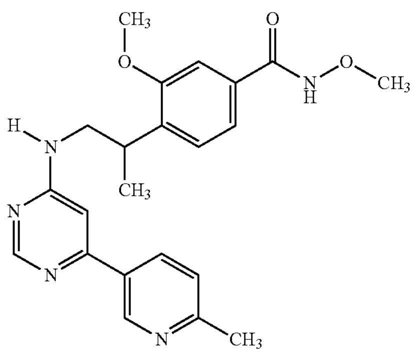 [SMILES: CONC(=O)c1ccc(C(C)CNc2cc(-c3ccc(C)nc3)ncn2)c(OC)c1] | 408.13 | (400 MHz, DMSO-d$_6$) δ 11.74 (s, 1H), 9.24-8.00 (m, 4H), 7.66 (d, J = 7.9 Hz, 1H), 7.34 (br. s, 3H), 7.21, 7.02 (2s, 1H), 3.82 (s, 1H), 3.71 (s, 3H), 3.71-3.33 (m, 3H), 2.63 (s, 1H), 1.23 (d, J = 6.6 Hz, 3H). [2] |
| 158 | 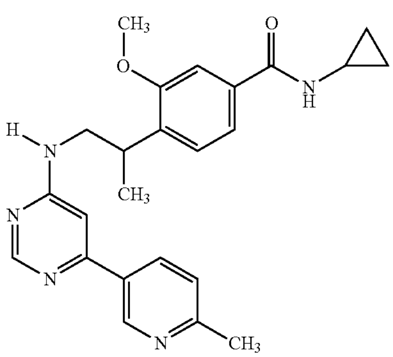 [SMILES: COc1cc(C(=O)NC2CC2)ccc1C(C)CNc1cc(-c2ccc(C)nc2)ncn1] | 418.18 | (400 MHz, DMSO-d$_6$) δ 9.14-8.22 (m, 5H), 7.65-7.00 (m, 5H), 3.81 (s, 3H), 3.76-3.41 (m, 3H), 2.81 (s, 1H), 2.63 (s, 3H), 1.22 (d, J = 6.5 Hz, 3H), 0.76-0.64 (m, 2H), 0.55 (s, 2H) |
| 159 | 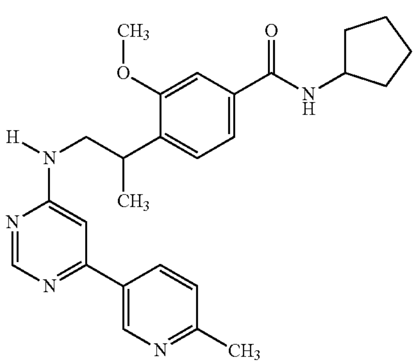 [SMILES: COc1cc(C(=O)NC2CCCC2)ccc1C(C)CNc1cc(-c2ccc(C)nc2)ncn1] | 446.53 | |

TABLE 1-continued

| Cmpnd No. | Structure | ESMS (M + H) | ¹H NMR (300 MHz, unless indicated otherwise) NMR peaks given as δ values |
|---|---|---|---|
| 160 | 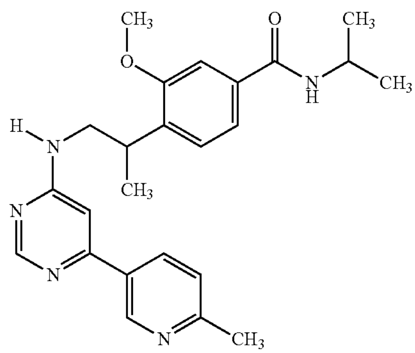 [SMILES: COc1cc(C(=O)NC(C)C)ccc1C(C)CNc1cc(-c2ccc(C)nc2)ncn1] | 420.42 | |
| 161 | 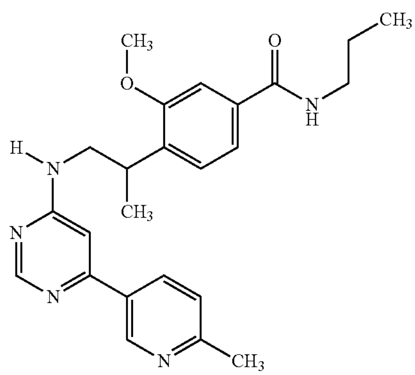 [SMILES: CCCNC(=O)c1ccc(C(C)CNc2cc(-c3ccc(C)nc3)ncn2)c(OC)c1] | 420.17 | (400 MHz, DMSO-d₆) δ 9.08-8.31 (m, 5H), 7.66-7.01 (m, 5H), 3.82 (s, 3H), 3.78-3.43 (m, 3H), 3.20 (t, J = 9.9 Hz, 2H), 2.63 (s, 3H), 1.52 (dd, J = 14.2, 7.2 Hz, 2H), 1.23 (d, J = 6.5 Hz, 3H), 0.88 (t, J = 7.4 Hz, 3H) |
| 162 | 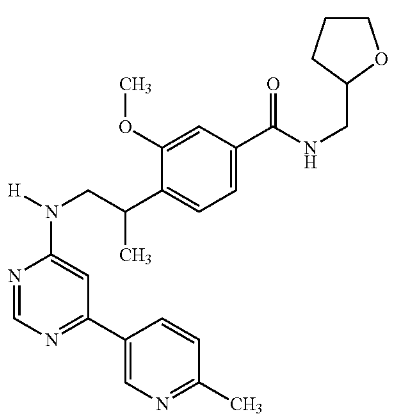 [SMILES: COc1cc(C(=O)NCC2CCCO2)ccc1C(C)CNc1cc(-c2ccc(C)nc2)ncn1] | 462.18 | |
| 163 | 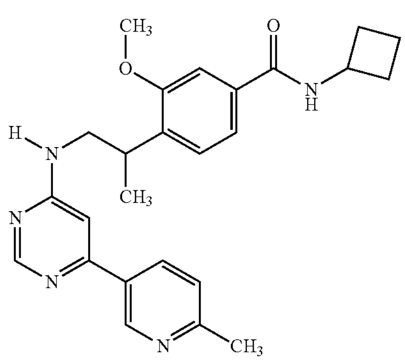 [SMILES: COc1cc(C(=O)NC2CCC2)ccc1C(C)CNc1cc(-c2ccc(C)nc2)ncn1] | 432.42 | |

TABLE 1-continued

| Cmpnd No. | Structure | ESMS (M + H) | ¹H NMR (300 MHz, unless indicated otherwise) NMR peaks given as δ values |
|---|---|---|---|
| 164 | 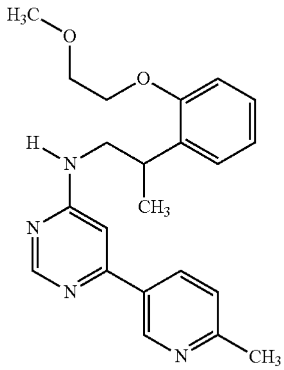 [SMILES: COCCOc1ccccc1C(C)CNc1cc(-c2ccc(C)nc2)ncn1] | 379.54 | (CDCl₃) δ 8.97 (s, 1H), 8.58 (s, 1H), 8.18 (d, J = 8.1 Hz, 1H), 7.26-7.15 (m, 3H), 6.97 (t, J = 7.5 Hz, 1H), 6.86 (d, J = 8.2 Hz, 1H), 6.73 (s, 1H), 4.17 (t, J = 4.3 Hz, 2H), 3.79 (m, 2H), 3.72-3.35 (m, 6H), 2.61 (s, 3H), 1.38 (d, J = 6.8 Hz, 3H) |
| 165 | 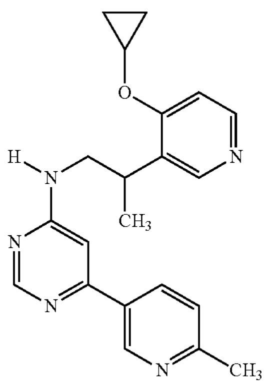 [SMILES: Cc1ccc(-c2cc(NCC(C)c3cnccc3OC3CC3)ncn2)cn1] | | (400 MHz, methanol-d₄) δ 9.02 (s, 1H), 8.68 (d, J = 6.6 Hz, 1H), 8.64 (s, 1H), 8.60 (s, 1H), 8.47 (s, 1H), 7.93 (d, J = 6.8 Hz, 1H), 7.75 (d, J = 8.2 Hz, 1H), 7.00 (s, 1H), 4.29 (s, 1H), 4.02-3.73 (m, 2H), 3.72-3.57 (m, 1H), 2.75 (s, 3H), 1.43 (d, J = 7.0 Hz, 3H), 1.04 (s, 2H), 0.92 (s, 2H) |
| 166 | 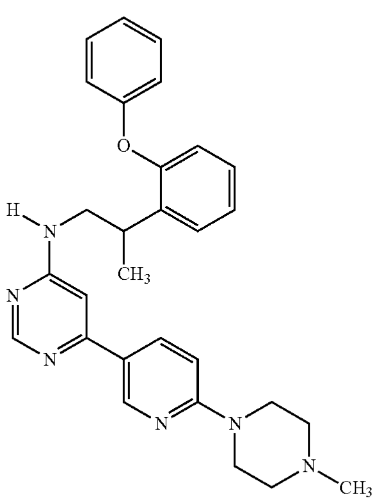 [SMILES: CC(CNc1cc(-c2ccc(N3CCN(C)CC3)nc2)ncn1)c1ccccc1Oc1ccccc1] | 509.22 | (400 MHz, DMSO-d₆) δ 9.32-9.22 (m, 1H), 8.71-8.58 (m, 2H), 8.02, 7.92 (2d, J = 8.7 Hz, 1H), 7.65-7.42 (m, 1H), 7.35-7.12 (m, 4H), 7.15-6.70 (m, 6H), 3.87-3.37 (m, 11H), 2.06 (s, 3H), 1.34-1.16 (m, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 167 | 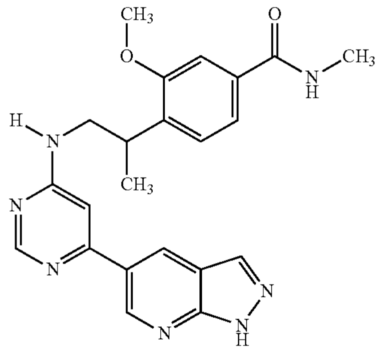 [SMILES: CNC(=O)c1ccc(C(C)CNc2cc(-c3cnc4[nH]ncc4c3)ncn2)c(OC)c1] | 418.34 | (400 MHz, methanol-d₄) δ 9.03 (s, 1H), 8.70 (d, J = 1.7 Hz, 1H), 8.46 (s, 1H), 8.37 (s, 1H), 8.21 (s, 1H), 7.39-7.31 (m, 3H), 6.86 (s, 1H), 3.90-3.81 (m, 3H), 3.63 (d, J = 6.2 Hz, 2H), 2.89 (s, 3H) and 1.32 (s, 3H) |
| 168 | 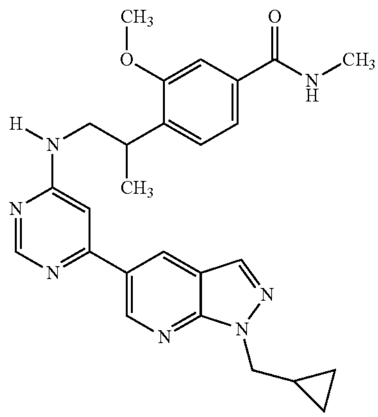 [SMILES: CNC(=O)c1ccc(C(C)CNc2cc(-c3cnc4c(cnn4CC4CC4)c3)ncn2)c(OC)c1] | 473.19 | |
| 169 | 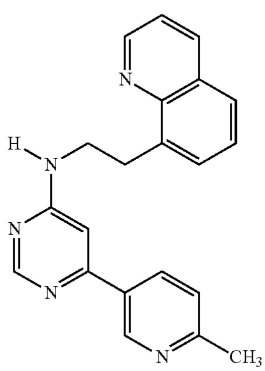 [SMILES: Cc1ccc(-c2cc(NCCc3cccc4cccnc34)ncn2)cn1] | 342 | (DMSO-d₆) δ 8.99 (s, 2H), 8.50 (s, 1H), 8.38 (dd, J = 8.3, 1.6 Hz, 1H), 8.22 (s, 1H), 7.87 (dd, J = 8.2, 1.2 Hz, 1H), 7.58 (dd, J = 27.2, 19.2 Hz, 4H), 7.38 (d, J = 8.1 Hz, 1H), 6.99 (d, J = 30.2 Hz, 1H), 3.74 (s, 2H), 3.50 (t, J = 7.0 Hz, 2H), 2.53 (d, J = 4.9 Hz, 3H) |
| 170 | 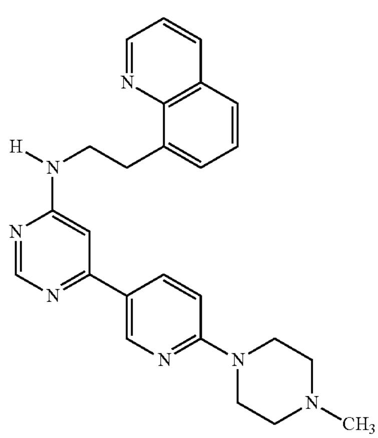 [SMILES: CN1CCN(c2ccc(-c3cc(NCCc4cccc5cccnc45)ncn3)cn2)CC1] | 426 | (DMSO-d₆) δ 8.99 (s, 1H), 8.77 (s, 1H), 8.47-8.31 (m, 2H), 8.09 (d, J = 7.0 Hz, 1H), 7.87 (dd, J = 8.1, 1.3 Hz, 1H), 7.73-7.42 (m, 4H), 6.92 (d, J = 9.1 Hz, 1H), 3.85-3.36 (m, 8H), 2.46-2.31 (m, 4H), 2.22 (s, 3H) |

| Cmpnd No. | Structure | ESMS (M + H) | $^1$H NMR (300 MHz, unless indicated otherwise) NMR peaks given as δ values |
|---|---|---|---|
| 171 | 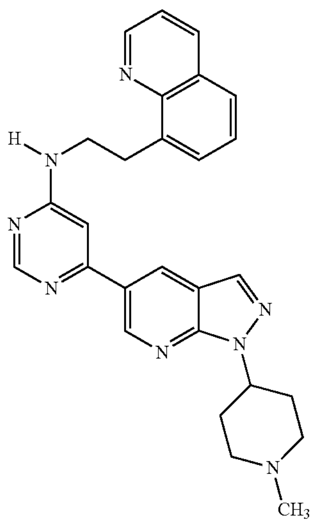 [SMILES: CN1CCC(n2ncc3cc(-c4cc(NCCc5cccc6cccnc56)ncn4)cnc32)CC1] | 464 | (DMSO-d$_6$) δ 9.15 (s, 1H), 8.98 (s, 1H), 8.79 (d, J = 2.0 Hz, 1H), 8.52 (s, 1H), 8.38 (dd, J = 8.3, 1.7 Hz, 1H), 8.29 (s, 1H), 7.87 (dd, J = 8.2, 1.3 Hz, 1H), 7.77-7.44 (m, 4H), 7.01 (s, 1H), 4.91-4.76 (m, 1H), 3.75 (s, 2H), 3.52 (t, J = 7.1 Hz, 2H), 2.94 (d, J = 9.6 Hz, 2H), 2.36-2.03 (m, 7H), 1.93 (d, J = 9.5 Hz, 2H) |
| 172 | 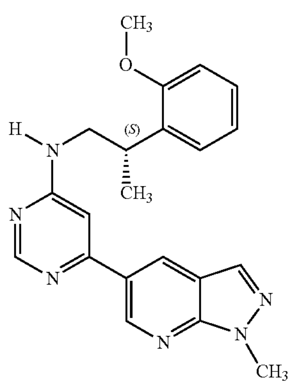 | 375.11 | (400 MHz, CDCl$_3$) δ 9.11 (s, 1H), 8.68 (s, 1H), 8.54 (s, 1H), 7.95 (s, 1H), 7.20-7.16 (m, 2H), 6.89-6.82 (m, 2H), 6.72 (s, 1H), 5.35 (s, 1H), 4.21 (s, 3H), 3.79 (s, 3H), 3.53 (d, J = 6.8 Hz, 3H) and 1.29 (d, J = 4.9 Hz, 3H) |
| 173 | 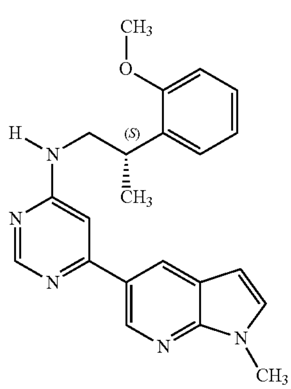 | 373.34 | (400 MHz, CDCl$_3$) δ 8.91 (s, 1H), 8.62 (s, 1H), 8.55 (s, 1H), 7.24 (s, 4H), 6.98 (s, 1H), 6.91 (d, J = 4.2 Hz, 1H), 6.54 (s, 1H), 5.33 (s, 1H), 3.93 (s, 3H), 3.86 (s, 3H), 3.57 (s, 3H) and 1.36 (s, 3H) |

TABLE 1-continued
| Cmpnd No. | Structure | ESMS (M + H) | $^1$H NMR (300 MHz, unless indicated otherwise) NMR peaks given as δ values |
|---|---|---|---|
| 174 | 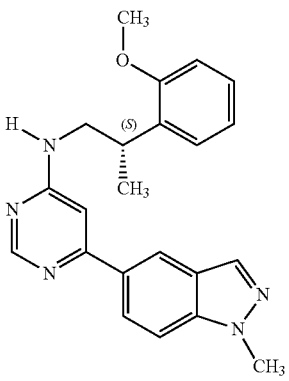 | 375.11 | (400 MHz, CDCl$_3$) δ 8.62 (s, 1H), 8.39 (s, 1H), 8.07 (s, 2H), 7.47 (d, J = 8.3 Hz, 1H), 7.26 (d, J = 10.0 Hz, 2H), 7.01-6.97 (m, 1H), 6.92 (d, J = 7.7 Hz, 1H), 6.76 (s, 1H), 5.25 (s, 1H), 4.13 (s, 3H), 3.87 (s, 3H), 3.62-3.49 (m, 3H) and 1.38 (d, J = 5.2 Hz, 3H) |
| 175 | 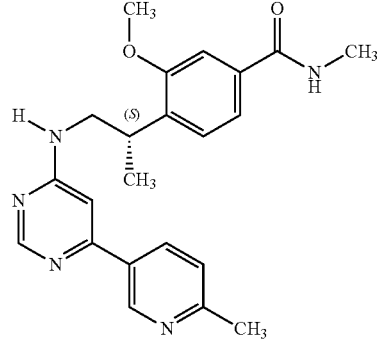 | 392.46 | (400 MHz, DMSO-d$_6$) δ 9.11-8.33 (m, 5H), 7.65 (br. s, 1H), 7.54-6.82 (m, 4H), 3.82 (s, 3H), 3.72-3.52 (m, 4H), 2.77 (d, J = 3.5 Hz, 3H), 2.63 (s, 3H), 1.23 (d, J = 6.6 Hz, 3H) |
| 176 | 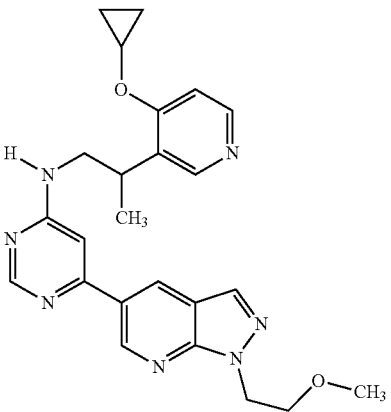 [SMILES: COCCn1ncc2cc(-c3cc(NCC(C)c4cnccc4OC4CC4)ncn3)cnc21] | 446.18 | (400 MHz, methanol-d$_4$) δ 8.92 (s, 1H), 8.78-8.63 (m, 3H), 8.59 (s, 1H), 8.28 (s, 1H), 7.91 (d, J = 6.9 Hz, 1H), 7.00 (s, 1H), 4.74 (t, J = 5.2 Hz, 2H), 4.27 (s, 1H), 4.02-3.71 (m, 4H), 3.71-3.56 (m, 1H), 3.28 (s, 3H), 1.42 (d, J = 7.0 Hz, 3H), 1.03 (s, 2H), 0.91 (s, 2H) |

| Cmpnd No. | Structure | ESMS (M + H) | ¹H NMR (300 MHz, unless indicated otherwise) NMR peaks given as δ values |
|---|---|---|---|
| 177 | 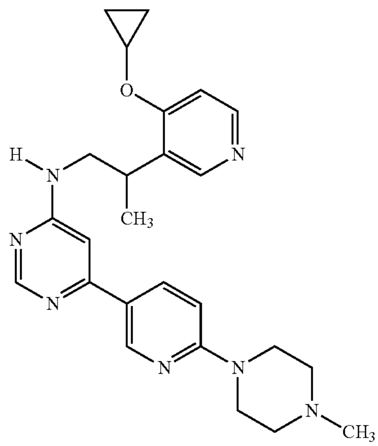 [SMILES: CC(CNc1cc(-c2ccc(N3CCN(C)CC3)nc2)ncn1)c1cnccc1OC1CC1] | 446.18 | (400 MHz, methanol-d₄) δ 8.68-8.60 (m, 3H), 8.58 (s, 1H), 8.01 (dd, J = 9.1, 2.4 Hz, 1H), 7.90 (d, J = 6.8 Hz, 1H), 7.10 (d, J = 9.1 Hz, 1H), 6.91 (s, 1H), 4.72 (s, 2H), 4.34-4.19 (m, 1H), 3.95 (dd, J = 14.1, 6.4 Hz, 1H), 3.85 (dd, J = 13.5, 7.6 Hz, 1H), 3.69-3.53 (m, 3H), 3.46-3.33 (m, 2H), 3.27-3.06 (m, 2H), 2.96 (s, 3H), 1.40 (d, J = 7.1 Hz, 3H), 1.07-0.85 (m, 4H) |
| 178 | 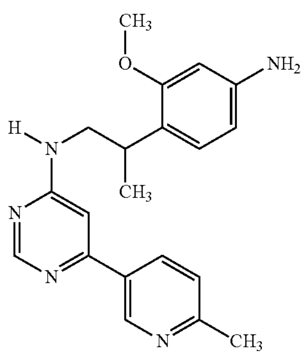 [SMILES: COc1cc(N)ccc1C(C)CNc1cc(-c2ccc(C)nc2)ncn1] | 350.34 | (400 MHz, CDCl₃) δ 8.93 (s, 1H), 8.52 (s, 1H), 8.12 (dd, J = 8.1, 2.1 Hz, 1H), 7.18 (d, J = 5.9 Hz, 1H), 6.91 (d, J = 8.0 Hz, 1H), 6.58 (s, 1H), 6.22 (dd, J = 8.0, 2.1 Hz, 1H), 6.18 (d, J = 2.0 Hz, 1H), 3.72 (s, 3H), 3.37 (br. s, 3H), 2.55 (s, 3H), 1.23 (d, J = 6.0 Hz, 3H) |
| 179 | 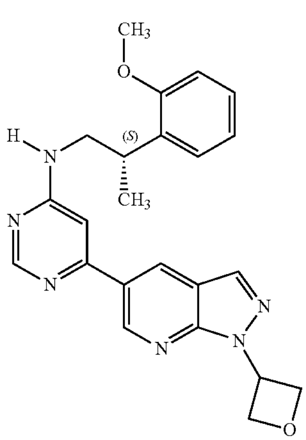 | 417.29 | (400 MHz, CDCl₃) δ 9.01 (s, 1H), 8.63 (s, 1H), 8.54 (s, 1H), 8.13 (s, 1H), 7.18 (d, J = 9.9 Hz, 2H), 6.90 (s, 1H), 6.84 (d, J = 5.9 Hz, 1H), 6.65 (s, 1H), 6.18 (s, 1H), 5.28 (s, 2H), 5.08 (s, 2H), 3.79 (s, 3H), 3.51 (s, 3H), 1.81 (s, 3H), 1.29 (s, 1H) and 1.17 (s, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 180 | 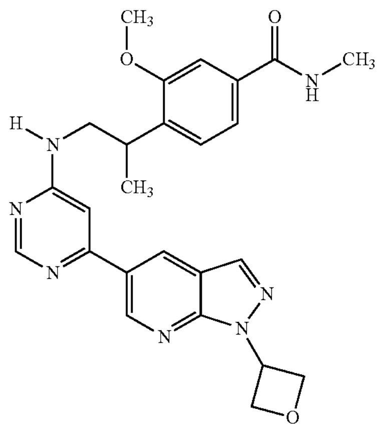 [SMILES: CNC(=O)c1ccc(C(C)CNc2cc(-c3cnc4c(cnn4C4COC4)c3)ncn2)c(OC)c1] | 475.17 | (400 MHz, CDCl$_3$) δ 8.99 (s, 1H), 8.62 (s, 1H), 8.53 (s, 1H), 8.13 (s, 1H), 7.34 (s, 1H), 7.19-7.16 (m, 1H), 6.62 (s, 1H), 6.17-6.14 (m, 2H), 5.27 (s, 2H), 5.08 (d, J = 5.9 Hz, 2H), 3.83 (s, 3H), 3.53 (s, 2H), 3.41 (d, J = 6.7 Hz, 1H), 2.92 (s, 3H), 1.76 (s, 2H) and 1.20-1.12 (m, 3H) |
| 181 | 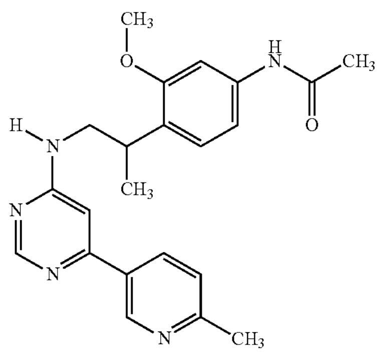 [SMILES: COc1cc(NC(C)=O)ccc1C(C)CNc1cc(-c2ccc(C)nc2)ncn1] | 392.39 | (400 MHz, DMSO-d$_6$) δ 9.92, 9.87 (2s, 1H), 9.19-8.58 (m, 3H), 8.47-8.12 (m, 1H), 7.63 (d, J = 7.8 Hz, 1H), 7.39-6.89 (m, 4H), 3.81-3.27 (m, 6H), 2.62 (s, 3H), 2.02 (s, 3H), 1.20 (d, J = 6.7 Hz, 3H) |
| 182 | 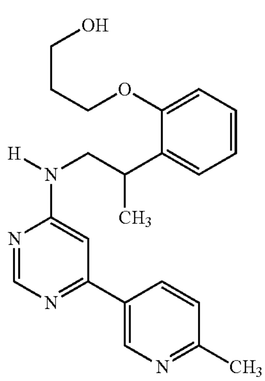 [SMILES: Cc1ccc(-c2cc(NCC(C)c3ccccc3OCCCO)ncn2)cn1] | 379.46 | (CDCl$_3$) δ 8.99 (d, J = 2.1 Hz, 1H), 8.53 (s, 1H), 8.18 (dd, J = 8.1, 2.3 Hz, 1H), 7.30-7.14 (m, 3H), 6.96 (dd, J = 16.4, 7.9 Hz, 2H), 6.59 (d, J = 1.0 Hz, 1H), 4.29 (m, 1H), 4.20-4.05 (m, 1H), 4.05-3.89 (m, 1H), 3.91-3.76 (m, 1H), 3.70 (s, 1H), 3.42 (m, 2H), 2.62 (s, 3H), 2.18-2.00 (m, 2H), 1.40 (d, J = 7.0 Hz, 3H) |
| 183 | 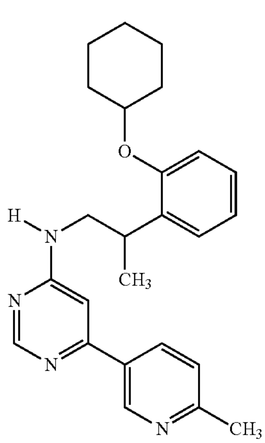 [SMILES: Cc1ccc(-c2cc(NCC(C)c3ccccc3OC3CCCCC3)ncn2)cn1] | 403.21 | (CDCl$_3$) δ 8.97 (s, 1H), 8.60 (s, 1H), 8.16 (dd, J = 8.1, 2.4 Hz, 1H), 7.25-7.11 (m, 3H), 6.92 (dd, J = 11.7, 7.6 Hz, 2H), 6.59 (s, 1H), 4.31 (m, 1H), 3.57 (dd, J = 19.1, 13.1 Hz, 3H), 2.62 (s, 3H), 1.96 (m, 2H), 1.74 (m, 2H), 1.50 (m, 4H), 1.32 (m, 5H) |

| Cmpnd No. | Structure | ESMS (M + H) | $^1$H NMR (300 MHz, unless indicated otherwise) NMR peaks given as δ values |
|---|---|---|---|
| 184 | 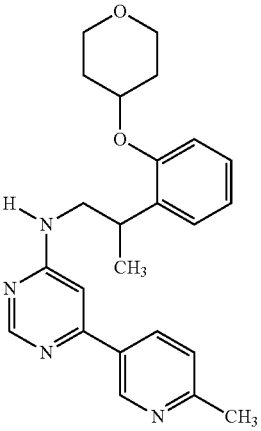 [SMILES: Cc1ccc(-c2cc(NCC(C)c3ccccc3OC3CCOCC3)ncn2)cn1] | 405.06 | (CDCl$_3$) δ 8.98 (d, J = 2.0 Hz, 1H), 8.60 (s, 1H), 8.17 (dd, J = 8.1, 2.3 Hz, 1H), 7.26-7.12 (m, 3H), 6.96 (dd, J = 8.0, 6.9 Hz, 1H), 6.90 (d, J = 8.7 Hz, 1H), 6.60 (s, 1H), 4.62-4.46 (m, 1H), 4.06-3.84 (m, 2H), 3.79-3.40 (m, 5H), 2.62 (s, 3H), 2.03 (m, 2H), 1.80 (m, 2H), 1.36 (d, J = 6.7 Hz, 3H) |
| 185 | 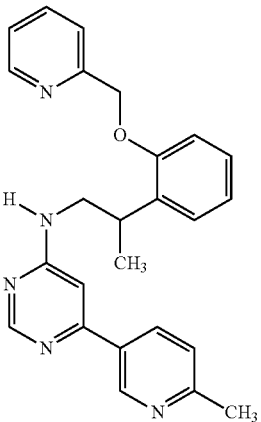 [SMILES: Cc1ccc(-c2cc(NCC(C)c3ccccc3OCc3ccccn3)ncn2)cn1] | 412.42 | (CDCl$_3$) δ 8.95 (s, 1H), 8.60 (m, 2H), 8.21 (d, J = 7.0 Hz, 1H), 7.69 (m, 1H), 7.46 (d, J = 7.8 Hz, 1H), 7.30-7.13 (m, 4H), 7.00 (t, J = 7.5 Hz, 1H), 6.93 (d, J = 8.2 Hz, 1H), 6.75 (s, 1H), 5.22 (s, 2H), 3.83-3.51 (m, 3H), 2.63 (s, 3H), 1.40 (d, J = 6.8 Hz, 3H) |
| 186 | 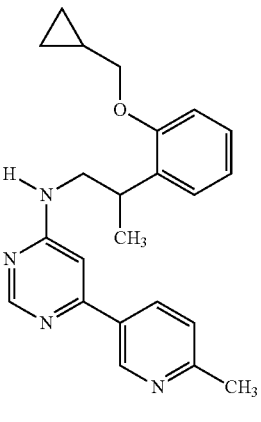 [SMILES: Cc1ccc(-c2cc(NCC(C)c3ccccc3OCC3CC3)ncn2)cn1] | 375.05 | (CDCl$_3$) δ 8.98 (d, J = 1.9 Hz, 1H), 8.60 (s, 1H), 8.17 (dd, J = 8.1, 2.3 Hz, 1H), 7.20 (m, 3H), 6.94 (tt, J = 4.3, 2.2 Hz, 1H), 6.85 (d, J = 8.2 Hz, 1H), 6.62 (s, 1H), 3.90-3.79 (d, 2H), 3.61 (m, 3H), 2.62 (s, 3H), 1.38 (d, J = 6.7 Hz, 3H), 1.30-1.19 (m, 1H), 0.60 (m, 2H), 0.33 (m, 2H) |

TABLE 1-continued

| Cmpnd No. | Structure | ESMS (M + H) | ¹H NMR (300 MHz, unless indicated otherwise) NMR peaks given as δ values |
|---|---|---|---|
| 187 | 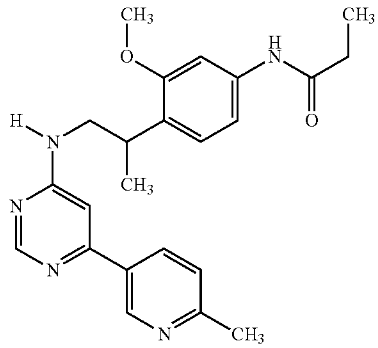 [SMILES: CCC(=O)Nc1ccc(C(C)CNc2cc(-c3ccc(C)nc3)ncn2)c(OC)c1] | 406.41 | (400 MHz, DMSO-d$_6$) δ 9.85, 9.80 (2s, 1H), 9.06-8.28 (m, 4H), 7.62 (d, J = 7.9 Hz, 1H), 7.35-6.81 (m, 4H), 3.72 (s, 3H), 3.70-3.24 (m, 3H), 2.62 (s, 3H), 2.29 (m, 2H), 1.20 (d, J = 6.7 Hz, 3H), 1.07 (t, J = 7.4 Hz, 3H) |
| 188 | 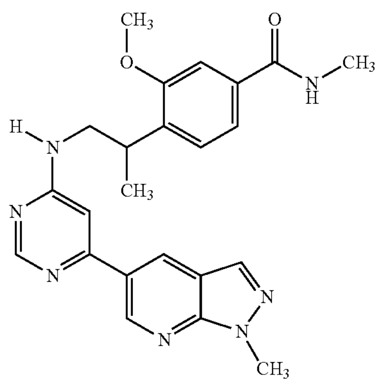 [SMILES: CNC(=O)c1ccc(C(C)CNc2cc(-c3cnc4c(cnn4C)c3)ncn2)c(OC)c1] | 432.17 | (400 MHz, DMSO-d$_6$) δ 9.13 (s, 1H), 8.77 (s, 1H), 8.56 (s, 2H), 8.42 (s, 1H), 7.51 (s, 1H), 7.43 (s, 2H), 7.34 (s, 1H), 7.02 (s, 1H), 4.23 (s, 3H), 3.83 (s, 3H), 3.58 (s, 1H), 3.51 (s, 1H), 3.34 (s, 1H), 2.78 (s, 3H) and 1.23 (s, 3H) |
| 189 | 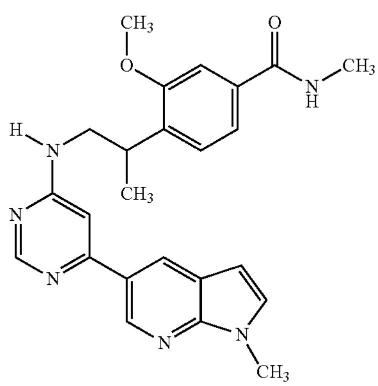 [SMILES: CNC(=O)c1ccc(C(C)CNc2cc(-c3cnc4c(ccn4C)c3)ncn2)c(OC)c1] | 431.4 | (CDCl$_3$) δ 8.79 (s, 1H), 8.51 (s, 1H), 8.44 (s, 1H), 7.32 (s, 1H), 7.20 (s, 1H), 7.16 (s, 2H), 6.64 (s, 1H), 6.46 (s, 1H), 6.26 (s, 1H), 5.35 (d, J = 3.8 Hz, 1H), 3.85 (s, 3H), 3.81 (s, 3H), 3.54 (t, J = 6.4 Hz, 3H), 2.90 (d, J = 4.0 Hz, 3H) and 1.28 (d, J = 5.4 Hz, 3H) |
| 190 | 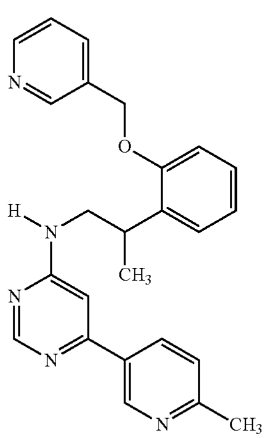 [SMILES: Cc1ccc(-c2cc(NCC(C)c3ccccc3OCc3cccnc3)ncn2)cn1] | 412.42 | (CDCl$_3$) δ 8.95 (d, J = 2.0 Hz, 1H), 8.69 (s, 1H), 8.57 (m, 2H), 8.13 (dd, J = 8.1, 2.3 Hz, 1H), 7.72 (d, J = 7.9 Hz, 1H), 7.26-7.18 (m, 4H), 7.08-6.92 (m, 2H), 6.55 (s, 1H), 5.10 (s, 2H), 3.61 (dd, J = 12.4, 6.3 Hz, 3H), 2.62 (s, 3H), 1.35 (d, J = 6.6 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 191 | 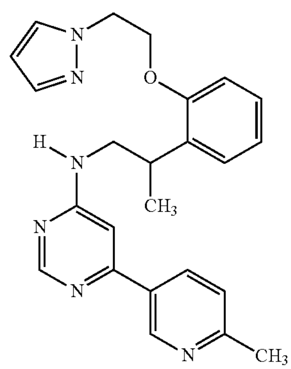 [SMILES: Cc1ccc(-c2cc(NCC(C)c3ccccc3OCCn3cccn3)ncn2)cn1] | 415.46 | |
| 192 | 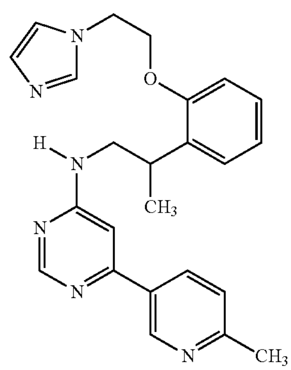 | 415.53 | (CDCl₃) δ 9.01 (d, J = 1.9 Hz, 1H), 8.60 (s, 1H), 8.18 (dd, J = 8.1, 2.3 Hz, 1H), 7.70 (s, 1H), 7.24 (s, 1H), 7.22-7.15 (m, 1H), 7.12-6.96 (m, 3H), 6.81 (d, J = 8.2 Hz, 1H), 6.62 (s, 1H), 5.28 (s, 1H), 4.43-4.30 (m, 2H), 4.24 (t, J = 5.1 Hz, 2H), 3.45 (m, 3H), 2.62 (s, 3H), 1.28 (dd, J = 6.4, 3.2 Hz, 3H) |
| 193 | 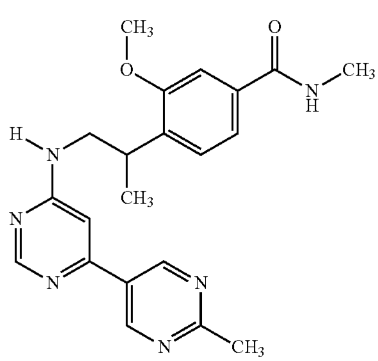 [SMILES: CNC(=O)c1ccc(C(C)CNc2cc(-c3cnc(C)nc3)ncn2)c(OC)c1] | 393 | (400 MHz, DMSO-d₆) δ 9.23 (d, J = 53.2 Hz, 2H), 8.59-8.31 (m, 2H), 7.58 (s, 1H), 7.45-7.25 (m, 3H), 6.97 (s, 1H), 3.81 (s, 3H), 3.68-3.40 (m, 3H), 2.77 (d, J = 4.4 Hz, 3H), 2.68 (s, 3H), 1.20 (d, J = 5.5 Hz, 3H) |
| 194 | 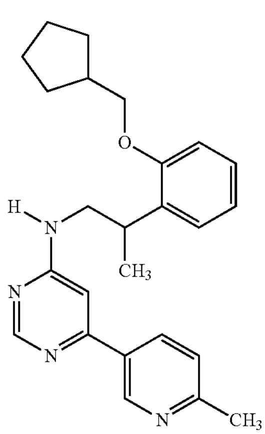 [SMILES: Cc1ccc(-c2cc(NCC(C)c3ccccc3OCC3CCCC3)ncn2)cn1] | 403.18 | (CDCl₃) δ 8.97 (d, J = 2.0 Hz, 1H), 8.60 (s, 1H), 8.16 (dd, J = 8.1, 2.3 Hz, 1H), 7.25-7.12 (m, 2H), 7.00-6.90 (m, 1H), 6.88 (d, J = 8.1 Hz, 1H), 6.59 (s, 1H), 5.18 (s, 1H), 3.87 (ddd, J = 20.9, 8.9, 7.0 Hz, 2H), 3.71-3.43 (m, 3H), 2.62 (s, 3H), 2.34 (dp, J = 14.8, 7.6 Hz, 1H), 1.82 (d, J = 5.2 Hz, 2H), 1.67-1.47 (m, 5H), 1.36 (d, J = 6.4 Hz, 4H) |

TABLE 1-continued

| Cmpnd No. | Structure | ESMS (M + H) | ¹H NMR (300 MHz, unless indicated otherwise) NMR peaks given as δ values |
|---|---|---|---|
| 195 | 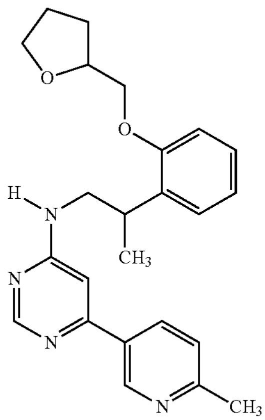 | 405.03 | |
| 196 | 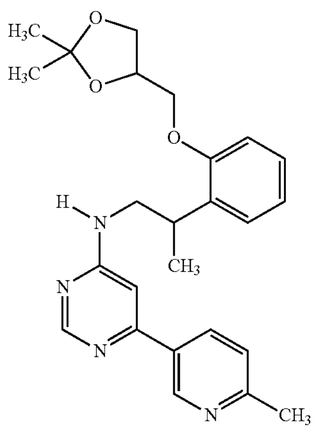 | 435.11 | |
| 197 | 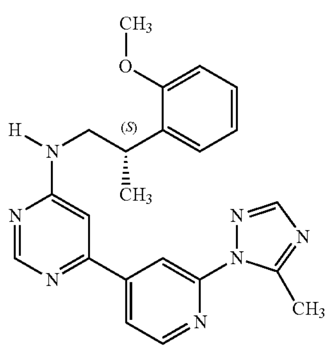 | 403.16 | |
| 198 | 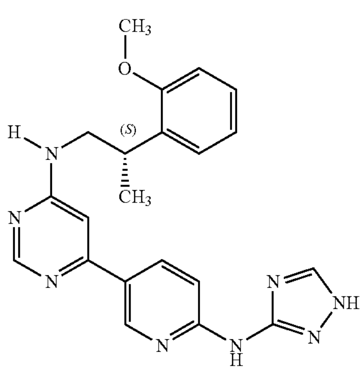 | 403.16 | |

TABLE 1-continued

| Cmpnd No. | Structure | ESMS (M + H) | ¹H NMR (300 MHz, unless indicated otherwise) NMR peaks given as δ values |
|---|---|---|---|
| 199 | 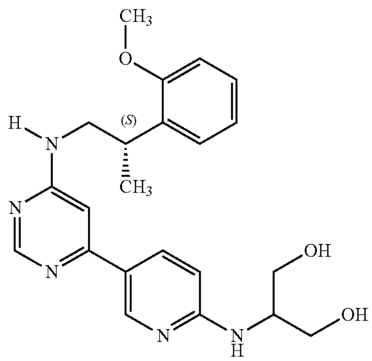 | 410.19 | |
| 200 | 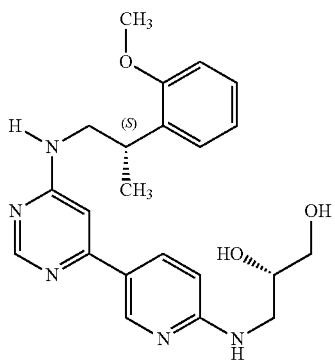 | 410.19 | |
| 201 | 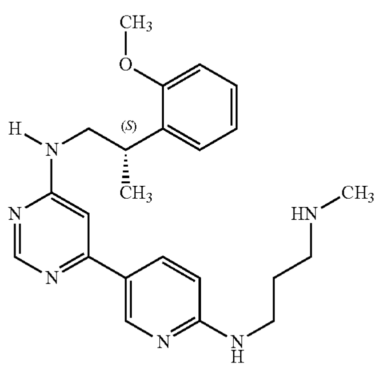 | 407.2 | |
| 202 | 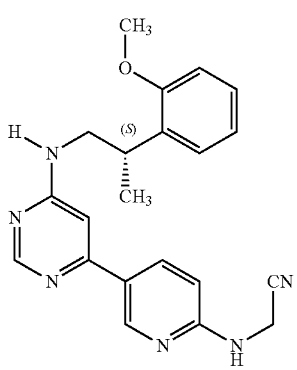 | 375.18 | |

TABLE 1-continued

| Cmpnd No. | Structure | ESMS (M + H) | $^1$H NMR (300 MHz, unless indicated otherwise) NMR peaks given as δ values |
|---|---|---|---|
| 203 | 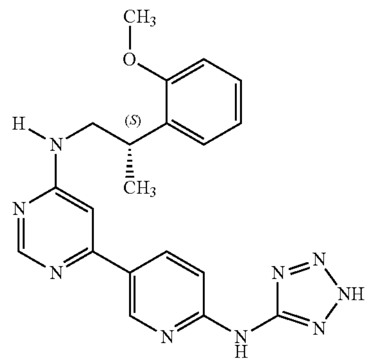 | 404.17 | |
| 204 | 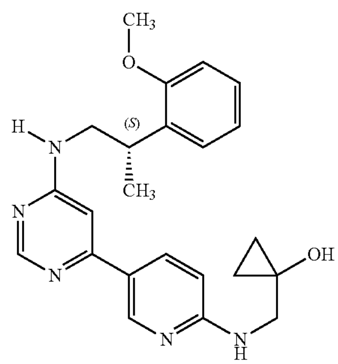 | 406.16 | |
| 205 | 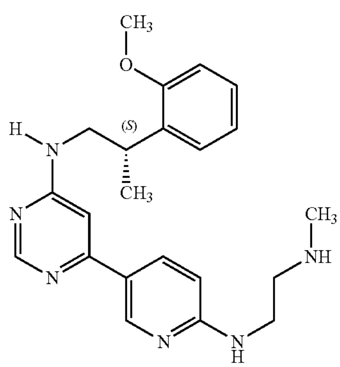 | 393.21 | |
| 206 | 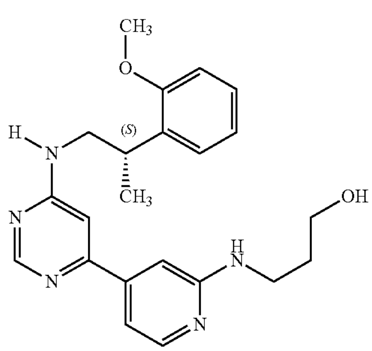 | 394.18 | |

TABLE 1-continued

| Cmpnd No. | Structure | ESMS (M + H) | ¹H NMR (300 MHz, unless indicated otherwise) NMR peaks given as δ values |
|---|---|---|---|
| 207 | 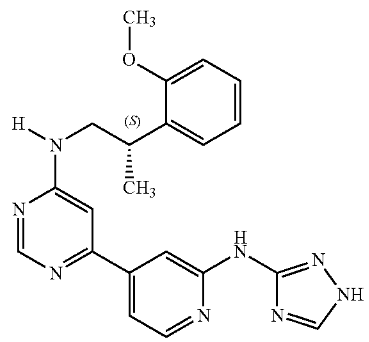 | 403.2 | |
| 208 | 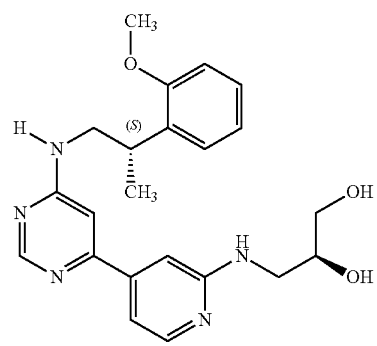 | 410.16 | |
| 209 | 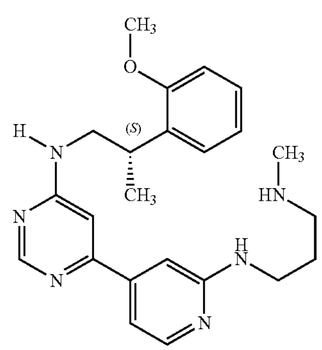 | 407.24 | |
| 210 | 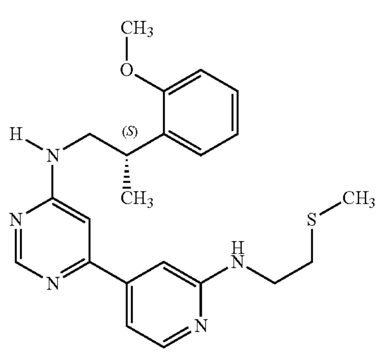 | 410.19 | |

TABLE 1-continued

| Cmpnd No. | Structure | ESMS (M + H) | ¹H NMR (300 MHz, unless indicated otherwise) NMR peaks given as δ values |
|---|---|---|---|
| 211 | 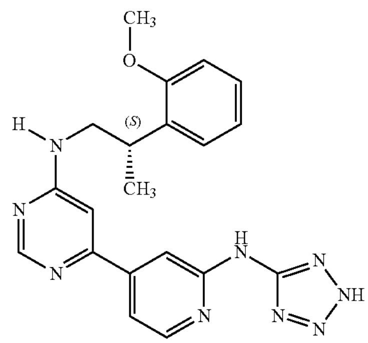 | 404.17 | |
| 212 | 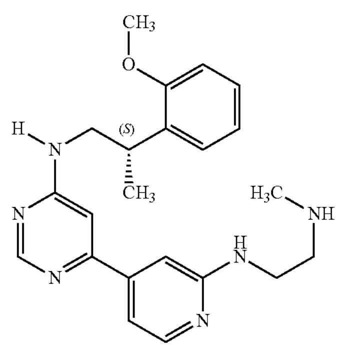 | 393.24 | |
| 213 | 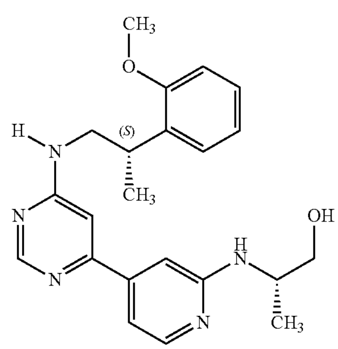 | 394.22 | |
| 214 | 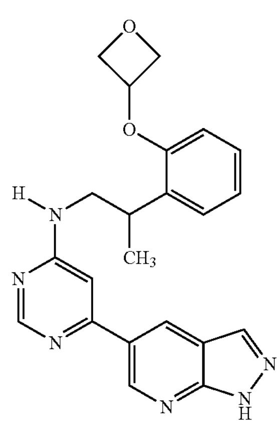 [SMILES: CC(CNc1cc(-c2cnc3[nH]ncc3c2)ncn1)c1ccccc1OC1COC1] | 403.34 | (400 MHz, methanol-$d_4$) δ 9.04 (d, J = 1.9 Hz, 1H), 8.73 (s, 1H), 8.49 (s, 1H), 8.21 (s, 1H), 7.31 (d, J = 7.6 Hz, 1H), 7.12 (t, J = 7.7 Hz, 1H), 6.96 (t, J = 7.5 Hz, 1H), 6.88 (d, J = 1.1 Hz, 1H), 6.46 (d, J = 8.2 Hz, 1H), 5.28-5.13 (m, 1H), 5.00-4.89 (m, 2H), 4.57 (dd, J = 11.7, 5.0 Hz, 2H), 3.88-3.63 (m, 2H), 3.60-3.51 (m, 1H), 1.34 (d, J = 6.4 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 215 | 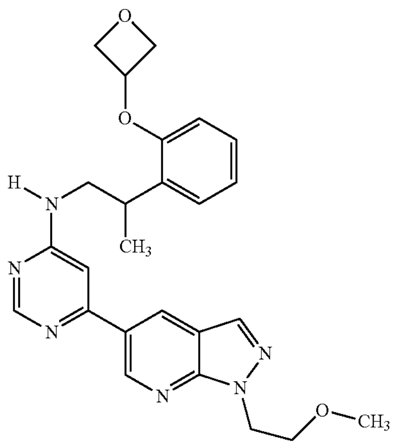 [SMILES: COCCn1ncc2cc(-c3cc(NCC(C)c4ccccc4OC4COC4)ncn3)cnc21] | 461.31 | (400 MHz, CDCl₃) δ 10.22 (s, 1H), 8.92 (s, 1H), 8.66 (s, 1H), 8.39 (s, 1H), 8.12 (s, 1H), 7.24 (d, J = 7.5 Hz, 1H), 7.09-6.99 (m, 1H), 6.99-6.87 (m, 1H), 6.71 (s, 1H), 6.27 (d, J = 8.0 Hz, 1H), 5.21-5.07 (m, 1H), 4.94-4.83 (m, 2H), 4.75-4.67 (m, 2H), 4.62-4.53 (m, 2H), 3.86 (s, 2H), 3.70-3.62 (m, 1H), 3.59-3.48 (m, 2H), 3.27 (s, 3H), 1.39 (d, J = 6.8 Hz, 3H) |
| 216 | 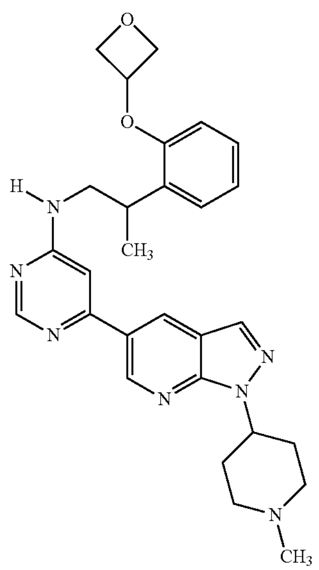 [SMILES: CC(CNc1cc(-c2cnc3c(cnn3C3CCN(C)CC3)c2)ncn1)c1ccccc1OC1COC1] | 500.41 | (400 MHz, CDCl₃) δ 8.99 (s, 1H), 8.59 (d, J = 1.9 Hz, 1H), 8.56 (s, 1H), 8.01 (s, 1H), 7.24-7.20 (m, 1H), 7.09 (t, J = 7.8 Hz, 1H), 6.94 (t, J = 7.5 Hz, 1H), 6.63 (s, 1H), 6.34-6.29 (m, 1H), 5.18-5.05 (m, 2H), 4.96-4.75 (m, 3H), 4.63-4.58 (m, 2H), 3.67-3.44 (m, 3H), 2.97 (d, J = 11.6 Hz, 2H), 2.46-2.32 (m, 2H), 2.30 (s, 3H), 2.18 (t, J = 11.8 Hz, 2H), 1.97 (t, J = 5.6 Hz, 2H), 1.32 (d, J = 6.5 Hz, 3H) |
| 217 | 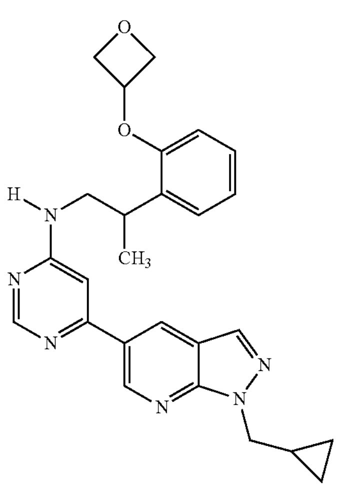 [SMILES: CC(CNc1cc(-c2cnc3c(cnn3CC3CC3)c2)ncn1)c1ccccc1OC1COC1] | 457.35 | (400 MHz, CDCl₃) δ 10.33 (s, 1H), 8.90 (s, 1H), 8.65 (d, J = 2.0 Hz, 1H), 8.38 (s, 1H), 8.09 (s, 1H), 7.23 (t, J = 7.8 Hz, 1H), 7.12-6.98 (m, 1H), 6.93 (t, J = 7.3 Hz, 1H), 6.73 (s, 1H), 6.28 (d, J = 8.0 Hz, 1H), 5.19-5.06 (m, 1H), 4.90 (s, 2H), 4.72-4.48 (m, 2H), 4.36 (t, J = 7.5 Hz, 2H), 3.71-3.53 (m, 4H), 1.39 (d, J = 6.3 Hz, 3H), 0.56-0.38 (m, 4H) |

TABLE 1-continued

| Cmpnd No. | Structure | ESMS (M + H) | ¹H NMR (300 MHz, unless indicated otherwise) NMR peaks given as δ values |
|---|---|---|---|
| 218 | 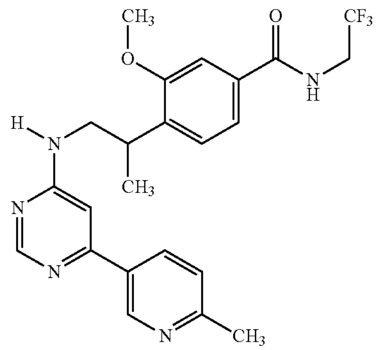 [SMILES: COc1cc(C(=O)NCC(F)(F)F)ccc1C(C)CNc1cc(-c2ccc(C)nc2)ncn1] | 460.29 | (400 MHz, CDCl$_3$) δ 8.85 (s, 1H), 8.52 (s, 1H), 8.14 (d, J = 7.4 Hz, 1H), 7.37 (s, 1H), 7.22 (s, 2H), 6.53 (s, 2H), 4.06 (dd, J = 8.7, 15.7 Hz, 2H), 3.84 (s, 3H), 3.54 (t, J= 6.5 Hz, 2H), 2.56 (d, J = 4.6 Hz, 3H), 1.84 (s, 3H) and 1.29 (d, J = 6.0 Hz, 3H) |
| 219 | 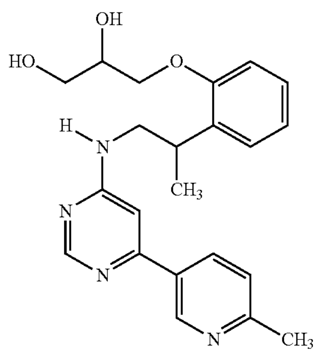 [SMILES: Cc1ccc(-c2cc(NCC(C)c3ccccc3OCC(O)CO)ncn2)cn1] | 395.14 | |
| 220 | 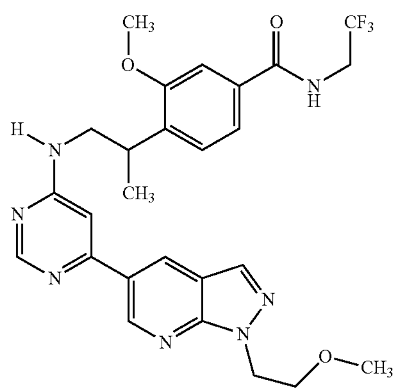 [SMILES: COCCn1ncc2cc(-c3cc(NCC(C)c4ccc(C(=O)NCC(F)(F)F)cc4OC)ncn3)cnc21] | 544.62 | |
| 221 | 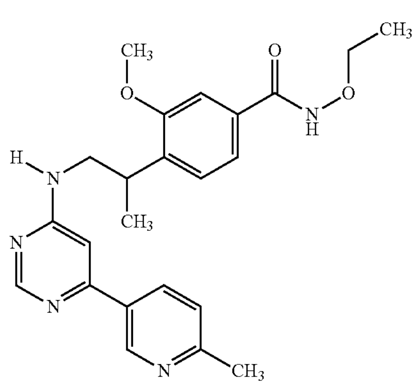 | 422.31 | (400 MHz, DMSO-d$_6$) δ 11.62 (s, 1H), 9.32-8.50 (m, 3H), 8.47-8.12 (m, 1H), 7.64 (d, J = 7.6 Hz, 1H), 7.34 (br. s, 3H), 7.10 (2s, 1H), 3.92 (q, J = 6.8 Hz, 2H), 3.81 (s, 3H), 3.75-3.31 (m, 3H), 2.62 (s, 3H), 1.21 (m, 5H) |

TABLE 1-continued

| Cmpnd No. | Structure | ESMS (M + H) | ¹H NMR (300 MHz, unless indicated otherwise) NMR peaks given as δ values |
|---|---|---|---|
| 222 | 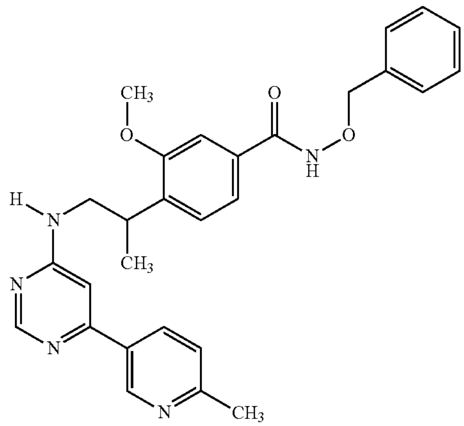 [SMILES: COc1cc(C(=O)NOCc2ccccc2)ccc1C(C)CNc1cc(-c2ccc(C)nc2)ncn1] | 484.33 | (400 MHz, DMSO-d₆) δ 11.76 (s, 1H), 9.18-8.13 (m, 4H), 7.61 (d, J = 7.5 Hz, 1H), 7.51-6.75 (m, 8H), 4.92 (s, 2H), 3.81 (s, 2H), 3.74-3.52 (m, 3H), 2.61 (s, 3H), 1.22 (d, J = 6.2 Hz, 3H) |
| 223 | 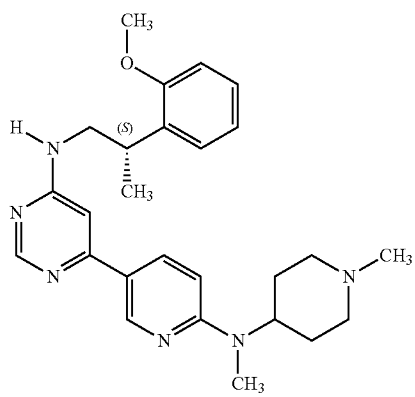 | 447.53 | (400 MHz, CDCl₃) δ 8.74 (d, J = 2.1 Hz, 1H), 8.53 (s, 1H), 8.11 (dd, J = 9.0, 2.5 Hz, 1H), 7.25-7.17 (m, 2H), 6.96 (t, J = 7.4 Hz, 1H), 6.90 (d, J = 7.8 Hz, 1H), 6.55 (m, 2H), 5.03 (s, 1H), 4.72-4.49 (m, 2H), 3.85 (s, 3H), 3.63-3.43 (m, 3H), 2.96 (m, 4H), 2.33 (s, 3H), 2.16 (t, J = 10.7 Hz, 2H), 1.89 (dt, J = 12.0, 10.6 Hz, 2H), 1.70 (d, J = 10.1 Hz, 2H), 1.34 (d, J = 6.8 Hz, 3H) |
| 224 | 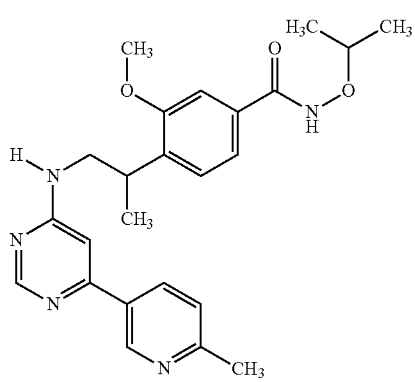 [SMILES: COc1cc(C(=O)NOC(C)C)ccc1C(C)CNc1cc(-c2ccc(C)nc2)ncn1] | 436.62 | (400 MHz, DMSO-d₆) δ 11.43 (br s, 1H), 9.11-8.34 (m, 4H), 7.68 (d, J = 8.1 Hz, 1H), 7.35 (br. s, 3H), 7.22, 7.03 (2d, 1H), 4.38-4.02 (m, 1H), 3.83 (s, 3H), 3.76-3.27 (m, 3H), 2.64 (s, 3H), 1.24-1.19 (m, 9H) |

| Cmpnd No. | Structure | ESMS (M + H) | ¹H NMR (300 MHz, unless indicated otherwise) NMR peaks given as δ values |
|---|---|---|---|
| 225 | 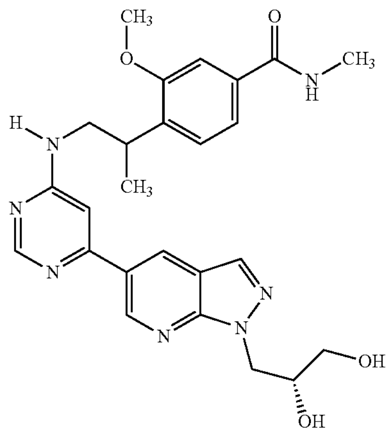 [SMILES: CNC(=O)c1ccc(C(C)CNc2cc(-c3cnc4c(cnn4C[C@@H](O)CO)c3)ncn2)c(OC)c1] | 492.33 | |
| 226 | 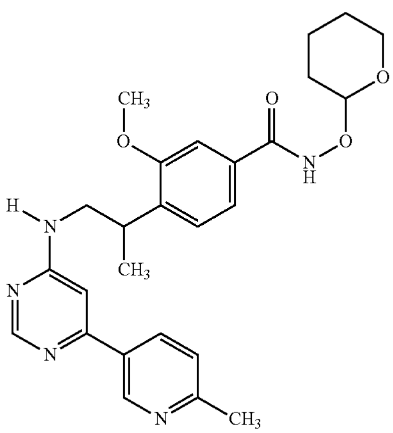 [SMILES: COc1cc(C(=O)NOC2CCCCO2)ccc1C(C)CNc1cc(-c2ccc(C)nc2)ncn1] | 478.32 | (400 MHz, DMSO-d$_6$) δ 11.62 (s, 1H), 9.46-8.08 (m, 4H), 7.87-6.77 (m, 5H), 4.98 (s, 1H), 3.81 (s, 3H), 4.11-3.29 (m, 5H), 2.58 (s, 3H), 1.72 (br. s, 3H), 1.54 (br.s, 3H), 1.22 (br. s, 3H) |
| 227 | 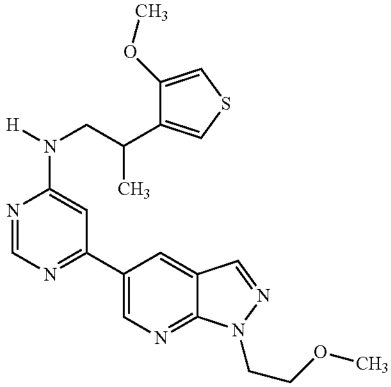 [SMILES: COCCn1ncc2cc(-c3cc(NCC(C)c4cscc4OC)ncn3)cnc21] | 424.94 | (400 MHz, methanol-d$_4$) δ 9.05 (s, 1H), 8.69 (s, 1H), 8.45 (s, 1H), 8.19 (s, 1H), 7.05 (s, 1H), 6.91 (s, 1H), 6.37 (d, J = 3.1 Hz, 1H), 4.70 (t, J = 5.4 Hz, 2H), 3.90 (t, J = 5.5 Hz, 2H), 3.82 (s, 3H), 3.76-3.45 (m, 2H), 3.29 (s, 3H), 3.20 (dd, J = 14.0, 7.0 Hz, 1H), 1.43-1.16 (m, 4H) |

| Cmpnd No. | Structure | ESMS (M + H) | $^1$H NMR (300 MHz, unless indicated otherwise) NMR peaks given as δ values |
|---|---|---|---|
| 228 | 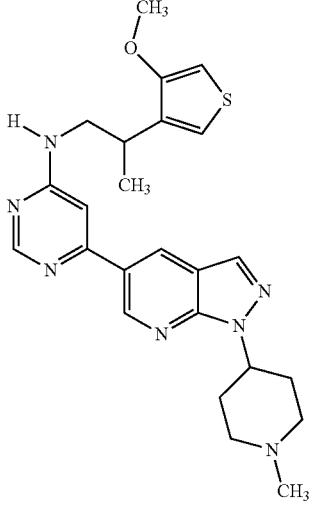 [SMILES: COc1cscc1C(C)CNc1cc(-c2cnc3c(cnn3C3CCN(C)CC3)c2)ncn1] | | (400 MHz, methanol-d$_4$) δ 9.05 (s, 1H), 8.70 (s, 1H), 8.45 (s, 1H), 8.18 (s, 1H), 7.05 (s, 1H), 6.93 (s, 1H), 6.38 (d, J = 3.1 Hz, 1H), 4.98-4.91 (m, 1H), 3.82 (s, 3H), 3.70-3.49 (m, 2H), 3.07 (d, 2H), 2.50-2.26 (m, 7H), 2.03 (d, J = 12.8 Hz, 2H), 1.29 (d, J = 7.9 Hz, 5H) |
| 229 | 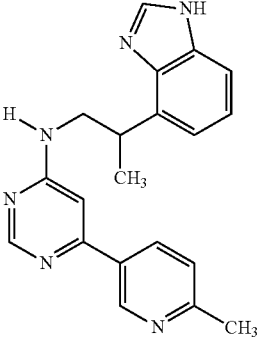 [SMILES: Cc1ccc(-c2cc(NCC(C)c3cccc4[nH]cnc34)ncn2)cn1] | | (400 MHz, DMSO-d$_6$) δ 9.13 (d, J = 115.9 Hz, 1H), 8.59-8.06 (m, 3H), 7.62 (s, 1H), 7.42 (t, J = 14.2 Hz, 2H), 7.19-6.84 (m, 3H), 3.71 (d, J = 51.5 Hz, 3H), 2.52 (d, J = 6.0 Hz, 3H), 1.39 (d, J = 6.1 Hz, 3H) |
| 230 | 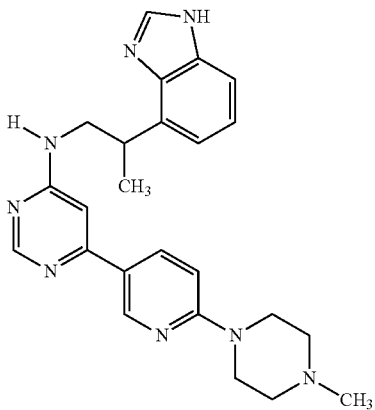 [SMILES: CC(CNc1cc(-c2ccc(N3CCN(C)CC3)nc2)ncn1)c1cccc2[nH]cnc12] | | (400 MHz, DMSO-d$_6$) δ 8.72 (s, 1H), 8.55-7.94 (m, 3H), 7.43 (d, J = 7.6 Hz, 2H), 7.14 (dd, J = 20.0, 12.4 Hz, 2H), 6.93 (s, 1H), 3.67 (d, J = 65.6 Hz, 7H), 2.40 (s, 4H), 2.22 (s, 3H), 1.39 (d, J = 6.3 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 231 | 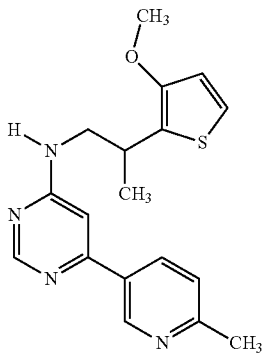 [SMILES: COc1ccsc1C(C)CNc1cc(-c2ccc(C)nc2)ncn1] | 341.24 | (400 MHz, CDCl$_3$) δ 9.01 (s, 1H), 8.61 (s, 1H), 8.20 (dd, J = 8.1, 2.2 Hz, 1H), 7.25 (d, J = 6.0 Hz, 1H), 7.07 (d, J = 5.5 Hz, 1H), 6.83 (d, J = 5.5 Hz, 1H), 6.68 (s, 1H), 5.44 (s, 1H), 3.84 (s, 3H), 3.73-3.22 (m, 3H), 2.62 (s, 3H), 1.39 (d, J = 6.7 Hz, 3H) |
| 232 | 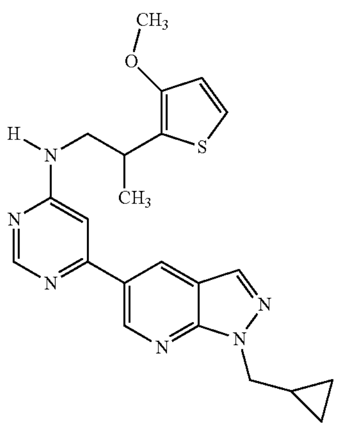 [SMILES: COc1ccsc1C(C)CNc1cc(-c2cnc3c(cnn3CC3CC3)c2)ncn1] | 421.32 | (400 MHz, CDCl$_3$) δ 9.09 (s, 1H), 8.70 (d, J = 2.0 Hz, 1H), 8.63 (s, 1H), 8.09 (s, 1H), 7.08 (d, J = 5.5 Hz, 1H), 6.85 (d, J = 5.5 Hz, 1H), 6.75 (s, 1H), 5.46 (s, 1H), 4.43 (d, J = 7.1 Hz, 2H), 3.86 (s, 3H), 3.72-3.35 (m, 3H), 1.50-1.42 (m, 1H), 1.40 (d, J = 6.7 Hz, 3H), 0.63-0.52 (m, 2H), 0.52-0.42 (m, 2H) |
| 233 | 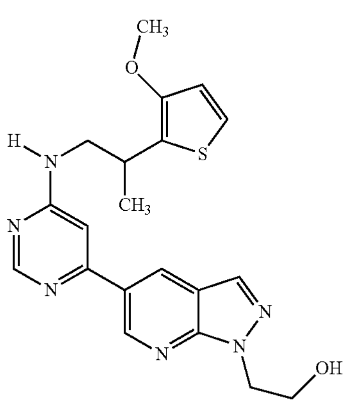 [SMILES: COc1ccsc1C(C)CNc1cc(-c2cnc3c(cnn3CCO)c2)ncn1] | 411.28 | (400 MHz, CDCl$_3$) δ 9.07 (s, 1H), 8.71 (d, J = 1.5 Hz, 1H), 8.59 (s, 1H), 8.08 (s, 1H), 7.06 (d, J = 5.5 Hz, 1H), 6.83 (d, J = 5.5 Hz, 1H), 6.72 (s, 1H), 5.54 (s, 1H), 4.80-4.60 (m, 2H), 4.28 (s, 1H), 4.15 (s, 2H), 3.85 (s, 3H), 3.75-3.07 (m, 4H), 1.39 (d, J = 6.6 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 234 | 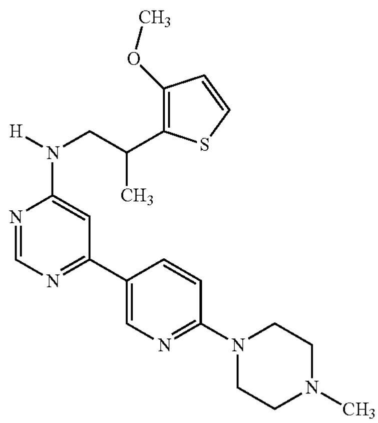 [SMILES: COc1ccsc1C(C)CNc1cc(-c2ccc(N3CCN(C)CC3)nc2)ncn1] | 425.35 | (400 MHz, CDCl₃) δ 8.74 (s, 1H), 8.54 (s, 1H), 8.13 (dd, J = 9.0, 2.4 Hz, 1H), 7.05 (d, J = 5.5 Hz, 1H), 6.83 (d, J = 5.5 Hz, 1H), 6.69 (d, J = 9.0 Hz, 1H), 6.58 (s, 1H), 5.30 (s, 1H), 3.83 (s, 3H), 3.72-3.60 (m, 4H), 3.60-3.31 (m, 3H), 2.58-2.43 (m, 4H), 2.34 (s, 3H), 1.37 (d, J = 6.7 Hz, 3H) |
| 235 | 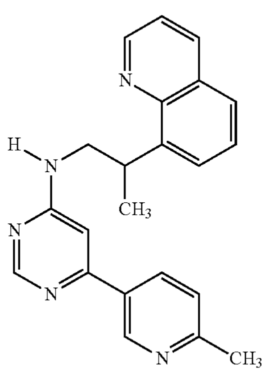 [SMILES: Cc1ccc(-c2cc(NCC(C)c3cccc4cccnc34)ncn2)cn1] | 356 | (400 MHz, DMSO-d₆) δ 9.04 (d, J = 71.6 Hz, 2H), 8.34 (dd, J = 66.8, 58.8 Hz, 3H), 7.85 (d, J = 8.1 Hz, 1H), 7.79-7.46 (m, 4H), 7.15 (d, J = 184.9 Hz, 2H), 4.49 (s, 1H), 3.78 (s, 2H), 2.52 (d, J = 5.4 Hz, 3H), 1.39 (s, 3H) |
| 236 | 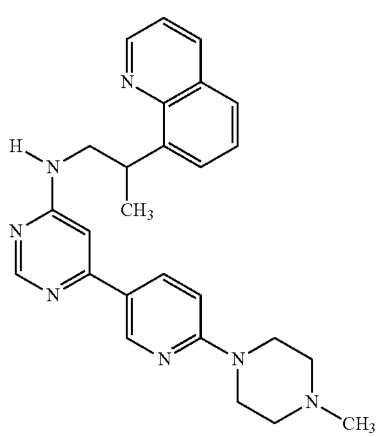 | 440 | (400 MHz, DMSO-d₆) δ 8.83 (d, J = 100.2 Hz, 2H), 8.38 (d, J = 7.9 Hz, 2H), 8.05 (s, 1H), 7.85 (d, J = 8.0 Hz, 1H), 7.72 (s, 1H), 7.65-7.51 (m, 2H), 7.40 (s, 1H), 7.20-6.65 (m, 2H), 4.48 (s, 1H), 3.66 (d, J = 59.0 Hz, 6H), 2.40 (s, 4H), 2.22 (s, 3H), 1.38 (d, J = 6.4 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 237 | 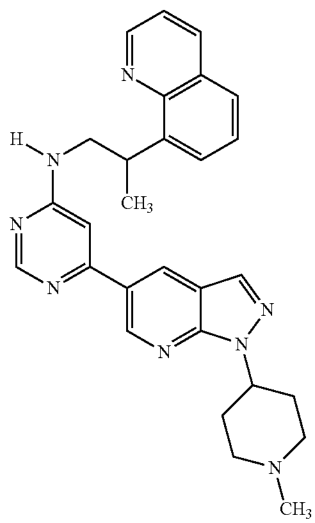 [SMILES: CC(CNc1cc(-c2cnc3c(cnn3C3CCN(C)CC3)c2)ncn1)c1cccc2cccnc12] | 479 | (400 MHz, DMSO-d$_6$) δ 9.09 (s, 1H), 8.96 (s, 1H), 8.76 (s, 1H), 8.38 (dd, J = 46.9, 38.8 Hz, 3H), 7.85 (d, J = 8.2 Hz, 1H), 7.63 (dd, J = 35.9, 28.2 Hz, 4H), 7.15 (d, J = 130.8 Hz, 1H), 4.83 (s, 1H), 4.51 (s, 1H), 3.80 (s, 2H), 2.93 (d, J = 10.6 Hz, 2H), 2.31-2.05 (m, 7H), 1.93 (s, 2H), 1.40 (s, 3H) |
| 238 | 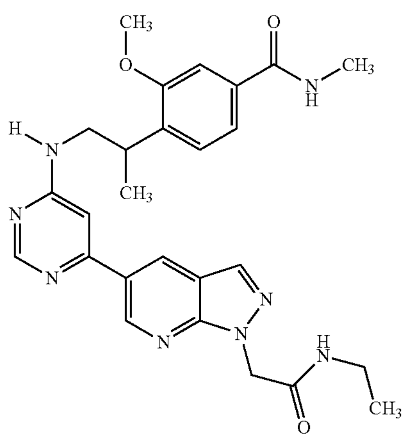 [SMILES: CCNC(=O)Cn1ncc2cc(-c3cc(NCC(C)c4ccc(C(=O)NC)cc4OC)ncn3)cnc21] | 503.31 | (400 MHz, DMSO-d$_6$) δ 9.10 (s, 1H), 8.79 (s, 1H), 8.53 (s, 1H), 8.38 (d, J = 3.4 Hz, 1H), 8.29 (s, 1H), 8.21 (s, 1H), 7.50 (s, 1H), 7.41 (s, 3H), 7.01 (s, 1H), 5.11 (s, 2H), 3.82 (s, 3H), 3.67-3.38 (m, 2H), 3.33 (s, 3H), 3.11 (t, J = 6.2 Hz, 2H), 2.78 (d, J = 3.6 Hz, 3H) and 1.32-0.90 (m, 4H) |
| 239 | 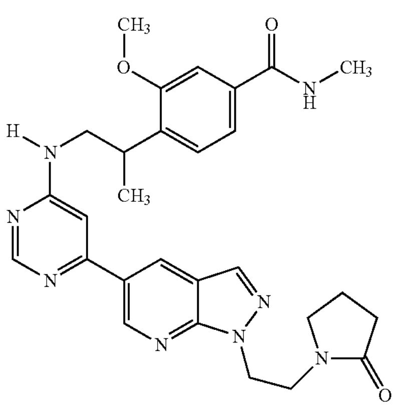 [SMILES: CNC(=O)c1ccc(C(C)CNc2cc(-c3cnc4c(cnn4CCN4CCCC4=O)c3)ncn2)c(OC)c1] | 529.36 | (400 MHz, DMSO-d$_6$) δ 9.11 (s, 1H), 8.77 (s, 1H), 8.53 (s, 1H), 8.39 (s, 1H), 8.27 (s, 1H), 7.49-7.34 (m, 3H), 7.01 (s, 1H), 4.63 (s, 2H), 3.82 (s, 3H), 3.65-3.51 (m, 4H), 3.33 (s, 1H), 3.22 (s, 2H), 2.78 (s, 3H), 1.98 (s, 2H), 1.76 (d, J = 6.9 Hz, 2H), 1.22 (s, 3H) and 1.10 (d, J = 6.6 Hz, 1H) |

TABLE 1-continued
| Cmpnd No. | Structure | ESMS (M + H) | ¹H NMR (300 MHz, unless indicated otherwise) NMR peaks given as δ values |
|---|---|---|---|
| 240 | 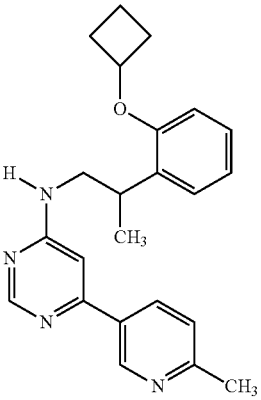 [SMILES: Cc1ccc(-c2cc(NCC(C)c3ccccc3OC3CCC3)ncn2)cn1] | 375.11 | (CDCl$_3$) δ 8.98 (s, 1H), 8.61 (s, 1H), 8.17 (dd, J = 8.1, 2.3 Hz, 1H), 7.25-7.09 (m, 3H), 7.00-6.89 (m, 1H), 6.72 (d, J = 7.5 Hz, 1H), 6.61 (s, 1H), 4.71-4.56 (m, 1H), 3.56 (m, 3H), 2.62 (s, 3H), 2.50-2.33 (m, 2H), 2.20-1.98 (m, 2H), 1.89-1.61 (m, 2H), 1.42-1.30 (m, 3H) |
| 241 | 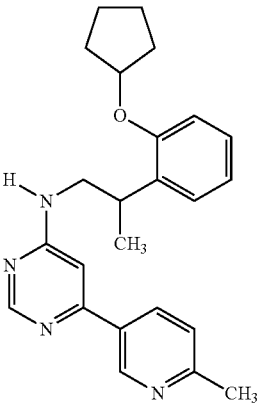 [SMILES: Cc1ccc(-c2cc(NCC(C)c3ccccc3OC3CCCC3)ncn2)cn1] | 389.06 | (CDCl$_3$) δ 8.98 (s, 1H), 8.59 (s, 1H), 8.19 (dd, J = 8.1, 2.2 Hz, 1H), 7.24-7.12 (m, 3H), 6.98-6.82 (m, 2H), 6.57 (s, 1H), 4.81 (dt, J = 8.2, 2.7 Hz, 1H), 3.53 (m, 3H), 2.63 (s, 3H), 2.03-1.54 (m, 10H), 1.33 (t, J = 10.1 Hz, 3H) |
| 242 | 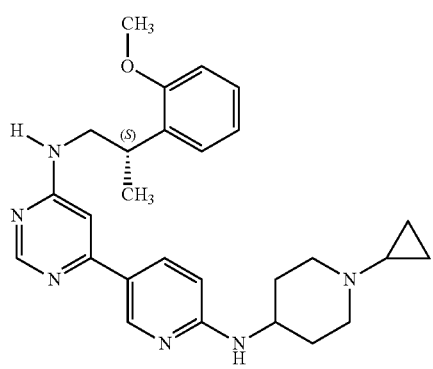 | 459.56 | (CDCl$_3$) δ 8.66 (d, J = 2.0 Hz, 1H), 8.53 (s, 1H), 8.07 (dd, J = 8.8, 2.4 Hz, 1H), 7.26-7.16 (m, 3H), 7.02-6.85 (m, 2H), 6.55 (s, 1H), 6.43 (d, J = 8.7 Hz, 1H), 4.67 (d, J = 8.0 Hz, 1H), 3.85 (s, 3H), 3.69 (d, J = 8.3 Hz, 2H), 3.63-3.43 (m, 3H), 3.01 (d, J = 12.0 Hz, 2H), 2.39 (t, J = 10.3 Hz, 2H), 2.06 (d, J = 11.9 Hz, 2H), 1.34 (d, J = 6.7 Hz, 3H), 0.53-0.37 (m, 4H) |

TABLE 1-continued

| Cmpnd No. | Structure | ESMS (M + H) | ¹H NMR (300 MHz, unless indicated otherwise) NMR peaks given as δ values |
|---|---|---|---|
| 243 | 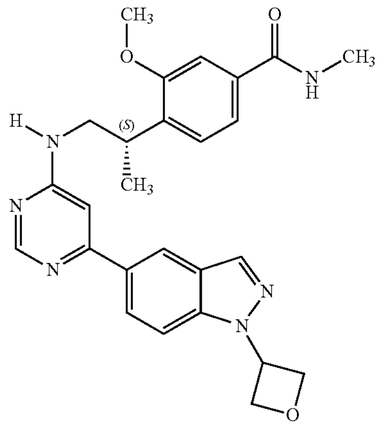 | 473.51 | (CDCl₃) δ 8.53 (s, 1H), 8.32 (s, 1H), 8.09 (s, 1H), 7.95 (dd, J = 8.9, 1.5 Hz, 1H), 7.51 (d, J = 8.9 Hz, 1H), 7.34 (d, J = 1.3 Hz, 1H), 7.14 (dd, J = 7.9, 1.5 Hz, 1H), (s, 1H), 6.11 (d, J = 4.5 Hz, 1H), 5.75 (t, J = 7.0 Hz, 1H), 5.25 (t, J = 6.6 Hz, 2H), 5.09 (t, J = 7.3 Hz, 2H), 3.83 (s, 3H), 3.54 (dd, J = 12.9, 6.4 Hz, 3H), 2.92 (d, J = 4.9 Hz, 3H), 2.66 (q, J = 7.1 Hz, 3H), 2.34 (s, 2H) |
| 244 | 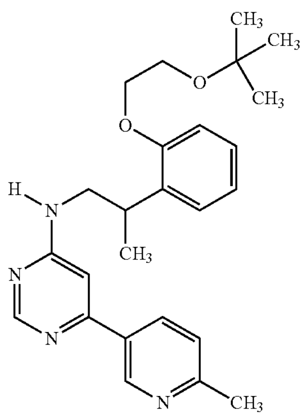 [SMILES: Cc1ccc(-c2cc(NCC(C)c3ccccc3OCCOC(C)(C)C)ncn2)cn1] | 421.54 | (CDCl₃) δ 8.98 (s, 1H), 8.53 (s, 1H), 8.23 (dd, J = 8.1, 2.2 Hz, 1H), 8.14 (s, 1H), 7.23 (d, J = 6.7 Hz, 1H), 7.15 (td, J = 7.8, 1.6 Hz, 1H), 6.93 (dd, J = 10.3, 4.6 Hz, 1H), 6.83 (d, J = 8.2 Hz, 1H), 6.72 (s, 1H), 4.24-4.00 (m, 2H), 3.86-3.50 (m, 5H), 2.63 (s, 3H), 1.38 (d, J = 6.3 Hz, 3H), 1.24 (s, 9H) |
| 245 | 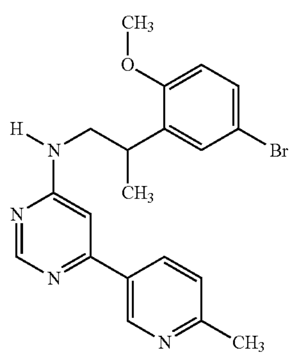 [SMILES: COc1ccc(Br)cc1C(C)CNc1cc(-c2ccc(C)nc2)ncn1] | 413.35 | |
| 246 | 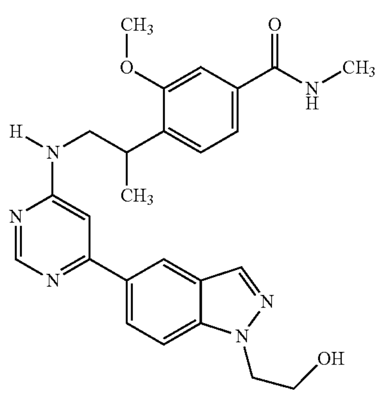 [SMILES: CNC(=O)c1ccc(C(C)CNc2cc(-c3ccc4c(cnn4CCO)c3)ncn2)c(OC)c1] | 461.55 | |

| Cmpnd No. | Structure | ESMS (M + H) | ¹H NMR (300 MHz, unless indicated otherwise) NMR peaks given as δ values |
|---|---|---|---|
| 247 | 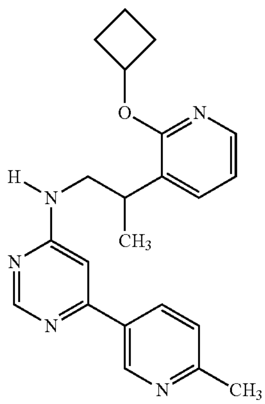 [SMILES: Cc1ccc(-c2cc(NCC(C)c3cccnc3OC3CCC3)ncn2)cn1] | 376 | (400 MHz, DMSO-d₆) δ 8.99 (s, 1H), 8.52 (s, 1H), 8.18 (s, 1H), 8.01-7.88 (m, 1H), 7.61 (d, J = 6.5 Hz, 1H), 7.49 (t, J = 5.4 Hz, 1H), 7.37 (d, J = 8.1 Hz, 1H), 6.92 (dd, J = 7.1, 5.0 Hz, 2H), 5.10 (p, J = 7.3 Hz, 1H), 3.76-3.37 (m, 3H), 2.52 (d, J = 3.7 Hz, 3H), 2.30 (d, J = 6.9 Hz, 2H), 1.98-1.78 (m, 2H), 1.56 (dq, J = 18.6, 10.2 Hz, 2H), 1.20 (dd, J = 22.7, 6.7 Hz, 3H) |
| 248 | 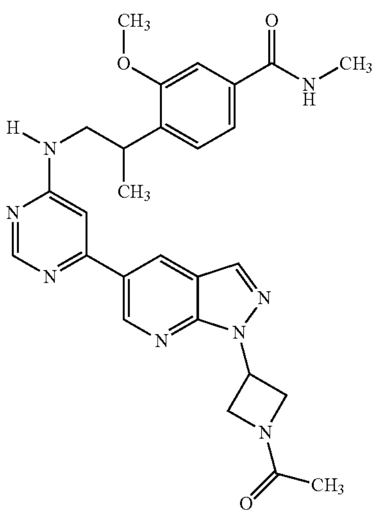 [SMILES: CNC(=O)c1ccc(C(C)CNc2cc(-c3cnc4c(cnn4C4CN(C(C)=O)C4)c3)ncn2)c(OC)c1] | 515.31 | (400 MHz, CDCl₃) δ 9.00 (s, 1H), 8.62 (s, 1H), 8.54 (s, 1H), 8.11 (s, 1H), 7.35 (s, 1H), 7.17 (dd, J = 7.5, 12.4 Hz, 2H), 6.63 (s, 1H), 6.15 (s, 1H), 5.85-5.82 (m, 1H), 5.23 (s, 1H), 4.74-4.71 (m, 1H), 4.59 (t, J = 8.5 Hz, 1H), 4.52-4.47 (m, 2H), 3.83 (s, 3H), 3.64-3.53 (m, 3H), 2.93 (d, J = 4.6 Hz, 3H), 1.92 (s, 3H) and 1.29 (d, J = 5.7 Hz, 3H) |
| 249 | 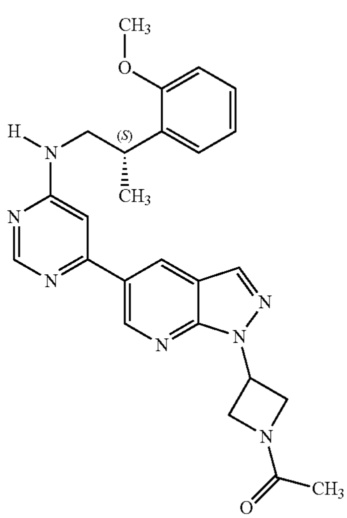 | 458.31 | (400 MHz, CDCl₃) δ 9.02 (s, 1H), 8.64 (s, 1H), 8.55 (s, 1H), 8.11 (s, 1H), 7.30-7.13 (m, 3H), 6.91 (t, J = 7.4 Hz, 1H), 6.84 (d, J = 8.3 Hz, 1H), 6.65 (s, 1H), 5.84 (dd, J = 7.1, 19.8 Hz, 1H), 4.74-4.71 (m, 1H), 4.59 (t, J = 8.4 Hz, 1H), 4.52 (d, J = 6.1 Hz, 2H), 3.79 (s, 3H), 3.68-3.49 (m, 3H), 1.92 (s, 3H) and 1.30 (d, J = 6.2 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 250 | 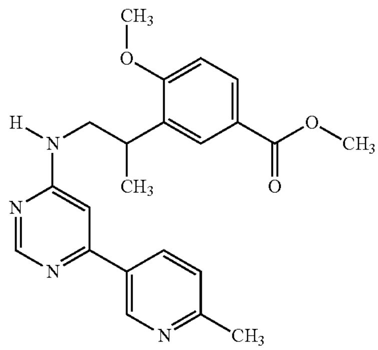 [SMILES: COC(=O)c1ccc(OC)c(C(C)CNc2cc(-c3ccc(C)nc3)ncn2)c1] | 393.45 | (CDCl$_3$) δ 9.00 (s, 1H), 8.61 (s, 1H), 8.18 (dd, J = 8.1, 2.3 Hz, 1H), 7.99-7.90 (m, 1H), 7.26-7.19 (m, 2H), 6.92 (m, 1H), 6.67 (s, 1H), 3.89 (d, J = 2.5 Hz, 3H), 3.61 (m, 3H), 2.62 (s, 2H), 1.36 (t, J = 6.0 Hz, 3H) |
| 251 | 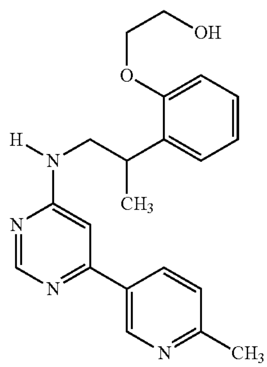 [SMILES: Cc1ccc(-c2cc(NCC(C)c3ccccc3OCCO)ncn2)cn1] | 365.03 | (CDCl$_3$) δ 10.45 (s, 1H), 9.67 (s, 1H), 9.00 (d, 1H), 8.73 (s, 1H), 7.79 (d, 1H), 7.26 (m, 2H), 7.17-6.97 (m, 1H), 6.91-6.84 (m, 1H), 4.31-3.59 (m, 7H), 2.91 (s, 3H), 1.45 (s, 3H) |
| 252 | 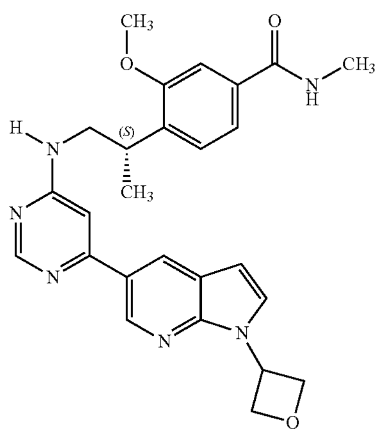 | 473.32 | (CDCl$_3$) δ 8.78 (d, J = 1.9 Hz, 1H), 8.54 (s, 1H), 8.47 (d, J = 2.0 Hz, 1H), 7.66 (d, J = 3.6 Hz, 1H), 7.34 (d, J = 1.3 Hz, 1H), 7.18-7.11 (m, 2H), 6.70-6.54 (m, 2H), 6.08 (t, J = 6.3 Hz, 2H), 5.14 (t, J = 7.4 Hz, 2H), 4.98 (t, J = 6.7 Hz, 2H), 3.83 (s, 3H), 3.61-3.42 (m, 3H), 2.93 (d, J = 4.8 Hz, 3H), 1.98 (s, 1H), 1.60 (s, 3H) |
| 253 | 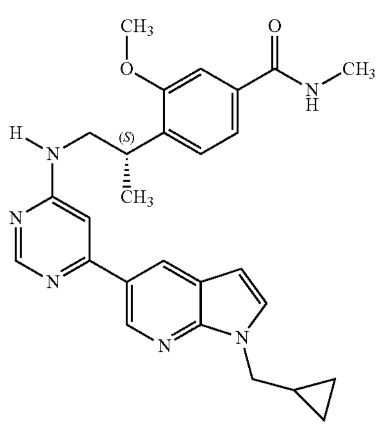 | 471.72 | (CDCl$_3$) δ 8.87 (d, J = 2.0 Hz, 1H), 8.63 (s, 1H), 8.54 (d, J = 2.1 Hz, 1H), 7.43-7.39 (m, 2H), 7.24 (dd, J = 8.1, 6.6 Hz, 2H), 6.73 (s, 1H), 6.56 (d, J = 3.5 Hz, 1H), 6.15 (d, J = 4.4 Hz, 1H), 4.21 (d, J = 7.0 Hz, 2H), 3.92 (s, 3H), 3.73-3.52 (m, 3H), 3.01 (d, J = 4.9 Hz, 3H), 1.67 (s, 2H), 1.37 (d, J = 6.6 Hz, 3H), 0.70-0.59 (m, 2H), 0.46 (t, J = 5.3 Hz, 2H) |

TABLE 1-continued

| Cmpnd No. | Structure | ESMS (M + H) | ¹H NMR (300 MHz, unless indicated otherwise) NMR peaks given as δ values |
|---|---|---|---|
| 254 | 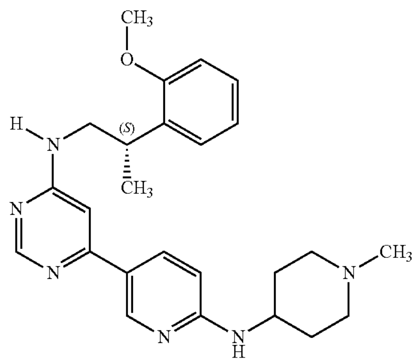 | 433.51 | |
| 255 | 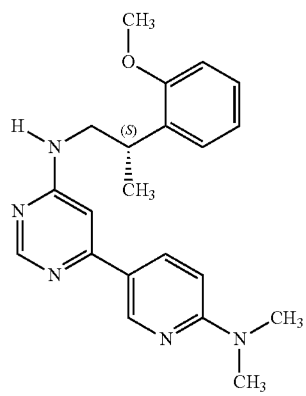 | 364.42 | |
| 256 | 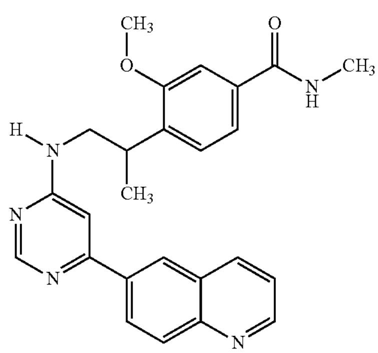 [SMILES: CNC(=O)c1ccc(C(C)CNc2cc(-c3ccc4ncccc4c3)ncn2)c(OC)c1] | 428 | (400 MHz, DMSO-d₆) δ 8.95 (d, J = 2.9 Hz, 1H), 8.74-8.22 (m, 5H), 8.12 (d, J = 8.8 Hz, 1H), 7.64-7.48 (m, 2H), 7.38 (d, J = 30.7 Hz, 3H), 7.10 (s, 1H), 3.83 (s, 3H), 3.70-3.42 (m, 3H), 2.76 (t, J = 9.9 Hz, 3H), 1.21 (d, J = 25.1 Hz, 3H) |
| 257 | 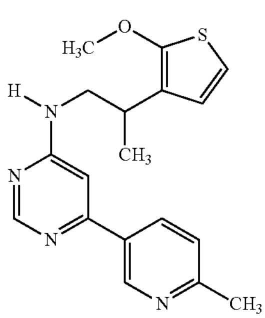 [SMILES: COc1sccc1C(C)CNc1cc(-c2ccc(C)nc2)ncn1] | 341.16 | (400 MHz, CDCl₃) δ 9.03 (s, 1H), 8.62 (s, 1H), 8.22 (d, J = 8.1 Hz, 1H), 7.27 (d, J = 5.4 Hz, 1H), 6.73 (d, J = 5.8 Hz, 1H), 6.67 (s, 1H), 6.61 (d, J = 5.8 Hz, 1H), 5.24 (s, 1H), 3.92 (s, 3H), 3.67-3.36 (m, 2H), 3.34-3.22 (m, 1H), 2.64 (s, 3H), 1.33 (d, J = 6.9 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 258 | 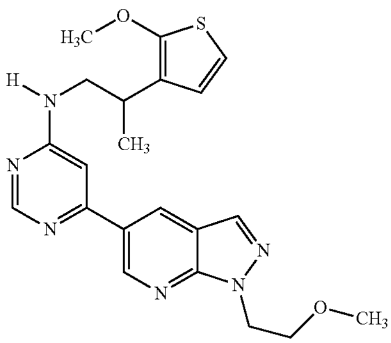 [SMILES: COCCn1ncc2cc(-c3cc(NCC(C)c4ccsc4OC)ncn3)cnc21] | 425.61 | (400 MHz, methanol-d₄) δ 9.05 (s, 1H), 8.69 (s, 1H), 8.45 (s, 1H), 8.19 (s, 1H), 6.88 (s, 1H), 6.78 (d, J = 5.3 Hz, 1H), 6.64 (d, J = 5.8 Hz, 1H), 4.70 (t, J = 5.4 Hz, 2H), 3.90 (t, J = 5.4 Hz, 2H), 3.84 (s, 3H), 3.80-3.32 (m, 3H), 3.29 (s, 3H), 1.26 (d, J = 6.3 Hz, 3H) |
| 259 | 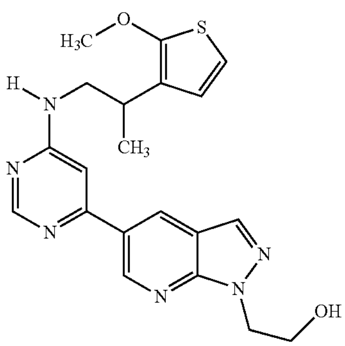 [SMILES: COc1sccc1C(C)CNc1cc(-c2cnc3c(cnn3CCO)c2)ncn1] | 410.92 | (400 MHz, methanol-d4) δ 9.04 (s, 1H), 8.68 (s, 1H), 8.44 (s, 1H), 8.18 (s, 1H), 6.87 (s, 1H), 6.78 (d, J = 5.6 Hz, 1H), 6.63 (d, J = 5.8 Hz, 1H), 4.64 (t, J = 5.6 Hz, 2H), 4.04 (t, J = 5.6 Hz, 2H), 3.84 (s, 3H), 3.74-3.52 (m, 1H), 3.49-3.41 (m, 1H), 3.26 (dd, J = 14.4, 7.3 Hz, 1H), 1.26 (d, J = 6.3 Hz, 3H) |
| 260 | 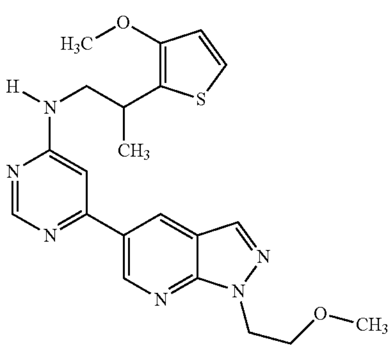 [SMILES: COCCn1ncc2cc(-c3cc(NCC(C)c4sccc4OC)ncn3)cnc21] | 425.29 | (400 MHz, methanol-d4) δ 9.07 (s, 1H), 8.71 (s, 1H), 8.46 (s, 1H), 8.20 (s, 1H), 7.12 (d, J = 5.5 Hz, 1H), 6.93 (s, 1H), 6.88 (d, J = 5.5 Hz, 1H), 4.71 (t, J = 5.4 Hz, 2H), 3.90 (t, J = 5.4 Hz, 2H), 3.86-3.54 (m, 4H), 3.55-3.44 (m, 2H), 3.29 (s, 3H), 1.34 (s, 3H) |
| 261 | 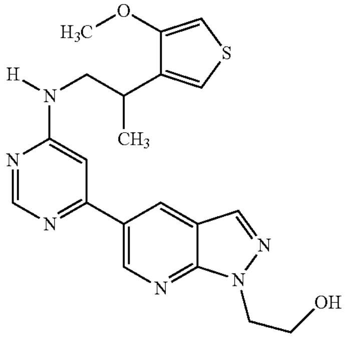 [SMILES: COc1cscc1C(C)CNc1cc(-c2cnc3c(cnn3CCO)c2)ncn1] | 410.86 | (400 MHz, methanol-d₄) δ 9.05 (s, 1H), 8.69 (s, 1H), 8.45 (s, 1H), 8.20 (s, 1H), 7.04 (s, 1H), 6.91 (s, 1H), 6.37 (d, J = 3.1 Hz, 1H), 4.64 (t, J = 5.6 Hz, 2H), 4.04 (t, J = 5.6 Hz, 2H), 3.82 (s, 3H), 3.74-3.44 (m, 2H), 3.24-3.18 (m, 1H), 1.31 (s, 3H) |

| Cmpnd No. | Structure | ESMS (M + H) | ¹H NMR (300 MHz, unless indicated otherwise) NMR peaks given as δ values |
|---|---|---|---|
| 262 | 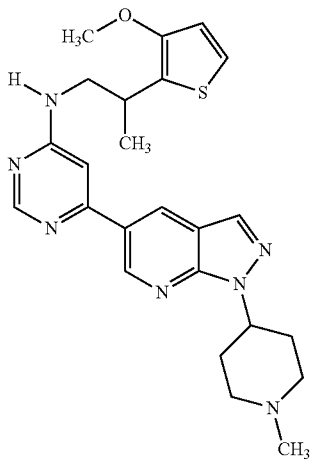 [SMILES: COc1ccsc1C(C)CNc1cc(-c2cnc3c(cnn3C3CCN(C)CC3)c2)ncn1] | 464.27 | (400 MHz, methanol-d₄) δ 9.05 (s, 1H), 8.68 (s, 1H), 8.46 (s, 1H), 8.17 (s, 1H), 7.11 (d, J = 5.5 Hz, 1H), 6.92 (s, 1H), 6.88 (d, J = 5.4 Hz, 1H), 4.93 (t, J = 12.0 Hz, 1H), 3.78 (s, 3H), 3.73-3.37 (m, 4H), 3.35 (s, 3H), 3.06 (d, J = 11.2 Hz, 2H), 2.52-2.23 (m, 4H), 2.03 (d, J = 12.3 Hz, 2H), 1.34 (s, 3H) |
| 263 | 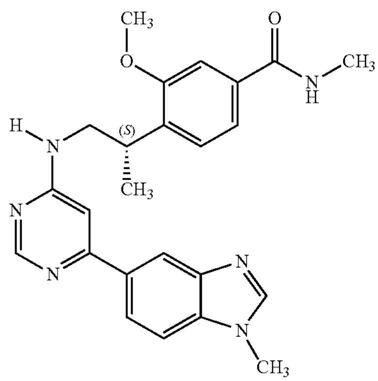 | 431.31 | |
| 264 | 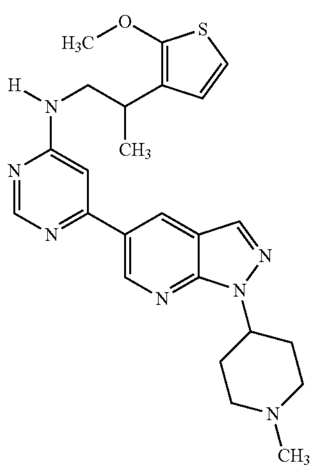 [SMILES: COc1sccc1C(C)CNc1cc(-c2cnc3c(cnn3C3CCN(C)CC3)c2)ncn1] | 464.23 | (400 MHz, methanol-d₄) δ 9.05 (s, 1H), 8.69 (s, 1H), 8.46 (s, 1H), 8.18 (s, 1H), 6.90 (s, 1H), 6.78 (d, J = 5.3 Hz, 1H), 6.64 (d, J = 5.8 Hz, 1H), 4.99-4.90 (m, 1H), 3.84 (s, 3H), 3.77-3.37 (m, 3H), 3.07 (d, J = 10.9 Hz, 2H), 2.57-2.16 (m, 8H), 2.03 (d, J = 12.5 Hz, 2H), 1.27 (d, J = 6.0 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 265 | 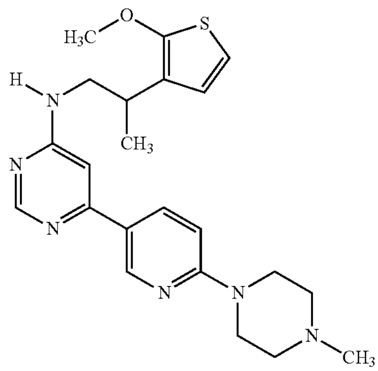 [SMILES: COc1sccc1C(C)CNc1cc(-c2ccc(N3CCN(C)CC3)nc2)ncn1] | 425.1 | (400 MHz, methanol-d₄) δ 8.66 (s, 1H), 8.36 (s, 1H), 8.04 (d, J = 8.2 Hz, 1H), 6.88 (d, J = 9.0 Hz, 1H), 6.76 (d, J = 5.8 Hz, 1H), 6.72 (s, 1H), 6.63 (d, J = 5.8 Hz, 1H), 3.83 (s, 3H), 3.66 (s, 4H), 3.61-3.37 (m, 3H), 2.59-2.52 (m, 4H), 2.35 (s, 3H), 1.25 (d, J = 6.7 Hz, 3H) |
| 266 | 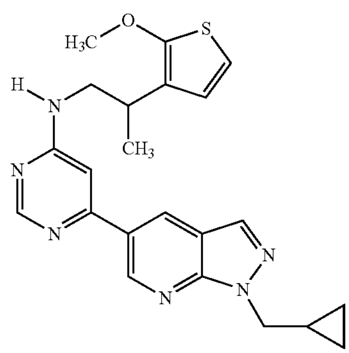 [SMILES: COc1sccc1C(C)CNc1cc(-c2cnc3c(cnn3CC3CC3)c2)ncn1] | 421.26 | (400 MHz, CDCl₃) δ 9.02 (s, 1H), 8.62 (s, 1H), 8.55 (s, 1H), 8.02 (s, 1H), 6.74-6.61 (m, 2H), 6.54 (d, J = 5.8 Hz, 1H), 5.18 (s, 1H), 4.36 (d, J = 7.0 Hz, 2H), 3.84 (s, 3H), 3.49 (s, 1H), 3.40-3.29 (m, 1H), 3.27-3.15 (m, 1H), 1.42-1.32 (m, 1H), 1.26 (d, J = 6.9 Hz, 3H), 0.54-0.45 (m, 2H), 0.45-0.37 (m, 2H) |
| 267 | 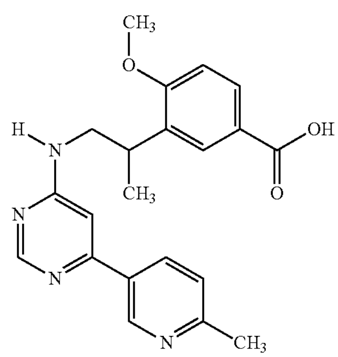 [SMILES: COc1ccc(C(=O)O)cc1C(C)CNc1cc(-c2ccc(C)nc2)ncn1] | 379.14 | |
| 268 | 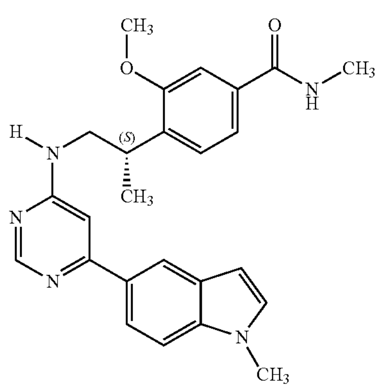 | 430.35 | (CDCl₃) δ 8.51 (s, 1H), 8.19 (d, J = 1.2 Hz, 1H), 7.79 (dd, J = 8.6, 1.6 Hz, 1H), 7.31 (d, J = 8.5 Hz, 2H), 7.17-7.09 (m, 2H), 7.02 (d, J = 3.1 Hz, 1H), 6.66 (s, 1H), 6.49 (dd, J = 3.1, 0.6 Hz, 1H), 6.06 (d, J = 4.3 Hz, 1H), 3.83 (s, 3H), 3.76 (s, 3H), 3.61-3.40 (m, 4H), 2.90 (d, J = 4.9 Hz, 3H), 1.28 (d, J = 6.6 Hz, 3H) |

TABLE 1-continued
| Cmpnd No. | Structure | ESMS (M + H) | $^1$H NMR (300 MHz, unless indicated otherwise) NMR peaks given as δ values |
|---|---|---|---|
| 269 | 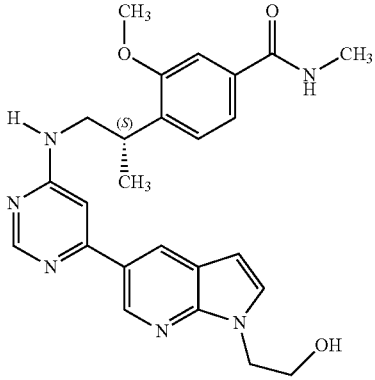 | 461.61 | |
| 270 | 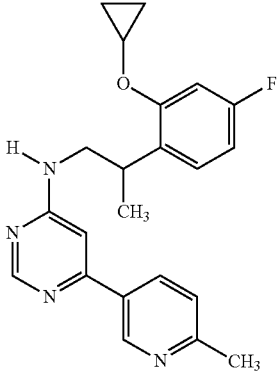 [SMILES: Cc1ccc(-c2cc(NCC(C)c3ccc(F)cc3OC3CC3)ncn2)cn1] | 379 | (400 MHz, DMSO-d$_6$) δ 8.97 (s, 1H), 8.49 (s, 1H), 8.17 (s, 1H), 7.38 (t, J = 6.6 Hz, 2H), 7.21 (d, J = 21.9 Hz, 1H), 7.07 (d, J = 11.2 Hz, 1H), 6.91 (d, J = 8.9 Hz, 1H), 6.74 (dd, J = 16.9, 8.5 Hz, 1H), 3.85 (s, 1H), 3.46 (d, J = 86.9 Hz, 3H), 2.52 (d, J = 3.5 Hz, 3H), 1.18 (d, J = 10.8 Hz, 3H), 0.73 (d, J = 4.9 Hz, 2H), 0.53 (s, 2H) |
| 271 | 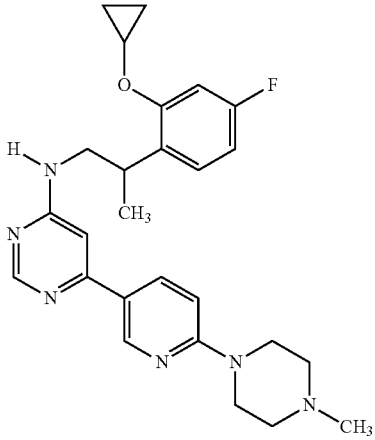 [SMILES: CC(CNc1cc(-c2ccc(N3CCN(C)CC3)nc2)ncn1)c1ccc(F)cc1OC1CC1] | 463 | (400 MHz, DMSO-d$_6$) δ 8.71 (s, 1H), 8.40 (s, 1H), 8.06 (s, 1H), 7.31-7.13 (m, 2H), 7.07 (d, J = 11.3 Hz, 1H), 6.91 (d, J = 9.0 Hz, 1H), 6.74 (d, J = 9.6 Hz, 2H), 3.85 (s, 1H), 3.46 (d, J = 95.5 Hz, 7H), 2.38 (t, J = 14.6 Hz, 4H), 2.22 (s, 3H), 1.17 (dd, J = 13.2, 6.2 Hz, 3H), 0.75 (t, J = 7.6 Hz, 2H), 0.56 (d, J = 13.6 Hz, 2H) |

TABLE 1-continued

| Cmpnd No. | Structure | ESMS (M + H) | $^1$H NMR (300 MHz, unless indicated otherwise) NMR peaks given as δ values |
|---|---|---|---|
| 272 | 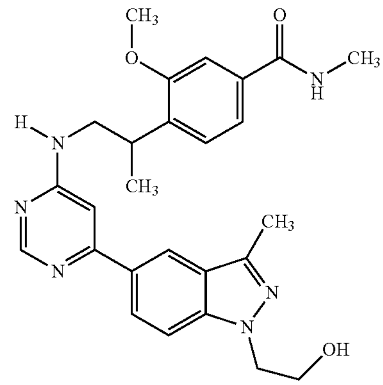 [SMILES: CNC(=O)c1ccc(C(C)CNc2cc(-c3ccc4c(c3)c(C)nn4CCO)ncn2)c(OC)c1] | 475.34 | (400 MHz, CDCl$_3$) δ 8.63 (s, 1H), 8.37 (s, 1H), 7.95 (d, J = 8.9 Hz, 1H), 7.44 (d, J = 11.4 Hz, 2H), 7.21 (d, J = 8.0 Hz, 1H), 6.67 (s, 1H), 6.08 (s, 1H), 4.47-4.41 (m, 2H), 4.14 (d, J = 7.1 Hz, 2H), 3.91 (d, J = 7.7 Hz, 3H), 3.69-3.54 (m, 3H), 3.00 (d, J = 4.7 Hz, 3H), 2.64 (s, 3H), 1.38 (d, J = 6.2 Hz, 3H), 1.27 (d, J = 7.1 Hz, 3H) |
| 273 | 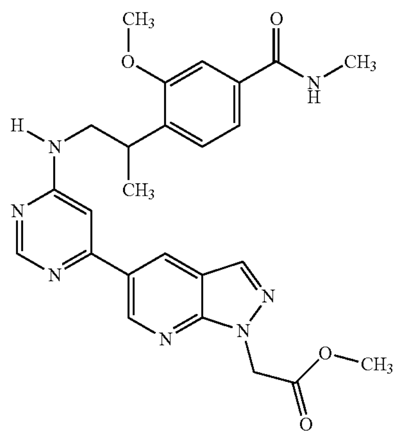 [SMILES: CNC(=O)c1ccc(C(C)CNc2cc(-c3cnc4c(cnn4CC(=O)OC)c3)ncn2)c(OC)c1] | 490.32 | (400 MHz, CDCl$_3$) δ 9.00 (s, 1H), 8.61 (s, 1H), 8.54 (s, 1H), 8.08 (s, 1H), 7.33 (s, 1H), 7.16 (q, J = 7.9 Hz, 2H), 6.62 (s, 1H), 6.19 (d, J = 3.9 Hz, 1H), 5.28 (s, 2H), 3.81 (s, 3H), 3.70 (s, 3H), 3.58-3.45 (m, 4H), 2.91 (d, J = 4.0 Hz, 3H), 1.28 (d, J = 5.9 Hz, 3H) |
| 274 | 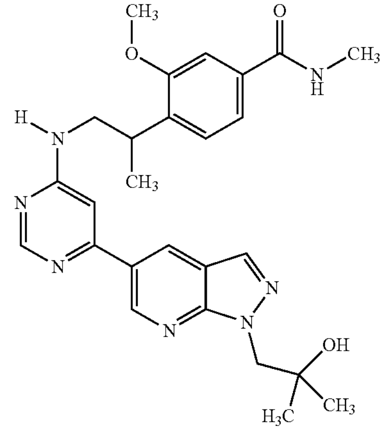 [SMILES: CNC(=O)c1ccc(C(C)CNc2cc(-c3cnc4c(cnn4CC(C)(C)O)c3)ncn2)c(OC)c1] | 490.73 | (400 MHz, CDCl$_3$) δ 9.09 (s, 1H), 8.73 (d, J = 1.6 Hz, 1H), 8.64 (s, 1H), 8.15 (s, 1H), 7.44 (s, 1H), 7.25-7.21 (m, 1H), 6.71 (s, 1H), 6.11 (s, 1H), 4.61 (s, 2H), 4.41 (s, 1H), 3.93 (s, 3H), 3.72-3.50 (m, 3H), 3.03 (d, J = 4.8 Hz, 3H), 1.60 (s, 2H), 1.38 (d, J = 6.4 Hz, 3H), 1.24 (s, 6H) |

TABLE 1-continued

| Cmpnd No. | Structure | ESMS (M + H) | ¹H NMR (300 MHz, unless indicated otherwise) NMR peaks given as δ values |
|---|---|---|---|
| 275 | 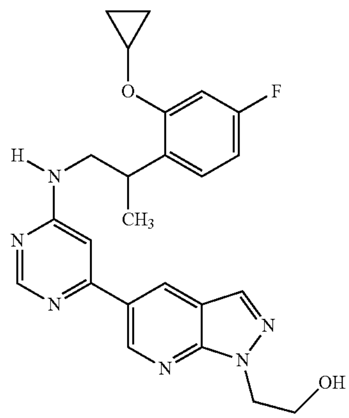 [SMILES: CC(CNc1cc(-c2cnc3c(cnn3CCO)c2)ncn1)c1ccc(F)cc1OC1CC1] | 449 | (400 MHz, DMSO-d₆) δ 9.10 (s, 1H), 8.71 (d, J = 45.6 Hz, 1H), 8.52 (s, 1H), 8.28 (s, 1H), 7.42 (s, 1H), 7.26 (s, 1H), 7.12-6.92 (m, 2H), 6.76 (t, J = 8.4 Hz, 1H), 4.54 (t, J = 5.5 Hz, 2H), 3.88 (t, J = 5.7 Hz, 3H), 3.48 (d, J = 79.9 Hz, 3H), 1.17 (s, 3H), 0.72 (s, 2H), 0.54 (s, 2H) |
| 276 | 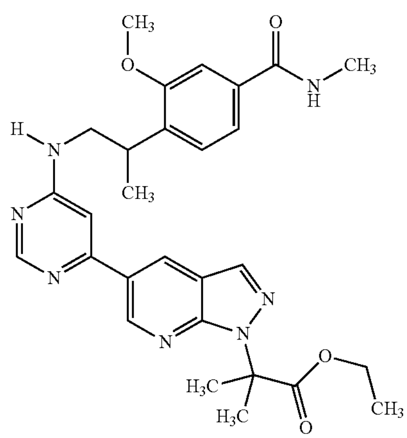 [SMILES: CCOC(=O)C(C)(C)n1ncc2cc(-c3cc(NCC(C)c4ccc(C(=O)NC)cc4OC)ncn3)cnc21] | 532.37 | (400 MHz, CDCl₃) δ 9.16 (s, 1H), 8.76 (s, 1H), 8.61 (s, 1H), 8.21 (s, 1H), 7.41 (s, 1H), 7.22 (d, J = 8.3 Hz, 1H), 6.71 (s, 1H), 6.15 (s, 1H), 4.23-4.15 (m, 2H), 3.92 (s, 3H), 3.69-3.51 (m, 4H), 2.99 (d, J = 4.7 Hz, 3H), 1.58 (s, 7H), 1.37 (d, J = 6.2 Hz, 3H), 1.19 (td, J = 7.1, 1.4 Hz, 3H) |
| 277 | 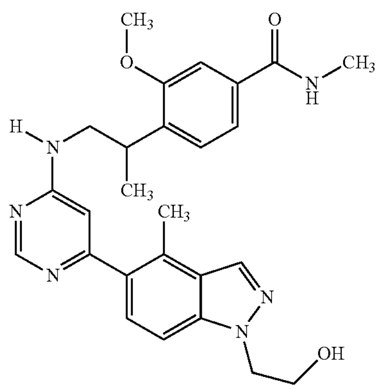 [SMILES: CNC(=O)c1ccc(C(C)CNc2cc(-c3ccc4c(cnn4CCO)c3C)ncn2)c(OC)c1] | 475.34 | (400 MHz, CDCl₃) δ 8.46 (s, 1H), 7.97 (s, 1H), 7.37-7.16 (m, 4H), 6.42-6.25 (m, 2H), 4.38 (t, J = 4.6 Hz, 2H), 4.01-3.94 (m, 2H), 3.78 (d, J = 5.6 Hz, 1H), 3.71 (s, 3H), 3.56-3.33 (m, 4H), 2.88 (d, J = 4.7 Hz, 4H), 2.53 (s, 3H), 1.25 (d, J = 6.6 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 278 | 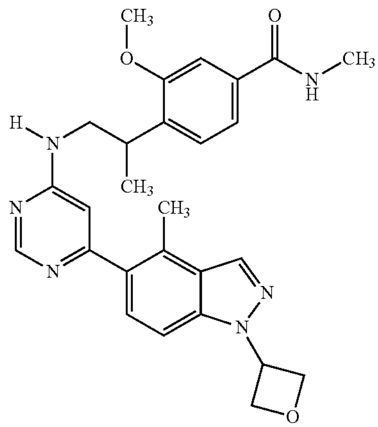 [SMILES: CNC(=O)c1ccc(C(C)CNc2cc(-c3ccc4c(cnn4C4COC4)c3C)ncn2)c(OC)c1] | 487.34 | (400 MHz, CDCl$_3$) δ 8.52 (s, 1H), 8.10 (s, 1H), 7.40 (d, J = 8.6 Hz, 1H), 7.33 (d, J = 12.1 Hz, 2H), 7.14 (d, J = 8.7 Hz, 2H), 6.35 (s, 1H), 6.21 (d, J = 4.1 Hz, 1H), 5.77-5.67 (m, 1H), 5.24 (t, J = 6.4 Hz, 2H), 5.08 (t, J = 7.2 Hz, 2H), 3.74 (s, 3H), 3.49 (dd, J = 21.0, 14.2 Hz, 3H), 2.91 (d, J = 4.8 Hz, 3H), 2.58 (s, 3H), 1.81 (s, 1H), 1.27 (d, J = 6.6 Hz, 3H) |
| 279 | 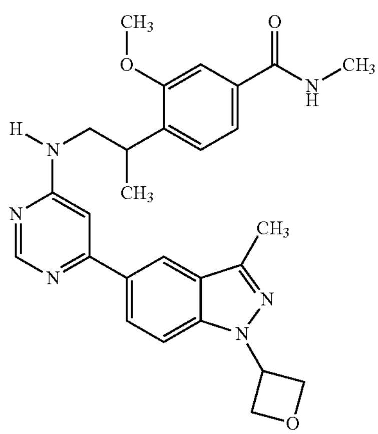 [SMILES: CNC(=O)c1ccc(C(C)CNc2cc(-c3ccc4c(c3)c(C)nn4C3COC3)ncn2)c(OC)c1] | 487.72 | (400 MHz, CDCl$_3$) δ 8.61 (s, 1H), 8.36 (s, 1H), 7.96 (d, J = 8.8 Hz, 1H), 7.51 (d, J = 8.8 Hz, 1H), 7.41 (s, 1H), 7.24 (q, J = 7.9 Hz, 2H), 6.71 (s, 1H), 6.30 (d, J = 4.2 Hz, 1H), 5.79-5.67 (m, 1H), 5.30 (t, J = 6.4 Hz, 2H), 5.13 (t, J = 7.1 Hz, 2H), 3.89 (s, 3H), 3.68-3.52 (m, 3H), 2.98 (d, J = 4.4 Hz, 3H), 2.65 (s, 3H), 1.91 (s, 1H), 1.36 (d, J = 6.0 Hz, 3H) |
| 280 | 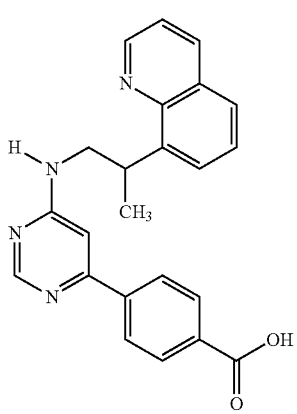 [SMILES: CC(CNc1cc(-c2ccc(C(=O)O)cc2)ncn1)c1cccc2cccnc12] | 385 | (400 MHz, DMSO-d$_6$) δ 9.02 (s, 1H), 8.92 (d, J = 14.2 Hz, 1H), 8.72 (d, J = 30.6 Hz, 1H), 8.40 (d, J = 8.1 Hz, 1H), 8.01 (ddd, J = 27.2, 20.5, 10.9 Hz, 5H), 7.75 (d, J = 6.1 Hz, 1H), 7.62 (t, J = 7.7 Hz, 2H), 7.44 (s, 1H), 6.98 (s, 1H), 4.52 (s, 1H), 3.71 (d, J = 159.2 Hz, 2H), 1.42 (d, J = 6.3 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 281 | 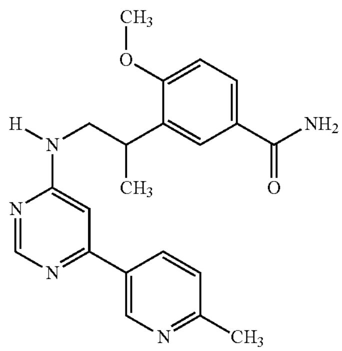 [SMILES: COc1ccc(C(N)=O)cc1C(C)CNc1cc(-c2ccc(C)nc2)ncn1] | 378.44 | (CDCl₃) δ 9.00 (s, 1H), 8.60 (s, 1H), 8.18 (dd, J = 8.1, 2.3 Hz, 1H), 7.76 (m, 1H), 7.65 (dt, J = 11.3, 7.5 Hz, 1H), 7.25 (m, 1H), 6.95-6.86 (m, 1H), 6.66 (s, 1H), 3.89 (s, 3H), 3.60 (m, 3H), 2.62 (s, 3H), 1.43-1.32 (d, 3H) |
| 282 | 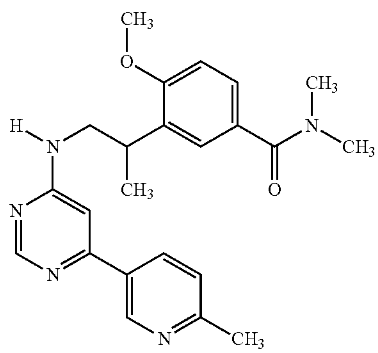 [SMILES: COc1ccc(C(=O)N(C)C)cc1C(C)CNc1cc(-c2ccc(C)nc2)ncn1] | 406.79 | |
| 283 | 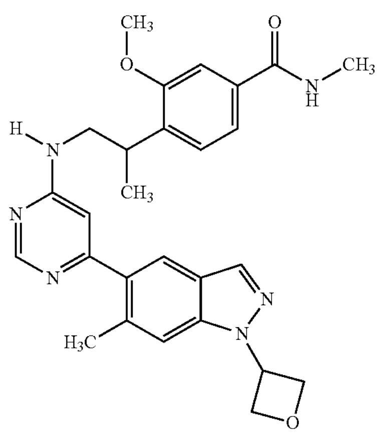 [SMILES: CNC(=O)c1ccc(C(C)CNc2cc(-c3cc4cnn(C5COC5)c4cc3C)ncn2)c(OC)c1] | 487.34 | (400 MHz, CDCl₃) δ 8.57 (s, 1H), 8.07 (s, 1H), 7.71 (s, 1H), 7.39 (s, 2H), 7.28 (d, J = 1.7 Hz, 1H), 7.21 (s, 1H), 6.35 (d, J = 3.1 Hz, 1H), 5.78 (d, J = 6.6 Hz, 1H), 5.32 (t, J = 6.0 Hz, 2H), 5.15 (t, J = 6.7 Hz, 2H), 3.81 (s, 3H), 3.66-3.33 (m, 3H), 3.02-2.93 (m, 3H), 2.52 (s, 3H), 1.96 (s, 2H), 1.40-1.31 (m, 3H) |
| 284 | 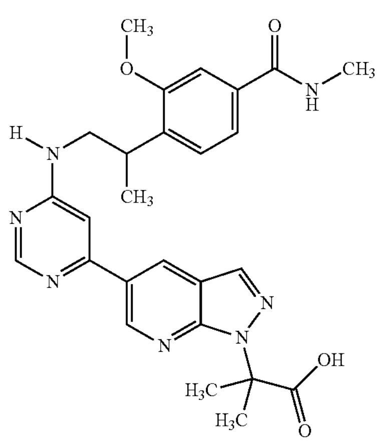 [SMILES: CNC(=O)c1ccc(C(C)CNc2cc(-c3cnc4c(cnn4C(C)(C)C(=O)O)c3)ncn2)c(OC)c1] | 504.33 | (400 MHz, DMSO-d₆) δ 9.17 (s, 1H), 9.06 8.84 (m, 2H), 8.86-8.66 (m, 2H), 8.39 (s, 1H), 7.42 (d, J = 7.2 Hz, 2H), 7.29 (d, J = 40.3 Hz, 1H), 7.03 (s, 1H), 3.82 (s, 3H), 3.72 (s, 2H), 3.54 (s, 2H), 2.72 (d, J = 41.3 Hz, 3H), 1.97 (d, J = 16.4 Hz, 6H), 1.25 (d, J = 5.9 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 285 | 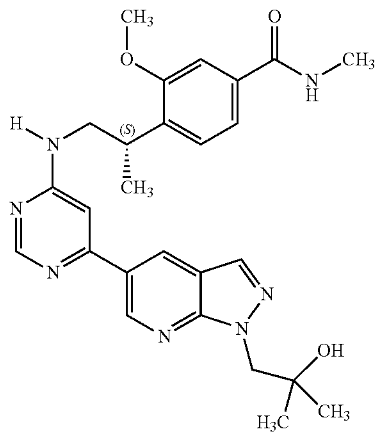 | 490.35 | (400 MHz, CDCl₃) δ 9.01 (s, 1H), 8.64 (d, J = 1.3 Hz, 1H), 8.55 (s, 1H), 8.06 (s, 1H), 7.35 (s, 1H), 7.18 (s, 1H), 7.14 (d, J = 7.7 Hz, 1H), 6.62 (s, 1H), 6.02 (s, 1H), 5.08 (s, 1H), 4.52 (s, 2H), 4.32 (s, 1H), 3.84 (s, 3H), 3.56 (dd, J = 13.3, 6.9 Hz, 3H), 2.94 (d, J = 4.8 Hz, 3H), 1.29 (d, J = 6.4 Hz, 3H), 1.15 (s, 6H) |
| 286 | 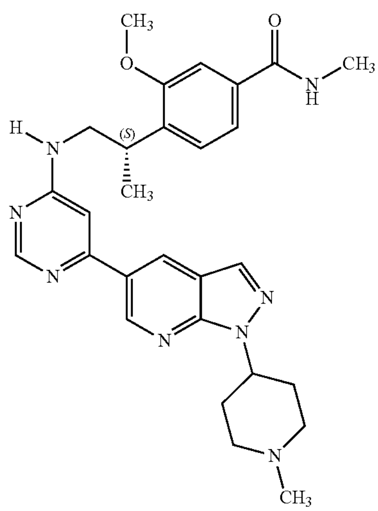 | 515.32 | (CDCl₃) δ 9.07 (d, J = 2.0 Hz, 1H), 8.69-8.57 (m, 2H), 8.10 (s, 1H), 7.43 (d, J = 1.3 Hz, 1H), 7.26-7.18 (m, 2H), 6.71 (s, 1H), 6.19 (d, J = 4.8 Hz, 1H), 4.97-4.84 (m, 1H), 3.92 (s, 3H), 3.62 (d, J = 6.3 Hz, 3H), 3.04 (dd, J = 13.4, 8.4 Hz, 5H), 2.51-2.20 (m, 6H), 2.06 (t, J = 5.8 Hz, 2H), 1.80 (s, 2H), 1.37 (d, J = 6.4 Hz, 3H) |
| 287 | 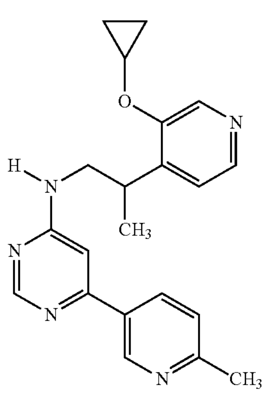 [SMILES: Cc1ccc(-c2cc(NCC(C)c3ccncc3OC3CC3)ncn2)cn1] | 362.27 | (400 MHz, CDCl₃) δ 8.92 (s, 1H), 8.55 (s, 1H), 8.51 (s, 1H), 8.17 (d, J = 4.8 Hz, 1H), 8.12 (dd, J = 8.1, 2.1 Hz, 1H), 7.19 (d, J = 6.4 Hz, 1H), 7.07 (d, J = 4.8 Hz, 1H), 6.58 (s, 1H), 5.12 (s, 1H), 3.83-3.73 (m, 1H), 3.60-3.33 (m, 3H), 2.55 (s, 3H), 1.24 (d, J = 6.1 Hz, 3H), 0.79-0.70 (m, 2H), 0.70-0.56 (m, 2H) |

TABLE 1-continued

| Cmpnd No. | Structure | ESMS (M + H) | ¹H NMR (300 MHz, unless indicated otherwise) NMR peaks given as δ values |
|---|---|---|---|
| 288 | 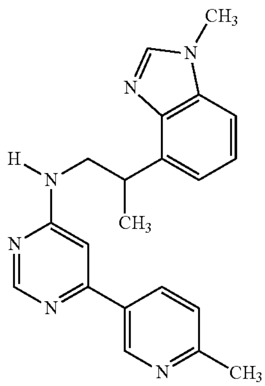 [SMILES: Cc1ccc(-c2cc(NCC(C)c3cccc4c3ncn4C)ncn2)cn1] | 359 | (400 MHz, DMSO-d$_6$) δ 9.10 (d, J = 104.4 Hz, 1H), 8.58-8.05 (m, 3H), 7.80-6.82 (m, 6H), 3.84 (s, 3H), 3.75 (d, J = 29.4 Hz, 2.33H), 3.31-3.16 (m, 0.66H), 2.52 (d, J = 8.7 Hz, 3H), 1.41 (s, 3H) |
| 289 | 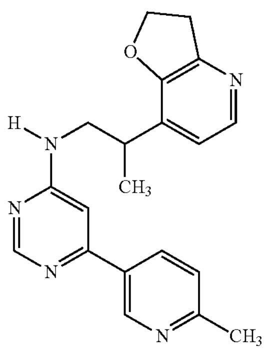 [SMILES: Cc1ccc(-c2cc(NCC(C)c3ccnc4c3OCC4)ncn2)cn1] | 348.21 | (400 MHz, CDCl$_3$) δ 9.04 (s, 1H), 8.64 (s, 1H), 8.25 (dd, J = 8.1, 2.0 Hz, 1H), 8.03 (d, J = 5.1 Hz, 1H), 7.29 (d, J = 7.9 Hz, 1H), 6.92 (d, J = 5.2 Hz, 1H), 6.77 (s, 1H), 5.29 (s, 1H), 4.72 (t, J = 9.0 Hz, 2H), 3.76-3.50 (m, 2H), 3.36 (t, J = 8.9 Hz, 2H), 3.33-3.21 (m, 1H), 2.65 (s, 3H), 1.39 (d, J = 7.0 Hz, 3H) |
| 290 | 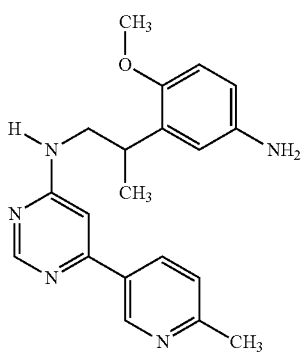 [SMILES: COc1ccc(N)cc1C(C)CNc1cc(-c2ccc(C)nc2)ncn1] | 350.37 | (CDCl$_3$) δ 9.00 (s, 1H), 8.61 (d, J = 7.1 Hz, 1H), 8.18 (dd, J = 8.1, 2.3 Hz, 1H), 7.24 (s, 1H), 6.74 (d, J = 8.5 Hz, 1H), 6.67 (m, 1H), 6.62-6.51 (m, 2H), 3.77 (s, 3H), 3.49 (m, 5H), 2.62 (s, 3H), 1.30 (d, 3H) |
| 291 | 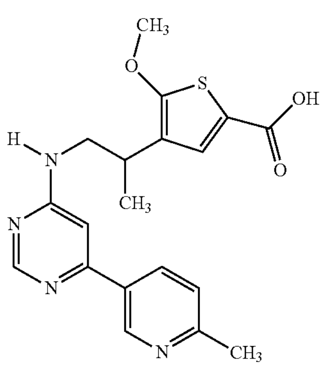 [SMILES: COc1sc(C(=O)O)cc1C(C)CNc1cc(-c2ccc(C)nc2)ncn1] | 385.22 | (methanol-d4) δ 8.99-8.86 (m, 1H), 8.72-8.49 (m, 1H), 8.29 (d, J = 8.1 Hz, 1H), 7.75-7.50 (m, 2H), 6.94 (s, 1H), 4.09-3.87 (m, 3H), 3.88-3.52 (m, 3H), 2.70 (s, 3H), 1.30 (d, J = 6.7 Hz, 3H) |

TABLE 1-continued

| Cmpnd No. | Structure | ESMS (M + H) | $^1$H NMR (300 MHz, unless indicated otherwise) NMR peaks given as δ values |
|---|---|---|---|
| 292 | 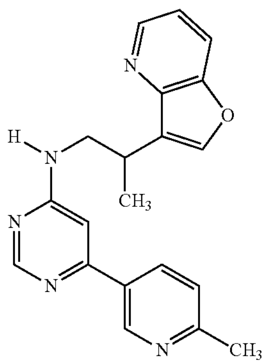 [SMILES: Cc1ccc(-c2cc(NCC(C)c3coc4cccnc34)ncn2)cn1] | 346 | (DMSO-d6) δ 9.10 (d, J = 66.6 Hz, 1H), 8.53 (d, J = 18.5 Hz, 2H), 8.16 (s, 2H), 8.01 (d, J = 8.2 Hz, 1H), 7.62 (s, 1H), 7.38 (d, J = 6.9 Hz, 2H), 6.95 (s, 1H), 4.21-3.63 (m, 2H), 3.38 (d, J = 9.5 Hz, 1H), 2.58-2.51 (m, 3H), 1.41 (d, J = 6.7 Hz, 3H) |
| 293 | 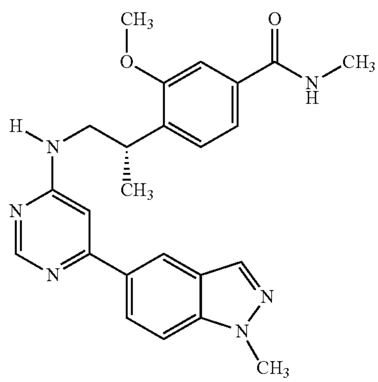 [SMILES: CNC(=O)c1ccc([C@H](C)CNc2cc(-c3ccc4c(cnn4C)c3)ncn2)c(OC)c1] | 431.63 | (CDCl$_3$) δ 8.54 (s, 1H), 8.30 (s, 1H), 7.98 (s, 1H), 7.95 (dd, J = 8.8, 1.5 Hz, 1H), 7.39 (d, J = 8.8 Hz, 2H), 7.35 (d, J = 1.4 Hz, 1H), 7.18-7.08 (m, 2H), 6.64 (s, 1H), 6.02 (s, 1H), 4.05 (d, J = 5.5 Hz, 2H), 3.83 (d, J = 4.4 Hz, 3H), 3.59-3.37 (m, 3H), 2.93 (d, J = 4.9 Hz, 3H), 1.29 (d, J = 6.6 Hz, 3H) |
| 294 | 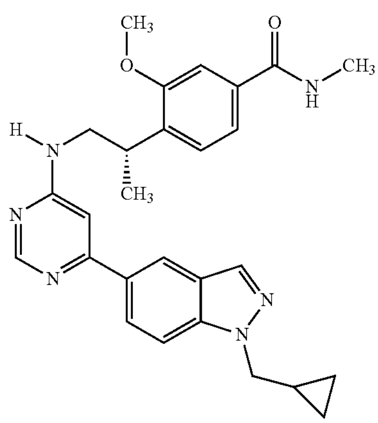 [SMILES: CNC(=O)c1ccc([C@H](C)CNc2cc(-c3ccc4c(cnn4CC4CC4)c3)ncn2)c(OC)c1] | 471.72 | (CDCl$_3$) δ 8.52 (s, 1H), 8.29 (d, J = 0.7 Hz, 1H), 7.99 (d, J = 0.6 Hz, 1H), 7.92 (dd, J = 8.9, 1.5 Hz, 1H), 7.41 (d, J = 8.9 Hz, 1H), 7.33 (d, J = 1.2 Hz, 1H), 7.19-7.11 (m, 2H), 6.63 (s, 1H), 6.17 (d, J = 4.7 Hz, 1H), 4.22 (d, J = 6.8 Hz, 2H), 3.81 (s, 3H), 3.61-3.42 (m, 3H), 2.90 (t, J = 4.4 Hz, 3H), 1.76 (s, 1H), 1.28 (d, J = 6.5 Hz, 4H), 0.58-0.47 (m, 2H), 0.36 (q, J = 4.8 Hz, 2H) |
| 295 | 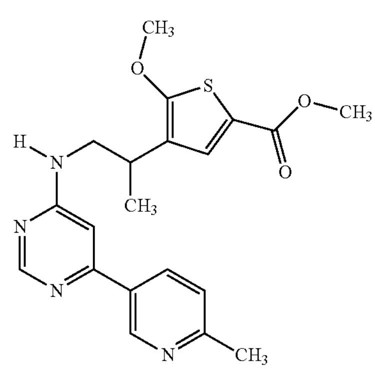 [SMILES: COC(=O)c1cc(C(C)CNc2cc(-c3ccc(C)nc3)ncn2)c(OC)s1] | 398.86 | (CDCl$_3$) δ 9.02 (d, J = 1.9 Hz, 1H), 8.63 (s, 1H), 8.20 (dd, J = 8.1, 2.3 Hz, 1H), 7.52 (s, 1H), 7.28 (s, 1H), 6.72 (s, 1H), 5.37 (bs, J = 34.0 Hz, 1H), 3.87 (s, 6H), 3.70-3.40 (m, 3H), 2.63 (s, 3H), 1.41 (d, J = 6.2 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 296 | 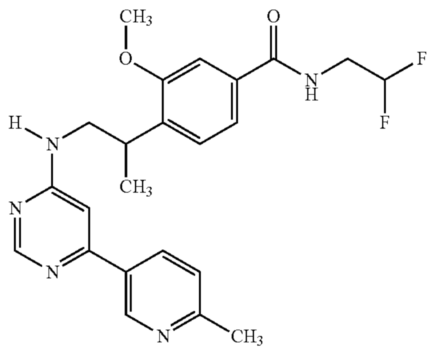 [SMILES: COc1cc(C(=O)NCC(F)F)ccc1C(C)CNc1cc(-c2ccc(C)nc2)ncn1] | 442.09 | (DMSO-d₆) δ 9.10-8.67 (m, 4H), 8.49-8.16 (m, 1H), 8.08-7.31 (m, 7H), 7.20, 7.04 (2s, 1H), 6.11 (t, J = 56.0 Hz, 1H), 3.83 (s, 3H), 3.73-3.50 (m, 5H), 2.64 (s, 3H), 1.24 (d, J = 6.7 Hz, 3H) |
| 297 | 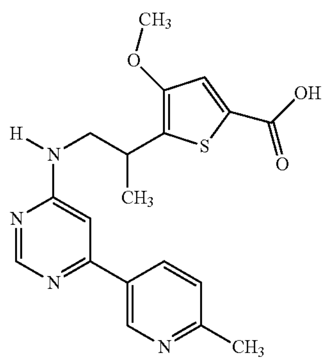 [SMILES: COc1cc(C(=O)O)sc1C(C)CNc1cc(-c2ccc(C)nc2)ncn1] | 385.19 | (CDCl₃) δ 8.96 (s, 1H), 8.77-8.50 (m, 1H), 8.36 (d, J = 8.0 Hz, 1H), 7.71 (d, J = 8.2 Hz, 1H), 7.59-7.36 (m, 1H), 6.99 (s, 1H), 4.00-3.65 (m, 5H), 3.65-3.54 (m, 1H), 2.72 (s, 3H), 1.38 (d, J = 6.7 Hz, 3H) |
| 298 | 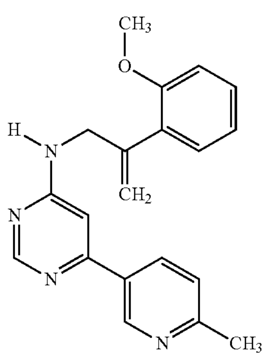 [SMILES: C=C(CNc1cc(-c2ccc(C)nc2)ncn1)c1ccccc1OC] | 332.97 | (CDCl₃) δ 10.19, 8.37 (2s, 1H), 9.41 (2s, 1H), 9.15-8.80 (m, 1H), 8.65 (2s, 1H), 7.89 (2d, J = 7.4 Hz, 1H), 7.36 (m, 2H), 7.18 (d, J = 7.0 Hz, 1H), 7.03-6.75 (m, 2H), 5.38 (s, 1H), 5.31 (d, J = 5.3 Hz, 1H), 4.72 (d, J = 3.4 Hz, 1H), 4.53 (d, J = 4.9 Hz, 1H), 3.87 (d, J = 7.3 Hz, 3H), 2.93 (d, J = 7.1 Hz, 3H) |
| 299 | 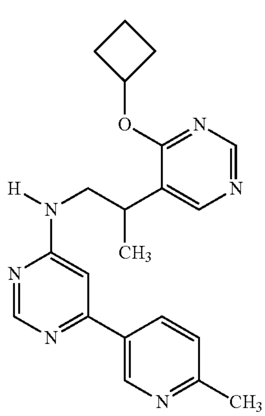 [SMILES: Cc1ccc(-c2cc(NCC(C)c3cncnc3OC3CCC3)ncn2)cn1] | 377 | (DMSO-d₆) δ 8.99 (s, 1H), 8.62-8.10 (m, 4H), 7.54 (t, J = 5.9 Hz, 1H), 7.37 (d, J = 8.1 Hz, 1H), 6.89 (s, 1H), 5.14 (p, J = 7.3 Hz, 1H), 3.71 (s, 1H), 3.56-3.26 (m, 5H), 2.38-2.23 (m, 2H), 2.02-1.83 (m, 2H), 1.57 (ddt, J = 20.8, 18.2, 8.9 Hz, 2H), 1.23 (dd, J = 25.1, 7.0 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 300 | 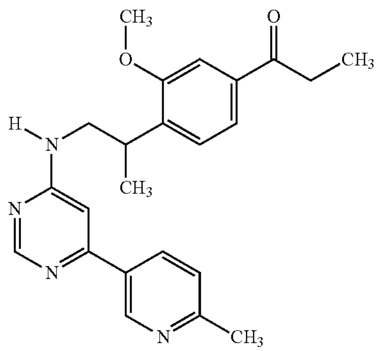 [SMILES: CCC(=O)c1ccc(C(C)CNc2cc(-c3ccc(C)nc3)ncn2)c(OC)c1] | 391.37 | (CDCl₃) δ 9.01 (s, 1H), 8.63 (s, 1H), 8.19 (dd, J = 8.1, 2.1 Hz, 1H), 7.62-7.49 (m, 2H), 7.32 (d, J = 7.8 Hz, 1H), 7.26 (s, 1H), 6.67 (s, 1H), 5.15 (s, 1H), 3.93 (s, 3H), 3.72-3.53 (m, 3H), 3.00 (q, J = 7.2 Hz, 2H), 2.64 (s, 3H), 1.38 (d, J = 6.2 Hz, 3H), 1.24 (t, J = 7.2 Hz, 3H) |
| 301 | 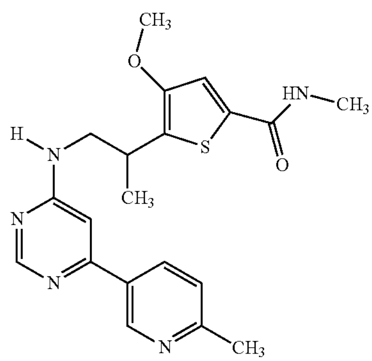 [SMILES: CNC(=O)c1cc(OC)c(C(C)CNc2cc(-c3ccc(C)nc3)ncn2)s1] | 398.16 | (CDCl₃) δ 8.99 (d, J = 1.9 Hz, 1H), 8.60 (s, 1H), 8.18 (dd, J = 8.1, 2.3 Hz, 1H), 7.27 (s, 1H), 7.25 (d, J = 7.4 Hz, 1H), 6.68 (s, 1H), 6.04 (d, J = 4.6 Hz, 1H), 5.44 (s, 1H), 3.81 (s, 3H), 3.78-3.48 (m, 3H), 2.94 (d, J 4.9 Hz, 3H), 2.61 (s, 3H), 1.37 (d, J = 6.3 Hz, 3H) |
| 302 | 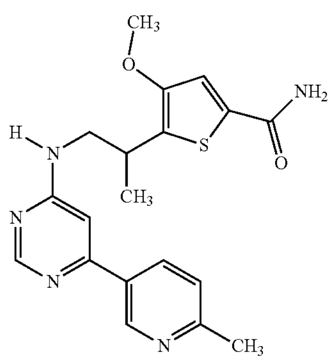 [SMILES: COc1cc(C(N)=O)sc1C(C)CNc1cc(-c2ccc(C)nc2)ncn1] | 384.21 | (methanol-d₄) δ 8.89 (s, 1H), 8.37 (d, J = 31.0 Hz, 1H), 8.17 (dd, J = 8.2, 2.3 Hz, 1H), 7.51 (s, 1H), 7.38 (d, J = 8.2 Hz, 1H), 6.82 (d, J = 1.1 Hz, 1H), 3.77 (s, 3H), 3.74-3.39 (m, 3H), 2.56 (s, 3H), 1.32 (d, J = 5.5 Hz, 3H) |
| 303 | 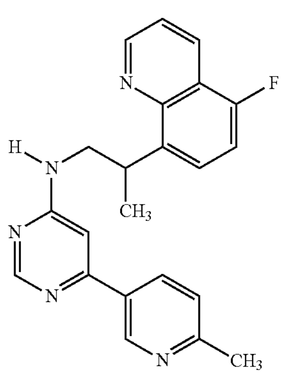 [SMILES: Cc1ccc(-c2cc(NCC(C)c3ccc(F)c4cccnc34)ncn2)cn1] | 374 | (400 MHz, DMSO-d₆) δ 8.99 (d, J = 26.7 Hz, 2H), 8.57-8.36 (m, 2H), 8.15 (s, 1H), 7.82-7.31 (m, 5H), 7.05 (d, J = 129.1 Hz, 1H), 4.42 (s, 1H), 3.56 (d, J = 152.0 Hz, 2H), 2.52 (d, J = 5.4 Hz, 3H), 1.38 (d, J = 5.1 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 304 | 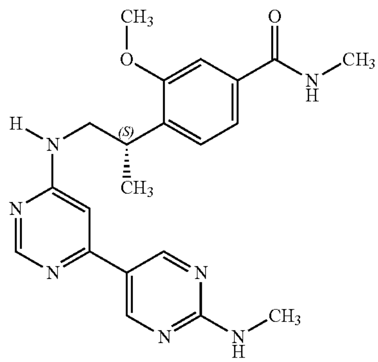 | 408 | (400 MHz, DMSO-d$_6$) δ 9.37 (s, 1H), 9.02-8.57 (m, 3H), 8.45 (d, J = 4.4 Hz, 1H), 8.09 (d, J = 29.3 Hz, 1H), 7.48-7.27 (m, 3H), 6.99 (d, J = 66.1 Hz, 1H), 3.81 (d, J = 7.9 Hz, 3H), 3.57 (s, 3H), 2.89 (d, J = 5.0 Hz, 3H), 2.78 (d, J = 4.3 Hz, 3H), 1.23 (d, J = 6.9 Hz, 3H) |
| 305 | 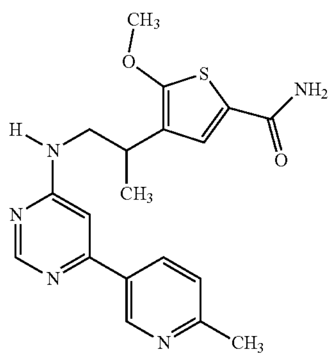 [SMILES: COc1sc(C(N)=O)cc1C(C)CNc1cc(-c2ccc(C)nc2)ncn1] | 384.58 | (methanol-d$_4$) δ 8.91 (s, 1H), 8.44 (s, 1H), 8.19 (dd, J = 8.2, 2.2 Hz, 1H), 7.54 (s, 1H), 7.41 (d, J = 8.2 Hz, 1H), 6.83 (s, 1H), 3.91 (s, 3H), 3.72-3.42 (m, 2H), 3.30-3.16 (m, 1H), 2.59 (s, 3H), 1.28 (d, J = 6.7 Hz, 3H) |
| 306 | 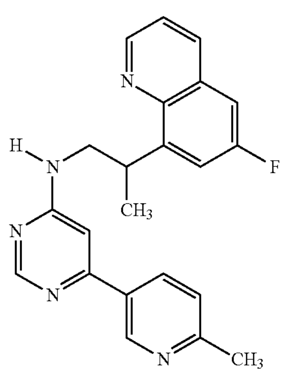 [SMILES: Cc1ccc(-c2cc(NCC(C)c3cc(F)cc4cccnc34)ncn2)cn1] | 374 | (400 MHz, DMSO-d$_6$) δ 9.19-8.82 (m, 2H), 8.33 (dd, J = 67.2, 59.3 Hz, 3H), 7.77-7.47 (m, 4H), 7.44-6.79 (m, 2H), 4.52 (s, 1H), 3.59 (d, J = 168.0 Hz, 2H), 2.51 (s, 3H), 1.38 (d, J = 4.8 Hz, 3H) |
| 307 | 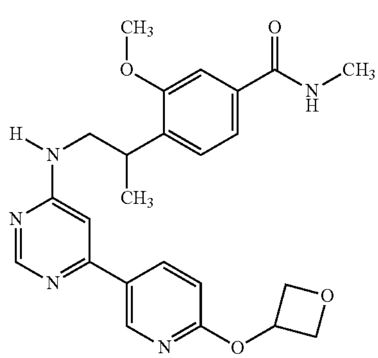 [SMILES: CNC(=O)c1ccc(C(C)CNc2cc(-c3ccc(OC4COC4)nc3)ncn2)c(OC)c1] | 449.99 | (400 MHz, CDCl$_3$) δ 8.56 (d, J = 1.8 Hz, 1H), 8.50 (s, 1H), 8.13 (dd, J = 8.7, 2.3 Hz, 1H), 7.34 (d, J = 1.0 Hz, 1H), 7.15 (dt, J = 7.9, 4.6 Hz, 2H), 6.80 (d, J = 8.7 Hz, 1H), 6.50 (s, 1H), 6.04 (d, J = 3.9 Hz, 1H), 5.60 (t, J = 5.8 Hz, 1H), 4.94 (t, J = 7.0 Hz, 2H), 4.74-4.63 (m, 2H), 3.82 (s, 3H), 3.51 (dd, J = 20.0, 13.2 Hz, 2H), 2.94 (d, J = 4.8 Hz, 3H), 2.55 (s, 2H), 1.27 (d, J = 6.7 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 308 | 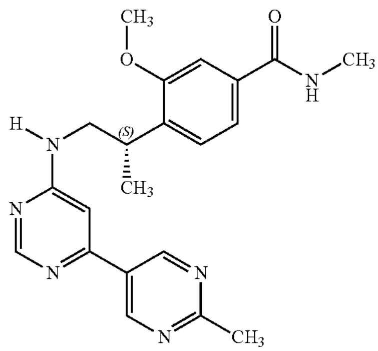 | 393 | (400 MHz, DMSO-$d_6$) δ 9.23 (d, J = 53.2 Hz, 2H), 8.59-8.31 (m, 2H), 7.58 (s, 1H), 7.45-7.25 (m, 3H), 6.97 (s, 1H), 3.81 (s, 3H), 3.68-3.40 (m, 3H), 2.77 (d, J = 4.4 Hz, 3H), 2.68 (s, 3H), 1.20 (d, J = 5.5 Hz, 3H) |
| 309 | 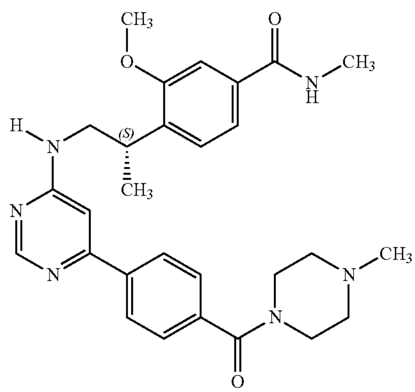 | 503.6 | (methanol-$d_4$) δ 8.61 (s, 1H), 7.89 (d, J = 7.7 Hz, 2H), 7.71 (d, J = 8.0 Hz, 2H), 7.42-7.24 (m, 3H), 6.89 (s, 1H), 3.93-3.54 (m, 8H), 3.35 (s, 3H), 2.93 (m, 6H), 1.40-1.26 (d, 3H) |
| 310 | 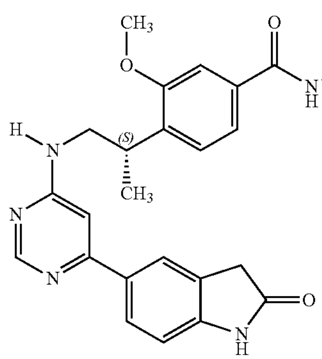 | 432.52 | (methanol-$d_4$) δ 8.39 (s, 1H), 7.75 (s, 2H), 7.34 (m, 3H), 6.98 (d, J = 9.2 Hz, 1H), 6.72 (s, 1H), 3.85 (s, 3H), 3.61 (m, 5H), 2.90 (s, 3H), 1.30 (d, 3H) |
| 311 | 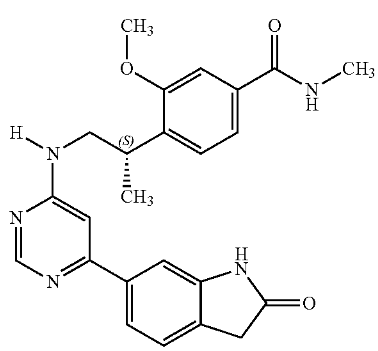 | 432.52 | |

TABLE 1-continued

| Cmpnd No. | Structure | ESMS (M + H) | ¹H NMR (300 MHz, unless indicated otherwise) NMR peaks given as δ values |
|---|---|---|---|
| 312 | 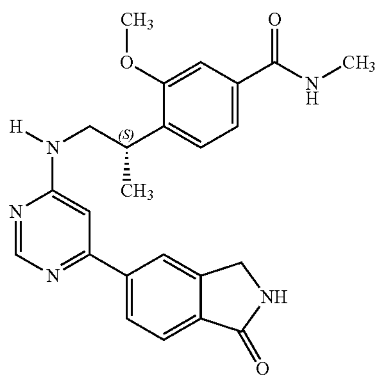 | 432.52 | (methanol-d₄) δ 8.61 (s, 1H), 8.02-7.80 (m, 3H), 7.43-7.27 (m, 3H), 6.85 (s, 1H), 4.57 (s, 2H), 3.92-3.57 (m, 6H), 2.88 (s, 3H), 1.32 (d, 3H) |
| 313 | 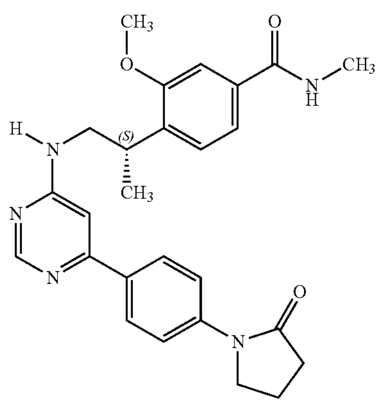 | 460.3 | (methanol-d₄) δ 8.60 (s, 1H), 7.93 (d, J = 8.5 Hz, 2H), 7.78 (d, J = 8.7 Hz, 2H), 7.41-7.27 (m, 3H), 6.80 (s, 1H), 3.98 (t, J = 7.1 Hz, 2H), 3.86 (s, 3H), 3.58 (m, 3H), 2.88 (s, 3H), 2.63 (m, 2H), 2.28-2.13 (m, 2H), 1.36 (d, 3H) |
| 314 | 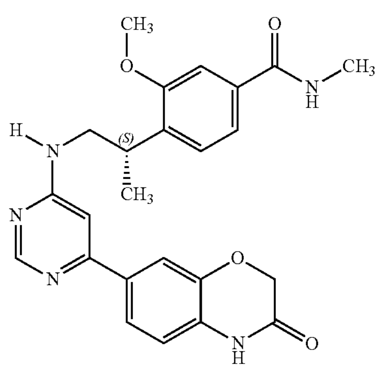 | 448.2 | (methanol-d₄) δ 8.51 (s, 1H), 7.43-7.27 (m, 5H), 7.09 (m, 1H), 6.74 (s, 1H), 4.69 (s, 2H), 3.90-3.49 (m, 6H), 2.89 (s, 3H), 1.35 (d, 3H) |
| 315 | 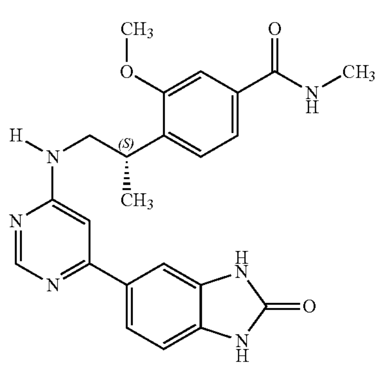 | 433.51 | |

TABLE 1-continued

| Cmpnd No. | Structure | ESMS (M + H) | ¹H NMR (300 MHz, unless indicated otherwise) NMR peaks given as δ values |
|---|---|---|---|
| 316 | 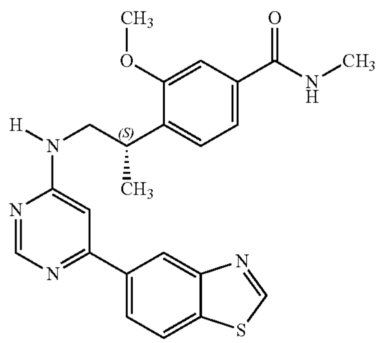 | 434.15 | (methanol-d₄) δ 9.43 (s, 1H), 8.68 (s, 1H), 8.49 (s, 1H), 8.34 (d, J = 8.4 Hz, 1H), 7.84 (d, J = 8.3 Hz, 1H), 7.36 (m, 3H), 6.93 (s, 1H), 3.95-3.56 (m, 6H), 2.86 (s, 3H), 1.38 (d, 3H) |
| 317 | 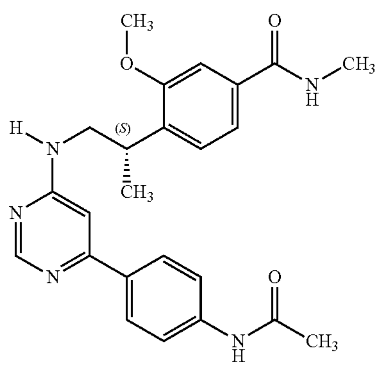 | 434.51 | (methanol-d₄) δ 8.37 (m, 3H), 7.82 (d, J = 8.7 Hz, 2H), 7.68 (d, J = 8.9 Hz, 2H), 7.34 (m, 3H), 6.76 (s, 1H), 3.85 (s, 3H), 3.59 (m, 3H), 2.90 (s, 3H), 2.13 (s, 3H), 1.30 (d, 3H) |
| 318 | 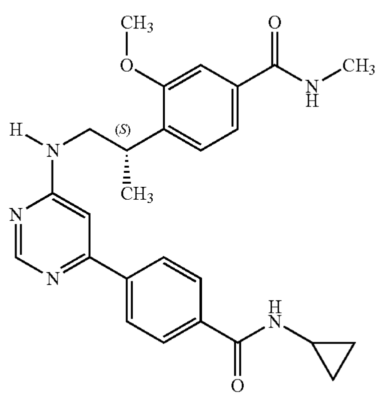 | 460.52 | (methanol-d₄) δ 8.64 (s, 1H), 8.00 (d, J = 8.0 Hz, 2H), 7.81 (d, 2H), 7.38 (m, 3H), 6.88 (s, 1H), 3.87 (s, 3H), 3.77-3.50 (m, 3H), 2.89 (m, 4H), 1.41-1.24 (m, 3H), 0.83 (m, 2H), 0.66 (m, 2H) |
| 319 | 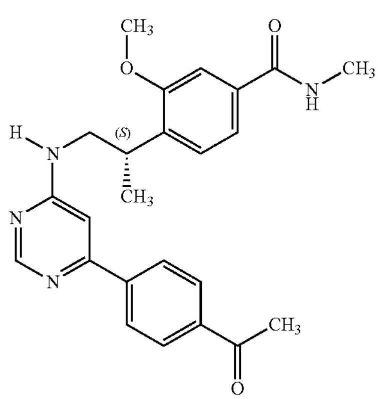 | 419.27 | (methanol-d₄) δ 8.49 (s, 1H), 8.11 (d, J = 8.3 Hz, 2H), 7.96 (d, J = 8.4 Hz, 2H), 7.34 (m, 3H), 6.84 (s, 1H), 3.85 (s, 3H), 3.61 (m, 3H), 2.89 (s, 3H), 2.65 (s, 3H), 1.33 (d, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 320 | 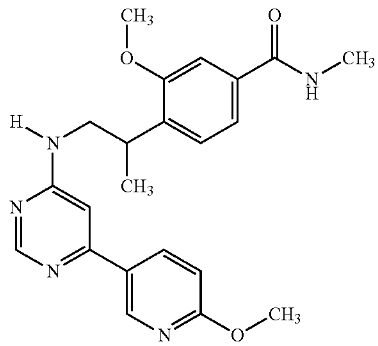 [SMILES: CNC(=O)c1ccc(C(C)CNc2cc(-c3ccc(OC)nc3)ncn2)c(OC)c1] | 408.36 | (400 MHz, CDCl₃) δ 8.69 (s, 1H), 8.53 (s, 1H), 8.15 (dd, J = 8.6, 1.9 Hz, 1H), 7.37 (s, 1H), 7.21 (s, 2H), 6.81 (d, J = 8.7 Hz, 1H), 6.59 (s, 1H), 6.46 (d, J = 4.5 Hz, 1H), 3.98 (s, 3H), 3.84 (s, 3H), 3.61-3.46 (m, 3H), 2.97 (d, J = 4.6 Hz, 3H), 2.16 (s, 1H), 1.32 (d, J = 6.4 Hz, 3H) |
| 321 | 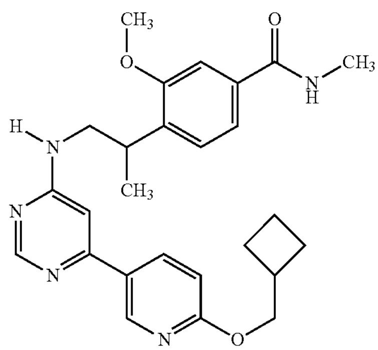 [SMILES: CNC(=O)c1ccc(C(C)CNc2cc(-c3ccc(OCC4CCC4)nc3)ncn2)c(OC)c1] | 462.03 | (400 MHz, CDCl₃) δ 8.70 (d, J = 1.6 Hz, 1H), 8.57 (s, 1H), 8.17 (dd, J = 8.7, 2.3 Hz, 1H), 7.40 (s, 1H), 7.23 (q, J = 7.9 Hz, 2H), 6.82 (d, J = 8.7 Hz, 1H), 6.59 (s, 1H), 6.22 (d, J = 4.4 Hz, 1H), 5.20 (s, 1H), 4.33 (d, J = 6.8 Hz, 2H), 3.89 (s, 3H), 3.66-3.44 (m, 3H), 3.01 (d, J = 4.8 Hz, 3H), 2.86-2.72 (m, 1H), 2.23-2.08 (m, 2H), 2.02-1.84 (m, 4H), 1.35 (d, J = 6.5 Hz, 3H) |
| 322 | 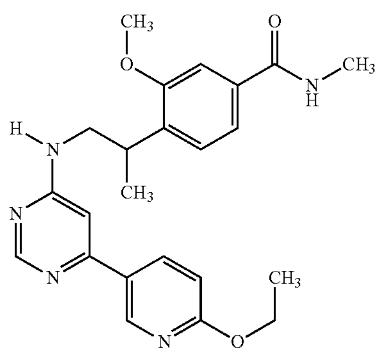 [SMILES: CCOc1ccc(-c2cc(NCC(C)c3ccc(C(=O)NC)cc3OC)ncn2)cn1] | 422.38 | (400 MHz, CDCl₃) δ 8.69 (s, 1H), 8.55 (s, 1H), 8.16 (dd, J = 8.6, 2.3 Hz, 1H), 7.39 (s, 1H), 7.22 (s, 2H), 6.80 (d, J = 8.8 Hz, 1H), 6.59 (s, 1H), 6.31 (d, J = 4.4 Hz, 1H), 4.42 (q, J = 7.0 Hz, 2H), 3.89 (d, J = 9.9 Hz, 3H), 3.66-3.47 (m, 3H), 2.99 (d, J = 4.7 Hz, 3H), 1.91 (s, 1H), 1.42 (t, J = 7.0 Hz, 3H), 1.34 (d, J = 6.5 Hz, 3H) |
| 323 | 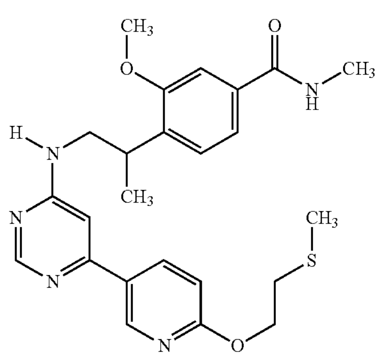 [SMILES: CNC(=O)c1ccc(C(C)CNc2cc(-c3ccc(OCCSC)nc3)ncn2)c(OC)c1] | 468.65 | (400 MHz, CDCl₃) δ 8.72 (s, 1H), 8.59 (s, 1H), 8.19 (dd, J = 8.7, 2.5 Hz, 1H), 7.42 (s, 1H), 7.27-7.19 (m, 2H), 6.84 (d, J = 8.6 Hz, 1H), 6.60 (s, 1H), 6.10 (s, 1H), 5.09 (s, 1H), 4.58 (t, J = 6.8 Hz, 2H), 3.92 (s, 3H), 3.60 (dd, J = 18.4, 11.6 Hz, 3H), 3.03 (d, J = 4.8 Hz, 3H), 2.92 (t, J = 6.8 Hz, 2H), 2.24 (s, 3H), 1.37 (d, J = 6.7 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 324 | 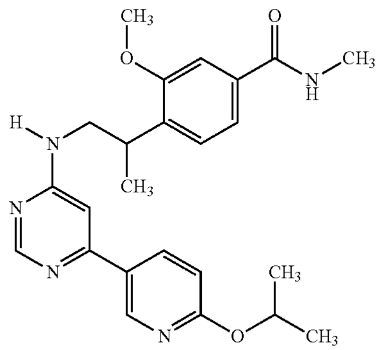 [SMILES: CNC(=O)c1ccc(C(C)CNc2cc(-c3ccc(OC(C)C)nc3)ncn2)c(OC)c1] | 436.71 | (400 MHz, CDCl₃) δ 8.70 (d, J = 1.8 Hz, 1H), 8.57 (s, 1H), 8.15 (dd, J = 8.7, 2.4 Hz, 1H), 7.41 (s, 1H), 7.23 (q, J = 7.8 Hz, 2H), 6.76 (d, J = 8.7 Hz, 1H), 6.59 (s, 1H), 6.20 (d, J = 4.2 Hz, 1H), 5.37 (dt, J = 12.3, 6.2 Hz, 1H), 5.19 (s, 1H), 3.90 (s, 3H), 3.66-3.50 (m, 3H), 3.01 (d, J = 4.8 Hz, 3H), 1.38 (d, J = 6.2 Hz, 6H), 1.35 (d, J = 6.7 Hz, 3H) |
| 325 | 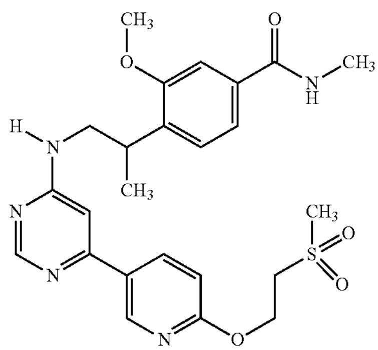 [SMILES: CNC(=O)c1ccc(C(C)CNc2cc(-c3ccc(OCCS(C)(=O)=O)nc3)ncn2)c(OC)c1] | 500.01 | (400 MHz, CDCl₃) δ 8.63 (d, J = 1.8 Hz, 1H), 8.50 (s, 1H), 8.14 (dd, J = 8.6, 2.4 Hz, 1H), 7.34 (s, 1H), 7.19-7.10 (m, 2H), 6.76 (d, J = 8.6 Hz, 1H), 6.52 (s, 1H), 6.16 (d, J = 4.3 Hz, 1H), 5.14 (s, 1H), 4.78 (t, J = 5.6 Hz, 2H), 3.82 (s, 3H), 3.53 (s, 3H), 3.43 (t, J = 5.5 Hz, 2H), 2.97 (s, 3H), 2.93 (d, J = 4.8 Hz, 3H), 1.28 (d, J = 6.5 Hz, 3H) |
| 326 | 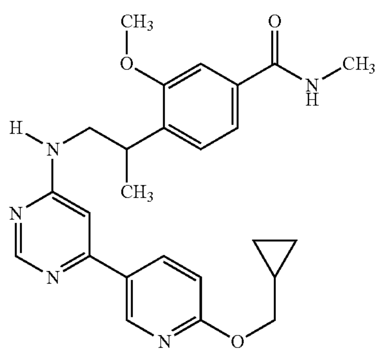 [SMILES: CNC(=O)c1ccc(C(C)CNc2cc(-c3ccc(OCC4CC4)nc3)ncn2)c(OC)c1] | 448.01 | (400 MHz, CDCl₃) δ 8.69 (d, J = 1.7 Hz, 1H), 8.56 (s, 1H), 8.17 (dd, J = 8.7, 2.4 Hz, 1H), 7.40 (s, 1H), 7.26-7.20 (m, 2H), 6.85 (d, J = 8.7 Hz, 1H), 6.59 (s, 1H), 6.24 (d, J = 4.3 Hz, 1H), 5.23 (s, 1H), 4.20 (d, J = 7.1 Hz, 2H), 3.89 (s, 3H), 3.66-3.49 (m, 4H), 3.00 (d, J = 4.8 Hz, 3H), 1.35 (d, J = 6.6 Hz, 3H), 0.71-0.58 (m, 2H), 0.44-0.33 (m, 2H) |
| 327 | 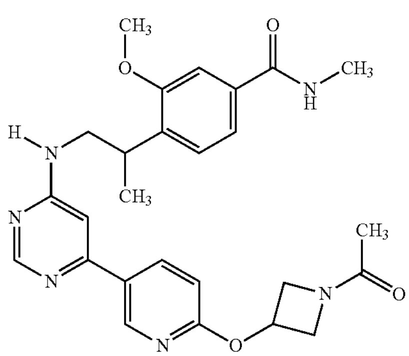 [SMILES: CNC(=O)c1ccc(C(C)CNc2cc(-c3ccc(OC4CN(C(C)=O)C4)nc3)ncn2)c(OC)c1] | 491.66 | (400 MHz, CDCl₃) δ 8.59 (s, 1H), 8.49 (s, 1H), 8.13 (d, J = 8.5 Hz, 1H), 7.33 (s, 1H), 7.17 (d, J = 7.8 Hz, 2H), 6.80 (d, J = 8.6 Hz, 1H), 6.52 (s, 1H), 6.21 (d, J = 4.5 Hz, 1H), 5.41-5.31 (m, 1H), 5.16 (s, 1H), 4.52-4.43 (m, 1H), 4.34 (dd, J = 10.9, 6.9 Hz, 1H), 3.81 (s, 3H), 3.59-3.38 (m, 3H), 2.93 (d, J = 4.8 Hz, 3H), 1.84 (s, 3H), 1.27 (d, J = 6.6 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 328 | 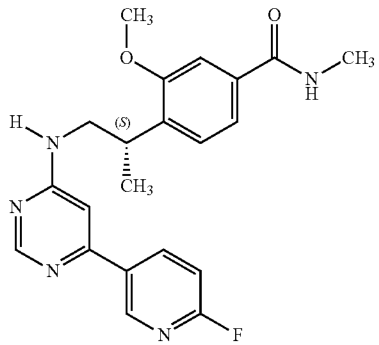 | 396.14 | |
| 329 | 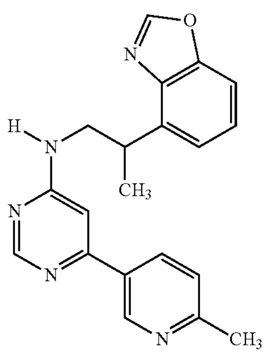 [SMILES: Cc1ccc(-c2cc(NCC(C)c3cccc4ocnc34)ncn2)cn1] | 346 | (400 MHz, DMSO-d₆) δ 9.33-8.98 (m, 2H), 8.62-8.22 (m, 2H), 7.66-7.29 (m, 2H), 7.07 (t, J = 8.0 Hz, 1H), 6.91 (t, J = 16.5 Hz, 1H), 6.87-6.67 (m, 2H), 3.39 (d, J = 36.6 Hz, 2H), 3.19 (dd, J = 13.9, 6.8 Hz, 1H), 2.52 (d, J = 3.9 Hz, 3H), 1.21-1.15 (m, 3H)., (400 MHz, DMSO-d₆) δ 8.98 (s, 1H), 8.73 (s, 1H), 8.33 (d, J = 133.8 Hz, 2H), 7.70-7.25 (m, 6H), 6.90 (s, 1H), 3.60 (t, J = 73.0 Hz, 3H), 2.52 (d, J = 4.3 Hz, 3H), 1.40 (d, J = 5.9 Hz, 3H) |
| 330 | 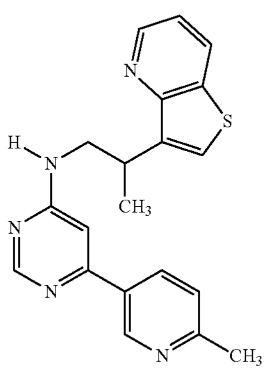 [SMILES: Cc1ccc(-c2cc(NCC(C)c3csc4cccnc34)ncn2)cn1] | 362 | (400 MHz, DMSO-d₆) δ 9.33-8.55 (m, 2H), 8.48 (s, 2H), 8.24 (d, J = 47.7 Hz, 1H), 7.97-7.52 (m, 2H), 7.51-6.88 (m, 3H), 3.92-3.58 (m, 2.5H), 3.17 (s, 0.5H), 2.53 (d, J = 8.1 Hz, 3H), 1.40 (s, 3H) |
| 331 | 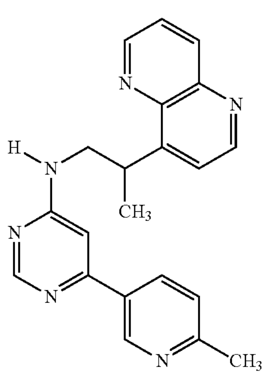 [SMILES: Cc1ccc(-c2cc(NCC(C)c3ccnc4cccnc34)ncn2)cn1] | 357 | (400 MHz, DMSO-d₆) δ 9.20-8.87 (m, 3H), 8.52-8.37 (m, 2H), 8.15 (s, 1H), 7.70 (t, J = 49.6 Hz, 3H), 7.37 (s, 1H), 6.87 (s, 1H), 4.48 (d, J = 6.7 Hz, 1H), 3.60 (d, J = 170.7 Hz, 2H), 2.52 (d, J = 4.2 Hz, 3H), 1.40 (d, J = 6.2 Hz, 3H) |

| Cmpnd No. | Structure | ESMS (M + H) | ¹H NMR (300 MHz, unless indicated otherwise) NMR peaks given as δ values |
|---|---|---|---|
| 332 | 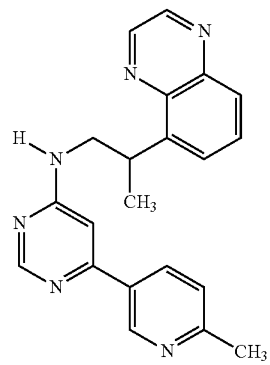 [SMILES: Cc1ccc(-c2cc(NCC(C)c3cccc4nccnc34)ncn2)cn1] | 357 | (400 MHz, DMSO-d₆) δ 8.96 (s, 3H), 8.46 (s, 1H), 8.15 (s, 1H), 8.01-7.92 (m, 1H), 7.90-7.76 (m, 2H), 7.52 (s, 1H), 7.37 (s, 1H), 7.05 (d, J = 135.9 Hz, 1H), 4.44 (s, 1H), 3.66 (t, J = 94.2 Hz, 2H), 2.52 (d, J = 4.3 Hz, 3H), 1.40 (d, J = 5.7 Hz, 3H) |
| 333 | 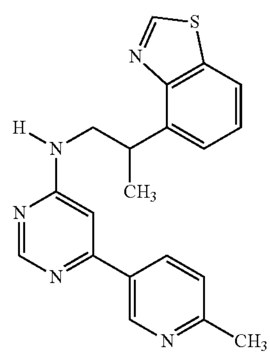 | 362 | (400 MHz, DMSO-d₆) δ 9.40 (s, 1H), 9.08 (d, J = 92.7 Hz, 1H), 8.49 (s, 1H), 8.25 (d, J = 72.8 Hz, 1H), 8.08-7.97 (m, 1H), 7.43 (t, J = 18.1 Hz, 4H), 6.91 (s, 1H), 4.02 (s, 1H), 3.58 (d, J = 173.1 Hz, 2H), 2.52 (d, J = 6.3 Hz, 3H), 1.41 (d, J = 6.4 Hz, 3H) |
| 334 | 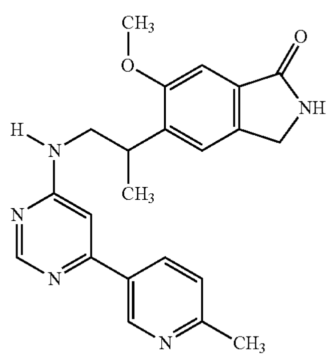 [SMILES: COc1cc2c(cc1C(C)CNc1cc(-c3ccc(C)nc3)ncn1)CNC2=O] | 390.25 | (DMSO-d₆) δ 9.08-8.29 (m, 5H), 7.64 (d, J = 8.0 Hz, 1H), 7.50 (br.s, 1H), 7.17, 7.00 (2s, 2H), 4.28 (s, 2H), 3.83 (s, 3H), 3.78-3.31 (m, 3H), 2.63 (s, 3H), 1.26 (d, J = 6.2 Hz, 3H) |
| 335 | 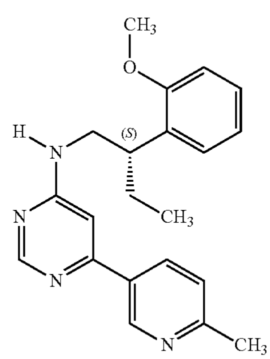 | 349.55 | (400 MHz, CDCl₃) δ 8.98 (s, 1H), 8.58 (s, 1H), 8.17 (dd, J = 8.1, 2.1 Hz, 1H), 7.26-7.14 (m, 3H), 6.95 (t, J = 7.4 Hz, 1H), 6.90 (d, J = 8.2 Hz, 1H), 6.61 (s, 1H), 5.16 (s, 1H), 3.82 (s, 3H), 3.77-3.41 (m, 2H), 3.41-3.26 (m, 1H), 2.61 (s, 3H), 1.81-1.75 (m, 2H), 0.87 (t, J = 7.4 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 336 | 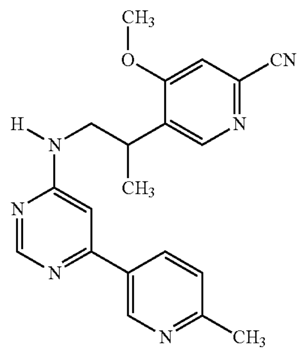 [SMILES: COc1cc(C#N)ncc1C(C)CNc1cc(-c2ccc(C)nc2)ncn1] | 361.35 | (CDCl₃) δ 8.98 (d, J = 1.9 Hz, 1H), 8.62 (s, 1H), 8.41 (s, 1H), 8.19 (dd, J = 8.1, 1.9 Hz, 1H), 7.27 (dd, J = 4.4, 3.6 Hz, 2H), 7.17 (s, 1H), 6.67 (s, 1H), 5.29 (s, 1H), 3.93 (s, 3H), 3.85-3.31 (m, 3H), 2.62 (s, 3H), 1.39 (d, J = 6.8 Hz, 3H) |
| 337 | 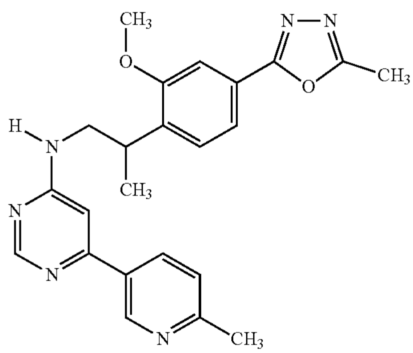 [SMILES: COc1cc(-c2nnc(C)o2)ccc1C(C)CNc1cc(-c2ccc(C)nc2)ncn1] | 417.48 | (CDCl₃) δ 9.00 (s, 1H), 8.61 (s, 1H), 8.17 (dd, J = 8.1, 2.0 Hz, 1H), 7.62-7.51 (m, 2H), 7.34 (d, J = 7.8 Hz, 1H), 7.24 (s, 1H), 6.65 (s, 1H), 3.92 (s, 3H), 3.73-3.49 (m, 3H), 2.62 (s, 6H), 1.38 (d, J = 6.1 Hz, 3H) |
| 338 | 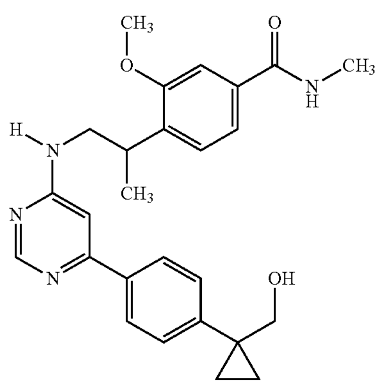 [SMILES: CNC(=O)c1ccc(C(C)CNc2cc(-c3ccc(C4(CO)CC4)cc3)ncn2)c(OC)c1] | 447.66 | (400 MHz, CDCl₃) δ 8.46 (s, 1H), 7.77 (d, J = 8.2 Hz, 2H), 7.35 (d, J = 8.2 Hz, 2H), 7.30 (s, 1H), 7.10 (dd, J = 14.4, 6.4 Hz, 2H), 6.49 (s, 1H), 6.17 (d, J = 4.4 Hz, 1H), 5.16 (s, 1H), 3.80 (s, 3H), 3.65 (s, 2H), 3.50 (dd, J = 18.6, 11.9 Hz, 4H), 2.90 (d, J = 4.8 Hz, 3H), 1.26 (d, J = 6.7 Hz, 3H), 0.84 (d, J = 4.6 Hz, 4H) |
| 339 | 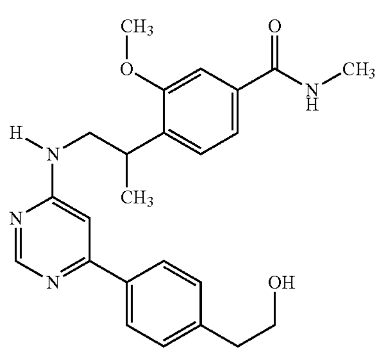 [SMILES: CNC(=O)c1ccc(C(C)CNc2cc(-c3ccc(CCO)cc3)ncn2)c(OC)c1] | 421.06 | (400 MHz, CDCl₃) δ 8.47 (s, 1H), 7.78 (d, J = 8.1 Hz, 2H), 7.30 (s, 1H), 7.24 (d, J = 8.0 Hz, 2H), 7.12 (q, J = 7.8 Hz, 2H), 6.51 (s, 1H), 6.18 (d, J = 4.4 Hz, 1H), 5.17 (s, 1H), 3.86-3.75 (m, 6H), 3.50 (dd, J = 19.1, 12.3 Hz, 3H), 2.91 (t, J = 5.8 Hz, 3H), 2.84 (t, J = 6.4 Hz, 2H), 1.26 (d, J = 6.7 Hz, 3H) |

| Cmpnd No. | Structure | ESMS (M + H) | ¹H NMR (300 MHz, unless indicated otherwise) NMR peaks given as δ values |
|---|---|---|---|
| 340 | 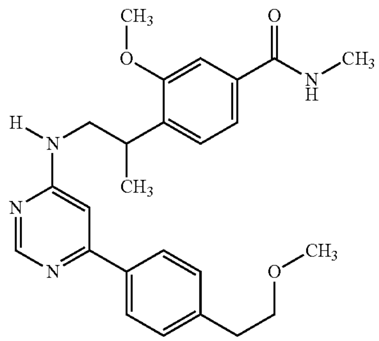 [SMILES: CNC(=O)c1ccc(C(C)CNc2cc(-c3ccc(CCOC)cc3)ncn2)c(OC)c1] | 435.72 | (400 MHz, CDCl₃) δ 8.51 (s, 1H), 7.80 (d, J = 8.1 Hz, 2H), 7.33 (s, 1H), 7.25 (d, J = 8.0 Hz, 2H), 7.17-7.06 (m, 2H), 6.57 (s, 1H), 6.07 (s, 1H), 5.07 (s, 1H), 3.82 (s, 3H), 3.56 (t, J = 6.9 Hz, 5H), 3.29 (s, 3H), 2.93 (d, J = 4.8 Hz, 3H), 2.87 (t, J = 6.9 Hz, 2H), 1.27 (d, J = 6.7 Hz, 3H) |
| 341 | 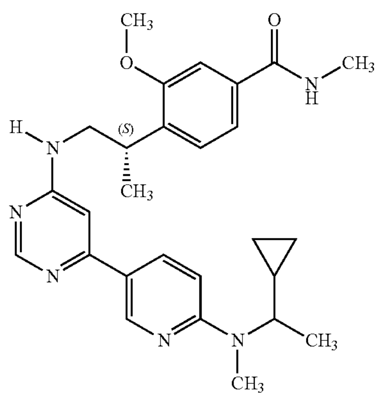 | 475.56 | (CDCl₃) δ 8.68 (d, J = 2.2 Hz, 1H), 8.52 (s, 1H), 8.07 (dd, J = 9.0, 2.3 Hz, 1H), 7.39 (s, 1H), 7.24-7.13 (m, 2H), 6.51 (s, 1H), 6.50 (s, 1H), 6.13 (s, 1H), 5.01 (s, 1H), 4.20-4.07 (m, 1H), 3.89 (s, 3H), 3.70-3.38 (m, 3H), 3.08-2.91 (m, 6H), 1.33 (d, J = 6.6 Hz, 3H), 1.23 (d, 3H), 1.06-0.95 (m, 1H), 0.60 (m, 1H), 0.40 (m, 2H), 0.25 (m, 1H) |
| 342 | 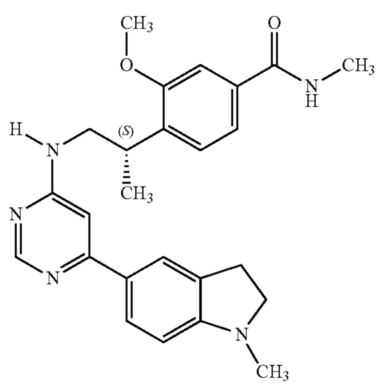 | 432.3 | (CDCl₃) δ 8.51 (s, 1H), 7.73 (m, 2H), 7.40 (s, 1H), 7.26-7.12 (m, 2H), 6.52 (d, J = 13.1 Hz, 1H), 6.47 (d, J = 8.7 Hz, 1H), 6.09 (s, 1H), 4.97 (s, 1H), 3.87 (s, 3H), 3.68-3.46 (m, 3H), 3.42 (t, J = 8.3 Hz, 2H), 3.01 (m, 5H), 2.83 (d, J = 0.6 Hz, 3H), 1.32 (t, J = 10.0 Hz, 3H) |
| 343 | 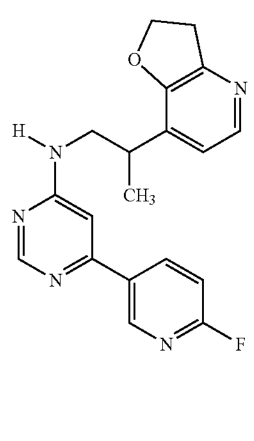 [SMILES: CC(CNc1cc(-c2ccc(F)nc2)ncn1)c1ccnc2c1OCC2] | 352.29 | (400 MHz, CDCl₃) δ 8.77 (s, 1H), 8.62 (s, 1H), 8.45 (t, J = 7.1 Hz, 1H), 8.01 (d, J = 5.1 Hz, 1H), 7.04 (dd, J = 8.5, 2.8 Hz, 1H), 6.91 (d, J = 5.1 Hz, 1H), 6.75 (s, 1H), 5.34 (s, 1H), 4.77-4.62 (m, 2H), 3.74-3.51 (m, 2H), 3.35 (t, J = 8.9 Hz, 2H), 3.31-3.22 (m, 1H), 1.37 (d, J = 6.9 Hz, 3H) |

TABLE 1-continued
| Cmpnd No. | Structure | ESMS (M + H) | ¹H NMR (300 MHz, unless indicated otherwise) NMR peaks given as δ values |
|---|---|---|---|
| 344 | 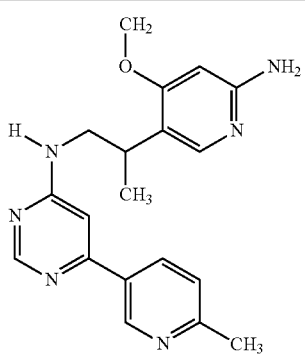 | 352.55 | (methanol-d₄) δ 8.77-8.44 (m, 2H), 8.13-7.86 (m, 1H), 7.64, 7.58 (2s, 1H), 7.03 (t, J = 8.4 Hz, 1H), 6.87 (s, 1H), 6.39 (s, 1H), 3.99 (s, 3H), 3.84 (d, J = 6.7 Hz, 3H), 3.31 (s, 3H), 2.16 (s, 3H), 1.32 (d, J = 7.1 Hz, 3H). , (methanol-d4) δ 8.94 (s, 1H), 8.63 (s, 1H), 8.35 (d, J = 8.2 Hz, 1H), 7.66 (d, J = 8.3 Hz, 1H), 7.58 (s, 1H), 6.96 (s, 1H), 6.38 (s, 1H), 3.98 (s, 3H), 3.82 (m, 2H), 3.34 (m, 1H), 2.70 (s, 3H), 1.32 (d, J = 7.1 Hz, 3H) |
| 345 | 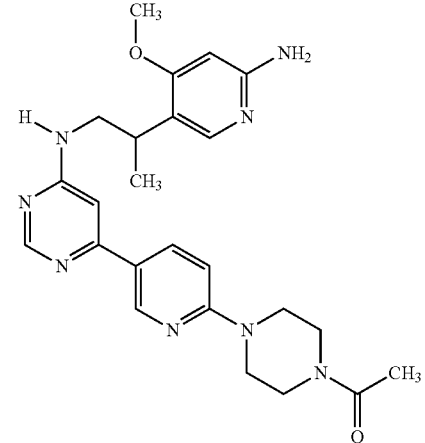 | 463.2 | (methanol-d₄) δ 8.96 (s, 1H), 8.67 (s, 1H), 8.39 (d, J = 7.4 Hz, 1H), 7.72 (d, J = 8.3 Hz, 1H), 7.58 (s, 1H), 7.00 (s, 1H), 6.38 (s, 1H), 3.99 (s, 3H), 3.83 (d, J = 6.5 Hz, 2H), 3.48-3.32 (m, 1H), 2.72 (s, 3H), 1.32 (d, J = 7.0 Hz, 3H) |
| 346 | 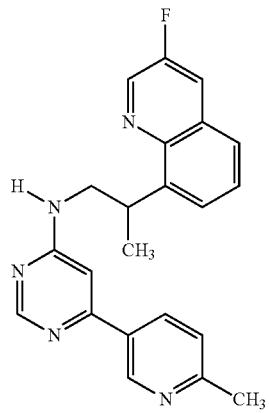 [SMILES: Cc1ccc(-c2cc(NCC(C)c3cccc4cc(F)cnc34)ncn2)cn1] | 374 | (400 MHz, DMSO-d₆) δ 8.95 (d, J = 2.8 Hz, 2H), 8.47 (s, 1H), 8.30-8.08 (m, 2H), 7.86 (d, J = 8.2 Hz, 1H), 7.76-7.44 (m, 3H), 7.37 (d, J = 6.8 Hz, 1H), 7.03 (d, J = 100.6 Hz, 1H), 4.45 (s, 1H), 3.58 (d, J = 153.4 Hz, 2H), 1.38 (d, J = 5.6 Hz, 3H) |

| Cmpnd No. | Structure | ESMS (M + H) | ¹H NMR (300 MHz, unless indicated otherwise) NMR peaks given as δ values |
|---|---|---|---|
| 347 | 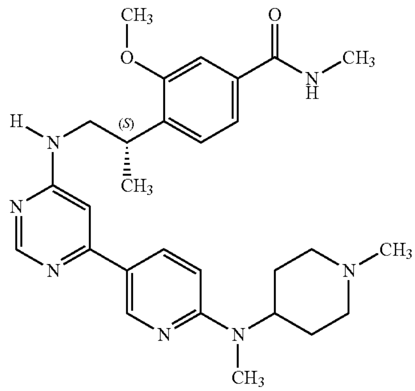 | 504.59 | |
| 348 | 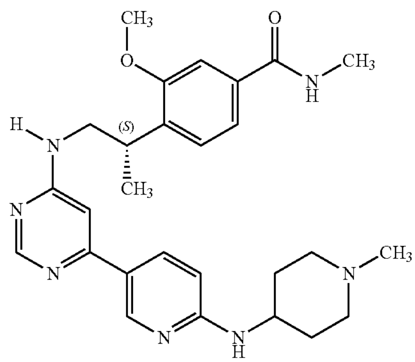 | 490.57 | |
| 349 | 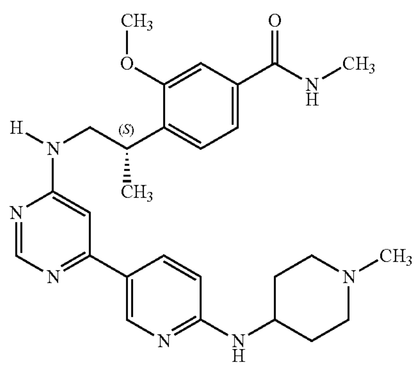 | 476.56 | |
| 350 | 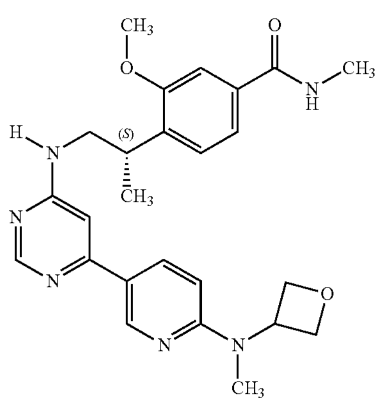 | 463.5 | |

TABLE 1-continued

| Cmpnd No. | Structure | ESMS (M + H) | ¹H NMR (300 MHz, unless indicated otherwise) NMR peaks given as δ values |
|---|---|---|---|
| 351 | 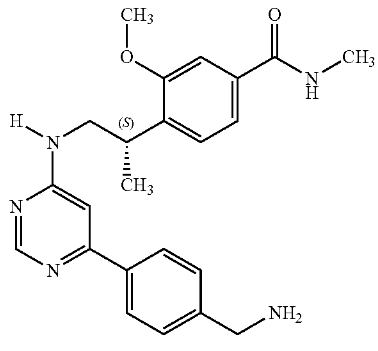 | 406.5 | (methanol-d₄) δ 8.34 (s, 3H), 7.93 (d, J = 8.3 Hz, 2H), 7.56 (d, J = 8.2 Hz, 2H), 7.34 (dd, J = 16.3, 7.8 Hz, 3H), 6.79 (s, 1H), 4.18 (s, 2H), 3.85 (s, 3H), 3.69-3.51 (m, 3H), 2.90 (s, 3H), 1.31 (d, 3H) |
| 352 | 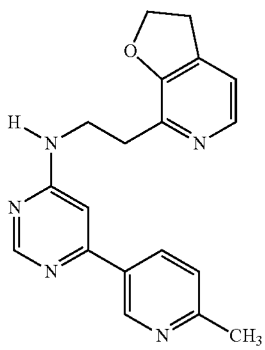 | 348.24 | (400 MHz, CDCl₃) δ 9.03 (s, 1H), 8.61 (s, 1H), 8.20 (dd, J = 8.1, 2.2 Hz, 1H), 8.11 (d, J = 4.7 Hz, 1H), 7.26 (d, J = 8.2 Hz, 1H), 7.07 (d, J = 4.7 Hz, 1H), 6.72 (s, 1H), 5.80 (s, 1H), 4.70-4.52 (m, 2H), 4.05-3.54 (m, 2H), 3.50-3.42 (m, 1H), 3.25 (t, J = 8.8 Hz, 2H), 2.63 (s, 3H), 1.36 (t, J = 10.4 Hz, 3H) |
| 353 | 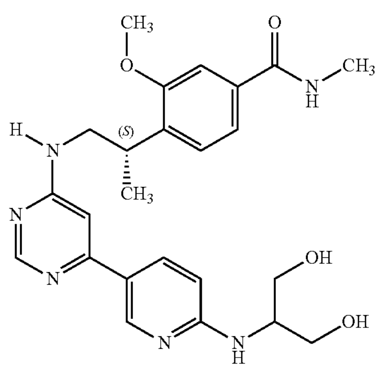 | 467.27 | |
| 354 | 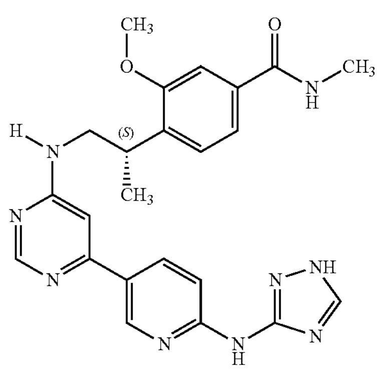 | 460.24 | |

TABLE 1-continued

| Cmpnd No. | Structure | ESMS (M + H) | ¹H NMR (300 MHz, unless indicated otherwise) NMR peaks given as δ values |
|---|---|---|---|
| 355 | 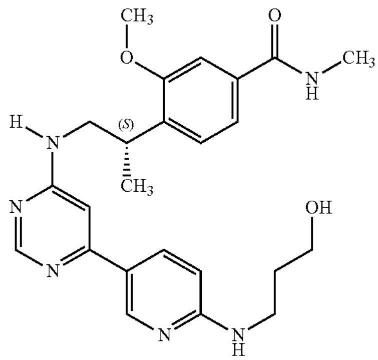 | 451.26 | |
| 356 | 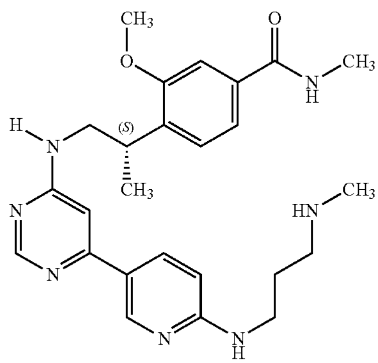 | 464.28 | |
| 357 | 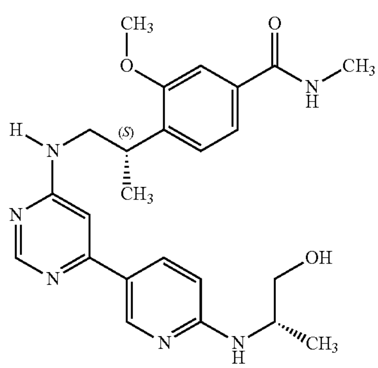 | 451.26 | |
| 358 | 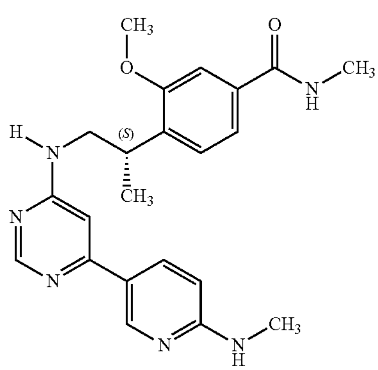 | 407.23 | |

TABLE 1-continued

| Cmpnd No. | Structure | ESMS (M + H) | ¹H NMR (300 MHz, unless indicated otherwise) NMR peaks given as δ values |
|---|---|---|---|
| 359 | 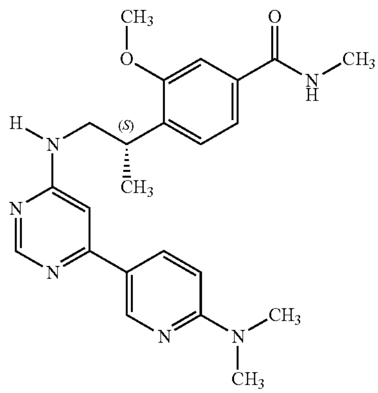 | 421.29 | |
| 360 | 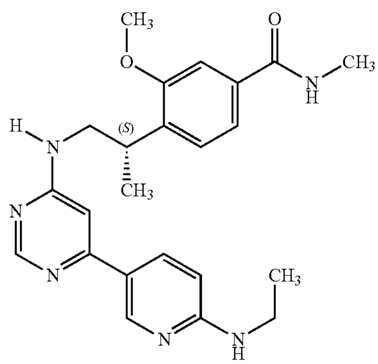 | 421.26 | |
| 361 | 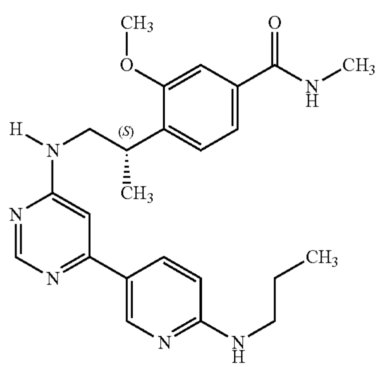 | 435.29 | |
| 362 | 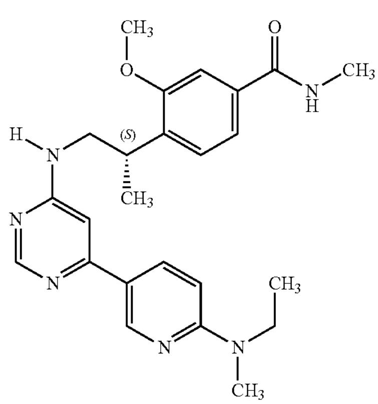 | 435.25 | |

TABLE 1-continued
| Cmpnd No. | Structure | ESMS (M + H) | $^1$H NMR (300 MHz, unless indicated otherwise) NMR peaks given as δ values |
|---|---|---|---|
| 363 | 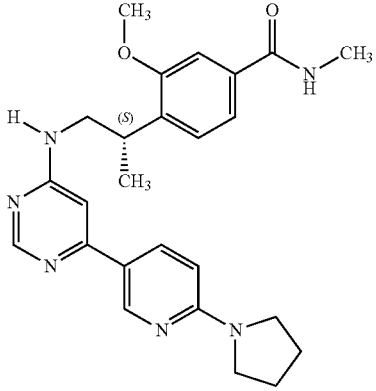 | 447.26 | |
| 364 | 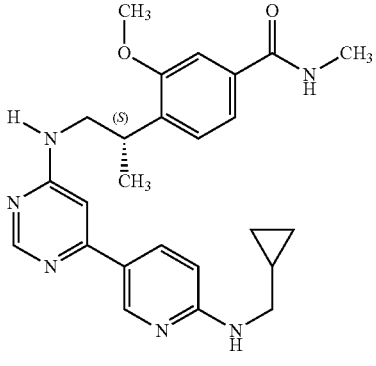 | 447.29 | |
| 365 | 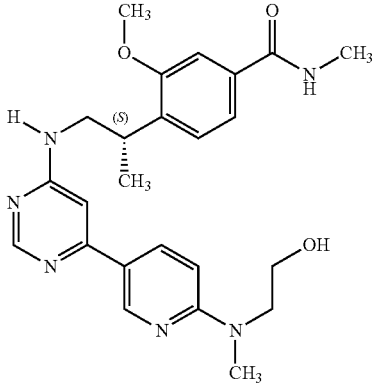 | 451.26 | |
| 366 | 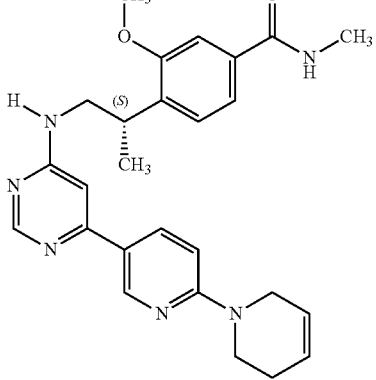 | 459.27 | |

TABLE 1-continued

| Cmpnd No. | Structure | ESMS (M + H) | ¹H NMR (300 MHz, unless indicated otherwise) NMR peaks given as δ values |
|---|---|---|---|
| 367 | 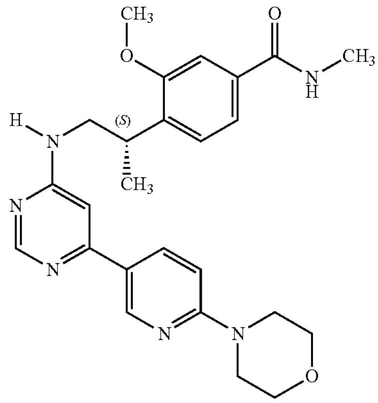 | 463.27 | |
| 368 | 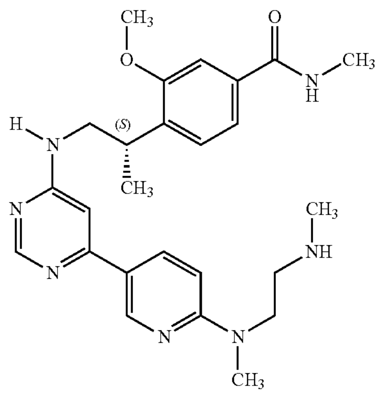 | 464.32 | |
| 369 | 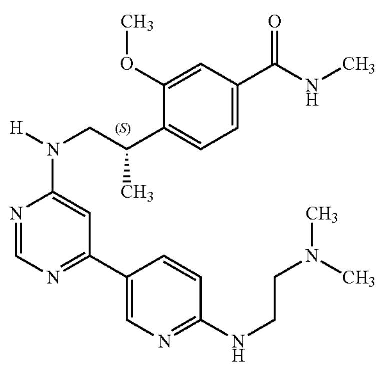 | 464.35 | |
| 370 | 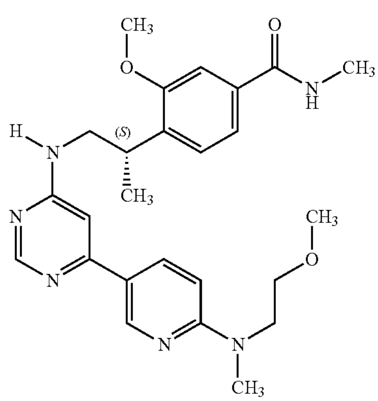 | 465.33 | |

| Cmpnd No. | Structure | ESMS (M + H) | ¹H NMR (300 MHz, unless indicated otherwise) NMR peaks given as δ values |
|---|---|---|---|
| 371 | 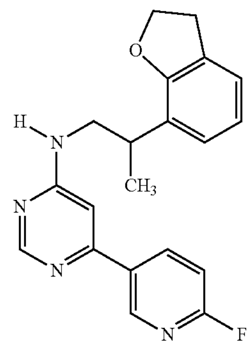 [SMILES: CC(CNc1cc(-c2ccc(F)nc2)ncn1)c1cccc2c1OCC2] | | |
| 372 | 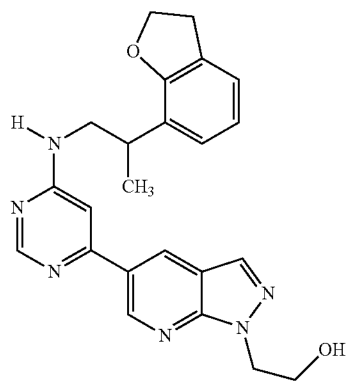 [SMILES: CC(CNc1cc(-c2cnc3c(cnn3CCO)c2)ncn1)c1cccc2c1OCC2] | 418.34 | (methanol-d₄) δ 9.05 (s, 1H), 8.70 (s, 1H), 8.44 (s, 1H), 8.20 (s, 1H), 7.98 (d, J = 4.4 Hz, 1H), 7.16 (d, J = 4.5 Hz, 1H), 6.90 (s, 1H), 4.78-4.39 (m, 4H), 4.04 (t, J = 5.5 Hz, 2H), 3.75 (s, 2H), 3.58-3.44 (m, 1H), 3.24 (t, J = 8.8 Hz, 2H), 1.34 (d, J = 6.8 Hz, 3H) |
| 373 | 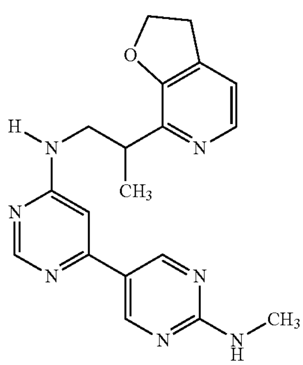 [SMILES: CNc1ncc(-c2cc(NCC(C)c3nccc4c3OCC4)ncn2)cn1] | 364.33 | |
| 374 | 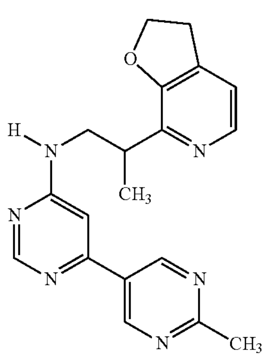 [SMILES: Cc1ncc(-c2cc(NCC(C)c3nccc4c3OCC4)ncn2)cn1] | 349.26 | (400 MHz, CDCl₃) δ 9.18 (s, 2H), 8.62 (s, 1H), 8.11 (d, J = 4.2 Hz, 1H), 7.08 (d, J = 3.7 Hz, 1H), 6.71 (s, 1H), 5.94 (s, 1H), 4.62 (t, J = 8.4 Hz, 2H), 4.12-3.49 (m, 3H), 3.25 (t, J = 8.5 Hz, 2H), 2.82 (s, 3H), 1.37 (d, J = 6.2 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 375 | 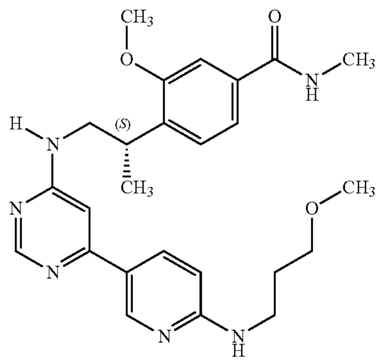 | 465.29 | |
| 376 | 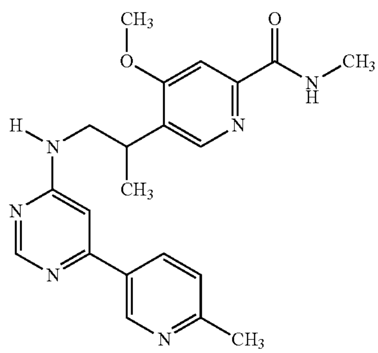 [SMILES: CNC(=O)c1cc(OC)c(C(C)CNc2cc(-c3ccc(C)nc3)ncn2)cn1] | 393.38 | (methanol-d₄) δ 8.89 (s, 1H), 8.43 (s, 1H), 8.31 (s, 1H), 8.18 (d, J = 7.3 Hz, 1H), 7.64 (s, 1H), 7.40 (d, J = 8.0 Hz, 1H), 6.79 (s, 1H), 3.94 (s, 3H), 3.80-3.43 (m, 3H), 2.92 (s, 3H), 2.58 (s, 3H), 1.36 (d, J = 6.7 Hz, 3H) |
| 377 | 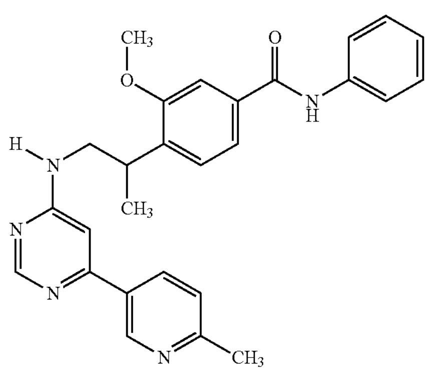 [SMILES: COc1cc(C(=O)Nc2ccccc2)ccc1C(C)CNc1cc(-c2ccc(C)nc2)ncn1] | 454.54 | (methanol-d₄) δ 8.88 (d, J = 1.9 Hz, 1H), 8.65, 8.53 (2s, 1H), 8.23 (dd, J = 8.3, 2.3 Hz, 1H), 7.83-7.29 (m, 7H), 7.15 (t, J = 7.4 Hz, 1H), 6.89 (s, 1H), 3.91 (s, m, 4H), 3.75-3.54 (m, 2H), 2.67 (s, 3H), 1.36 (d, J = 6.8 Hz, 3H) |
| 378 | 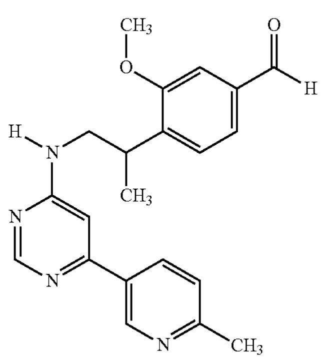 [SMILES: COc1cc(C=O)ccc1C(C)CNc1cc(-c2ccc(C)nc2)ncn1] | 363.14 | (methanol-d₄) δ 9.89 (s, 1H), 8.90 (s, 1H), 8.44 (s, 1H), 8.19 (d, J = 8.1 Hz, 1H), 7.74-7.11 (m, 4H), 6.81 (s, 1H), 3.88 (s, 3H), 3.65 (m, 3H), 2.59 (s, 3H), 1.32 (s, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 379 | 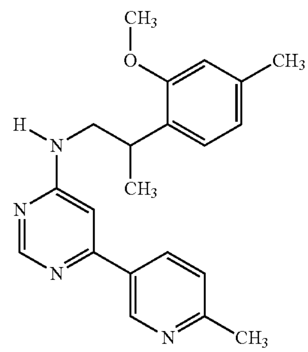 | 349.68 | (methanol-d₄) δ 8.89 (s, 1H), 8.67, 8.51 (2s, 1H), 8.26 (d, J = 8.3 Hz, 1H), 7.66 (d, J = 8.1 Hz, 1H), 7.29-6.44 (m, 4H), 4.01-3.67 (m, 1H), 3.78 (s, 3H), 3.54 (dd, J = 13.8, 6.7 Hz, 2H), 2.69 (s, 3H), 2.68 (s, 3H), 2.29, 2.19 (2s, 3H), 1.31 (d, J = 6.3 Hz, 3H) |
| 380 | 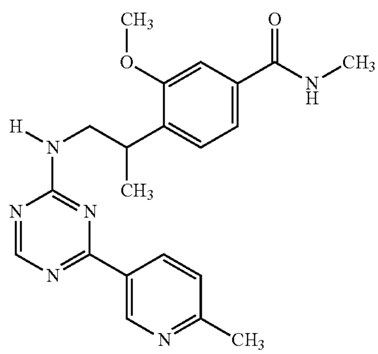 [SMILES: CNC(=O)c1ccc(C(C)CNc2ncnc(-c3ccc(C)nc3)n2)c(OC)c1] | 393.64 | |
| 381 | 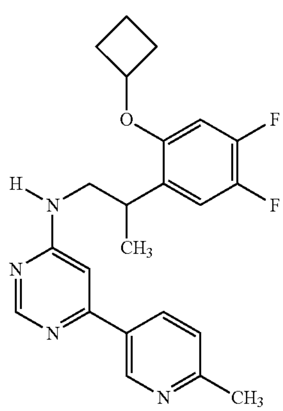 [SMILES: Cc1ccc(-c2cc(NCC(C)c3cc(F)c(F)cc3OC3CCC3)ncn2)cn1] | 411 | (400 MHz, DMSO-d₆) δ 8.98 (s, 1H), 8.59-8.08 (m, 2H), 7.51-7.22 (m, 3H), 6.93 (d, J = 12.5 Hz, 1H), 6.82 (dd, J = 12.8, 7.1 Hz, 1H), 4.59 (p, J = 7.0 Hz, 1H), 3.72-3.35 (m, 3H), 2.52 (d, J = 3.2 Hz, 3H), 2.29 (d, J = 3.7 Hz, 2H), 1.89-1.68 (m, 2H), 1.62-1.42 (m, 2H), 1.18 (d, J = 6.8 Hz, 3H) |
| 382 | 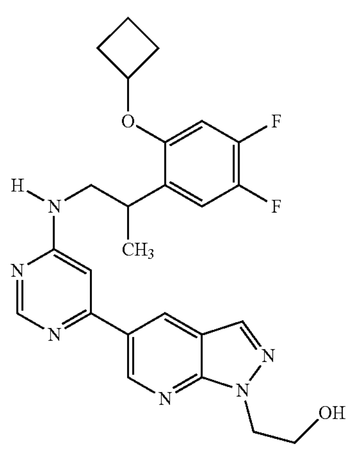 [SMILES: CC(CNc1cc(-c2cnc3c(cnn3CCO)c2)ncn1)c1cc(F)c(F)cc1OC1CCC1] | 481 | (400 MHz, DMSO-d₆) δ 9.11 (s, 1H), 8.82 (d, J = 34.3 Hz, 1H), 8.60-8.32 (m, 1H), 8.32-8.21 (m, 1H), 7.58-7.22 (m, 2H), 6.99 (s, 1H), 6.83 (dd, J = 12.8, 7.1 Hz, 1H), 4.93 (s, 1H), 4.67-4.43 (m, 3H), 3.88 (t, J = 5.8 Hz, 2H), 3.73-3.37 (m, 3H), 2.30 (s, 2H), 1.81 (dd, J = 19.0, 9.6 Hz, 2H), 1.62-1.40 (m, 2H), 1.18 (dd, J = 15.4, 6.5 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 383 | 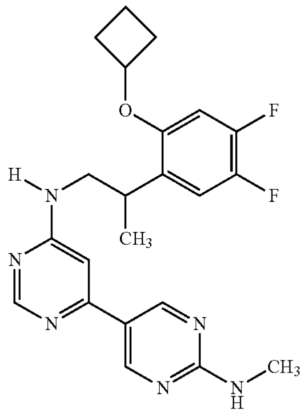 [SMILES: CNc1ncc(-c2cc(NCC(C)c3cc(F)c(F)cc3OC3CCC3)ncn2)cn1] | 427 | |
| 384 | 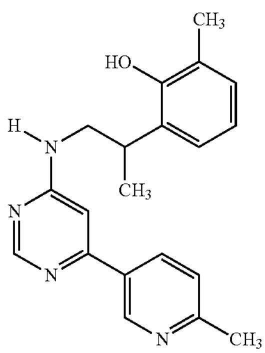 [SMILES: Cc1ccc(-c2cc(NCC(C)c3cccc(C)c3O)ncn2)cn1] | 335.22 | |
| 385 | 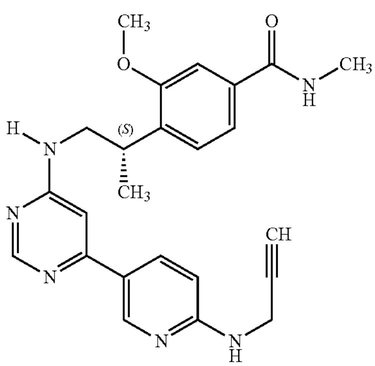 | 431.25 | |
| 386 | 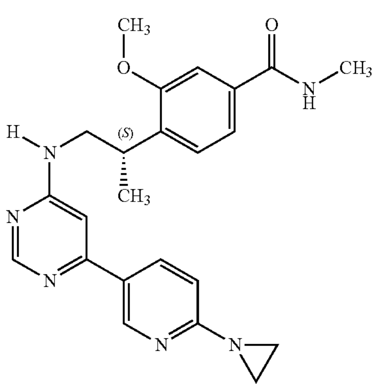 | 419.5 | |

TABLE 1-continued

| Cmpnd No. | Structure | ESMS (M + H) | ¹H NMR (300 MHz, unless indicated otherwise) NMR peaks given as δ values |
|---|---|---|---|
| 387 | 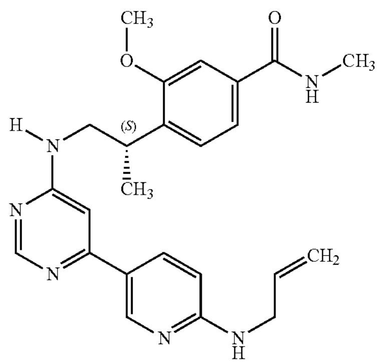 | 433.23 | |
| 388 | 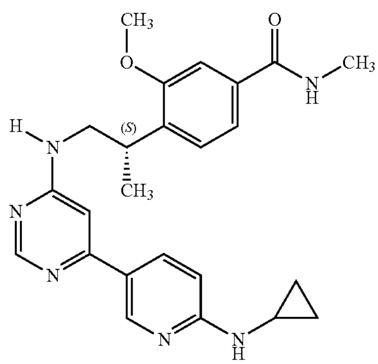 | 433.27 | |
| 389 | 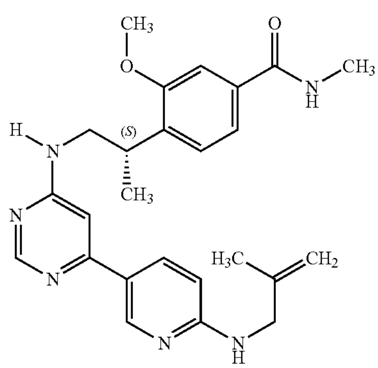 | 447.26 | |
| 390 | 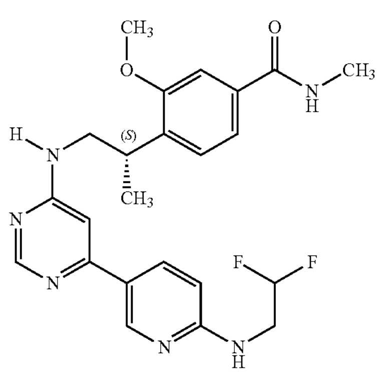 | 457.25 | |

TABLE 1-continued

| Cmpnd No. | Structure | ESMS (M + H) | ¹H NMR (300 MHz, unless indicated otherwise) NMR peaks given as δ values |
|---|---|---|---|
| 391 | 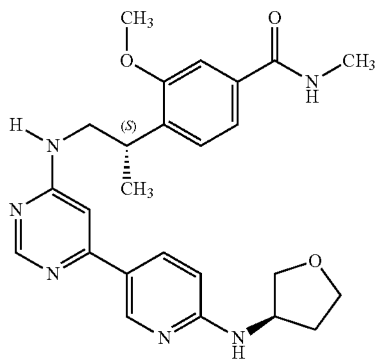 | 463.27 | |
| 392 | 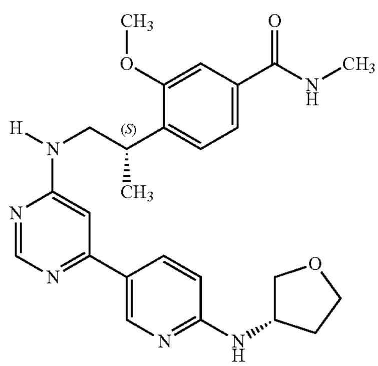 | 463.31 | |
| 393 | 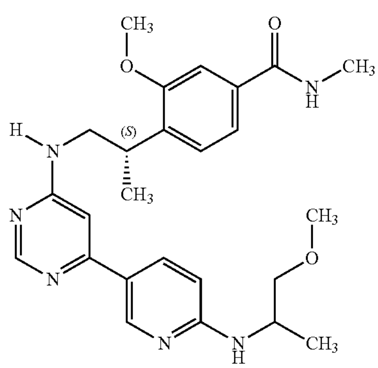 | 465.29 | |
| 394 | 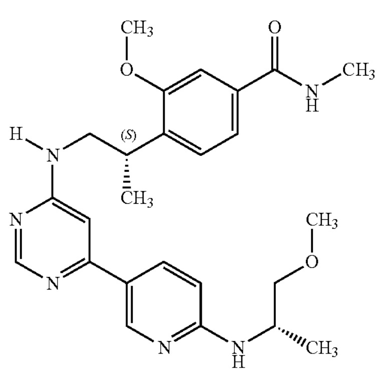 | 465.51 | |

TABLE 1-continued

| Cmpnd No. | Structure | ESMS (M + H) | ¹H NMR (300 MHz, unless indicated otherwise) NMR peaks given as δ values |
|---|---|---|---|
| 395 | 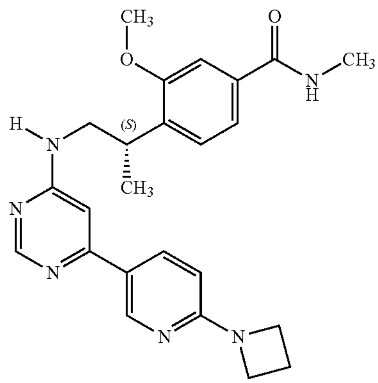 | 433.27 | |
| 396 | 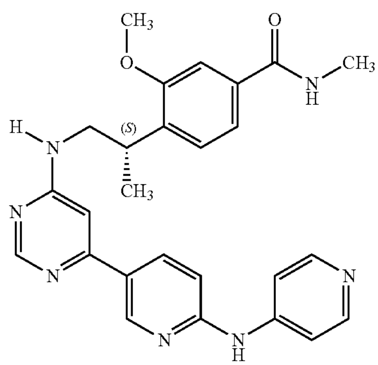 | 470.3 | |
| 397 | 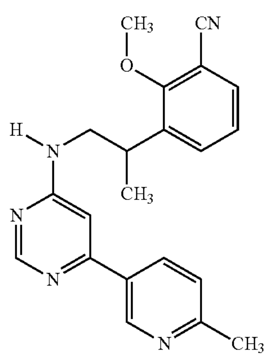 [SMILES: COc1c(C#N)cccc1C(C)CNc1cc(-c2ccc(C)nc2)ncn1] | 360.07 | (methanol-d₄) δ 8.96 (s, 1H), 8.69 (s, 1H), 8.38 (d, J = 8.1 Hz, 1H), 7.91-7.64 (m, 2H), 7.55 (d, J = 7.6 Hz, 1H), 7.26 (t, J = 7.8 Hz, 1H), 6.97 (s, 1H), 4.00 (s, 3H), 3.93-3.40 (m, 3H), 2.72 (s, 3H), 1.35 (d, J = 6.9 Hz, 3H) |
| 398 | 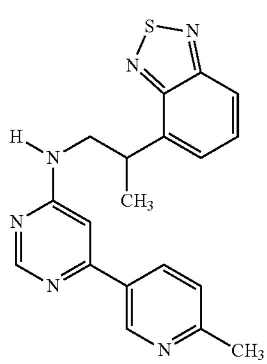 [SMILES: Cc1ccc(-c2cc(NCC(C)c3cccc4nsnc34)ncn2)cn1] | 363.37 | (methanol-d₄) δ 8.85 (s, 1H), 8.21 (s, 1H), 7.90 (d, J = 8.6 Hz, 1H), 7.73-7.39 (m, 3H), 6.80 (s, 1H), 4.28-3.86 (m, 3H), 2.67 (s, 3H), 1.56 (d, J = 6.8 Hz, 3H) |

| Cmpnd No. | Structure | ESMS (M + H) | ¹H NMR (300 MHz, unless indicated otherwise) NMR peaks given as δ values |
|---|---|---|---|
| 399 | 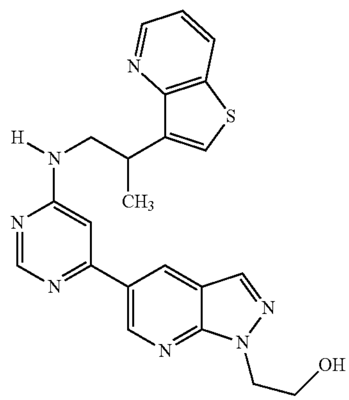 [SMILES: CC(CNc1cc(-c2cnc3c(cnn3CCO)c2)ncn1)c1csc2cccnc12] | | (400 MHz, DMSO-$d_6$) δ 9.21 (d, J = 85.0 Hz, 1H), 8.75 (d, J = 29.4 Hz, 2H), 8.47 (d, J = 8.3 Hz, 2H), 8.29 (s, 1H), 7.90 (s, 1H), 7.62 (s, 1H), 7.21 (d, J = 163.1 Hz, 2H), 4.92 (s, 1H), 4.55 (s, 2H), 3.99-3.34 (m, 5H), 1.41 (s, 3H) |
| 400 | 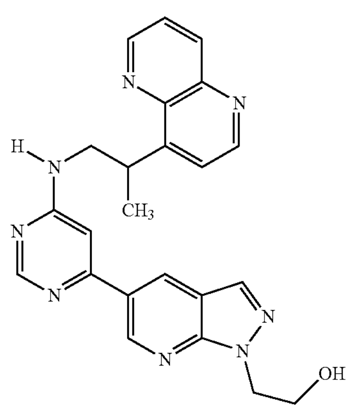 [SMILES: CC(CNc1cc(-c2cnc3c(cnn3CCO)c2)ncn1)c1ccnc2cccnc12] | | (400 MHz, DMSO-$d_6$) δ 9.31-8.67 (m, 3H), 8.44 (dd, J = 20.4, 12.8 Hz, 2H), 8.27 (s, 1H), 7.87-7.54 (m, 3H), 7.12 (d, J = 143.8 Hz, 1H), 4.73 (d, J = 155.3 Hz, 3H), 3.62 (d, J = 206.7 Hz, 4H), 1.41 (d, J = 6.0 Hz, 3H) |
| 401 | 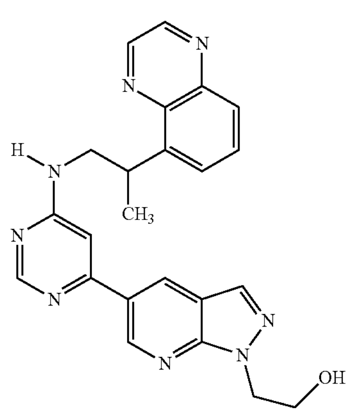 [SMILES: CC(CNc1cc(-c2cnc3c(cnn3CCO)c2)ncn1)c1cccc2nccnc12] | | (400 MHz, DMSO-$d_6$) δ 9.23-8.91 (m, 3H), 8.75 (s, 1H), 8.49 (d, J = 9.4 Hz, 1H), 8.28 (s, 1H), 8.04-7.93 (m, 1H), 7.85 (d, J = 5.2 Hz, 2H), 7.55 (s, 1H), 6.95 (s, 1H), 4.50 (d, J = 33.8 Hz, 3H), 3.95-3.42 (m, 4H), 1.42 (s, 3H). |

TABLE 1-continued

| Cmpnd No. | Structure | ESMS (M + H) | ¹H NMR (300 MHz, unless indicated otherwise) NMR peaks given as δ values |
|---|---|---|---|
| 402 | 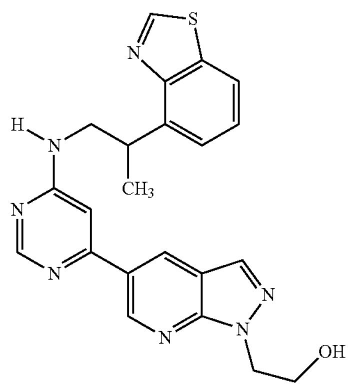 [SMILES: CC(CNc1cc(-c2cnc3c(cnn3CCO)c2)ncn1)c1cccc2scnc12] | | (400 MHz, DMSO-d$_6$) δ 9.25 (d, J = 124.9 Hz, 2H), 8.76 (s, 1H), 8.51 (s, 1H), 8.28 (s, 1H), 8.04 (d, J = 8.5 Hz, 1H), 7.50 (t, J = 18.9 Hz, 3H), 6.98 (s, 1H), 4.90 (s, 1H), 4.54 (s, 2H), 4.13-3.38 (m, 5H), 1.42 (d, J = 5.8 Hz, 3H) |
| 403 | 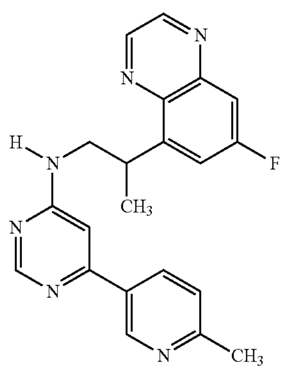 | | (400 MHz, DMSO-d$_6$) δ 8.95 (d, J = 20.7 Hz, 3H), 8.47 (d, J = 14.4 Hz, 1H), 8.14 (s, 1H), 7.88-7.70 (m, 2H), 7.52 (s, 1H), 7.37 (s, 1H), 6.84 (s, 1H), 4.55-4.36 (m, 1H), 3.61 (dd, J = 148.3, 33.8 Hz, 2H), 2.51 (s, 3H), 1.39 (d, J = 6.5 Hz, 3H) |
| 404 | 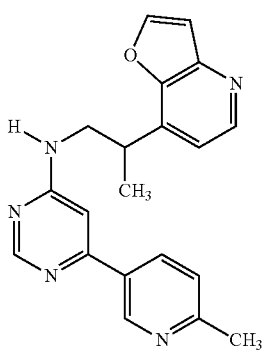 [SMILES: Cc1ccc(-c2cc(NCC(C)c3ccnc4ccoc34)ncn2)cn1] | 346.19 | (400 MHz, CDCl$_3$) δ 8.90 (s, 1H), 8.57 (s, 1H), 8.40 (d, J = 4.9 Hz, 1H), 8.10 (dd, J = 8.1, 2.1 Hz, 1H), 7.78 (d, J = 2.0 Hz, 1H), 7.18 (d, J = 10.6 Hz, 1H), 7.02 (d, J = 4.9 Hz, 1H), 6.91 (d, J = 2.1 Hz, 1H), 6.60 (s, 1H), 5.17 (s, 1H), 3.96-3.63 (m, 2H), 3.57 (dd, J = 14.1, 7.0 Hz, 1H), 2.54 (s, 3H), 1.44 (d, J = 6.9 Hz, 3H) |
| 405 | 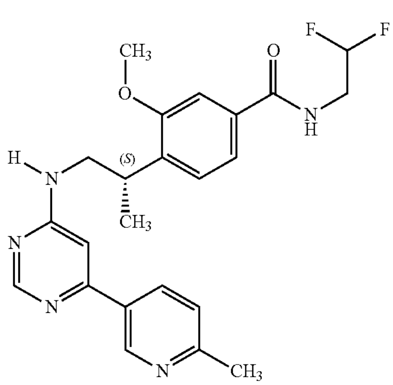 | 442.44 | (methanol-d$_4$) δ 8.89 (d, J = 2.3 Hz, 1H), 8.44 (s, 1H), 8.18 (dd, J = 8.2, 2.4 Hz, 1H), 7.63-7.25 (m, 4H), 6.81 (d, J = 1.1 Hz, 1H), 5.98 (tt, J = 56.2, 4.1 Hz, 1H), 3.86 (s, 3H), 3.71 (td, J = 14.9, 4.2 Hz, 2H), 3.61 (m, 2H), 2.59 (s, 3H), 1.31 (d, J = 5.6 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 406 | 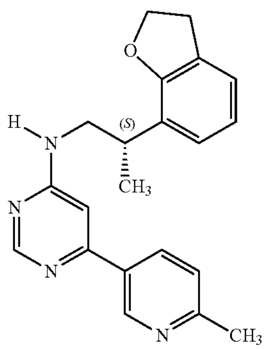 | 348.21 | (400 MHz, CDCl$_3$) δ 9.01 (s, 1H), 8.62 (s, 1H), 8.20 (dd, J = 8.0, 1.8 Hz, 1H), 8.00 (d, J = 5.1 Hz, 1H), 7.26 (d, J = 10.0 Hz, 1H), 6.90 (d, J = 5.1 Hz, 1H), 6.76 (s, 1H), 5.44 (s, 1H), 4.69 (t, J = 8.9 Hz, 2H), 3.63 (dd, J = 13.3, 7.0 Hz, 2H), 3.36-3.22 (m, 3H), 2.62 (s, 3H), 1.36 (d, J = 7.0 Hz, 3H) |
| 407 | 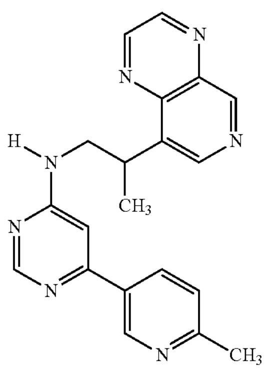 [SMILES: Cc1ccc(-c2cc(NCC(C)c3cncc4nccnc34)ncn2)cn1] | | (400 MHz, DMSO-d$_6$) δ 9.39 (s, 1H), 9.20-8.76 (m, 4H), 8.43 (s, 1H), 8.18 (d, J = 33.4 Hz, 1H), 7.53 (s, 1H), 7.37 (s, 1H), 7.23-6.74 (m, 1H), 4.24 (d, J = 6.4 Hz, 1H), 3.77 (t, J = 78.1 Hz, 2H), 2.51 (s, 3H), 1.47 (d, J = 6.8 Hz, 3H) |
| 408 | 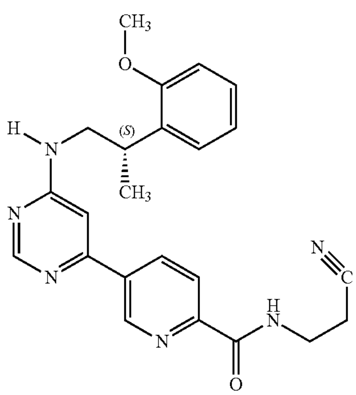 | 416.42 | (CDCl$_3$) δ 9.31 (s, 1H), 8.56 (s, 1H), 7.94 (s, 2H), 7.76 (s, 1H), 7.62 (m, 1H), 7.25-7.15 (m, 2H), 7.09-6.70 (m, 4H), 3.86 (s, 3H), 3.76 (m, 2H), 3.56 (m, 3H), 2.78 (m, 2H), 1.39 (d, 3H) |
| 409 | 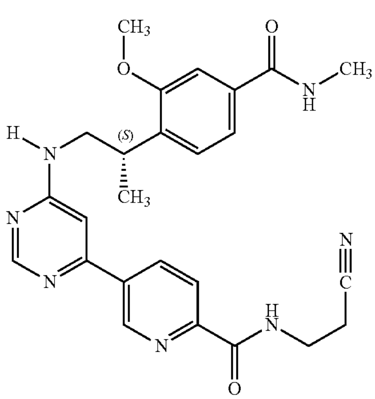 | 473.45 | (methanol-d$_4$) δ 9.10 (m, 1H), 8.60 (s, 1H), 8.10-8.00 (m, 2H), 7.90-7.80 (m, 2H), 7.38 (s, 1H), 7.37-7.27 (m, 2H), 6.85 (s, 1H), 4.00-3.79 (m, 5H), 3.72-3.58 (m, 3H), 2.89 (s, 3H), 2.82 (t, J = 6.4 Hz, 2H), 1.37 (d, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 410 | 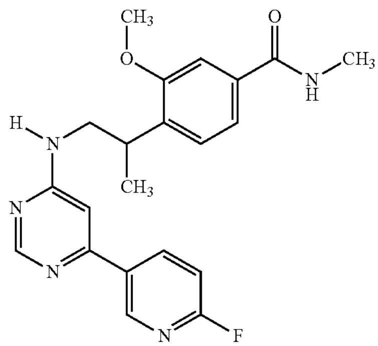 [SMILES: CNC(=O)c1ccc(C(C)CNc2cc(-c3ccc(F)nc3)ncn2)c(OC)c1] | 397.29 | (400 MHz, CDCl₃) δ 9.20-9.04 (m, 1H), 8.65 (ddd, J = 18.3, 15.3, 8.1 Hz, 1H), 8.59-8.39 (m, 1H), 7.37-7.28 (m, 1H), 7.18-7.08 (m, 2H), 7.01-6.88 (m, 1H), 6.10 (s, 1H), 5.71-5.42 (m, 1H), 3.79 (d, J = 14.0 Hz, 3H), 3.73-3.51 (m, 2H), 3.01-2.89 (m, 3H), 1.61 (s, 1H), 1.35-1.22 (m, 3H) |
| 411 | 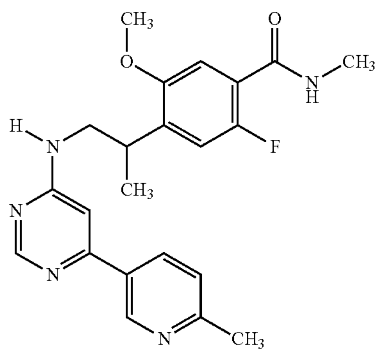 [SMILES: CNC(=O)c1cc(OC)c(C(C)CNc2cc(-c3ccc(C)nc3)ncn2)cc1F] | 410.31 | (400 MHz, CDCl₃) δ 9.01 (s, 1H), 8.63 (s, 1H), 8.18 (dd, J = 8.1, 2.0 Hz, 1H), 7.61 (d, J = 6.4 Hz, 1H), 7.26 (d, J = 5.9 Hz, 1H), 6.99 (d, J = 12.5 Hz, 1H), 6.78 (d, J = 9.0 Hz, 1H), 6.68 (s, 1H), 5.14 (s, 1H), 3.90 (s, 3H), 3.68-3.47 (m, 3H), 3.04 (d, J = 4.6 Hz, 3H), 2.63 (s, 3H), 1.34 (d, J = 5.8 Hz, 3H) |
| 412 | 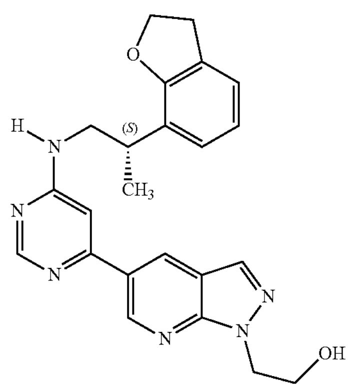 | 418.19 | (methanol-d₄) δ 9.00 (s, 1H), 8.67 (s, 1H), 8.54 (s, 1H), 8.22 (s, 1H), 7.90 (d, J = 5.3 Hz, 1H), 7.10 (d, J = 5.2 Hz, 1H), 6.91 (s, 1H), 4.80-4.55 (m, 4H), 4.04 (t, J = 5.6 Hz, 2H), 3.93-3.56 (m, 2H), 3.41-3.22 (m, 3H), 1.35 (d, J = 6.9 Hz, 3H) |
| 413 | 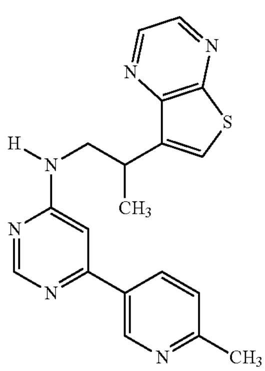 | 363 | (400 MHz, DMSO-d₆) δ 9.07 (d, J = 78.5 Hz, 1H), 8.78 (s, 1H), 8.64 (s, 1H), 8.46 (s, 1H), 8.12 (d, J = 37.5 Hz, 2H), 7.52 (dd, J = 18.2, 10.5 Hz, 1H), 7.14 (d, J = 195.7 Hz, 2H), 3.87-3.34 (m, 3H), 2.52 (d, J = 6.1 Hz, 3H), 1.41 (d, J = 5.0 Hz, 3H) |

| Cmpnd No. | Structure | ESMS (M + H) | ¹H NMR (300 MHz, unless indicated otherwise) NMR peaks given as δ values |
|---|---|---|---|
| 414 | 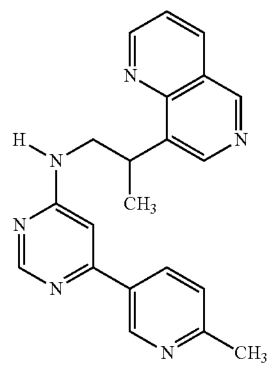 [SMILES: Cc1ccc(-c2cc(NCC(C)c3cncc4cccnc34)ncn2)cn1] | 357 | (400 MHz, DMSO-d₆) δ 9.28 (s, 1H), 9.06 (d, J = 82.8 Hz, 2H), 8.71 (s, 1H), 8.58 (d, J = 7.6 Hz, 1H), 8.47 (d, J = 14.4 Hz, 1H), 8.15 (s, 1H), 7.81-7.30 (m, 3H), 6.87 (s, 1H), 4.29 (s, 1H), 3.63 (d, J = 198.8 Hz, 2H), 2.52 (d, J = 3.5 Hz, 3H), 1.45 (d, J = 6.6 Hz, 3H) |
| 415 | 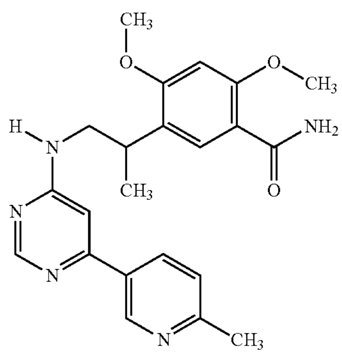 [SMILES: COc1cc(OC)c(C(C)CNc2cc(-c3ccc(C)nc3)ncn2)cc1C(N)=O] | 408.39 | (CDCl₃) δ 9.02 (s, 1H), 8.59 (s, 1H), 8.17 (dd, J = 8.1, 2.3 Hz, 1H), 8.10 (s, 1H), 7.61 (s, 1H), 6.65 (s, 1H), 6.47 (s, 1H), 5.64 (s, 1H), 3.98 (s, 3H), 3.89 (s, 3H), 3.51 (s, 3H), 2.62 (s, 3H), 1.35 (d, J = 6.2 Hz, 3H) |
| 416 | 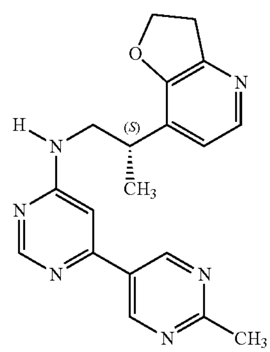 | 349.19 | (400 MHz, CDCl₃) δ 9.18 (s, 2H), 8.64 (s, 1H), 8.01 (d, J = 5.1 Hz, 1H), 6.90 (d, J = 5.1 Hz, 1H), 6.74 (s, 1H), 5.30 (s, 1H), 4.71 (t, J = 8.8 Hz, 2H), 3.84-3.42 (m, 2H), 3.35 (t, J = 8.9 Hz, 2H), 3.27 (dd, J = 14.1, 7.0 Hz, 1H), 2.81 (s, 3H), 1.37 (d, J = 6.9 Hz, 3H) |
| 417 | 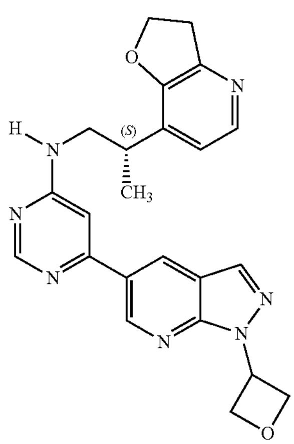 | 430.31 | (methanol-d₄) δ 9.05 (s, 1H), 8.71 (s, 1H), 8.47 (s, 1H), 8.31 (s, 1H), 7.87 (d, J = 5.2 Hz, 1H), 7.06 (d, J = 5.0 Hz, 1H), 6.90 (s, 1H), 6.32-6.18 (m, 1H), 5.27 (t, J = 6.5 Hz, 2H), 5.21-5.06 (m, 2H), 4.67 (t, J = 8.8 Hz, 2H), 3.88-3.57 (m, 2H), 3.37-3.21 (m, 3H), 1.34 (d, J = 6.9 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 418 | 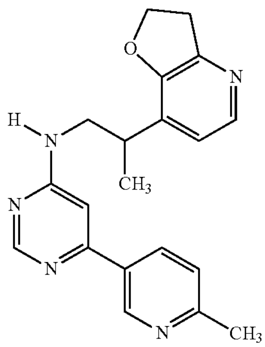 [SMILES: Cc1ccc(-c2cc(NCC(C)c3ccnc4c3OCC4)ncn2)cn1] | 348.21 | (methanol-d₄) δ 8.90 (s, 1H), 8.44 (s, 1H), 8.20 (d, J = 7.1 Hz, 1H), 8.13 (s, 1H), 8.06 (s, 1H), 7.42 (d, J = 8.2 Hz, 1H), 6.83 (s, 1H), 4.70 (t, J = 8.8 Hz, 2H), 3.70 (s, 2H), 3.33-3.19 (m, 3H), 2.59 (s, 3H), 1.36 (d, J = 7.0 Hz, 3H) |
| 419 | 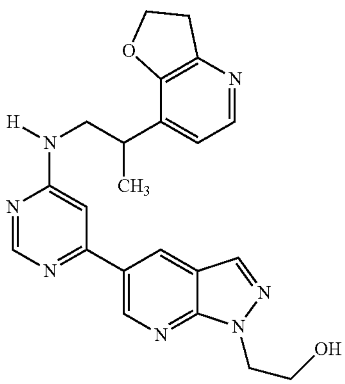 [SMILES: CC(CNc1cc(-c2cnc3c(cnn3CCO)c2)ncn1)c1ccnc2c1OCC2] | 418.31 | (methanol-d₄) δ 9.05 (s, 1H), 8.69 (s, 1H), 8.46 (s, 1H), 8.20 (s, 1H), 8.13 (s, 1H), 8.08 (s, 1H), 6.89 (s, 1H), 4.71 (t, J = 8.8 Hz, 2H), 4.64 (t, J = 5.7 Hz, 2H), 4.04 (t, J = 5.6 Hz, 2H), 3.80-3.52 (m, 2H), 3.29-3.18 (m, 3H), 1.38 (d, J = 6.9 Hz, 3H) |
| 420 | 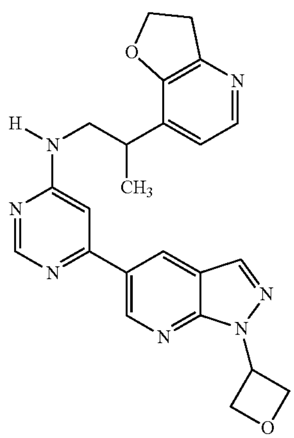 [SMILES: CC(CNc1cc(-c2cnc3c(cnn3C3COC3)c2)ncn1)c1ccnc2c1OCC2] | 430.31 | (methanol-d₄) δ 9.04 (s, 1H), 8.69 (s, 1H), 8.45 (s, 1H), 8.30 (s, 1H), 8.13 (s, 1H), 8.08 (s, 1H), 6.88 (s, 1H), 6.35-6.16 (m, 1H), 5.27 (t, J = 6.6 Hz, 2H), 5.18-5.08 (m, 2H), 4.71 (t, J = 8.8 Hz, 2H), 3.72 (s, 2H), 3.25 (t, J = 8.4 Hz, 3H), 1.38 (d, J = 7.0 Hz, 3H) |
| 421 | 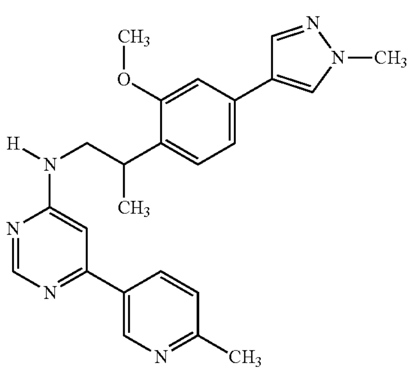 [SMILES: COc1cc(-c2cnn(C)c2)ccc1C(C)CNc1cc(-c2ccc(C)nc2)ncn1] | 415.46 | (methanol-d₄) δ 9.02 (s, 1H), 8.71 (s, 1H), 8.32 (s, 1H), 8.09 (s, 1H), 7.94 (s, 1H), 7.64 (d, J = 8.2 Hz, 1H), 7.37 (d, J = 7.7 Hz, 1H), 7.24 (br.s 2H), 7.01 (m, 1H), 4.07 (s, 3H), 4.02 (s, 3H), 3.97-3.65 (m, 3H), 2.79 (s, 3H), 1.50 (s, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 422 | 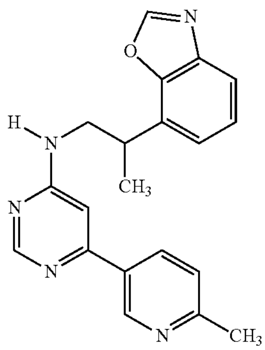 [SMILES: Cc1ccc(-c2cc(NCC(C)c3cccc4ncoc34)ncn2)cn1] | 346 | (400 MHz, DMSO-d₆) δ 8.98 (s, 1H), 8.73 (s, 1H), 8.50 (s, 1H), 8.22 (d, J = 40.4 Hz, 1H), 7.68-7.61 (m, 1H), 7.55 (t, J = 5.6 Hz, 1H), 7.35 (t, J = 7.6 Hz, 3H), 6.96 (d, J = 53.8 Hz, 1H), 3.70 (d, J = 5.2 Hz, 2H), 3.55 (dd, J = 14.1, 7.0 Hz, 1H), 2.52 (d, J = 2.2 Hz, 3H), 1.39 (d, J = 6.8 Hz, 3H) |
| 423 | 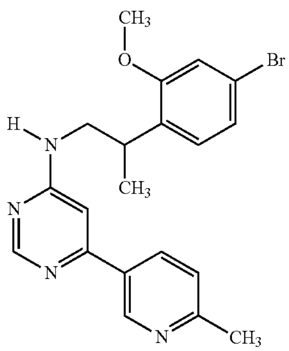 [SMILES: COc1cc(Br)ccc1C(C)CNc1cc(-c2ccc(C)nc2)ncn1] | 415.3 | (methanol-d₄) δ 8.90 (s, 1H), 8.67 (s, 1H), 8.27 (dd, J = 8.1, 2.5 Hz, 1H), 7.66 (d, J = 8.4 Hz, 1H), 7.29-6.96 (m, 2H), 6.91 (s, 1H), 3.80 (s, 3H), 3.80 (m, 2H), 3.56 (q, J = 6.7 Hz, 1H), 2.69 (s, 3H), 1.30 (d, J = 7.1 Hz, 3H) |
| 424 | 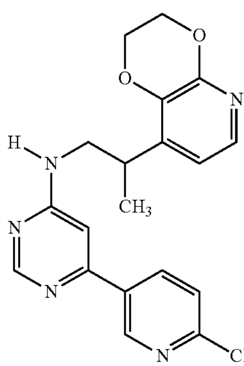 | 364.39 | (CDCl₃) δ 9.00 (d, J = 2.0 Hz, 1H), 8.63 (s, 1H), 8.20 (dd, J = 8.1, 2.3 Hz, 1H), 7.81 (d, J = 5.0 Hz, 1H), 7.27 (d, J = 4.2 Hz, 1H), 6.82 (d, J = 5.1 Hz, 1H), 6.71 (s, 1H), 4.43 (dd, J = 5.1, 3.0 Hz, 2H), 4.27 (dd, J = 5.1, 3.0 Hz, 2H), 3.56 (m, 3H), 2.62 (s, 3H), 1.32 (d, 3H) |
| 425 | 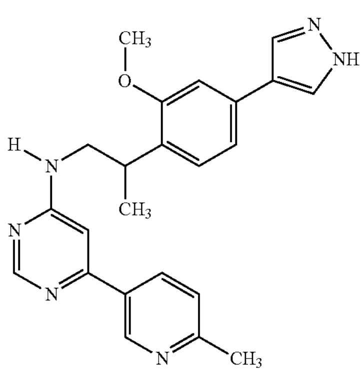 [SMILES: COc1cc(-c2cn[nH]c2)ccc1C(C)CNc1cc(-c2ccc(C)nc2)ncn1] | 401.19 | (methanol-d₄) δ 9.03 (s, 1H), 8.68 (br. s, 1H), 8.32 (d, J = 7.9 Hz, 1H), 8.08 (br. s, 2H), 7.61 (d, J = 8.2 Hz, 1H), 7.37 (d, J = 7.2 Hz, 1H), 7.27 (br. s, 2H), 7.00 (m, 1H), 4.02 (s, 3H), 3.94-3.59 (m, 3H), 2.77 (s, 3H), 1.48 (d, J = 6.2 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 426 | 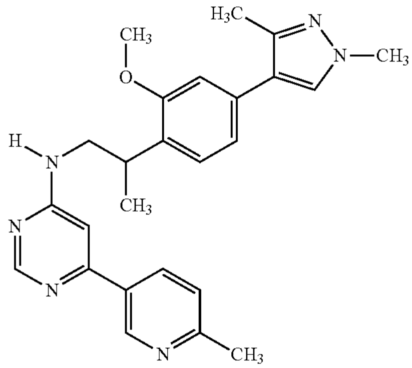 [SMILES: COc1cc(-c2cn(C)nc2C)ccc1C(C)CNc1cc(-c2ccc(C)nc2)ncn1] | 429.48 | (methanol-$d_4$) δ 9.21-8.97 (m, 1H), 8.85, 8.71 (2s, 1H), 8.57-8.31 (m, 1H), 8.00-7.72 (m, 2H), 7.42 (d, J = 7.8 Hz, 1H), 7.29-6.77 (m, 3H), 4.19-3.62 (m, 8H), 2.87 (s, 3H), 2.53, 2.43 (2s, 3H), 1.67-1.35 (m, 3H) |
| 427 | 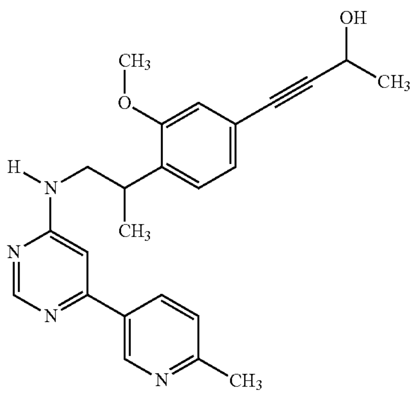 [SMILES: COc1cc(C#CC(C)O)ccc1C(C)CNc1cc(-c2ccc(C)nc2)ncn1] | 403.43 | (methanol-$d_4$) δ 8.91 (s, 1H), 8.67, 8.54 (2s, 1H), 8.26 (d, J = 8.4 Hz, 1H), 7.65 (d, J = 8.4 Hz, 1H), 7.20 (d, J = 7.9 Hz, 1H), 7.08-6.73 (m, 3H), 4.67 (q, J = 6.5 Hz, 1H), 4.04-3.44 (m, 3H), 3.81 (s, 3H), 2.70 (s, 3H), 1.47 (d, J = 6.6 Hz, 3H), 1.31 (d, J = 7.0 Hz, 3H) |
| 428 | 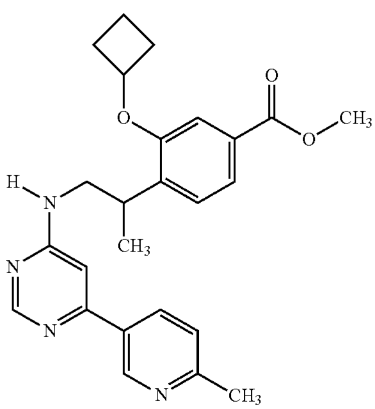 [SMILES: COC(=O)c1ccc(C(C)CNc2cc(-c3ccc(C)nc3)ncn2)c(OC2CCC2)c1] | 433.07 | (methanol-$d_4$) δ 9.08 (d, J = 2.4 Hz, 1H), 8.86 (s, 1H), 8.47 (dd, J = 8.2, 2.4 Hz, 1H), 7.85 (dd, J = 8.4, 4.2 Hz, 1H), 7.80-7.62 (m, 1H), 7.62-7.31 (m, 2H), 7.21-6.91 (m, 1H), 4.91 (t, J = 7.0 Hz, 1H), 4.29-3.68 (m, 3H), 2.88 (d, J = 3.1 Hz, 3H), 2.65 (m, 2H), 2.37-2.10 (m, 2H), 2.12-1.67 (m, 2H), 1.52 (d, J = 7.0 Hz, 3H) |
| 429 | 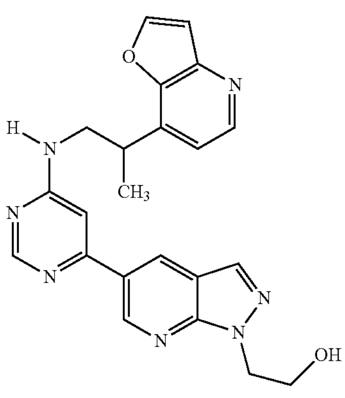 [SMILES: CC(CNc1cc(-c2cnc3c(cnn3CCO)c2)ncn1)c1ccnc2ccoc12] | 416.27 | (400 MHz, DMSO-$d_6$) δ 9.10 (s, 1H), 8.77 (s, 1H), 8.53 (s, 1H), 8.44 (d, J = 4.9 Hz, 1H), 8.31-8.24 (m, 2H), 7.59 (t, 1H), 7.28 (s, 1H), 7.11 (d, J = 2.0 Hz, 1H), 6.96 (s, 1H), 4.88 (t, J = 5.6 Hz, 1H), 4.52 (t, J = 5.7 Hz, 2H), 3.87 (q, J = 5.7 Hz, 2H), 3.75 (s, 2H), 3.66-3.55 (m, 1H), 1.40 (d, J = 6.7 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 430 | 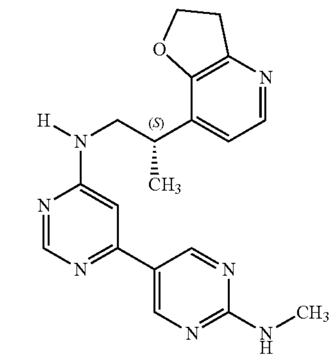 | 364.12 | (400 MHz, DMSO-d₆) δ 8.83 (s, 2H), 8.41 (s, 1H), 7.90 (d, J = 5.1 Hz, 1H), 7.55 (s, 1H), 7.39 (s, 1H), 7.01 (s, 1H), 6.77 (s, 1H), 4.61 (t, J = 8.4 Hz, 2H), 3.66-3.40 (m, 2H), 3.26-3.12 (m, 3H), 2.86 (d, J = 4.5 Hz, 3H), 1.21 (d, J = 6.6 Hz, 3H) |
| 431 | 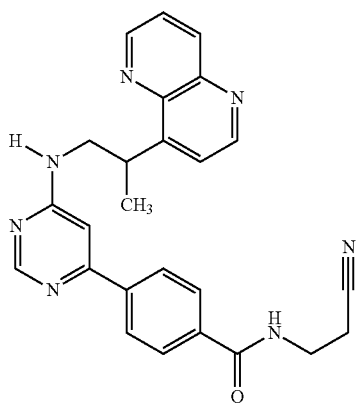 [SMILES: CC(CNc1cc(-c2ccc(C(=O)NCCC#N)cc2)ncn1)c1ccnc2cccnc12] | 438.41 | (DMSO-d₆) δ 8.98 (m, 3H), 8.51-8.39 (m, 2H), 7.97 (m, 3H), 7.78 (m, 2H), 7.57 (s, 1H), 7.21 (m, 1H), 6.92 (s, 1H), 4.48 (m, 1H), 3.83 (m, 2H), 3.52 (m, 2H), 2.80 (t, J = 6.3 Hz, 2H), 1.40 (d, J = 6.3 Hz, 3H) |
| 432 | 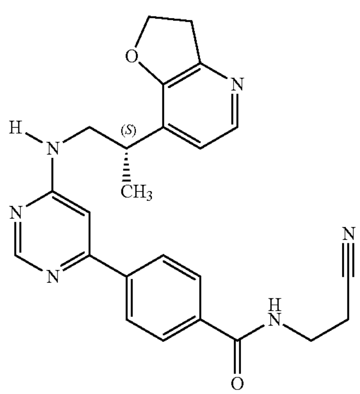 | 429.45 | (DMSO-d₆) δ 8.95 (m, 1H), 8.52 (s, 1H), 8.05 (s, 1H), 7.97 (m, 2H), 7.91 (d, J = 5.1 Hz, 1H), 7.58-7.49 (m, 2H), 7.02 (m, 2H), 4.62 (m, 2H), 3.67-3.44 (m, 4H), 3.28-3.12 (m, 3H), 2.80 (t, J = 6.4 Hz, 2H), 1.23 (d, J = 6.7 Hz, 3H) |
| 433 | 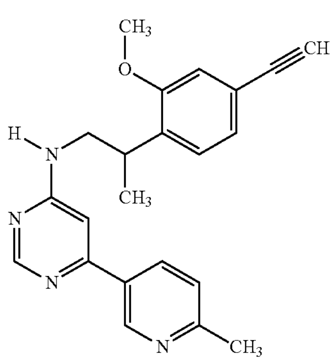 [SMILES: C#Cc1ccc(C(C)CNc2cc(-c3ccc(C)nc3)ncn2)c(OC)c1] | 359.05 | |

| Cmpnd No. | Structure | ESMS (M + H) | ¹H NMR (300 MHz, unless indicated otherwise) NMR peaks given as δ values |
|---|---|---|---|
| 434 | 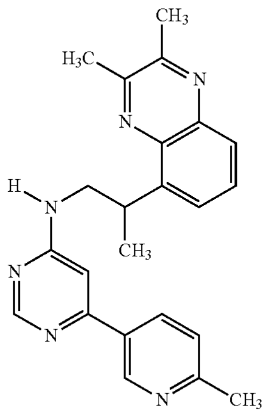 [SMILES: Cc1ccc(-c2cc(NCC(C)c3cccc4nc(C)c(C)nc34)ncn2)cn1] | 385 | (400 MHz, DMSO-$d_6$) δ 8.96 (s, 1H), 8.49 (s, 1H), 8.16 (s, 1H), 7.86-7.75 (m, 1H), 7.72-7.61 (m, 2H), 7.51 (d, J = 37.1 Hz, 1H), 7.36 (d, J = 8.1 Hz, 1H), 6.86 (s, 1H), 4.42 (dd, J = 14.0, 7.0 Hz, 1H), 3.74 (d, J = 63.7 Hz, 2H), 2.65 (s, 3H), 2.60 (s, 3H), 2.52 (d, J = 3.5 Hz, 3H), 1.38 (d, J = 6.3 Hz, 3H) |
| 435 | 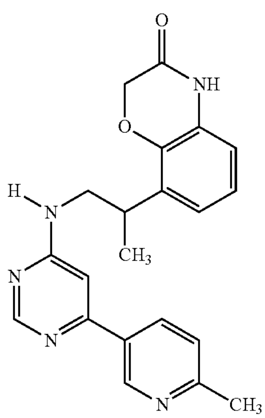 [SMILES: Cc1ccc(-c2cc(NCC(C)c3cccc4c3OCC(=O)N4)ncn2)cn1] | 376 | (400 MHz, DMSO-$d_6$) δ 10.65 (s, 1H), 8.99 (s, 1H), 8.50 (s, 1H), 8.18 (s, 1H), 7.47 (s, 1H), 7.37 (d, J = 8.1 Hz, 1H), 7.04-6.83 (m, 3H), 6.81-6.69 (m, 1H), 4.59-4.45 (m, 2H), 3.69-3.34 (m, 3H), 2.52 (d, J = 3.9 Hz, 3H), 1.19 (dd, J = 19.6, 6.9 Hz, 3H) |
| 436 | 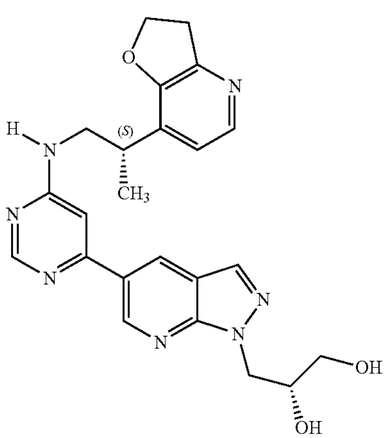 | 448.26 | (400 MHz, methanol-$d_4$) δ 9.01 (s, 1H), 8.69 (s, 1H), 8.54 (s, 1H), 8.50 (d, J = 1.2 Hz, 1H), 8.23 (s, 1H), 7.92 (d, J = 1.3 Hz, 1H), 7.90 (d, J = 5.2 Hz, 1H), 7.10 (d, J = 5.0 Hz, 1H), 6.91 (s, 1H), 4.69 (t, J = 8.6 Hz, 2H), 4.63 (d, J = 5.4 Hz, 2H), 4.27-4.17 (m, 1H), 3.89-3.67 (m, 2H), 3.59 (d, J = 5.3 Hz, 2H), 3.40-3.33 (m, 1H), 3.29-3.25 (m, 1H), 1.36 (d, J = 6.6 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 437 | 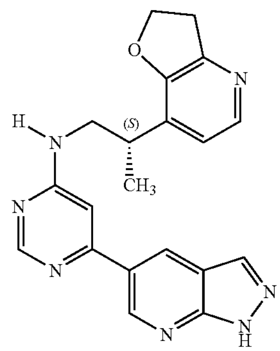 | 374.23 | (400 MHz, methanol-d₄) δ 9.16 (s, 1H), 8.78 (s, 1H), 8.65 (s, 1H), 8.18 (s, 1H), 8.03 (d, J = 4.8 Hz, 1H), 6.92 (d, J = 5.0 Hz, 1H), 6.84 (s, 1H), 5.30 (s, 1H), 4.72 (t, J = 8.7 Hz, 2H), 3.73-3.52 (m, 2H), 3.41-3.23 (m, 3H), 1.39 (d, J = 6.9 Hz, 3H) |
| 438 | 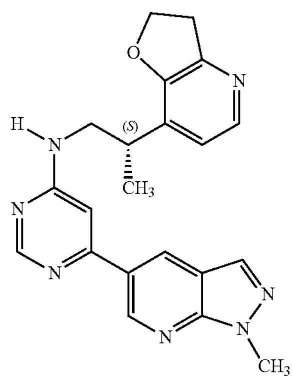 | 388.37 | (400 MHz, CDCl₃) δ 9.20 (s, 1H), 8.78 (d, J = 1.4 Hz, 1H), 8.62 (s, 1H), 8.04-7.98 (m, 2H), 6.91 (d, J = 5.1 Hz, 1H), 6.87 (s, 1H), 5.37 (s, 1H), 4.72 (t, J = 8.6 Hz, 2H), 4.28 (s, 3H), 3.77-3.40 (m, 2H), 3.38-3.23 (m, 3H), 1.37 (d, J = 6.9 Hz, 3H) |
| 439 | 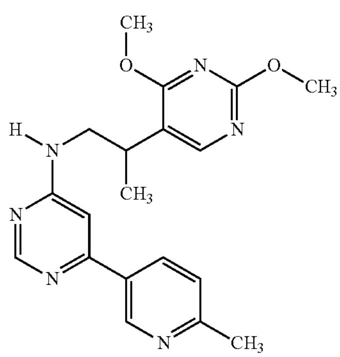 [SMILES: COc1ncc(C(C)CNc2cc(-c3ccc(C)nc3)ncn2)c(OC)n1] | 367.4 | (methanol-d₄) δ 9.11 (br. s, 1H), 8.81 (br. s, 1H), 8.53 (br. s, 1H), 8.32 (br. s, 1H), 7.89 (dd, J = 7.2, 3.2 Hz, 1H), 7.13 (br. s, 1H), 4.27 (s, 3H), 4.21 (s, 3H), 4.02 (m, 2H), 3.37 (m, 1H), 2.88 (d, J = 4.9 Hz, 3H), 1.72-1.19 (m, 3H) |
| 440 | 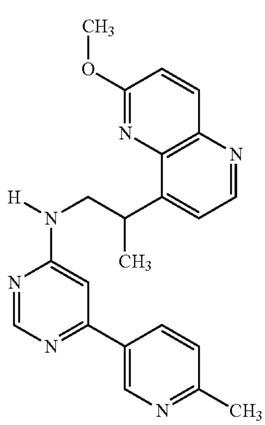 [SMILES: COc1ccc2nccc(C(C)CNc3cc(-c4ccc(C)nc4)ncn3)c2n1] | 387 | (400 MHz, DMSO-d₆) δ 8.96 (s, 1H), 8.73 (d, J = 4.5 Hz, 1H), 8.49 (s, 1H), 8.25 (d, J = 9.0 Hz, 1H), 8.15 (d, J = 6.7 Hz, 1H), 7.63 (d, J = 3.7 Hz, 1H), 7.50 (t, J = 5.5 Hz, 1H), 7.35 (d, J = 8.1 Hz, 1H), 7.24 (d, J = 9.0 Hz, 1H), 6.87 (s, 1H), 4.30 (dd, J = 14.0, 7.0 Hz, 1H), 3.95 (s, 3H), 3.80 (s, 2H), 2.52 (s, 3H), 1.40 (t, J = 9.4 Hz, 3H) |

| Cmpnd No. | Structure | ESMS (M + H) | ¹H NMR (300 MHz, unless indicated otherwise) NMR peaks given as δ values |
|---|---|---|---|
| 441 | 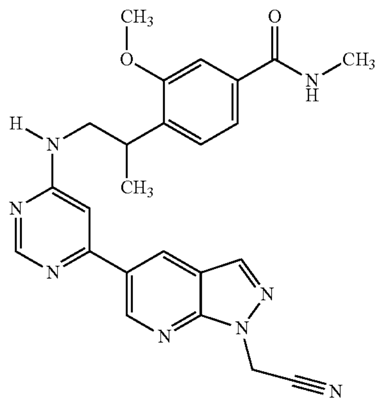 [SMILES: CNC(=O)c1ccc(C(C)CNc2cc(-c3cnc4c(cnn4CC#N)c3)ncn2)c(OC)c1] | 457.67 | (400 MHz, CDCl₃) δ 9.06 (s, 1H), 8.66 (d, J = 7.0 Hz, 1H), 8.56 (s, 1H), 8.19-8.05 (m, 1H), 7.34 (d, J = 8.9 Hz, 1H), 7.15 (d, J = 7.7 Hz, 1H), 6.60 (d, J = 21.2 Hz, 1H), 6.03 (s, 1H), 5.41 (s, 2H), 5.18 (s, 1H), 3.83 (d, J = 11.9 Hz, 3H), 3.55 (dt, J = 36.6, 18.1 Hz, 4H), 2.94 (d, J = 4.7 Hz, 3H), 1.30 (d, J = 6.2 Hz, 3H) |
| 442 | 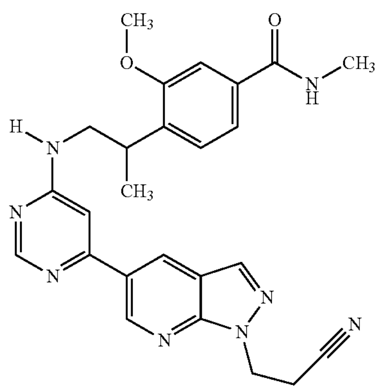 [SMILES: CNC(=O)c1ccc(C(C)CNc2cc(-c3cnc4c(cnn4CCC#N)c3)ncn2)c(OC)c1] | 471.34 | (400 MHz, CDCl₃) δ 9.00 (s, 1H), 8.62 (dd, J = 9.7, 1.5 Hz, 1H), 8.55 (d, J = 10.6 Hz, 1H), 8.44 (d, J = 11.8 Hz, 1H), 8.14-7.93 (m, 1H), 7.32 (d, J = 5.1 Hz, 1H), 7.16 (d, J = 5.3 Hz, 1H), 7.12 (d, J = 8.1 Hz, 1H), 6.59 (d, J = 20.4 Hz, 1H), 6.17 (d, J = 4.2 Hz, 1H), 5.14 (dd, J = 118.6, 43.4 Hz, 1H), 4.80 (t, J = 6.9 Hz, 2H), 3.81 (d, J = 6.2 Hz, 3H), 3.66-3.45 (m, 2H), 3.05-2.96 (m, 2H), 2.93 (d, J = 6.1 Hz, 3H), 1.29 (d, J = 6.3 Hz, 3H) |
| 443 | 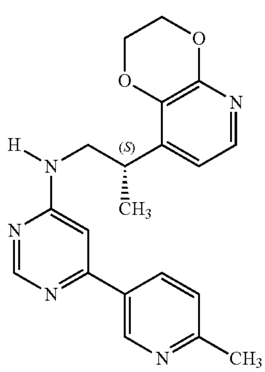 | 364.42 | (CDCl₃) δ 9.02 (d, J = 5.4 Hz, 1H), 8.64 (s, 1H), 8.28 (d, J = 7.6 Hz, 1H), 7.80 (d, J = 5.1 Hz, 1H), 7.31 (d, J = 8.2 Hz, 1H), 6.82 (d, J = 5.1 Hz, 1H), 6.72 (s, 1H), 4.44 (m, 2H), 4.32-4.21 (m, 2H), 3.53 (m, 3H), 2.65 (s, 3H), 1.33 (d, 3H) |
| 444 | 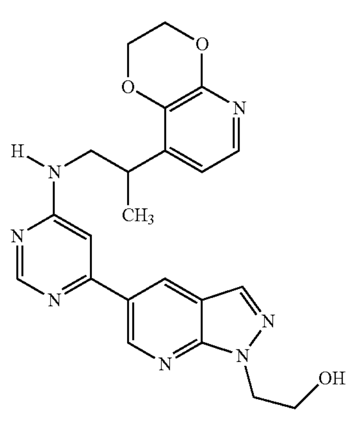 [SMILES: CC(CNc1cc(-c2cnc3c(cnn3CCO)c2)ncn1)c1ccnc2c1OCCO2] | 434.41 | (methanol-d₄) δ 8.89 (s, 1H), 8.73 (s, 1H), 8.65 (s, 1H), 8.29 (s, 1H), 7.68 (d, J = 5.3 Hz, 1H), 7.03-6.91 (m, 2H), 4.67 (m, 2H), 4.43 (m, 2H), 4.30 (m, 2H), 4.06 (m, 2H), 3.59 (m, 3H), 1.36 (d, J = 7.2 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 445 | 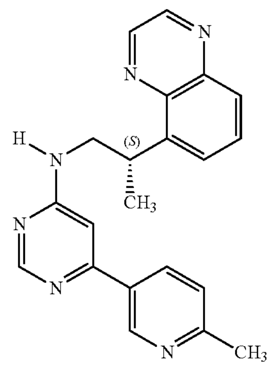 | 357 | (400 MHz, DMSO-d$_6$) δ 8.96 (s, 3H), 8.46 (s, 1H), 8.15 (s, 1H), 8.01-7.92 (m, 1H), 7.90-7.76 (m, 2H), 7.52 (s, 1H), 7.37 (s, 1H), 7.05 (d, J = 135.9 Hz, 1H), 4.44 (s, 1H), 3.66 (t, J = 94.2 Hz, 2H), 2.52 (d, J = 4.3 Hz, 3H), 1.40 (d, J = 5.7 Hz, 3H) |
| 446 | 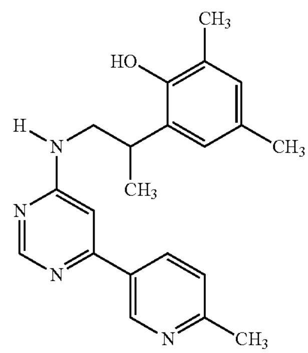 [SMILES: Cc1cc(C)c(O)c(C(C)CNc2cc(-c3ccc(C)nc3)ncn2)c1] | 349.03 | |
| 447 | 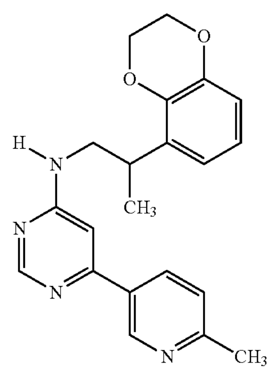 [SMILES: Cc1ccc(-c2cc(NCC(C)c3cccc4c3OCCO4)ncn2)cn1] | 363.37 | (CDCl$_3$) δ 9.02 (d, J = 1.6 Hz, 1H), 8.64 (s, 1H), 8.24 (dd, J = 8.1, 2.3 Hz, 1H), 7.30 (m, 1H), 6.89-6.77 (m, 3H), 6.71 (s, 1H), 4.30 (m, 4H), 3.49 (m, 3H), 2.65 (s, 3H), 1.35 (d, 3H) |
| 448 | 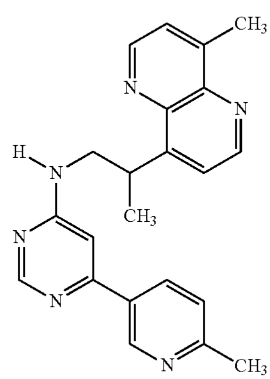 [SMILES: Cc1ccc(-c2cc(NCC(C)c3ccnc4c(C)ccnc34)ncn2)cn1] | 371 | (400 MHz, DMSO-d$_6$) δ 9.18-8.78 (m, 3H), 8.49 (s, 1H), 8.16 (s, 1H), 7.77-7.35 (m, 4H), 6.87 (s, 1H), 4.49 (d, J = 6.8 Hz, 1H), 3.63 (d, J = 141.0 Hz, 2H), 2.77 (d, J = 10.8 Hz, 3H), 2.53 (d, J = 6.1 Hz, 3H), 1.38 (d, J = 5.4 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 449 | 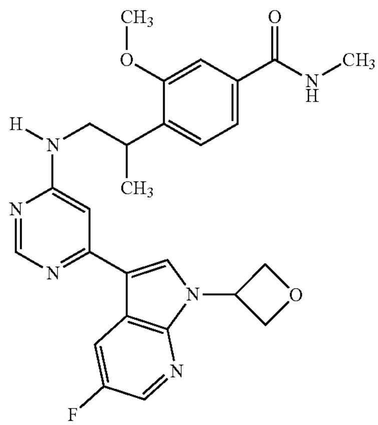 [SMILES: CNC(=O)c1ccc(C(C)CNc2cc(-c3cn(C4COC4)c4ncc(F)cc34)ncn2)c(OC)c1] | 490.73 | (400 MHz, CDCl₃) δ 8.51 (d, J = 13.1 Hz, 1H), 8.31 (s, 1H), 8.24 (dd, J = 9.1, 2.5 Hz, 1H), 8.16 (s, 1H), 7.34 (d, J = 5.3 Hz, 1H), 7.21 (d, J = 4.2 Hz, 1H), 7.14 (dd, J = 11.8, 5.2 Hz, 1H), 6.45 (s, 1H), 6.09-5.95 (m, 2H), 5.16 (t, J = 7.3 Hz, 2H), 4.97 (dt, J = 10.5, 5.2 Hz, 3H), 3.83 (d, J = 7.6 Hz, 3H), 3.62-3.44 (m, 3H), 2.93 (d, J = 4.8 Hz, 3H), 1.31 (d, J = 6.5 Hz, 3H) |
| 450 | 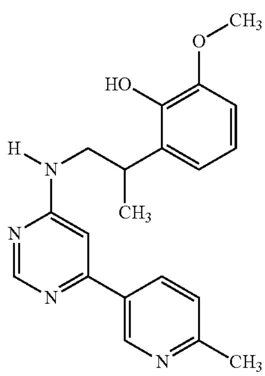 [SMILES: COc1cccc(C(C)CNc2cc(-c3ccc(C)nc3)ncn2)c1O] | 351.33 | |
| 451 | 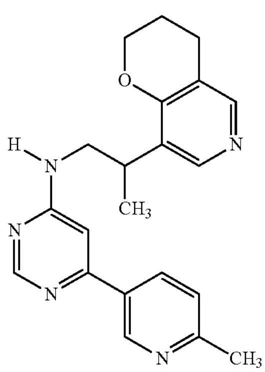 [SMILES: Cc1ccc(-c2cc(NCC(C)c3cncc4c3OCCC4)ncn2)cn1] | 362.18 | (400 MHz, methanol-d₄) δ 8.91 (s, 1H), 8.44 (s, 1H), 8.20 (d, J = 7.7 Hz, 1H), 8.05 (s, 1H), 7.99 (s, 1H), 7.42 (d, J = 8.1 Hz, 1H), 6.83 (s, 1H), 4.36-4.19 (m, 2H), 3.94-3.50 (m, 2H), 3.50-3.38 (m, 1H), 2.85-2.69 (m, 2H), 2.60 (s, 3H), 2.09-1.92 (m, 2H), 1.34 (d, J = 6.7 Hz, 3H) |
| 452 | 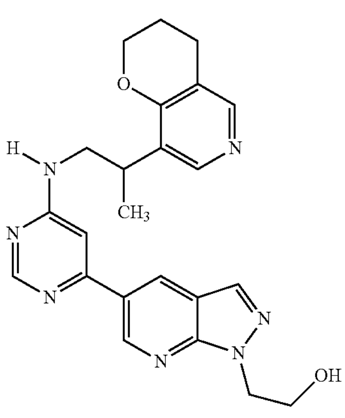 [SMILES: CC(CNc1cc(-c2cnc3c(cnn3CCO)c2)ncn1)c1cncc2c1OCCC2] | 432.23 | (400 MHz, CDCl₃) δ 9.01 (s, 1H), 8.65 (s, 1H), 8.43 (s, 1H), 8.17 (s, 1H), 8.05 (s, 1H), 7.97 (s, 1H), 6.84 (s, 1H), 4.62 (t, J = 5.6 Hz, 2H), 4.33-4.20 (m, 2H), 4.03 (t, J = 5.6 Hz, 2H), 3.61 (dd, J = 37.7, 25.6 Hz, 2H), 3.44 (dq, J = 20.8, 7.0 Hz, 1H), 2.74 (s, 2H), 2.06-1.92 (m, 2H), 1.31 (t, J = 15.0 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 453 | 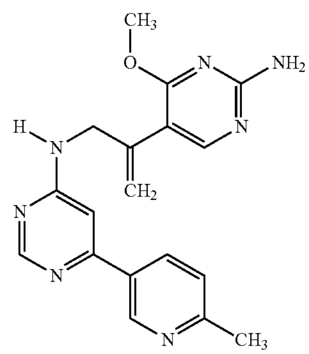 [SMILES: C=C(CNc1cc(-c2ccc(C)nc2)ncn1)c1cnc(N)nc1OC] | 350.28 | (methanol-d₄) δ 8.92 (d, J = 2.2 Hz, 1H), 8.46 (d, J = 1.1 Hz, 1H), 8.21 (dd, J = 8.3, 2.4 Hz, 1H), 7.86 (s, 1H), 7.41 (d, J = 8.2 Hz, 1H), 6.90 (d, J = 1.2 Hz, 1H), 5.30 (d, J = 1.5 Hz, 1H), 5.23 (d, J = 1.3 Hz, 1H), 4.38 (br. s, 2H), 3.93 (s, 3H), 2.59 (s, 3H) |
| 454 | 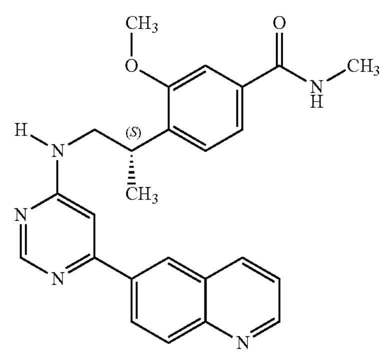 | 428 | (400 MHz, DMSO-d₆) δ 8.95 (d, J = 2.9 Hz, 1H), 8.74-8.22 (m, 5H), 8.12 (d, J = 8.8 Hz, 1H), 7.64-7.48 (m, 2H), 7.38 (d, J = 30.7 Hz, 3H), 7.10 (s, 1H), 3.83 (s, 3H), 3.70-3.42 (m, 3H), 2.76 (t, J = 9.9 Hz, 3H), 1.21 (d, J = 25.1 Hz, 3H) |
| 455 | 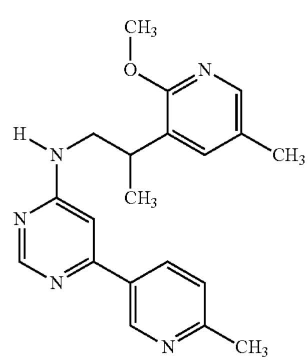 [SMILES: COc1ncc(C)cc1C(C)CNc1cc(-c2ccc(C)nc2)ncn1] | 350.43 | (400 MHz, CDCl₃) δ 9.01 (s, 1H), 8.61 (s, 1H), 8.20 (d, J = 6.8 Hz, 1H), 7.85 (s, 1H), 7.29 (d, J = 1.7 Hz, 1H), 7.27 (d, J = 4.7 Hz, 1H), 6.68 (s, 1H), 5.27 (s, 1H), 3.95 (s, 3H), 3.65-3.34 (m, 3H), 2.64 (d, J = 13.9 Hz, 3H), 2.22 (d, J = 8.8 Hz, 3H), 1.33 (d, J = 6.8 Hz, 3H) |
| 456 | 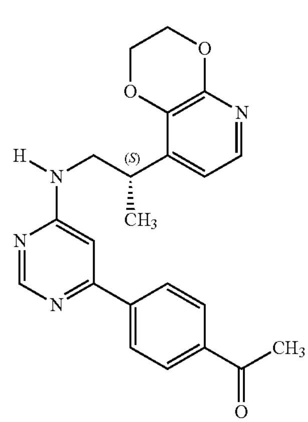 | 391.41 | (CDCl₃) δ 8.64 (s, 1H), 8.11-8.02 (m, 4H), 7.81 (d, J = 5.9 Hz, 1H), 6.84 (s, H), 6.82 (d, J = 5.1 Hz, 1H), 4.43 (m, 2H), 4.33-4.22 (m, 2H), 3.67-3.51 (m, 3H), 2.65 (s, 3H), 1.37 (d, J = 5.6 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 457 | 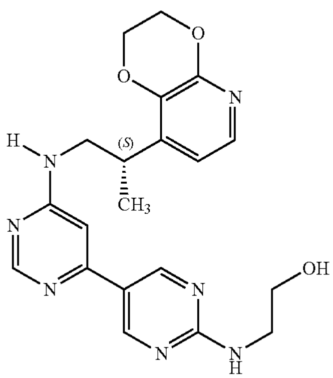 | 410.44 | |
| 458 | 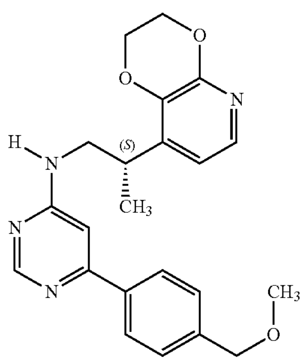 | 393.35 | (methanol-d₄) δ 8.43 (s, 1H), 7.86 (d, J = 8.0 Hz, 2H), 7.65 (d, J = 5.2 Hz, 1H), 7.45 (d, J = 8.1 Hz, 2H), 6.94 (d, J = 5.2 Hz, 1H), 6.82 (s, 1H), 4.51 (s, 2H), 4.39 (m, 2H), 4.28-4.18 (m, 2H), 3.58 (m, 3H), 3.40 (s, 3H), 1.31 (d, J = 6.1 Hz, 3H) |
| 459 | 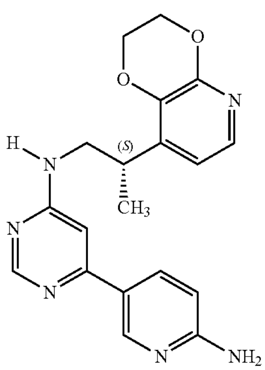 | 365.41 | (CDCl₃) δ 8.54 (s, 1H), 8.48-8.38 (m, 2H), 7.79 (d, J = 5.2 Hz, 1H), 6.89 (m, 1H), 6.82 (d, J = 5.1 Hz, 1H), 6.67 (s, 1H), 4.50-4.40 (m, 2H), 4.31 (m, 2H), 3.57 (m, 3H), 1.36 (d, J = 6.5 Hz, 3H) |
| 460 | 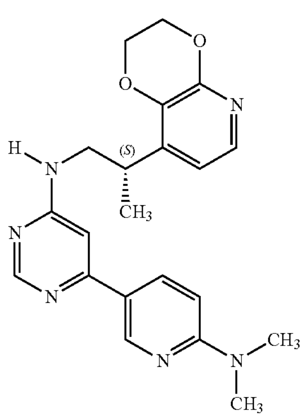 | 393.42 | (methanol-d₄) δ 8.62 (d, J = 2.1 Hz, 1H), 8.38 (s, 1H), 8.01 (dd, J = 9.2, 2.3 Hz, 1H), 7.65 (d, J = 5.2 Hz, 1H), 6.94 (d, J = 5.1 Hz, 1H), 6.74 (m, 2H), 4.40 (m, 2.9 Hz, 2H), 4.29-4.20 (m, 2H), 3.64-3.50 (m, 3H), 3.15 (s, 6H), 1.31 (d, J = 6.2 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 461 | 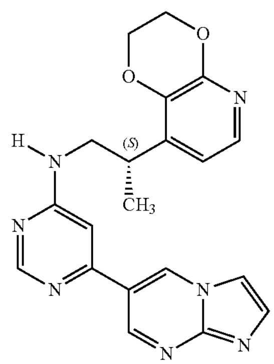 | 390.38 | |
| 462 | 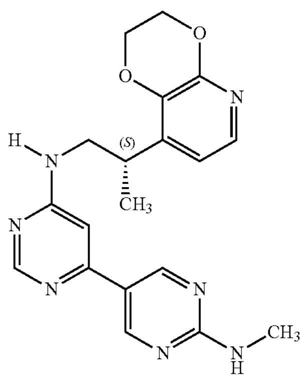 | 380.39 | (methanol-d₄) δ 8.75 (s, 2H), 8.47 (s, 1H), 7.65 (d, J = 5.3 Hz, 1H), 6.94 (d, J = 5.2 Hz, 1H), 6.76 (s, 1H), 4.46-4.34 (m, 2H), 4.32-4.19 (m, 2H), 3.59 (ddd, J = 12.0, 11.5, 7.3 Hz, 3H), 2.99 (s, 3H), 1.32 (d, J = 6.7 Hz, 3H) |
| 463 | 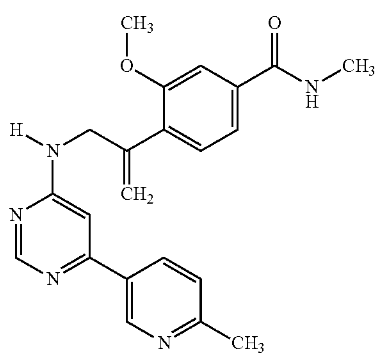 [SMILES: C=C(CNc1cc(-c2ccc(C)nc2)ncn1)c1ccc(C(=O)NC)cc1OC] | 390.38 | |
| 464 | 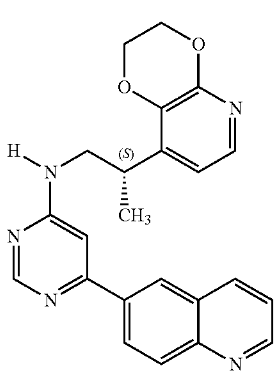 | 400.39 | |

TABLE 1-continued

| Cmpnd No. | Structure | ESMS (M + H) | ¹H NMR (300 MHz, unless indicated otherwise) NMR peaks given as δ values |
|---|---|---|---|
| 465 | 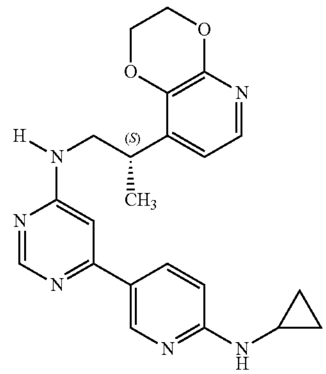 | 405.42 | |
| 466 | 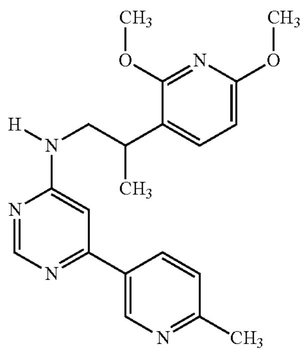 [SMILES: COc1ccc(C(C)CNc2cc(-c3ccc(C)nc3)ncn2)c(OC)n1] | 366.41 | (methanol-$d_4$) δ 8.88 (s, 1H), 8.66 (s, 1H), 8.38-8.01 (m, 1H), 7.64 (d, J = 8.3 Hz, 1H), 7.48 (d, J = 8.1 Hz, 1H), 6.90 (s, 1H), 6.28 (d, J = 8.3 Hz, 1H), 4.08-3.63 (m, 8H), 3.52-3.34 (m, 1H), 2.68 (s, 3H), 1.29 (d, J = 7.0 Hz, 3H) |
| 467 | 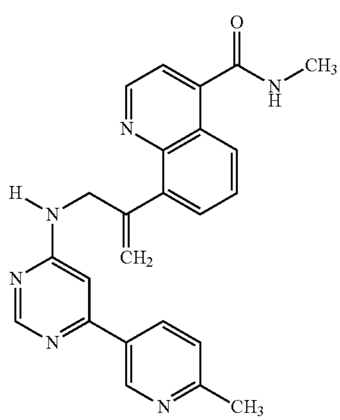 [SMILES: C=C(CNc1cc(-c2ccc(C)nc2)ncn1)c1cccc2c(C(=O)NC)ccnc12] | 411.43 | (methanol-$d_4$) δ 8.99 (d, J = 4.3 Hz, 1H), 8.94 (br. s, 1H), 8.44 (s, 1H), 8.25 (m, 1H), 8.13 (d, J = 7.1, 1H), 7.69 (dd, J = 7.1, 1.6 Hz, 1H), 7.61 (dd, J = 8.4, 7.1 Hz, 1H), 7.55 (d, J = 4.3 Hz, 1H), 7.43 (d, J = 8.2 Hz, 1H), 6.96 (m, 1H), 5.49 (s, 1H), 5.26 (d, J = 1.6 Hz, 1H), 4.61 (m, 2H), 3.02 (s, 3H), 2.60 (s, 3H) |
| 468 | 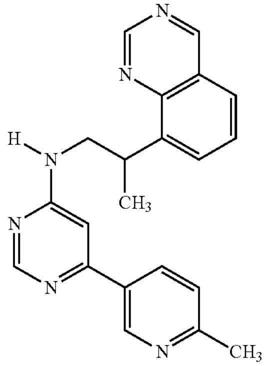 [SMILES: Cc1ccc(-c2cc(NCC(C)c3cccc4cncnc34)ncn2)cn1] | 357 | (400 MHz, DMSO-d6) δ 9.60 (s, 1H), 9.35 (d, J = 14.9 Hz, 1H), 8.96 (s, 1H), 8.47 (d, J = 13.3 Hz, 1H), 8.16 (s, 2H), 8.03 (d, J = 8.3 Hz, 2H), 7.37 (s, 2H), 6.88 (s, 1H), 4.36 (s, 1H), 3.76 (s, 2H), 2.52 (s, 3H), 1.40 (s, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 469 | 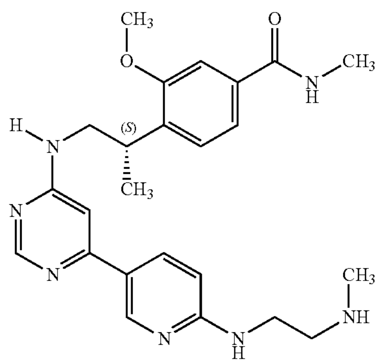 | 450.44 | |
| 470 | 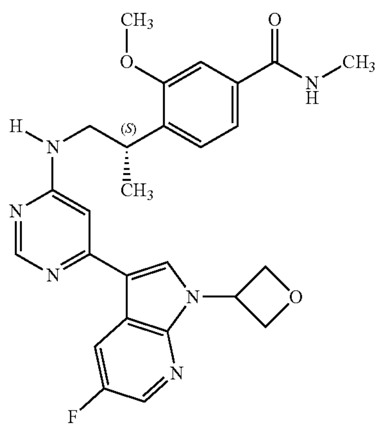 | 491.26 | (400 MHz, CDCl₃) δ 8.57 (s, 1H), 8.40 (s, 1H), 8.32 (dd, J = 9.0, 2.1 Hz, 1H), 8.23 (s, 1H), 7.42 (s, 1H), 7.27-7.22 (m, 2H), 6.56 (s, 1H), 6.29 (s, 1H), 6.18-6.00 (m, 1H), 5.23 (t, J = 7.3 Hz, 2H), 5.05 (dd, J = 10.2, 6.4 Hz, 2H), 3.91 (s, 3H), 3.72-3.50 (m, 3H), 2.99 (s, 3H), 2.05 (s, 1H), 1.38 (d, J = 6.2 Hz, 3H) |
| 471 | 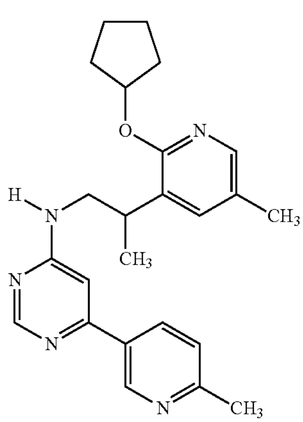 [SMILES: Cc1cnc(OC2CCCC2)c(C(C)CNc2cc(-c3ccc(C)nc3)ncn2)c1] | 404.14 | (400 MHz, CDCl₃) δ 8.98 (s, 1H), 8.61 (s, 1H), 8.18 (d, J = 7.8 Hz, 1H), 7.83 (s, 1H), 6.59 (s, 1H), 5.46 (s, 1H), 5.19 (s, 1H), 3.55 (s, 2H), 3.39-3.28 (m, 1H), 2.62 (s, 3H), 2.21 (s, 3H), 2.02-1.84 (m, 3H), 1.79-1.60 (m, 6H), 1.32 (d, J = 6.8 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 472 | 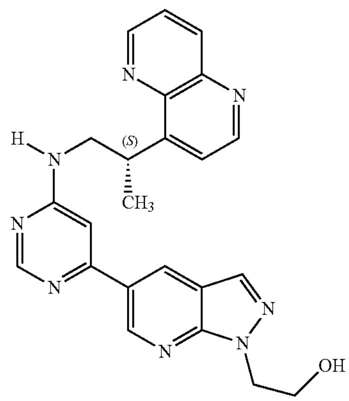 | 427 | (400 MHz, DMSO-d$_6$) δ 9.31-8.67 (m, 3H), 8.44 (dd, J = 20.4, 12.8 Hz, 2H), 8.27 (s, 1H), 7.87-7.54 (m, 3H), 7.12 (d, J = 143.8 Hz, 1H), 4.73 (d, J = 155.3 Hz, 3H), 3.62 (d, J = 206.7 Hz, 4H), 1.41 (d, J = 6.0 Hz, 3H) |
| 473 | 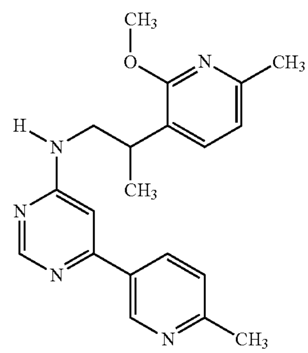 | 350.34 | (methanol-d$_4$) δ 8.95 (s, 1H), 8.67 (s, 1H), 8.33 (d, J = 8.5 Hz, 1H), 7.71 (d, J = 7.4 Hz, 1H), 7.47 (dd, J = 7.5, 2.6 Hz, 1H), 6.94 (s, 1H), 6.86-6.58 (m, 1H), 3.92 (s, 3H), 3.87-3.54 (m, 2H), 3.44 (qd, J = 7.0, 2.5 Hz, 1H), 2.72 (s, 3H), 2.39 (s, 3H), 1.31 (d, J = 7.0 Hz, 3H) |
| 474 | 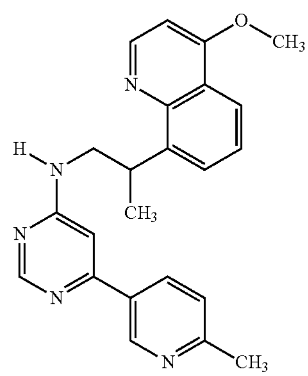 [SMILES: COc1ccnc2c(C(C)CNc3cc(-c4ccc(C)nc4)ncn3)cccc12] | 386.45 | (methanol-d$_4$) δ 9.26 (d, J = 2.2 Hz, 1H), 9.12 (d, J = 6.8 Hz, 1H), 8.93-8.75 (m, 2H), 8.42 (dd, J = 8.4, 1.3 Hz, 1H), 8.30-8.14 (m, 1H), 8.11 (d, J = 8.5 Hz, 1H), 7.89 (t, J = 8.0 Hz, 1H), 7.62 (d, J = 6.8 Hz, 1H), 7.25 (s, 1H), 4.41 (s, 3H), 4.27-3.69 (m, 3H), 2.89 (s, 3H), 1.59 (d, J = 6.6 Hz, 3H) |
| 475 | 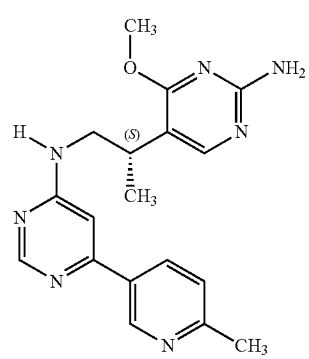 | 352.41 | |

TABLE 1-continued

| Cmpnd No. | Structure | ESMS (M + H) | ¹H NMR (300 MHz, unless indicated otherwise) NMR peaks given as δ values |
|---|---|---|---|
| 476 | 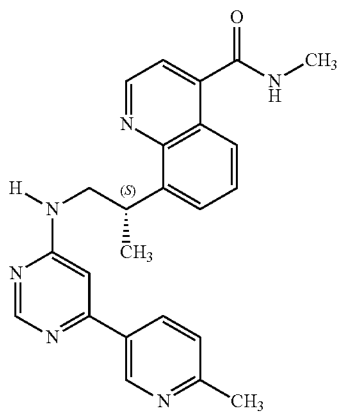 | 413.45 | (methanol-d₄) δ 9.32, 9.20 (2d, J = 5.4 Hz, 1H), 9.41, 9.27 (2d, J = 2.1 Hz, 1H), 8.95, 8.86 (2d, J = 8.1 Hz, 1H), 8.79, 8.67 (2s, 1H), 8.29 (dd, J = 8.5, 1.3 Hz, 1H), 8.22 (d, J = 7.1 Hz, 1H), 8.14 (d, J = 8.6 Hz, 1H), 8.08 (d, J = 5.5 Hz, 1H), 7.97 (t, J = 8.0 Hz, 1H), 7.48, 7.22 (2s, 1H), 4.39 (q, J = 6.7 Hz, 1H), 4.12 (d, J = 6.5 Hz, 2H), 3.07 3.05 (2s, 3H), 2.94, 2.90 (2s, 3H), 1.61 (d, J = 6.8 Hz, 3H) |
| 477 | 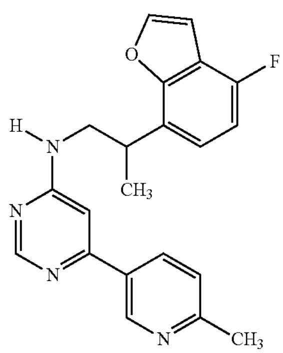 [SMILES: Cc1ccc(-c2cc(NCC(C)c3ccc(F)c4ccoc34)ncn2)cn1] | 363.17 | (400 MHz, CDCl₃) δ 10.05 (s, 1H), 9.04 (s, 1H), 8.50 (s, 1H), 8.31 (s, 1H), 7.53 (t, J = 35.5 Hz, 2H), 7.05 (s, 1H), 6.82-6.71 Hz, 1H), 3.55 (d, J = 6.2 Hz, 2H), 2.76 (s, 3H), 1.47 (s, 3H) |
| 478 | 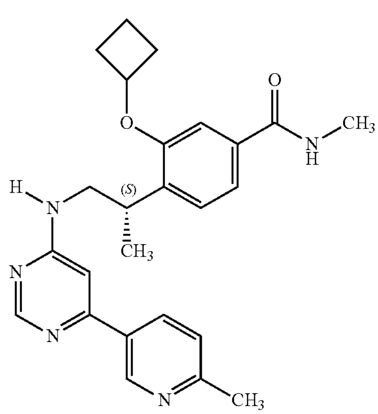 | 432.46 | (methanol-d₄) δ 9.27 (d, J = 1.9 Hz, 1H), 8.86 (dd, J = 8.5, 2.0 Hz, 1H), 8.77, 8.65 (2s, 1H), 8.16 (d, J = 8.5 Hz, 1H), 7.48-6.75 (m, 4H), 4.78 (t, J = 7.1 Hz, 1H), 4.09-3.52 (m, 3H), 3.02-2.72 (m, 6H), 2.59-2.47 (m, 2H), 2.26-1.96 (m, 2H), 1.94-1.60 (m, 2H), 1.37 (d, J = 6.9 Hz, 3H) |

TABLE 1-continued

| Cmpnd No. | Structure | ESMS (M + H) | $^{1}$H NMR (300 MHz, unless indicated otherwise) NMR peaks given as δ values |
|---|---|---|---|
| 479 | 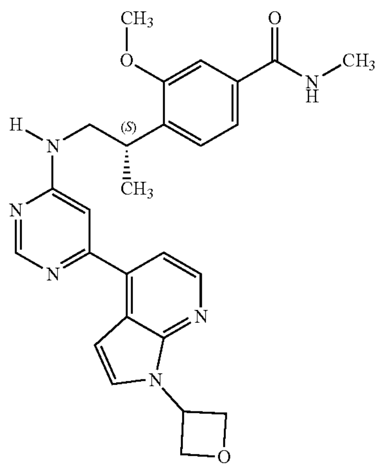 | 473.19 | (400 MHz, CDCl$_3$) δ 8.62 (s, 1H), 8.32 (d, J = 4.9 Hz, 1H), 7.72 (d, J = 3.5 Hz, 1H), 7.42 (d, J = 4.8 Hz, 1H), 7.33 (s, 1H), 7.18-7.12 (m, 2H), 6.98 (d, J = 3.5 Hz, 1H), 6.75 (s, 1H), 6.09 (td, J = 13.3, 6.3 Hz, 2H), 5.15 (t, J = 7.3 Hz, 2H), 4.96 (t, J = 6.6 Hz, 2H), 3.78 (s, 3H), 3.56 (dd, J = 13.6, 6.9 Hz, 3H), 2.92 (t, J = 10.5 Hz, 3H), 1.30 (d, J = 6.4 Hz, 3H) |
| 480 | 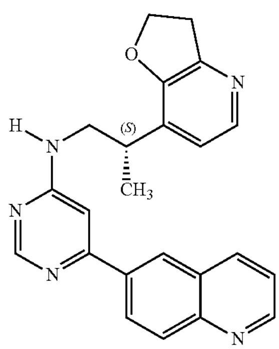 | 384.39 | (400 MHz, CDCl$_3$) δ 8.99-8.88 (m, 1H), 8.67 (s, 1H), 8.54 (s, 1H), 8.24 (t, J = 8.6 Hz, 2H), 8.16 (d, J = 8.8 Hz, 1H), 8.00 (d, J = 5.1 Hz, 1H), 7.44 (dd, J = 8.2, 4.2 Hz, 1H), 6.91 (d, J = 5.2 Hz, 2H), 5.45 (s, 1H), 4.81-4.55 (m, 2H), 3.67 (dd, J = 24.2, 18.6 Hz, 2H), 3.37-3.24 (m, 3H), 1.37 (d, J = 6.9 Hz, 3H) |
| 481 | 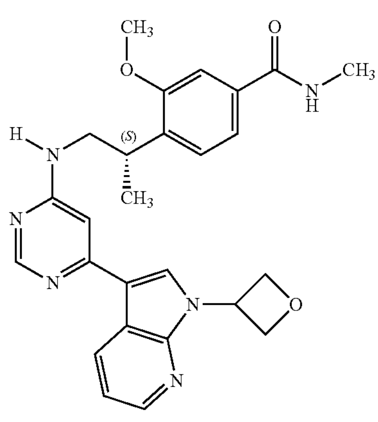 | 473.07 | |

TABLE 1-continued

| Cmpnd No. | Structure | ESMS (M + H) | ¹H NMR (300 MHz, unless indicated otherwise) NMR peaks given as δ values |
|---|---|---|---|
| 482 | 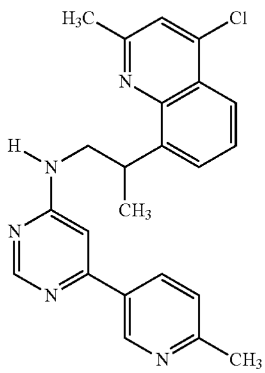 [SMILES: Cc1ccc(-c2cc(NCC(C)c3cccc4c(Cl)cc(C)nc34)ncn2)cn1] | 404.39 | (methanol-d₄) δ 8.92, 8.85 (2s, 1H), 8.66, 8.49 (2s, 1H), 8.41-7.92 (m, 2H), 7.87-7.38 (m, 4H), 6.87, 6.80 (2s, 1H), 4.63 (q, J = 7.0 Hz, 1H), 4.15-3.67 (m, 2H), 2.73 (s, 3H), 2.69 (s, 3H), 1.51 (d, J = 7.0 Hz, 3H) |
| 483 | 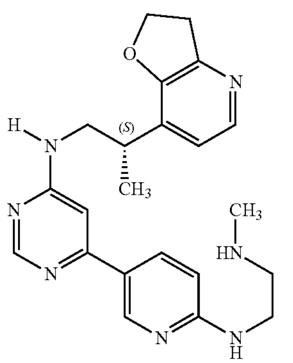 | 406.18 | (400 MHz, CDCl₃) δ 8.66 (s, 1H), 8.53 (s, 1H), 8.04-8.00 (m, 1H), 7.99 (d, J = 5.1 Hz, 1H), 6.89 (d, J = 5.1 Hz, 1H), 6.59 (s, 1H), 6.48 (d, J = 8.8 Hz, 1H), 5.54 (s, 1H), 5.23 (s, 1H), 4.77-4.56 (m, 2H), 3.63-3.50 (m, 4H), 3.32 (t, J = 8.9 Hz, 2H), 3.25 (dd, J = 14.1, 7.0 Hz, 1H), 2.93 (t, J = 5.6 Hz, 2H), 2.51 (s, 3H), 1.34 (d, J = 6.9 Hz, 3H) |
| 484 | 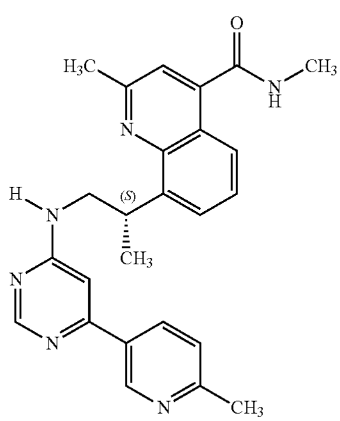 | 427.43 | (methanol-d₄) δ 9.25 (d, J = 2.0 Hz, 1H), 8.83 (dd, J = 8.6, 1.9 Hz, 1H), 8.75 (s, 1H), 8.34-8.05 (m, 3H), 7.96 (s, 1H), 7.90 (t, J = 7.9 Hz, 1H), 7.21 (s, 1H), 4.54 (q, J = 6.7 Hz, 1H), 4.26-3.90 (m, 2H), 3.16 (s, 3H), 3.05 (s, 3H), 2.89 (s, 3H), 1.59 (d, J = 6.8 Hz, 3H) |
| 485 | 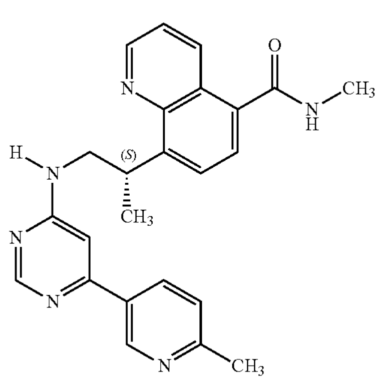 | 413 | (400 MHz, DMSO-d₆) δ 9.07 (d, J = 77.4 Hz, 2H), 8.71 (d, J = 8.4 Hz, 1H), 8.56-8.41 (m, 2H), 8.19 (d, J = 22.4 Hz, 1H), 7.69 (dd, J = 30.6, 23.4 Hz, 4H), 7.14 (d, J = 187.5 Hz, 2H), 4.53 (s, 1H), 3.57 (d, J = 187.8 Hz, 2H), 2.85 (d, J = 4.5 Hz, 3H), 2.52 (d, J = 5.8 Hz, 3H), 1.39 (s, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 486 | (structure) | 377.16 | (400 MHz, CDCl₃) δ 8.68 (s, 1H), 8.57 (s, 1H), 8.15 (dd, J = 8.8, 2.1 Hz, 1H), 8.02 (d, J = 5.1 Hz, 1H), 6.91 (d, J = 5.1 Hz, 1H), 6.64 (s, 1H), 6.49 (d, J = 8.8 Hz, 1H), 5.15 (s, 2H), 4.81-4.61 (m, 2H), 3.74-3.45 (m, 2H), 3.45-3.32 (m, 4H), 3.27 (dt, J = 13.7, 6.9 Hz, 1H), 1.37 (d, J = 6.9 Hz, 3H), 1.31 (t, J = 7.2 Hz, 3H) |
| 487 | (structure) | 376.23 | (400 MHz, methanol-d₄) δ 8.92 (s, 1H), 8.45 (s, 1H), 8.20 (d, J = 7.1 Hz, 1H), 7.42 (d, J = 8.0 Hz, 1H), 6.99 (s, 1H), 6.84 (s, 1H), 4.14 (s, 2H), 3.75-3.47 (m, 3H), 2.95-2.74 (m, 2H), 2.60 (s, 3H), 2.37 (s, 3H), 2.16-1.90 (m, 2H), 1.28 (d, J = 5.8 Hz, 3H) |
| 488 | (structure) | 414.44 | (methanol-d₄) δ 9.01 (d, J = 4.5 Hz, 1H), 8.85 (br. s, 1H), 8.57 (m, 2H), 7.91 (d, J = 4.3 Hz, 1H), 8.22 (m, 1H), 7.91 (d, J = 4.6 Hz, 1H), 7.81 (dd, J = 7.3, 1.4 Hz, 1H), 7.68 (m, 2H), 6.82 (s, 1H), 4.65 (q, J = 7.0 Hz, 1H), 4.02 (s, 3H), 4.03 (m, 2H), 2.71 (2s, 3H), 1.52 (d, J = 6.9 Hz, 3H) |
| 489 | (structure) | 381.38 | (methanol-d₄) δ 9.05 (d, J = 4.4 Hz, 1H), 8.86 (s, 1H), 8.60 (s, 1H), 8.24 (d, J = 7.7 Hz, 1H), 8.09 (d, J = 8.3 Hz, 1H), 7.91 (d, J = 7.9 Hz, 2H), 7.81 (t, J = 7.8 Hz, 1H), 7.64 (d, J = 8.1 Hz, 1H), 6.82 (s, 1H), 4.64 (q, J = 7.1 Hz, 1H), 4.29-3.78 (m, 2H), 2.72 (s, 3H), 1.52 (d, J = 7.3 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 490 | 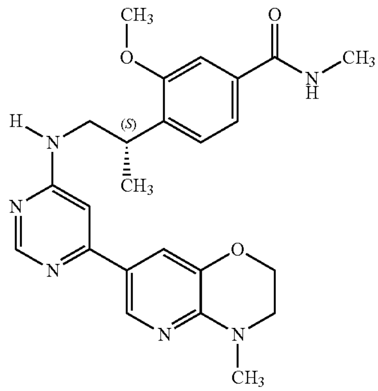 | 449.45 | |
| 491 | 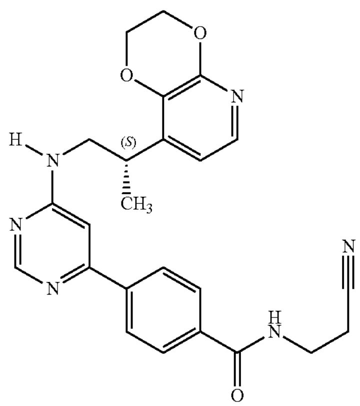 | 445.39 | (methanol-d₄) δ 8.67 (s, 1H), 8.05 (d, J = 8.2 Hz, 2H), 7.90 (d, J = 7.9 Hz, 2H), 7.67 (d, J = 5.2 Hz, 1H), 7.03-6.87 (m, 2H), 4.41 (m, 2H), 4.28 (m, 2H), 3.88 (m, 2H), 3.63 (m, 3H), 2.82 (t, J = 6.5 Hz, 2H), 1.35 (d, J = 6.9 Hz, 3H) |
| 492 | 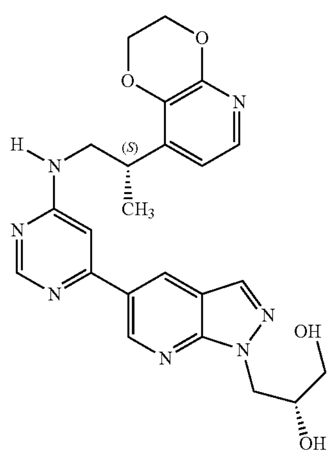 | 464.52 | (methanol-d₄) δ 8.93 (s, 1H), 8.67 (s, 2H), 8.28 (s, 1H), 7.67 (d, J = 5.2 Hz, 1H), 6.97 (m, 2H), 4.71-4.58 (m, 2H), 4.42 (m, 2H), 4.33-4.13 (m, 3H), 3.66 (m, 5H), 1.36 (d, J = 6.8 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 493 | 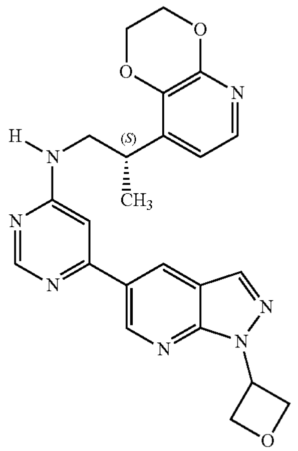 | 446.44 | (methanol-$d_4$) δ 8.90 (s, 1H), 8.69 (m, 2H), 8.40 (s, 1H), 7.67 (d, J = 5.3 Hz, 1H), 6.94 (m, 2H), 6.37-6.20 (m, 1H), 5.28 (t, J = 6.5 Hz, 2H), 5.15 (t, J = 7.3 Hz, 2H), 4.42 (m, 2H), 4.29 (m, 2H), 4.04-3.53 (m, 4H), 1.36 (d, J = 6.7 Hz, 3H) |
| 494 | 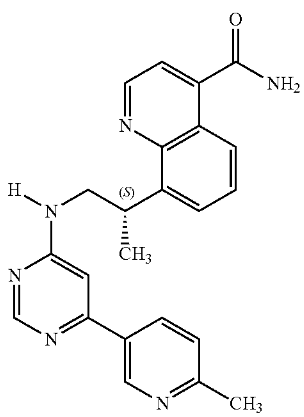 | 399.4 | (methanol-$d_4$) δ 9.29 (d, J = 5.2 Hz, 1H), 9.25 (s, 1H), 8.85 (dd, J = 8.6, 2.1 Hz, 1H), 8.79 (s, 1H), 8.32 (d, J = 8.5 Hz, 1H), 8.15 (d, J = 6.7 Hz, 1H), 8.10 (d, J = 8.4 Hz, 1H), 8.02 (d, J = 5.1 Hz, 1H), 7.93 (t, J = 8.0 Hz, 1H), 7.9 (m, 1H), 7.22 (s, 1H), 4.41 (q, J = 6.7 Hz, 1H), 4.08 (qd, J = 13.9, 6.6 Hz, 2H), 2.89 (s, 3H), 1.61 (d, J = 6.8 Hz, 3H) |
| 495 | 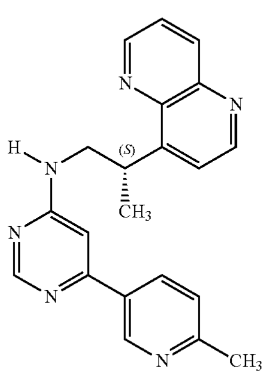 | 357 | (400 MHz, DMSO-$d_6$) δ 9.20-8.84 (m, 3H), 8.51-8.37 (m, 2H), 8.16 (s, 1H), 7.69 (t, J = 52.3 Hz, 3H), 7.38 (s, 1H), 6.87 (s, 1H), 4.48 (d, J = 6.4 Hz, 1H), 3.58 (d, J = 177.4 Hz, 2H), 2.52 (d, J = 4.2 Hz, 3H), 1.40 (d, J = 6.6 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 496 | 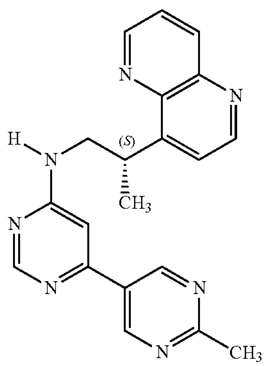 | 358 | (400 MHz, DMSO-d$_6$) δ 9.14 (s, 2H), 9.06-8.89 (m, 2H), 8.55-8.35 (m, 2H), 7.72 (t, J = 31.2 Hz, 3H), 7.11 (d, J = 159.7 Hz, 1H), 4.48 (d, J = 7.1 Hz, 1H), 3.64 (d, J = 154.6 Hz, 2H), 2.68 (s, 3H), 1.40 (d, J = 6.3 Hz, 3H) |
| 497 | 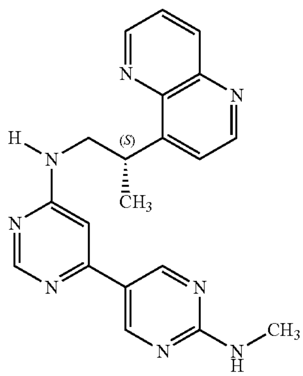 | 373 | (400 MHz, DMSO-d$_6$) δ 9.04-8.67 (m, 4H), 8.45-8.34 (m, 2H), 7.87-7.65 (m, 2H), 7.49 (d, J = 33.7 Hz, 2H), 6.73 (s, 1H), 4.46 (d, J = 6.7 Hz, 1H), 3.77 (s, 2H), 2.86 (d, J = 4.4 Hz, 3H), 1.39 (d, J = 6.7 Hz, 3H) |
| 498 | 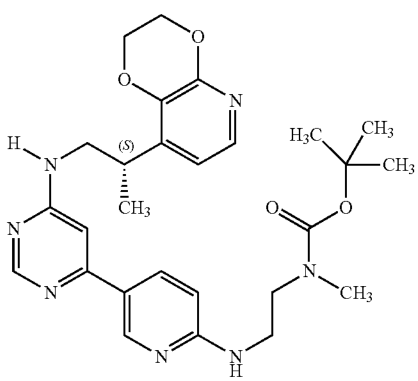 | 522.55 | |
| 499 | 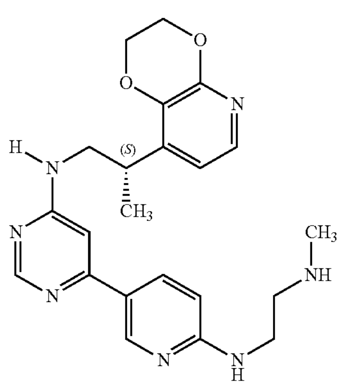 | 422.47 | |

TABLE 1-continued

| Cmpnd No. | Structure | ESMS (M + H) | ¹H NMR (300 MHz, unless indicated otherwise) NMR peaks given as δ values |
|---|---|---|---|
| 500 | 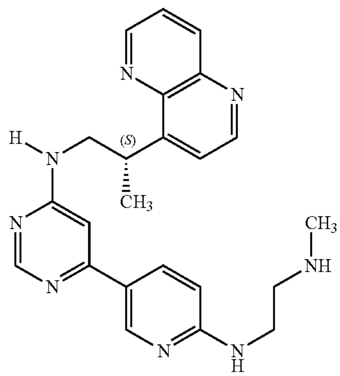 | 416 | (400 MHz, DMSO-d₆) δ 9.46 (d, J = 57.9 Hz, 1H), 9.23 (d, J = 32.8 Hz, 2H), 9.07 (d, J = 4.2 Hz, 2H), 8.65 (s, 1H), 8.57 (dd, J = 18.4, 8.7 Hz, 2H), 7.94 (dd, J = 23.9, 10.8 Hz, 3H), 7.14 (d, J = 143.7 Hz, 1H), 6.86 (d, J = 9.2 Hz, 1H), 4.54 (d, J = 7.2 Hz, 1H), 3.98 (dd, J = 25.5, 6.9 Hz, 2H), 3.69 (dd, J = 13.2, 5.1 Hz, 3H), 3.48 (dd, J = 10.9, 4.2 Hz, 1H), 3.13 (s, 2H), 2.57 (s, 3H), 1.45 (d, J = 6.7 Hz, 3H) |
| 501 | 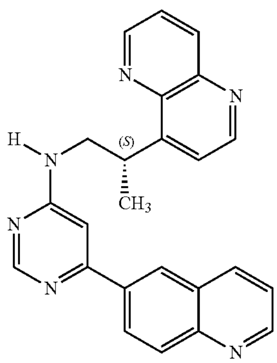 | 393 | (400 MHz, DMSO-d₆) δ 9.03 (s, 1H), 8.96 (d, J = 4.2 Hz, 2H), 8.62 (s, 1H), 8.55-8.46 (m, 2H), 8.43 (d, J = 8.5 Hz, 1H), 8.28 (s, 1H), 8.13 (s, 1H), 7.84-7.56 (m, 4H), 7.34-6.98 (m, 1H), 4.51 (d, J = 6.3 Hz, 1H), 3.75 (d, J = 76.6 Hz, 2H), 1.42 (d, J = 6.1 Hz, 3H) |
| 502 | 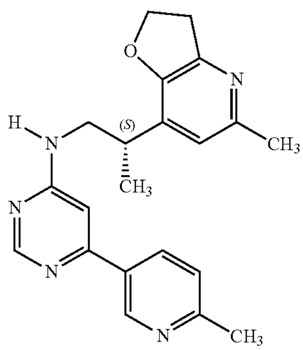 | 362.12 | (400 MHz, CDCl₃) δ 9.02 (s, 1H), 8.62 (s, 1H), 8.20 (d, J = 8.1 Hz, 1H), 7.24 (d, 1H), 6.74 (s, 2H), 5.25 (s, 1H), 4.66 (t, J = 9.2 Hz, 2H), 3.84-3.51 (m, 2H), 3.29 (t, J = 8.8 Hz, 2H), 3.26-3.13 (m, 1H), 2.61 (s, 3H), 2.45 (s, 3H), 1.34 (d, J = 6.9 Hz, 3H) |
| 503 | 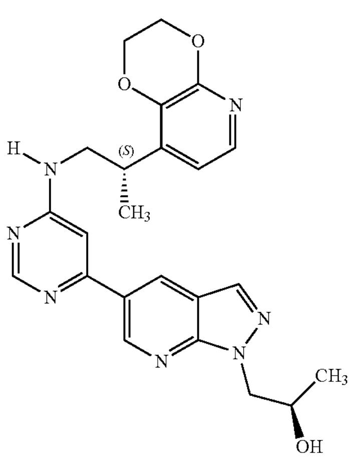 | 448.17 | (400 MHz, CDCl₃) δ 9.08 (s, 1H), 8.74 (s, 1H), 8.65 (s, 1H), 8.12 (d, J = 5.4 Hz, 1H), 7.80 (d, J = 5.0 Hz, 1H), 6.83 (d, J = 5.0 Hz, 1H), 6.77 (s, 1H), 5.34 (s, 1H), 4.69 (dd, J = 14.2, 2.3 Hz, 1H), 4.54-4.46 (m, 1H), 4.43 (d, J = 4.0 Hz, 2H), 4.38 (dd, J = 9.5, 4.1 Hz, 1H), 4.27 (s, 2H), 3.60 (t, J = 15.9 Hz, 3H), 1.36 (d, J = 5.8 Hz, 3H), 1.30 (d, J = 6.3 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 504 | 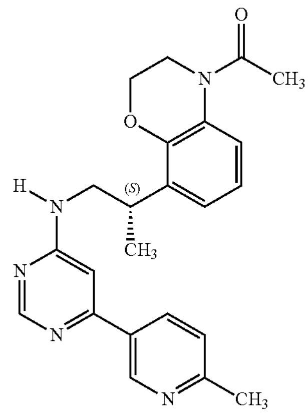 | 404.49 | (methanol-d₄) δ 9.44 (d, J = 2.1 Hz, 1H), 9.04 (dd, J = 8.5, 2.2 Hz, 1H), 8.92, 8.80 (2s, 1H), 8.32 (d, J = 8.4 Hz, 1H), 7.57-7.18 (m, 2H), 7.04 (t, J = 7.8 Hz, 1H), 4.66-4.33 (m, 2H), 4.28-3.62 (m, 5H), 3.08 (s, 3H), 2.45 (s, 2H), 1.52 (d, J = 7.1 Hz, 3H) |
| 505 | 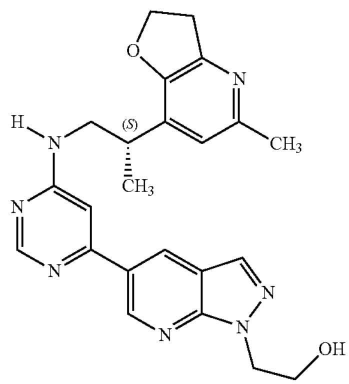 | 432.11 | (CDCl₃) δ 9.10 (s, 1H), 8.74 (s, 1H), 8.62 (s, 1H), 8.09 (s, 1H), 6.79 (s, 1H), 6.75 (s, 1H), 5.29 (s, 1H), 4.85-4.54 (m, 4H), 4.14 (s, 3H), 3.72-3.40 (m, 2H), 3.41-3.10 (m, 3H), 2.45 (s, 3H), 1.36 (d, J = 6.9 Hz, 3H) |
| 506 | 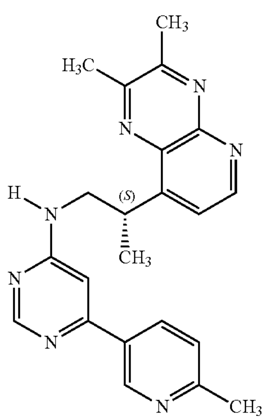 | 386 | (400 MHz, DMSO-d₆) δ 8.95 (d, J = 4.5 Hz, 2H), 8.48 (s, 1H), 8.15 (s, 1H), 7.70 (d, J = 4.2 Hz, 1H), 7.39 (t, J = 19.4 Hz, 2H), 6.81 (s, 1H), 4.43 (dd, J = 14.2, 7.1 Hz, 1H), 3.94-3.56 (m, 2H), 2.69 (s, 3H), 2.61 (s, 3H), 2.52 (d, J = 3.4 Hz, 3H), 1.38 (d, J = 6.8 Hz, 3H) |
| 507 | 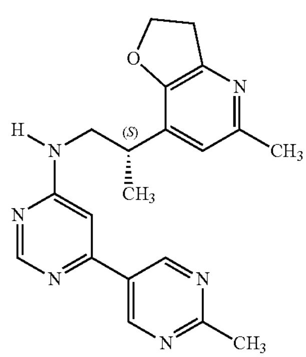 | 363.12 | (CDCl₃) δ 9.18 (s, 2H), 8.63 (s, 1H), 6.74 (s, 2H), 5.32 (s, 1H), 4.67 (t, J = 8.5 Hz, 2H), 3.55 (d, J = 36.2 Hz, 2H), 3.40-3.10 (m, 3H), 2.81 (s, 3H), 2.45 (s, 3H), 1.51-1.28 (m, 3H) |

| Cmpnd No. | Structure | ESMS (M + H) | ¹H NMR (300 MHz, unless indicated otherwise) NMR peaks given as δ values |
|---|---|---|---|
| 508 | 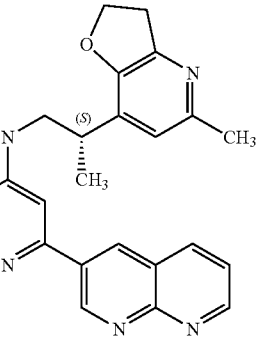 | 398.22 | |
| 509 | 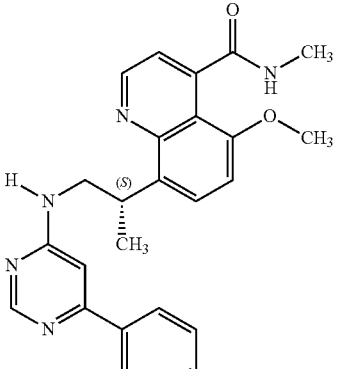 | 443.15 | (400.0 MHz, CDCl₃) δ 8.90 (s, 1H), 8.36 (s, 1H), 8.04 (d, J = 7.9 Hz, 1H), 7.45 (d, J = 6.4 Hz, 1H), 7.32 (s, 1H), 7.13 (d, J = 7.8 Hz, 1H), 6.73 (s, 1H), 5.81 (s, 1H), 5.55 (s, 1H), 4.33 (s, 1H), 3.76 (s, 3H), 3.65-3.62 (m, 1H), 3.43-3.40 (m, 1H), 3.02 (d, J = 3.0 Hz, 3H), 2.53 (s, 3H), 1.56 (s, 1H), 1.46 (d, J = 6.6 Hz, 3H) and 1.14 (t, J = 6.7 Hz, 1H) |
| 510 | 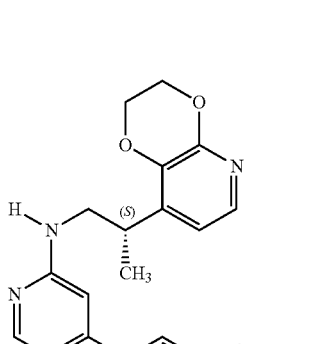 | 448.17 | (400 MHz, CDCl₃) δ 9.00 (d, J = 1.9 Hz, 1H), 8.65 (d, J = 2.0 Hz, 1H), 8.56 (s, 1H), 8.03 (s, 1H), 7.71 (t, J = 6.6 Hz, 1H), 6.73 (t, J = 6.1 Hz, 1H), 6.69-6.62 (m, 1H), 5.11 (s, 1H), 4.61 (dd, J = 14.1, 2.4 Hz, 1H), 4.38-4.32 (m, 3H), 4.32-4.24 (m, 1H), 4.23-4.15 (m, 2H), 3.48 (d, J = 14.8 Hz, 3H), 1.27 (d, J = 6.1 Hz, 3H), 1.22 (d, J = 6.3 Hz, 3H) |

TABLE 1-continued

| Cmpnd No. | Structure | ESMS (M + H) | $^1$H NMR (300 MHz, unless indicated otherwise) NMR peaks given as δ values |
|---|---|---|---|
| 511 | 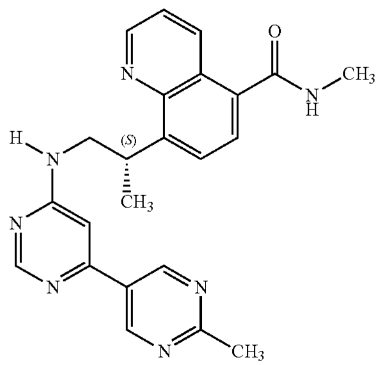 | 414 | (400 MHz, DMSO-d$_6$) δ 9.22 (d, J = 58.5 Hz, 2H), 9.01-8.91 (m, 1H), 8.70 (d, J = 8.6 Hz, 1H), 8.50 (d, J = 4.4 Hz, 2H), 7.68 (dd, J = 29.4, 22.2 Hz, 4H), 7.15 (d, J = 165.0 Hz, 1H), 4.53 (s, 1H), 3.59 (d, J = 175.3 Hz, 2H), 2.85 (d, J = 4.3 Hz, 3H), 2.69 (s, 3H), 1.39 (s, 3H) |
| 512 | 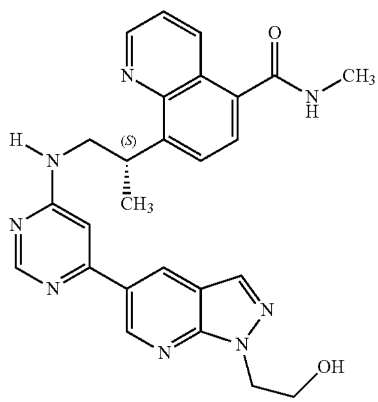 | 483 | (400 MHz, DMSO-d$_6$) δ 9.04 (d, J = 44.3 Hz, 2H), 8.86-8.66 (m, 2H), 8.50 (d, J = 4.3 Hz, 2H), 8.27 (s, 1H), 7.72 (t, J = 11.5 Hz, 2H), 7.61 (s, 2H), 7.16 (d, J = 143.2 Hz, 1H), 4.87 (t, J = 5.3 Hz, 1H), 4.54 (s, 3H), 3.86 (t, J = 15.9 Hz, 4H), 2.85 (d, J = 4.5 Hz, 3H), 1.40 (s, 3H) |
| 513 | 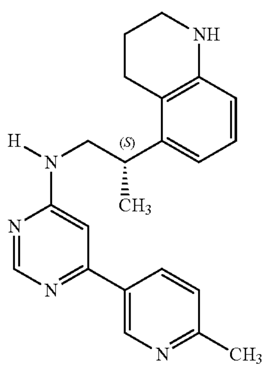 | 362.24 | (methanol-d$_4$) δ 9.11 (d, J = 2.4 Hz, 1H), 8.84 (s, 1H), 8.52 (dd, J = 8.3, 2.5 Hz, 1H), 7.88 (d, J = 8.3 Hz, 1H), 7.42-6.71 (m, 4H), 4.70-4.33 (m, 2H), 4.02 (qd, J = 13.3, 7.2 Hz, 2H), 3.90-3.55 (m, 3H), 2.89 (s, 3H), 1.49 (d, J = 7.1 Hz, 3H) |
| 514 | 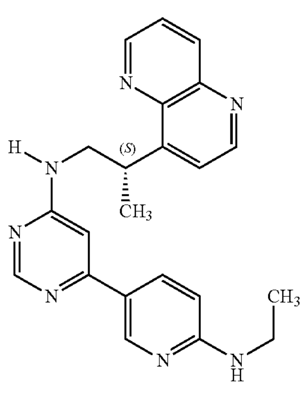 | 386 | (400 MHz, DMSO-d$_6$) δ 9.03 (s, 1H), 8.94 (d, J = 4.4 Hz, 1H), 8.63 (s, 1H), 8.43 (d, J = 8.3 Hz, 1H), 8.36 (s, 1H), 7.91 (s, 1H), 7.80 (dd, J = 8.4, 3.8 Hz, 1H), 7.73 (s, 1H), 7.35 (s, 1H), 6.83 (d, J = 74.6 Hz, 2H), 6.50 (d, J = 8.9 Hz, 1H), 4.46 (d, J = 6.8 Hz, 1H), 3.59 (d, J = 138.5 Hz, 2H), 3.32 (s, 2H), 1.39 (d, J = 6.8 Hz, 3H), 1.15 (t, J = 7.1 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 515 | 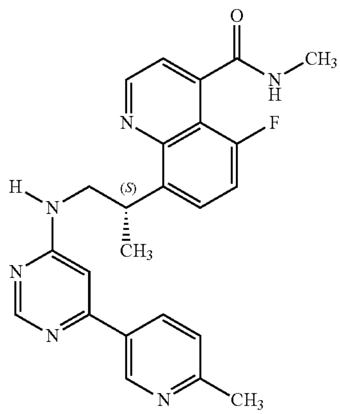 | 431.53 | (400.0 MHz, CDCl₃) δ 8.94 (s, 1H), 8.35 (s, 1H), 8.05 (d, J = 7.4 Hz, 1H), 7.48 (s, 1H), 7.40 (s, 1H), 7.13 (d, J = 8.0 Hz, 1H), 7.07 (t, J = 9.2 Hz, 1H), 5.83 (s, 1H), 5.65 (s, 1H), 4.36 (d, J = 5.0 Hz, 1H), 3.78-3.75 (m, 1H), 3.69-3.65 (m, 1H), 3.02 (d, J = 4.3 Hz, 3H), 2.53 (d, J = 9.3 Hz, 3H), 1.70 (s, 1H) and 1.47 (d, J = 6.9 Hz, 3H) |
| 516 | 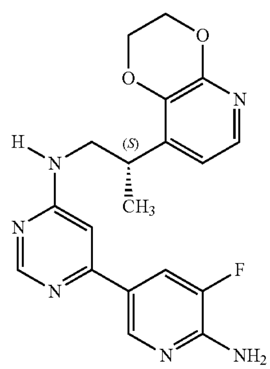 | 383.06 | (400 MHz, CDCl₃) δ 8.50 (s, 1H), 8.39 (s, 1H), 7.84 (d, J = 11.7 Hz, 1H), 7.73 (d, J = 4.9 Hz, 1H), 6.74 (d, J = 5.0 Hz, 1H), 6.52 (d, J = 18.1 Hz, 1H), 5.09 (s, 1H), 4.80 (s, 2H), 4.36 (d, J = 4.1 Hz, 2H), 3.48 (s, 2H), 1.68 (s, 2H), 1.27 (s, 3H) |
| 517 | 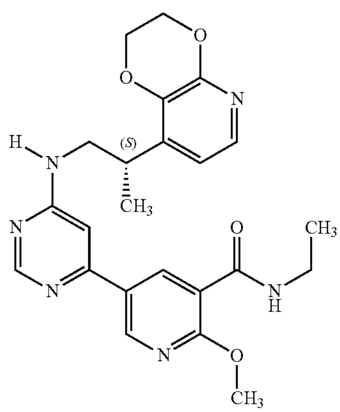 | 451.07 | (400 MHz, CDCl₃) δ 9.04 (s, 1H), 8.95 (s, 1H), 8.60 (s, 1H), 7.90 (s, 1H), 6.86-6.75 (m, 2H), 5.38 (s, 1H), 4.45 (s, 2H), 4.39-4.27 (m, 2H), 4.18 (s, 3H), 3.60-3.47 (m, 5H), 1.35 (d, J = 4.0 Hz, 3H), 1.29-1.24 (m, 3H) |
| 518 | 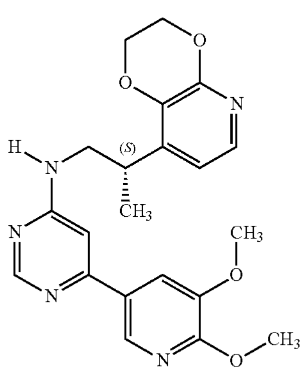 | 410.06 | (400 MHz, CDCl₃) δ 8.62 (s, 1H), 8.24 (s, 1H), 7.77 (d, J = 23.9 Hz, 2H), 6.82 (d, J = 4.9 Hz, 1H), 6.67 (d, J = 18.8 Hz, 1H), 5.23 (s, 1H), 4.43 (s, 2H), 4.27 (s, 2H), 4.08 (s, 3H), 3.98 (s, 3H), 3.64-3.50 (m, 3H), 1.33 (t, J = 12.6 Hz, 3H) |

TABLE 1-continued

| Cmpnd No. | Structure | ESMS (M + H) | $^1$H NMR (300 MHz, unless indicated otherwise) NMR peaks given as δ values |
|---|---|---|---|
| 519 | 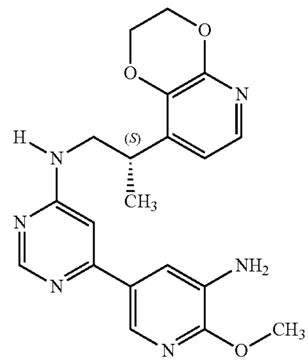 | 392.93 | (400 MHz, CDCl$_3$) δ 8.60 (s, 1H), 8.10 (s, 1H), 7.81 (s, 1H), 7.54 (s, 1H), 6.82 (d, J = 3.9 Hz, 1H), 6.65 (s, 1H), 5.17 (s, 1H), 4.43 (s, 2H), 4.27 (s, 2H), 4.05 (s, 3H), 3.91 (s, 2H), 3.50 (dd, J = 20.8, 13.9 Hz, 3H), 1.35 (s, 3H) |
| 520 | 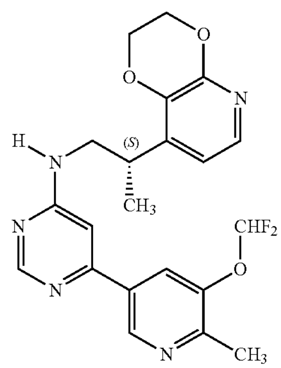 | 444.08 | (400 MHz, CDCl$_3$) δ 8.61 (d, J = 15.0 Hz, 2H), 7.84 (s, 1H), 7.75 (dd, J = 12.7, 5.0 Hz, 1H), 6.85-6.75 (m, 2H), 6.16 (tt, J = 54.9, 4.0 Hz, 1H), 5.43 (s, 1H), 4.47-4.39 (m, 2H), 4.31 (ddd, J = 12.3, 10.6, 3.0 Hz, 4H), 3.74-3.51 (m, 3H), 2.55 (s, 3H), 1.35 (d, J = 5.9 Hz, 3H) |
| 521 | 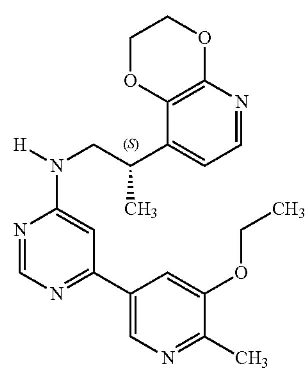 | 408.12 | (400 MHz, CDCl$_3$) δ 8.62 (s, 1H), 8.48 (s, 1H), 7.76 (d, J = 12.8 Hz, 2H), 6.78 (d, J = 7.8 Hz, 2H), 5.55 (s, 1H), 4.40 (s, 2H), 4.24 (s, 2H), 4.14 (s, 2H), 3.55 (s, 3H), 2.51 (s, 3H), 1.47 (s, 3H) |
| 522 | 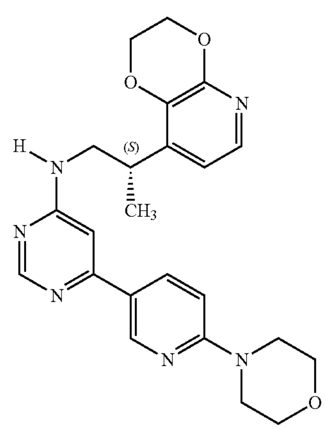 | 435.34 | (methanol-d$_4$) δ 8.61 (d, J = 5.7 Hz, 1H), 8.56 (d, J = 2.4 Hz, 1H), 7.92 (dd, J = 9.2, 2.7 Hz, 1H), 7.69 (d, J = 5.3 Hz, 1H), 6.99 (m, 2H), 6.80 (s, 1H), 4.46 (m, 2H), 4.34-4.27 (m, 2H), 3.97-3.59 (m, 11H), 1.34 (d, J = 7.0 Hz, 3H) |

TABLE 1-continued
| Cmpnd No. | Structure | ESMS (M + H) | $^1$H NMR (300 MHz, unless indicated otherwise) NMR peaks given as δ values |
|---|---|---|---|
| 523 | 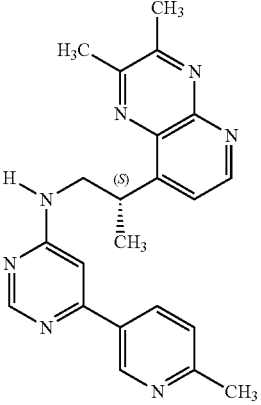 | 406.31 | (methanol-$d_4$) δ 8.67 (s, 1H), 8.40 (d, J = 2.2 Hz, 1H), 7.95 (s, 1H), 7.68 (d, J = 5.3 Hz, 1H), 6.99 (d, J = 5.3 Hz, 1H), 6.84 (s, 1H), 4.46 (m, 4H), 4.30 (m, 2H), 3.98-3.78 (m, 2H), 3.62 (m, 1H), 2.94 (m, 2H), 2.17-2.01 (m, 2H), 1.34 (d, J = 7.0 Hz, 3H) |
| 524 | 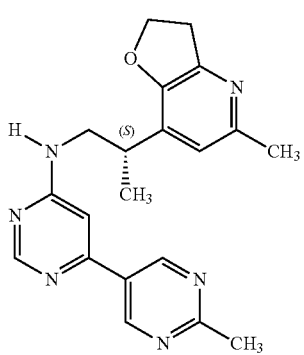 | 421.3 | (methanol-$d_4$) δ 8.55 (s, 1H), 8.15 (d, J = 2.1 Hz, 1H), 7.67 (d, J = 5.2 Hz, 1H), 7.30 (d, J = 2.1 Hz, 1H), 6.97 (d, J = 5.4 Hz, 1H), 6.74 (s, 1H), 4.43 (m, 2H), 4.33-4.21 (m, 4H), 3.98-3.72 (m, 2H), 3.62 (d, J = 4.6 Hz, 3H), 3.34 (s, 3H), 1.33 (d, J = 7.0 Hz, 3H) |
| 525 | 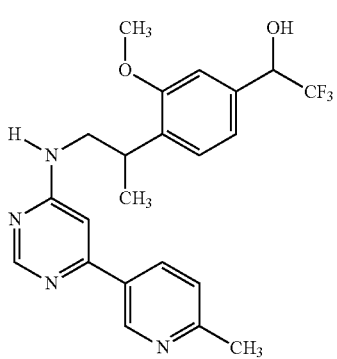 [SMILES: COc1cc(C(O)C(F)(F)F)ccc1C(C)CNc1cc(-c2ccc(C)nc2)ncn1] | 433.63 | (methanol-$d_4$) δ 9.20-8.92 (m, 1H), 8.76 (d, J = 3.9 Hz, 1H), 8.40 (d, J = 8.2 Hz, 1H), 7.77 (d, J = 8.0 Hz, 1H), 7.42 (d, J = 7.7 Hz, 1H), 7.34-7.12 (m, 2H), 7.09 (d, J = 1.0 Hz, 1H), 5.16 (q, J = 7.0 Hz, 1H), 4.00 (s, 3H), 4.04-3.76 (m, 3H), 2.84 (d, J = 2.9 Hz, 3H), 2.20 (s, 1H), 1.50 (d, J = 7.0 Hz, 3H) |

| Cmpnd No. | Structure | ESMS (M + H) | ¹H NMR (300 MHz, unless indicated otherwise) NMR peaks given as δ values |
|---|---|---|---|
| 526 | 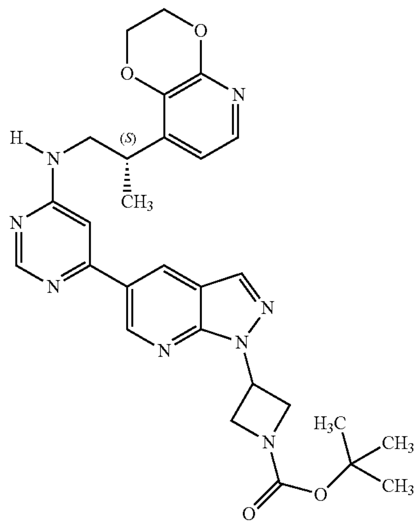 | | (400.0 MHz, CDCl₃) δ 9.08 (s, 1H), 8.71 (d, J = 1.4 Hz, 1H), 8.65 (s, 1H), 8.17 (s, 1H), 7.79 (d, J = 4.9 Hz, 1H), 6.82 (d, J = 5.0 Hz, 1H), 6.77 (s, 1H), 5.84 (dd, J = 7.7, 19.3 Hz, 1H), 5.35 (s, 1H), 4.59-4.55 (m, 2H), 4.49-4.43 (m, 4H), 4.27 (s, 2H), 3.58 (s, 2H), 1.86 (s, 1H), 1.50 (s, 9H) and 1.36 (d, J = 5.3 Hz, 3H) |
| 527 | 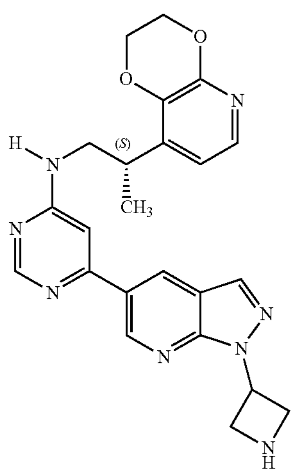 | 445.45 | |
| 528 | 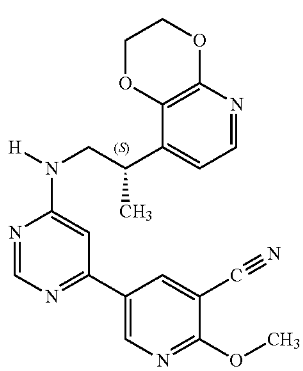 | 404.99 | (400 MHz, CDCl₃) δ 8.93 (d, J = 1.3 Hz, 1H), 8.60 (s, 1H), 8.50 (d, J = 1.8 Hz, 1H), 7.72 (d, J = 4.5 Hz, 1H), 6.79 (t, J = 6.9 Hz, 1H), 6.73 (d, J = 7.2 Hz, 1H), 5.64 (s, 1H), 4.42 (s, 2H), 4.25 (d, J = 3.2 Hz, 2H), 4.10 (d, J = 7.6 Hz, 3H), 3.63-3.39 (m, 3H), 1.32 (t, J = 8.5 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 529 | 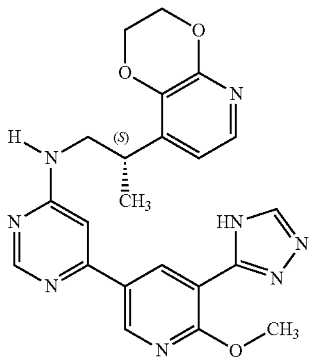 | 447.03 | (400 MHz, CDCl$_3$) δ 11.79 (s, 1H), 8.96 (d, J = 10.2 Hz, 2H), 8.55 (s, 1H), 7.99 (s, 1H), 7.74 (d, J = 5.1 Hz, 1H), 6.71 (dd, J = 31.5, 12.7 Hz, 2H), 5.12 (s, 1H), 4.43-4.30 (m, 2H), 4.29-4.21 (m, 2H), 4.19 (s, 3H), 3.64-3.33 (m, 3H), 1.28 (d, J = 6.2 Hz, 3H) |
| 530 | 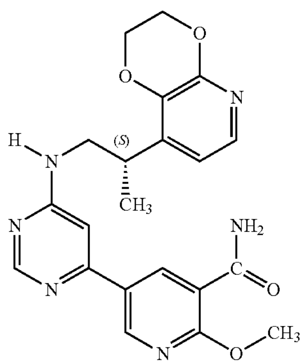 | 423.13 | (400 MHz, CDCl$_3$) δ 9.06 (s, 1H), 8.93 (d, J = 1.7 Hz, 1H), 8.60 (s, 1H), 6.86-6.77 (m, 2H), 6.25 (s, 1H), 5.69 (s, 1H), 4.42 (d, J = 3.7 Hz, 2H), 4.27 (dd, J = 8.4, 2.8 Hz, 2H), 4.17 (s, 3H), 3.63-3.44 (m, 3H), 1.32 (t, J = 9.4 Hz, 3H) |
| 531 | 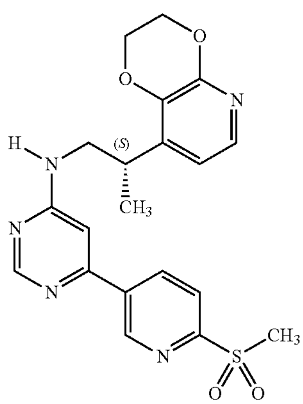 | 427.92 | (400 MHz, CDCl$_3$) δ 9.23 (d, J = 1.3 Hz, 1H), 8.67 (s, 1H), 8.55 (dd, J = 8.2, 2.1 Hz, 1H), 8.16 (d, J = 8.2 Hz, 1H), 7.73 (t, J = 4.9 Hz, 1H), 6.88-6.79 (m, 2H), 5.67 (s, 1H), 4.47-4.37 (m, 2H), 4.25 (d, J = 3.7 Hz, 2H), 3.87-3.51 (m, 3H), 3.25 (s, 3H), 1.34 (d, J = 6.1 Hz, 3H) |
| 532 | 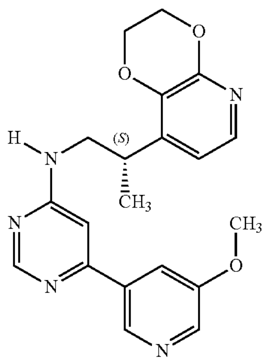 | 380 | (400 MHz, CDCl$_3$) δ 8.58 (d, J = 12.3 Hz, 2H), 8.29 (d, J = 2.1 Hz, 1H), 7.80 (s, 1H), 7.66 (t, J = 6.8 Hz, 1H), 6.80-6.69 (m, 2H), 5.57 (s, 1H), 4.33 (d, J = 3.9 Hz, 2H), 4.18 (s, 2H), 3.86 (s, 3H), 3.65-3.42 (m, 3H), 1.26 (d, J = 5.8 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 533 | 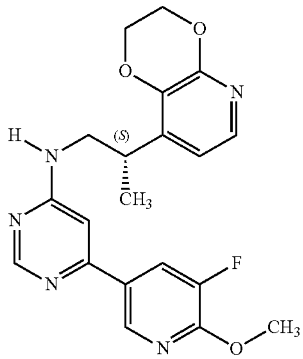 | 398 | (400 MHz, CDCl₃) δ 8.62 (d, J = 16.0 Hz, 1H), 8.50 (d, J = 1.5 Hz, 1H), 7.98 (dt, J = 11.6, 5.8 Hz, 1H), 7.75 (dd, J = 11.2, 5.0 Hz, 1H), 6.81 (d, J = 5.1 Hz, 1H), 6.68 (s, 1H), 5.42 (s, 1H), 4.42 (dd, J = 5.0, 3.0 Hz, 2H), 4.30-4.23 (m, 2H), 4.08 (s, 3H), 3.54 (ddd, J = 15.8, 14.0, 6.9 Hz, 3H), 1.34 (d, J = 6.3 Hz, 3H) |
| 534 | 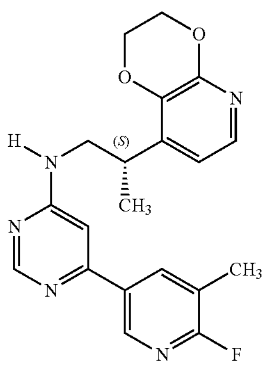 | 382.05 | (400 MHz, CDCl₃) δ 8.62 (s, 1H), 8.51 (s, 1H), 8.26 (dd, J = 9.4, 1.3 Hz, 1H), 7.74 (t, J = 6.8 Hz, 1H), 6.81 (d, J = 5.1 Hz, 1H), 6.74 (s, 1H), 5.51 (s, 1H), 4.41 (dd, J = 4.9, 3.1 Hz, 2H), 4.25 (d, J = 3.8 Hz, 2H), 3.79-3.49 (m, 3H), 2.35 (s, 3H), 1.34 (d, J = 6.2 Hz, 3H) |
| 535 | 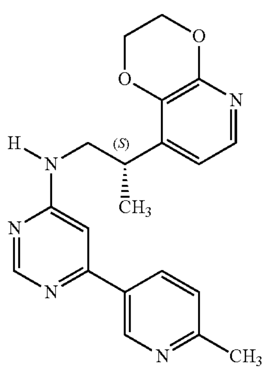 | 362 | (400 MHz, CDCl₃) δ 9.00 (s, 1H), 8.62 (s, 1H), 8.20 (dd, J = 8.1, 2.3 Hz, 1H), 8.09 (d, J = 5.0 Hz, 1H), 7.28-7.24 (d, 1H), 7.01 (d, J = 4.9 Hz, 1H), 6.70 (s, 1H), 5.27 (s, 1H), 4.29-4.16 (m, 2H), 3.75-3.51 (m, 3H), 3.00 (t, J = 6.5 Hz, 2H), 2.62 (s, 3H), 2.17-2.06 (m, 2H), 1.33 (d, J = 6.4 Hz, 3H) |
| 536 | 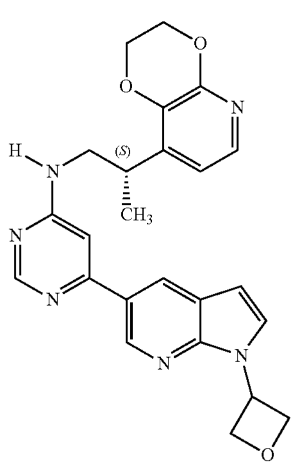 | 444.91 | (400 MHz, CDCl₃) δ 8.65 (s, 1H), 8.32 (dd, J = 8.8, 5.0 Hz, 1H), 7.75-7.69 (m, 2H), 7.42 (t, J = 4.8 Hz, 1H), 6.99 (t, J = 4.7 Hz, 1H), 6.79 (s, 1H), 6.74 (d, J = 5.0 Hz, 1H), 6.09 (p, J = 6.9 Hz, 1H), 5.34 (s, 1H), 5.13 (t, J = 7.3 Hz, 2H), 4.95 (t, J = 6.6 Hz, 2H), 4.36-4.27 (m, 2H), 4.20-4.11 (m, 2H), 3.52 (dd, J = 19.4, 12.2 Hz, 3H), 1.26 (t, J = 10.6 Hz, 3H) |

| Cmpnd No. | Structure | ESMS (M + H) | ¹H NMR (300 MHz, unless indicated otherwise) NMR peaks given as δ values |
|---|---|---|---|
| 537 | 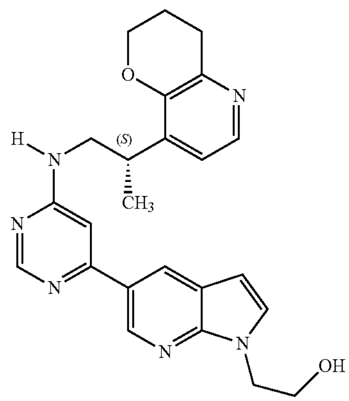 | 431.99 | (400 MHz, methanol-d₄) δ 9.06 (s, 1H), 8.71 (s, 1H), 8.47 (s, 1H), 8.20 (s, 1H), 7.95 (d, J = 4.9 Hz, 1H), 7.15 (d, J = 5.1 1H), 6.90 (s, 1H), 4.65 (t, J = 5.6 Hz, 2H), 4.24-4.13 (m, 2H), 4.05 (t, J = 5.6 Hz, 2H), 3.84-3.51 (m, 3H), 3.35 (s, 2H), 2.88 (t, J = 6.2 Hz, 2H), 2.13-2.01 (m, 2H), 1.31 (d, J = 5.9 Hz, 3H) |
| 538 | 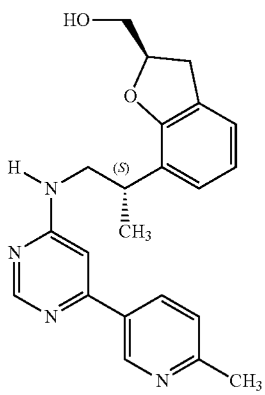 | 377.61 | (CDCl₃) δ 9.01 (d, J = 2.0 Hz, 1H), 8.48 (s, 1H), 8.18 (dd, J = 8.1, 2.3 Hz, 1H), 7.25 (d, J = 7.2 Hz, 1H), 7.09 (d, J = 7.0 Hz, 2H), 7.04-6.81 (m, 2H), 6.57 (s, 2H), 5.10-4.93 (m, 1H), 3.80 (ddd, J = 19.7, 12.8, 4.7 Hz, 2H), 3.63-3.46 (m, 2H), 3.32 (dt, J = 36.8, 18.4 Hz, 1H), 3.05 (dd, J = 15.8, 5.4 Hz, 2H), 2.62 (s, 3H), 1.61 (s, 1H), 1.46 (d, J = 7.0 Hz, 3H) |
| 539 | 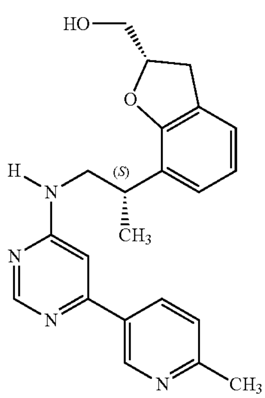 | 377.61 | (CDCl₃) δ 9.04 (d, J = 2.1 Hz, 1H), 8.54 (s, 1H), 8.24 (dd, J = 8.3, 2.2 Hz, 1H), 7.29 (s, 1H), 7.09 (d, J = 7.3 Hz, 1H), 6.96 (t, J = 13.4 Hz, 1H), 6.83 (t, J = 7.5 Hz, 1H), 6.68 (d, J = 0.9 Hz, 1H), 5.05 (dd, J = 6.5, 3.0 Hz, 1H), 3.93-3.67 (m, 3H), 3.60 (s, 1H), 3.51-3.16 (m, 4H), 2.97 (dd, J = 15.7, 6.3 Hz, 2H), 2.64 (s, 3H), 1.55 (d, J = 7.2 Hz, 3H) |
| 540 | 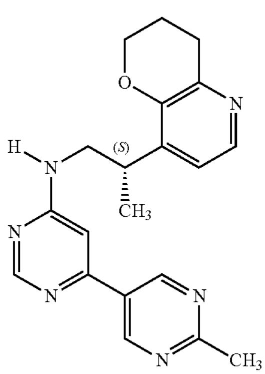 | 363.15 | (400 MHz, CDCl₃) δ 9.16 (s, 2H), 8.63 (s, 1H), 8.07 (d, J = 4.4 Hz, 1H), 7.00 (d, J = 4.4 Hz, 1H), 6.70 (s, 1H), 5.35 (s, 1H), 4.31-4.16 (m, 2H), 3.72-3.48 (m, 3H), 2.98 (t, J = 6.3 Hz, 2H), 2.80 (s, 3H), 2.20-2.07 (m, 2H), 1.33 (d, J = 4.8 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 541 | 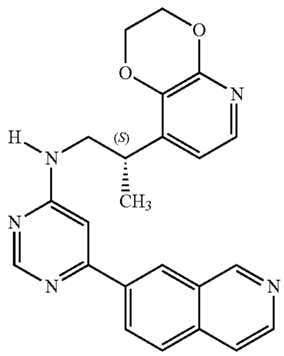 | 400.14 | (methanol-d₄) δ 9.62 (s, 1H), 8.76 (s, 2H), 8.65 (d, J = 6.1 Hz, 1H), 8.31 (s, 2H), 8.21 (d, J = 6.2 Hz, 1H), 7.69 (d, J = 5.3 Hz, 1H), 7.12-6.96 (m, 2H), 4.44 (m, 2H), 4.31 (m, 2H), 4.03-3.78 (m, 2H), 3.75-3.58 (m, 1H), 1.37 (d, J = 6.9 Hz, 3H) |
| 542 | 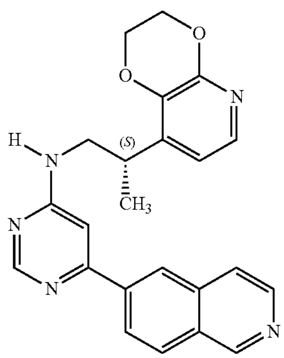 | 400.14 | (methanol-d₄) δ 9.59 (s, 1H), 8.73 (s, 1H), 8.64 (d, J = 6.1 Hz, 1H), 8.57 (s, 1H), 8.49 (d, J = 9.2 Hz, 1H), 8.21 (m, 2H), 7.68 (d, J = 5.3 Hz, 1H), 7.11-6.95 (m, 2H), 4.43 (m, 2H), 4.30 (m, 2H), 3.89 (m, 2H), 3.64 (m, 1H), 1.36 (d, J = 6.9 Hz, 3H) |
| 543 | 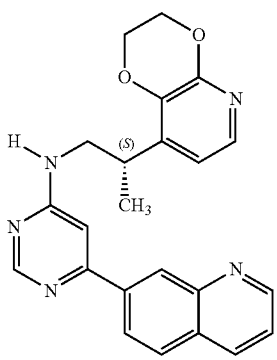 | 400.19 | (methanol-d₄) δ 9.04 (d, J = 3.1 Hz, 1H), 8.75 (s, 1H), 8.54 (d, J = 8.3 Hz, 1H), 8.49 (s, 1H), 8.23 (d, J = 8.5 Hz, 1H), 7.97 (d, J = 7.2 Hz, 1H), 7.78-7.65 (m, 2H), 7.06 (s, 1H), 7.00 (d, J = 5.4 Hz, 1H), 4.44 (m, 2H), 4.31 (m, 2H), 4.02-3.77 (m, 2H), 3.67 (m, 1H), 1.37 (d, J = 7.0 Hz, 3H) |
| 544 | 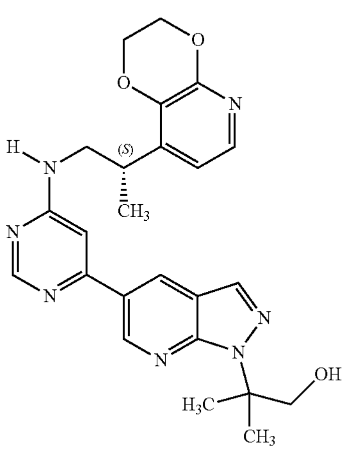 | 462.12 | |

TABLE 1-continued

| Cmpnd No. | Structure | ESMS (M + H) | ¹H NMR (300 MHz, unless indicated otherwise) NMR peaks given as δ values |
|---|---|---|---|
| 545 | 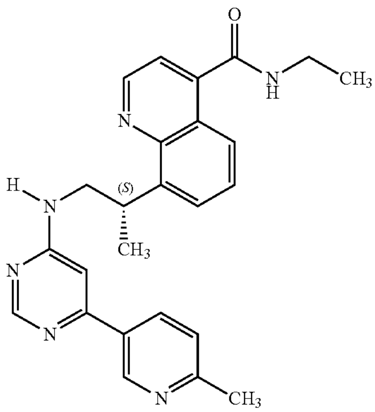 | 427.29 | (methanol-d₄) δ 9.30 (d, J = 5.2 Hz, 1H), 9.27 (d, J = 2.1 Hz, 1H), 8.86 (dd, J = 8.5, 2.3 Hz, 1H), 8.80 (s, 1H), 8.25 (dd, J = 8.5, 1.3 Hz, 1H), 8.17 (d, J = 6.5 Hz, 1H), 8.12 (d, J = 8.6 Hz, 1H), 8.01 (d, J = 5.2 Hz, 1H), 7.99-7.76 (m, 1H), 7.32-7.08 (m, 1H), 4.40 (q, J = 6.7 Hz, 1H), 4.09 (t, J = 6.2 Hz, 2H), 3.56 (q, J = 7.3 Hz, 2H), 2.89 (s, 3H), 1.61 (d, J = 6.9 Hz, 3H), 1.32 (t, J = 7.3 Hz, 3H) |
| 546 | 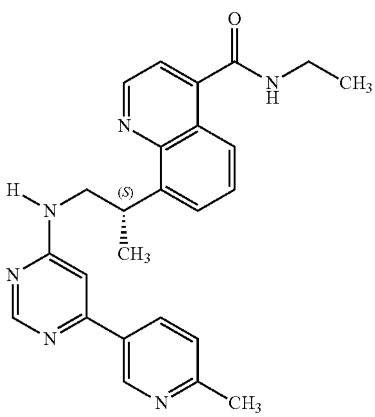 | 481.21 | (methanol-d₄) δ 9.64-9.02 (m, 2H), 8.86 (dd, J = 8.5, 2.2 Hz, 1H), 8.33-8.00 (m, 3H), 7.98-7.68 (m, 2H), 7.20 (s, 1H), 4.47 (q, J = 6.8 Hz, 1H), 4.09 (t, J = 7.3 Hz, 2H), 2.89 (s, 3H), 1.60 (d, J = 6.9 Hz, 3H) |
| 547 | 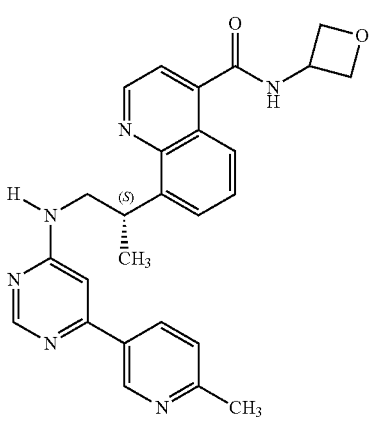 | 455.28 | (methanol-d₄) δ 9.32 (d, J = 5.3 Hz, 1H), 9.27 (d, J = 2.1 Hz, 1H), 8.86 (dd, J = 8.5, 2.1 Hz, 1H), 8.80 (d, J = 4.7 Hz, 1H), 8.33 (d, J = 8.5 z, 1H), 8.18 (d, J = 7.0 Hz, 1H), 8.11 (s, 1H), 8.06 (dd, J = 5.3, 1.3 Hz, 1H), 7.94 (t, J = 7.9 Hz, 1H), 7.22 (s, 1H), 4.59-4.46 (m, 1H), 4.41 (q, J = 6.7 Hz, 1H), 4.28-3.89 (m, 3H), 3.89-3.71 (m, 3H), 2.90 (s, 3H), 1.62 (d, J = 6.7 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 548 | 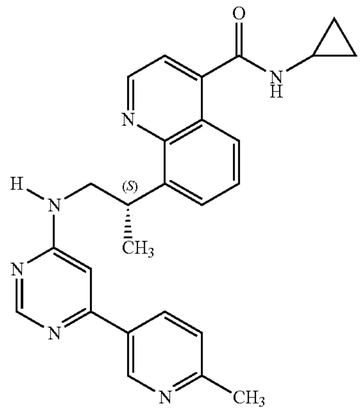 | 439.26 | (methanol-d₄) δ 9.75-9.24 (m, 2H), 9.03 (dd, J = 8.4, 2.2 Hz, 1H), 8.99, 8.80 (2s, 1H), 8.42 (d, J = 1.2 Hz, 1H), 8.31 (td, J = 8.2, 2.6 Hz, 2H), 8.22-7.96 (m, 2H), 7.7.57, 7.39 (2s, 1H), 4.80-4.37 (m, 1H), 4.46-3.96 (m, 2H), 3.23 (tt, J = 7.4, 3.9 Hz, 1H), 3.06 (s, 3H), 1.77 (d, J = 6.8 Hz, 3H), 1.06 (m, 2H), 0.91 (dt, J = 4.2, 1.7 Hz, 2H) |
| 549 | 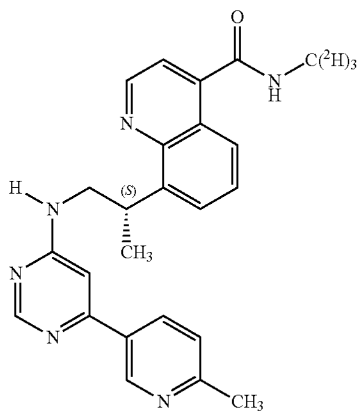 | 416.26 | (methanol-d₄) δ 9.34-9.26 (m, 2H), 8.86 (dd, J = 8.4, 1.9 Hz, 1H), 8.80 (s, 1H), 8.25 (d, J = 8.4 Hz, 1H), 8.13 (t, J = 8.7 Hz, 2H), 7.99 (d, J = 5.1 Hz, 1H), 7.96-7.67 (m, 1H), 7.39, 7.21 (2s, 1H), 4.65-4.29 (m, 1H), 4.09 (m, 2H), 2.89 (s, 3H), 1.61 (d, J = 6.6 Hz, 3H) |
| 550 | 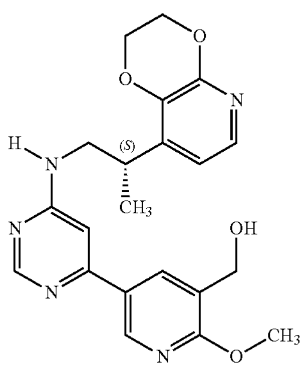 | 410.31 | (400 MHz, CDCl₃) δ 8.60 (d, J = 2.0 Hz, 1H), 8.53 (s, 1H), 8.12 (d, J = 2.1 Hz, 1H), 7.73 (d, J = 5.1 Hz, 1H), 6.74 (d, J = 5.1 Hz, 1H), 6.56 (s, 1H), 5.04 (s, 1H), 4.65 (d, J = 6.2 Hz, 2H), 4.35 (dd, J = 4.9, 3.1 Hz, 2H), 4.18 (dd, J = 9.5, 6.5 Hz, 2H), 3.98 (s, 3H), 3.46 (d, J = 18.5 Hz, 3H), 1.27 (d, J = 5.9 Hz, 3H) |
| 551 | 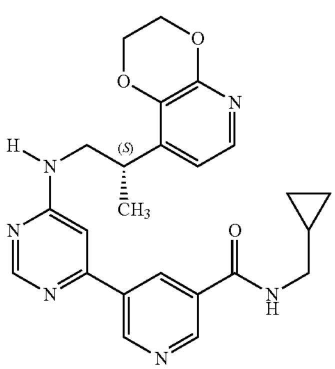 | 447 | (400 MHz, CDCl₃) δ 9.16 (s, 1H), 8.97 (d, J = 2.0 Hz, 1H), 8.57-8.47 (m, 2H), 7.69 (d, J = 5.1 Hz, 1H), 6.75-6.64 (m, 2H), 6.31 (s, 1H), 5.16 (s, 1H), 4.35-4.27 (m, 2H), 4.17 (t, J = 8.2 Hz, 2H), 3.42 (d, J = 25.9 Hz, 3H), 3.25 (dd, J = 7.0, 5.5 Hz, 2H), 1.23 (t, J = 8.4 Hz, 3H), 0.98 (ddd, J = 12.5, 7.6, 4.8 Hz, 1H), 0.54-0.44 (m, 2H), 0.20 (q, J = 5.1 Hz, 2H) |

TABLE 1-continued

| Cmpnd No. | Structure | ESMS (M + H) | ¹H NMR (300 MHz, unless indicated otherwise) NMR peaks given as δ values |
|---|---|---|---|
| 552 | 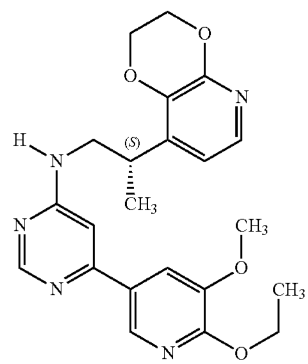 | 424.14 | (400 MHz, CDCl₃) δ 8.62 (s, 1H), 8.24 (s, 1H), 7.86-7.75 (m, 2H), 6.83 (d, J = 5.1 Hz, 1H), 6.67 (d, J = 15.2 Hz, 1H), 5.07 (s, 1H), 4.54 (q, J = 7.0 Hz, 2H), 4.44 (d, J = 4.0 Hz, 2H), 4.28 (s, 2H), 3.99 (s, 3H), 3.55 (d, J = 18.6 Hz, 3H), 1.49 (t, J = 7.1 Hz, 3H), 1.35 (d, J = 5.4 Hz, 3H) |
| 553 | 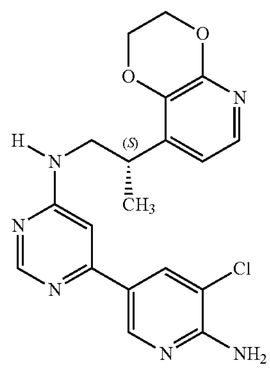 | 399.01 | (400 MHz, CDCl₃) δ 8.59 (s, 2H), 8.21 (d, J = 1.8 Hz, 1H), 7.83 (d, J = 5.1 Hz, 1H), 6.81 (t, J = 12.7 Hz, 1H), 6.62 (s, 1H), 5.13 (s, 3H), 4.45 (d, J = 4.0 Hz, 2H), 4.30 (d, J = 2.9 Hz, 2H), 3.66-3.49 (m, 3H), 1.35 (d, J = 4.6 Hz, 3H) |
| 554 | 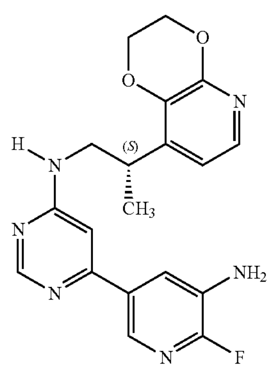 | 383.06 | (400 MHz, CDCl₃) δ 8.61 (s, 1H), 8.04 (s, 1H), 7.82 (d, J = 4.5 Hz, 1H), 7.78 (d, J = 10.4 Hz, 1H), 6.83 (d, J = 4.5 Hz, 1H), 6.68 (s, 1H), 5.13 (s, 1H), 4.50-4.40 (m, 2H), 4.29 (s, 2H), 3.93 (s, 2H), 3.68-3.47 (m, 3H), 1.36 (d, J = 5.5 Hz, 3H) |
| 555 | 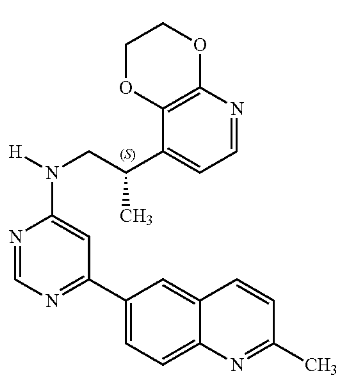 | 414.23 | (methanol-d₄) δ 8.78-8.66 (m, 2H), 8.55 (s, 1H), 8.23 (s, 2H), 7.80 (d, J = 8.6 Hz, 1H), 7.69 (d, J = 5.3 Hz, 1H), 7.11-6.96 (m, 2H), 4.44 (m, 2H), 4.30 (m, 2H), 4.01-3.78 (m, 2H), 3.65 (m, 1H), 2.90 (s, 3H), 1.36 (d, J = 7.0 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 556 | 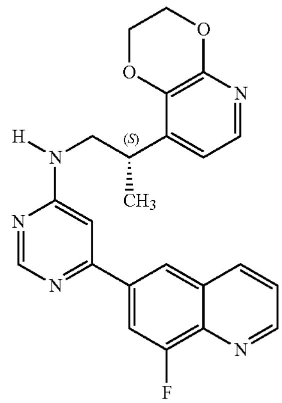 | 418.19 | (methanol-d$_4$) δ 9.06 (d, J = 3.2 Hz, 1H), 8.76 (s, 1H), 8.58 (d, J = 8.4 Hz, 1H), 8.29 (s, 1H), 7.93 (d, J = 10.9 Hz, 1H), 7.78 (m, 1H), 7.70 (d, J = 5.3 Hz, 1H), 7.02 (m, 2H), 4.45 (m, 2H), 4.31 (m, 2H), 3.93 (m, 2H), 3.65 (m, 1H), 1.37 (d, J = 7.0 Hz, 3H) |
| 557 | 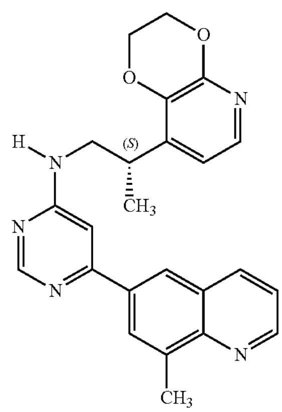 | 468.11 | (methanol-d$_4$) δ 9.11 (dd, J = 4.2, 1.6 Hz, 1H), 8.70 (s, 2H), 8.63-8.47 (m, 2H), 7.76 (dd, J = 8.3, 4.2 Hz, 1H), 7.67 (d, J = 5.2 Hz, 1H), 7.03 (m, 2H), 4.42 (m, 2H), 4.28 (m, 2H), 3.99-3.73 (m, 2H), 3.62 (m, 1H), 1.36 (d, J = 6.8 Hz, 3H) |
| 558 | 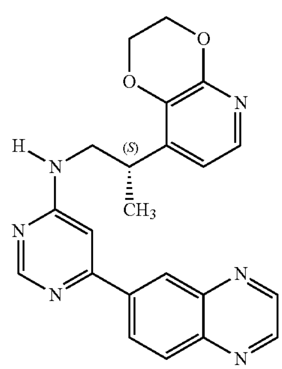 | 401.18 | (methanol-d$_4$) δ 9.03 (s, 2H), 8.77 (s, 1H), 8.62 (s, 1H), 8.33 (d, J = 8.7 Hz, 1H), 8.18 (d, J = 9.0 Hz, 1H), 7.70 (d, J = 5.2 Hz, 1H), 7.08 (s, 1H), 7.01 (d, J = 5.2 Hz, 1H), 4.45 (m, 2H), 4.31 (m, 2H), 4.06-3.82 (m, 2H), 3.65 (m, 1H), 1.37 (d, J = 7.1 Hz, 3H) |
| 559 | 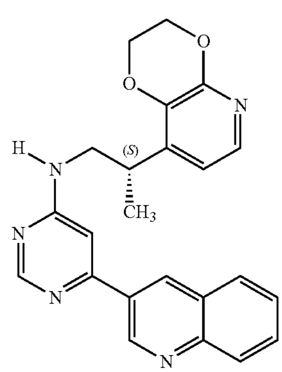 | 400.14 | (methanol-d$_4$) δ 9.23 (s, 1H), 8.87 (s, 1H), 8.76 (s, 1H), 8.16 (dd, J = 16.0, 7.5 Hz, 2H), 7.97 (t, J = 7.4 Hz, 1H), 7.79 (t, J = 7.6 Hz, 1H), 7.68 (d, J = 5.3 Hz, 1H), 7.07 (s, 1H), 7.00 (d, J = 5.0 Hz, 1H), 4.43 (m, 2H), 4.34-4.23 (m, 2H), 3.99-3.77 (m, 2H), 3.65 (m, 1H), 1.37 (d, J = 6.9 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 560 | 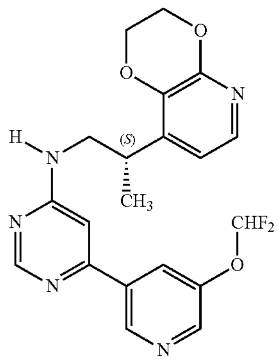 | 416 | (400 MHz, CDCl₃) δ 8.90 (s, 1H), 8.57 (s, 1H), 8.47 (s, 1H), 8.06 (s, 1H), 7.68 (dd, J = 11.2, 4.9 Hz, 1H), 7.19 (d, J = 1.5 Hz, 1H), 6.79-6.69 (m, 2H), 5.38 (s, 1H), 4.34 (d, J = 3.6 Hz, 2H), 4.18 (s, 2H), 3.47 (t, J = 12.6 Hz, 3H), 1.27 (d, J = 5.3 Hz, 3H) |
| 561 | 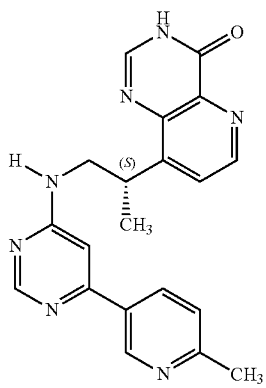 | 373.18 | (DMSO-d₆) δ 12.27 (s, 1H), 8.97 (s, 1H), 8.47 (s, 1H), 8.12 (s, 1H), 8.01 (dd, J = 7.9, 1.3 Hz, 1H), 7.78 (d, 1H), 7.50 (t, J = 7.7 Hz, 2H), 7.37 (d, J = 8.0 Hz, 1H), 7.07 (s, 1H), 4.16 (m, 1H), 3.66 (m, 2H), 3.33 (s, 3H), 1.31 (d, J = 6.5 Hz, 3H) |
| 562 | 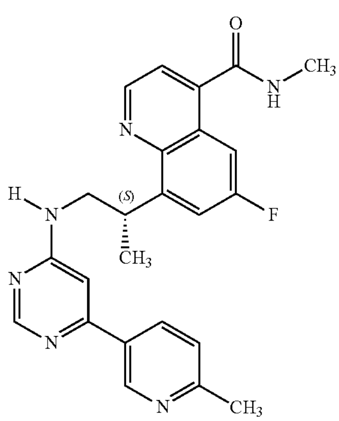 | 431.05 | (400 MHz, CDCl₃) δ 8.89 (s, 1H), 8.39 (s, 1H), 8.07 (d, J = 7.0 Hz, 1H), 7.62 (d, J = 7.8 Hz, 1H), 7.47 (s, 1H), 7.35 (d, J = 7.8 Hz, 1H), 7.19-7.13 (m, 3H), 6.00 (s, 1H), 5.61 (s, 1H), 4.41 (s, 1H), 3.79 (d, J = 5.6 Hz, 1H), 3.72-3.68 (m, 1H), 3.03 (d, J = 4.1 Hz, 3H), 2.53 (s, 3H) and 1.48 (d, J = 6.4 Hz, 3H) |
| 563 | 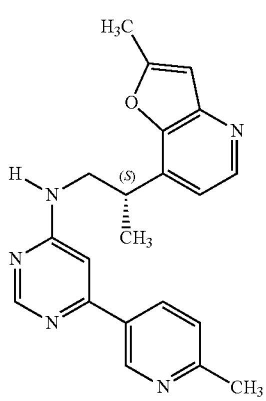 | 360.06 | (400 MHz, CDCl₃) δ 8.95 (s, 1H), 8.65 (s, 1H), 8.35 (d, J = 3.4 Hz, 1H), 8.17 (d, J = 7.7 Hz, 1H), 7.28-7.23 (m, 1H), 6.99 (d, J = 3.6 Hz, 1H), 6.66 (s, 1H), 6.55 (s, 1H), 5.39 (s, 1H), 3.89 (s, 1H), 3.76 (d, J = 5.2 Hz, 1H), 3.62 (d, J = 6.3 Hz, 1H), 2.61 (s, 3H), 2.48 (s, 3H) and 1.50 (d, J = 6.1 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 564 | 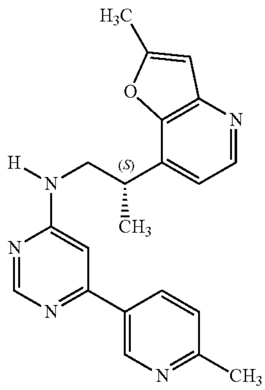 | 361.5 | (methanol-d₄) δ 8.88 (s, 1H), 8.77-8.65 (m, 1H), 8.38 (t, J = 10.5 Hz, 2H), 8.16 (dd, J = 8.2, 2.3 Hz, 1H), 7.62 (s, 1H), 7.41 (dd, J = 8.0, 4.3 Hz, 1H), 6.80 (d, J = 31.8 Hz, 1H), 4.02-3.71 (m, 1H), 3.73-3.36 (m, 2H), 2.66 (d, J = 3.1 Hz, 3H), 2.59 (d, J = 3.5 Hz, 3H), 2.19 (s, 1H), 1.53 (d, J = 7.0 Hz, 3H) |
| 565 | 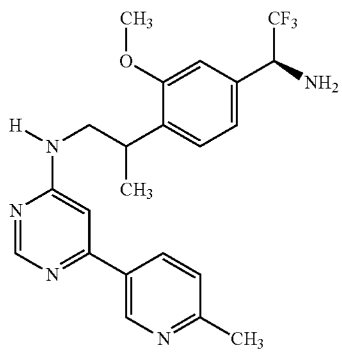 [SMILES: COc1cc([C@H](N)C(F)(F)F)ccc1C(C)CNc1cc(-c2ccc(C)nc2)ncn1] | 432.19 | (methanol-d₄) δ 9.00-8.83 (m, 1H), 8.65 (s, 1H), 8.29 (dd, J = 8.2, 2.3 Hz, 1H), 7.66 (d, J = 8.2 Hz, 1H), 7.48-7.28 (m, 1H), 7.15 (m, 2H), 6.95 (s, 1H), 5.31 (q, J = 7.4 Hz, 1H), 3.88 (s, 2H), 3.91-3.46 (m, 3H), 2.71 (d, J = 2.7 Hz, 3H), 1.33 (d, J = 6.9 Hz, 3H) |
| 566 | 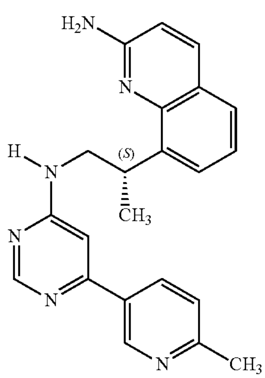 | 371.2 | |
| 567 | 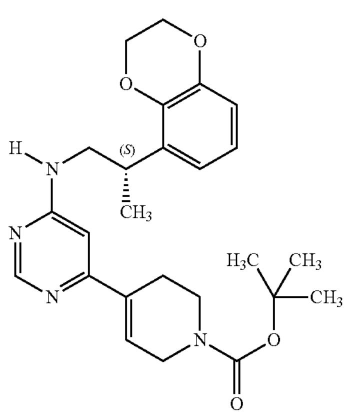 | 454.29 | (methanol-d₄) δ 8.30 (s, 1H), 7.62 (d, 1H), 6.90 (d, 1H), 6.67 (m, 1H), 6.41 (s, 1H), 4.45-4.33 (m, 2H), 4.24 (m, 2H), 4.10 (m, 2H), 3.79-3.46 (m, 5H), 2.44 (m, 2H), 1.48 (s, 9H), 1.33-1.25 (d, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 568 | 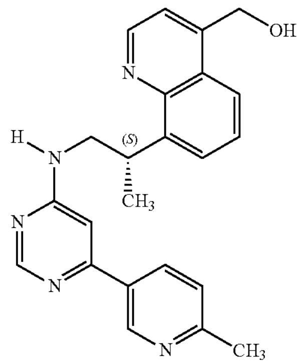 | 386.52 | (methanol-d₄) δ 8.89 (d, J = 8.2 Hz, 2H), 8.42 (s, 1H), 8.15 (dd, J = 8.2, 2.4 Hz, 1H), 7.91 (d, J = 8.4 Hz, 1H), 7.73 (d, J = 7.2 Hz, 1H), 7.62 (dd, J = 16.5, 6.2 Hz, 2H), 7.43 (d, J = 8.2 Hz, 1H), 5.15 (d, J = 20.2 Hz, 2H), 4.56 (s, 1H), 3.91-3.65 (m, 3H), 2.61 (s, 3H) |
| 569 | 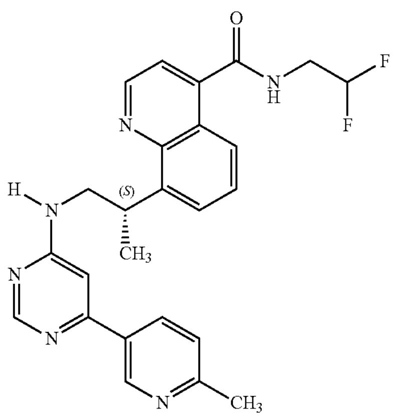 | 463.25 | (methanol-d₄) δ 8.87 (s, 1H), 8.78 (s, 1H), 8.33 (s, 1H), 8.09 (s, 1H), 7.93 (dd, J = 8.4, 1.4 Hz, 1H), 7.69 (d, J = 6.7 Hz, 1H), 7.53 (dd, J = 8.4, 7.2 Hz, 1H), 7.44 (s, 1H), 7.33 (d, J = 7.5 Hz, 1H), 6.64 (M, 1H), 6.02 (tt, J = 55.8, 3.8 Hz, 1H), 4.51 (q, J = 7.0 Hz, 1H), 3.93-3.53 (m, 4H), 2.50 (s, 3H), 1.40 (d, J = 6.4 Hz, 3H) |
| 570 | 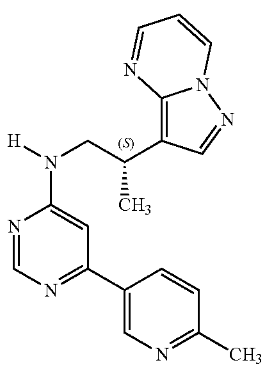 | 346.52 | (methanol-d₄) δ 8.91 (s, 1H), 8.81 (dd, J = 7.1, 1.7 Hz, 1H), 8.45 (d, J = 22.5 Hz, 2H), 8.20 (s, 1H), 8.10 (s, 1H), 7.42 (d, J = 8.2 Hz, 1H), 6.94 (dd, J = 7.1, 4.0 Hz, 1H), 6.81 (s, 1H), 3.76 (dd, J = 12.8, 7.4 Hz, 1H), 3.55 (h, J = 7.1 Hz, 1H), 2.59 (s, 3H), 1.48 (d, J = 6.9 Hz, 3H) |
| 571 | 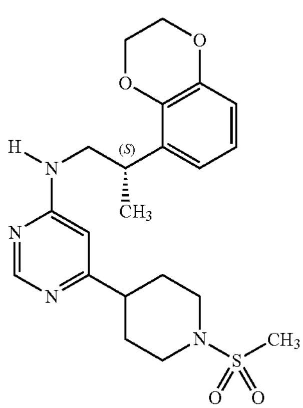 | 434.57 | (methanol-d₄) δ 8.51 (s, 1H), 7.65 (d, J = 5.2 Hz, 1H), 6.93 (d, 1H), 6.46 (s, 1H), 4.47-4.35 (m, 2H), 4.26 (m, 2H), 3.93-3.46 (m, 5H), 2.93-2.59 (m, 6H), 1.98 (m, 2H), 1.75 (m, 2H), 1.31 (d, J = 7.0 Hz, 3H) |

| Cmpnd No. | Structure | ESMS (M + H) | ¹H NMR (300 MHz, unless indicated otherwise) NMR peaks given as δ values |
|---|---|---|---|
| 572 | 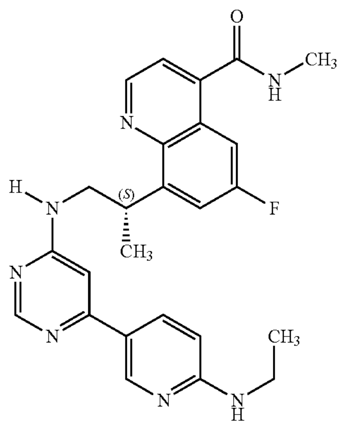 | 460.1 | (400 MHz, CDCl₃) δ 8.87 (s, 1H), 8.35 (s, 1H), 7.99 (s, 1H), 7.64 (s, 1H), 7.40 (s, 2H), 7.27 (s, 1H), 7.20 (s, 1H), 6.39 (s, 1H), 6.23 (s, 1H), 5.89 (s, 1H), 4.87 (s, 1H), 4.52 (s, 1H), 3.71 (s, 2H), 3.34 (s, 2H), 3.05 (s, 3H) and 1.29 (s, 6H) |
| 573 | 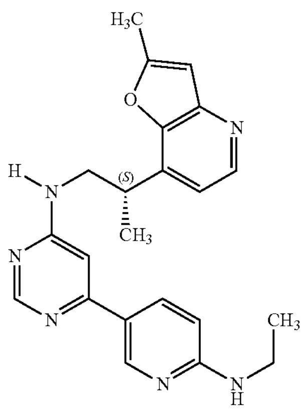 | 389.07 | (400 MHz, CDCl₃) δ 8.57 (s, 1H), 8.50 (s, 1H), 8.29 (d, J = 4.7 Hz, 1H), 7.99 (dd, J = 1.5, 8.7 Hz, 1H), 6.91 (d, J = 4.9 Hz, 1H), 6.48 (d, J = 13.7 Hz, 2H), 6.35 (d, J = 8.8 Hz, 1H), 5.07 (s, 1H), 4.75 (s, 1H), 3.74-3.60 (m, 2H), 3.54 (q, J = 7.0 Hz, 1H), 3.28 (s, 2H), 2.41 (s, 3H), 1.41 (d, J = 6.8 Hz, 3H) and 1.19 (q, J = 7.3 Hz, 3H) |
| 574 | 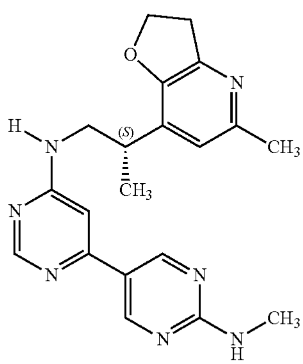 | 378.13 | (400 MHz, methanol-d₄) δ 8.80 (s, 2H), 8.39 (s, 1H), 6.92 (s, 1H), 6.73 (s, 1H), 4.73-4.59 (m, 2H), 3.65 (s, 2H), 3.27-3.17 (m, 3H), 2.98 (s, 3H), 2.40 (s, 3H), 1.31 (d, J = 6.5 Hz, 3H) |
| 575 | 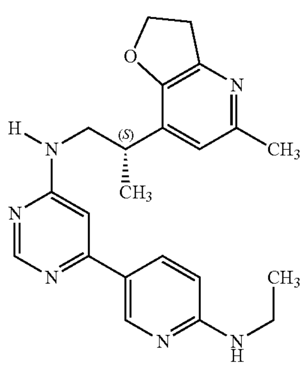 | 391.13 | (400 MHz, CDCl₃) δ 8.69 (s, 1H), 8.55 (s, 1H), 8.11 (d, 1H), 6.74 (s, 1H), 6.62 (s, 1H), 6.45 (d, 1H), 5.13 (s, 1H), 4.95-4.75 (m, 1H), 4.75-4.54 (m, 2H), 3.74-3.45 (m, 2H), 3.45-3.14 (m, 5H), 2.45 (s, 3H), 1.41-1.24 (m, 6H) |

| Cmpnd No. | Structure | ESMS (M + H) | ¹H NMR (300 MHz, unless indicated otherwise) NMR peaks given as δ values |
|---|---|---|---|
| 576 | 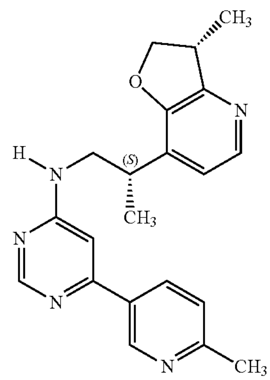 | 362.11 | (400 MHz, CDCl₃) δ 9.01 (s, 1H), 8.61 (s, 1H), 8.21 (d, J = 7.2 Hz, 1H), 8.03 (d, J = 4.3 Hz, 1H), 7.26 (m, 1H), 6.91 (s, 1H), 6.74 (s, 1H), 5.34 (s, 1H), 4.83 (t, 1H), 4.20 (t, 1H), 3.72-3.43 (m, 3H), 3.38-3.18 (m, 1H), 2.62 (s, 3H), 1.40 (d, J = 6.7 Hz, 3H), 1.36 (d, J = 6.5 Hz, 3H) |
| 577 | 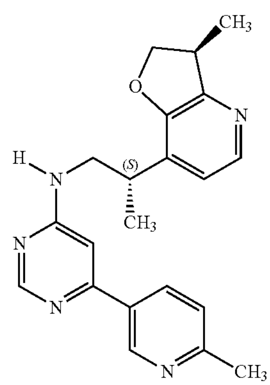 | 362.14 | (400 MHz, CDCl₃) δ 9.02 (s, 1H), 8.62 (s, 1H), 8.22 (dd, J = 8.1, 2.0 Hz, 1H), 8.04 (d, J = 5.1 Hz, 1H), 7.27 (d, J = 4.9 Hz, 1H), 6.91 (d, J = 5.1 Hz, 1H), 6.74 (s, 1H), 5.25 (s, 1H), 4.83 (t, J = 9.1 Hz, 1H), 4.21 (t, J = 8.3 Hz, 1H), 3.78-3.51 (m, 3H), 3.36-3.18 (m, 1H), 2.63 (s, 3H), 1.41 (d, J = 6.9 Hz, 3H), 1.37 (d, J = 7.0 Hz, 3H) |
| 578 | 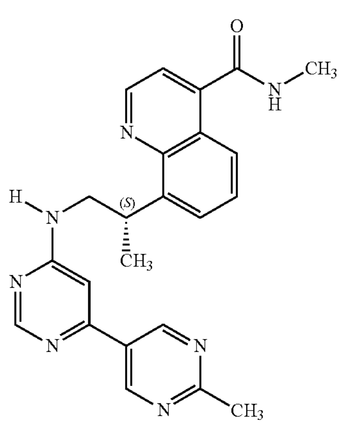 | 414.57 | (DMSO-d₆, 70°C.) δ 9.14 (s, 2H), 8.95 (d, J = 4.3 Hz, 1H), 8.47 (s, 1H), 8.34 (br. s, 1H), 8.02 (d, J = 8.4 Hz, 1H), 7.74 (d, J = 7.3 Hz, 1H), 7.59 (t, J = 7.8 Hz, 1H), 7.50 (d, J = 4.3 Hz, 1H), 7.28 (br. s, 1H), 7.04 (s, 1H), 4.52 (h, J = 7.0 Hz, 1H), 3.83-3.66 (m, 2H), 2.88 (d, J = 4.4 Hz, 3H), 2.68 (s, 3H), 1.42 (d, J = 6.9 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 579 | 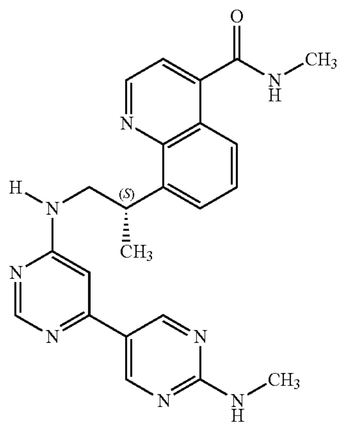 | 429.62 | (DMSO-d$_6$) δ 8.96 (d, J = 4.3 Hz, 1H), 8.79 (s, 2H), 8.50 (s, 1H), 8.22 (bs, 1H), 8.05 (d, J = 7.7 Hz, 1H), 7.75 (d, J = 6.9 Hz, 1H), 7.66-7.54 (m, 1H), 7.51 (d, J = 4.3 Hz, 1H), 6.91 (s, 1H), 4.55 (m, 1H), 3.89-3.74 (m, 2H), 2.99-2.83 (m, 6H), 1.46 (d, J = 7.0 Hz, 3H) |
| 580 | 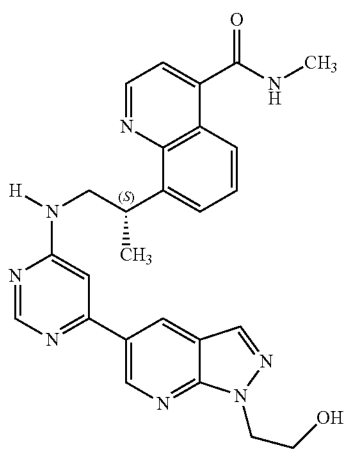 | 483.61 | (DMSO-d$_6$) δ 9.07 (s, 1H), 8.97 (d, J = 4.1 Hz, 1H), 8.74 (s, 1H), 8.58 (s, 1H), 8.36 (s, 1H), 8.28 (s, 1H), 8.04 (d, J = 8.7 Hz, 1H), 7.96 (s, 1H), 7.78 (d, J = 6.9 Hz, 1H), 7.62 (t, J = 7.9 Hz, 1H), 7.52 (d, J = 4.2 Hz, 1H), 7.12 (s, 1H), 4.57 (m, 3H), 3.93 (t, J = 5.9 Hz, 2H), 3.83 (m, 2H), 2.90 (d, J = 4.4 Hz, 3H), 1.45 (d, J = 7.0 Hz, 3H) |
| 581 | 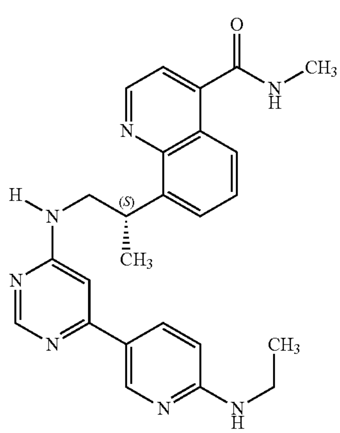 | 442.62 | (DMSO-d$_6$) δ 8.96 (d, J = 4.3 Hz, 1H), 8.54 (s, 1H), 8.52 (s, 1H), 8.36 (m, 2H), 8.04 (d, J = 9.2 Hz, 1H), 7.91 (d, J = 9.6 Hz, 1H), 7.76 (d, J = 7.2 Hz, 1H), 7.66-7.58 (m, 1H), 7.52 (d, J = 4.4 Hz, 1H), 6.90 (s, 1H), 6.71 (d, J = 9.0 Hz, 1H), 4.61-4.47 (m, 1H), 3.83 (m, 2H), 3.40 (q, J = 7.1 Hz, 2H), 2.90 (d, J = 4.6 Hz, 3H), 1.44 (d, J = 7.0 Hz, 3H), 1.21 (t, J = 7.2 Hz, 3H) |

TABLE 1-continued

| Cmpnd No. | Structure | ESMS (M + H) | $^1$H NMR (300 MHz, unless indicated otherwise) NMR peaks given as δ values |
|---|---|---|---|
| 582 | 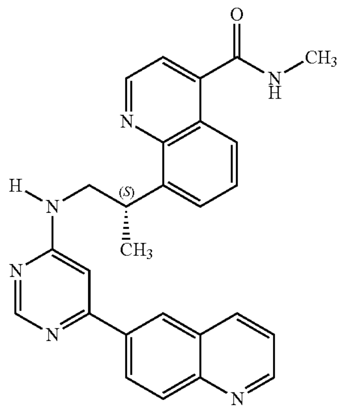 | 449.62 | (DMSO-d$_6$) δ 9.06 (s, 1H), 8.96 (s, 1H), 8.75 (s, 1H), 8.64 (d, J = 4.8 Hz, 1H), 8.56 (d, J = 8.2 Hz, 1H), 8.22 (s, 3H), 8.02 (d, J = 7.2 Hz, 1H), 7.81 (s, 1H), 7.73-7.60 (m, 2H), 7.54 (d, J = 4.3 Hz, 1H), 7.07 (s, 1H), 4.56 (m, 1H), 3.90 (m, 2H), 2.87 (d, J = 4.6 Hz, 3H), 1.44 (d, 3H) |
| 583 | 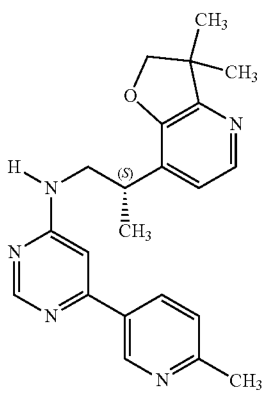 | 376.11 | (400 MHz, CDCl$_3$) δ 9.02 (s, 1H), 8.62 (s, 1H), 8.22 (d, J = 8.1 Hz, 1H), 8.06 (d, J = 5.1 Hz, 1H), 7.27 (d, J = 2.3 Hz, 1H), 6.92 (d, J = 5.2 Hz, 1H), 6.73 (s, 1H), 5.21 (s, 1H), 4.37 (s, 2H), 3.83-3.52 (m, 2H), 3.36-3.24 (m, 1H), 2.63 (s, 3H), 1.46-1.30 (m, 9H) |
| 584 | 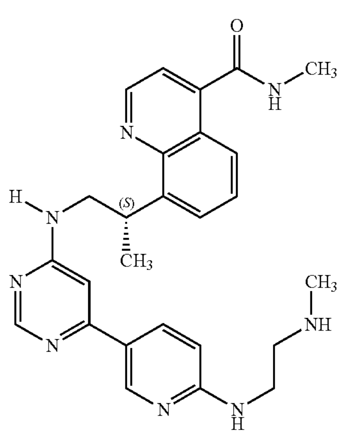 | 471.26 | |

| Cmpnd No. | Structure | ESMS (M + H) | ¹H NMR (300 MHz, unless indicated otherwise) NMR peaks given as δ values |
|---|---|---|---|
| 585 | 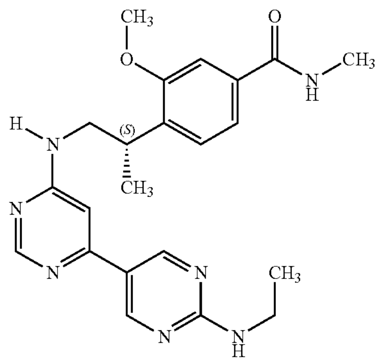 | 422.29 | (DMSO-d$_6$) δ 8.83 (s, 2H), 8.40 (s, 1H), 8.34 (d, J = 4.4 Hz, 1H), 7.58 (t, J = 5.4 Hz, 1H), 7.40 (d, J = 2.6 Hz, 2H), 7.36-7.20 (m, 2H), 6.79 (s, 1H), 3.82 (s, 3H), 3.60-3.32 (m, 5H), 2.78 (d, J = 4.4 Hz, 3H), 1.28-1.09 (m, 6H) |
| 586 | 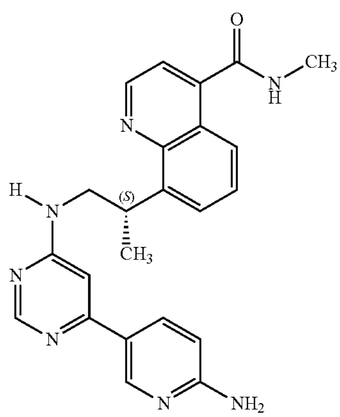 | 414.23 | (DMSO-d$_6$) δ 8.99 (d, J = 4.3 Hz, 1H), 8.68-8.51 (m, 2H), 8.36 (s, 1H), 7.99 (m, 2H), 7.76 (d, J = 7.2 Hz, 1H), 7.68-7.57 (t, 1H), 7.53 (d, J = 4.1 Hz, 1H), 7.31 (s, 1H), 6.50 (d, J = 8.9 Hz, 1H), 6.34 (s, 2H), 4.50 (m, 1H), 3.69 (m, 2H), 2.87 (d, J = 4.6 Hz, 3H), 1.37 (d, J = 6.9 Hz, 3H) |
| 587 | 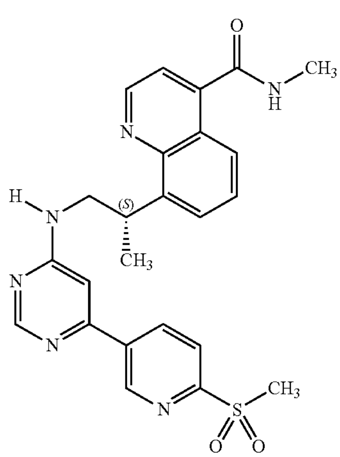 | 477.2 | (DMSO-d$_6$) δ 9.23 (s, 1H), 8.97 (d, J = 4.3 Hz, 1H), 8.69-8.52 (m, 3H), 8.20 (m, 1H), 7.99 (d, 1H), 7.77 (m, 1H), 7.69-7.57 (m, 1H), 7.51 (m, 1H), 3.90 (m, 3H), 3.34 (s, 3H), 2.87 (d, J = 4.6 Hz, 3H), 1.40 (d, J = 6.4 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 588 | 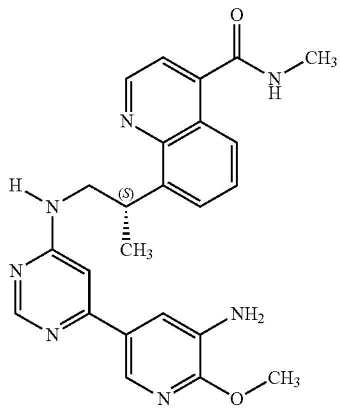 | 441.91 | (DMSO-d₆) δ 8.98 (d, J = 4.3 Hz, 1H), 8.63 (d, J = 4.5 Hz, 1H), 8.41 (s, 1H), 7.99 (d, J = 8.3 Hz, 1H), 7.76 (d, J = 7.1 Hz, 1H), 7.68-7.58 (m, 1H), 7.53 (d, J = 4.3 Hz, 1H), 7.46 (m, 2H), 5.09 (s, 2H), 4.50 (m, 1H), 3.92 (s, 3H), 3.72 (m, 2H), 2.87 (d, J = 4.6 Hz, 3H), 1.38 (d, J = 6.9 Hz, 3H) |
| 589 | 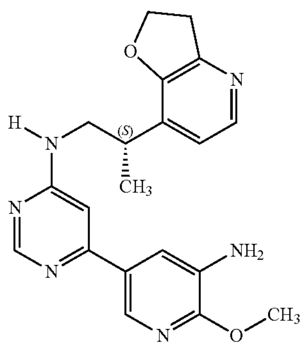 | 379.25 | |
| 590 | 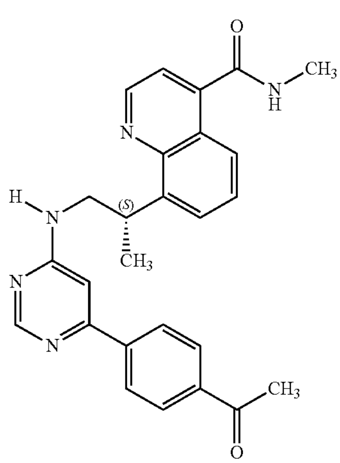 | 440.25 | (DMSO-d₆) δ 8.98 (d, J = 4.2 Hz, 1H), 8.63 (d, J = 4.6 Hz, 1H), 8.50 (s, 1H), 8.07 (m, 4H), 8.00 (d, J = 8.2 Hz, 1H), 7.77 (d, J = 7.2 Hz, 1H), 7.61 (m, 3H), 4.51 (m, 1H), 3.76 (m, 2H), 2.87 (d, J = 4.6 Hz, 3H), 2.59 (s, 3H), 1.39 (d, J = 6.8 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 591 | 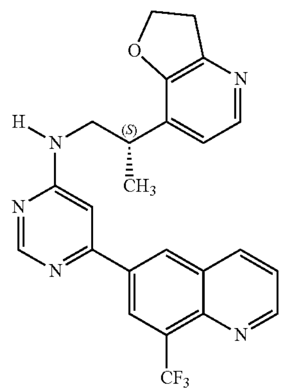 | 452.22 | (DMSO-d₆) δ 9.11 (dd, J = 4.2, 1.6 Hz, 1H), 8.93 (s, 1H), 8.68 (m, 2H), 8.61 (s, 1H), 7.95 (d, J = 5.2 Hz, 1H), 7.77 (dd, J = 8.4, 4.2 Hz, 2H), 7.19 (s, 1H), 7.09 (d, J = 5.3 Hz, 1H), 4.64 (t, J = 8.9 Hz, 2H), 3.65 (m, 3H), 3.24 (t, 2H), 1.26 (d, J = 6.9 Hz, 3H) |
| 592 | 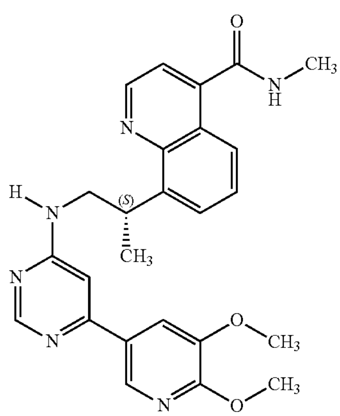 | 459.24 | (DMSO-d₆) δ 8.97 (d, J = 4.3 Hz, 1H), 8.63 (m, 1H), 8.50 (s, 1H), 8.28 (s, 1H), 8.04-7.97 (dd, 1H), 7.77 (m, 3H), 7.67-7.58 (t, 1H), 7.52 (d, 1H), 6.91 (s, 1H), 4.52 (m, 1H), 3.93 (s, 3H), 3.86 (s, 3H), 3.77 (m, 2H), 2.87 (d, J = 4.6 Hz, 3H), 1.39 (d, J = 6.9 Hz, 3H) |
| 593 | 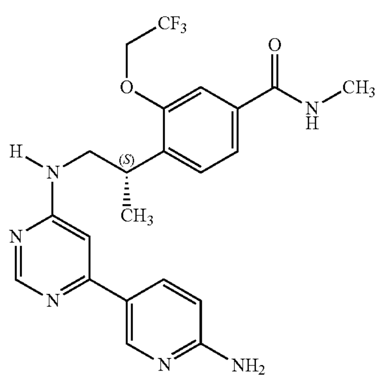 | 460.28 | |
| 594 | 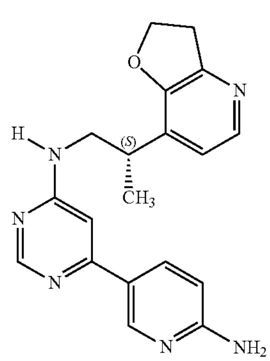 | 348.01 | (DMSO-d₆) δ 8.53 (s, 2H), 8.15 (s, 2H), 7.93 (d, J = 5.2 Hz, 1H), 7.55 (s, 2H), 7.04 (d, J = 4.7 Hz, 1H), 6.83 (d, J = 8.9 Hz, 2H), 4.62 (t, J = 8.9 Hz, 2H), 3.62 (m, 3H), 3.27-3.14 (m, 2H), 1.23 (d, J = 6.9 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 595 | 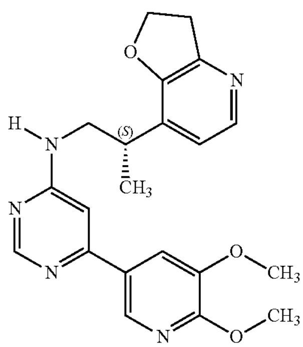 | 394.2 | (DMSO-d₆) δ 8.47 (s, 1H), 8.31 (s, 1H), 7.91 (d, J = 5.1 Hz, 1H), 7.77 (s, 1H), 7.44 (m, 1H), 7.01 (d, J = 4.9 Hz, 1H), 6.91 (s, 1H), 4.61 (t, J = 8.9 Hz, 2H), 3.92 (s, 3H), 3.86 (s, 3H), 3.57 (m, 2H), 3.18 (m, 3H), 1.22 (d, J = 6.9 Hz, 3H) |
| 596 | 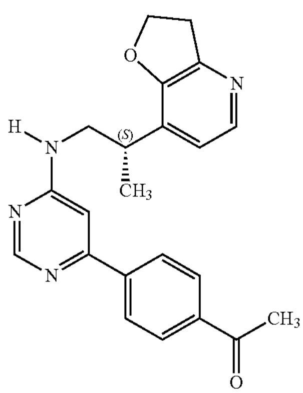 | 375.2 | (DMSO-d₆) δ 8.52 (s, 1H), 8.06 (m, 4H), 7.90 (d, 1H), 7.53 (m, 1H), 7.02 (m, 2H), 4.62 (t, J = 8.5 Hz, 2H), 4.06 (q, J = 5.3 Hz, 1H), 3.59 (m, 2H), 3.26-3.18 (m, 2H), 2.62 (s, 3H), 1.22 (d, 3H) |
| 597 | 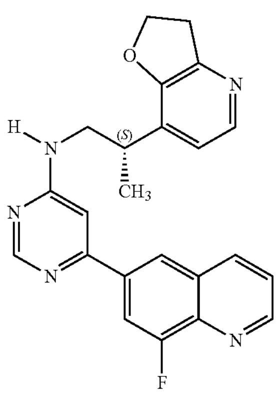 | 402.44 | (DMSO-d₆) δ 9.00 (dd, J = 4.2, 1.6 Hz, 1H), 8.63-8.46 (m, 3H), 8.12 (s, 1H), 7.91 (d, 1H), 7.69 (dd, J = 8.4, 4.2 Hz, 1H), 7.57 (m, 1H), 7.12 (s, 1H), 7.03 (d, J = 4.7 Hz, 1H), 4.63 (t, J = 8.9 Hz, 2H), 3.60 (s, 2H), 3.22 (m, 3H), 1.23 (d, 3H) |
| 598 | 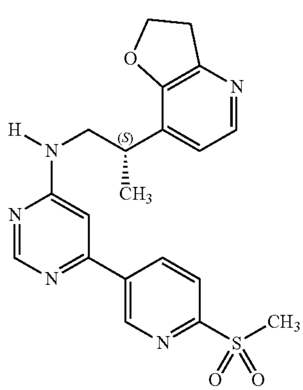 | 412.25 | (DMSO-d₆) δ 9.28 (s, 1H), 8.59 (m, 2H), 8.16 (d, 1H), 7.94 (d, 1H), 7.85-7.72 (m, 1H), 7.10 (m, 2H), 4.64 (t, J = 8.9 Hz, 2H), 3.62 (m, 2H), 3.33 (s, 3H), 3.31-3.20 (m, 3H), 1.24 (d, J = 6.9 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 599 | 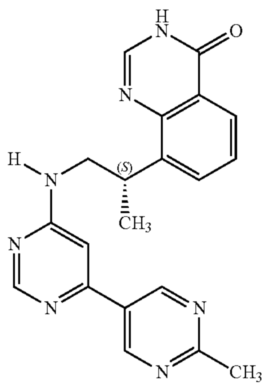 | 374.21 | (DMSO-d$_6$) δ 12.28 (s, 1H), 9.24 (s, 1H), 9.15 (s, 1H), 8.50 (s, 1H), 8.12 (s, 1H), 8.01 (dd, J = 7.9, 1.5 Hz, 1H), 7.80 (s, 1H), 7.60 (s, 1H), 7.50 (t, J = 7.7 Hz, 1H), 6.95 (s, 1H), 4.21-4.08 (m, 1H), 3.68 (m, 2H), 2.69 (s, 3H), 1.28 (d, 3H) |
| 600 | 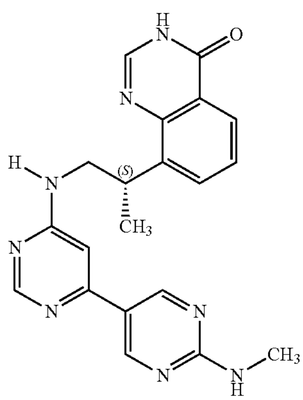 | 389.25 | (DMSO-d$_6$) δ 12.42 (s, 1H), 9.51 (m, 1H), 9.04 (m, 1H), 8.82 (m, 1H), 8.65 (s, 1H), 8.11 (s, 1H), 8.03 (d, 1H), 7.84 (d, 1H), 7.57-7.44 (m, 1H), 7.00 (s, 2H), 3.95-3.50 (m, 3H), 2.90 (s, 3H), 1.34 (d, 3H) |
| 601 | 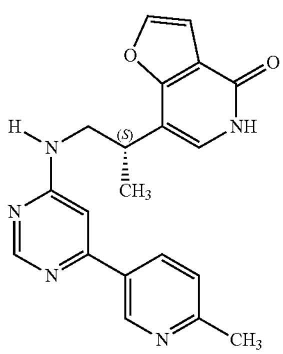 | 362.24 | (methanol-d$_4$) δ 8.89 (d, J = 2.2 Hz, 1H), 8.45-8.38 (m, 1H), 8.17 (dd, J = 8.2, 2.4 Hz, 1H), 7.77 (d, J = 2.2 Hz, 1H), 7.41 (d, J = 8.2 Hz, 1H), 7.14 (s, 1H), 4.86-4.79 (m, 1H), 6.97 (d, J = 2.2 Hz, 1H), 6.79 (d, J = 1.2 Hz, 1H), 3.77 (d, J = 8.2 Hz, 2H), 3.44-3.31 (m, 1H), 2.59 (s, 3H), 1.43 (d, J = 7.0 Hz, 3H) |
| 602 | 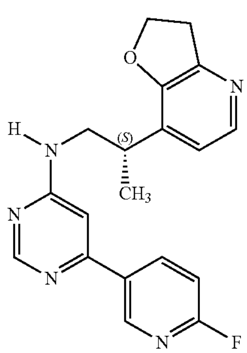 | 352.33 | (CDCl$_3$) δ 8.79 (d, J = 2.2 Hz, 1H), 8.64 (s, 1H), 8.52-8.39 (m, 1H), 8.03 (d, J = 5.2 Hz, 1H), 7.05 (dd, J = 8.6, 2.7 Hz, 1H), 6.93 (d, J = 5.2 Hz, 1H), 6.76 (s, 1H), 5.32 (s, 1H), 4.80-4.65 (m, 2H), 3.80-3.53 (m, 2H), 3.46-3.20 (m, 3H), 1.39 (d, J = 7.0 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 603 | 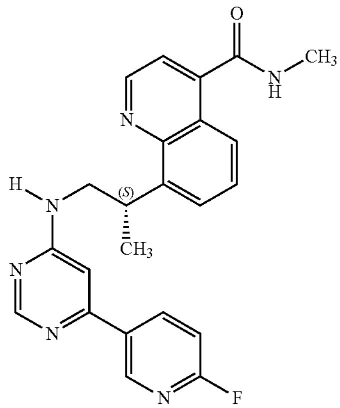 | 417.25 | |
| 604 | 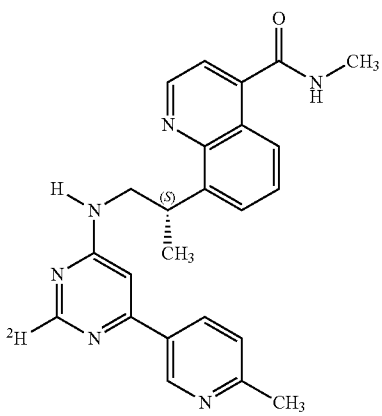 | 414.23 | |
| 605 | 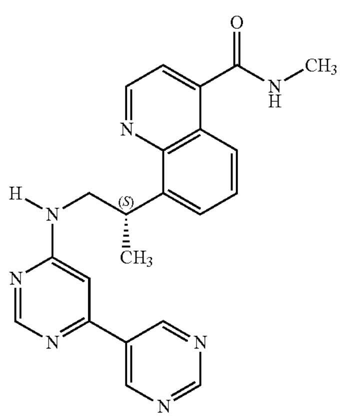 | 400.44 | (DMSO-d$_6$) δ 9.35 (m, 3H), 8.97 (d, J = 4.3 Hz, 1H), 8.68 (d, J = 4.5 Hz, 1H), 8.54 (s, 1H), 7.99 (d, J = 8.0 Hz, 1H), 7.76 (m, 2H), 7.62 (dd, J = 17.0, 9.6 Hz, 1H), 7.54 (s, 1H), 6.98 (s, 1H), 4.53 (m, 1H), 3.81 (m, 2H), 2.87 (d, J = 4.6 Hz, 3H), 1.39 (d, 3H) |

| Cmpnd No. | Structure | ESMS (M + H) | ¹H NMR (300 MHz, unless indicated otherwise) NMR peaks given as δ values |
|---|---|---|---|
| 606 | 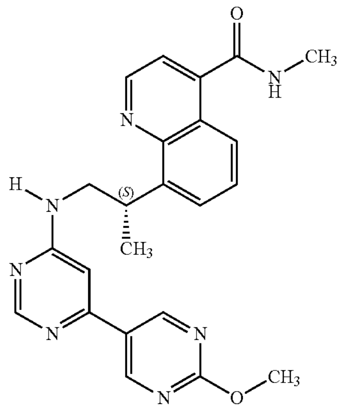 | 430.41 | (DMSO-d$_6$) δ 9.15 (m, 2H), 8.97 (d, J = 4.3 Hz, 1H), 8.68 (d, J = 4.6 Hz, 1H), 8.48 (s, 1H), 7.99 (d, J = 8.1 Hz, 1H), 7.76 (s, 1H), 7.69-7.57 (m, 2H), 7.54 (s, 1H), 6.88 (s, 1H), 4.52 (m, 1H), 3.99 (s, 3H), 3.78 (m, 2H), 2.87 (d, J = 4.6 Hz, 3H), 1.37 (d, J = 5.9 Hz, 3H) |
| 607 | 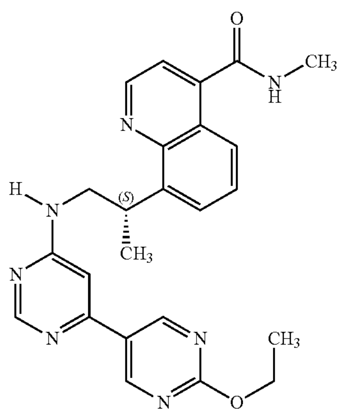 | 444.47 | (DMSO-d$_6$) δ 9.14 (m, 2H), 8.97 (d, J = 4.3 Hz, 1H), 8.68 (d, J = 4.5 Hz, 1H), 8.48 (s, 1H), 7.99 (d, J = 8.0 Hz, 1H), 7.76 (s, 1H), 7.68-7.58 (m, 2H), 7.54 (s, 1H), 6.87 (s, 1H), 4.42 (m, 3H), 3.79 (m, 2H), 2.87 (d, J = 4.6 Hz, 3H), 1.36 (m, 6H) |
| 608 | 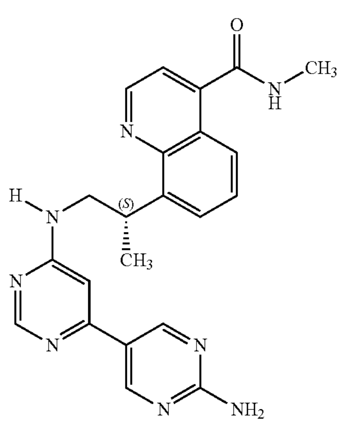 | 415.43 | (DMSO-d$_6$) δ 8.98 (d, J = 4.3 Hz, 1H), 8.83 (m, 2H), 8.67 (d, J = 4.5 Hz, 1H), 8.41 (s, 1H), 7.99 (d, J = 8.3 Hz, 1H), 7.76 (m, 1H), 7.68-7.59 (m, 1H), 7.54 (m, 1H), 7.12 (m, 2H), 6.75 (s, 1H), 4.50 (m, 1H), 3.72 (m, 2H), 2.87 (d, J = 4.6 Hz, 3H), 1.39 (d, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 609 | 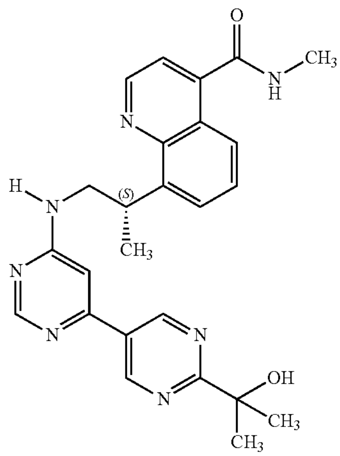 | 458.46 | (DMSO-d$_6$) δ 9.33 (s, 1H), 9.22 (m, 1H), 8.97 (s, 1H), 8.69 (m, 2H), 8.50 (s, 1H), 7.99 (d, 1H), 7.78 (m, 1H), 7.69-7.59 (m, 1H), 7.59-7.49 (m, 1H), 6.98 (s, 1H), 4.55 (m, 1H), 3.87 (m, 2H), 3.55 (s, 1H), 2.87 (d, J = 4.6 Hz, 3H), 1.54 (s, 6H), 1.39 (d, J = 6.0 Hz, 3H) |
| 610 | 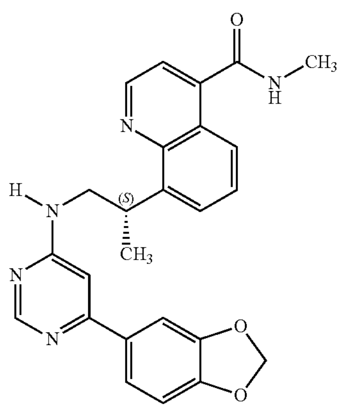 | 442.42 | |
| 611 | 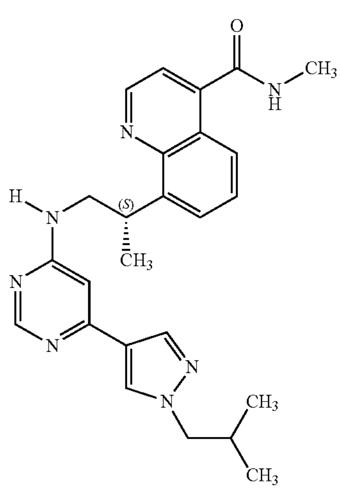 | 444.47 | (DMSO-d$_6$) δ 8.98 (d, J = 4.2 Hz, 1H), 8.67 (m, 1H), 8.31 (s, 1H), 8.21 (s, 1H), 7.97 d, 1H), 7.90 (s, 1H), 7.76 (m, 1H), 7.68-7.58 (m, 1H), 7.54 (d, J = 4.2 Hz, 1H), 7.35 (m, 1H), 6.59 (s, 1H), 4.49 (m, 1H), 3.95 (d, J = 7.2 Hz, 2H), 3.68 (m, 2H), 2.87 (d, J = 4.6 Hz, 3H), 2.13 (dt, J = 13.5, 6.7 Hz, 1H), 1.36 (d, J = 6.8 Hz, 3H), 0.84 (d, J = 6.7 Hz, 6H) |

TABLE 1-continued

| Cmpnd No. | Structure | ESMS (M + H) | ¹H NMR (300 MHz, unless indicated otherwise) NMR peaks given as δ values |
|---|---|---|---|
| 612 | 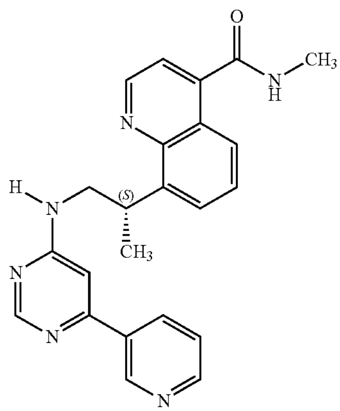 | 399.24 | |
| 613 | 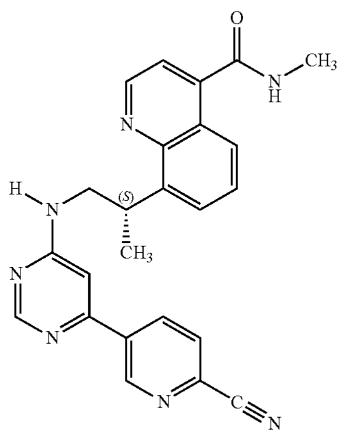 | 424.27 | (DMSO-d₆) δ 9.20 (s, 1H), 8.96 (s, 1H), 8.65 (m, 2H), 8.49 (m, 1H), 8.42-8.16 (m, 2H), 7.99 (m, 1H), 7.78 (m, 1H), 7.62 (m, 1H), 7.52 (m, 1H), 7.02 (s, 1H), 4.54 (m, 1H), 3.85 (m, 2H), 2.87 (d, J = 4.6 Hz, 3H), 1.40 (d, 3H) |
| 614 | 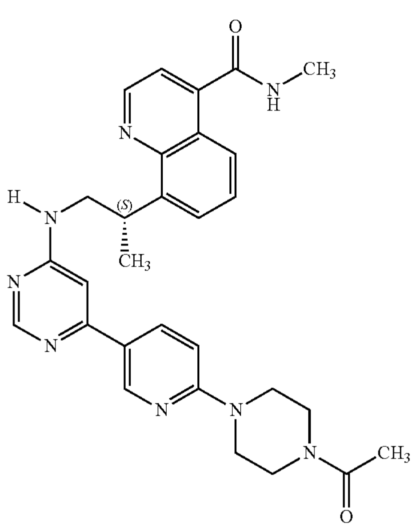 | 525.52 | (DMSO-d₆) δ 8.97 (d, J = 4.3 Hz, 1H), 8.69 (m, 2H), 8.60 (s, 1H), 8.10 (m, 1H), 8.01 (d, J = 7.9 Hz, 1H), 7.98-7.89 (m, 1H), 7.80 (m, 1H), 7.64 (t, J = 7.8 Hz, 1H), 7.52 (m, 1H), 7.04 (m, 1H), 6.81 (s, 1H), 4.54 (m, 2H), 3.98-3.53 (m, 10H), 2.87 (d, J = 4.6 Hz, 3H), 2.06 (s, 3H), 1.40 (d, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 615 | 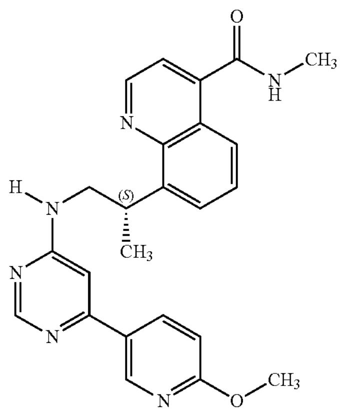 | 429.27 | (DMSO-d$_6$) δ 8.96 (m, 1H), 8.68 (m, 3H), 8.15 (s, 1H), 8.00 (d, J = 8.4 Hz, 1H), 7.78 (s, 1H), 7.69-7.59 (m, 1H), 7.55 (s, 1H), 7.01 (s, 1H), 6.85 (s, 1H), 4.53 (m, 1H), 3.93 (m, 5H), 2.87 (d, J = 4.6 Hz, 3H), 1.39 (d, J = 5.2 Hz, 3H) |
| 616 | 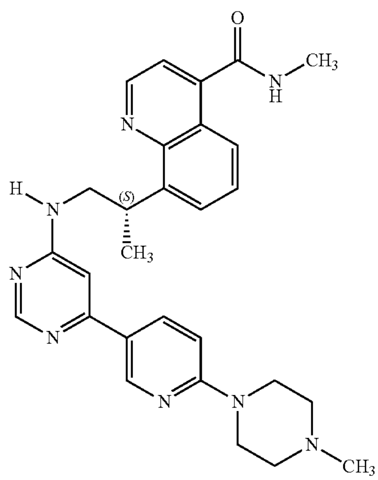 | 497.53 | (DMSO-d$_6$) δ 9.97 (s, 1H), 8.97 (d, J = 4.3 Hz, 1H), 8.85 (s, 1H), 8.69 (m, 3H), 8.01 (d, J = 8.4 Hz, 1H), 7.78 (m, 1H), 7.64 (m, 1H), 7.53 (m, 1H), 7.13 (m, 1H), 6.85 (s, 1H), 4.55 (m, 3H), 3.89 (m, 3H), 3.53 (m, 2H), 3.25 (m, 2H), 3.09 (m, 2H), 2.87 (m, 6H), 1.40 (d, 3H) |
| 617 | 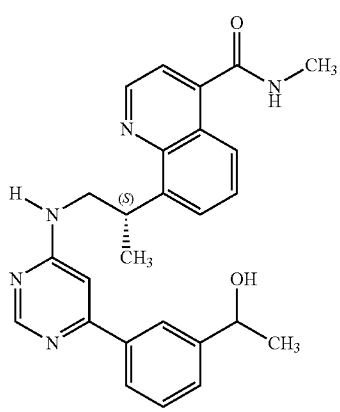 | 442.27 | (DMSO-d$_6$) δ 9.10 (s, 1H), 8.96 (m, 1H), 8.79-8.64 (m, 2H), 8.06-7.97 (m, 1H), 7.78 (m, 2H), 7.65 (m, 2H), 7.54 m, 2H), 6.95 (s, 1H), 4.81 (m, 1H), 4.54 (dd, J = 13.8, 7.0 Hz, 1H), 3.94 (m, 2H), 2.87 (d, J = 4.6 Hz, 3H), 1.38 (m, 6H) |

TABLE 1-continued

| Cmpnd No. | Structure | ESMS (M + H) | ¹H NMR (300 MHz, unless indicated otherwise) NMR peaks given as δ values |
|---|---|---|---|
| 618 | 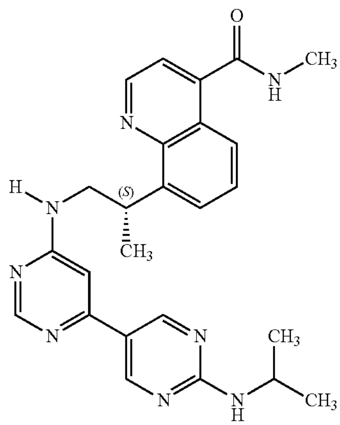 | 457.31 | (DMSO-d₆) δ 9.21 (m, 1H), 8.93 (m, 2H), 8.68 (m, 3H), 8.17-7.94 (m, 2H), 7.79 (m, 1H), 7.65 (t, J = 7.7 Hz, 1H), 7.53 (m, 1H), 6.79 (s, 1H), 4.54 (m, 1H), 4.13 (m, 1H), 3.90 (m, 2H), 2.87 (d, J = 4.6 Hz, 3H), 1.40 (m, 3H), 1.24-1.11 (m, 6H) |
| 619 | 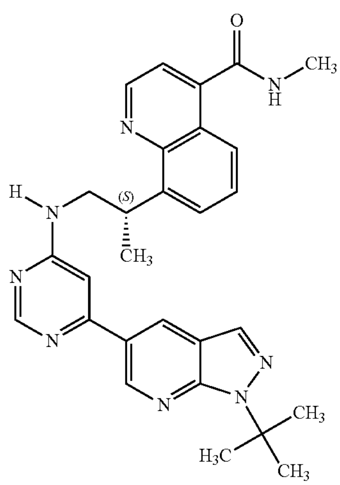 | 495.34 | |
| 620 | 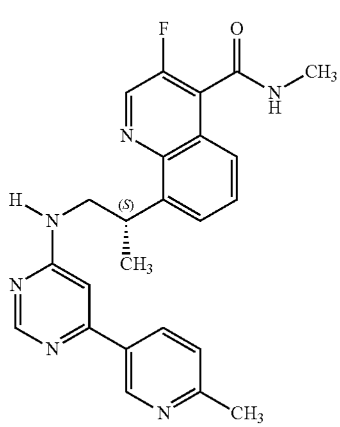 | 431.29 | (methanol-d₄) δ 9.04 (s, 2H), 8.58 (s, 1H), 8.35 (s, 1H), 8.12-7.74 (m, 3H), 7.58 (d, J = 8.2 Hz, 1H), 6.92 (m, 1H), 4.73 (q, J = 6.9 Hz, 1H), 3.96 (dd, J = 13.2, 7.0 Hz, 2H), 3.20 (s, 3H), 2.76 (s, 3H), 1.64 (d, J = 7.0 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 621 | 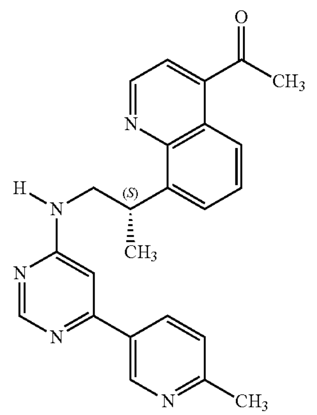 | 398.53 | (methanol-$d_4$) δ 9.02 (d, J = 4.4 Hz, 1H), 8.86 (d, J = 7.1 Hz, 1H), 8.58 (s, 1H), 8.30-8.12 (m, 2H), 7.86-7.74 (m, 2H), 7.63 (s, 2H), 4.63 (q, J = 7.0 Hz, 1H), 2.70 (d, J = 12.9 Hz, 6H), 1.52 (d, J = 7.4 Hz, 3H) |
| 622 | 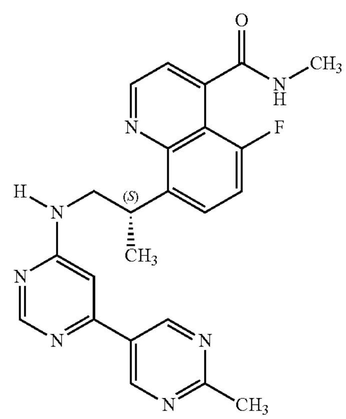 | 432.13 | (400 MHz, $CDCl_3$) δ 8.93 (s, 1H), 8.67 (s, 2H), 8.40 (s, 1H), 7.51 (s, 1H), 7.39 (s, 1H), 7.12 (d, J = 8.2 Hz, 1H), 6.17 (s, 1H), 5.85 (s, 1H), 4.39 (d, J = 5.3 Hz, 1H), 3.67 (s, 2H), 3.03 (d, J = 2.9 Hz, 3H), 2.72 (s, 3H), 1.88 (s, 1H) and 1.46 (d, J = 5.1 Hz, 3H) |
| 623 | 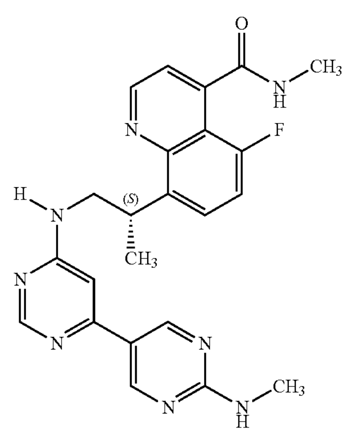 | 447.14 | (400 MHz, DMSO-$d_6$) δ 9.00 (d, J = 2.8 Hz, 2H), 8.84 (d, J = 3.6 Hz, 1H), 8.45 (s, 1H), 8.39 (s, 1H), 7.75 (s, 1H), 7.50-7.41 (m, 4H), 6.75 (s, 1 H), 4.43 (s, 1H), 3.70 (s, 2H), 2.86 (d, J = 2.6 Hz, 3H), 2.82 (d, J = 3.4 Hz, 3H) and 1.36 (d, J = 5.0 Hz, 3H) |

| Cmpnd No. | Structure | ESMS (M + H) | ¹H NMR (300 MHz, unless indicated otherwise) NMR peaks given as δ values |
|---|---|---|---|
| 624 | 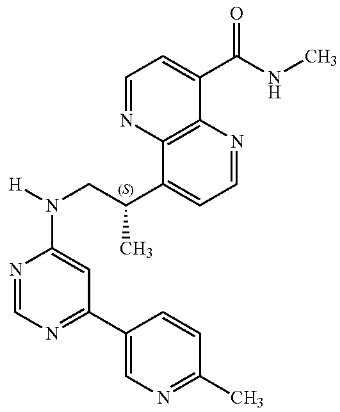 | 414 | (400 MHz, DMSO-d₆) δ 10.23 (s, 1H), 9.14 (d, J = 4.2 Hz, 1H), 9.01 (t, J = 15.1 Hz, 2H), 8.45 (s, 1H), 8.22 (t, J = 21.0 Hz, 2H), 7.85 (s, 1H), 7.55 (s, 1H), 7.36 (d, J = 7.1 Hz, 1H), 6.85 (s, 1H), 4.61-4.44 (m, 1H), 4.12-3.68 (m, 2H), 2.97 (d, J = 4.7 Hz, 3H), 2.52 (d, J = 4.2 Hz, 3H), 1.40 (d, J = 6.6 Hz, 3H) |
| 625 | 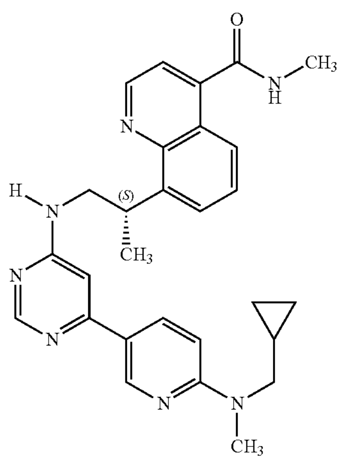 | 482.47 | |
| 626 | 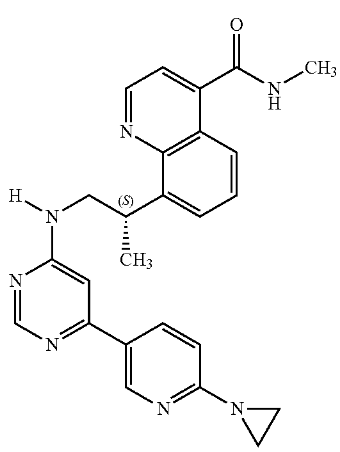 | 440.29 | |

TABLE 1-continued
| Cmpnd No. | Structure | ESMS (M + H) | ¹H NMR (300 MHz, unless indicated otherwise) NMR peaks given as δ values |
|---|---|---|---|
| 627 | 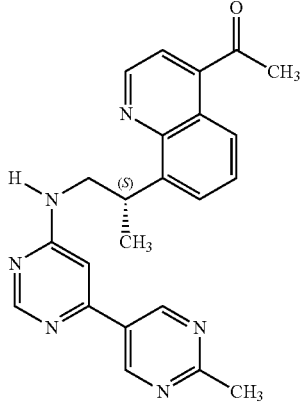 | 405.32 | (CDCl₃) δ 9.18 (s, 2H), 8.62 (s, 1H), 7.08 (d, J = 7.7 Hz, 1H), 6.93 (dd, J = 8.3, 7.3 Hz, 1H), 6.69 (s, 1H), 4.37 (t, J = 4.8 Hz, 2H), 3.96 (s, 2H), 3.58 (s, 3H), 2.84 (s, 3H), 2.33 (s, 3H), 1.38 (d, J = 6.0 Hz, 3H). |
| 628 | 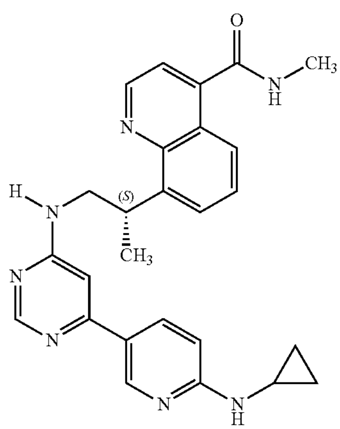 | 454.43 | |
| 629 | 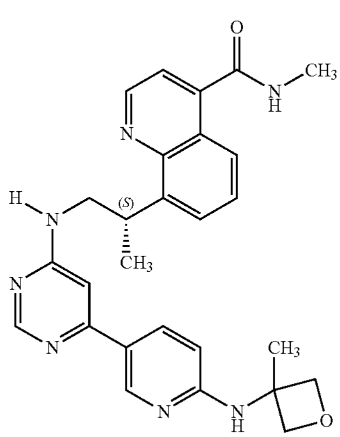 | 484.36 | |

TABLE 1-continued

| Cmpnd No. | Structure | ESMS (M + H) | ¹H NMR (300 MHz, unless indicated otherwise) NMR peaks given as δ values |
|---|---|---|---|
| 630 | 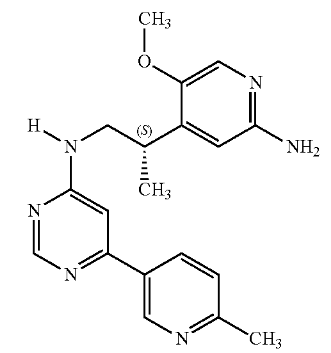 | 351.16 | (400 MHz, CDCl$_3$) δ 9.01 (s, 1H), 8.62 (s, 1H), 8.18 (d, 1H), 7.71 (s, 1H), 7.25 (d, J = 5.6 Hz, 1H), 6.68 (s, 1H), 6.41 (s, 1H), 5.25 (s, 1H), 4.16 (s, 2H), 3.83 (s, 3H), 3.59-3.38 (m, 3H), 2.62 (s, 3H), 1.30 (d, J = 6.8 Hz, 3H) |
| 631 | 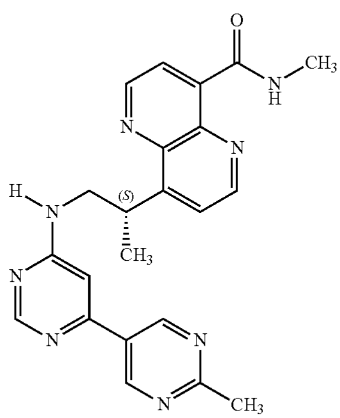 | 415 | (400 MHz, DMSO-d$_6$) δ 10.23 (s, 1H), 9.13 (d, J = 4.3 Hz, 3H), 9.02 (t, J = 8.8 Hz, 1H), 8.47 (s, 1H), 8.25 (d, J = 4.1 Hz, 1H), 7.84 (s, 1H), 7.65 (s, 1H), 6.88 (s, 1H), 4.53 (dd, J = 13.5, 6.6 Hz, 1H), 3.82 (s, 2H), 2.97 (d, J = 4.7 Hz, 3H), 2.68 (s, 3H), 1.40 (d, J = 6.3 Hz, 3H) |
| 632 | 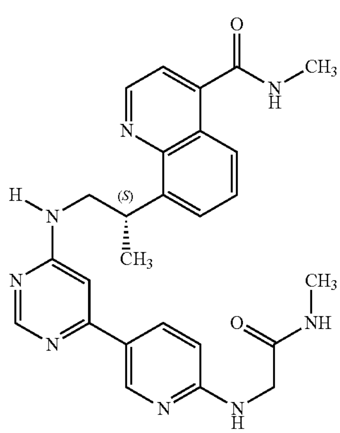 | 485.59 | |

TABLE 1-continued

| Cmpnd No. | Structure | ESMS (M + H) | ¹H NMR (300 MHz, unless indicated otherwise) NMR peaks given as δ values |
|---|---|---|---|
| 633 | 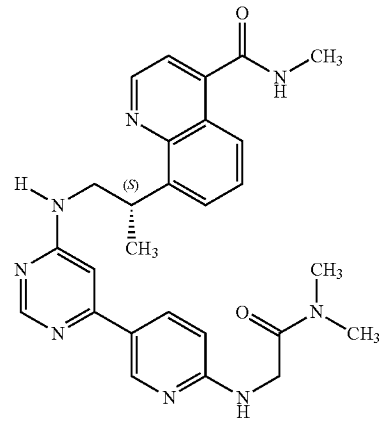 | 498.72 | |
| 634 | 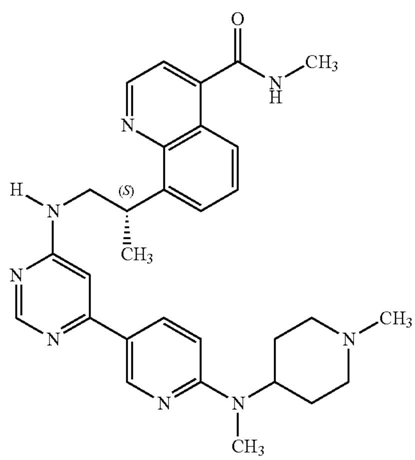 | 525.59 | |
| 635 | 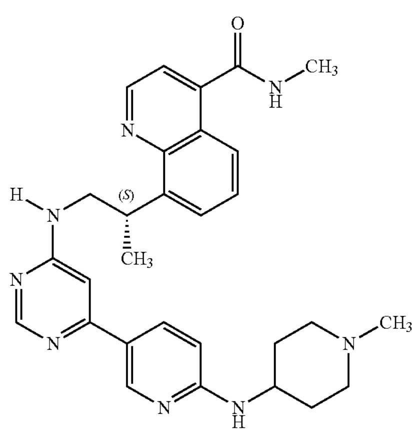 | 511.41 | |

TABLE 1-continued

| Cmpnd No. | Structure | ESMS (M + H) | ¹H NMR (300 MHz, unless indicated otherwise) NMR peaks given as δ values |
|---|---|---|---|
| 636 | 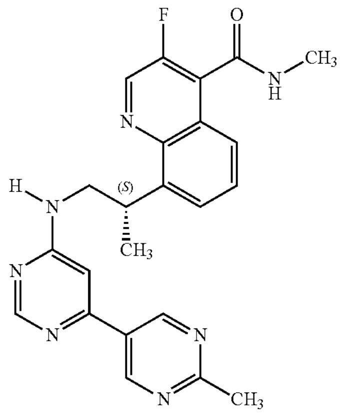 | 432.37 | (methanol-d₄) δ 9.30 (s, 2H), 9.03 (s, 1H), 8.61 (s, 1H), 8.30-7.72 (m, 3H), 6.98 (br.s, 1H), 4.78 (m, 2H), 4.00 (m, 1H), 3.20 (s, 3H), 2.92 (s, 3H), 1.64 (d, J = 6.1 Hz, 3H) |
| 637 | 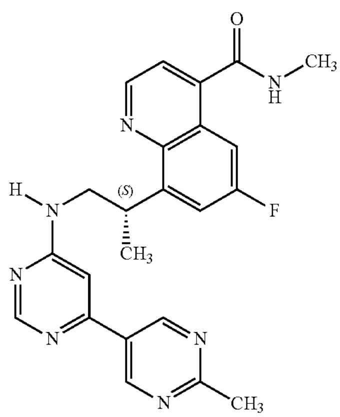 | 432 | (400 MHz, DMSO-d₆) δ 9.20 (d, J = 53.7 Hz, 2H), 8.96 (t, J = 10.2 Hz, 1H), 8.71 (d, J = 4.6 Hz, 1H), 8.50 (s, 1H), 7.71 (dd, J = 29.3, 27.0 Hz, 4H), 7.39-6.87 (m, 1H), 4.55 (d, J = 5.5 Hz, 1H), 3.91-3.40 (m, 2H), 2.86 (d, J = 4.6 Hz, 3H), 2.68 (s, 3H), 1.35 (t, J = 15.3 Hz, 3H) |
| 638 | 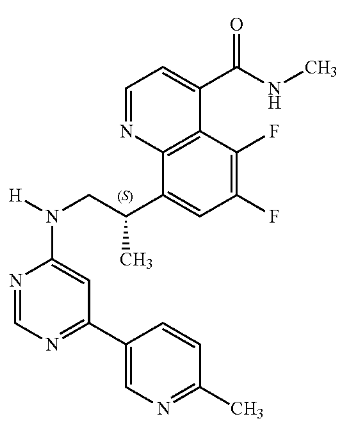 | 449.16 | (400 MHz, DMSO-d₆) δ 8.96 (d, J = 4.3 Hz, 2H), 8.53-8.48 (m, 2H), 8.16 (s, 1H), 7.93 (s, 1H), 7.57 (s, 2H), 7.38 (s, 1H), 6.87 (s, 1H), 4.51 (d, J = 6.9 Hz, 1H), 3.33 (d, J = 8.9 Hz, 2H), 2.83 (d, J = 4.6 Hz, 3H), 2.53 (s, 3H) and 1.36 (d, J = 6.6 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 639 | 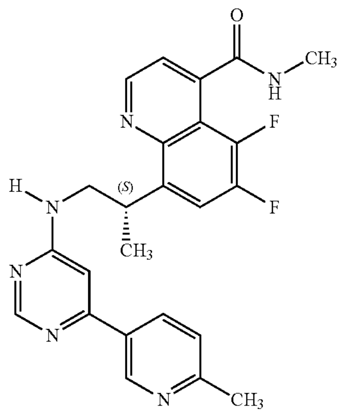 | 449.23 | (400 MHz, DMSO-d₆) δ 9.32 (d, J = 4.7 Hz, 1H), 9.13 (s, 1H), 8.96 (d, J = 4.1 Hz, 1H), 8.52-8.50 (m, 2H), 7.93 (s, 1H), 7.61 (s, 1H), 7.56 (s, 1H), 6.90 (s, 1H), 4.52 (d, J = 6.2 Hz, 1H), 3.77 (s, 2H), 2.83 (d, J = 4.5 Hz, 3H), 2.68 (s, 3H) and 1.36 (d, J = 6.1 Hz, 3H) |
| 640 | 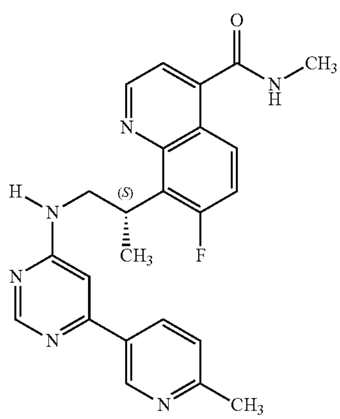 | 431.12 | |
| 641 | 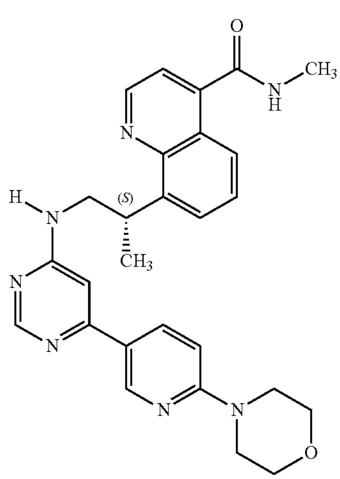 | 484.41 | |

| Cmpnd No. | Structure | ESMS (M + H) | ¹H NMR (300 MHz, unless indicated otherwise) NMR peaks given as δ values |
|---|---|---|---|
| 642 | 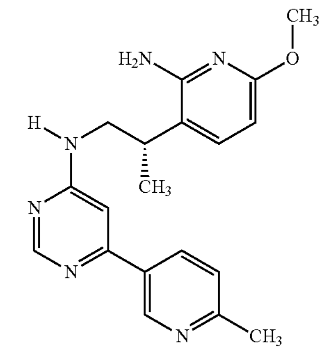 [SMILES: COc1ccc([C@H](C)CNc2cc(-c3ccc(C)nc3)ncn2)c(N)n1] | 351.43 | (CDCl₃) δ 9.02 (d, J = 2.3 Hz, 1H), 8.61 (s, 1H), 8.20 (dd, J = 8.1, 2.4 Hz, 1H), 7.34-7.22 (m, 1H), 6.67 (s, 1H), 6.08 (d, J = 7.9 Hz, 1H), 5.22 (br. s, 1H), 4.24 (s, 2H), 3.89 (s, 3H), 3.61-3.19 (m, 3H), 2.64 (s, 3H), 1.76 (br. s, 2H), 1.30 (d, J = 7.0 Hz, 2H) |
| 643 | 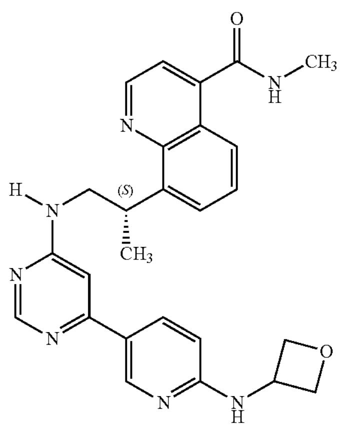 | 470.27 | |
| 644 | 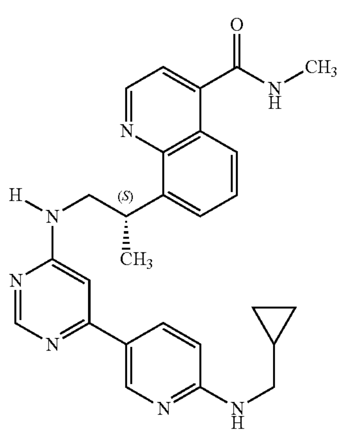 | 468.43 | |

TABLE 1-continued

| Cmpnd No. | Structure | ESMS (M + H) | $^1$H NMR (300 MHz, unless indicated otherwise) NMR peaks given as δ values |
|---|---|---|---|
| 645 | 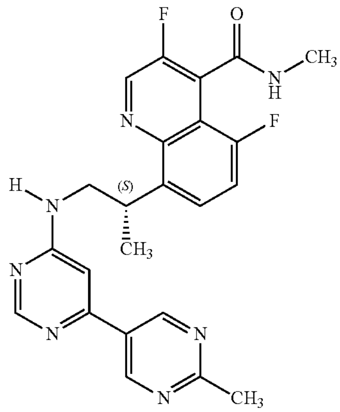 | 450.33 | (methanol-d$_4$) δ 9.12 (br. s, 2H), 8.91 (s, 1H), 8.40 (s, 1H), 7.70 (br. s, 1H), 7.36 (dd, J = 11.4, 8.2 Hz, 1H), 6.83 (br. s, 1H), 4.49 (q, J = 7.4 Hz, 1H), 3.81 (m, 2H), 2.99 (s, 3H), 2.75 (s, 3H), 1.44 (d, J = 7.1 Hz, 3H) |
| 646 | 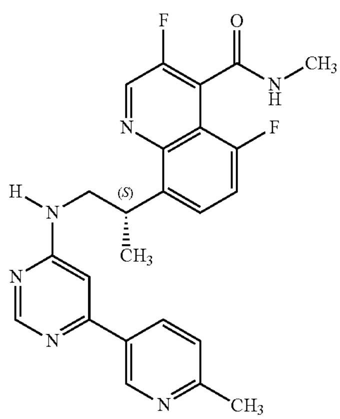 | 449.43 | (methanol-d$_4$) δ 8.92 (s, 1H), 8.87 (s, 1H), 8.41 (s, 1H), 8.19 (br. s, 1H), 7.71 (t, J = 7.1 Hz, 1H), 7.39 (m, 2H), 6.74 (br. s, 1H), 4.52 (m, 1H), 3.71 (m, 2H), 2.98 (s, 3H), 2.60 (s, 3H), 1.46 (d, J = 6.7 Hz, 3H) |
| 647 | 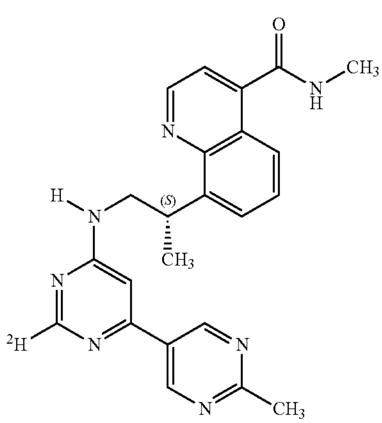 | 415.36 | |

TABLE 1-continued

| Cmpnd No. | Structure | ESMS (M + H) | ¹H NMR (300 MHz, unless indicated otherwise) NMR peaks given as δ values |
|---|---|---|---|
| 648 | 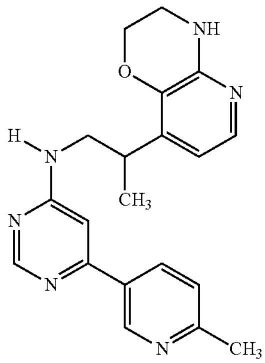 [SMILES: Cc1ccc(-c2cc(NCC(C)c3ccnc4c3OCCN4)ncn2)cn1] | 363.32 | (methanol-d₄) δ 8.91 (s, 1H), 8.45 (s, 1H), 8.20 (dd, J = 8.5, 2.3 Hz, 1H), 7.47 (d, J = 5.4 Hz, 1H), 7.42 (d, J = 8.2 Hz, 1H), 6.86 (s, 1H), 6.55 (d, J = 5.5 Hz, 1H), 4.13 (t, J = 4.5 Hz, 2H), 3.84-3.50 (m, 3H), 3.46 (dd, J = 5.3, 3.7 Hz, 2H), 2.59 (s, 3H), 1.27 (d, J = 5.8 Hz, 3H) |
| 649 | 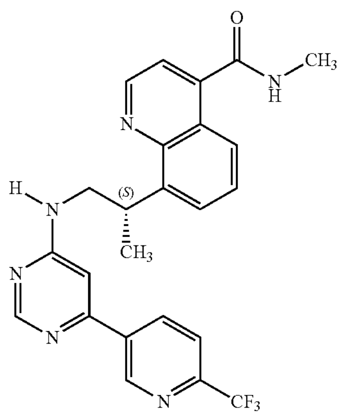 | 467.73 | (DMSO-d₆) δ 9.25 (s, 1H), 8.98 (d, J = 4.3 Hz, 1H), 8.68 (m, 1H), 8.55 (m, 2H), 7.99 (m, 2H), 7.77 (m, 2H), 7.64 (t, J = 8.0 Hz, 1H), 7.54 (s, 1H), 7.03 (s, 1H), 4.53 (m, 1H), 3.81 (m, 2H), 2.87 (d, J = 4.5 Hz, 3H), 1.39 (d, 3H) |
| 650 | 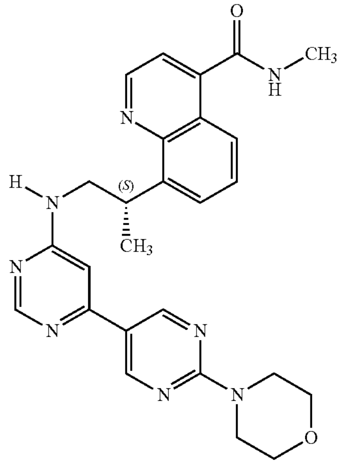 | 485.82 | (DMSO-d₆) δ 8.98 (d, J = 4.3 Hz, 1H), 8.90 (s, 1H), 8.67 (d, J = 4.6 Hz, 1H), 8.42 (s, 1H), 7.99 (d, J = 8.3 Hz, 1H), 7.77 (s, 1H), 7.63 (t, J = 7.8 Hz, 1H), 7.54 (m, 2H), 4.51 (m, 2H), 3.90-3.61 (m, 10H), 2.87 (d, J = 4.6 Hz, 3H), 1.36 (d, J = 6.9 Hz, 3H) |

TABLE 1-continued
| Cmpnd No. | Structure | ESMS (M + H) | ¹H NMR (300 MHz, unless indicated otherwise) NMR peaks given as δ values |
|---|---|---|---|
| 651 | 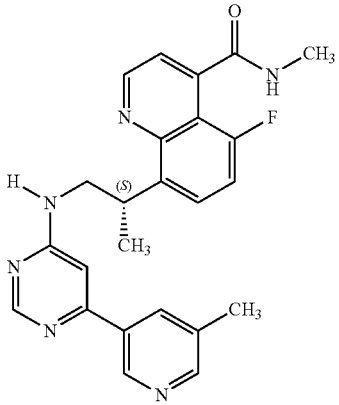 | 431.12 | (400 MHz, CDCl₃) δ 8.92 (s, 1H), 8.35 (s, 2H), 8.00 (s, 1H), 7.69-7.32 (m, 4H), 7.07 (t, J = 8.9 Hz, 1H), 6.04 (s, 1H), 5.86 (s, 1H), 4.38 (dd, J = 5.8, 12.0 Hz, 1H), 3.67 (t, J = 5.8 Hz, 2H), 2.99 (d, J = 4.7 Hz, 3H), 2.30 (s, 3H) and 1.46 (d, J = 6.8 Hz, 3H) |
| 652 | 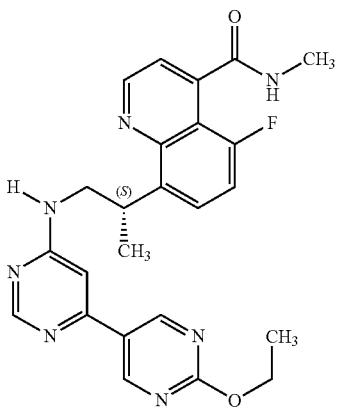 | 462.19 | (400 MHz, CDCl₃) δ 8.93 (d, J = 2.6 Hz, 1H), 8.60 (s, 2H), 8.36 (s, 1H), 7.52-7.49 (m, 1H), 7.38 (s, 1H), 7.12-7.08 (m, 2H), 6.21 (s, 1H), 5.80 (s, 1H), 4.45-4.36 (m, 3H), 3.64 (s, 2H), 3.01 (d, J = 4.8 Hz, 3H), 1.45 (d, J = 7.0 Hz, 3H) and 1.39 (t, J = 7.1 Hz, 3H) |
| 653 | 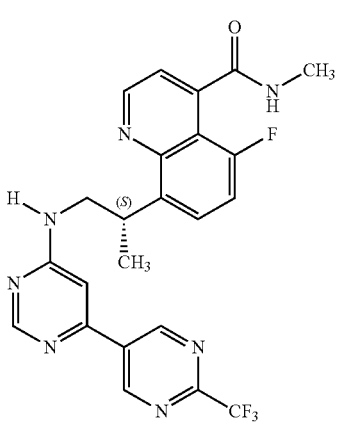 | 486.31 | (400 MHz, CDCl₃) δ 8.95 (s, 1H), 8.49 (s, 1H), 7.55 (s, 1H), 7.43 (s, 1H), 7.15 (s, 1H), 6.38 (s, 1H), 5.84 (s, 1H), 4.42 (q, J = 6.6 Hz, 1H), 3.68 (s, 2H), 2.98 (s, 3H), 1.59 (s, 3H) and 1.47 (d, J = 6.6 Hz, 3H) |

| Cmpnd No. | Structure | ESMS (M + H) | ¹H NMR (300 MHz, unless indicated otherwise) NMR peaks given as δ values |
|---|---|---|---|
| 654 | 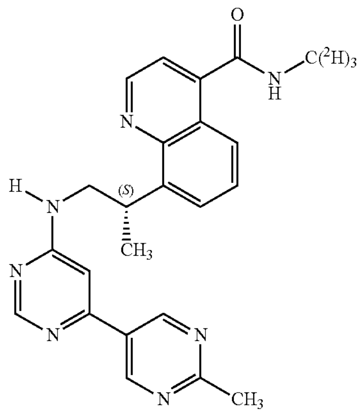 | 417 | (400 MHz, DMSO-d₆) δ 9.23 (d, J = 68.9 Hz, 2H), 8.98 (d, J = 4.3 Hz, 1H), 8.64 (s, 1H), 8.51 (s, 1H), 8.00 (d, J = 7.9 Hz, 1H), 7.75 (s, 1H), 7.66-7.56 (m, 2H), 7.40 (t, J = 7.2 Hz, 1H), 7.03 (d, J = 61.5 Hz, 1H), 4.52 (s, 1H), 3.59 (d, J = 162.7 Hz, 2H), 2.69 (s, 3H), 1.38 (s, 3H) |
| 655 | 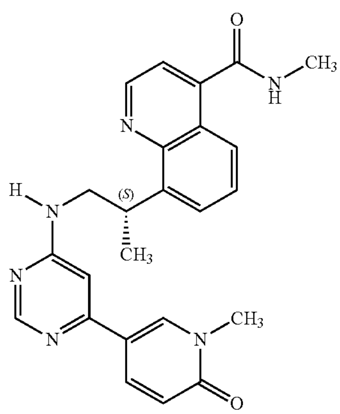 | 429 | (400 MHz, DMSO-d₆) δ 8.98 (d, J = 4.3 Hz, 1H), 8.67 (d, J = 4.8 Hz, 1H), 8.47 (s, 1H), 8.37 (s, 1H), 7.99 (d, J = 8.1 Hz, 1H), 7.75 (s, 1H), 7.63 (t, J = 7.7 Hz, 1H), 7.49 (d, J = 36.2 Hz, 2H), 6.69 (s, 1H), 6.50 (s, 1H), 4.50 (s, 1H), 3.70 (s, 2H), 3.52 (s, 3H), 2.87 (d, J = 4.6 Hz, 3H), 1.36 (s, 3H) |
| 656 | 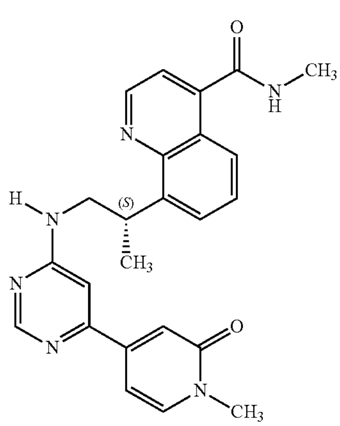 | 429 | (400 MHz, DMSO-d₆) δ 8.98 (s, 1H), 8.68 (s, 1H), 8.44 (d, J = 35.7 Hz, 1H), 7.99 (d, J = 8.4 Hz, 1H), 7.89-6.51 (m, 8H), 4.50 (s, 1H), 3.75 (s, 2H), 3.42 (d, J = 22.6 Hz, 3H), 2.87 (d, J = 4.5 Hz, 3H), 1.38 (s, 3H) |

| Cmpnd No. | Structure | ESMS (M + H) | ¹H NMR (300 MHz, unless indicated otherwise) NMR peaks given as δ values |
|---|---|---|---|
| 657 | 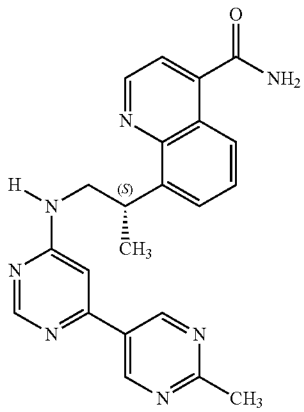 | | (400 MHz, DMSO-d₆) δ 9.23 (d, J = 68.7 Hz, 2H), 8.97 (d, J = 4.3 Hz, 1H), 8.51 (s, 1H), 8.20 (s, 1H), 8.06 (d, J = 8.4 Hz, 1H), 7.90 (s, 1H), 7.65 (t, J = 41.9 Hz, 4H), 7.44-6.89 (m, 1H), 4.48 (d, J = 32.8 Hz, 1H), 3.94-3.38 (m, 2H), 2.68 (s, 3H), 1.38 (s, 3H) |
| 658 | 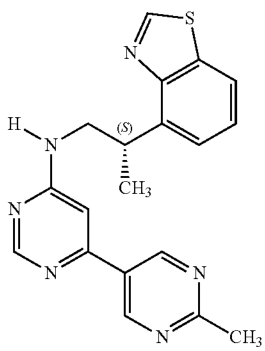 | 363 | (400 MHz, DMSO-d₆) δ 9.41-9.08 (m, 3H), 8.53 (s, 1H), 8.11-7.95 (m, 1H), 7.71 (d, J = 50.7 Hz, 1H), 7.45 (s, 2H), 7.37-6.87 (m, 1H), 4.02 (s, 1H), 3.91-3.37 (m, 2H), 2.69 (s, 3H), 1.41 (s, 3H) |
| 659 | 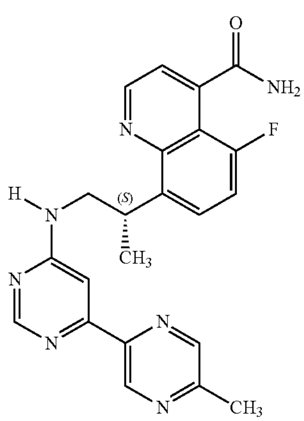 | 432.38 | (400 MHz, CDCl₃) δ 9.27 (s, 1H), 8.94 (s, 1H), 8.42 (d, J = 1.1 Hz, 2H), 7.56 (dd, J = 5.9, 7.8 Hz, 1H), 7.33 (d, J = 3.4 Hz, 1H), 7.13 (s, 1 H), 6.50 (s, 1H), 6.39 (s, 1H), 6.08 (s, 1H), 4.45 (q, J = 6.9 Hz, 1H), 3.41 (m, 2H), 3.02 (d, J = 4.8 Hz, 3H), 2.58 (s, 3H) and 1.44 (d, J = 6.9 Hz, 3H) |
| 660 | 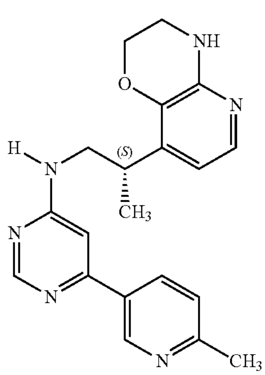 | 363.16 | (methanol-d₄) δ 8.92 (s, 1H), 8.45 (s, 1H), 8.21 (d, J = 8.1 Hz, 1H), 7.47 (d, J = 5.4 Hz, 1H), 7.42 (d, J = 8.2 Hz, 1H), 6.86 (s, 1H), 6.55 (d, J = 5.4 Hz, 1H), 4.13 (t, J = 4.5 Hz, 2H), 3.77-3.44 (m, 5H), 2.59 (s, 3H), 1.27 (d, J = 6.0 Hz, 3H) |

| Cmpnd No. | Structure | ESMS (M + H) | ¹H NMR (300 MHz, unless indicated otherwise) NMR peaks given as δ values |
|---|---|---|---|
| 661 | 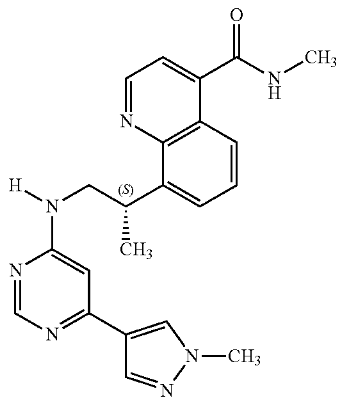 | 402 | (400 MHz, DMSO-d₆) δ 8.98 (d, J = 4.1 Hz, 1H), 8.67 (d, J = 4.4 Hz, 1H), 8.31 (s, 1H), 8.19 (s, 1H), 7.98 (d, J = 8.4 Hz, 1H), 7.81 (d, J = 45.6 Hz, 2H), 7.63 (t, J = 7.8 Hz, 1H), 7.53 (s, 1H), 7.32 (s, 1H), 6.56 (s, 1H), 4.44 (d, J = 34.6 Hz, 1H), 3.87 (s, 3H), 3.69 (s, 2H), 2.87 (d, J = 4.6 Hz, 3H), 1.36 (d, J = 6.5 Hz, 3H) |
| 662 | 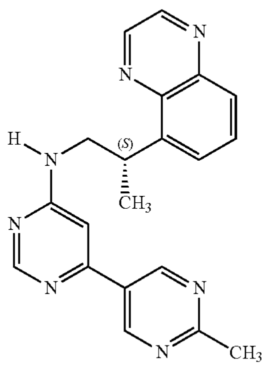 | 358 | (400 MHz, DMSO-d₆) δ 9.21 (d, J = 64.0 Hz, 2H), 8.95 (d, J = 1.7 Hz, 2H), 8.49 (s, 1H), 7.97 (d, J = 9.8 Hz, 1H), 7.91-7.56 (m, 3H), 7.32-6.82 (m, 1H), 4.44 (s, 1H), 3.94-3.38 (m, 2H), 2.68 (s, 3H), 1.40 (s, 3H) |
| 663 | 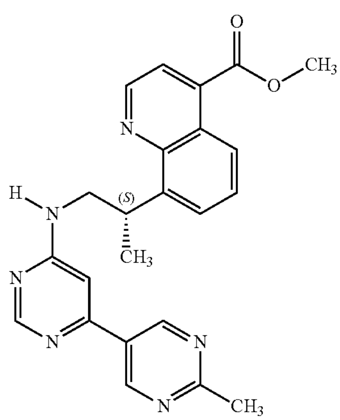 | 415.39 | (CDCl₃) δ 9.17 (s, 2H), 9.09 (d, J = 4.4 Hz, 1H), 8.64 (dd, J = 8.5, 1.5 Hz, 1H), 8.60 (s, 1H), 7.95 (d, J = 4.4 Hz, 1H), 7.74 (dd, J = 7.3, 1.5 Hz, 1H), 7.66 (dd, J = 8.4, 7.2 Hz, 1H), 6.93 (s, 1H), 5.82 (s, 1H), 4.66 (q, J = 7.1 Hz, 1H), 4.06 (s, 3H), 3.79 (dt, J = 13.1, 6.8 Hz, 1H), 3.61 (s, 1H), 2.86 (t, J = 0.8 Hz, 3H), 1.56 (d, J = 7.0 Hz, 3H) |
| 664 | 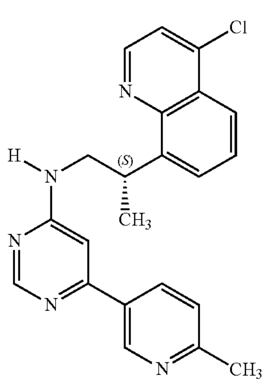 | 388.93 | (CDCl₃) δ 9.18 (s, 2H), 8.87 (d, J = 4.7 Hz, 1H), 8.66-8.50 (m, 1H), 8.19 (dd, J = 8.3, 1.5 Hz, 1H), 7.75 (dd, J = 7.3, 1.6 Hz, 1H), 7.66 (dd, J = 8.3, 7.3 Hz, 1H), 7.59 (d, J = 4.6 Hz, 1H), 6.9 (br s, 1H), 5.86 (br. s, 1H), 4.63 (q, J = 7.1 Hz, 1H), 3.79 (dt, J = 13.1, 6.7 Hz, 1H), 3.6 (br. s, 1H), 2.83 (s, 3H), 1.56 (d, J = 7.0 Hz, 3H) |

| Cmpnd No. | Structure | ESMS (M + H) | ¹H NMR (300 MHz, unless indicated otherwise) NMR peaks given as δ values |
|---|---|---|---|
| 665 | 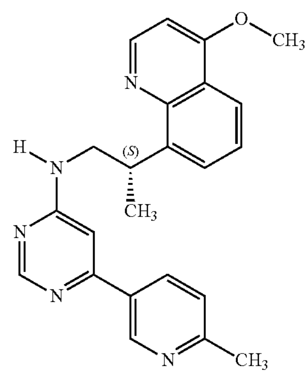 | 385.78 | (CDCl₃) δ 9.15 (s, 2H), 8.88 (d, J = 5.2 Hz, 1H), 8.58 (s, 1H), 8.14 (dd, J = 8.3, 1.5 Hz, 1H), 7.69 (d, J = 7.2 Hz, 1H), 7.52 (t, J = 7.8 Hz, 1H), 6.86 (d, J = 5.2 Hz, 1H), 6.2 (br. s, 1H), 4.71-4.49 (m, 1H), 3.73 (dt, J = 13.1, 6.8 Hz, 1H), 3.49 (d, J = 10.4 Hz, 1H), 2.83 (s, 3H), 1.55 (d, J = 7.1 Hz, 3H) |
| 666 | 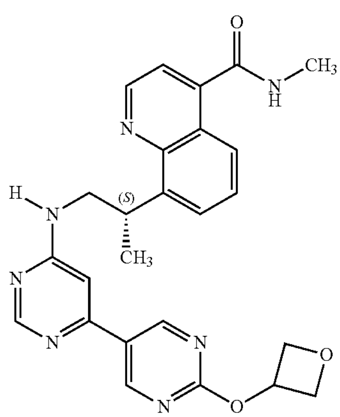 | 472.27 | (DMSO-d₆) δ 9.08 (m, 2H), 8.96 (d, J = 4.3 Hz, 1H), 8.65 (d, J = 5.0 Hz, 1H), 8.47 (s, 1H), 7.99 (d, J = 8.9 Hz, 1H), 7.77 (m, 1H), 7.63 (t, J = 7.7 Hz 1H), 7.54 (m, 1H), 6.8 (s, 1H), 5.64 (m, 1H), 4.92 (t, J = 6.9 Hz, 2H), 4.63 (m, 2H), 4.52 (m, 1H), 3.76 (m, 2H), 2.87 (d, J = 4.6 Hz, 3H), 1.37 (d, J = 6.9 Hz, 3H) |
| 667 | 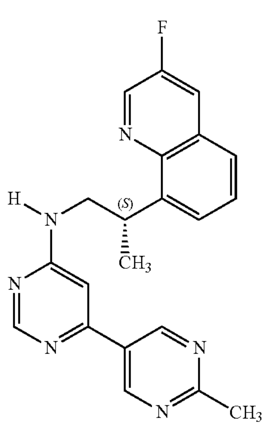 | 375.09 | (methanol-d₄) δ 9.12 (s, 1H), 9.02 (s, 1H), 8.82 (s, 1H), 8.66, 8.57 (2s, 1H), 8.00 (dd, J = 9.2, 2.9 Hz, 1H), 7.81 (dd, J = 8.1, 1.5 Hz, 1H), 7.70 (d, J = 7.4 Hz, 1H), 7.61 (t, J = 7.7 Hz, 1H), 7.36, 6.86 (2s, 1H), 4.58 (q, J = 7.1 Hz, 1H), 4.14-3.86 (m, 2H), 2.84, 2.78 (2s, 3H), 1.51 (d, J = 7.2 Hz, 3H) |

TABLE 1-continued

| Cmpnd No. | Structure | ESMS (M + H) | $^1$H NMR (300 MHz, unless indicated otherwise) NMR peaks given as δ values |
|---|---|---|---|
| 668 | 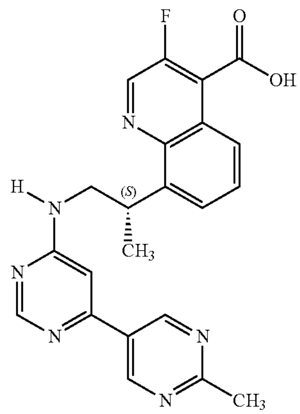 | 419.11 | (methanol-$d_4$) δ 9.08 (s, 1H), 9.01 (s, 1H), 8.89 (s, 1H), 8.59 (s, 1H), 7.96 (d, J = 10.6 Hz, 2H), 7.67 (t, J = 7.7 Hz, 1H), 7.13, 6.80 (2s, 1H), 4.62 (q, J = 7.1 Hz, 1H), 4.05 (m, 2H), 2.60 (s, 3H), 1.52 (d, J = 7.4 Hz, 3H) |
| 669 | 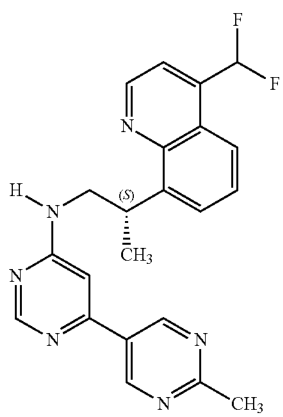 | 407 | (400 MHz, DMSO-$d_6$) δ 9.13 (dd, J = 46.6, 24.4 Hz, 3H), 8.50 (s, 1H), 8.05 (d, J = 7.5 Hz, 1H), 7.71 (ddd, J = 57.0, 44.1, 24.1 Hz, 5H), 7.07 (d, J = 112.0 Hz, 1H), 4.54 (s, 1H), 3.93-3.35 (m, 2H), 2.68 (s, 3H), 1.39 (s, 3H) |
| 670 | 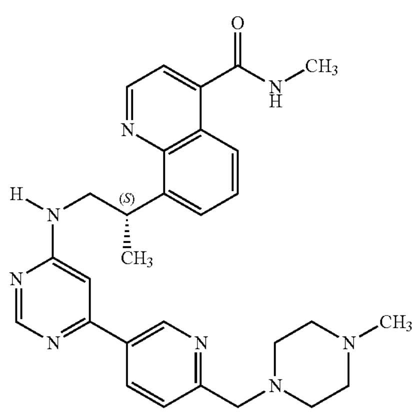 | 511.33 | (DMSO-$d_6$) δ 8.98 (m, 2H), 8.65 (m, 1H), 8.48 (s, 1H), 8.27 (m, 1H), 7.99 (dd, J = 8.4, 1.3 Hz, 1H), 7.77 (m, 1H), 7.69-7.49 (m, 3H), 7.00 (m, 1H), 4.52 (m, 1H), 3.64 (m, 4H), 2.87 (d, J = 4.5 Hz, 3H), 2.39 (m, 6H), 2.15 (s, 3H), 1.38 (d, J = 7.0 Hz, 3H) |

| Cmpnd No. | Structure | ESMS (M + H) | ¹H NMR (300 MHz, unless indicated otherwise) NMR peaks given as δ values |
|---|---|---|---|
| 671 | 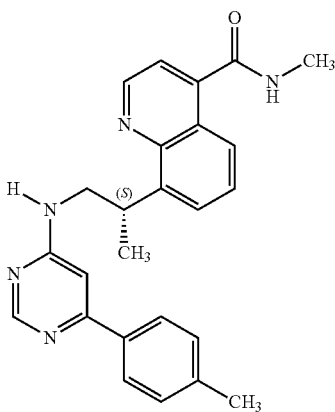 | 412.39 | (DMSO-d$_6$) δ 8.96 (d, J = 4.2 Hz, 1H), 8.66 (m, 2H), 8.06-7.97 (m, 1H), 7.76 (m, 3H), 7.64 (t, J = 7.8 Hz, 1H), 7.55 (m, 1H), 7.41 (m, 2H), 6.89 (s, 1H), 4.54 (m, 1H), 3.75 (m, 2H), 2.87 (d, J = 4.5 Hz, 3H), 2.40 (s, 3H), 1.41 (d, J = 6.9 Hz, 3H) |
| 672 | 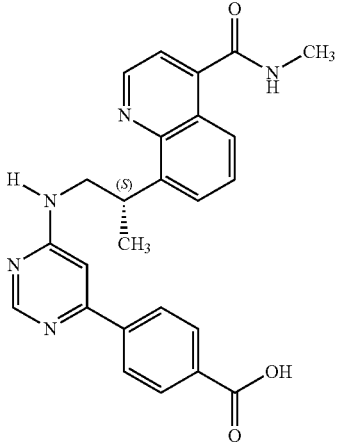 | 442.32 | (DMSO-d$_6$) δ 9.65 (m, 1H), 9.01-8.87 (m, 1H), 8.79 (s, 1H), 8.69 (m, 1H), 8.11 (m, 4H), 7.93 (d, J = 8.2 Hz, 1H), 7.89-7.73 (m, 1H), 7.65 (t, J = 7.8 Hz, 1H), 7.55 (m, 1H), 7.07 (s, 1H), 4.60 (m, 1H), 3.95 (m, 2H), 2.87 (d, J = 4.5 Hz, 3H), 1.42 (d, J = 6.8 Hz, 3H) |
| 673 | 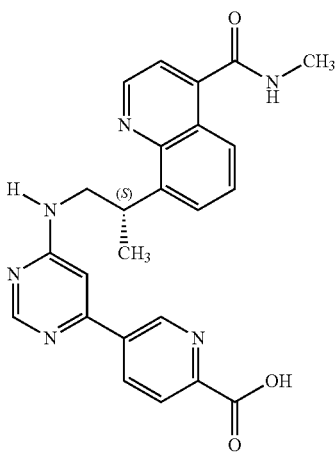 | 443.27 | (DMSO-d$_6$) δ 9.13 (m, 1H), 8.97 (m, 1H), 8.67 (m, 2H), 8.38 (m, 1H), 8.21 (m, 1H), 8.01 (dd, J = 8.3, 1.3 Hz, 1H), 7.79 (m, 1H), 7.69-7.60 (m, 1H), 7.55 (m, 1H), 7.03 (s, 1H), 4.54 (m, 1H), 3.80 (m, 2H), 2.87 (d, J = 4.6 Hz, 3H), 1.40 (d, J = 7.1 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 674 | 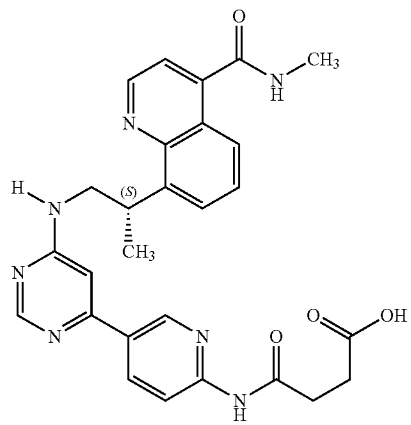 | 513.26 | (DMSO-d$_6$) δ.10.38 (s, 1H), 9.24 (s, 1H), 8.96 (m, 1H), 8.66 (m, 1H), 8.02 (d, J = 8.3 Hz, 1H), 7.97-7.73 (m, 5H), 7.64 (t, J = 7.9 Hz, 1H), 7.54 (d, J = 4.9 Hz, 1H), 6.87 (s, 1H), 4.55 (m, 1H), 3.97 (m, 2H), 2.87 (d, J = 4.5 Hz, 3H), 2.70-2.52 (m, 4H), 1.41 (d, J = 7.2 Hz, 3H) |
| 675 | 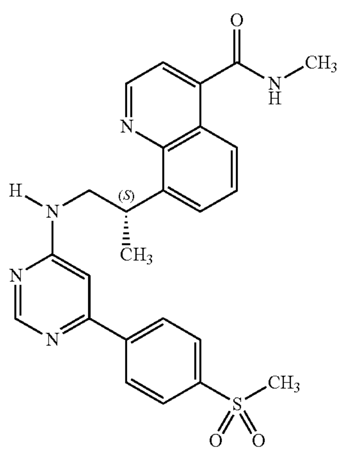 | 476.22 | (DMSO-d$_6$) δ.8.98 (d, J = 4.3 Hz, 1H), 8.65 (d, J = 4.8 Hz, 1H), 8.52 (s, 1H), 8.19 (m, 2H), 8.07-7.96 (m, 2H), 7.77 (m, 1H), 7.63 (t, J = 7.8 Hz, 1H), 7.54 (m, 1H), 7.01 (s, 1H), 4.52 (s, 1H), 3.75 (m, 2H), 3.26 (s, 3H), 2.87 (d, J = 4.6 Hz, 3H), 1.39 (d, J = 6.9 Hz, 3H) |
| 676 | 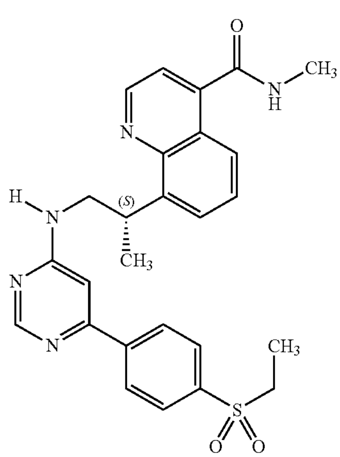 | 490.22 | (DMSO-d$_6$) δ.8.98 (d, J = 4.3 Hz, 1H), 8.65 (d, J = 5.3 Hz, 1H), 8.52 (s, 1H), 8.20 (m, 2H), 8.00 (d, J = 8.2 Hz, 3H), 7.77 (m, 1H), 7.63 (t, J = 7.8 Hz, 1H), 7.54 (s, 1H), 7.01 (s, 1H), 4.52 (m, 1H), 3.76 (m, 2H), 3.40 (q, 2H), 2.87 (d, J = 4.5 Hz, 3H), 1.39 (d, J = 6.9 Hz, 3H), 1.13 (t, J = 7.3 Hz, 3H) |

| Cmpnd No. | Structure | ESMS (M + H) | ¹H NMR (300 MHz, unless indicated otherwise) NMR peaks given as δ values |
|---|---|---|---|
| 677 | 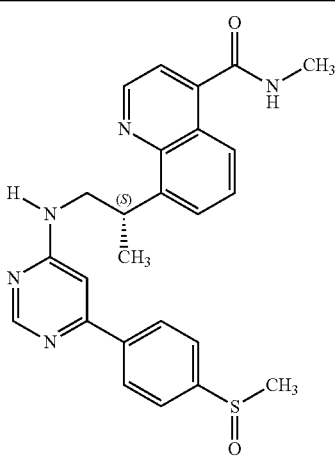 | 460.28 | (DMSO-d₆) δ 8.96 (d, J = 4.2 Hz, 1H), 8.67 (m, 2H), 8.01 (m, 3H), 7.83 (m, 3H), 7.72-7.49 (m, 3H), 6.97 (s, 1H), 4.62-4.48 (m, 1H), 3.80 (m, 2H), 2.91-2.76 (6H), 1.41 (d, J = 6.9 Hz, 3H) |
| 678 | 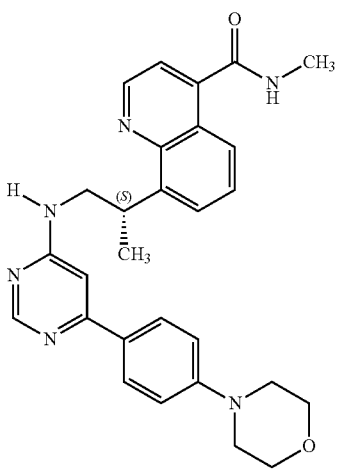 | 483.28 | (DMSO-d₆) δ 9.00 (d, J = 4.3 Hz, 1H), 8.65 (s, 1H), 8.39 (s, 1H), 7.99 (d, J = 8.6 Hz, 1H), 7.88 (s, 1H), 7.77 (d, J = 7.2 Hz, 1H), 7.68-7.59 (m, 1H), 7.58-7.50 (m, 1H), 7.34 (s, 1H), 7.02 (d, J = 8.6 Hz, 2H), 4.51 (m, 1H), 3.74 (m, 5H), 3.26-3.13 (m, 5H), 2.87 (d, 3H), 1.38 (d, J = 7.0 Hz, 3H) |
| 679 | 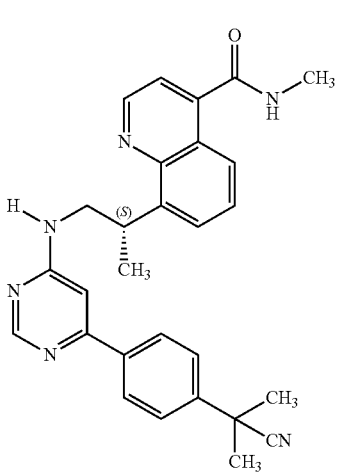 | 465.32 | (DMSO-d₆) δ 8.98 (d, J = 4.3 Hz, 1H), 8.65 (d, J = 5.2 Hz, 1H), 8.47 (s, 1H), 8.00 (d, J = 8.4 Hz, 2H), 7.77 (d, J = 7.3 Hz, 1H), 7.64 (m, 3H), 7.54 (m, 2H), 6.93 (s, 1H), 4.51 (m, 1H), 3.75 (m, 2H), 2.87 (d, J = 4.4 Hz, 3H), 1.72 (s, 6H), 1.38 (d, J = 6.9 Hz, 3H) |

… TABLE 1-continued
| Cmpnd No. | Structure | ESMS (M + H) | $^1$H NMR (300 MHz, unless indicated otherwise) NMR peaks given as δ values |
|---|---|---|---|
| 680 | 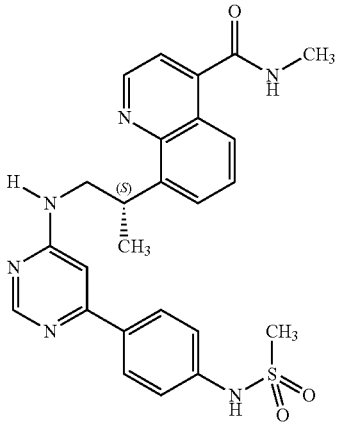 | 491.21 | (DMSO-d$_6$) δ.10.28 (s, 1H), 8.95 (m, 1H), 8.71-8.56 (m, 2H), 8.01 (dd, J = 8.4, 1.4 Hz, 1H), 7.80 (m, 2H), 7.70-7.58 (m, 1H), 7.54 (d, J = 4.3 Hz, 1H), 7.37 (m, 2H), 6.87 (s, 1H), 4.54 (m, 1H), 3.80 (m, 2H), 3.12 (s, 3H), 2.87 (d, J = 4.5 Hz, 3H), 1.40 (d, J = 6.9 Hz, 3H) |
| 681 | 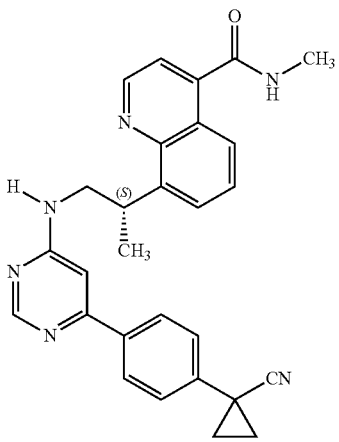 | 463.21 | (DMSO-d$_6$) δ.8.98 (d, J = 4.3 Hz, 1H), 8.65 (m, 1H), 8.46 (s, 1H), 8.06-7.95 (m, 2H), 7.77 (d, J = 7.0 Hz, 1H), 7.68-7.58 (m, 1H), 7.54 (m, 2H), 7.44 (m, 2H), 6.92 (s, 1H), 4.50 (m, 1H), 3.75 (m, 2H), 2.87 (d, J = 4.5 Hz, 3H), 1.81 (m, 2H), 1.59 (m, 2H), 1.38 (d, J = 6.9 Hz, 3H) |
| 682 | 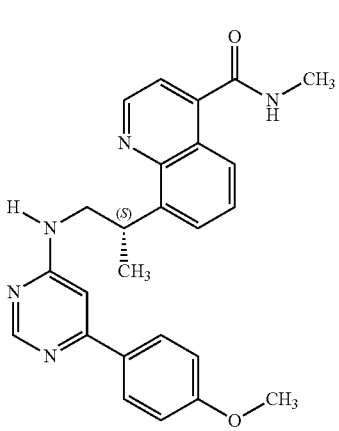 | 428.28 | (DMSO-d$_6$) δ.8.99 (d, J = 4.3 Hz, 1H), 8.65 (d, J = 5.4 Hz, 1H), 8.43 (s, 1H), 7.99 (d, J = 8.4 Hz, 1H), 7.84-7.71 (m, 2H), 7.67-7.59 (m, 1H), 7.54 (m, 2H), 7.05 (d, J = 8.3 Hz, 2H), 4.51 (m, 1H), 3.79 (m, 5H), 2.87 (d, J = 4.6 Hz, 3H), 1.38 (d, J = 6.9 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 683 | 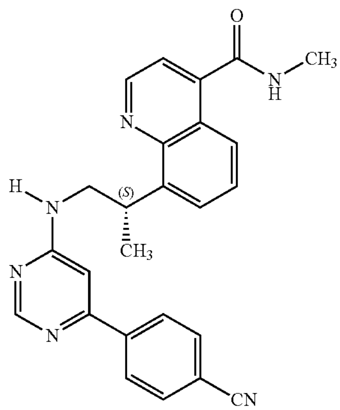 | 423.28 | (DMSO-d$_6$) δ 8.98 (d, J = 4.3 Hz, 1H), 8.65 (d, J = 5.3 Hz, 1H), 8.51 (s, 1H), 8.12 (m, 2H), 7.99 (m, 3H), 7.76 (m, 1H), 7.66-7.58 (m, 1H), 7.54 (m, 1H), 6.99 (s, 1H), 4.52 (m, 1H), 3.76 (m, 2H), 2.87 (d, J = 4.4 Hz, 3H), 1.38 (d, J = 6.8 Hz, 3H) |
| 684 | 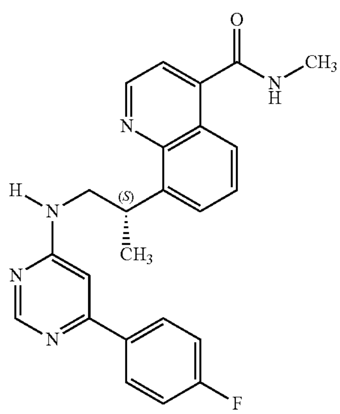 | 416.26 | (DMSO-d$_6$) δ 8.98 (d, J = 4.3 Hz, 1H), 8.65 (d, J = 5.2 Hz, 1H), 8.45 (s, 1H), 8.03-7.95 (m, 2H), 7.77 (m, 1H), 7.63 (t, J = 7.8 Hz, 1H), 7.54 (m, 2H), 7.32 (t, J = 8.8 Hz, 2H), 6.89 (s, 1H), 4.51 (m, 1H), 3.75 (m, 2H), 2.87 (d, J = 4.3 Hz, 3H), 1.38 (d, J = 6.9 Hz, 3H) |
| 685 | 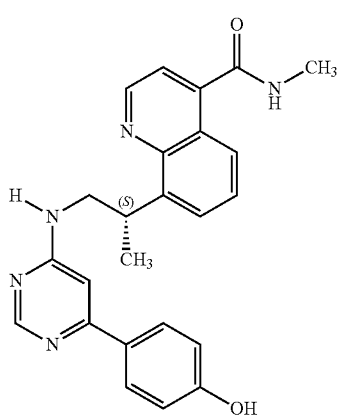 | 414.23 | (DMSO-d$_6$) δ 8.99 (d, J = 4.3 Hz, 1H), 8.65 (m, 1H), 8.36 (s, 1H), 7.99 (dd, J = 8.4, 1.4 Hz, 1H), 7.77 (m, 3H), 7.63 (m, 1H), 7.54 (d, J = 4.2 Hz, 1H), 7.29 (m, 1H), 6.74 (d, J = 8.4 Hz, 2H), 4.50 (m, 1H), 3.70 (m, 2H), 2.87 (d, J = 4.5 Hz, 3H), 1.37 (d, J = 6.9 Hz, 3H) |

| Cmpnd No. | Structure | ESMS (M + H) | ¹H NMR (300 MHz, unless indicated otherwise) NMR peaks given as δ values |
|---|---|---|---|
| 686 | 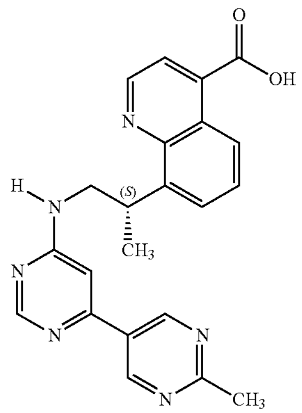 | 401.15 | (DMSO-d₆) δ.13.84 (br. s, 1H), 9.15 (br. s, 2H), 9.05 (d, J = 4.3 Hz, 1H), 8.51 (dd, J = 8.8, 1.6 Hz, 2H), 7.91 (d, J = 4.3 Hz, 1H), 7.86-7.75 (m, 1H), 7.69 (dd, J = 8.5, 7.2 Hz, 1H), 7.07 (m, 1H), 4.54 (q, J = 7.3 Hz, 1H), 3.78 (s, 2H), 2.69 (s, 3H), 1.39 (d, J = 6.9 Hz, 3H) |
| 687 | 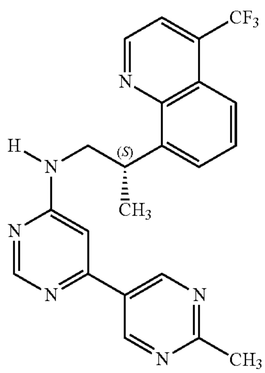 | 425.14 | (DMSO-d₆) δ.9.14 (d, J = 4.4 Hz, 3H), 8.47 (s, 1H), 7.98 (m, 2H), 7.90 (m, 1H), 7.85-7.75 (m, 1H), 7.62 (s, 1H), 6.92 (s, 1H), 4.54 (m, 1H), 3.80 (m, 2H), 2.68 (s, 3H), 1.40 (d, J = 6.9 Hz, 3H) |
| 688 | 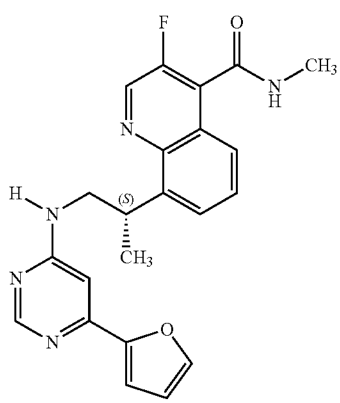 | 406.15 | (methanol-d₄) δ 9.00, 8.87 (2s, 1H), 8.45, 8.40 (2s, 1H), 8.07-7.59 (m, 5H), 7.34 (d, J = 3.7 Hz, 1H), 6.75 (d, J = 3.3 Hz, 2H), 4.59 (q, J = 7.0 Hz, 1H), 4.09 (dd, J = 13.4, 6.4 Hz, 1H), 3.96 (dd, J = 13.4, 7.7 Hz, 1H), 3.03 (s, 3H), 1.55, 1.49 (2d, J = 7.1 Hz, 3H) |
| 689 | 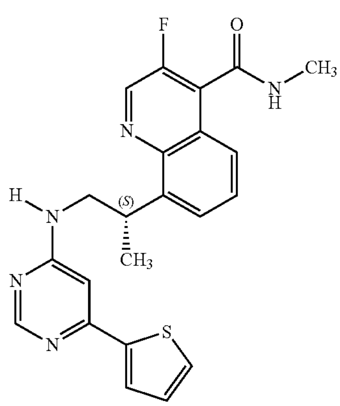 | 422.17 | (methanol-d₄) δ 8.87 (s, 1H), 8.46 (s, 1H), 8.10-7.45 (m, 5H), 7.39-7.14 (m, 1H), 6.70 (s, 1H), 4.58 (q, J = 7.1 Hz, 1H), 4.23-3.78 (m, 2H), 3.03 (s, 3H), 1.49 (d, J = 7.2 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 690 | 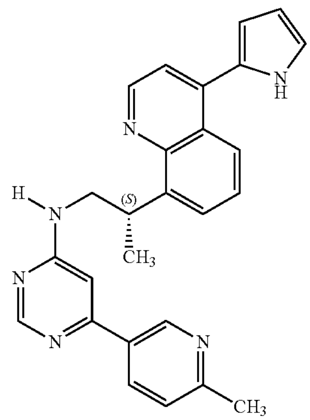 | 420.15 | (methanol-$d_4$) δ 9.20 (s, 2H), 9.16 (s, 1H), 8.93 (s, 1H), 8.71 (d, J = 8.4 Hz, 1H), 8.10 (d, J = 7.3 Hz, 1H), 7.94 (t, J = 11.4 Hz, 2H), 7.40 (s, 1H), 7.19 (s, 1H), 7.17-7.02 (m, 1H), 6.57 (s, 1H), 4.12 (m, 1H), 3.99 (dd, J = 14.3, 3.6 Hz, 1H), 3.65-3.42 (m, 1H), 2.78 (s, 3H), 1.65 (d, J = 6.6 Hz, 3H) |
| 691 | 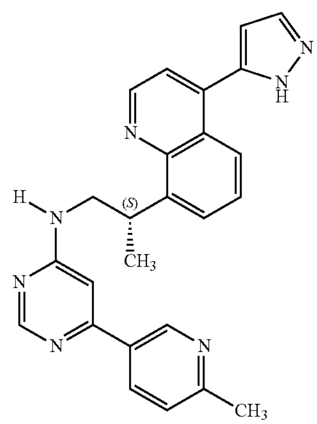 | 421.54 | (methanol-$d_4$) δ 9.16 (m, 3H), 8.93 (d, J = Hz, 1H), 8.82 (s, 1H), 8.55 (br.s, 1H), 8.23-7.65 (m, 5H), 7.02 (d, J = 9.0 Hz, 2H), 4.37 (m, 1H), 4.05 (m, 1H), 3.79 (m, 1H), 2.79 (s, 3H), 1.62 (d, J = 6.8 Hz, 3H) |
| 692 | 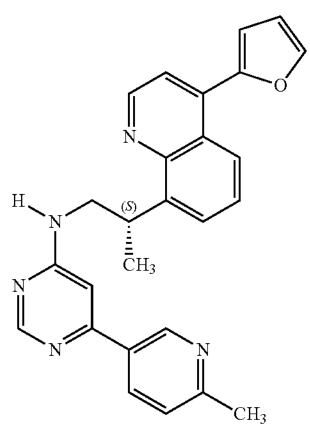 | 421.5 | (methanol-$d_4$) δ 9.39-8.42 (m, 5H), 8.41-7.69 (m, 4H), 7.55 (s, 1H), 7.04 (s, 1H), 6.85 (s, 1H), 4.44 (m, 1H), 4.03 (m, 1H), 3.80 (dd, J = 13.9, 7.7 Hz, 1H), 2.66 (s, 3H), 1.60 (d, J = 6.8 Hz, 3H) |

TABLE 1-continued
| Cmpnd No. | Structure | ESMS (M + H) | ¹H NMR (300 MHz, unless indicated otherwise) NMR peaks given as δ values |
|---|---|---|---|
| 693 | 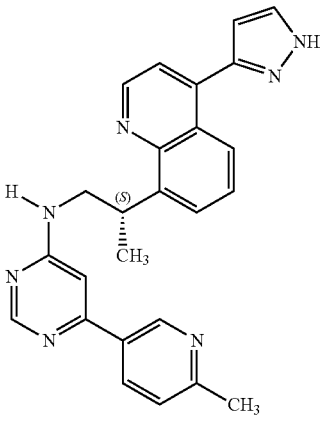 | 422.67 | (methanol-$d_4$) δ 9.21-9.11 (m, 3H), 8.83 (m, 2H), 8.53 (m, 1H), 8.04-7.73 (m, 4H), 7.03 (s, 1H), 6.97 (s, 1H), 4.39 (m, 1H), 4.0 (m, 1H), 3.76-3.68 (m, 1H), 2.78 (s, 3H), 1.61 (d, J = 6.8 Hz, 3H) |
| 694 | 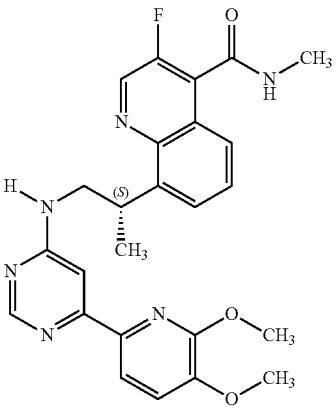 | 477.18 | (methanol-$d_4$) δ 8.92, 8.87 (2s, 1H), 8.52, 8.46 (2d, J = 0.9 Hz, 1H), 7.95-7.59 (m, 4H), 7.48, 7.39 (2d, J = 8.2 Hz, 1H), 7.26, 7.04 (2d, J = 0.9 Hz, 1H), 4.62 (p, J = 7.0 Hz, 1H), 4.22-3.79 (m, 8H), 3.08-2.87 (m, 3H), 1.56, 1.50 (d, J = 7.0 Hz, 3H) |
| 695 | 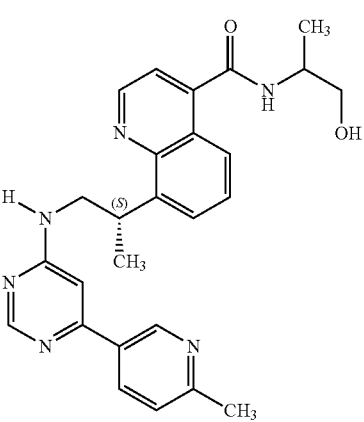 | 456.47 | (methanol-$d_4$) δ 9.0 (m, 4H), 8.61 (dd, J = 8.6, 1.4 Hz, 1H), 8.48-8.24 (m, 1H), 8.07 (d, J = 4.2 Hz, 1H), 7.85-7.74 (m, 1H), 7.64 (ddd, J = 10.9, 8.4, 7.1 Hz, 1H), 6.79 (s, 1H), 4.64 (dt, J = 12.2, 3.9 Hz, 2H), 4.49 (ddd, J = 12.2, 7.0, 4.2 Hz, 1H), 3.82 (m, 3H), 2.75 (s, 3H), 1.52-1.42 (m, 6H) |

TABLE 1-continued
| Cmpnd No. | Structure | ESMS (M + H) | ¹H NMR (300 MHz, unless indicated otherwise) NMR peaks given as δ values |
|---|---|---|---|
| 696 | 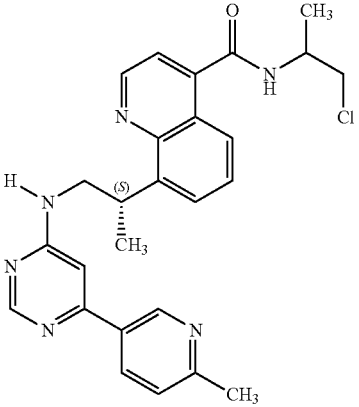 | 474.52 | (methanol-d₄) δ 9.13-9.86 (m, 3H), 8.45 (s, 1H), 8.14-8.00 (m, 1H), 7.87-7.77 (m, 1H), 7.69-7.42 (m, 3H), 6.80 (s, 1H), 4.64-4.34 (m, 2H), 4.01-3.58 (m, 4H), 2.76 (s, 3H), 1.57-1.43 (m, 3H), 1.59, 1.37 (d, J = 6.8 Hz, 3H) |
| 697 | 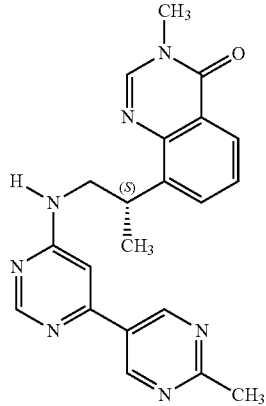 | 388.17 | (CDCl₃) δ 9.12 (s, 2H), 8.53 (s, 1H), 8.16 (dd, J = 8.0, 1.5 Hz, 1H), 8.08 (s, 1H), 7.64 (dd, J = 7.6, 1.5 Hz, 1H), 7.43 (t, J = 7.7 Hz, 1H), 6.84 (br. s, 1H), 6.04 (br. s, 1H), 4.19 (q, J = 7.1 Hz, 1H), 3.55 (s, 3H), 3.4 (m, 2H), 2.74 (s, 3H), 1.40 (d, J = 7.0 Hz, 3H) |
| 698 | 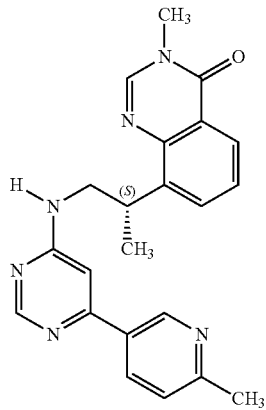 | 387.18 | (CDCl₃) δ 8.96 (s, 1H), 8.51 (d, J = 1.2 Hz, 1H), 8.31-8.01 (m, 3H), 7.63 (dd, J = 7.6, 1.5 Hz, 1H), 7.42 (t, J = 7.7 Hz, 1H), 7.23 (d, J = 8.2 Hz, 1H), 6.83 (br.s, 1H), 5.79 (br. s, 1H), 4.19 (q, J = 7.1 Hz, 1H), 3.55 (s, 3H), 3.43 (br. s, 2H), 2.58 (s, 3H), 1.39 (d, J = 7.2 Hz, 3H) |

TABLE 1-continued

| Cmpnd No. | Structure | ESMS (M + H) | $^1$H NMR (300 MHz, unless indicated otherwise) NMR peaks given as δ values |
|---|---|---|---|
| 699 | 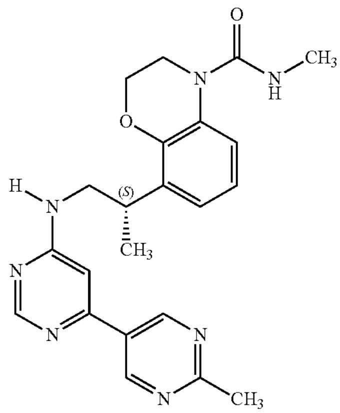 | 420.27 | (CDCl$_3$) δ 11.21 (s, 1H), 9.09 (s, 2H), 8.53 (s, 1H), 7.09 (dd, J = 8.0, 1.6 Hz, 1H), 6.94 (dd, J = 7.7, 1.7 Hz, 1H), 6.83 (t, J = 7.8 Hz, 1H), 6.61 (d, J = 1.2 Hz, 1H), 5.48 (br. s, 1H), 5.27 (q, J = 4.7 Hz, 1H)., 4.22 (t, J = 4.6 Hz, 2H), 3.91-3.72 (m, 2H), 3.50 (br.s, 2H), 2.78 (d, J = 4.6 Hz, 3H), 2.74 (s, 3H), 1.28 (d, J = 6.0 Hz, 3H) |
| 700 | 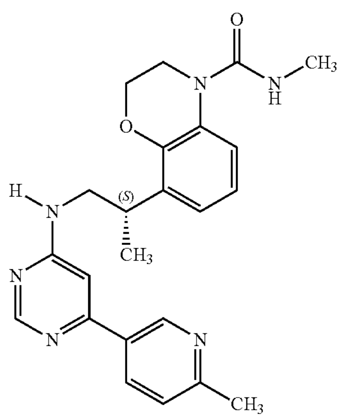 | 419.23 | (CDCl$_3$) δ 8.88 (s, 1H), 8.52 (s, 1H), 8.20 (dd, J = 8.1, 2.4 Hz, 1H), 7.23 (d, J = 8.2 Hz, 1H), 7.08 (dd, J = 7.9, 1.6 Hz, 1H), 6.95 (dd, J = 7.7, 1.7 Hz, 1H), 6.83 (t, J = 7.8 Hz, 1H), 6.65-6.52 (m, 1H), 5.3 (m, 1H), 5.26 (q, J = 4.8 Hz, 2H), 4.21 (t, J = 4.6 Hz, 2H), 3.81 (td, J = 4.3, 1.4 Hz, 2H), 3.49 (s, 3H), 2.78 (d, J = 4.6 Hz, 3H), 2.59 (s, 3H), 1.28 (d, J = 6.1 Hz, 3H) |
| 701 | 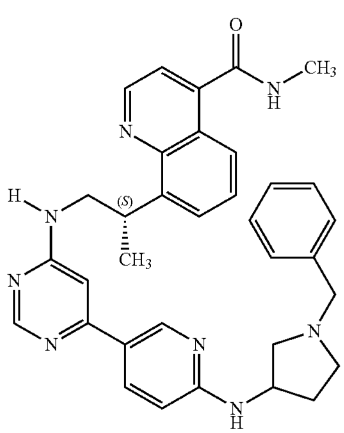 | 573.27 | |

TABLE 1-continued
| Cmpnd No. | Structure | ESMS (M + H) | $^1$H NMR (300 MHz, unless indicated otherwise) NMR peaks given as δ values |
|---|---|---|---|
| 702 | 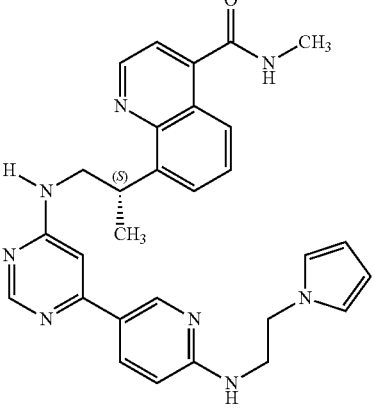 | 507.46 | (DMSO-d$_6$) δ 8.99 (d, J = 4.1 Hz, 1H), 8.65 (d, J = 4.6 Hz, 2H), 8.37 (s, 1H), 7.99 (d, J = 8.3 Hz, 2H), 7.77 (d, J = 7.0 Hz, 1H), 7.67-7.59 (m, 1H), 7.54 (d, J = 4.2 Hz, 1H), 7.40-7.30 (m, 1H), 7.13-7.04 (m, 1H), 6.75 (t, J = 2.0 Hz, 2H), 6.55 (d, J = 8.7 Hz, 1H), 5.98 (t, J = 2.1 Hz, 2H), 4.58-4.43 (m, 1H), 4.07 (t, J = 6.3 Hz, 2H), 3.86-3.56 (m, 4H), 2.87 (d, J = 4.6 Hz, 3H), 1.37 (d, J = 6.9 Hz, 3H) |
| 703 | 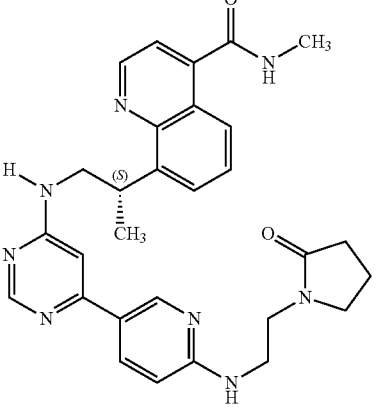 | 525.43 | (DMSO-d$_6$) δ 8.99 (d, J = 4.2 Hz, 1H), 8.66 (d, J = 4.5 Hz, 2H), 8.37 (s, 1H), 8.13-7.84 (m, 2H), 7.77 (d, J = 6.7 Hz, 1H), 7.71-7.59 (m, 1H), 7.54 (d, J = 4.2 Hz, 1H), 7.47-7.26 (m, 1H), 7.11-6.93 (m, 1H), 6.77 (s, 1H), 6.53 (d, J = 8.8 Hz, 1H), 4.56-4.42 (m, 1H), 3.69 (s, 2H), 3.51-3.28 (m, 10H), 2.87 (d, J = 4.5 Hz, 3H), 2.17 (t, J = 8.0 Hz, 2H), 1.96-1.80 (m, 2H), 1.37 (d, J = 6.9 Hz, 3H) |
| 704 | 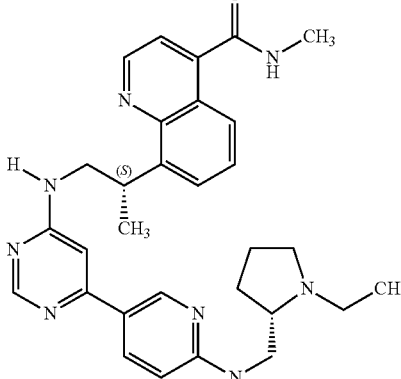 | 525.43 | |

TABLE 1-continued

| Cmpnd No. | Structure | ESMS (M + H) | $^1$H NMR (300 MHz, unless indicated otherwise) NMR peaks given as δ values |
|---|---|---|---|
| 705 | 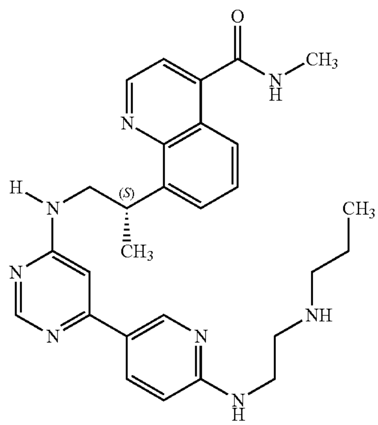 | 499.47 | |
| 706 | 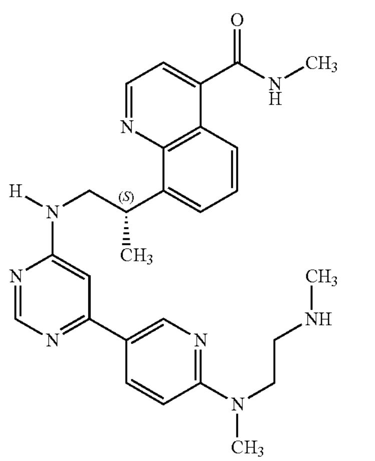 | 485.36 | |
| 707 | 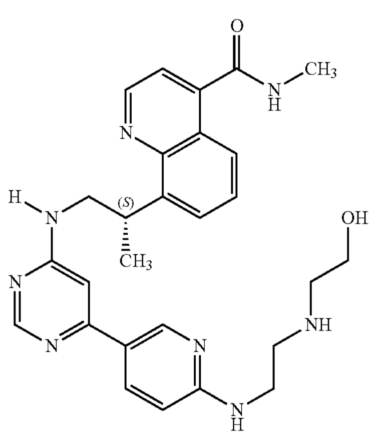 | 501.42 | |

| Cmpnd No. | Structure | ESMS (M + H) | $^1$H NMR (300 MHz, unless indicated otherwise) NMR peaks given as δ values |
|---|---|---|---|
| 708 | 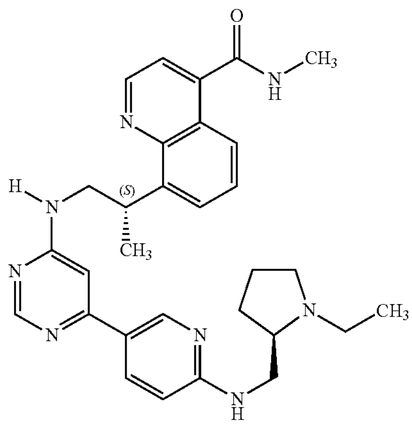 | 525.43 | (DMSO-d$_6$) δ 8.99 (d, J = 4.2 Hz, 1H), 8.65 (dd, J = 8.8, 4.2 Hz, 2H), 8.36 (s, 1H), 8.06-7.83 (m, 2H), 7.77 (d, J = 6.6 Hz, 1H), 7.71-7.58 (m, 1H), 7.53 (d, J = 4.3 Hz, 1H), 7.32 (t, J = 5.8 Hz, 1H), 6.79 (s, 1H), 6.58 (d, J = 8.8 Hz, 1H), 4.59-4.41 (m, 1H), 3.69 (s, 2H), 3.60-3.46 (m, 1H), 3.16-3.01 (m, 2H), 2.97-2.79 (m, 4H), 2.68-2.53 (m, 2H), 2.25 (dq, J = 13.9, 7.0 Hz, 1H), 2.11 (dd, J = 16.7, 8.4 Hz, 1H), 1.90-1.73 (m, 1H), 1.73-1.49 (m, 3H), 1.37 (d, J = 6.9 Hz, 3H), 1.05 (t, J = 7.2 Hz, 3H) |
| 709 | 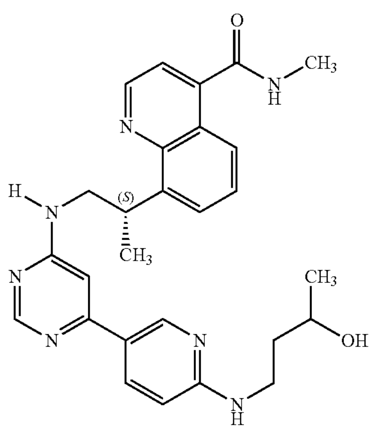 | 486.37 | |
| 710 | 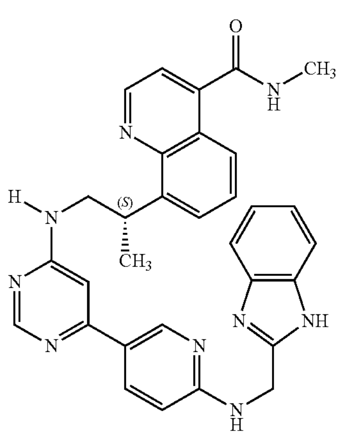 | 544.36 | |

TABLE 1-continued

| Cmpnd No. | Structure | ESMS (M + H) | ¹H NMR (300 MHz, unless indicated otherwise) NMR peaks given as δ values |
|---|---|---|---|
| 711 | 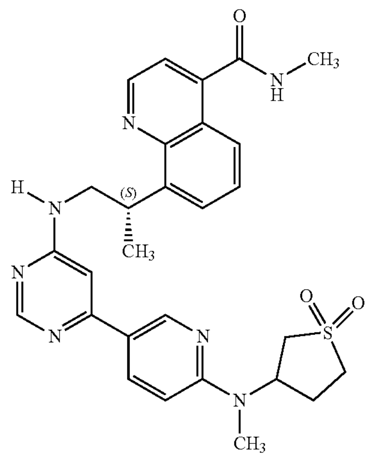 | 546.19 | |
| 712 | 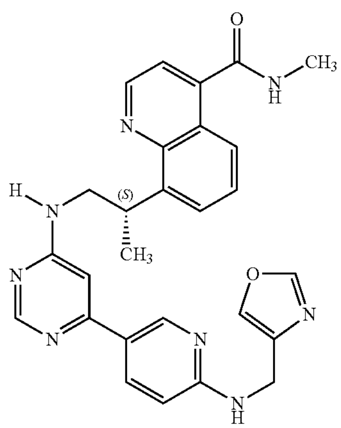 | 495.22 | |
| 713 | 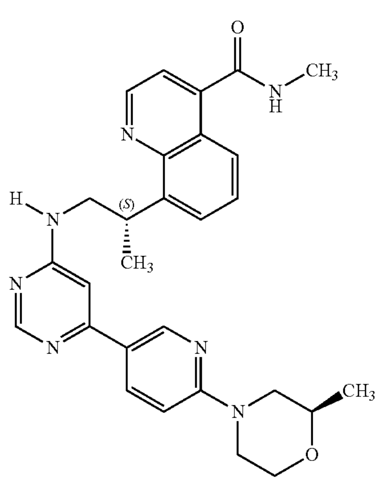 | 498.26 | |

TABLE 1-continued

| Cmpnd No. | Structure | ESMS (M + H) | ¹H NMR (300 MHz, unless indicated otherwise) NMR peaks given as δ values |
|---|---|---|---|
| 714 | 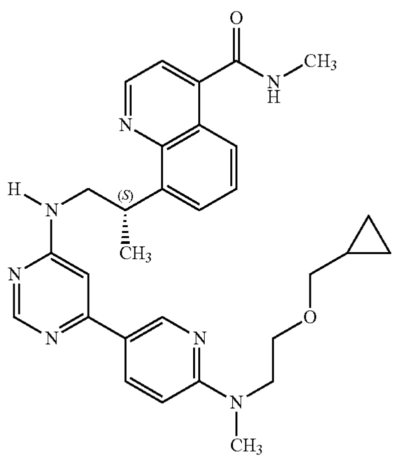 | 526.27 | |
| 715 | 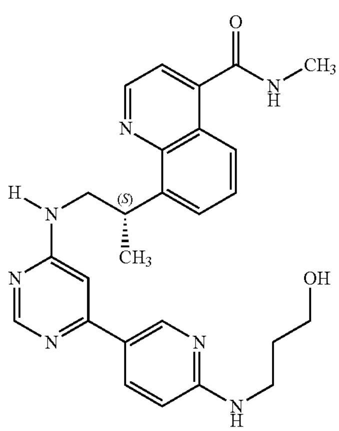 | 472.25 | |
| 716 | 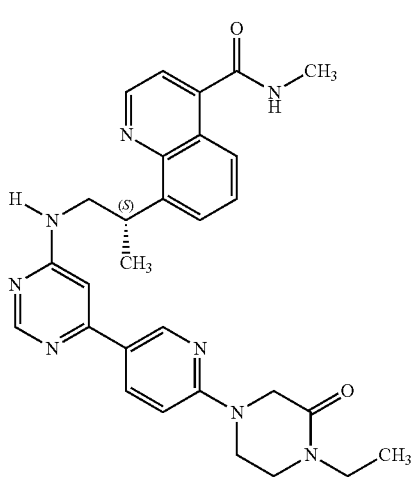 | 525.26 | |

TABLE 1-continued

| Cmpnd No. | Structure | ESMS (M + H) | ¹H NMR (300 MHz, unless indicated otherwise) NMR peaks given as δ values |
|---|---|---|---|
| 717 | 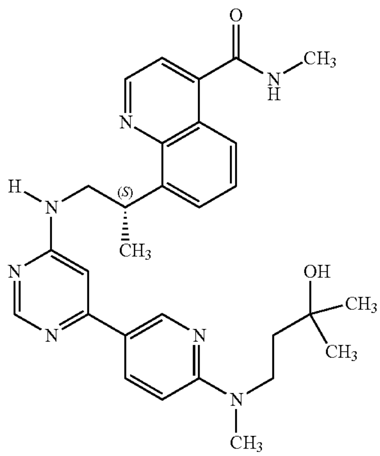 | 514.3 | |
| 718 | 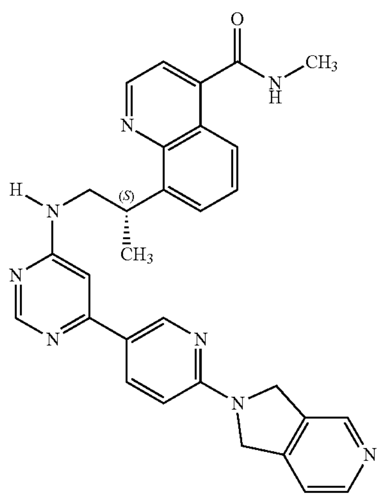 | 517.33 | |
| 719 | 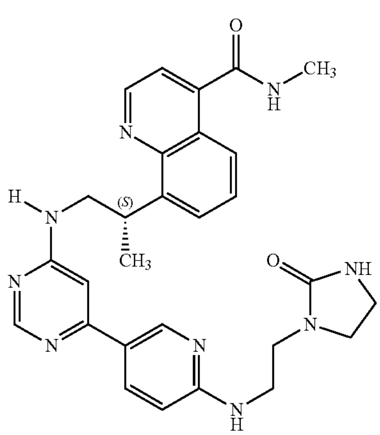 | 526.4 | |

TABLE 1-continued

| Cmpnd No. | Structure | ESMS (M + H) | ¹H NMR (300 MHz, unless indicated otherwise) NMR peaks given as δ values |
|---|---|---|---|
| 720 | 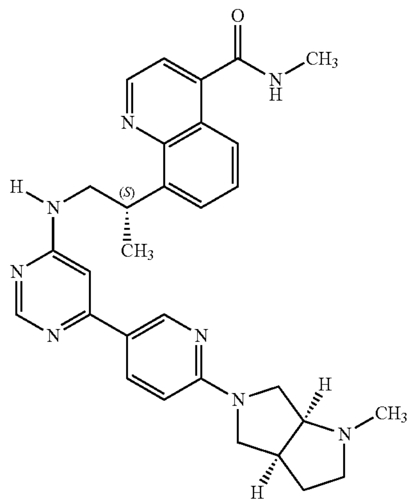 | 523.45 | |
| 721 | 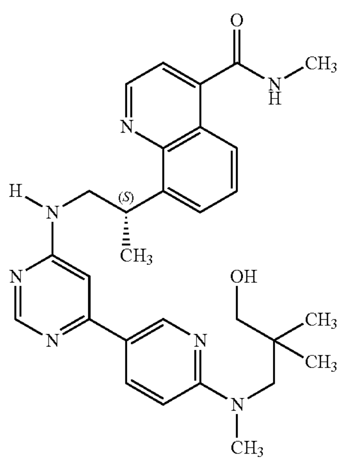 | 500.37 | |
| 722 | 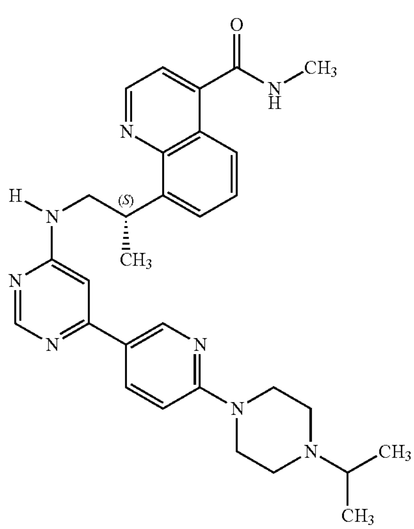 | 525.43 | |

| Cmpnd No. | Structure | ESMS (M + H) | ¹H NMR (300 MHz, unless indicated otherwise) NMR peaks given as δ values |
|---|---|---|---|
| 723 | 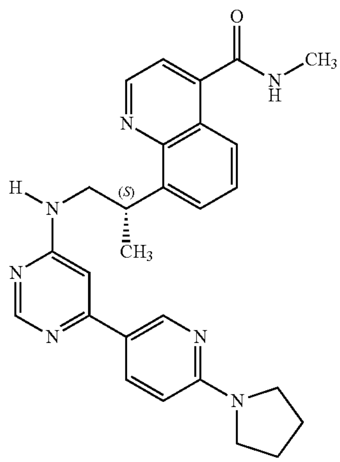 | 468.4 | |
| 724 | 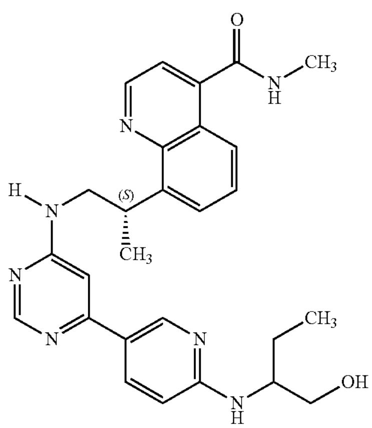 | 486.37 | |
| 725 | 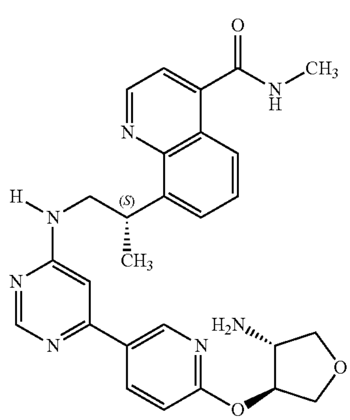 | 500.24 | |

TABLE 1-continued

| Cmpnd No. | Structure | ESMS (M + H) | $^1$H NMR (300 MHz, unless indicated otherwise) NMR peaks given as δ values |
|---|---|---|---|
| 726 | 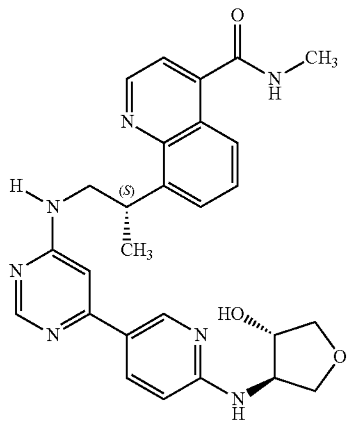 | 500.24 | |
| 727 | 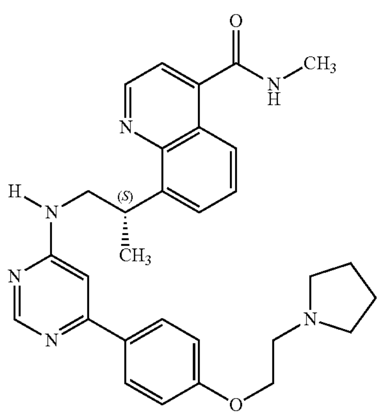 | 511.21 | (DMSO-d$_6$) δ 8.99 (d, J = 4.2 Hz, 1H), 8.68 (d, J = 4.9 Hz, 1H), 8.42 (s, 1H), 7.99 (m, 3H), 7.76 (m, 1H), 7.64 (t, J = 7.8 Hz, 1H), 7.56 (m, 1H), 7.45 (m, 1H), 7.13-6.80 (m, 3H), 4.51 (m, 1H), 4.24 (m, 2H), 3.75 (m, 2H), 3.34 (s, 2H), 3.17 (m, 2H), 2.96 (m, 2H), 2.75 (d, 3H), 1.82 (m, 4H), 1.38 (d, J = 6.8 Hz, 3H) |
| 728 | 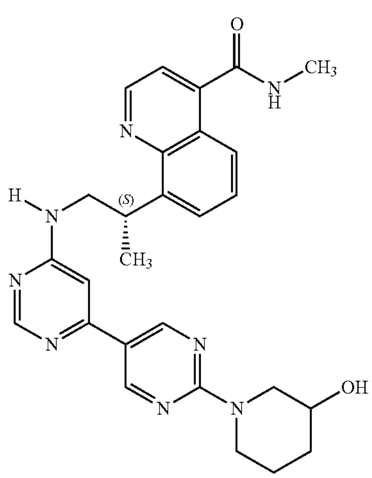 | 499.23 | (DMSO-d$_6$) δ 9.11-8.77 (m, 3H), 8.68 (m, 1H), 8.40 (s, 1H), 7.99 (d, J = 8.4 Hz, 1H), 7.77 (m, 1H), 7.63 (t, J = 7.8 Hz, 1H), 7.51 (m, 2H), 4.95 (m, 1H), 4.50 (m, 2H), 4.30 (m, 1H), 3.25 (m, 2H), 3.5 (m, 1H), 3.16 (m, 1H), 3.08-2.95 (m, 1H), 2.87 (d, J = 4.5 Hz, 3H), 1.90 (m, 1H), 1.74 (m, 1H), 1.38 (m, 4H) |

TABLE 1-continued

| Cmpnd No. | Structure | ESMS (M + H) | ¹H NMR (300 MHz, unless indicated otherwise) NMR peaks given as δ values |
|---|---|---|---|
| 729 | 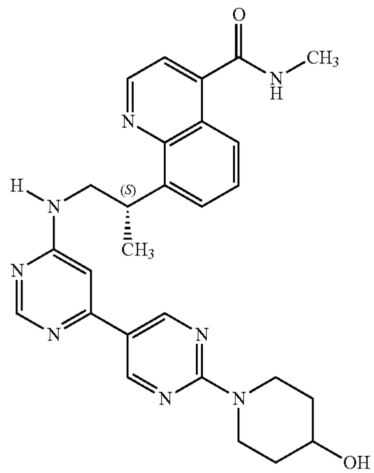 | 499.14 | (DMSO-d₆) δ 9.07-8.77 (m, 3H), 8.68 (d, J = 4.9 Hz, 1H), 8.41 (s, 1H), 7.99 (d, J = 8.4 Hz, 1H), 7.77 (s, 1H), 7.63 (t, J = 7.8 Hz, 1H), 7.51 (m, 2H), 4.78 (m, 1H), 4.50 (m, 1H), 4.31 (m, 2H), 3.75 (m, 3H), 3.38 (s, 2H), 2.87 (d, J = 4.5 Hz, 3H), 1.78 (m, 2H), 1.36 (m, 4H) |
| 730 | 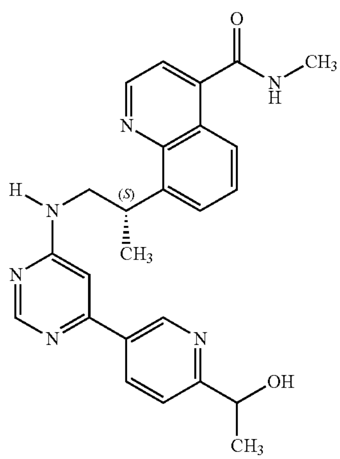 | 443.19 | (DMSO-d₆) δ 8.98 (d, J = 4.3 Hz, 1H), 8.68 (m, 1H), 8.49 (s, 1H), 8.27 (m, 1H), 7.99 (d, J = 8.4 Hz, 1H), 7.77 (m, 1H), 7.68-7.49 (m, 3H), 6.90 (s, 1H), 5.48 (m, 1H), 4.78 (m, 1H), 4.52 (m, 1H), 3.75 (m, 2H), 2.87 (d, J = 4.5 Hz, 3H), 1.39 (m, 6H) |
| 731 | 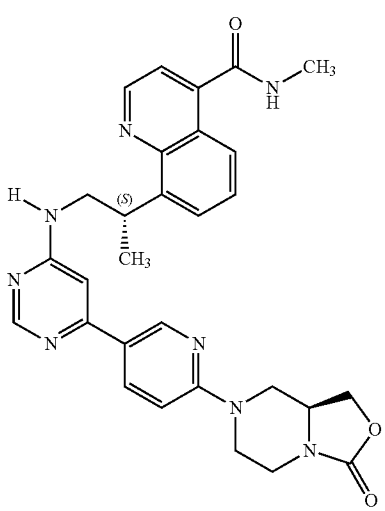 | 539.26 | |

| Cmpnd No. | Structure | ESMS (M + H) | ¹H NMR (300 MHz, unless indicated otherwise) NMR peaks given as δ values |
|---|---|---|---|
| 732 | 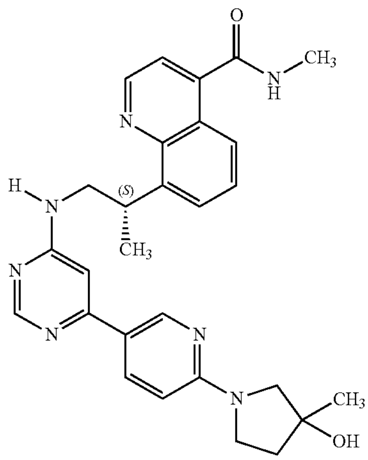 | 498.19 | |
| 733 | 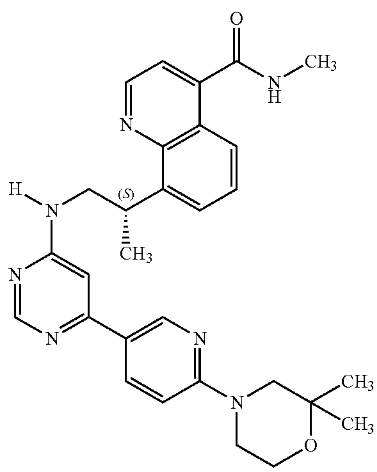 | 512.26 | |
| 734 | 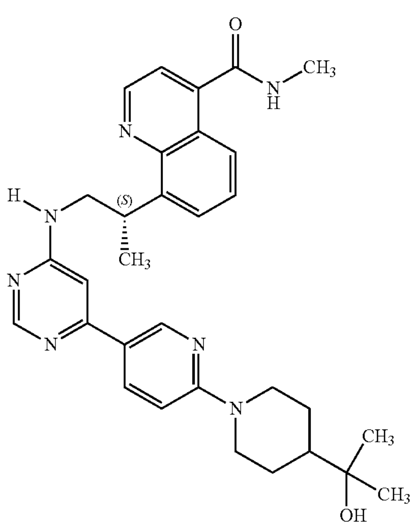 | 540.32 | |

TABLE 1-continued

| Cmpnd No. | Structure | ESMS (M + H) | ¹H NMR (300 MHz, unless indicated otherwise) NMR peaks given as δ values |
|---|---|---|---|
| 735 | 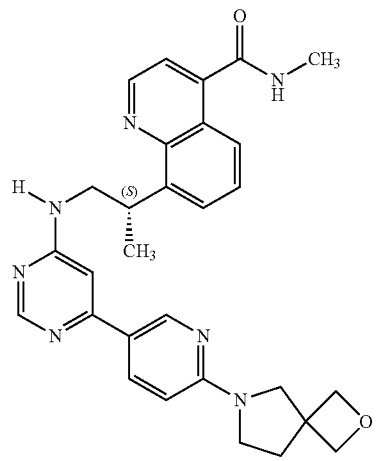 | 510.28 | |
| 736 | 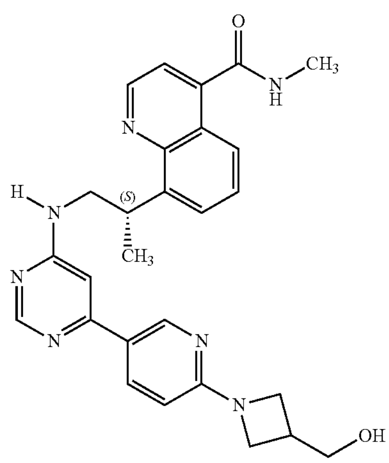 | 484.2 | |
| 737 | 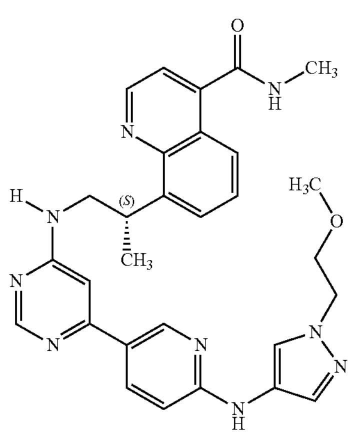 | 538.26 | |

TABLE 1-continued

| Cmpnd No. | Structure | ESMS (M + H) | ¹H NMR (300 MHz, unless indicated otherwise) NMR peaks given as δ values |
|---|---|---|---|
| 738 | 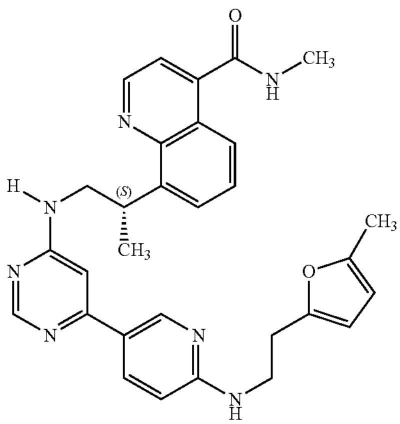 | 522.19 | |
| 739 | 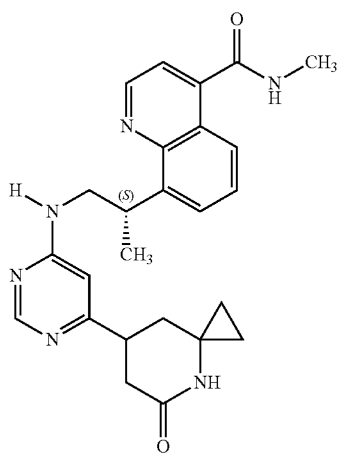 | 446 | (400 MHz, DMSO-$d_6$) δ 9.06 (s, 1H), 8.68 (d, J = 4.6 Hz, 1H), 8.29 (s, 1H), 8.03-7.91 (m, 2H), 7.74 (d, J = 7.0 Hz, 1H), 7.68-7.58 (m, 1H), 7.54 (d, J = 4.2 Hz, 1H), 6.89 (s, 1H), 5.71 (s, 1H), 4.49 (s, 1H), 4.05 (s, 2H), 3.49 (d, J = 104.6 Hz, 4H), 2.87 (d, J = 4.5 Hz, 3H), 1.35 (d, J = 6.8 Hz, 3H), 0.75 (s, 4H) |
| 740 | 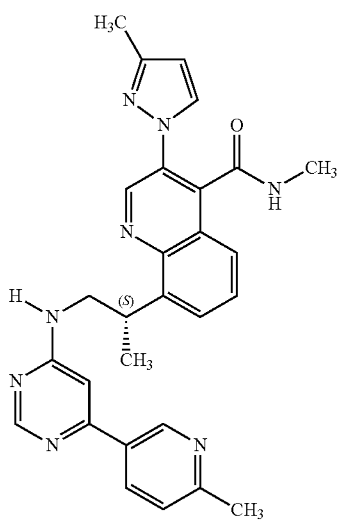 | 493.28 | (methanol-$d_4$) δ 9.15 (d, J = 1.9 Hz, 1H), 8.87, 8.82 (2s, 1H), 8.53 (s, 1H), 8.34-7.46 (m, 6H), 7.33, 6.75 (2s, 1H), 6.42, 6.37 (2s, 1H), 4.66 (m, 1H), 4.22-3.81 (m, 2H), 2.90 (s, 3H), 2.69, 2.66 (2s, 3H), 2.38, 2.34 (2s, 3H), 1.58, 1.53 (2d, J = 7.1 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 741 | 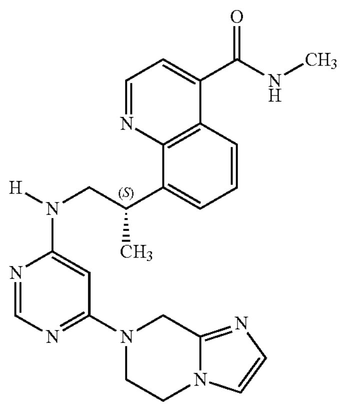 | 443 | (400 MHz, DMSO-$d_6$) δ 9.02 (d, J = 4.3 Hz, 1H), 8.68 (d, J = 4.6 Hz, 1H), 8.36 (s, 1H), 8.17 (s, 1H), 8.02 (dd, J = 8.4, 1.2 Hz, 1H), 7.79 (d, J = 6.9 Hz, 1H), 7.74-7.60 (m, 3H), 7.56 (d, J = 4.3 Hz, 1H), 6.07 (s, 1H), 5.11 (s, 2H), 4.49 (s, 1H), 4.22 (d, J = 50.5 Hz, 4H), 3.67 (t, J = 29.0 Hz, 2H), 2.87 (d, J = 4.6 Hz, 3H), 1.40 (d, J = 6.9 Hz, 3H) |
| 742 | 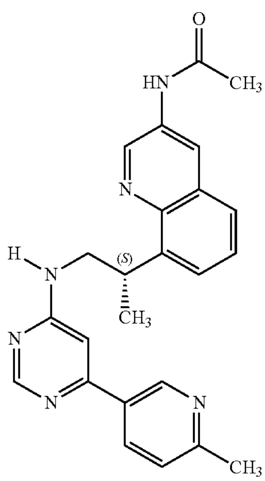 | 413.17 | (methanol-$d_4$) δ 8.93 (s, 2H), 8.61 (d, J = 2.5 Hz, 1H), 8.40 (s, 1H), 8.18 (m, 1H), 7.88-7.30 (m, 5H), 4.51 (d, J = 6.4 Hz, 1H), 3.81 (dd, J = 13.3, 6.6 Hz, 2H), 2.60 (s, 3H), 2.22 (s, 3H), 1.49 (s, 3H) |
| 743 | 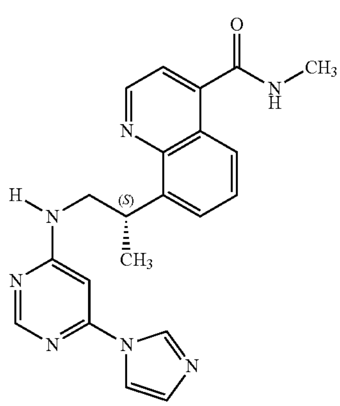 | 388.19 | (DMSO-$d_6$) δ 8.98 (d, J = 4.3 Hz, 1H), 8.68 (d, J = 5.1 Hz, 1H), 8.34 (m, 2H), 8.06-7.69 (m, 4H), 7.65 (m, 1H), 7.54 (m, 1H), 7.12 (m, 1H), 6.56 (s, 1H), 4.52 (m, 1H), 3.78 (m, 2H), 2.87 (d, J = 4.4 Hz, 3H), 1.38 (d, 3H) |

| Cmpnd No. | Structure | ESMS (M + H) | ¹H NMR (300 MHz, unless indicated otherwise) NMR peaks given as δ values |
|---|---|---|---|
| 744 | 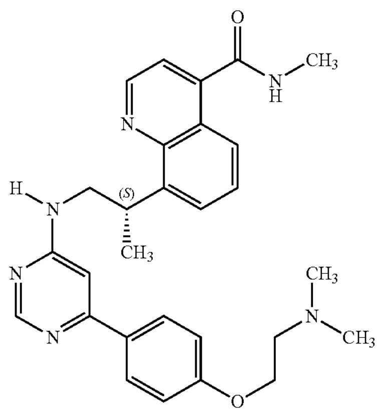 | 485.23 | (DMSO-d₆) δ 9.75 (s, 1H), 8.98 (d, J = 4.3 Hz, 1H), 8.66 (d, J = 4.9 Hz, 1H), 8.50 (s, 1H), 8.04-7.84 (m, 3H), 7.77 (d, J = 7.3 Hz, 1H), 7.63 (t, J = 7.8 Hz, 1H), 7.54 (d, J = 4.3 Hz, 1H), 7.14 (d, J = 8.4 Hz, 2H), 6.87 (s, 1H), 4.51 (m, 1H), 4.40 (t, J = 4.8 Hz, 2H), 3.80 (m, 2H), 3.55 (t, J = 4.8 Hz, 2H), 2.87 (m, 9H), 1.39 (d, J = 6.9 Hz, 3H) |
| 745 | 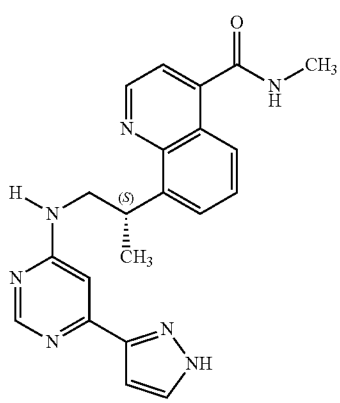 | 388 | (400 MHz, DMSO-d₆) δ 9.49 (d, J = 91.1 Hz, 1H), 9.04 (dd, J = 60.1, 4.1 Hz, 1H), 8.62 (d, J = 38.4 Hz, 2H), 8.04 (dd, J = 17.3, 14.8 Hz, 2H), 7.87-7.70 (m, 1H), 7.69-7.59 (m, 1H), 7.59-7.49 (m, 1H), 7.05 (dd, J = 53.3, 29.8 Hz, 2H), 4.54 (dd, J = 14.1, 7.3 Hz, 1H), 4.05-3.48 (m, 2H), 2.87 (d, J = 4.5 Hz, 3H), 1.42 (dd, J = 15.8, 7.0 Hz, 3H) |
| 746 | 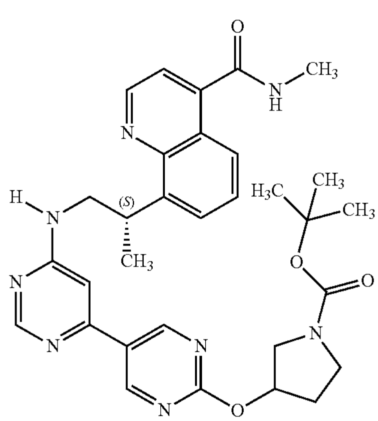 | 585.16 | |

TABLE 1-continued

| Cmpnd No. | Structure | ESMS (M + H) | ¹H NMR (300 MHz, unless indicated otherwise) NMR peaks given as δ values |
|---|---|---|---|
| 747 | 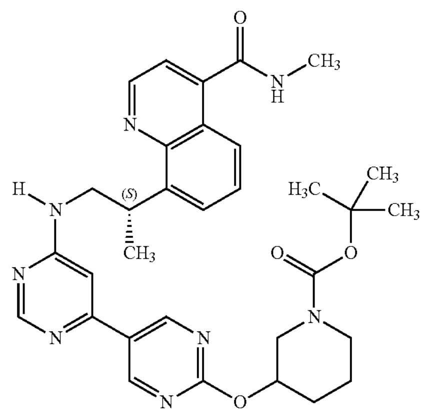 | 599.2 | |
| 748 | 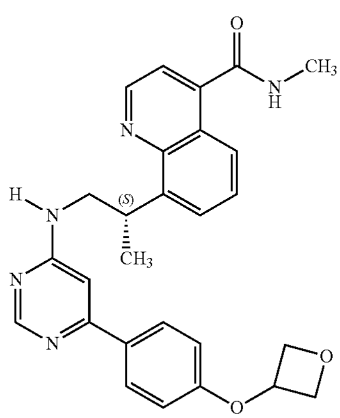 | 470.25 | (DMSO-d$_6$) δ 8.98 (d, J = 4.3 Hz, 1H), 8.65 (d, J = 5.1 Hz, 1H), 8.42 (s, 1H), 8.05-7.85 (m, 3H), 7.77 (d, J = 7.1 Hz, 1H), 7.68-7.59 (m, 1H), 7.55 (s, 1H), 7.43 (s, 1H), 6.90 (d, J = 8.4 Hz, 2H), 5.45-5.28 (m, 1H), 4.95 (t, J = 6.6 Hz, 2H), 4.57 (m, 3H), 3.70 (m, 2H), 3.17 (s, 1H), 2.87 (d, J = 4.5 Hz, 3H), 1.38 (d, J = 6.9 Hz, 3H) |
| 749 | 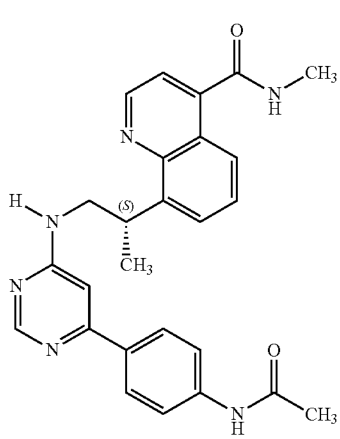 | 455.58 | (DMSO-d$_6$) δ 10.14 (s, 1H), 8.98 (d, J = 4.3 Hz, 1H), 8.68 (m, 1H), 8.43 (s, 1H), 8.04-7.43 (m, 8H), 6.85 (s, 1H), 4.51 (m, 1H), 3.75 (m, 2H), 2.87 (d, J = 4.5 Hz, 3H), 2.07 (s, 3H), 1.38 (d, J = 6.9 Hz, 3H) |

| Cmpnd No. | Structure | ESMS (M + H) | ¹H NMR (300 MHz, unless indicated otherwise) NMR peaks given as δ values |
|---|---|---|---|
| 750 | 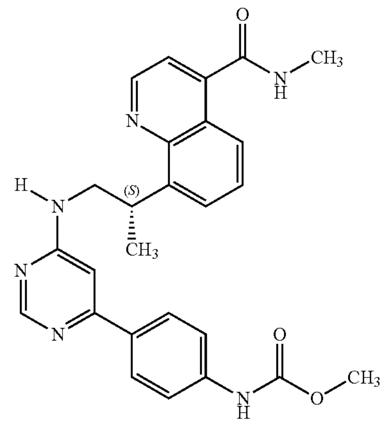 | 471.55 | (DMSO-d$_6$) δ 9.89 (s, 1H), 8.98 (d, J = 4.3 Hz, 1H), 8.69 (m, 1H), 8.42 (s, 1H), 7.99 (d, J = 8.3 Hz, 2H), 7.90 (s, 1H), 7.76 (m, 1H), 7.61 (m, 4H), 7.46 (m, 1H), 6.84 (s, 1H), 4.51 (m, 1H), 3.70 (m, 5H), 2.87 (d, J = 4.5 Hz, 3H), 1.37 (d, J = 6.9 Hz, 3H) |
| 751 | 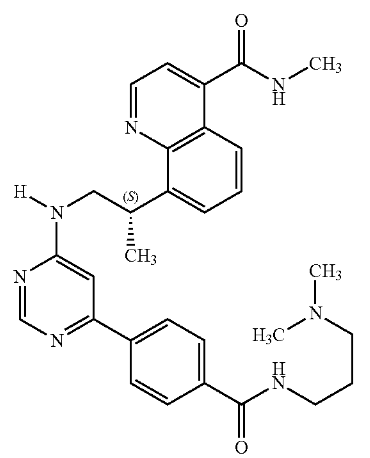 | 526.59 | (DMSO-d$_6$) δ 9.46 (s, 1H), 8.99 (d, J = 4.3 Hz, 1H), 8.69 (m, 2H), 8.50 (s, 1H), 8.20 (m, 1H), 8.03-7.92 (m, 3H), 7.77 (m, 1H), 7.64 (m, 1H), 7.55 (m, 1H), 6.97 (s, 1H), 4.52 (s, 1H), 3.75 (m, 2H), 3.35 (d, J = 5.7 Hz, 2H), 3.07 (t, J = 7.9 Hz, 2H), 2.87 (d, J = 4.5 Hz, 3H), 2.76 (s, 6H), 1.90 (m, 2H), 1.38 (d, J = 6.9 Hz, 3H) |
| 752 | 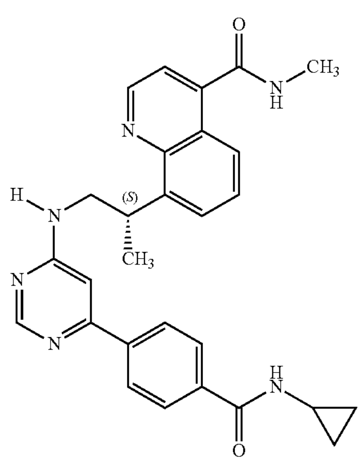 | 481.59 | (DMSO-d$_6$) δ 8.98 (d, J = 4.3 Hz, 1H), 8.68 (m, 1H), 8.54 (m, 2H), 8.05-7.87 (m, 4H), 7.78 (m, 1H), 7.64 (t, J = 7.8 Hz, 1H), 7.55 (s, 1H), 6.96 (s, 1H), 4.52 (m, 1H), 3.80 (m, 2H), 2.87 (m, 4H), 1.38 (d, J = 6.9 Hz, 3H), 0.70 (m, 2H), 0.59 (m, 2H) |

TABLE 1-continued

| Cmpnd No. | Structure | ESMS (M + H) | ¹H NMR (300 MHz, unless indicated otherwise) NMR peaks given as δ values |
|---|---|---|---|
| 753 | 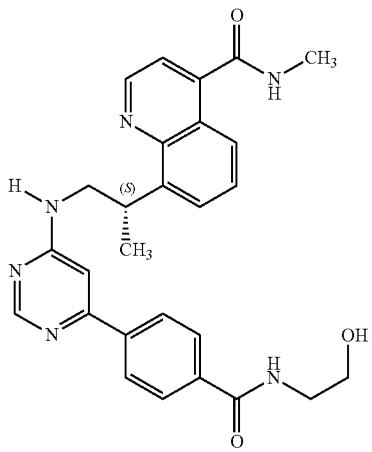 | 485.55 | (DMSO-d$_6$) δ 8.98 (d, J = 4.3 Hz, 1H), 8.69 (m, 1H), 8.58 (s, 2H), 7.99 (m, 5H), 7.87-7.72 (m, 1H), 7.64 (t, J = 7.8 Hz, 1H), 7.55 (s, 1H), 6.96 (s, 1H), 4.53 (m, 1H), 3.80 (m, 2H), 3.53 (t, J = 6.3 Hz, 2H), 3.35 (m, 2H), 2.87 (d, J = 4.5 Hz, 3H), 1.40 (d, 3H) |
| 754 | 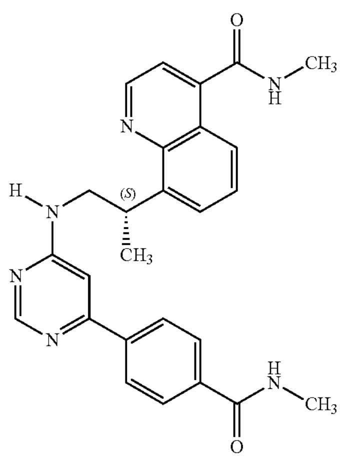 | 455.58 | (DMSO-d$_6$) δ 8.98 (d, J = 4.3 Hz, 1H), 8.68 (m, 1H), 8.57 (m, 2H), 8.19-7.88 (m, 5H), 7.78 (s, 1H), 7.64 (t, J = 7.8 Hz, 1H), 7.55 (s, 1H), 6.96 (s, 1H), 4.53 (m, 1H), 3.80 (m, 2H), 2.87 (d, J = 4.6 Hz, 3H), 2.81 (d, J = 4.1 Hz, 3H), 1.40 (d, 3H) |
| 755 | 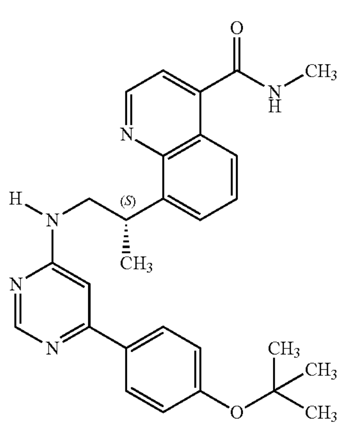 | 470.61 | (DMSO-d$_6$) δ 8.99 (d, J = 4.3 Hz, 1H), 8.68 (d, J = 5.1 Hz, 1H), 8.44 (s, 1H), 7.99 (d, J = 8.3 Hz, 2H), 7.88 (s, 2H), 7.76 (m, 1H), 7.64 (t, J = 7.8 Hz, 1H), 7.55 (s, 1H), 7.09 (m, 2H), 6.85 (s, 1H), 4.51 (m, 1H), 3.75 (m, 2H), 2.87 (d, J = 4.5 Hz, 3H), 1.35 (m, 12H) |

TABLE 1-continued

| Cmpnd No. | Structure | ESMS (M + H) | ¹H NMR (300 MHz, unless indicated otherwise) NMR peaks given as δ values |
|---|---|---|---|
| 756 | 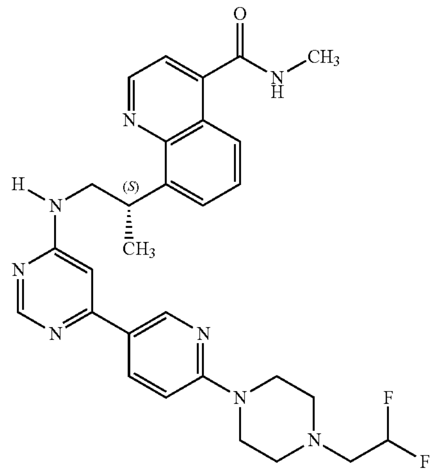 | 547.47 | (DMSO-d₆) δ 9.00 (d, 1H), 8.68 (m, 1H), 8.40 (s, 1H), 8.05 (s, 1H), 7.99 (d, J = 8.3 Hz, 1H), 7.77 (m, 1H), 7.63 (t, J = 7.8 Hz, 1H), 7.55 (s, 1H), 7.42 (s, 1H), 6.94 (s, 1H), 6.80 (s, 1H), 6.05- 6.40 (m, 1H), 4.51 (s, 1H), 3.60-3.80 (m, 6H), 2.87 (d, J = 4.6 Hz, 2H), 2.84-2.68 (m, 2H), 2.63 (m, 4H), 1.37 (d, J = 6.8 Hz, 3H) |
| 757 | 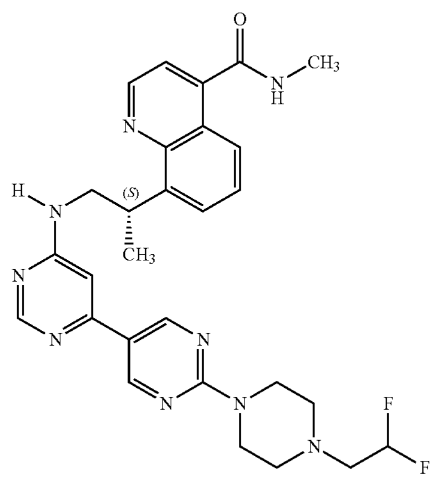 | 548.31 | (DMSO-d₆) δ 8.98 (d, J = 4.3 Hz, 1H), 8.88 (m, 1H), 8.67 (m, 1H), 8.41 (m, 1H), 7.99 (d, J = 8.6 Hz, 1H), 7.77 (s, 1H), 7.63 (t, J = 7.8 Hz, 1H), 7.54 (m, 2H), 6.75 (s, 1H), 6.00-6.40 (m, 1H), 4.50 (s, 1H), 3.80 (m, 6H), 2.86 (d, J = 4.6 Hz, 3H), 2.83-2.68 (m, 2H), 2.61 (m, 4H), 1.36 (d, J = 6.9 Hz, 3H) |
| 758 | 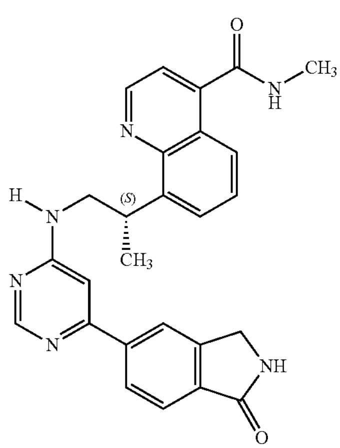 | 453.6 | (DMSO-d₆) δ 8.98 (d, J = 4.2 Hz, 1H), 8.68 (m, 2H), 8.51 (s, 1H), 8.14 (m, 1H), 8.00 (d, J = 8.2 Hz, 1H), 7.78 (m, 2H), 7.68-7.49 (m, 2H), 6.95 (s, 1H), 4.45 (m, 3H), 3.75 (m, 2H), 2.87 (d, J = 4.5 Hz, 3H), 1.39 (d, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 759 | 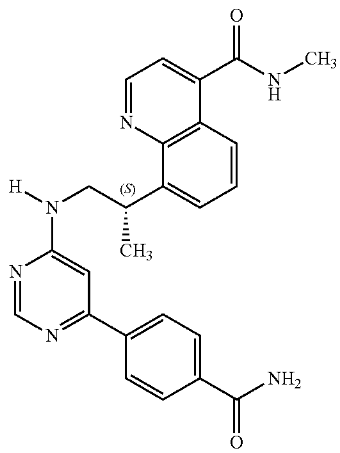 | 441.58 | (DMSO-d$_6$) δ 8.98 (d, J = 4.3 Hz, 1H), 8.68 (d, J = 5.4 Hz, 1H), 8.55 (s, 1H), 8.20-7.92 (m, 5H), 7.78 (s, 1H), 7.64 (t, J = 7.8 Hz, 1H), 7.54 (m, 2H), 6.95 (s, 1H), 4.53 (s, 1H), 3.80 (m, 2H), 3.35 (s, 2H), 2.87 (d, J = 4.5 Hz, 3H), 1.40 (d, 3H) |
| 760 | 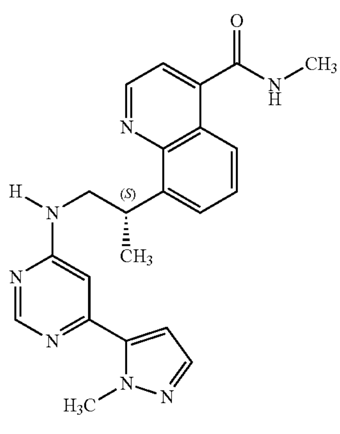 | 402 | (400 MHz, DMSO-d$_6$) δ 8.96 (s, 1H), 8.66 (d, J = 4.5 Hz, 3H), 8.01 (dd, J = 8.4, 1.1 Hz, 1H), 7.78 (s, 1H), 7.68-7.53 (m, 3H), 6.76 (d, J = 31.5 Hz, 2H), 4.52 (d, J = 6.9 Hz, 1H), 4.16-3.62 (m, 5H), 2.87 (d, J = 4.6 Hz, 3H), 1.40 (d, J = 6.7 Hz, 3H) |
| 761 | 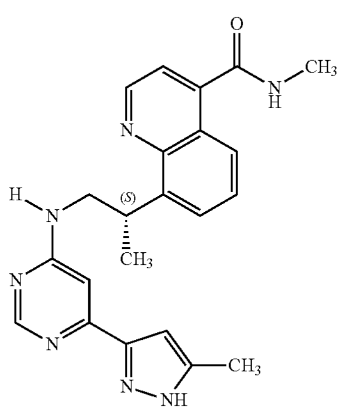 | 402 | (400 MHz, DMSO-d$_6$) δ 9.44 (d, J = 86.0 Hz, 1H), 9.13-8.91 (m, 1H), 8.62 (dd, J = 27.1, 22.0 Hz, 2H), 8.02 (d, J = 8.5 Hz, 1H), 7.88-7.71 (m, 1H), 7.71-7.59 (m, 1H), 7.53 (d, J = 4.1 Hz, 1H), 7.00 (dd, J = 167.5, 139.6 Hz, 2H), 4.53 (dd, J = 14.0, 7.0 Hz, 1H), 3.93 (dd, J = 36.4, 6.6 Hz, 2H), 2.87 (d, J = 4.5 Hz, 3H), 2.34 (d, J = 22.4 Hz, 3H), 1.40 (d, J = 6.9 Hz, 3H) |

TABLE 1-continued
| Cmpnd No. | Structure | ESMS (M + H) | $^1$H NMR (300 MHz, unless indicated otherwise) NMR peaks given as δ values |
|---|---|---|---|
| 762 | 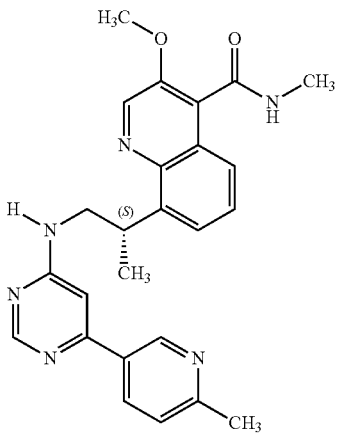 | 443.61 | (methanol-d$_4$) δ 8.93, 8.87 (2s, 2H), 8.61, 8.55 (2s, 1H), 8.38-8.19 (m, 1H), 7.90-7.44 (m, 4H), 7.34, 6.87 (2s, 1H), 4.55 (h, J = 7.1 Hz, 1H), 4.14-3.85 (m, 5H), 3.00 (s, 3H), 2.73, 2.70 (2s, 3H), 1.54, 1.48 (2d, J = 7.0 Hz, 3H) |
| 763 | 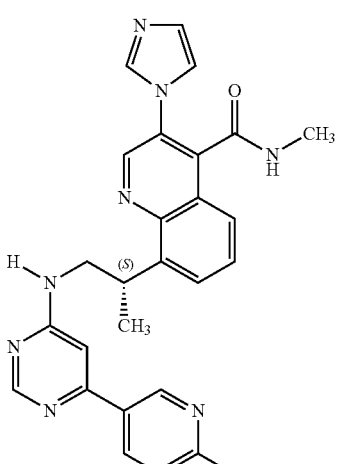 | 479.61 | (methanol-d$_4$) δ 9.36, 9.32 (2s, 1H), 9.11, 9.08 (2s, 1H), 8.98, 8.90 (2s, 1H), 8.62 8.57 (2s, 1H), 8.41-8.25 (m, 1H), 8.09-7.55 (m, 6H), 7.37, 6.93 (2s, 1H), 4.66 (q, J = 7.0 Hz, 1H), 4.10 (qd, J = 13.5, 7.2 Hz, 2H), 2.89 (s, 3H), 2.71 (s, 3H), 1.55 (d, J = 8.4 Hz, 3H) |
| 764 | 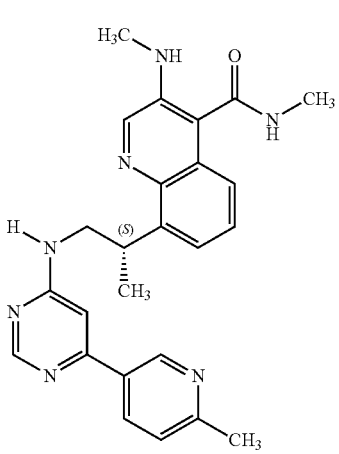 | 442.53 | (methanol-d$_4$) δ 8.99, 8.90 (2s, 1H), 8.71, 8.55 (2d, J = 9.5 Hz, 2H), 8.44, 8.24 (2d, J = 8.2 Hz, 1H), 8.02-7.36 (m, 4H), 7.30, 6.97 (2s, 1H), 4.54-4.22 (m, 1H), 4.10-3.71 (m, 2H), 3.02 (d, J = 4.1 Hz, 6H), 2.73 (s, 3H), 1.52 (d, J = 6.9 Hz, 3H) |

| Cmpnd No. | Structure | ESMS (M + H) | ¹H NMR (300 MHz, unless indicated otherwise) NMR peaks given as δ values |
|---|---|---|---|
| 765 | 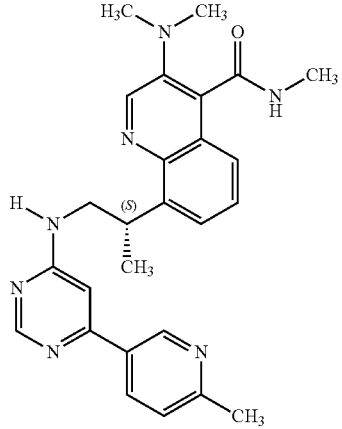 | 456.7 | (methanol-d₄) δ 8.91 (dd, J = 2.5, 0.8 Hz, 1H), 8.81, 8.71 (2s, 1H), 8.62, 8.55 (2s, 1H), 8.29 (m, 1H), 7.99-7.46 (m, 4H), 7.44, 6.86 (2s, 1H), 4.47 (q, J = 9.1 Hz, 1H), 3.96 (d, J = 6.9 Hz, 1H), 3.05 (s, 6H), 3.00 (s, 3H), 2.71 (d, J = 6.1 Hz, 3H), 1.51 (m, 3H) |
| 766 | 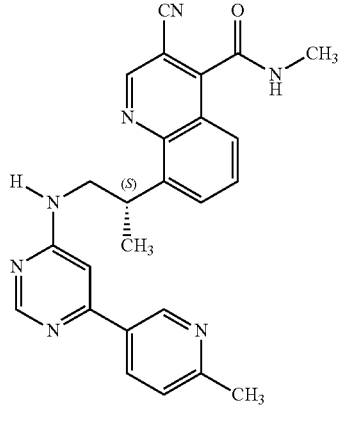 | 438.57 | (methanol-d₄) δ 9.28, 9.20 (2s, 1H), 8.84 (s, 1H), 8.75 (d, J = 8.3 Hz, 1H), 8.59, 8.53 (2s, 1H), 8.21 (d, J = 8.8 Hz, 2H), 8.02-7.90 (m, 1H), 7.81 (t, J = 7.8 Hz, 1H), 7.62 (d, J = 8.6 Hz, 1H), 7.14, 6.80 (2s, 1H), 4.65 (q, J = 7.3 Hz, 2H), 4.24-3.83 (m, 2H), 3.19 (s, 3H), 2.73 (s, 3H), 1.57, 1.53 (2d, J = 7.1 Hz, 3H) |
| 767 | 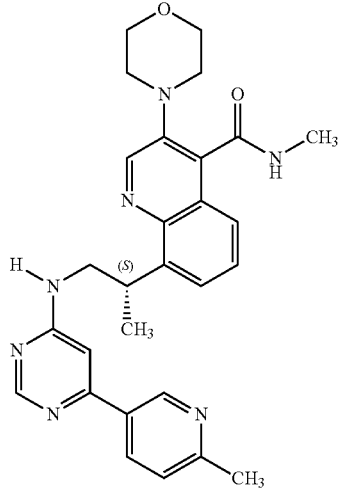 | 498.65 | (methanol-d₄) δ 8.91 (d, J = 7.1 Hz, 1H), 8.85, 8.76 (2s, 1H), 8.62, 8.56 (2s, 1H), 8.27 (dd, J = 8.3, 2.4 Hz, 1H), 7.76-7.46 (m, 4H), 6.84 (s, 1H), 4.54 (q, J = 7.1 Hz, 1H), 4.14-3.89 (m, 2H), 3.80 (q, J = 6.9, 4.2 Hz, 4H), 3.20 (q, J = 4.6 Hz, 4H), 3.02 (s, 3H), 2.74, 2.68 (2s, 3H), 1.54, 1.48 (d, J = 7.0 Hz, 3H) |

TABLE 1-continued
| Cmpnd No. | Structure | ESMS (M + H) | ¹H NMR (300 MHz, unless indicated otherwise) NMR peaks given as δ values |
|---|---|---|---|
| 768 | 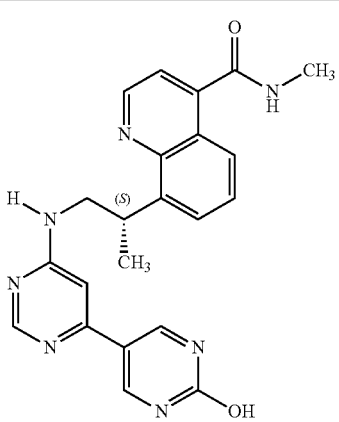 | 416.56 | (DMSO-$d_6$) δ 8.99 (m, 1H), 8.75 (m, 3H), 8.37 (m, 1H), 7.98 (dd, J = 8.4, 1.4 Hz, 1H), 7.76 (m, 1H), 7.70-7.58 (m, 1H), 7.54 (m, 2H), 6.73 (s, 1H), 4.50 (m, 1H), 3.75 (m, 2H), 2.87 (d, J = 4.5 Hz, 3H), 1.37 (d, J = 6.7 Hz, 3H) |
| 769 | 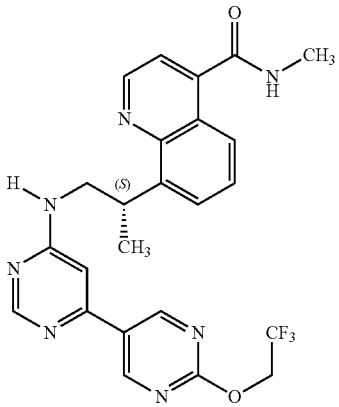 | 498.61 | (DMSO-$d_6$) δ 8.98 (d, J = 4.3 Hz, 1H), 8.85 (s, 1H), 8.68 (m, 1H), 8.35 (m, 1H), 7.98 (d, J = 8.4 Hz, 1H), 7.79-7.70 (m, H), 7.63 (m, 1H), 7.52 (m, 1H), 7.43 (m, 1H), 5.07-4.89 (m, 1H), 4.47 (m, 2H), 3.75 (m, 1H), 2.87 (d, J = 4.6 Hz, 3H), 1.34 (d, J = 7.9 Hz, 3H) |
| 770 | 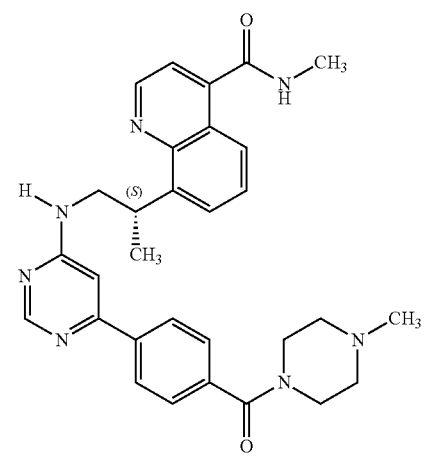 | 524.66 | (DMSO-$d_6$) δ 10.04 (s, 1H), 8.97 (d, J = 4.3 Hz, 1H), 8.74-8.55 (m, 2H), 8.00 (m, 3H), 7.78 (m, 1H), 7.68-7.52 (m, 4H), 6.95 (s, 1H), 4.54 (m, 1H), 4.00-3.03 (m, 10H), 2.93-2.76 (m, 6H), 1.41 (d, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 771 | 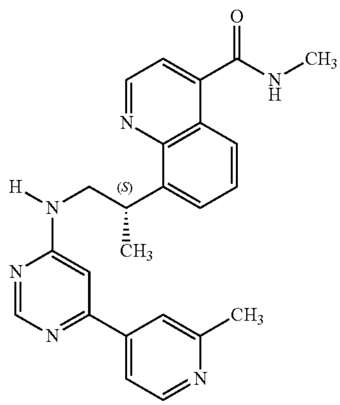 | 413.59 | |
| 772 | 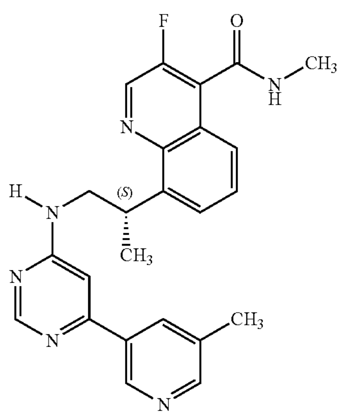 | 430.96 | (methanol-d₄) δ 8.86 (s, 1H), 8.80 (br.s, 1H), 8.48 (br.s, 1H), 8.41 (s, 1H), 8.13 (br.s, 1H), 7.84-7.56 (m, 3H), 6.76 (br. s, 1H), 4.57 (q, J = 7.1 Hz, 1H), 3.80 (dd, J = 13.2, 6.9 Hz, 2H), 3.03 (s, 3H), 2.44 (s, 3H), 1.48 (d, J = 6.9 Hz, 3H) |
| 773 | 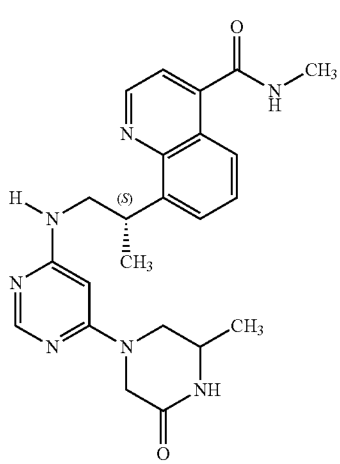 | 434 | (400 MHz, DMSO-d₆) δ 9.07 (d, J = 4.0 Hz, 1H), 8.68 (d, J = 4.6 Hz, 1H), 8.36 (s, 3H), 8.04 (dd, J = 8.4, 1.1 Hz, 1H), 7.80 (d, J = 7.0 Hz, 1H), 7.70-7.61 (m, 1H), 7.57 (d, J = 4.3 Hz, 1H), 6.01 (s, 1H), 4.51 (s, 1H), 4.10 (s, 3H), 3.76-3.38 (m, 4H), 2.88 (d, J = 4.6 Hz, 3H), 1.40 (d, J = 6.9 Hz, 3H), 1.13 (d, J = 6.3 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 774 | 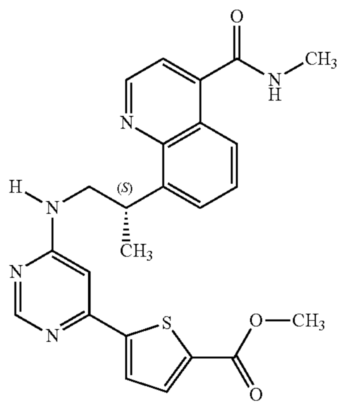 | 462 | (400 MHz, DMSO-d₆) δ 8.99 (s, 1H), 8.66 (d, J = 4.6 Hz, 1H), 8.48 (s, 1H), 7.90 (dd, J = 81.5, 16.4 Hz, 5H), 7.67-7.59 (m, 1H), 7.54 (s, 1H), 6.90 (s, 1H), 4.51 (s, 1H), 3.85 (s, 5H), 2.87 (d, J = 4.6 Hz, 3H), 1.38 (d, J = 5.4 Hz, 3H) |
| 775 | 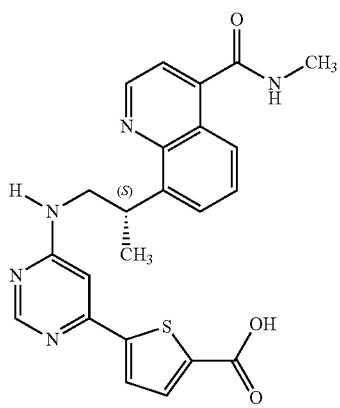 | 448 | (400 MHz, DMSO-d₆) δ 8.99 (s, 1H), 8.66 (d, J = 4.4 Hz, 1H), 8.48 (s, 1H), 8.21-7.97 (m, 2H), 7.66 (dd, J = 32.4, 24.6 Hz, 4H), 7.54 (s, 1H), 6.89 (s, 1H), 4.51 (s, 1H), 3.63 (d, J = 127.2 Hz, 2H), 2.87 (d, J = 4.6 Hz, 3H), 1.38 (d, J = 5.9 Hz, 3H) |
| 776 | 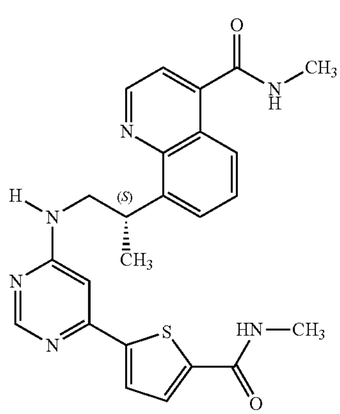 | 461 | (400 MHz, DMSO-d₆) δ 8.97 (s, 1H), 8.63 (d, J = 5.0 Hz, 1H), 8.51 (s, 1H), 8.35 (s, 1H), 7.97 (d, J = 8.4 Hz, 1H), 7.89-7.42 (m, 6H), 6.78 (s, 1H), 4.43 (d, J = 37.2 Hz, 1H), 3.72 (s, 2H), 2.85 (d, J = 4.6 Hz, 3H), 2.75 (d, J = 4.4 Hz, 3H), 1.35 (d, J = 5.4 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 777 | 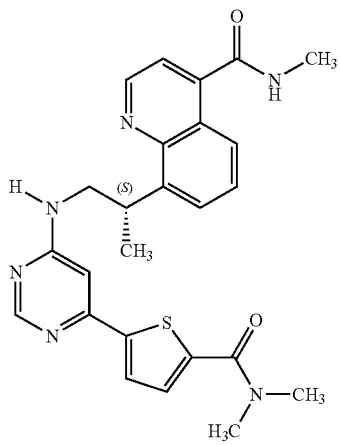 | 475 | (400 MHz, DMSO-$d_6$) δ 8.99 (s, 1H), 8.65 (d, J = 4.2 Hz, 1H), 8.37 (s, 1H), 7.99 (d, J = 8.1 Hz, 1H), 7.61 (dt, J = 47.4, 32.2 Hz, 6H), 6.83 (s, 1H), 4.50 (s, 1H), 3.74 (s, 2H), 3.14 (d, J = 22.5 Hz, 6H), 2.87 (d, J = 4.5 Hz, 3H), 1.37 (d, J = 6.0 Hz, 3H) |
| 778 | 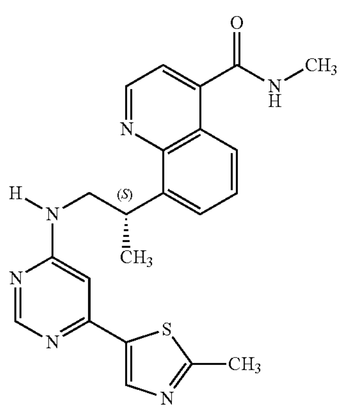 | 419.58 | (DMSO-$d_6$) δ 8.99 (s, 1H), 8.67 (m, 1H), 8.35 (s, 1H), 8.15 (s, 1H), 7.99 (d, J = 8.6 Hz, 1H), 7.75 (s, 1H), 7.68-7.52 (m, 2H), 6.76 (s, 1H), 4.49 (m, 1H), 3.74 (m, 2H), 2.87 (d, J = 4.5 Hz, 3H), 2.68 (s, 3H), 1.36 (d, J = 6.9 Hz, 3H) |
| 779 | 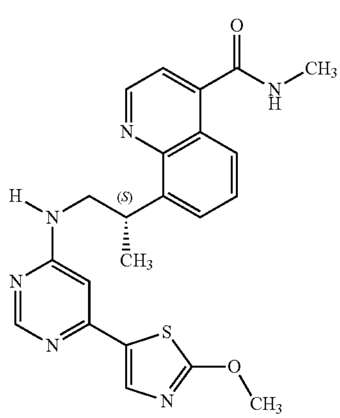 | 435.64 | |

| Cmpnd No. | Structure | ESMS (M + H) | ¹H NMR (300 MHz, unless indicated otherwise) NMR peaks given as δ values |
|---|---|---|---|
| 780 | 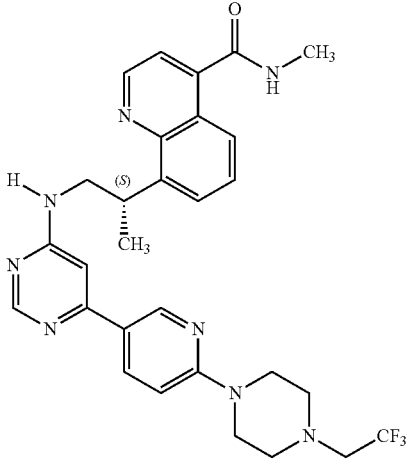 | 565.7 | (DMSO-d₆) δ 8.99 (d, J = 4.3 Hz, 1H) 8.67 (m, 1H), 8.40 (s, 1H), 8.07 (s, 1H), 8.02-7.95 (m, 1H), 7.77 (m, 1H), 7.68-7.59 (m, 1H), 7.55 (s, 1H), 7.41 (s, 1H), 6.93 (d, J = 9.1 Hz, 1H), 6.80 (s, 1H), 4.50 (s, 1H), 3.60-3.80 (m, 6H), 3.30-3.14 (m, 2H), 2.87 (d, J = 4.5 Hz, 3H), 2.71 (m, 4H), 1.37 (d, J = 6.9 Hz, 3H) |
| 781 | 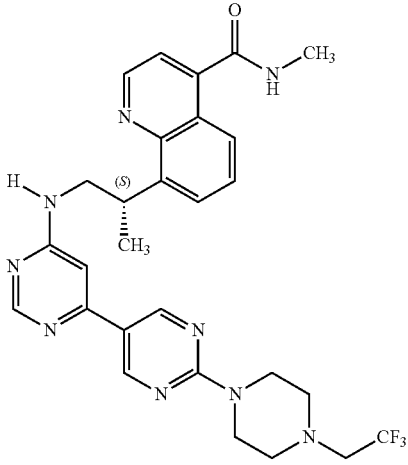 | 566.64 | (DMSO-d₆) δ 8.98 (d, J = 4.3 Hz, 1H), 8.88 (s, 1H), 8.67 (d, J = 4.9 Hz, 1H), 8.41 (s, 1H), 7.99 (dd, J = 8.4, 1.3 Hz, 1H), 7.77 (s, 1H), 7.69-7.58 (m, 1H), 7.54 (m, 2H), 6.75 (s, 1H), 4.51 (m, 1H), 3.83 (m, 6H), 3.29-3.18 (m, 2H), 2.87 (d, J = 4.6 Hz, 3H), 2.69 (m, 4H), 1.36 (d, J = 6.8 Hz, 3H) |
| 782 | 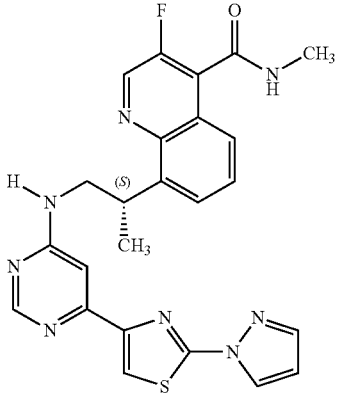 | 489.14 | (methanol-d₄) δ 8.88 (s, 1H), 8.45 (d, J = 2.6 Hz, 1H), 8.34 (s, 1H), 7.95 (s, 1H), 7.86-7.54 (m, 4H), 7.05 (s, 1H), 6.59 (s, 1H), 4.57 (q, J = 7.1 Hz, 1H), 3.80 (dd, J = 13.0, 7.3 Hz, 2H), 3.02 (s, 3H), 1.48 (d, J = 6.8 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 783 | 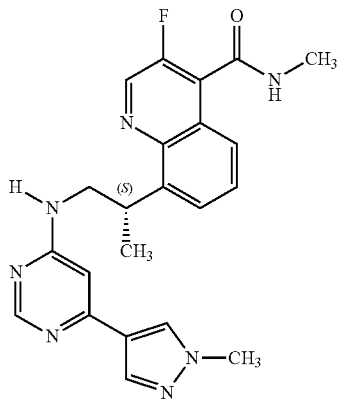 | 420.22 | (methanol-$d_4$) δ 8.88 (s, 1H), 8.26 (s, 1H), 8.06 (s, 1H), 7.92 (s, 1H), 7.86-7.55 (m, 3H), 6.55 (br.s, 1H), 4.55 (q, J = 7.1 Hz, 1H), 3.93 (s, 3H), 3.75 (m, 1H), 3.03 (s, 3H), 1.46 (d, J = 7.1 Hz, 3H) |
| 784 | 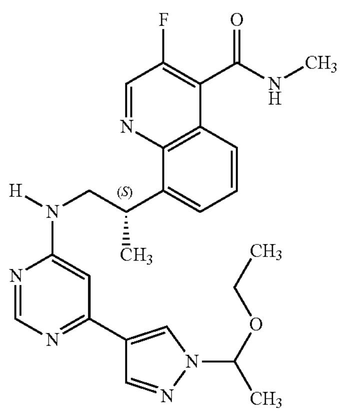 | 478.24 | (methanol-$d_4$) δ 8.88 (s, 1H), 8.27 (br.s, 2H), 7.99 (s, 1H), 7.88-7.55 (m, 3H), 6.56 (s, 1H), 5.72-5.47 (m, 1H), 4.67-4.42 (m, 1H), 3.77 (d, J = 8.8 Hz, 2H), 3.53-3.40 (m, 1H), 3.01 (s, 3H), 1.66 (d, J = 6.0 Hz, 3H), 1.46 (d, J = 7.0 Hz, 3H), 1.14 (t, J = 7.0 Hz, 3H) |
| 785 | 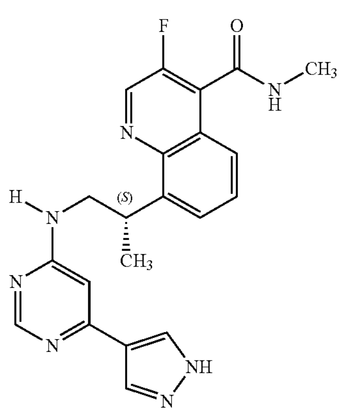 | 406.22 | (methanol-$d_4$) δ 8.89 (s, 1H), 8.27 (s, 1H), 8.09 (br.s, 2H), 7.91-7.53 (m, 3H), 6.59 (br.s, 2H), 4.56 (d, J = 7.7 Hz, 1H), 3.76 (m, 2H), 3.03 (s, 3H), 1.47 (d, J = 7.0 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 786 | 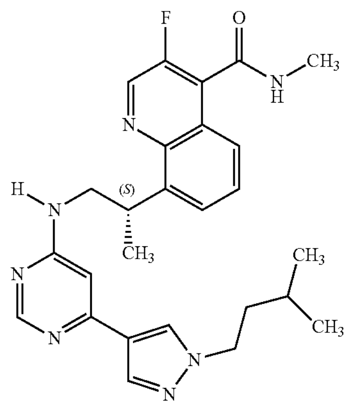 | 476.26 | (methanol-d₄) δ 8.88 (s, 1H), 8.26 (s, 1H), 8.11 (s, 1H), 7.93 (s, 1H), 7.87-7.56 (m, 3H), 4.55 (q, J = 7.1 Hz, 1H), 4.21 (t, J = 7.3 Hz, 2H), 3.76 (d, J = 9.6 Hz, 2H), 3.03 (s, 3H), 1.77 (q, J = 7.2 Hz, 2H), 1.55 (dt, J = 13.6, 6.7 Hz, 1H), 1.46 (d, J = 7.0 Hz, 3H), 0.96 (d, J = 6.6 Hz, 6H) |
| 787 | 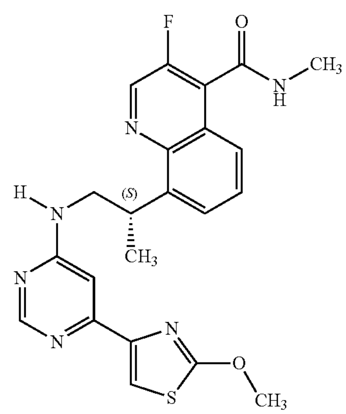 | 453.17 | (methanol-d₄) δ 8.89 (s, 1H), 8.23 (s, 1H), 7.88-7.52 (m, 4H), 4.55 (q, J = 7.4 Hz, 1H), 4.11 (s, 3H), 3.88-3.73 (m, 2H), 3.03 (s, 3H), 1.46 (d, J = 7.0 Hz, 3H) |
| 788 | 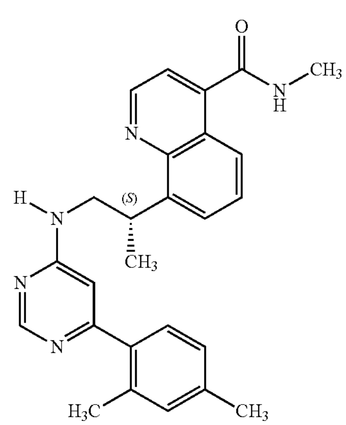 | 426.25 | (DMSO-d₆) δ 8.96 (s, 1H), 8.67 (d, J = 4.7 Hz, 1H), 8.44 (s, 1H), 7.99 (dd, J = 8.4, 1.4 Hz, 1H), 7.76 (d, J = 7.1 Hz, 1H), 7.63 (dd, J = 8.4, 7.2 Hz, 1H), 7.52 (d, J = 4.3 Hz, 1H), 7.24 (s, 1H), 7.10 (m, 2H), 6.48 (s, 1H), 4.48 (m, 1H), 2.86 (d, J = 4.6 Hz, 3H), 2.31 (s, 6H), 1.38 (d, J = 6.9 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 789 | 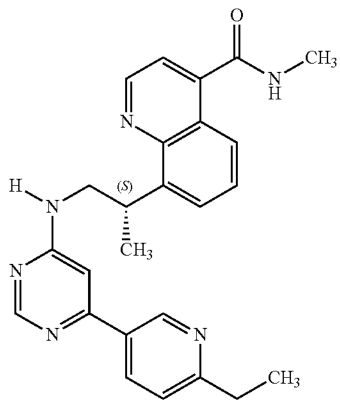 | 427.17 | (DMSO-d$_6$) δ 8.98 (d, J = 4.4 Hz, 1H), 8.68 (d, J = 5.4 Hz, 1H), 8.48 (s, 1H), 8.19 (s, 1H), 8.04-7.95 (m, 1H), 7.77 (s, 1H), 7.69-7.49 (m, 3H), 7.39 (m, 1H), 6.90 (s, 1H), 4.52 (s, 1H), 3.75 (m, 2H), 2.84 (m, 5H), 1.38 (d, J = 6.9 Hz, 3H), 1.26 (t, J = 7.5 Hz, 3H) |
| 790 | 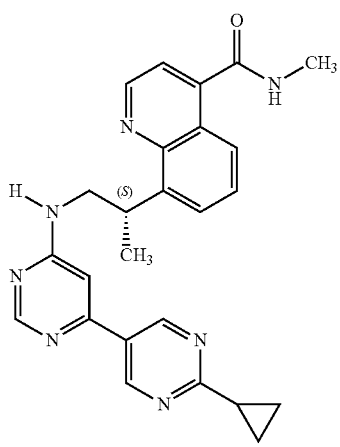 | 440.18 | (DMSO-d$_6$) δ 9.24 (s, 1H), 9.08 (s, 1H), 8.97 (d, J = 4.3 Hz, 1H), 8.67 (d, J = 4.8 Hz, 1H), 8.49 (s, 1H), 7.99 (d, J = 8.3 Hz, 1H), 7.84-7.58 (m, 3H), 7.54 (s, 1H), 6.91 (s, 1H), 4.52 (m, 1H), 3.80 (m, 2H), 2.87 (d, J = 4.5 Hz, 3H), 1.37 (d, J = 6.9 Hz, 3H), 1.19-0.99 (m, 4H) |
| 791 | 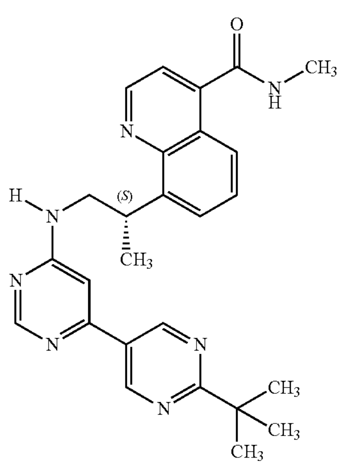 | 456.2 | (DMSO-d$_6$) δ 9.19 (m, 2H), 8.97 (d, J = 4.3 Hz, 1H), 8.67 (d, J = 4.8 Hz, 1H), 8.52 (s, 1H), 7.99 (d, J = 8.4 Hz, 1H), 7.72 (m, 2H), 7.67-7.58 (m, 1H), 7.53 (d, J = 4.1 Hz, 1H), 6.93 (s, 1H), 4.52 (m, 1H), 3.80 (m, 2H), 2.86 (d, J = 4.6 Hz, 3H), 1.39 (m, 12H) |

TABLE 1-continued

| Cmpnd No. | Structure | ESMS (M + H) | ¹H NMR (300 MHz, unless indicated otherwise) NMR peaks given as δ values |
|---|---|---|---|
| 792 | 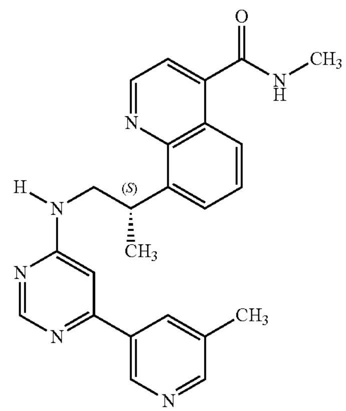 | 413.13 | (DMSO-d$_6$) δ 8.98 (d, J = 4.3 Hz, 1H), 8.88 (s, 1H), 8.68 (d, J = 5.0 Hz, 1H), 8.49 (m, 2H), 8.10 (m, 1H), 7.99 (d, J = 8.5 Hz, 1H), 7.77 (s, 1H), 7.64 (t, J = 7.8 Hz, 1H), 7.55 (s, 1H), 6.95 (s, 1H), 4.52 (s, 1H), 3.75 (m, 2H), 2.87 (d, J = 4.5 Hz, 3H), 2.38 (s, 3H), 1.38 (d, J = 6.7 Hz, 3H) |
| 793 | 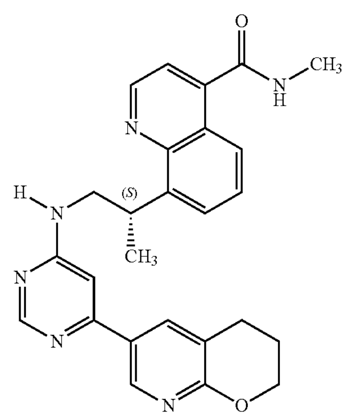 | 455.17 | (DMSO-d$_6$) δ 8.98 (d, J = 4.3 Hz, 1H), 8.68 (m, 1H), 8.54 (s, 1H), 8.43 (s, 1H), 7.99 (m, 2H), 7.77 (s, 1H), 7.63 (t, J = 7.8 Hz, 1H), 7.55 (m, 2H), 6.85 (s, 1H), 4.51 (s, 1H), 4.33 (m, 2H), 3.75 (m, 2H), 2.87 (m, 5H), 1.94 (m, 2H), 1.38 (d, J = 6.8 Hz, 3H) |
| 794 | 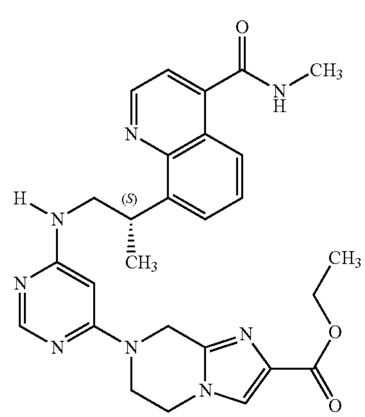 | 515 | (400 MHz, DMSO-d$_6$) δ 9.06 (d, J = 4.3 Hz, 1H), 8.69 (d, J = 4.5 Hz, 1H), 8.39 (s, 1H), 8.03 (dd, J = 8.4, 1.2 Hz, 1H), 7.93 (s, 1H), 7.80 (d, J = 6.9 Hz, 1H), 7.69-7.62 (m, 1H), 7.57 (d, J = 4.3 Hz, 1H), 6.13 (s, 1H), 4.88 (s, 2H), 4.51 (s, 1H), 4.29-4.06 (m, 6H), 3.80-3.66 (m, 1H), 3.56 (s, 1H), 2.87 (d, J = 4.6 Hz, 3H), 1.41 (d, J = 6.9 Hz, 3H), 1.26 (t, J = 7.1 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 795 | 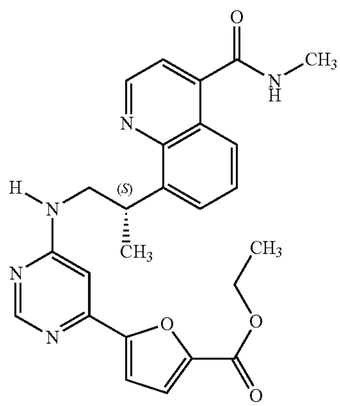 | 460 | (400 MHz, DMSO-$d_6$) δ 8.97 (s, 1H), 8.66 (s, 1H), 8.54 (s, 1H), 8.36 (s, 1H), 8.00 (d, J = 7.9 Hz, 1H), 7.74 (s, 1H), 7.63 (t, J = 7.6 Hz, 1H), 7.46 (dd, J = 60.3, 26.4 Hz, 3H), 6.95 (s, 1H), 4.53-4.30 (m, 3H), 3.96-3.71 (m, 2H), 2.87 (d, J = 4.6 Hz, 3H), 1.47-1.26 (m, 6H) |
| 796 | 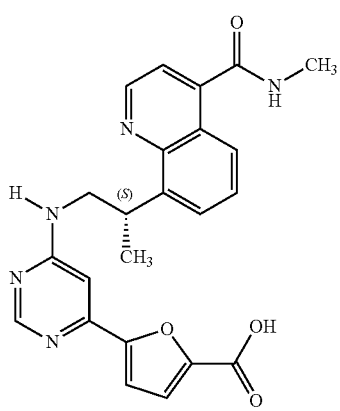 | 432 | (400 MHz, DMSO-$d_6$) δ 8.98 (s, 1H), 8.91-8.50 (m, 3H), 8.01 (d, J = 8.0 Hz, 1H), 7.75 (d, J = 6.7 Hz, 1H), 7.63 (t, J = 7.8 Hz, 1H), 7.55-7.34 (m, 3H), 6.97 (s, 1H), 4.49 (s, 1H), 3.84 (dd, J = 20.8, 14.3 Hz, 2H), 2.87 (d, J = 4.5 Hz, 3H), 1.39 (d, J = 6.3 Hz, 3H) |
| 797 | 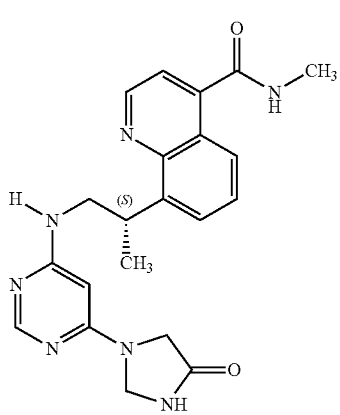 | 406 | (400 MHz, DMSO-$d_6$) δ 9.01 (d, J = 4.2 Hz, 1H), 8.83 (s, 1H), 8.67 (d, J = 4.7 Hz, 1H), 8.36 (s, 1H), 8.03 (d, J = 8.4 Hz, 1H), 7.79 (d, J = 7.6 Hz, 1H), 7.69-7.63 (m, 1H), 7.57 (d, J = 4.3 Hz, 1H), 5.84-5.61 (m, 1H), 4.88 (s, 2H), 4.49 (s, 1H), 3.95 (s, 2H), 3.68 (s, 1H), 3.53 (s, 1H), 2.87 (d, J = 4.6 Hz, 3H), 1.40 (d, J = 6.9 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 798 | 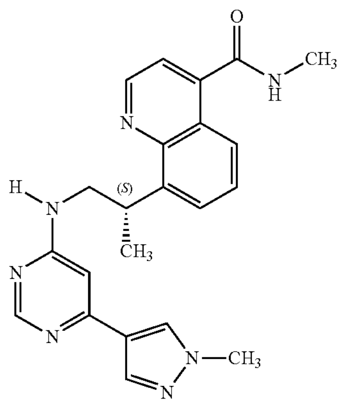 | 402 | (400 MHz, DMSO-d$_6$) δ 9.31 (d, J = 34.8 Hz, 1H), 8.96 (d, J = 4.3 Hz, 1H), 8.74-8.40 (m, 3H), 8.17 (d, J = 69.7 Hz, 1H), 8.01 (d, J = 8.4 Hz, 1H), 7.88-7.70 (m, 1H), 7.63 (s, 1H), 7.54 (s, 1H), 6.93 (d, J = 160.0 Hz, 1H), 4.54 (s, 1H), 3.85 (t, J = 64.7 Hz, 5H), 2.87 (d, J = 4.6 Hz, 3H), 1.39 (d, J = 6.9 Hz, 3H) |
| 799 | 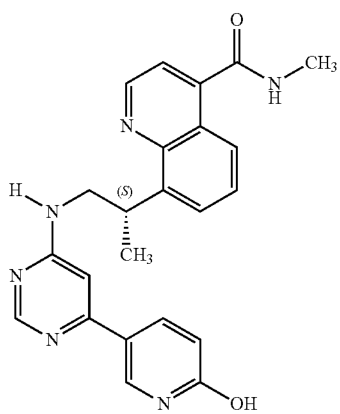 | 415.11 | |
| 800 | 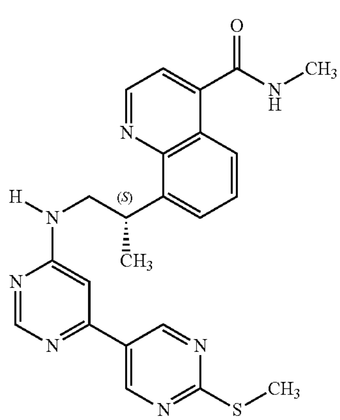 | 446.12 | |

TABLE 1-continued

| Cmpnd No. | Structure | ESMS (M + H) | ¹H NMR (300 MHz, unless indicated otherwise) NMR peaks given as δ values |
|---|---|---|---|
| 801 | 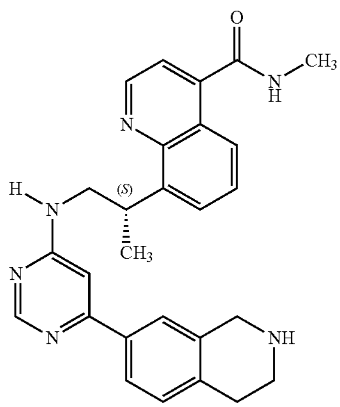 | 453 | (400 MHz, DMSO-$d_6$) δ 8.96 (d, J = 4.2 Hz, 1H), 8.43 (s, 1H), 8.01 (s, 1H), 7.66 (dd, J = 32.6, 24.9 Hz, 6H), 7.18 (s, 1H), 7.10-6.80 (m, 1H), 4.49 (s, 3H), 3.52 (s, 2H), 3.17 (s, 2H), 2.87 (d, J = 4.4 Hz, 3H), 2.70 (s, 2H), 1.38 (s, 3H) |
| 802 | 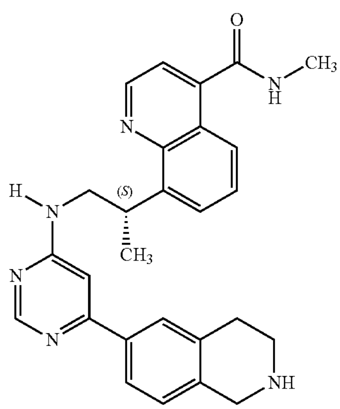 | 453 | (400 MHz, DMSO-$d_6$) δ 8.97 (d, J = 4.2 Hz, 1H), 8.69 (s, 1H), 8.43 (s, 1H), 8.00 (d, J = 8.4 Hz, 1H), 7.86-7.36 (m, 6H), 7.16 (s, 1H), 4.49 (s, 3H), 3.72 (s, 2H), 3.52 (s, 2H), 2.87 (d, J = 4.5 Hz, 3H), 2.70 (s, 2H), 1.38 (d, J = 6.6 Hz, 3H) |
| 803 | 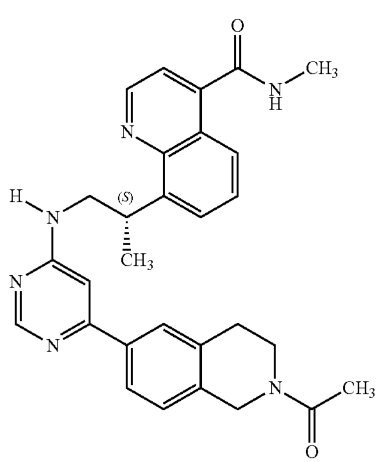 | 495 | (400 MHz, DMSO-$d_6$) δ 8.98 (d, J = 4.2 Hz, 1H), 8.65 (s, 1H), 8.45 (s, 1H), 8.00 (d, J = 7.9 Hz, 1H), 7.76 (s, 3H), 7.63 (t, J = 7.7 Hz, 1H), 7.42 (d, J = 99.1 Hz, 3H), 6.83 (d, J = 43.9 Hz, 1H), 4.69 (d, J = 24.6 Hz, 2H), 4.46 (d, J = 48.7 Hz, 1H), 3.68 (s, 4H), 2.99-2.71 (m, 5H), 2.10 (s, 3H), 1.38 (d, J = 5.9 Hz, 3H) |

TABLE 1-continued

| Cmpnd No. | Structure | ESMS (M + H) | $^1$H NMR (300 MHz, unless indicated otherwise) NMR peaks given as δ values |
|---|---|---|---|
| 804 | 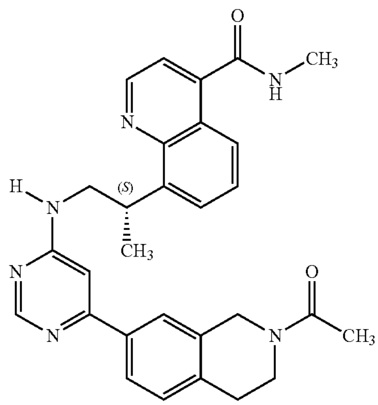 | 495 | (400 MHz, DMSO-d$_6$) δ 8.98 (d, J = 4.2 Hz, 1H), 8.65 (d, J = 4.3 Hz, 1H), 8.45 (s, 1H), 8.00 (d, J = 8.2 Hz, 1H), 7.76 (s, 3H), 7.68-7.59 (m, 1H), 7.43 (d, J = 94.8 Hz, 3H), 6.84 (d, J = 42.8 Hz, 1H), 4.67 (d, J = 23.4 Hz, 2H), 4.50 (s, 1H), 3.69 (s, 4H), 2.89 (t, J = 14.7 Hz, 5H), 2.10 (s, 3H), 1.38 (s, 3H) |
| 805 | 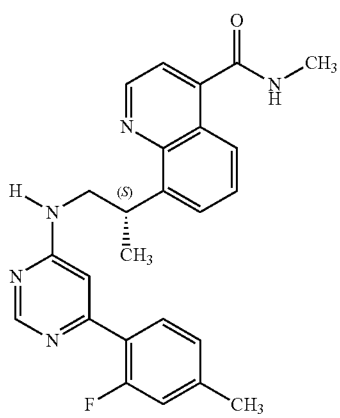 | 430.19 | (DMSO-d$_6$) δ 8.96 (s, 1H), 8.67 (d, J = 5.1 Hz, 1H), 8.47 (s, 1H), 7.98 (dd, J = 8.3, 1.4 Hz, 1H), 7.89 (d, J = 9.0 Hz, 1H), 7.75 (d, J = 7.1 Hz, 1H), 7.68-7.58 (m, 2H), 7.53 (d, J = 4.2 Hz, 1H), 7.22-7.07 (m, 2H), 6.90 (s, 1H), 4.47 (m, 1H), 3.75 (m, 2H), 2.86 (d, J = 4.5 Hz, 3H), 2.35 (s, 3H), 1.37 (d, J = 6.9 Hz, 3H) |
| 806 | 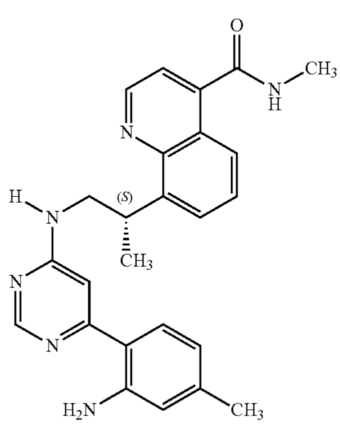 | 427.12 | (DMSO-d$_6$) δ 8.98 (d, J = 4.3 Hz, 1H), 8.68 (m, 1H), 8.40 (s, 1H), 7.99 (dd, J = 8.2, 1.2 Hz, 1H), 7.77 (m, 1H), 7.70-7.59 (m, 1H), 7.55 (s, 1H), 7.32 (m, 1H), 6.53 (m, 3H), 6.43 (s, 1H), 4.50 (m, 1H), 3.70 (m, 2H), 2.87 (d, J = 4.4 Hz, 3H), 2.19 (s, 3H), 1.38 (d, J = 6.8 Hz, 3H) |

| Cmpnd No. | Structure | ESMS (M + H) | ¹H NMR (300 MHz, unless indicated otherwise) NMR peaks given as δ values |
|---|---|---|---|
| 807 | 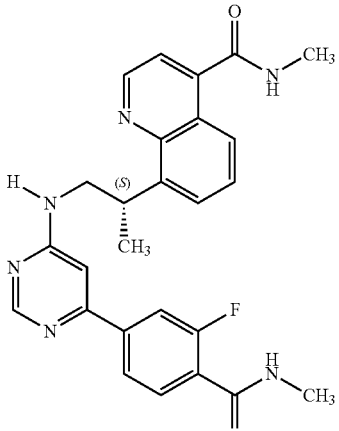 | 473.13 | (DMSO-d₆) δ 8.98 (d, J = 4.2 Hz, 1H), 8.69 (d, 1H), 8.49 (s, 1H), 8.33 (m, 1H), 8.00 (d, J = 8.4 Hz, 1H), 7.77 (m, 3H), 7.69-7.46 (m, 3H), 6.90 (s, 1H), 4.52 (m, 1H), 3.75 (m, 2H), 2.87 (d, J = 4.4 Hz, 3H), 2.84-2.74 (m, 3H), 1.39 (d, 3H) |
| 808 | 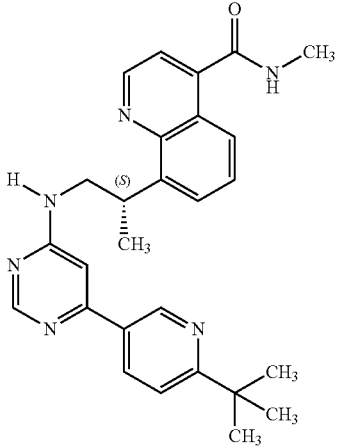 | 457.1 | (DMSO-d₆) δ 8.98 (d, J = 4.3 Hz, 2H), 8.68 (m, 1H), 8.49 (s, 1H), 8.25 (s, 1H), 7.99 (d, J = 8.2 Hz, 1H), 7.77 (m, 2H), 7.70-7.58 (m, 2H), 7.54 (s, 1H), 6.92 (s, 1H), 5.33 (s, 1H), 4.52 (m, 1H), 3.80 (m, 2H), 2.87 (d, J = 4.5 Hz, 3H), 1.47 (s, 6H), 1.38 (d, J = 6.7 Hz, 3H) |
| 809 | 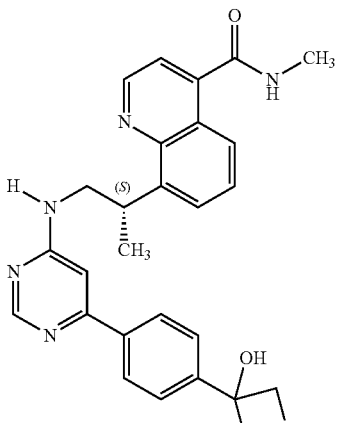 | 470.16 | (DMSO-d₆) δ 8.99 (m, 1H), 8.68 (d, J = 5.2 Hz, 1H), 8.47 (s, 1H), 8.00 (m, 2H), 7.74 (m, 3H), 7.68-7.47 (m, 3H), 6.92 (s, 1H), 6.46 (s, 1H), 4.80 (m, 2H), 4.71 (m, 2H), 4.51 (m, 1H), 3.75 (m, 2H), 2.87 (d, J = 4.5 Hz, 3H), 1.38 (d, J = 6.9 Hz, 3H) |

| Cmpnd No. | Structure | ESMS (M + H) | ¹H NMR (300 MHz, unless indicated otherwise) NMR peaks given as δ values |
|---|---|---|---|
| 810 | 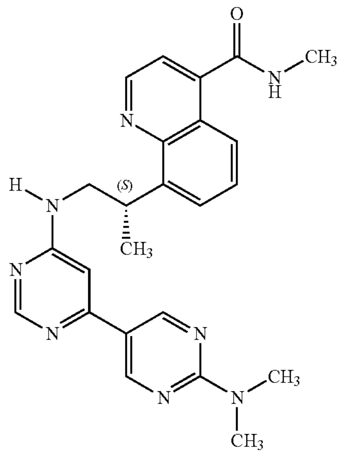 | 443.15 | (DMSO-d₆) δ 8.98 (d, J = 4.3 Hz, 1H), 8.87 (s, 1H), 8.68 (d, J = 4.9 Hz, 1H), 8.41 (s, 1H), 7.99 (d, J = 8.1 Hz, 1H), 7.77 (s, 1H), 7.63 (t, J = 7.8 Hz, 1H), 7.51 (m, 2H), 6.75 (s, 1H), 4.51 (m, 1H), 3.75 (m, 2H), 3.19 (s, 6H), 2.87 (d, J = 4.5 Hz, 3H), 1.36 (d, J = 6.9 Hz, 3H) |
| 811 | 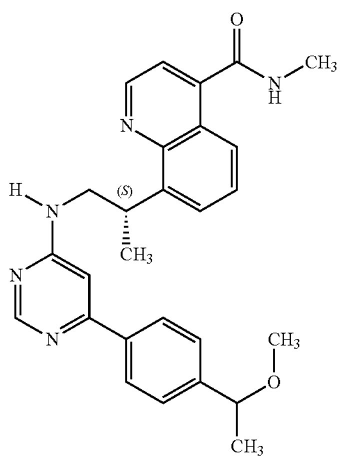 | 456.16 | (DMSO-d₆) δ 8.99 (d, J = 4.3 Hz, 1H), 8.68 (d, J = 5.3 Hz, 1H), 8.46 (s, 1H), 8.11-7.86 (m, 3H), 7.77 (m, 1H), 7.64 (t, J = 7.7 Hz, 1H), 7.49 (m, 4H), 6.90 (s, 1H), 4.52 (m, 1H), 4.37 (m, 1H), 3.75 (m, 2H), 3.15 (s, 3H), 2.87 (d, J = 4.5 Hz, 3H), 1.37 (m, 6H) |
| 812 | 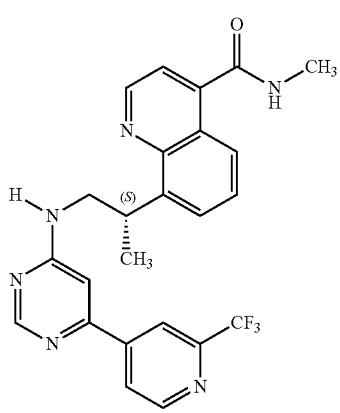 | 467.05 | (DMSO-d₆) δ 8.97 (d, J = 4.3 Hz, 1H), 8.90 (m, 1H), 8.68 (m, 1H), 8.57 (m, 1H), 8.31 (s, 1H), 8.18 (s, 1H), 7.99 (d, J = 8.4 Hz, 1H), 7.75 (m, 2H), 7.63 (t, J = 7.9 Hz, 1H), 7.53 (d, J = 4.3 Hz, 1H), 7.12 (s, 1H), 4.52 (m, 1H), 3.80 (m, 2H), 2.86 (d, J = 4.6 Hz, 3H), 1.38 (d, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 813 | 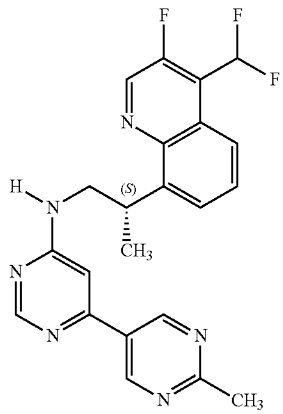 | 425 | (400 MHz, DMSO-$d_6$) δ 9.11 (d, J = 20.1 Hz, 3H), 8.48 (s, 1H), 8.16 (d, J = 8.4 Hz, 1H), 7.76 (dt, J = 60.6, 39.0 Hz, 4H), 6.92 (s, 1H), 4.57-4.38 (m, 1H), 3.77 (s, 2H), 2.68 (s, 3H), 1.38 (d, J = 5.5 Hz, 3H) |
| 814 | 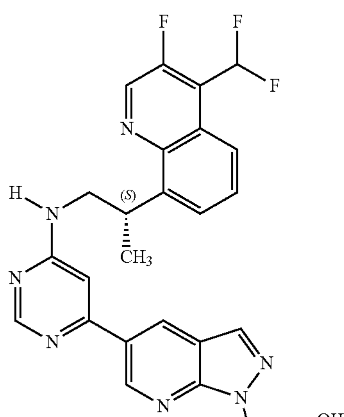 | 494 | (DMSO-$d_6$) δ 9.09 (s, 2H), 8.76 (s, 1H), 8.48 (s, 1H), 8.26 (s, 1H), 8.16 (d, J = 7.8 Hz, 1H), 7.97-7.62 (m, 3H), 7.54 (s, 1H), 6.91 (d, J = 42.4 Hz, 1H), 4.88 (s, 1H), 4.53 (d, J = 5.6 Hz, 3H), 3.82 (d, J = 47.8 Hz, 4H), 1.40 (d, J = 5.9 Hz, 3H) |
| 815 | 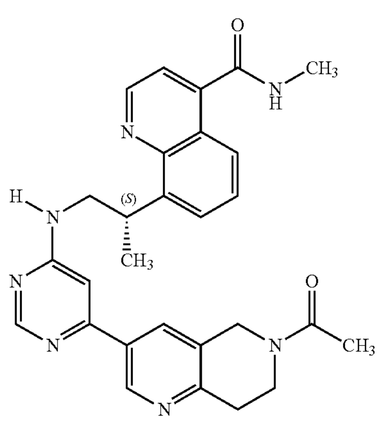 | 496.13 | (DMSO-$d_6$) δ 9.00-8.82 (m, 2H), 8.68 (m, 1H), 8.57 (s, 1H), 8.12 (m, 1H), 8.00 (d, J = 8.3 Hz, 1H), 7.78 (s, 1H), 7.64 (t, J = 7.8 Hz, 1H), 7.55 (s, 1H), 6.93 (s, 1H), 4.75 (m, 2H), 4.53 (m, 1H), 3.80 (m, 4H), 3.11 -2.81 (m, 5H), 2.12 (d, J = 6.7 Hz, 3H), 1.39 (s, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 816 | 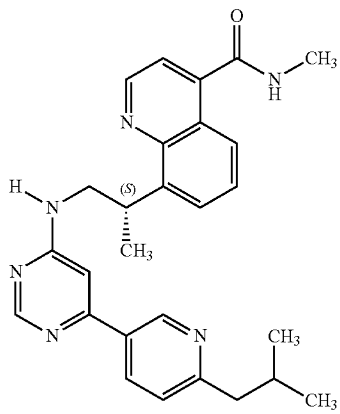 | 455.21 | (DMSO-d$_6$) δ 8.98 (m, 2H), 8.68 (m, 1H), 8.48 (s, 1H), 8.19 (m, 1H), 8.02-7.95 (m, 1H), 7.77 (s, 1H), 7.69-7.51 (m, 3H), 7.35 (m, 1H), 6.90 (s, 1H), 4.52 (m, 1H), 3.80 (m, 2H), 2.87 (d, J = 4.5 Hz, 3H), 2.66 (d, J = 7.1 Hz, 2H), 2.10 (m, 1H), 1.38 (d, J = 6.9 Hz, 3H), 0.90 (d, J = 6.6 Hz, 6H) |
| 817 | 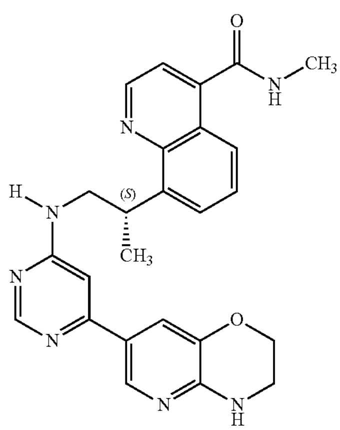 | 456.2 | (DMSO-d$_6$) δ 9.00 (m, 1H), 8.68 (m, 1H), 8.45 (s, 1H), 8.19 (m, 1H), 8.00 (dd, J = 8.3, 1.3 Hz, 1H), 7.78 (s, 1H), 7.64 (t, J = 7.8 Hz, 1H), 7.55 (s, 1H), 7.43 (s, 1H), 6.75 (s, 1H), 4.52 (m, 1H), 4.16 (m, 2H), 3.74 (m, 2H), 3.45 (m, 2H), 2.87 (d, J = 4.5 Hz, 3H), 1.38 (d, J = 6.8 Hz, 3H) |
| 818 | 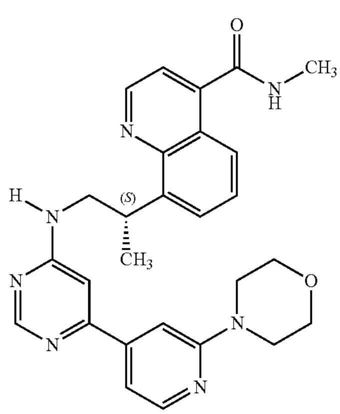 | 484.29 | (DMSO-d$_6$) δ 8.97 (d, J = 4.3 Hz, 1H), 8.67 (d, J = 4.7 Hz, 1H), 8.49 (s, 1H), 8.24 (s, 1H), 8.04-7.95 (m, 1H), 7.76 (s, 1H), 7.68-7.60 (m, 1H), 7.54 (s, 1H), 7.32 (s, 1H), 7.11 (s, 1H), 6.95 (s, 1H), 4.50 (s, 1H), 3.71 (m, 6H), 3.49 (m, 4H), 3.17 (d, J = 5.3 Hz, 3H), 1.37 (d, J = 7.0 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 819 | 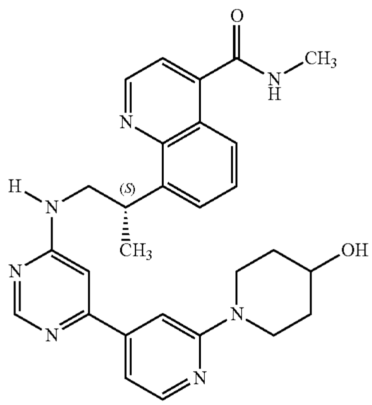 | 498.2 | (DMSO-$d_6$) δ 8.97 (d, J = 4.3 Hz, 1H), 8.66 (m, 1H), 8.48 (s, 1H), 8.19 (s, 1H), 7.99 (d, J = 8.4 Hz, 1H), 7.76 (m, 1H), 7.69-7.59 (m, 1H), 7.54 (m, 1H), 7.31 (s, 1H), 6.95 (m, 1H), 4.50 (m, 1H), 4.10 (m, 2H), 3.72 (m, 3H), 3.17 (m, 5H), 2.55 (m, 2H), 1.77 (m, 2H), 1.38 (d, 3H) |
| 820 | 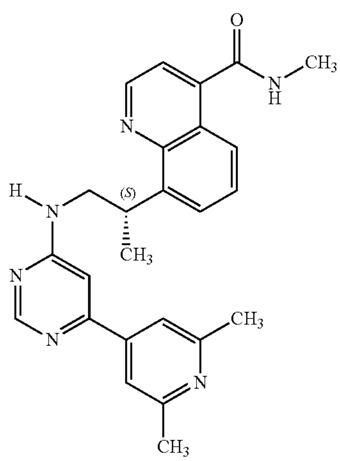 | 427.21 | (DMSO-$d_6$) δ 8.96 (d, J = 4.3 Hz, 1H), 8.68 (m, 1H), 8.52 (s, 1H), 7.99 (dd, J = 8.4, 1.4 Hz, 1H), 7.82-7.59 (m, 4H), 7.54 (s, 1H), 7.00 (s, 1H), 4.51 (m, 1H), 3.78 (m, 2H), 2.87 (d, J = 4.6 Hz, 3H), 2.55 (s, 6H), 1.39 (d, 3H) |
| 821 | 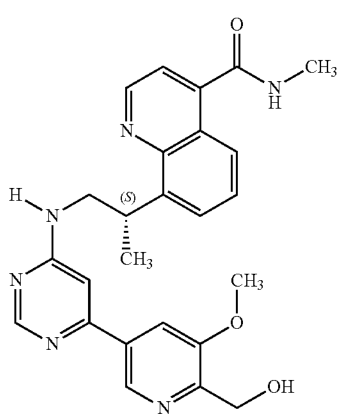 | 459.22 | (DMSO-$d_6$) δ 8.97 (d, J = 4.4 Hz, 1H), 8.68 (m, 3H), 8.00 (dd, J = 8.4, 1.3 Hz, 1H), 7.88 (m, 1H), 7.79 (m, 1H), 7.64 (m, 1H), 7.54 (m, 1H), 7.00 (s, 1H), 4.63 (s, 2H), 4.54 (m, 1H), 3.95 (s, 3H), 3.90 (m, 2H), 2.87 (d, J = 4.6 Hz, 3H), 1.40 (d, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 822 | 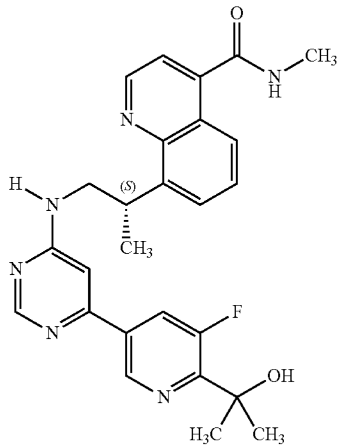 | 475.15 | (DMSO-d$_6$) δ 8.98 (d, J = 4.3 Hz, 1H), 8.85 (s, 1H), 8.67 (m, 1H), 8.52 (s, 1H), 8.10 (m, 1H), 8.00 (d, J = 8.3 Hz, 1H), 7.77 (m, 2H), 7.64 (t, J = 7.8 Hz, 1H), 7.54 (s, 1H), 6.96 (s, 1H), 4.53 (s, 1H), 3.75 (m, 2H), 2.87 (d, J = 4.5 Hz, 3H), 1.54 (s, 6H), 1.38 (d, J = 6.9 Hz, 3H) |
| 823 | 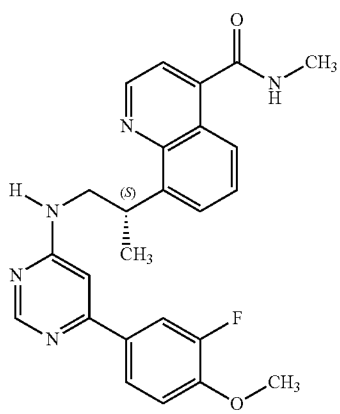 | 446.16 | (DMSO-d$_6$) δ 8.97 (d, J = 4.3 Hz, 1H), 8.68 (m, 1H), 8.59 (s, 1H), 8.39 (s, 1H), 8.01 (dd, J = 8.4, 1.4 Hz, 1H), 7.89-7.59 (m, 4H), 7.55 (s, 1H), 7.36 (s, 1H), 6.87 (s, 1H), 4.53 (m, 1H), 3.82 (m, 5H), 2.87 (d, J = 4.6 Hz, 3H), 1.39 (d, J = 6.9 Hz, 3H) |
| 824 | 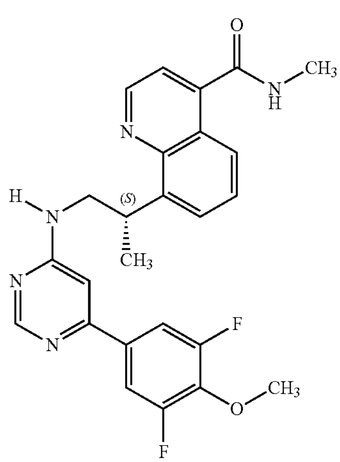 | 464.17 | (DMSO-d$_6$) δ 8.97 (d, J = 4.3 Hz, 1H), 8.67 (m, 1H), 8.52 (s, 1H), 8.04-7.96 (m, 1H), 7.94-7.58 (m, 4H), 7.55 (m, 1H), 6.80 (s, 1H), 4.53 (m, 1H), 4.01 (s, 3H), 3.80 (m, 2H), 2.87 (d, J = 4.6 Hz, 3H), 1.38 (d, J = 6.8 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 825 | 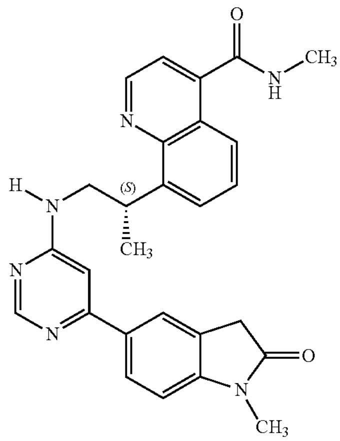 | 467.1 | (DMSO-$d_6$) δ 8.99 (d, J = 4.2 Hz, 1H), 8.68 (d, J = 5.1 Hz, 1H), 8.42 (s, 1H), 8.00 (d, J = 8.3 Hz, 1H), 7.91 (s, 1H), 7.78 (d, J = 7.1 Hz, 1H), 7.65 (m, 1H), 7.56 (s, 1H), 7.11 (d, J = 4.9 Hz, 1H), 6.85 (s, 1H), 4.52 (m, 1H), 3.64 (m, 4H), 3.17 (s, 3H), 2.87 (d, J = 4.5 Hz, 3H), 1.38 (d, J = 6.9 Hz, 3H) |
| 826 | 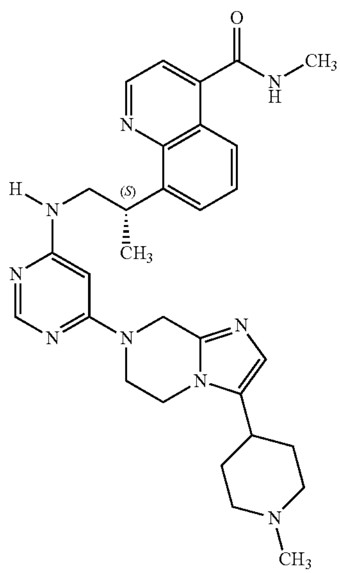 | 540 | (400 MHz, DMSO-$d_6$) δ 9.01 (d, J = 4.3 Hz, 1H), 8.68 (d, J = 4.9 Hz, 1H), 8.28 (s, 1H), 8.00 (d, J = 8.2 Hz, 1H), 7.77 (d, J = 6.9 Hz, 2H), 7.66-7.62 (m, 1H), 7.58-7.49 (m, 2H), 6.06-5.92 (m, 1H), 5.04 (s, 2H), 4.49 (s, 1H), 4.16 (d, J = 32.0 Hz, 4H), 3.78-3.45 (m, 4H), 3.19-2.94 (m, 3H), 2.85 (dd, J = 21.2, 4.2 Hz, 6H), 2.19-1.68 (m, 4H), 1.39 (d, J = 6.6 Hz, 3H) |
| 827 | 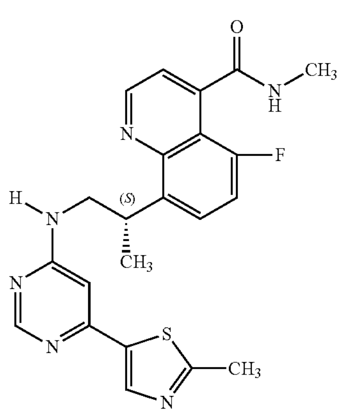 | 437.12 | (DMSO-$d_6$) δ 9.00 (d, J = 4.1 Hz, 1H), 8.47 (d, J = 4.9 Hz, 1H), 8.34 (m, 1H), 8.15 (m, 1H), 7.74 (m, 1H), 7.61-7.38 (m, 3H), 6.74 (s, 1H), 4.44 (m, 1H), 3.70 (m, 2H), 2.82 (d, J = 4.6 Hz, 3H), 2.68 (s, 3H), 1.35 (d, J = 6.8 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 828 | 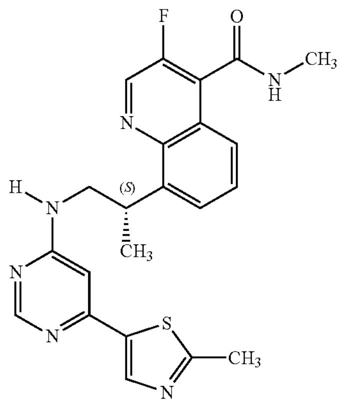 | 437.07 | (DMSO-d$_6$) δ 9.03 (s, 1H), 8.86 (d, J = 4.9 Hz, 1H), 8.35 (m, 1H), 8.15 (m, 1H), 7.71 (m, 3H), 7.58 (m, 1H), 6.75 (s, 1H), 4.45 (m, 1H), 3.75 (m, 2H), 2.94-2.85 (m, 3H), 2.67 (s, 3H), 1.36 (d, J = 6.9 Hz, 3H) |
| 829 | 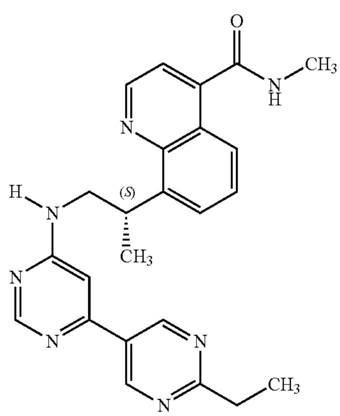 | 428.21 | (DMSO-d$_6$) δ 9.25 (m, 2H), 8.97 (d, J = 4.3 Hz, 1H), 8.68 (d, J = 5.1 Hz, 1H), 8.51 (s, 1H), 7.99 (d, J = 8.5 Hz, 1H), 7.87-7.59 (m, 3H), 7.54 (s, 1H), 6.95 (s, 1H), 4.55 (m, 1H), 3.80 (m, 2H), 2.96 (m, 2H), 2.87 (d, J = 4.5 Hz, 3H), 1.46-1.24 (m, 6H) |
| 830 | 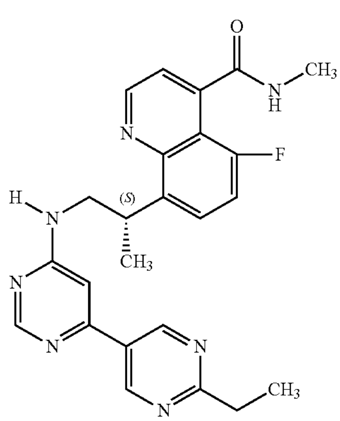 | 446.16 | (DMSO-d$_6$) δ 9.17 (m, 2H), 8.99 (d, J = 4.3 Hz, 1H), 8.55-8.41 (m, 2H), 7.75 (m, 2H), 7.46 (m, 2H), 6.93 (s, 1H), 4.45 (m, 1H), 3.80 (m, 2H), 2.96 (m, 2H), 2.82 (d, J = 4.5 Hz, 3H), 1.44-1.24 (m, 6H) |

TABLE 1-continued

| Cmpnd No. | Structure | ESMS (M + H) | ¹H NMR (300 MHz, unless indicated otherwise) NMR peaks given as δ values |
|---|---|---|---|
| 831 | 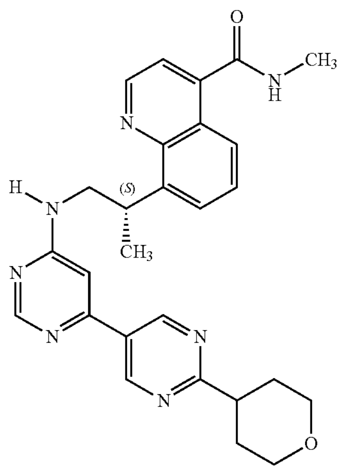 | 484.11 | (DMSO-d₆) δ 9.35 (s, 1H), 9.20 (s, 1H), 8.97 (d, J = 4.3 Hz, 1H), 8.68 (d, J = 4.8 Hz, 1H), 8.52 (m, 1H), 7.99 (d, J = 8.3 Hz, 1H), 7.76 (m, 2H), 7.63 (t, J = 7.8 Hz, 1H), 7.54 (s, 1H), 6.95 (s, 1H), 4.52 (m, 1H), 3.95 (m, 2H), 3.80 (m, 2H), 3.48 (t, J = 11.2 Hz, 2H), 3.18-3.08 (m, 1H), 2.87 (d, J = 4.5 Hz, 3H), 1.89 (m, 4H), 1.37 (d, J = 6.8 Hz, 3H) |
| 832 | 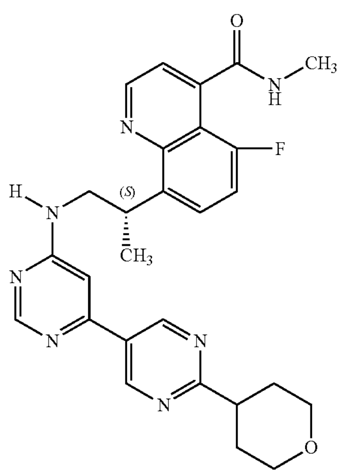 | 502.11 | (DMSO-d₆) δ 9.30 (s, 1H), 9.20 (s, 1H), 8.99 (d, J = 4.4 Hz, 1H), 8.56-8.42 (m, 2H), 7.70 (m, 2H), 7.47 (m, 2H), 6.95 (s, 1H), 4.45 (m, 1H), 3.95 (m, 2H), 3.80 (m, 2H), 3.48 (t, J = 11.0 Hz, 2H), 3.16 (m, 2H), 2.82 (d, J = 4.6 Hz, 3H), 1.89 (m, 4H), 1.36 (d, J = 6.9 Hz, 3H) |
| 833 | 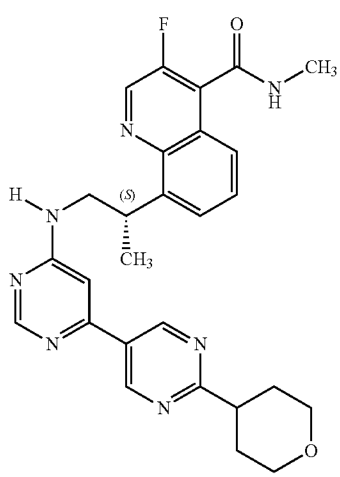 | 502.07 | (DMSO-d₆) δ 9.30 (s, 1H), 9.20 (s, 1H), 9.02 (s, 1H), 8.86 (d, J = 4.8 Hz, 1H), 8.51 (s, 1H), 7.71 (m, 4H), 6.94 (s, 1H), 4.48 (m, 1H), 3.95 (d, J = 10.5 Hz, 2H), 3.80 (m, 2H), 3.48 (t, J = 11.2 Hz, 2H), 3.17 (m, 1H), 2.90 (d, J = 4.6 Hz, 3H), 1.87 (m, 4H), 1.37 (d, J = 6.9 Hz, 3H) |

TABLE 1-continued

| Cmpnd No. | Structure | ESMS (M + H) | $^1$H NMR (300 MHz, unless indicated otherwise) NMR peaks given as δ values |
|---|---|---|---|
| 834 | 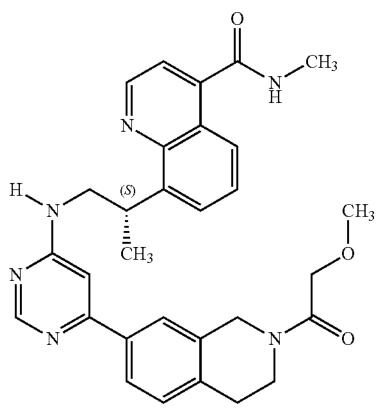 | 525 | (400 MHz, DMSO-$d_6$) δ 8.98 (d, J = 4.2 Hz, 1H), 8.65 (d, J = 4.1 Hz, 1H), 8.45 (s, 1H), 8.00 (d, J = 7.9 Hz, 1H), 7.76 (s, 3H), 7.64 (t, J = 7.8 Hz, 1H), 7.55 (s, 2H), 7.29 (s, 1H), 6.82 (d, J = 48.5 Hz, 1H), 4.67 (s, 2H), 4.50 (s, 1H), 4.19 (s, 2H), 3.67 (d, J = 21.2 Hz, 4H), 2.87 (d, J = 4.6 Hz, 5H), 2.51 (d, J = 1.8 Hz, 3H), 1.39 (d, J = 5.8 Hz, 3H) |
| 835 | 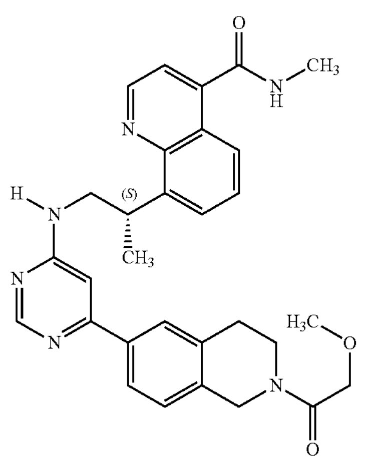 | 525 | (400 MHz, DMSO-$d_6$) δ 8.96 (d, J = 4.2 Hz, 1H), 8.63 (d, J = 4.5 Hz, 1H), 8.43 (s, 1H), 7.97 (d, J = 8.1 Hz, 1H), 7.75 (s, 3H), 7.61 (t, J = 7.8 Hz, 1H), 7.53 (s, 2H), 7.29 (s, 1H), 6.81 (d, J = 51.2 Hz, 1H), 4.63 (s, 2H), 4.49 (s, 1H), 4.17 (s, 2H), 3.65 (d, J = 24.1 Hz, 4H), 2.87 (t, J = 12.9 Hz, 5H), 2.49 (s, 3H), 1.36 (d, J = 5.9 Hz, 3H) |
| 836 | 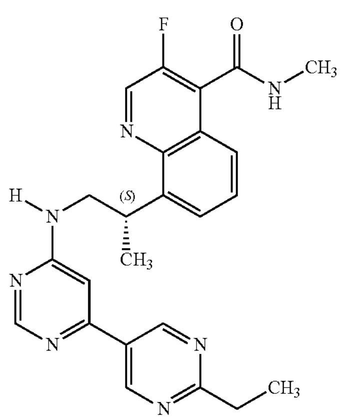 | 446.12 | (DMSO-$d_6$) δ 9.17 (s, 1H), 9.02 (s, 1H), 8.86 (d, J = 5.0 Hz, 1H), 8.51 (s, 1H), 7.72 (m, 4H), 6.90 (s, 1H), 4.47 (m, 1H), 3.80 (m, 2H), 2.93 (m, 5H), 1.45-1.24 (m, 6H) |

TABLE 1-continued

| Cmpnd No. | Structure | ESMS (M + H) | ¹H NMR (300 MHz, unless indicated otherwise) NMR peaks given as δ values |
|---|---|---|---|
| 837 | 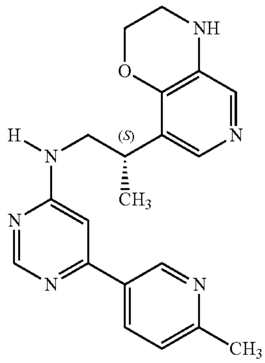 | 363.12 | (methanol-d₄) δ 8.91 (s, 1H), 8.44 (s, 1H), 8.19 (dd, J = 8.2, 2.4 Hz, 1H), 7.66 (s, 1H), 7.63 (s, 1H), 7.41 (d, J = 8.2 Hz, 1H), 6.83 (s, 1H), 4.27 (dd, J = 5.2, 3.6 Hz, 2H), 3.83-3.54 (m, 2H), 3.44-3.34 (m, 3H), 2.59 (s, 3H), 1.33 (d, J = 7.0 Hz, 3H) |
| 838 | 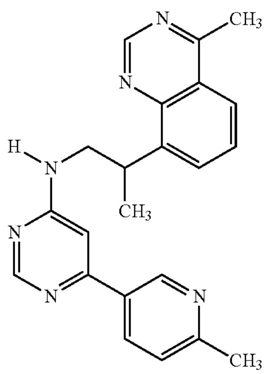 [SMILES: Cc1ccc(-c2cc(NCC(C)c3cccc4c(C)ncnc34)ncn2)cn1] | 371.08 | (methanol-d₄) δ 9.09 (d, J = 12.4 Hz, 1H), 8.88 (br. s, 1H), 8.36 (s, 1H), 8.28-8.03 (m, 2H), 7.94 (dd, J = 7.3, 1.4 Hz, 1H), 7.69 (dd, J = 8.4, 7.3 Hz, 1H), 7.40 (d, J = 7.9 Hz, 1H), 6.72 (s, 1H), 4.48 (q, J = 7.0 Hz, 1H), 3.78 (m, 2H), 2.92 (s, 3H), 2.59 (s, 3H), 1.48 (d, J = 7.0 Hz, 3H) |
| 839 | 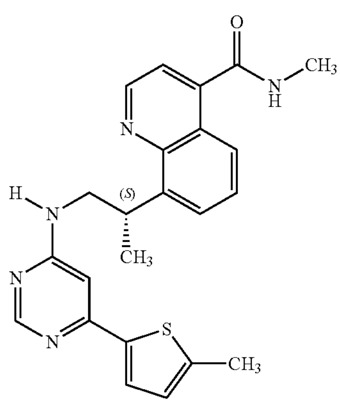 | 418 | (400 MHz, DMSO-d₆) δ 8.99 (s, 1H), 8.65 (d, J = 4.6 Hz, 1H), 8.30 (s, 1H), 7.99 (d, J = 7.4 Hz, 1H), 7.74 (s, 1H), 7.67-7.37 (m, 4H), 6.78 (d, J = 65.9 Hz, 2H), 4.43 (d, J = 41.7 Hz, 1H), 3.52 (d, J = 155.1 Hz, 2H), 2.87 (d, J = 4.6 Hz, 3H), 2.47 (s, 3H), 1.37 (d, J = 6.7 Hz, 3H) |
| 840 | 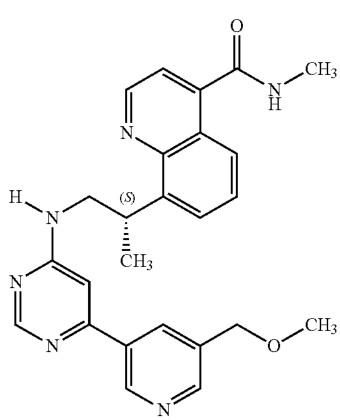 | 443 | (400 MHz, DMSO-d₆) δ 8.98 (d, J = 4.0 Hz, 2H), 8.65 (s, 2H), 8.50 (s, 1H), 8.22 (s, 1H), 8.00 (d, J = 8.0 Hz, 1H), 7.83-7.50 (m, 4H), 7.41-6.90 (m, 1H), 4.54 (s, 3H), 3.91-3.37 (m, 2H), 3.34 (d, J = 8.8 Hz, 3H), 2.87 (d, J = 4.6 Hz, 3H), 1.39 (s, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 841 | 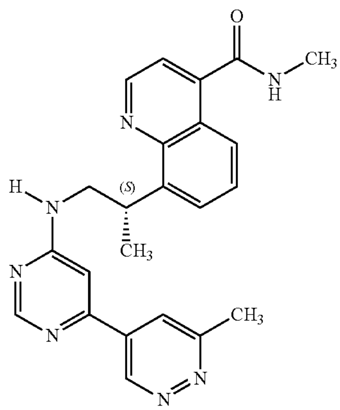 | 414 | (400 MHz, DMSO-$d_6$) δ 9.48 (s, 1H), 8.97 (d, J = 4.3 Hz, 1H), 8.65 (s, 1H), 8.50 (d, J = 35.3 Hz, 1H), 7.99 (d, J = 8.7 Hz, 2H), 7.75 (s, 2H), 7.64 (d, J = 7.3 Hz, 1H), 7.53 (s, 1H), 7.04 (d, J = 25.5 Hz, 1H), 4.52 (s, 1H), 3.69 (d, J = 71.7 Hz, 2H), 2.87 (d, J = 4.6 Hz, 3H), 2.70 (s, 3H), 1.39 (s, 3H) |
| 842 | 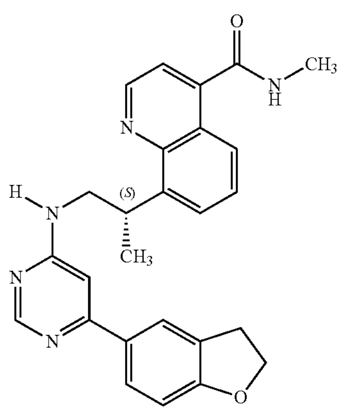 | 440 | (400 MHz, DMSO-$d_6$) δ 8.99 (d, J = 4.2 Hz, 1H), 8.65 (d, J = 4.6 Hz, 1H), 8.40 (s, 1H), 7.91 (dd, J = 71.2, 25.7 Hz, 4H), 7.63 (t, J = 7.8 Hz, 1H), 7.55 (s, 1H), 7.38 (s, 1H), 6.85 (s, 2H), 4.58 (dd, J = 26.3, 17.7 Hz, 3H), 3.51 (d, J = 152.5 Hz, 2H), 3.24 (s, 2H), 2.87 (d, J = 4.6 Hz, 3H), 1.38 (d, J = 6.5 Hz, 3H) |
| 843 | 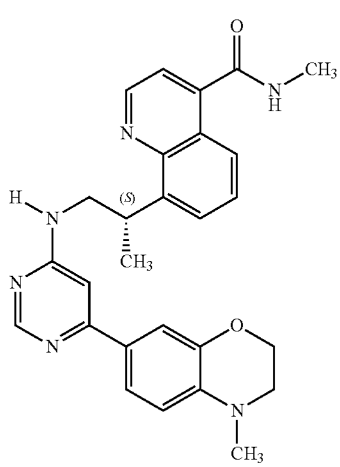 | 469 | (400 MHz, DMSO-$d_6$) δ 9.02 (s, 1H), 8.65 (d, J = 4.2 Hz, 1H), 8.36 (s, 1H), 7.99 (d, J = 8.1 Hz, 1H), 7.81-7.24 (m, 6H), 6.75 (d, J = 8.4 Hz, 2H), 4.49 (s, 1H), 4.25 (s, 2H), 3.51 (d, J = 140.3 Hz, 2H), 3.31 (s, 2H), 2.95-2.80 (m, 6H), 1.37 (d, J = 6.7 Hz, 3H) |

TABLE 1-continued
| Cmpnd No. | Structure | ESMS (M + H) | ¹H NMR (300 MHz, unless indicated otherwise) NMR peaks given as δ values |
|---|---|---|---|
| 844 | 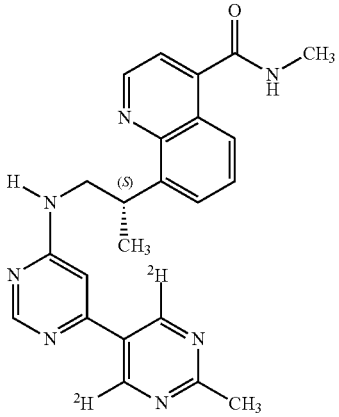 | 416.17 | (DMSO-d6, 70° C.) δ 8.95 (d, J = 4.2 Hz, 1H), 8.47 (s, 1H), 8.35 (s, 1H), 8.01 (d, J = 8.4 Hz, 1H), 7.74 (d, J = 7.1 Hz, 1H), 7.59 (t, J = 7.8 Hz, 1H), 7.50 (d, J = 4.3 Hz, 1H), 7.30 (s, 1H), 7.03 (s, 1H), 4.51 (h, J = 7.2 Hz, 1H), 3.78 (m, 2H), 2.88 (d, J = 4.6 Hz, 3H), 2.68 (s, 3H), 1.41 (d, J = 7.0 Hz, 3H) |
| 845 | 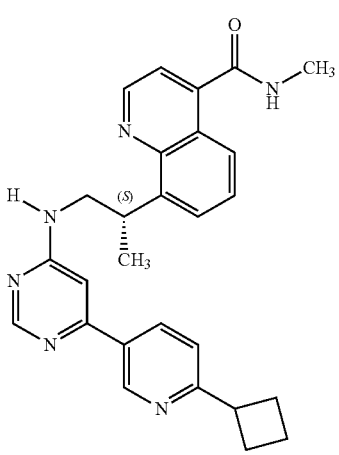 | 453.22 | (DMSO-$d_6$) δ 8.98 (m, 2H), 8.66 (d, J = 4.9 Hz, 1H), 8.52-8.43 (m, 1H), 8.20 (s, 1H), 8.04-7.96 (m, 1H), 7.77 (m, 1H), 7.68-7.52 (m, 3H), 7.36 (d, J = 8.1 Hz, 1H), 6.93 (s, 1H), 4.51 (m, 1H), 3.89-3.62 (m, 3H), 2.87 (d, J = 4.2 Hz, 3H), 2.37-2.21 (m, 4H), 2.10-1.95 (m, 1H), 1.87 (m, 1H), 1.38 (d, J = 6.8 Hz, 3H) |
| 846 | 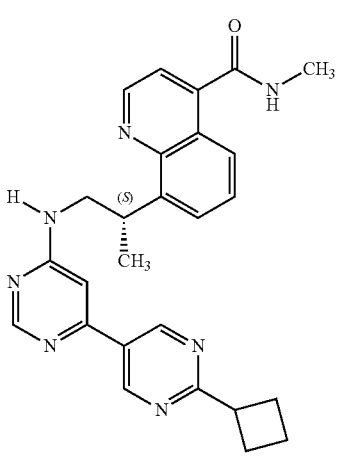 | 454.21 | (DMSO-$d_6$) δ 9.20 (m, 2H), 8.97 (d, J = 4.3 Hz, 1H), 8.66 (m, 1H), 8.51 (s, 1H), 7.99 (d, J = 8.3 Hz, 1H), 7.77 (m, 1H), 7.64 (m, 2H), 7.54 (m, 1H), 6.96 (s, 1H), 4.55 (m, 1H), 3.81 (m, 3H), 2.87 (d, J = 4.4 Hz, 3H), 2.36 (m, 4H), 2.05 (m, 1H), 1.90 (m, 1H), 1.38 (d, J = 6.9 Hz, 3H) |

| Cmpnd No. | Structure | ESMS (M + H) | ¹H NMR (300 MHz, unless indicated otherwise) NMR peaks given as δ values |
|---|---|---|---|
| 847 | 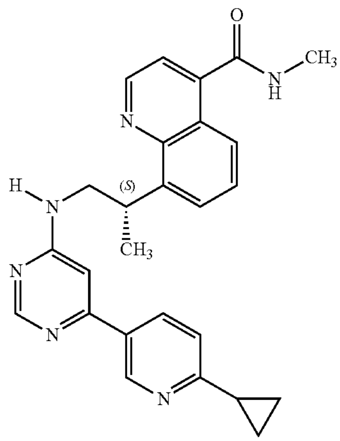 | 439.22 | (DMSO-d$_6$) δ 8.97 (d, J = 4.2 Hz, 2H), 8.66 (d, J = 4.8 Hz, 1H), 8.46 (s, 1H), 8.15 (s, 1H), 8.03-7.96 (m, 1H), 7.77 (m, 1H), 7.64 (m, 1H), 7.55 (m, 1H), 7.40 (d, J = 8.1 Hz, 1H), 6.90 (s, 1H), 4.51 (m, 1H), 3.74 (m, 2H), 2.87 (d, J = 4.2 Hz, 3H), 2.20 (m, 1H), 1.46-1.30 (d, 3H), 1.00 (m, 4H) |
| 848 | 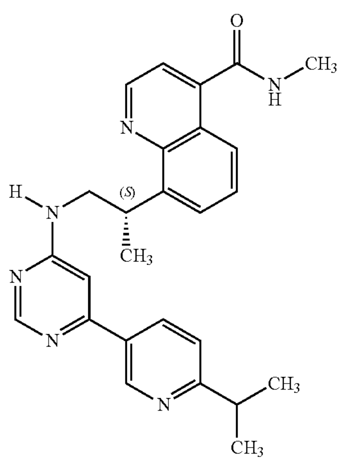 | 441.24 | (DMSO-d$_6$) δ 9.01 (s, 1H), 8.98 (d, J = 4.3 Hz, 1H), 8.66 (m, 1H), 8.48 (s, 1H), 8.21 (m, 1H), 8.00 (dd, J = 8.3, 1.3 Hz, 1H), 7.77 (m, 1H), 7.68-7.51 (m, 3H), 7.40 (d, J = 8.2 Hz, 1H), 6.93 (s, 1H), 4.51 (m, 1H), 3.75 (m, 2H), 3.12-3.03 (m, 1H), 2.87 (d, J = 4.1 Hz, 3H), 1.38 (d, J = 6.9 Hz, 3H), 1.26 (d, J = 6.9 Hz, 6H) |
| 849 | 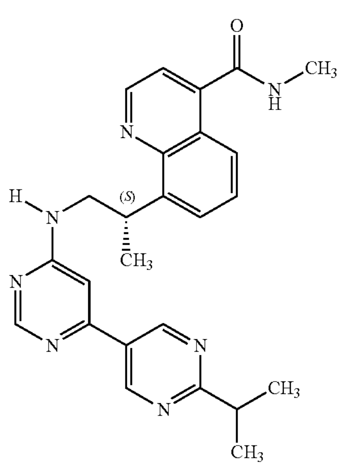 | 442.23 | (DMSO-d$_6$) δ 9.19 (m, 2H), 8.97 (d, J = 4.3 Hz, 1H), 8.66 (d, J = 5.0 Hz, 1H), 8.51 (s, 1H), 8.03-7.95 (m, 1H), 7.81-7.59 (m, 3H), 7.53 (d, J = 4.2 Hz, 1H), 6.95 (s, 1H), 4.52 (m, 1H), 3.75 (m, 2H), 3.27-3.17 (m, 1H), 2.87 (d, J = 4.2 Hz, 3H), 1.38 (d, J = 6.9 Hz, 3H), 1.31 (d, J = 6.9 Hz, 6H) |

TABLE 1-continued

| Cmpnd No. | Structure | ESMS (M + H) | ¹H NMR (300 MHz, unless indicated otherwise) NMR peaks given as δ values |
|---|---|---|---|
| 850 | 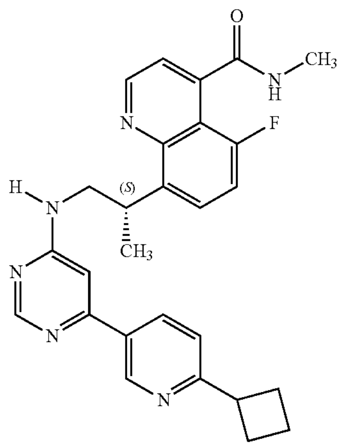 | 471.22 | (DMSO-$d_6$) δ 9.03 (s, 1H), 9.00 (d, J = 4.3 Hz, 1H), 8.46 (m, 2H), 8.20 (s, 1H), 7.76 (m, 1H), 7.62-7.32 (m, 4H), 6.93 (s, 1H), 4.45 (m, 1H), 3.85-3.61 (m, 3H), 2.82 (d, J = 4.5 Hz, 3H), 2.30 (m, 4H), 2.04 (m, 1H), 1.87 (m, 1H), 1.37 (d, J = 7.0 Hz, 3H) |
| 851 | 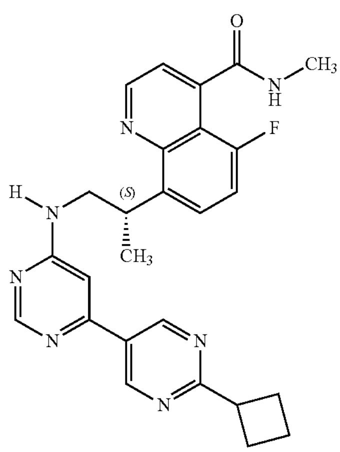 | 472.21 | (DMSO-$d_6$) δ 9.19 (s, 2H), 8.99 (d, J = 4.3 Hz, 1H), 8.54-8.41 (m, 2H), 7.76 (s, 1H), 7.67 (s, 1H), 7.54-7.38 (m, 2H), 6.95 (s, 1H), 4.45 (m, 1H), 3.90-3.62 (m, 3H), 2.82 (d, J = 4.5 Hz, 3H), 2.37 (m, 4H), 2.14-1.98 (m, 1H), 1.90 (m, 1H), 1.36 (d, J = 6.9 Hz, 3H) |
| 852 | 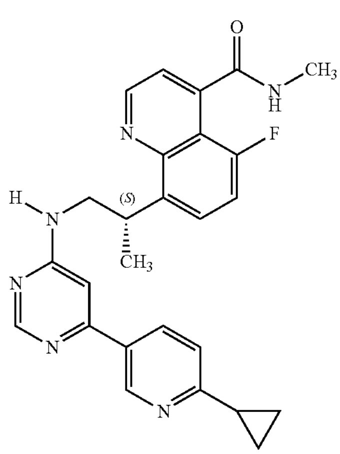 | 457.22 | (DMSO-$d_6$) δ 8.99 (d, J = 4.3 Hz, 1H), 8.96 (s, 1H), 8.45 (m, 2H), 8.14 (s, 1H), 7.76 (s, 1H), 7.57-7.35 (m, 4H), 6.89 (s, 1H), 4.44 (m, 1H), 3.75 (m, 2H), 2.82 (d, J = 4.5 Hz, 3H), 2.16 (m, 1H), 1.36 (d, J = 6.9 Hz, 3H), 1.00 (d, J = 8.0 Hz, 4H) |

| Cmpnd No. | Structure | ESMS (M + H) | ¹H NMR (300 MHz, unless indicated otherwise) NMR peaks given as δ values |
|---|---|---|---|
| 853 | 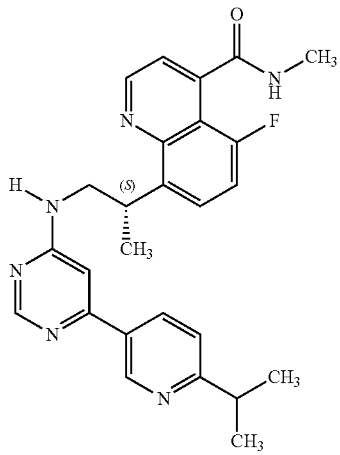 | 459.2 | (DMSO-d$_6$) δ 9.02 (s, 1H), 9.00 (d, J = 4.3 Hz, 1H), 8.46 (m, 2H), 8.21 (s, 1H), 7.76 (m, 1H), 7.60-7.36 (m, 4H), 6.92 (s, 1H), 4.45 (m, 1H), 3.73 (m, 2H), 3.07 (m, 1H), 2.82 (d, J = 4.4 Hz, 3H), 1.37 (d, J = 6.9 Hz, 3H), 1.26 (d, J = 6.9 Hz, 6H) |
| 854 | 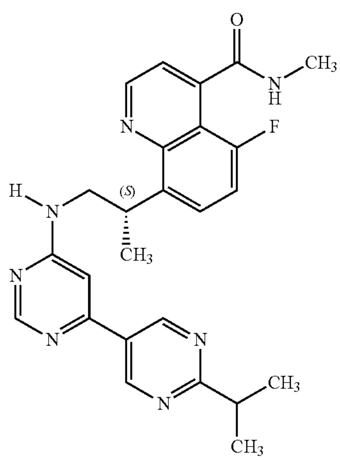 | 460.24 | (DMSO-d$_6$) δ 9.19 (m, 2H), 8.99 (d, J = 4.3 Hz, 1H), 8.54-8.40 (m, 2H), 7.71 (m, 2H), 7.54-7.39 (m, 2H), 6.95 (s, 1H), 4.45 (m, 1H), 3.75 (m, 2H), 3.28-3.18 (m, 1H), 2.82 (d, J = 4.5 Hz, 3H), 1.36 (d, J = 7.0 Hz, 3H), 1.31 (d, J = 6.9 Hz, 6H) |
| 855 | 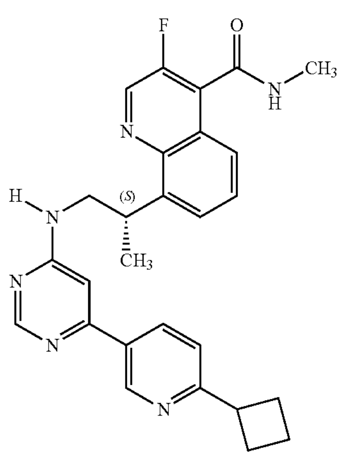 | 471.22 | (DMSO-d$_6$) δ 9.02 (m, 2H), 8.84 (d, J = 4.9 Hz, 1H), 8.48 (s, 1H), 8.20 (s, 1H), 7.81-7.67 (m, 3H), 7.57 (m, 1H), 7.36 (d, J = 8.2 Hz, 1H), 6.93 (s, 1H), 4.47 (m, 1H), 3.72 (m, 3H), 2.90 (d, J = 4.3 Hz, 3H), 2.37-2.22 (m, 4H), 2.02 (m, 1H), 1.86 (m, 1H), 1.37 (d, J = 6.9 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 856 | 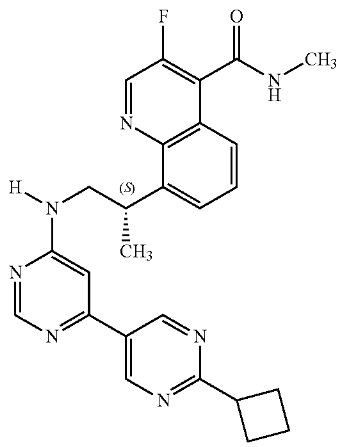 | 472.21 | (DMSO-d$_6$) δ 9.20 (m, 2H), 9.01 (s, 1H), 8.84 (d, J = 4.8 Hz, 1H), 8.50 (s, 1H), 7.70 (m, 4H), 6.95 (s, 1H), 4.47 (m, 1H), 3.94-3.66 (m, 3H), 2.90 (d, J = 4.1 Hz, 3H), 2.38 (m, 4H), 2.13-1.98 (m, 1H), 1.90 (m, 1H), 1.37 (d, J = 6.8 Hz, 3H) |
| 857 | 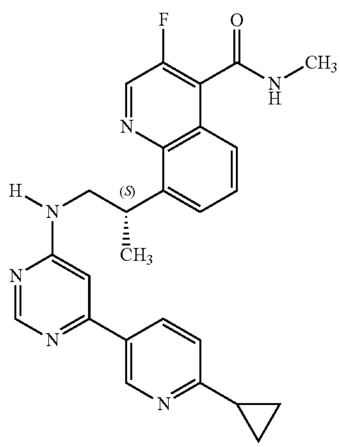 | 457.18 | (DMSO-d$_6$) δ 9.01 (m, 2H), 8.84 (m, 1H), 8.46 (s, 1H), 8.14 (s, 1H), 7.72 (q, J = 7.2, 6.5 Hz, 3H), 7.55 (s, 1H), 7.40 (d, J = 8.3 Hz, 1H), 6.90 (s, 1H), 4.57-4.39 (m, 1H), 3.75 (m, 2H), 2.90 (d, J = 4.1 Hz, 3H), 2.20 (m, 1H), 1.37 (d, J = 6.9 Hz, 3H), 1.07-0.91 (m, 4H) |
| 858 | 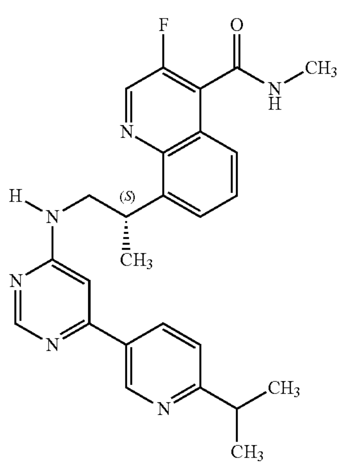 | 459.2 | (DMSO-d$_6$) δ 9.01 (m, 2H), 8.85 (d, J = 5.1 Hz, 1H), 8.48 (s, 1H), 8.21 (s, 1H), 7.81-7.66 (m, 3H), 7.57 (m, 1H), 7.39 (d, J = 8.2 Hz, 1H), 6.93 (s, 1H), 4.53-4.41 (m, 1H), 3.74 (m, 2H), 3.08 (m, 1H), 2.90 (d, J = 4.1 Hz, 3H), 1.37 (d, J = 6.9 Hz, 3H), 1.26 (d, J = 6.9 Hz, 6H) |

TABLE 1-continued

| Cmpnd No. | Structure | ESMS (M + H) | ¹H NMR (300 MHz, unless indicated otherwise) NMR peaks given as δ values |
|---|---|---|---|
| 859 | 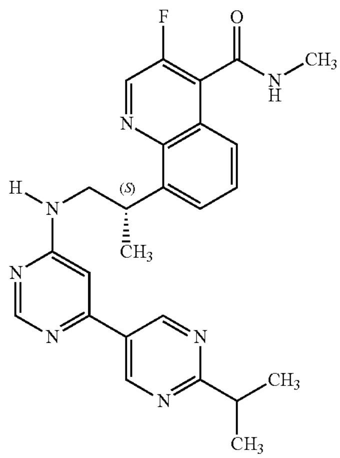 | 459.16 | (DMSO-$d_6$) δ 9.19 (m, 2H), 9.01 (s, 1H), 8.85 (m, 1H), 8.50 (s, 1H), 7.82-7.64 (m, 4H), 4.47 (s, 1H), 3.75 (m, 2H), 3.27-3.17 (m, 1H), 2.94-2.81 (d, 3H), 1.37 (d, J = 6.9 Hz, 3H), 1.31 (d, J = 6.9 Hz, 6H) |
| 860 | 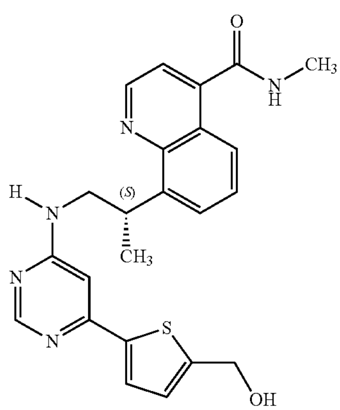 | 434 | (400 MHz, DMSO-$d_6$) δ 8.99 (s, 1H), 8.65 (d, J = 4.5 Hz, 1H), 8.32 (s, 1H), 7.99 (d, J = 8.3 Hz, 1H), 7.75 (s, 1H), 7.68-7.38 (m, 4H), 6.86 (d, J = 102.4 Hz, 2H), 4.73 (d, J = 72.8 Hz, 2H), 4.50 (s, 1H), 4.07-3.55 (m, 2H), 2.87 (d, J = 4.6 Hz, 3H), 1.37 (d, J = 6.6 Hz, 3H) |
| 861 | 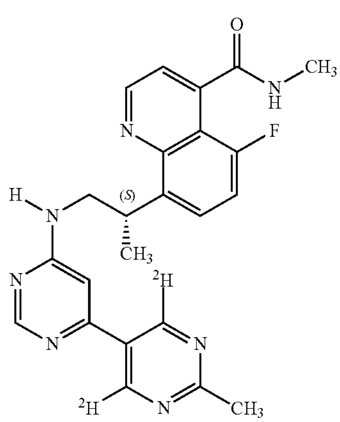 | 434.17 | (DMSO-$d_6$) δ 8.99 (d, J = 4.3 Hz, 1H), 8.53-8.41 (m, 2H), 7.71 (m, 2H), 7.54-7.38 (m, 2H), 6.96 (s, 1H), 4.45 (s, 1H), 3.75 (m, 2H), 2.82 (d, J = 4.3 Hz, 3H), 2.69 (s, 3H), 1.36 (d, J = 6.9 Hz, 3H) |

| Cmpnd No. | Structure | ESMS (M + H) | ¹H NMR (300 MHz, unless indicated otherwise) NMR peaks given as δ values |
|---|---|---|---|
| 862 | 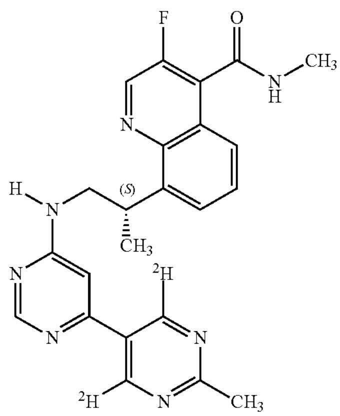 | 434.22 | (DMSO-d₆) δ 9.01 (s, 1H), 8.85 (m, 1H), 8.50 (s, 1H), 7.83-7.61 (m, 4H), 6.96 (s, 1H), 4.47 (s, 1H), 2.75 (m, 2H), 2.90 (d, J = 3.7 Hz, 3H), 2.68 (s, 3H), 1.37 (d, J = 7.0 Hz, 3H) |
| 863 | 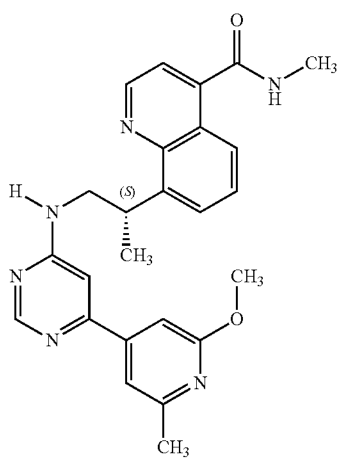 | 443 | (400 MHz, DMSO-d₆) δ 8.95 (d, J = 24.2 Hz, 1H), 8.66 (s, 1H), 8.43 (d, J = 43.2 1H), 8.00 (d, J = 8.6 Hz, 1H), 7.56 (dd, J = 111.4, 74.5 Hz, 6H), 6.99 (d, J = 39.4 Hz, 1H), 4.44 (d, J = 56.3 Hz, 1H), 3.88 (s, 5H), 2.87 (d, J = 4.6 Hz, 3H), 2.47 (s, 3H), 1.38 (s, 3H) |
| 864 | 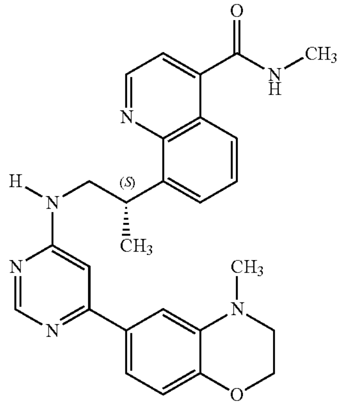 | 469 | (400 MHz, DMSO-d₆) δ 8.98 (d, J = 4.3 Hz, 1H), 8.65 (d, J = 4.7 Hz, 1H), 8.40 (s, 1H), 7.99 (d, J = 7.4 Hz, 1H), 7.76 (d, J = 6.6 Hz, 1H), 7.68-7.58 (m, 1H), 7.53 (s, 1H), 7.27 (d, J = 53.3 Hz, 3H), 6.76 (s, 2H), 4.45 (d, J = 30.3 Hz, 1H), 4.28 (s, 2H), 3.71 (s, 2H), 3.28-3.23 (m, 2H), 2.92-2.79 (m, 6H), 1.38 (d, J = 6.7 Hz, 3H) |

| Cmpnd No. | Structure | ESMS (M + H) | ¹H NMR (300 MHz, unless indicated otherwise) NMR peaks given as δ values |
|---|---|---|---|
| 865 | 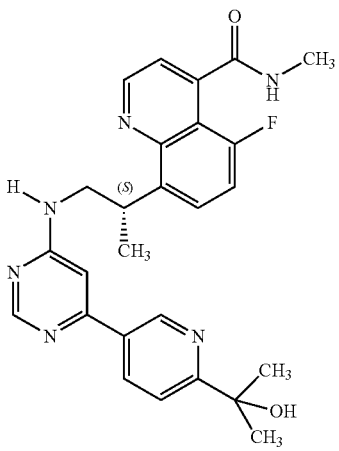 | 475.2 | (DMSO-d₆) δ 9.01 (m, 1H), 9.00 (d, J = 4.3 Hz, 1H), 8.47 (d, J = 5.0 Hz, 2H), 8.25 (s, 1H), 7.77 (m, 2H), 7.60 (m, 1H), 7.54-7.40 (m, 2H), 6.91 (s, 1H), 4.45 (m, 1H), 3.76 (m, 2H), 2.82 (d, J = 4.5 Hz, 3H), 1.47 (s, 6H), 1.37 (d, J = 6.9 Hz, 3H) |
| 866 | 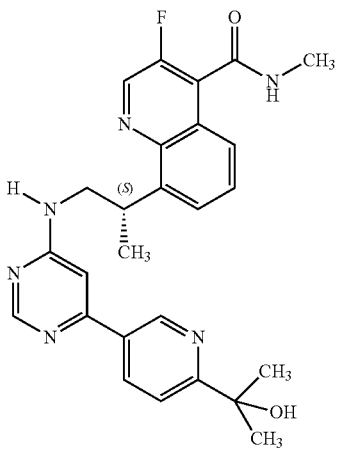 | 475.11 | (DMSO-d₆) δ 9.02 (m, 2H), 8.87 (m, 1H), 8.49 (s, 1H), 8.26 (m, 1H), 7.86-7.66 (m, 4H), 7.62 (s, 1H), 6.92 (s, 1H), 5.34 (s, 1H), 4.47 (m, 1H), 3.75 (m, 2H), 2.90 (d, J = 4.4 Hz, 3H), 1.47 (s, 6H), 1.37 (d, J = 6.9 Hz, 3H) |
| 867 | 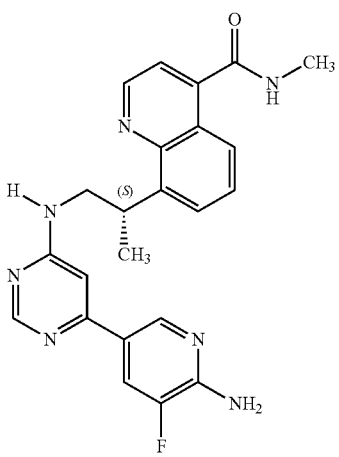 | 432.17 | (DMSO-d₆) δ 8.99 (d, J = 4.2 Hz, 1H), 8.68 (d, J = 5.2 Hz, 1H), 8.38 (s, 1H), 7.99 (dd, J = 8.3, 1.3 Hz, 1H), 7.77 (m, 2H), 7.64 (t, J = 7.8 Hz, 1H), 7.54 (d, J = 4.2 Hz, 1H), 7.41 (s, 1H), 6.70 (s, 2H), 4.51 (s, 1H), 3.72 (s, 2H), 2.87 (d, J = 4.5 Hz, 3H), 1.37 (d, J = 6.9 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 868 | 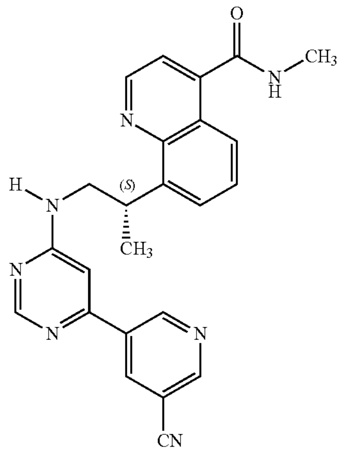 | 424.23 | (DMSO-d$_6$) δ 9.33 (m, 1H), 9.11 (m, 1H), 8.97 (d, J = 4.3 Hz, 1H), 8.68 (m, 2H), 8.51 (m, 1H), 8.03-7.95 (m, 1H), 7.78 (m, 2H), 7.64 (t, J = 7.8 Hz, 1H), 7.54 (d, J = 4.2 Hz, 1H), 7.01 (s, 1H), 4.54 (m, 1H), 3.83 (m, 2H), 2.87 (d, J = 4.5 Hz, 3H), 1.39 (m, 3H) |
| 869 | 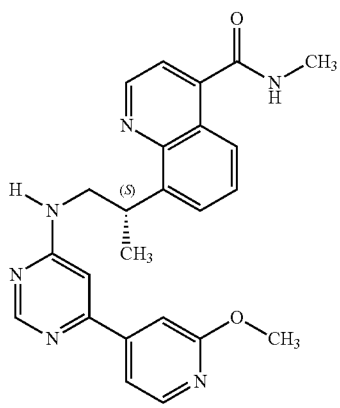 | 429.23 | (DMSO-d$_6$) δ 8.98 (s, 1H), 8.69 (m, 1H), 8.51 (s, 1H), 8.28 (m, 1H), 7.99 (d, J = 8.3 Hz, 1H), 7.78 (m, 1H), 7.70-7.58 (m, 2H), 7.54 (s, 1H), 7.43 (s, 1H), 7.27 (s, 1H), 4.52 (m, 1H), 3.84 (m, 5H), 2.87 (d, J = 4.3 Hz, 3H), 1.37 (d, J = 6.9 Hz, 3H) |
| 870 | 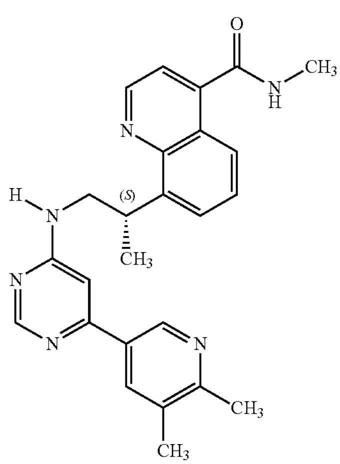 | 427.17 | (DMSO-d$_6$) δ 8.98 (d, J = 4.3 Hz, 1H), 8.78 (m, 1H), 8.69 (m, 1H), 8.47 (s, 1H), 7.99 (m, 2H), 7.77 (m, 1H), 7.68-7.48 (m, 3H), 6.92 (s, 1H), 4.51 (m, 1H), 3.76 (m, 2H), 2.87 (d, J = 4.3 Hz, 3H), 2.49-2.43 (s, 3H), 2.32 (s, 3H), 1.38 (d, J = 7.5 Hz, 3H) |

| Cmpnd No. | Structure | ESMS (M + H) | ¹H NMR (300 MHz, unless indicated otherwise) NMR peaks given as δ values |
|---|---|---|---|
| 871 | 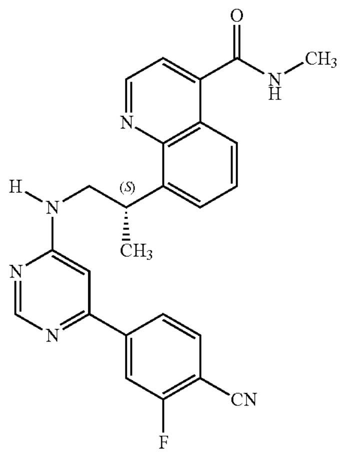 | 441.17 | (DMSO-d$_6$) δ 8.97 (d, J = 4.3 Hz, 1H), 8.68 (m, 1H), 8.52 (m, 1H), 8.19-7.94 (m, 4H), 7.77 (m, 2H), 7.63 (t, J = 7.8 Hz, 1H), 7.54 (s, 1H), 7.01 (s, 1H), 4.52 (m, 1H), 3.75 (m, 2H), 2.87 (d, J = 4.4 Hz, 3H), 1.38 (d, 3H) |
| 872 | 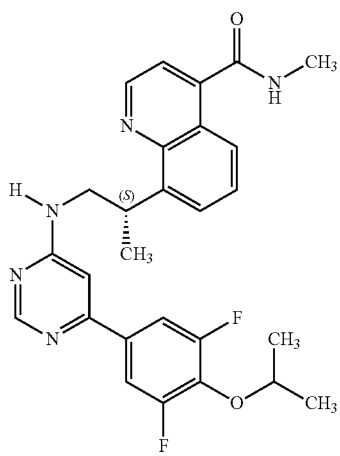 | 492.12 | (DMSO-d$_6$) δ 8.98 (d, J = 4.3 Hz, 1H), 8.68 (m, 1H), 8.45 (s, 1H), 7.99 (d, J = 8.4 Hz, 1H), 7.93-7.59 (m, 5H), 7.55 (s, 1H), 6.85 (s, 1H), 4.50 (m, 2H), 3.75 (m, 2H), 2.87 (d, J = 4.5 Hz, 3H), 1.37 (d, J = 6.8 Hz, 3H), 1.30 (d, J = 6.1 Hz, 6H) |
| 873 | 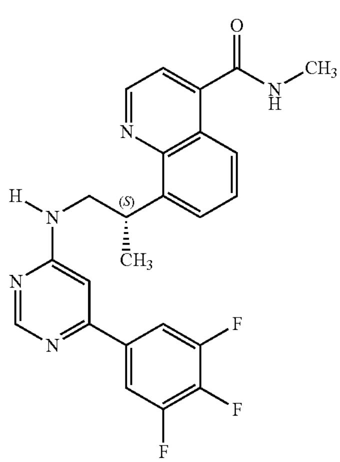 | 452.11 | (400 MHz, DMSO-d$_6$) δ 8.97 (d, J = 4.3 Hz, 1H), 8.68 (d, J = 4.9 Hz, 1H), 8.47 (s, 1H), 8.10-7.97 (m, 2H), 7.92-7.59 (m, 4H), 7.54 (s, 1H), 6.91 (s, 1H), 4.52 (m, 1H), 3.75 (m, 2H), 2.87 (d, J = 4.5 Hz, 3H), 1.37 (d, J = 6.8 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 874 | 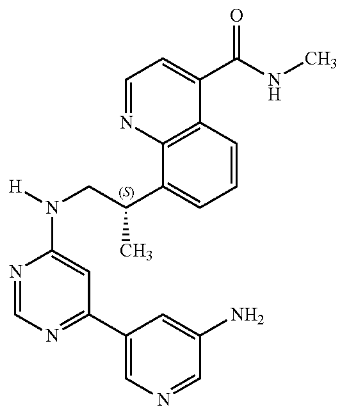 | 414.12 | 1H NMR (300 MHz, DMSO-d6) ? 8.98 (s, 1H), 8.68 (m, 1H), 8.45 (s, 1H), 7.99 (m, 2H), 7.76 (m, 1H), 7.63 (t, J = 7.8 Hz, 1H), 7.54 (m, 2H), 5.49 (s, 2H), 4.50 (m, 1H), 3.75 (m, 2H), 2.87 (d, J = 4.4 Hz, 3H), 1.37 (d, 3H) |
| 875 | 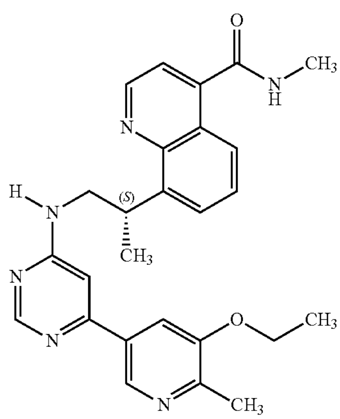 | 457.19 | 1H NMR (300 MHz, DMSO-d6) ? 8.98 (d, J = 4.3 Hz, 1H), 8.68 (m, 1H), 8.48 (m, 2H), 7.99 (dd, J = 8.4, 1.4 Hz, 1H), 7.77 (m, 2H), 7.69-7.49 (m, 3H), 6.90 (s, 1H), 4.51 (m, 1H), 4.14 (q, J = 6.9 Hz, 2H), 3.77 (m, 2H), 2.87 (d, J = 4.4 Hz, 3H), 2.41 (s, 3H), 1.38 (m, 6H) |
| 876 | 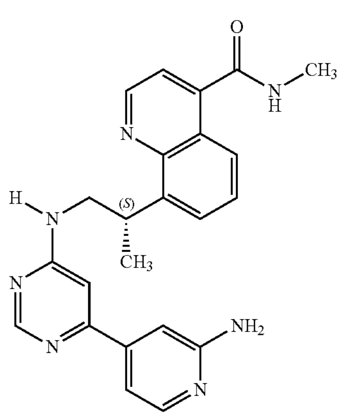 | 414.12 | |

| Cmpnd No. | Structure | ESMS (M + H) | $^1$H NMR (300 MHz, unless indicated otherwise) NMR peaks given as δ values |
|---|---|---|---|
| 877 | 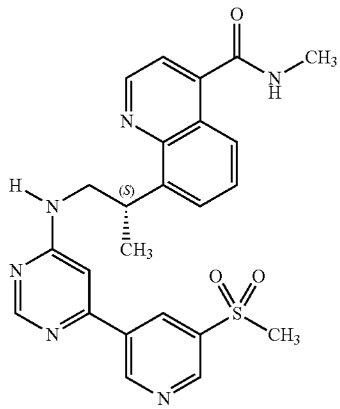 | 477 | (DMSO-d$_6$) δ 9.39 (s, 1H), 9.16 (s, 1H), 8.98 (m, 1H), 8.68 (m, 2H), 8.55 (m, 1H), 7.99 (d, J = 8.4 Hz, 1H), 7.89-7.58 (m, 3H), 7.53 (d, J = 4.2 Hz, 1H), 7.09 (s, 1H), 4.53 (m, 1H), 3.81 (m, 2H), 2.87 (d, J = 4.4 Hz, 3H), 1.39 (d, 3H) |
| 878 | 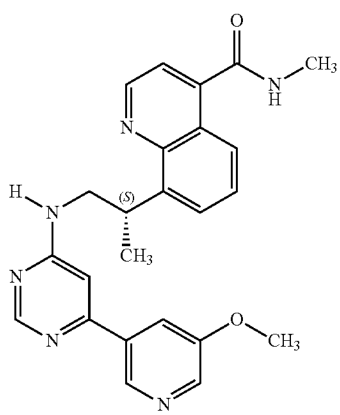 | 429.06 | (DMSO-d$_6$) δ 8.98 (d, J = 4.3 Hz, 1H), 8.68 (m, 2H), 8.50 (s, 1H), 8.38 (s, 1H), 8.02-7.95 (m, 1H), 7.79 (m, 2H), 7.68-7.49 (m, 3H), 6.97 (s, 1H), 4.52 (m, 1H), 3.90 (s, 3H), 3.70 (m, 2H), 2.87 (d, J = 4.4 Hz, 3H), 1.38 (d, J = 6.9 Hz, 3H) |
| 879 | 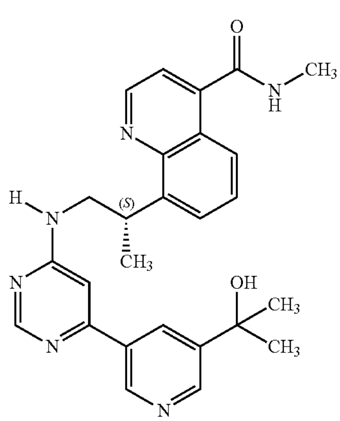 | 457.15 | (DMSO-d$_6$) δ 8.96 (m, 2H), 8.75 (s, 1H), 8.68 (m, 1H), 8.50 (s, 1H), 8.36 (m, 1H), 7.99 (d, J = 8.3 Hz, 1H), 7.77 (m, 1H), 7.64 (t, J = 7.8 Hz, 1H), 7.54 (m, 1H), 6.99 (s, 1H), 4.51 (m, 1H), 3.80 (m, 2H), (d, J = 4.4 Hz, 3H), 1.49 (s, 6H), 1.38 (d, J = 6.7 Hz, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 880 | 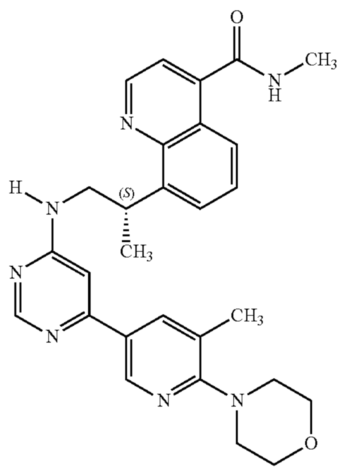 | 498.2 | (DMSO-d₆) δ 8.98 (d, J = 4.3 Hz, 1H), 8.68 (m, 2H), 8.44 (s, 1H), 7.99 (m, 2H), 7.78 (m, 1H), 7.64 (t, J = 7.8 Hz, 1H), 7.54 (m, 2H), 6.80 (s, 1H), 4.51 (m, 1H), (m, 6H), 3.22-3.11 (m, 4H), 2.87 (d, J = 4.4 Hz, 3H), 2.31 (s, 3H), 1.46-1.29 (d, 3H) |
| 881 | 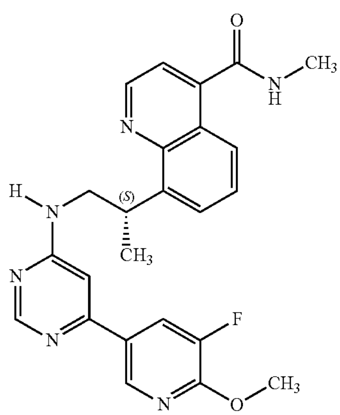 | 447.16 | (DMSO-d₆) δ 8.98 (d, J = 4.3 Hz, 1H), 8.68 (m, 1H), 8.46 (s, 1H), 8.12 (m, 1H), 8.03-7.96 (m, 1H), 7.78 (m, 1H), 7.69-7.51 (m, 3H), 6.85 (s, 1H), 4.52 (m, 1H), 4.01 (s, 3H), 3.75 (m, 2H), 2.87 (d, J = 4.5 Hz, 3H), 1.37 (d, J = 6.8 Hz, 3H) |
| 882 | 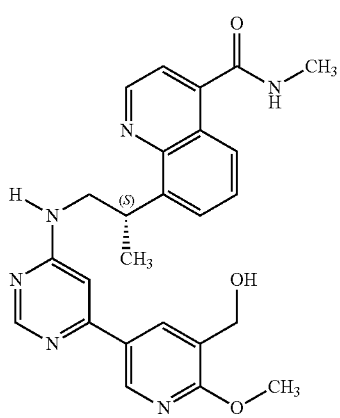 | 459.08 | (DMSO-d₆) δ 8.99 (s, 1H), 8.74-8.56 (m, 2H), 8.45 (s, 1H), 8.28 (s, 1H), 8.03-7.96 (m, 1H), 7.77 (m, 1H), 7.69-7.47 (m, 3H), 6.85 (s, 1H), 4.51 (m, 3H), 4.02-3.88 (s, 3H), 3.76 (m, 2H), 2.87 (d, J = 4.5 Hz, 3H), 1.38 (d, J = 6.9 Hz, 3H) |

| Cmpnd No. | Structure | ESMS (M + H) | ¹H NMR (300 MHz, unless indicated otherwise) NMR peaks given as δ values |
|---|---|---|---|
| 883 | 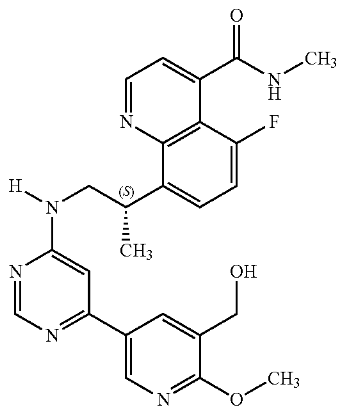 | 477.09 | (DMSO-d₆) δ 9.01 (s, 1H), 8.63 (s, 1H), 8.46 (m, 2H), 8.27 (s, 1H), 7.76 (m, 1H), 7.55-7.38 (m, 3H), 6.88 (s, 1H), 4.47 (m, 3H), 3.94 (s, 3H), 3.75 (m, 2H), 2.82 (d, J = 4.5 Hz, 3H), 1.37 (d, J = 6.9 Hz, 3H) |
| 884 | 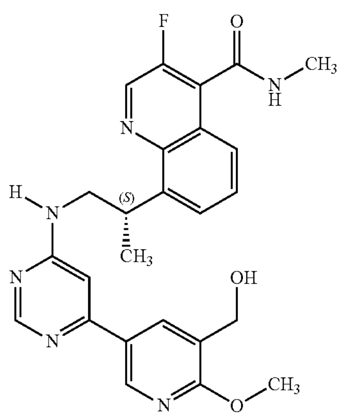 | 477.09 | (DMSO-d₆) δ 9.04 (s, 1H), 8.86 (m, 1H), 8.64 (m, 1H), 8.45 (s, 1H), 8.28 (m, 1H), 7.72 (m, 3H), 7.51 (m, 1H), 4.51 (s, 3H), 3.93 (s, 3H), 3.75 (m, 2H), 2.90 (d, J = 4.6 Hz, 3H), 1.37 (d, J = 6.9 Hz, 3H) |
| 885 | 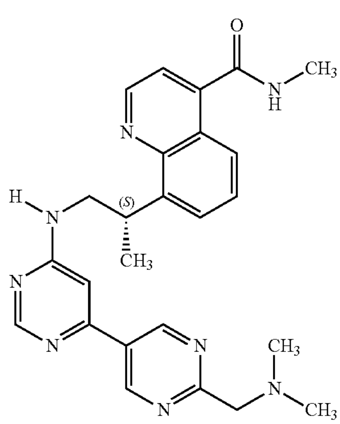 | 457 | (400 MHz, DMSO-d₆) δ 9.18 (d, J = 32.2 Hz, 2H), 8.97 (d, J = 4.2 Hz, 1H), 8.66 (s, 1H), 8.52 (s, 1H), 7.99 (d, J = 8.1 Hz, 1H), 7.86-7.43 (m, 4H), 6.94 (d, J = 22.1 Hz, 1H), 4.45 (d, J = 46.8 Hz, 1H), 3.71 (s, 4H), 2.87 (d, J = 4.6 Hz, 3H), 2.26 (s, 6H), 1.39 (s, 3H) |

TABLE 1-continued

| Cmpnd No. | Structure | ESMS (M + H) | ¹H NMR (300 MHz, unless indicated otherwise) NMR peaks given as δ values |
|---|---|---|---|
| 886 | 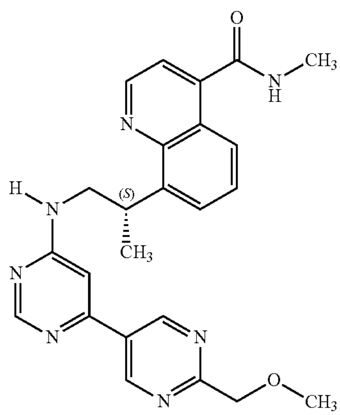 | 444 | (400 MHz, DMSO-$d_6$) δ 9.25 (s, 2H), 8.97 (d, J = 4.3 Hz, 1H), 8.65 (d, J = 4.6 Hz, 1H), 8.48 (d, J = 35.6 Hz, 1H), 7.99 (d, J = 8.2 Hz, 1H), 7.89-7.42 (m, 4H), 6.98 (s, 1H), 4.59 (d, J = 46.2 Hz, 3H), 3.59 (d, J = 150.7 Hz, 5H), 2.87 (d, J = 4.6 Hz, 3H), 1.39 (s, 3H) |

TABLE 2

| Cmpnd No. | Structure | ESMS (M + H) | ¹H NMR (300 MHz, unless indicated otherwise) NMR peaks given as δ values |
|---|---|---|---|
| 887 | 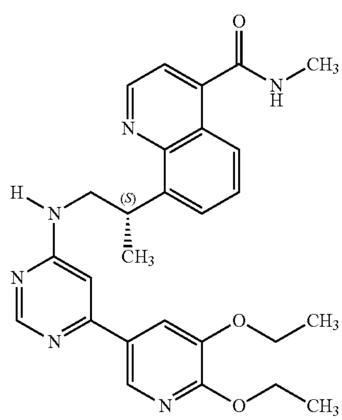 | 487 | (400 MHz, DMSO-$d_6$) δ 8.97 (d, J = 4.3 Hz, 1H), 8.65 (d, J = 4.7 Hz, 1H), 8.44 (s, 2H), 7.99 (d, J = 9.1 Hz, 1H), 7.76 (s, 2H), 7.66-7.60 (m, 1H), 7.54 (s, 2H), 7.26-6.80 (m, 1H), 4.50 (s, 1H), 4.40 (d, J = 7.3 Hz, 2H), 4.11 (q, J = 7.0 Hz, 2H), 3.72 (s, 2H), 2.87 (d, J = 4.6 Hz, 3H), 1.41-1.31 (m, 9H) |
| 888 | 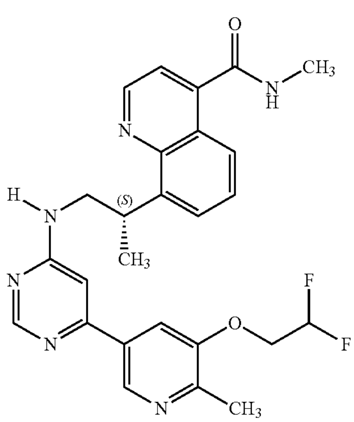 | 493 | (400 MHz, DMSO-$d_6$) δ 8.98 (d, J = 4.3 Hz, 1H), 8.65 (d, J = 4.7 Hz, 2H), 8.48 (s, 1H), 7.99 (d, J = 8.5 Hz, 1H), 7.81 (d, J = 47.1 Hz, 2H), 7.61 (dd, J = 25.7, 18.3 Hz, 3H), 6.90 (d, J = 39.4 Hz, 1H), 6.57-6.30 (m, 1H), 4.47 (td, J = 14.8, 3.4 Hz, 3H), 3.66 (d, J = 83.7 Hz, 2H), 2.87 (d, J = 4.6 Hz, 3H), 2.43 (d, J = 3.2 Hz, 3H), 1.38 (d, J = 6.2 Hz, 3H) |

TABLE 2-continued

| Cmpnd No. | Structure | ESMS (M + H) | ¹H NMR (300 MHz, unless indicated otherwise) NMR peaks given as δ values |
|---|---|---|---|
| 889 | 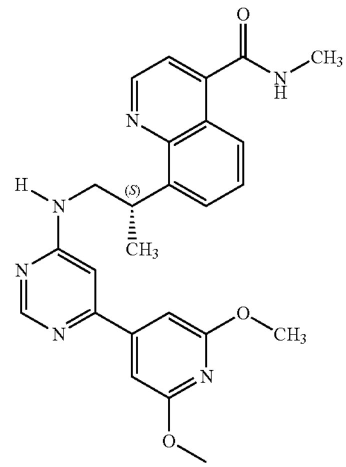 | 459 | (400 MHz, DMSO-$d_6$) δ 8.98 (s, 1H), 8.65 (s, 1H), 8.48 (s, 1H), 8.00 (d, J = 8.5 Hz, 1H), 7.85-7.47 (m, 4H), 7.01 (dd, J = 113.3, 57.0 Hz, 3H), 4.46 (d, J = 35.9 Hz, 1H), 3.90 (s, 8H), 2.87 (d, J = 4.6 Hz, 3H), 1.38 (s, 3H) |
| 890 | 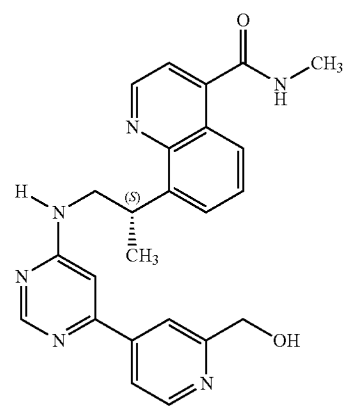 | 429 | (400 MHz, DMSO-$d_6$) δ 8.90 (d, J = 64.2 Hz, 1H), 8.61 (dd, J = 41.4, 15.8 Hz, 3H), 8.00 (d, J = 7.7 Hz, 1H), 7.85-7.49 (m, 5H), 7.11 (d, J = 51.8 Hz, 1H), 5.57 (s, 1H), 4.74 (d, J = 87.3 Hz, 2H), 4.51 (s, 1H), 3.91-3.33 (m, 2H), 2.87 (d, J = 4.6 Hz, 3H), 1.39 (s, 3H) |
| 891 | 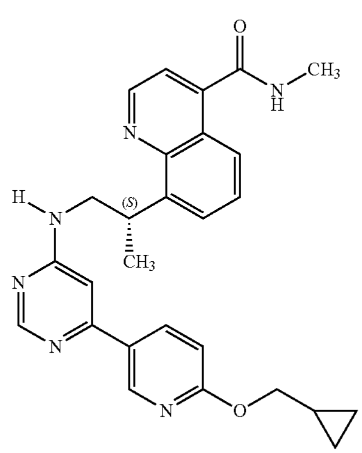 | 469 | (400 MHz, DMSO-$d_6$) δ 8.98 (d, J = 4.3 Hz, 1H), 8.65 (d, J = 4.6 Hz, 2H), 8.44 (s, 1H), 8.15 (d, J = 38.3 Hz, 1H), 7.99 (d, J = 8.4 Hz, 1H), 7.77 (s, 1H), 7.63 (t, J = 7.7 Hz, 1H), 7.54 (s, 2H), 6.93 (s, 2H), 4.51 (s, 1H), 4.16 (d, J = 6.6 Hz, 2H), 3.88-3.35 (m, 2H), 2.87 (d, J = 4.6 Hz, 3H), 1.38 (d, J = 6.7 Hz, 3H), 1.26 (s, 1H), 0.56 (d, J = 6.9 Hz, 2H), 0.34 (d, J = 4.5 Hz, 2H) |

TABLE 2-continued

| Cmpnd No. | Structure | ESMS (M + H) | ¹H NMR (300 MHz, unless indicated otherwise) NMR peaks given as δ values |
|---|---|---|---|
| 892 | 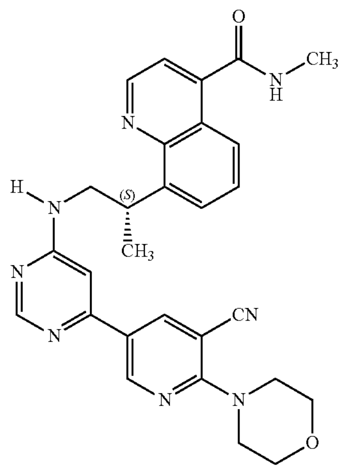 | 470 | (400 MHz, DMSO-d$_6$) δ 8.97 (d, J = 4.3 Hz, 1H), 8.65 (d, J = 4.5 Hz, 1H), 8.49 (s, 1H), 8.14 (s, 1H), 7.99 (d, J = 8.5 Hz, 1H), 7.75 (s, 1H), 7.61 (dd, J = 26.3, 18.8 Hz, 3H), 6.93 (t, J = 59.8 Hz, 3H), 4.45 (d, J = 32.4 Hz, 1H), 3.66 (d, J = 76.7 Hz, 2H), 3.53 (q, J = 6.7 Hz, 4H), 2.87 (d, J = 4.6 Hz, 3H), 1.38 (d, J = 6.1 Hz, 3H), 1.12 (t, J = 7.0 Hz, 6H) |
| 893 | 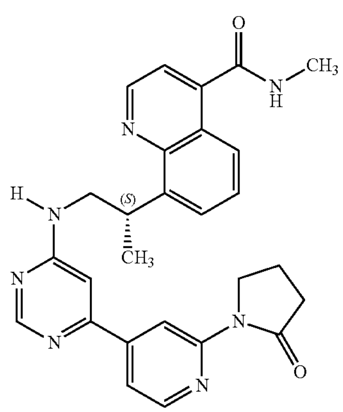 | 482 | (400 MHz, DMSO-d$_6$) δ 8.94 (t, J = 19.3 Hz, 2H), 8.65 (d, J = 4.6 Hz, 1H), 8.51 (d, J = 18.5 Hz, 2H), 8.00 (dd, J = 8.4, 1.1 Hz, 1H), 7.75 (s, 2H), 7.63 (t, J = 7.7 Hz, 2H), 7.53 (d, J = 3.9 Hz, 1H), 7.16 (d, J = 124.5 Hz, 1H), 4.51 (d, J = 6.7 Hz, 1H), 4.03 (t, J = 6.7 Hz, 2H), 3.57 (d, J = 164.4 Hz, 2H), 2.87 (d, J = 4.6 Hz, 3H), 2.61 (t, J = 8.0 Hz, 2H), 2.05 (dd, J = 22.0, 14.8 Hz, 2H), 1.39 (d, J = 5.9 Hz, 3H) |
| 894 | 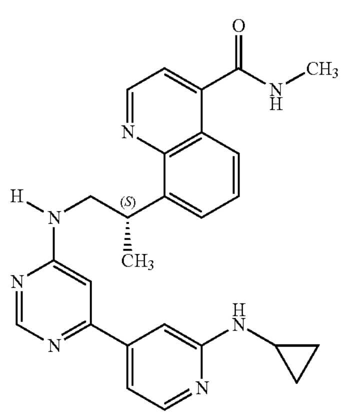 | 454 | (400 MHz, DMSO-d$_6$) δ 8.97 (d, J = 4.2 Hz, 1H), 8.65 (d, J = 4.8 Hz, 1H), 8.44 (d, J = 37.5 Hz, 1H), 8.08 (s, 1H), 7.99 (d, J = 8.5 Hz, 1H), 7.75 (s, 1H), 7.68-7.45 (m, 454 3H), 7.03 (d, J = 103.9 Hz, 4H), 4.46 (d, J = 41.8 Hz, 1H), 3.89-3.37 (m, 2H), 2.87 (d, J = 4.6 Hz, 3H), 2.52 (s, 1H), 1.38 (d, J = 5.8 Hz, 3H), 0.70 (d, J = 4.6 Hz, 2H), 0.50-0.38 (m, 2H) |

TABLE 2-continued

| Cmpnd No. | Structure | ESMS (M + H) | ¹H NMR (300 MHz, unless indicated otherwise) NMR peaks given as δ values |
|---|---|---|---|
| 895 | 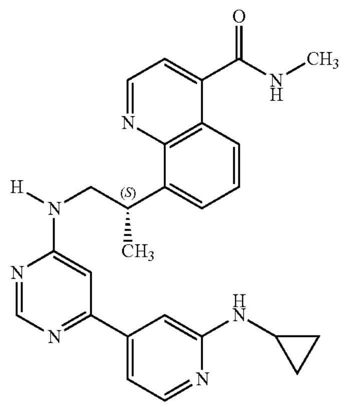 | 431 | (400 MHz, DMSO-d₆) δ 9.01 (s, 1H), 8.83 (d, J = 4.7 Hz, 1H), 8.53 (d, J = 22.7 Hz, 2H), 7.70 (dd, J = 27.5, 15.9 Hz, 6H), 6.95 (d, J = 26.8 Hz, 1H), 4.42 (d, J = 33.7 Hz, 1H), 3.66 (d, J = 83.3 Hz, 2H), 2.90 (d, J = 4.6 Hz, 3H), 2.53 (d, J = 10.9 Hz, 3H), 1.38 (d, J = 5.9 Hz, 3H) |
| 896 | 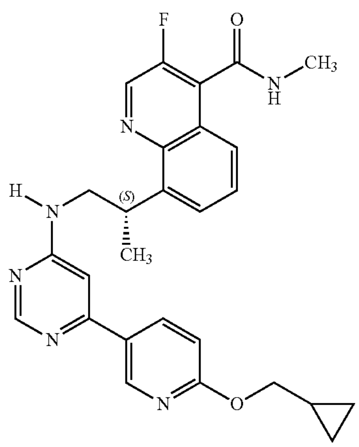 | 487 | (400 MHz, DMSO-d₆) δ 9.01 (s, 1H), 8.79 (t, J = 28.3 Hz, 2H), 8.44 (s, 1H), 8.20 (s, 1H), 7.82-7.62 (m, 3H), 7.49 (s, 1H), 6.92 (d, J = 8.0 Hz, 2H), 4.42 (d, J = 34.7 Hz, 1H), 4.16 (d, J = 6.9 Hz, 2H), 3.73 (s, 2H), 2.90 (d, J = 4.6 Hz, 3H), 1.37 (d, J = 6.8 Hz, 3H), 1.26 (s, 1H), 0.61-0.48 (m, 2H), 0.34 (d, J = 4.6 Hz, 2H) |
| 897 | 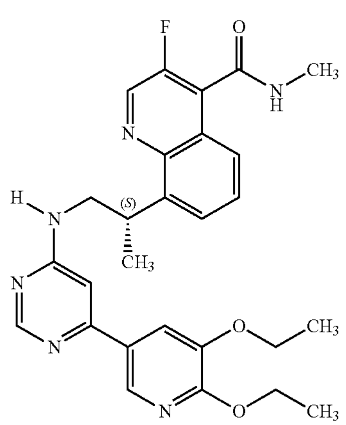 | 505 | (400 MHz, DMSO-d₆) δ 9.01 (s, 1H), 8.84 (d, J = 4.7 Hz, 1H), 8.34 (d, J = 77.6 Hz, 2H), 7.72 (dd, J = 9.4, 7.4 Hz, 4H), 7.45 (s, 1H), 6.84 (d, J = 39.9 Hz, 1H), 4.40 (d, J = 7.1 Hz, 3H), 4.11 (q, J = 7.0 Hz, 2H), 3.72 (s, 2H), 2.90 (d, J = 4.6 Hz, 3H), 1.35 (dd, J = 13.5, 6.6 Hz, 9H) |

TABLE 2-continued

| Cmpnd No. | Structure | ESMS (M + H) | ¹H NMR (300 MHz, unless indicated otherwise) NMR peaks given as δ values |
|---|---|---|---|
| 898 | 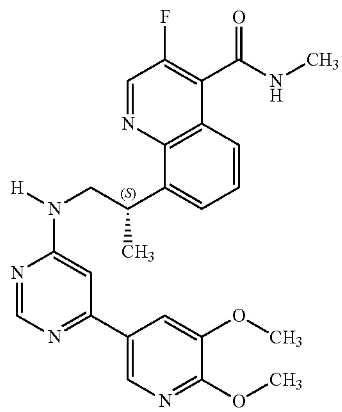 | 477 | (400 MHz, DMSO-d₆) δ 9.01 (s, 1H), 8.84 (d, J = 4.6 Hz, 1H), 8.45 (s, 1H), 8.27 (s, 1H), 7.85-7.62 (m, 4H), 7.48 (s, 1H), 6.83 (d, J = 33.7 Hz, 1H), 4.46 (s, 1H), 3.92 (s, 3H), 3.85 (s, 3H), 3.74 (s, 2H), 2.90 (d, J = 4.6 Hz, 3H), 1.37 (d, J = 6.5 Hz, 3H) |
| 899 | 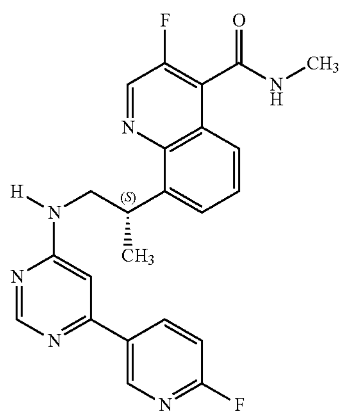 | 435 | (400 MHz, DMSO-d₆) δ 9.01 (s, 1H), 8.79 (t, J = 27.6 Hz, 2H), 8.40 (d, J = 71.4 Hz, 2H), 7.90-7.47 (m, 4H), 7.02 (dd, J = 151.1, 69.9 Hz, 2H), 4.41 (d, J = 46.6 Hz, 1H), 3.64 (d, J = 103.4 Hz, 2H), 2.90 (d, J = 4.6 Hz, 3H), 1.34 (t, J = 20.2 Hz, 3H) |
| 900 | 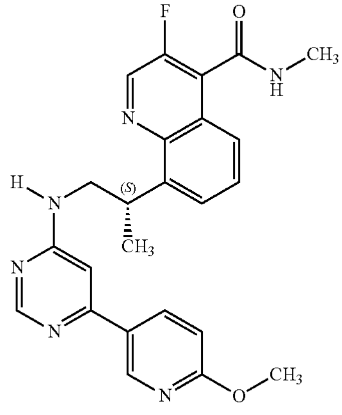 | | (400 MHz, DMSO-d₆) δ 9.02 (s, 1H), 8.84 (d, J = 4.5 Hz, 2H), 8.45 (s, 1H), 8.14 (d, J = 47.1 Hz, 1H), 7.84-7.62 (m, 3H), 7.50 (s, 1H), 6.86 (t, J = 41.5 Hz, 2H), 4.38 (d, J = 62.8 Hz, 1H), 3.82 (d, J = 73.3 Hz, 5H), 2.90 (d, J = 4.6 Hz, 3H), 1.37 (d, J = 6.6 Hz, 3H) |

TABLE 2-continued

| Cmpnd No. | Structure | ESMS (M + H) | ¹H NMR (300 MHz, unless indicated otherwise) NMR peaks given as δ values |
|---|---|---|---|
| 901 | 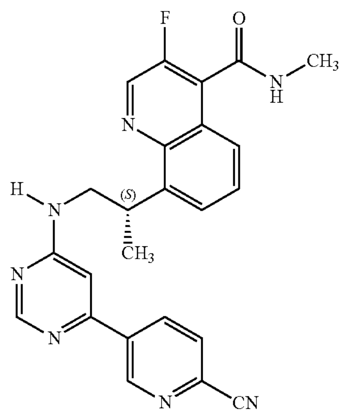 | 442 | (400 MHz, DMSO-d$_6$) δ 9.23 (s, 1H), 9.01 (s, 1H), 8.84 (d, J = 4.9 Hz, 1H), 8.54 (s, 2H), 8.09 (d, J = 59.0 Hz, 1H), 7.97-7.57 (m, 4H), 7.13 (d, J = 77.0 Hz, 1H), 4.41 (d, J = 60.7 Hz, 1H), 3.79 (s, 2H), 2.90 (d, J = 4.6 Hz, 3H), 1.37 (d, J = 6.4 Hz, 3H) |
| 902 | 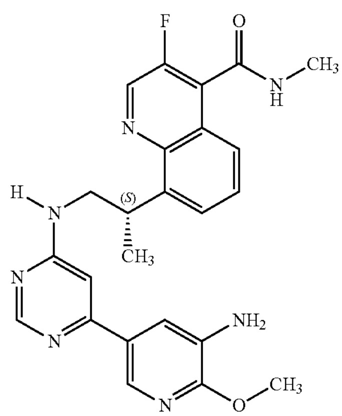 | 462 | (400 MHz, DMSO-d$_6$) δ 9.05-8.77 (m, 2H), 8.41 (s, 1H), 7.96 (s, 1H), 7.71 (dd, J = 10.2, 5.8 Hz, 3H), 7.46 (s, 2H), 6.71 (d, J = 42.2 Hz, 1H), 5.11 (s, 2H), 4.41 (d, J = 43.4 Hz, 1H), 3.92 (s, 3H), 3.70 (s, 2H), 2.90 (d, J = 4.6 Hz, 3H), 1.37 (d, J = 6.8 Hz, 3H) |
| 903 | 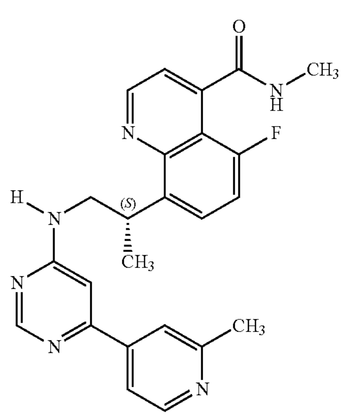 | 431 | (400 MHz, DMSO-d$_6$) δ 8.99 (d, J = 4.3 Hz, 1H), 8.49 (dd, J = 31.1, 13.2 Hz, 3H), 7.94-7.29 (m, 6H), 6.93 (d, J = 40.1 Hz, 1H), 4.40 (d, J = 43.1 Hz, 1H), 3.90-3.37 (m, 2H), 2.82 (d, J = 4.6 Hz, 3H), 2.53 (d, J = 11.6 Hz, 3H), 1.38 (s, 3H) |

TABLE 2-continued

| Cmpnd No. | Structure | ESMS (M + H) | ¹H NMR (300 MHz, unless indicated otherwise) NMR peaks given as δ values |
|---|---|---|---|
| 904 | 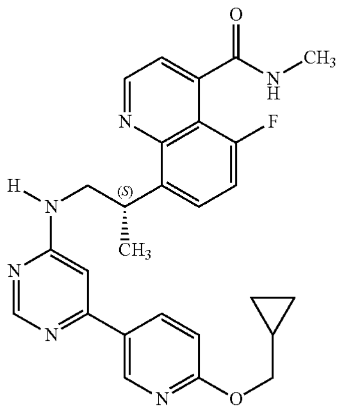 | 487 | (400 MHz, DMSO-d₆) δ 9.00 (d, J = 4.3 Hz, 1H), 8.70 (s, 1H), 8.45 (d, J = 5.1 Hz, 2H), 8.19 (s, 1H), 7.76 (s, 1H), 7.45 (dd, J = 21.7, 13.7 Hz, 3H), 6.92 (s, 2H), 4.44 (s, 1H), 4.16 (d, J = 6.6 Hz, 2H), 3.52 (d, J = 142.2 Hz, 2H), 2.82 (d, J = 4.6 Hz, 3H), 1.36 (d, J = 6.4 Hz, 3H), 1.26 (s, 1H), 0.56 (d, J = 6.5 Hz, 2H), 0.34 (d, J = 4.2 Hz, 2H) |
| 905 | 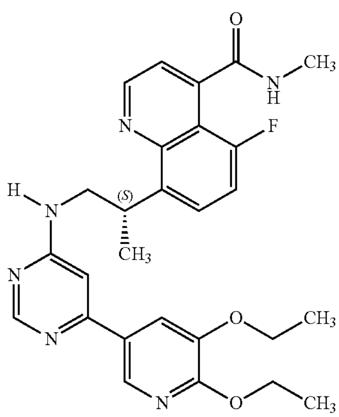 | 505 | (400 MHz, DMSO-d₆) δ 8.99 (d, J = 4.3 Hz, 1H), 8.31 (dd, J = 104.0, 26.1 Hz, 3H), 7.74 (s, 2H), 7.57-7.31 (m, 3H), 6.79 (d, J = 51.8 Hz, 1H), 4.40 (d, J = 7.1 Hz, 3H), 4.11 (q, J = 7.0 Hz, 2H), 3.91-3.36 (m, 2H), 2.77 (t, J = 30.8 Hz, 3H), 1.35 (dd, J = 13.3, 6.5 Hz, 9H) |
| 906 | 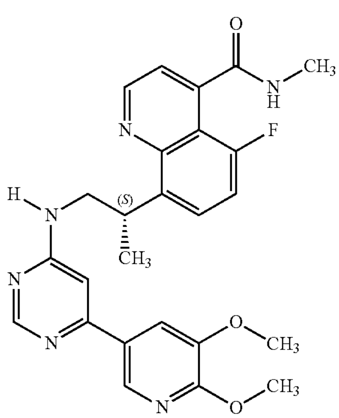 | 477 | (400 MHz, DMSO-d₆) δ 8.99 (d, J = 4.3 Hz, 1H), 8.36 (d, J = 69.8 Hz, 3H), 7.76 (s, 2H), 7.55-7.35 (m, 3H), 6.82 (d, J = 39.9 Hz, 1H), 4.43 (s, 1H), 3.92 (s, 3H), 3.85 (s, 3H), 3.74 (s, 2H), 2.82 (d, J = 4.6 Hz, 3H), 1.36 (d, J = 6.8 Hz, 3H) |

TABLE 2-continued

| Cmpnd No. | Structure | ESMS (M + H) | ¹H NMR (300 MHz, unless indicated otherwise) NMR peaks given as δ values |
|---|---|---|---|
| 907 | 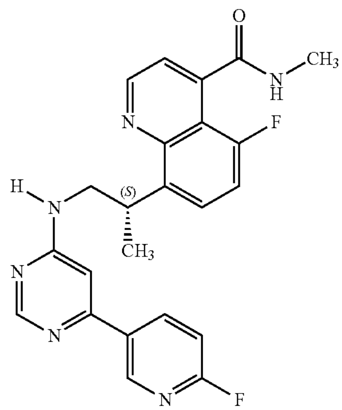 | 435 | (400 MHz, DMSO-d$_6$) δ 8.92 (t, J = 45.9 Hz, 2H), 8.69-8.34 (m, 3H), 7.83-7.24 (m, 5H), 6.86 (d, J = 39.9 Hz, 1H), 4.38 (d, J = 56.9 Hz, 1H), 3.54 (d, J = 152.8 Hz, 2H), 2.77 (t, J = 30.9 Hz, 3H), 1.32 (t, J = 28.3 Hz, 3H) |
| 908 | 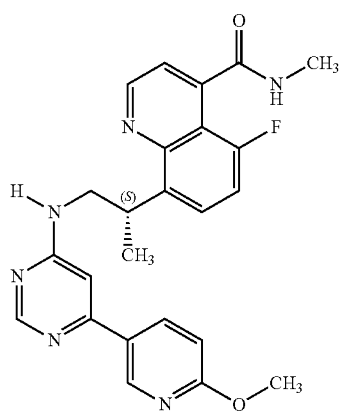 | 447 | (400 MHz, DMSO-d$_6$) δ 9.00 (d, J = 4.3 Hz, 1H), 8.75 (s, 1H), 8.44 (s, 2H), 8.21 (s, 1H), 7.76 (s, 1H), 7.45 (dd, J = 22.8, 12.0 Hz, 3H), 6.94 (s, 2H), 4.39 (d, J = 45.6 Hz, 1H), 4.04-3.41 (m, 5H), 2.82 (d, J = 4.6 Hz, 3H), 1.36 (d, J = 6.7 Hz, 3H) |
| 909 | 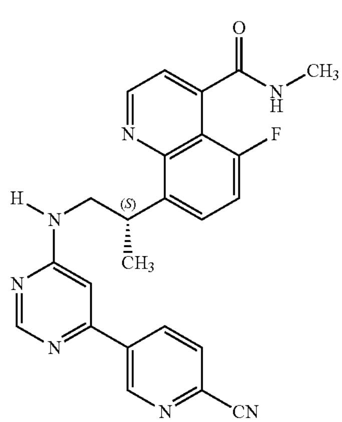 | 442 | (400 MHz, DMSO-d$_6$) δ 9.23 (s, 1H), 9.01 (dd, J = 15.9, 4.3 Hz, 1H), 8.76-8.34 (m, 3H), 8.16 (s, 1H), 7.75 (s, 2H), 7.59-6.92 (m, 3H), 4.40 (d, J = 48.5 Hz, 1H), 3.59 (d, J = 147.3 Hz, 2H), 2.82 (d, J = 4.6 Hz, 3H), 1.37 (s, 3H) |

TABLE 2-continued

| Cmpnd No. | Structure | ESMS (M + H) | ¹H NMR (300 MHz, unless indicated otherwise) NMR peaks given as δ values |
|---|---|---|---|
| 910 | 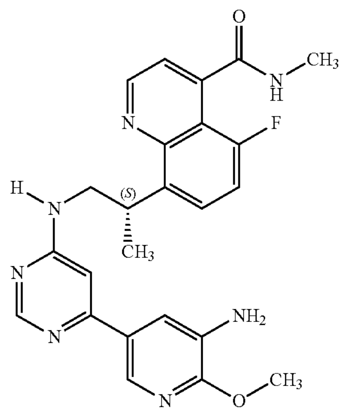 | 462 | (400 MHz, DMSO-d₆) δ 9.05-8.85 (m, 1H), 8.74-8.30 (m, 2H), 7.96 (t, J = 50.7 Hz, 1H), 7.74 (s, 1H), 7.59-7.28 (m, 4H), 6.67 (d, J = 59.3 Hz, 1H), 5.11 (s, 2H), 4.37 (d, J = 42.0 Hz, 1H), 4.04-3.35 (m, 5H), 2.77 (t, J = 31.1 Hz, 3H), 1.36 (d, J = 6.6 Hz, 3H) |
| 911 | 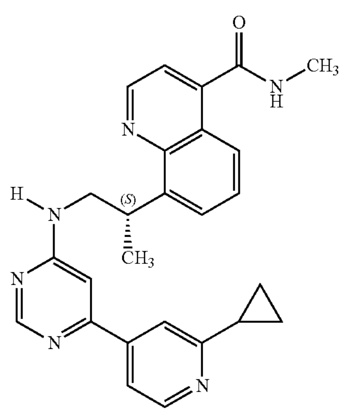 | 439.1 | (DMSO-d₆) δ 8.98 (d, J = 4.3 Hz, 1H), 8.68 (m, 1H), 8.51 (m, 2H), 7.99 (d, J = 8.4 Hz, 1H), 7.84-7.48 (m, 6H), 7.0 (s, 1H), 4.52 (m, 1H), 3.80 (m, 2H), 2.87 (d, J = 4.4 Hz, 3H), 2.18 (m, 1H), 1.39 (d, 3H), 0.97 (m, 4H) |
| 912 | 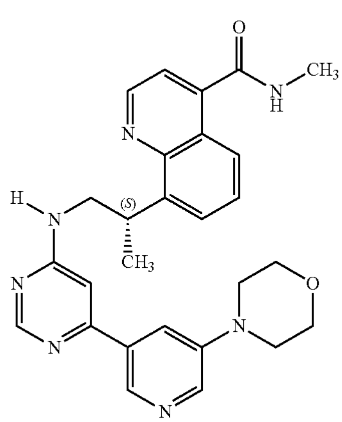 | 484.11 | (DMSO-d₆) δ 8.98 (d, J = 4.3 Hz, 1H), 8.68 (m, 1H), 8.44 (m, 3H), 7.99 (dd, J = 8.4, 1.3 Hz, 1H), 7.83-7.47 (m, 5H), 6.95 (s, 1H), 4.52 (m, 1H), 3.77 (m, 6H), 3.23 (m, 4H), 2.87 (d, J = 4.5 Hz, 3H), 1.38 (d, J = 6.9 Hz, 3H) |

TABLE 2-continued

| Cmpnd No. | Structure | ESMS (M + H) | ¹H NMR (300 MHz, unless indicated otherwise) NMR peaks given as δ values |
|---|---|---|---|
| 913 | 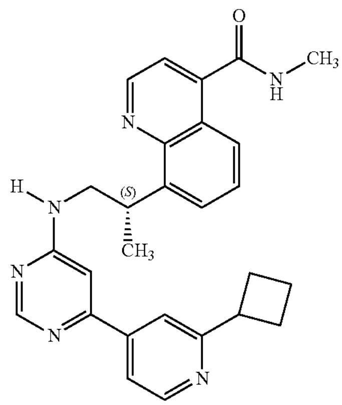 | 453.19 | (DMSO-d$_6$) δ 8.97 (d, J = 4.3 Hz, 1H), 8.75-8.58 (m, 2H), 8.51 (s, 1H), 8.03-7.95 (m, 1H), 7.87-7.59 (m, 5H), 7.54 (s, 1H), 7.01 (s, 1H), 4.53 (m, 1H), 3.89-3.66 (m, 3H), 2.87 (d, J = 4.3 Hz, 3H), 2.38-2.20 (m, 4H), 2.12-1.95 (m, 1H), 1.86 (m, 1H), 1.38 (d, J = 6.9 Hz, 3H) |
| 914 | 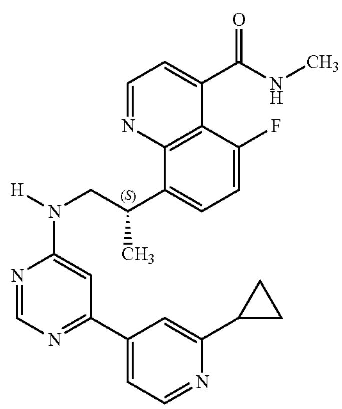 | 457.1 | (DMSO-d$_6$) δ 9.00 (d, J = 4.3 Hz, 1H), 8.57-8.42 (m, 3H), 7.82-7.38 (m, 6H), 6.98 (s, 1H), 4.45 (m, 1H), 3.80 (m, 2H), 2.82 (d, J = 4.5 Hz, 3H), 2.26-2.12 (m, 1H), 1.37 (d, J = 6.8 Hz, 3H), 0.97 (m, 4H) |
| 915 | 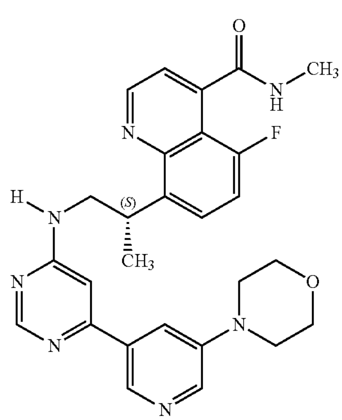 | 502.11 | (DMSO-d$_6$) δ 8.99 (d, J = 4.3 Hz, 1H), (m, 3H), 7.76 (m, 2H), 7.47 (m, 3H), 4.45 (s, 1H), 3.76 (m, 6H), 3.22 (m, 4H), 2.82 (d, J = 4.5 Hz, 3H), 1.37 (d, 3H) |

TABLE 2-continued

| Cmpnd No. | Structure | ESMS (M + H) | ¹H NMR (300 MHz, unless indicated otherwise) NMR peaks given as δ values |
|---|---|---|---|
| 916 | 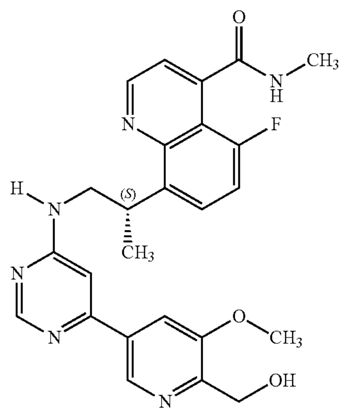 | 477.09 | (DMSO-d₆) δ 9.00 (d, J = 4.3 Hz, 1H), 8.63 (m, 1H), 8.48 (m, 2H), 7.80 (m, 2H), 7.63-7.39 (m, 3H), 6.98 (s, 1H), 4.59 (s, 2H), 4.45 (m, 1H), 3.89 (s, 3H), 3.75 (m, 2H), 2.82 (d, J = 4.5 Hz, 3H), 1.37 (d, J = 6.8 Hz, 3H) |
| 917 | 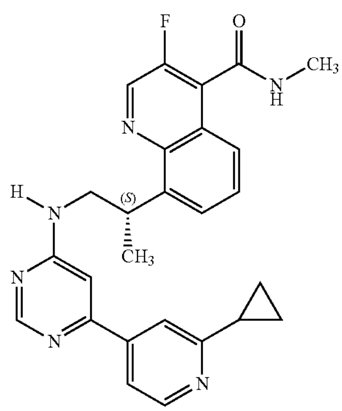 | 457.1 | (DMSO-d₆) δ 9.02 (s, 1H), 8.86 (m, 1H), 8.58-8.44 (m, 2H), 7.93-7.53 (m, 6H), 6.99 (s, 1H), 4.54-4.41 (m, 1H), 3.77 (m, 2H), 2.90 (d, J = 4.3 Hz, 3H), 2.25-2.14 (m, 1H), 1.37 (d, J = 6.9 Hz, 3H), 0.97 (m, 4H) |
| 918 | 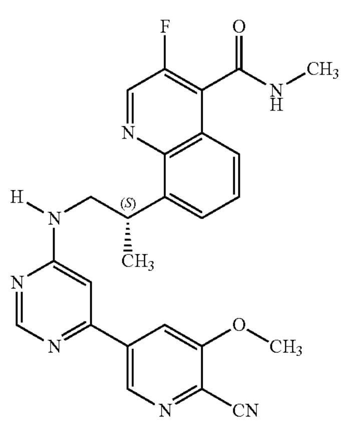 | 472.05 | (DMSO-d₆) δ 9.02 (m, 1H), 8.87 (m, 1H), 8.78 (m, 1H), 8.54 (m, 1H), 8.31 (dd, J = 4.4, 1.3 Hz, 1H), 7.83-7.69 (m, 4H), 4.48 (m, 1H), 4.06 (s, 3H), 3.79 (m, 3H), 2.90 (d, J = 4.5 Hz, 3H), 1.38 (d, 3H) |

TABLE 2-continued
| Cmpnd No. | Structure | ESMS (M + H) | ¹H NMR (300 MHz, unless indicated otherwise) NMR peaks given as δ values |
|---|---|---|---|
| 919 | 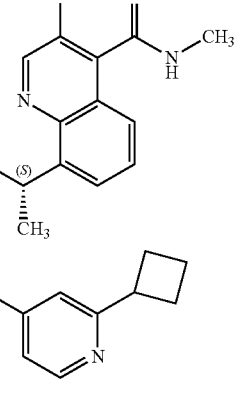 | 471.15 | (DMSO-d$_6$) δ 9.02 (s, 1H), 8.86 (m, 1H), 8.63 (m, 1H), 8.51 (s, 1H), 7.84-7.58 (m, 6H), 7.00 (s, 1H), 4.46 (m, 1H), 3.88-3.64 (m, 3H), 2.90 (d, J = 4.4 Hz, 3H), 2.30 (m, 4H), 2.03 (dq, J = 10.5, 8.5 Hz, 1.91-1.77 (m, 1H), 1.37 (d, J = 6.9 Hz, 3H) |
| 920 | 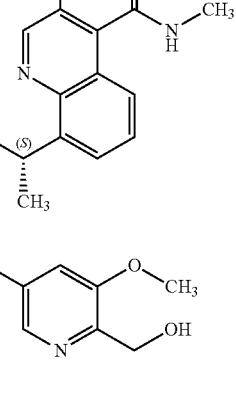 | 477.13 | (DMSO-d$_6$) δ 9.03 (s, 1H), 8.87 (m, 1H), 8.63 (m, 1H), 8.50 (m, 1H), 7.92-7.65 (m, 4H), 7.60 (s, 1H), 6.99 (s, 1H), 4.58 (s, 2H), 4.47 (m, 1H), 3.90 (s, 3H), 3.87 (m, 2H), 2.90 (d, J = 4.4 Hz, 3H), 1.37 (d, J = 6.9 Hz, 3H) |
| 921 | 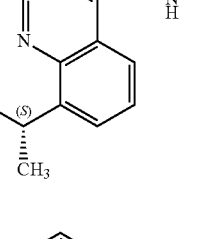 | 472.09 | |

TABLE 2-continued

| Cmpnd No. | Structure | ESMS (M + H) | ¹H NMR (300 MHz, unless indicated otherwise) NMR peaks given as δ values |
|---|---|---|---|
| 922 | 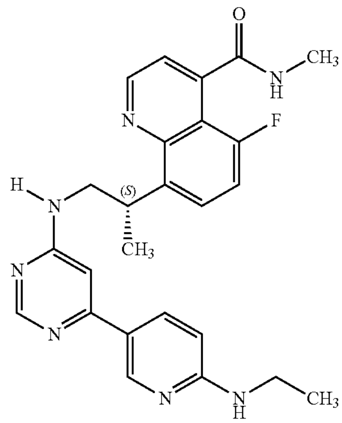 | 460.07 | |
| 923 | 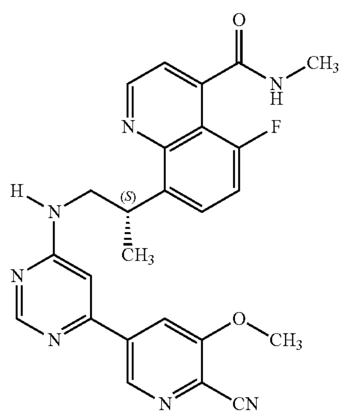 | 472.09 | |
| 924 | 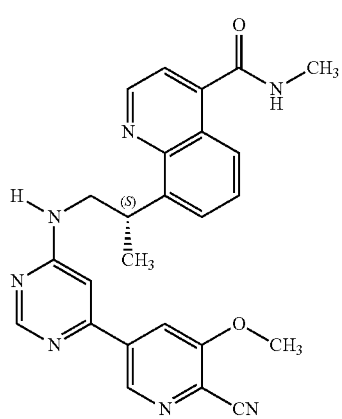 | 454.13 | |

TABLE 2-continued

| Cmpnd No. | Structure | ESMS (M + H) | ¹H NMR (300 MHz, unless indicated otherwise) NMR peaks given as δ values |
|---|---|---|---|
| 925 | 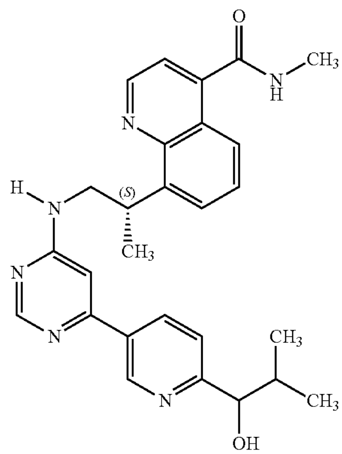 | 471.15 | (DMSO-d$_6$) δ 8.98 (m, 2H), 8.69 (m, 1H), 8.49 (s, 1H), 8.27 (m, 1H), 8.00 (d, J = 8.4 Hz, 1H), 7.77 (m, 1H), 7.69-7.49 (m, 4H), 6.94 (s, 1H), 4.47 (m, 2H), 3.77 (m, 2H), 3.07 (m, 1H), 2.87 (d, J = 4.4 Hz, 3H), 2.07 (m, 1H), 1.38 (d, J = 6.8 Hz, 3H), 0.87 (d, J = 6.9 Hz, 3H), 0.78 (d, J = 6.7 Hz, 3H) |
| 926 | 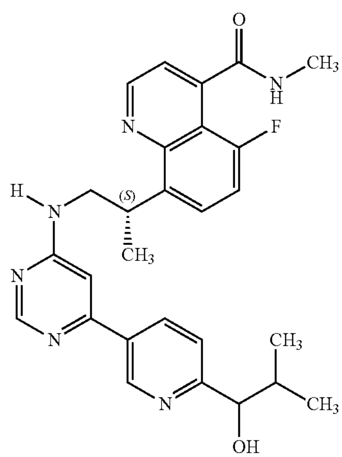 | 488.97 | (DMSO-d$_6$) δ 9.00 (d, J = 4.3 Hz, 2H), 8.48 (s, 2H), 8.26 (s, 1H), 7.76 (s, 1H), 7.48 (m, 4H), 6.90 (s, 1H), 4.42 (m, 2H), 3.75 (m, 2H), 2.82 (d, J = 4.5 Hz, 3H), 2.07 (m, 1H), 1.36 (d, J = 7.0 Hz, 3H), 0.87 (d, J = 6.8 Hz, 3H), 0.78 (d, J = 6.8 Hz, 3H) |
| 927 | 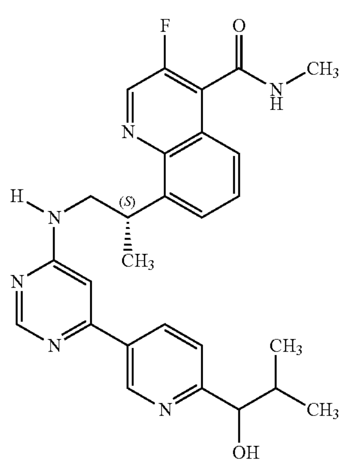 | 489.11 | (DMSO-d$_6$) δ 9.02 (m, 2H), 8.88 (m, 1H), 8.48 (s, 1H), 8.26 (m, 1H), 7.82-7.51 (m, 5H), 6.93 (s, 1H), 4.45 (m, 2H), 3.88-3.67 (m, 2H), 3.07 (m, 1H), 2.90 (d, J = 4.3 Hz, 3H), 2.07 (m, 1H), 1.37 (d, J = 6.8 Hz, 3H), 0.87 (d, J = 6.8 Hz, 3H), 0.78 (d, J = 6.7 Hz, 3H) |

TABLE 2-continued

| Cmpnd No. | Structure | ESMS (M + H) | ¹H NMR (300 MHz, unless indicated otherwise) NMR peaks given as δ values |
|---|---|---|---|
| 928 | 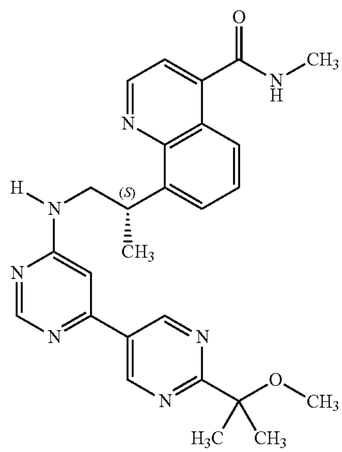 | 472.05 | (DMSO-d₆) δ 9.32 (m, 2H), 8.97 (d, J = 4.3 Hz, 1H), 8.68 (m, 1H), 8.53 (m, 1H), 8.03-7.96 (m, 1H), 7.76 (m, 2H), 7.63 (t, J = 7.8 Hz, 1H), 7.53 (d, J = 4.4 Hz, 1H), 6.97 (s, 1H), 4.52 (m, 1H), 3.80 (m, 2H), 3.02 (s, 3H), 2.87 (d, J = 4.5 Hz, 3H), 1.57 (s, 6H), 1.38 (d, J = 6.8 Hz, 3H) |
| 929 | 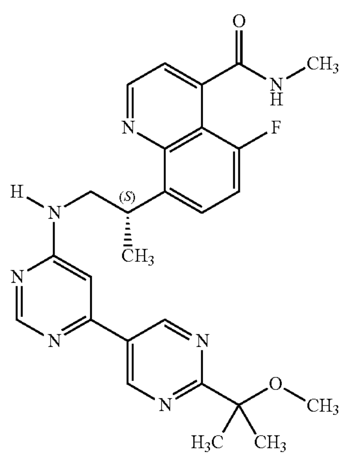 | 490.14 | (DMSO-d₆) δ 9.26 (m, 2H), 8.98 (m, 1H), 8.55-8.44 (m, 2H), 7.73 (m, 2H), 7.53-7.41 (m, 2H), 6.96 (s, 1H), 4.46 (m, 1H), 3.80 (m, 2H), 3.02 (s, 3H), 2.82 (d, J = 4.6 Hz, 3H), 1.57 (s, 6H), 1.36 (d, J = 6.9 Hz, 3H) |
| 930 | 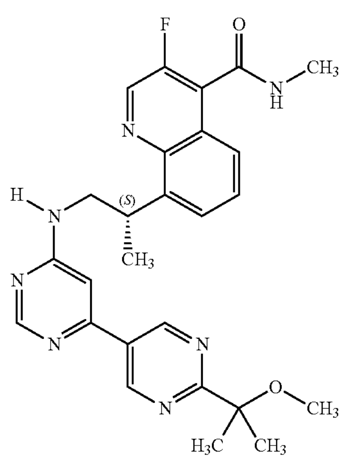 | 490.14 | (DMSO-d₆) δ 9.32 (m, 2H), 9.02 (s, 1H), 8.87 (m, 1H), 8.53 (m, 1H), 7.88-7.65 (m, 4H), 6.97 (s, 1H), 4.48 (m, 1H), 3.80 (m, 2H), 3.02 (s, 3H), 2.90 (d, J = 4.3 Hz, 3H), 1.57 (s, 6H), 1.37 (d, J = 6.8 Hz, 3H) |

TABLE 2-continued
| Cmpnd No. | Structure | ESMS (M + H) | ¹H NMR (300 MHz, unless indicated otherwise) NMR peaks given as δ values |
|---|---|---|---|
| 931 | 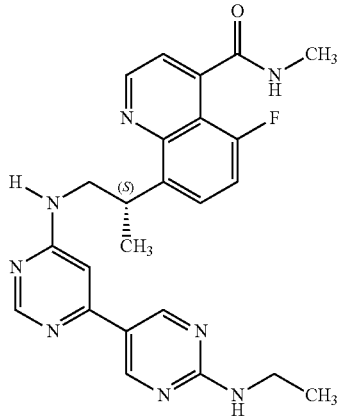 | 461.24 | |
| 932 | 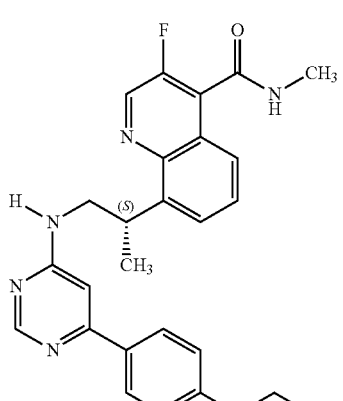 | 461.06 | |
| 933 | 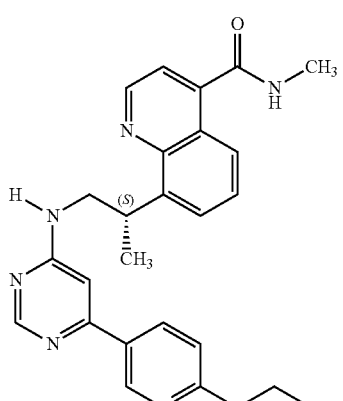 | 443.15 | |

TABLE 2-continued

| Cmpnd No. | Structure | ESMS (M + H) | $^1$H NMR (300 MHz, unless indicated otherwise) NMR peaks given as δ values |
|---|---|---|---|
| 934 | 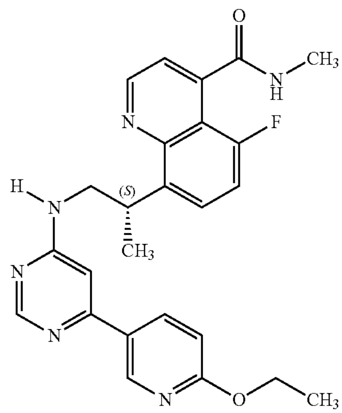 | 461.02 | |
| 935 | 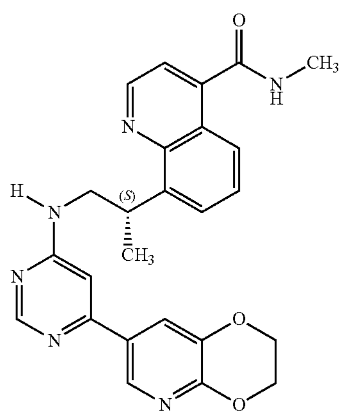 | 457.15 | (DMSO-d$_6$) δ 8.99 (d, J = 4.2 Hz, 1H), 8.69 (d, J = 5.1 Hz, 1H), 8.44 (m, 1H), 8.31 (m, 1H), 7.99 (dd, J = 8.6, 1.3 Hz, 1H), 7.85-7.45 (m, 5H), 6.85 (s, 1H), 4.47 (m, 3H), 4.31 (m, 2H), 3.80 (m, 2H), 2.87 (d, J = 4.2 Hz, 3H), 1.37 (d, J = 6.9 Hz, 3H) |
| 936 | 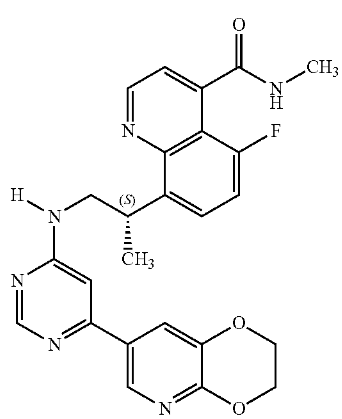 | 475.06 | (DMSO-d$_6$) δ 9.01 (d, J = 4.3 Hz, 1H), 8.30 (m, 1H), 8.52-8.39 (m, 2H), 7.76 (s, 2H), 7.60-7.38 (m, 3H), 6.84 (s, 1H), 4.47 (m, 3H), 4.31 (m, 2H), 3.75 (m, 2H), 2.82 (d, J = 4.5 Hz, 3H), 1.36 (d, J = 6.9 Hz, 3H) |

TABLE 2-continued
| Cmpnd No. | Structure | ESMS (M + H) | ¹H NMR (300 MHz, unless indicated otherwise) NMR peaks given as δ values |
|---|---|---|---|
| 937 | 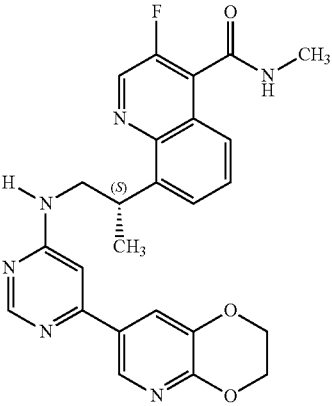 | 475.02 | (DMSO-d$_6$) δ 9.02 (s, 1H), 8.87 (m, 1H), 8.44 (s, 1H), 8.30 (m, 1H), 7.80-7.44 (m, 5H), 6.84 (s, 1H), 4.47 (m, 3H), 4.31 (m, 2H), 3.75 (m, 2H), 2.90 (d, J = 4.4 Hz, 3H), 1.36 (d, J = 6.9 Hz, 3H) |
| 938 | 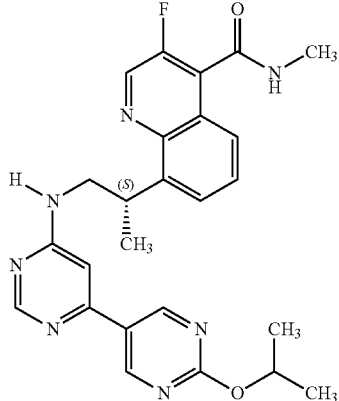 | 476.1 | (DMSO-d$_6$) δ 9.02 (m, 3H), 8.87 (m, 1H), 8.47 (s, 1H), 7.68 (m, 4H), 6.87 (s, 1H), 5.32-5.22 (m, 1H), 4.47 (m, 1H), 3.80 (m, 2H), 2.90 (d, J = 4.5 Hz, 3H), 1.36 (m, 9H) |
| 939 | 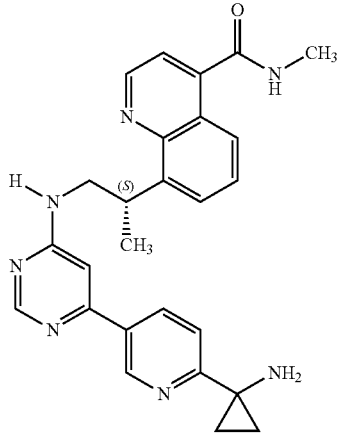 | 454.09 | (DMSO-d$_6$) δ 8.96 (m, 2H), 8.72 (m, 1H), 8.45 (m, 1H), 8.07 (d, J = 8.0 Hz, 1H), 8.00 (m, 1H), 7.76 (d, J = 7.0 Hz, 1H), 7.69-7.50 (m, 4H), 6.92 (s, 1H), 4.97 (m, 1H), 4.49 (m, 1H), 3.73 (m, 2H), 3.04 (m, 2H), 2.91-2.80 (d, 3H), 1.35 (m, 5H), 1.06 (dm, 2H) |

TABLE 2-continued

| Cmpnd No. | Structure | ESMS (M + H) | ¹H NMR (300 MHz, unless indicated otherwise) NMR peaks given as δ values |
|---|---|---|---|
| 940 | 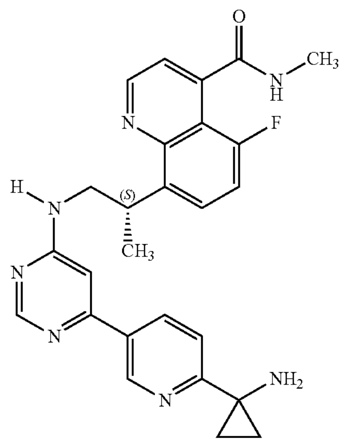 | 472.09 | (DMSO-d₆) δ 9.02-8.96 (m, 1H), 8.88 (m, 1H), 8.48 (m, 2H), 8.10 (m, 1H), 7.80-7.60 (m, 3H), 7.56-7.38 (m, 2H), 6.91 (s, 1H), 4.98 (m, 1H), 4.43 (m, 1H), 3.73 (m, 2H), 3.05 (m, 3H), 2.81 (d, J = 4.3 Hz, 3H), 1.36 (m, 4H), 1.08 (m, 2H) |
| 941 | 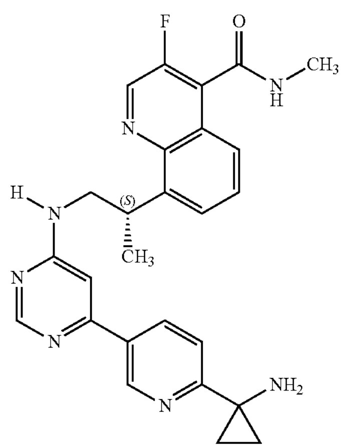 | 472.14 | (DMSO-d₆) δ 9.02 (s, 1H), 8.90 (m, 2H), 8.45 (m, 1H), 8.09 (m, 1H), 7.82-7.59 (m, 5H), 6.90 (s, 1H), 4.86 (m, 1H), 4.46 (m, 1H), 3.74 (m, 2H), 3.03 (m, 1H), 2.90 (d, J = 4.1 Hz, 3H), 1.43-1.21 (m, 5H), 1.05 (m, 2H) |
| 942 | 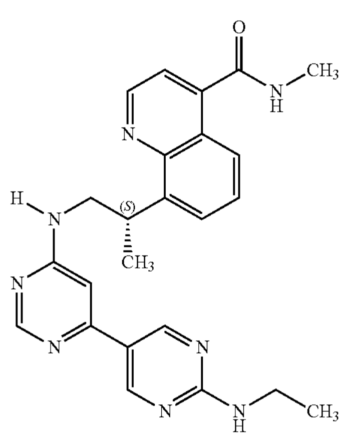 | 443.15 | |

TABLE 2-continued

| Cmpnd No. | Structure | ESMS (M + H) | ¹H NMR (300 MHz, unless indicated otherwise) NMR peaks given as δ values |
|---|---|---|---|
| 943 | 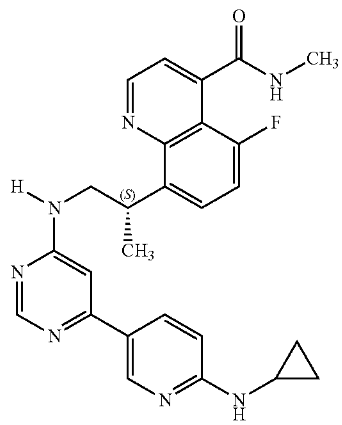 | 472.14 | |
| 944 | 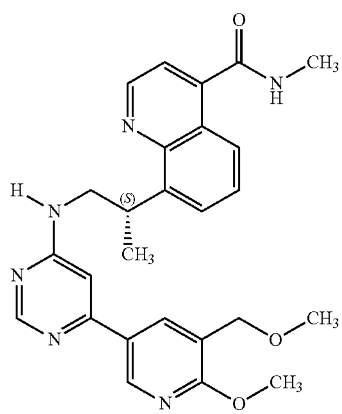 | 473 | (400 MHz, DMSO-d₆) δ 8.98 (d, J = 3.9 Hz, 1H), 8.73-8.41 (m, 2H), 8.22 (s, 1H), 8.00 (d, J = 7.9 Hz, 1H), 7.85-7.40 (m, 4H), 7.29-6.34 (m, 1H), 4.44 (s, 2H), 4.02-3.60 (m, 4H), 3.37-3.24 (m, 2H), 2.87 (d, J = 4.6 Hz, 3H), 2.50-2.43 (m, 3H), 1.38 (d, J = 6.1 Hz, 3H) |
| 945 | 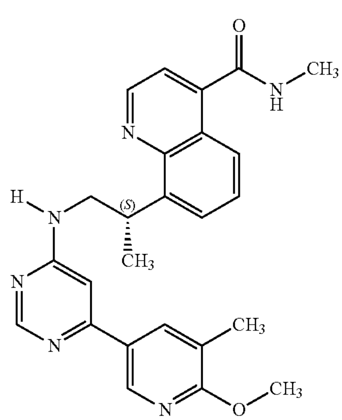 | 443 | (400 MHz, DMSO-d₆) δ 8.93 (t, J = 25.1 Hz, 1H), 8.52 (dd, J = 111.4, 25.8 Hz, 3H), 7.97 (t, J = 18.2 Hz, 2H), 7.82-7.40 (m, 4H), 6.81 (d, J = 36.2 Hz, 1H), 4.51 (s, 1H), 3.94 (s, 3H), 3.83-3.33 (m, 2H), 2.87 (d, J = 4.6 Hz, 3H), 2.21 (s, 3H), 1.38 (d, J = 6.5 Hz, 3H) |

| Cmpnd No. | Structure | ESMS (M + H) | ¹H NMR (300 MHz, unless indicated otherwise) NMR peaks given as δ values |
|---|---|---|---|
| 946 | 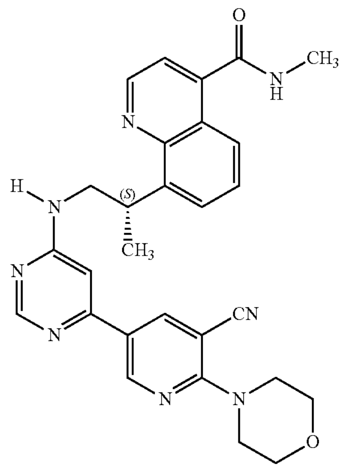 | 509 | (400 MHz, DMSO-d₆) δ 8.98 (d, J = 3.9 Hz, 2H), 8.51 (dd, J = 115.5, 32.4 Hz, 3H), 7.99 (d, J = 8.3 Hz, 1H), 7.87-7.40 (m, 4H), 6.79 (d, J = 50.9 Hz, 1H), 4.51 (s, 1H), 3.89-.33.34 (m, 10H), 2.87 (d, J = 4.6 Hz, 3H), 1.38 (s, 3H) |
| 947 | 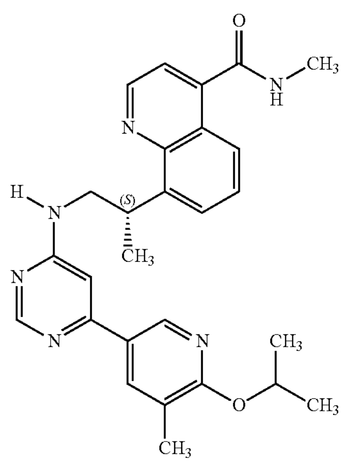 | 471 | (400 MHz, DMSO-d₆) δ 8.98 (d, J = 4.3 Hz, 1H), 8.57 (dd, J = 64.6, 27.4 Hz, 3H), 8.00 (d, J= 8.0 Hz, 2H), 7.87-7.36 (m, 4H), 6.77 (d, J = 44.7 Hz, 1H), 5.27 (d, J = 58.1 Hz, 1H), 4.45 (d, J = 48.3 Hz, 1H), 3.54 (d, J= 151.2 Hz, 2H), 2.86 (t, J = 8.1 Hz, 3H), 2.18 (s, 3H), 1.35 (dd, J = 20.4, 6.3 Hz, 9H) |
| 948 | 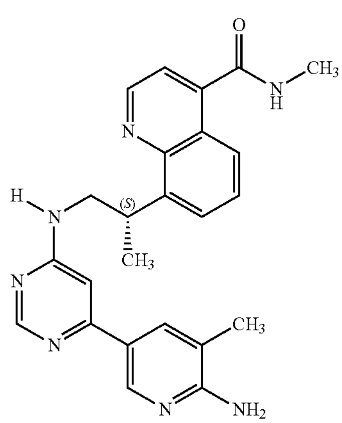 | 428 | (400 MHz, DMSO-d₆) δ 8.99 (d, J = 4.3 Hz, 1H), 8.66 (d, J = 4.7 Hz, 1H), 8.41 (d, J = 38.6 Hz, 2H), 7.99 (d, J = 7.3 Hz, 1H), 7.89-7.47 (m, 4H), 6.98 (d, J = 254.6 Hz, 2H), 6.09 (d, J = 53.2 Hz, 2H), 4.45 (d, J = 45.3 Hz, 1H), 3.70 (s, 2H), 2.87 (d, J = 4.6 Hz, 3H), 2.10 (s, 3H), 1.38 (d, J = 6.8 Hz, 3H) |

TABLE 2-continued

| Cmpnd No. | Structure | ESMS (M + H) | ¹H NMR (300 MHz, unless indicated otherwise) NMR peaks given as δ values |
|---|---|---|---|
| 949 | 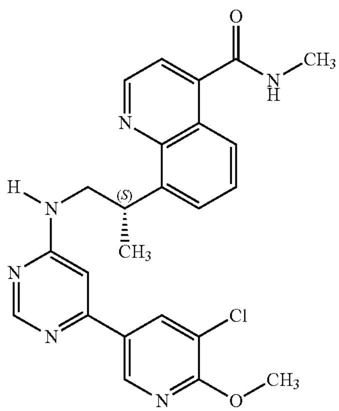 | 463 | (400 MHz, DMSO-d$_6$) δ 8.98 (d, J = 4.3 Hz, 1H), 8.65 (d, J = 4.5 Hz, 2H), 8.36 (d, J = 78.6 Hz, 2H), 8.00 (d, J = 8.6 Hz, 1H), 7.86-7.42 (m, 4H), 6.81 (d, J = 67.9 Hz, 1H), 4.44 (d, J = 64.3 Hz, 1H), 4.01 (s, 3H), 3.61 (d, J = 109.3 Hz, 2H), 2.87 (d, J = 4.6 Hz, 3H), 1.37 (s, 3H) |
| 950 | 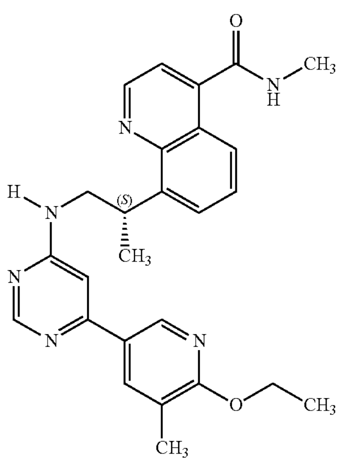 | 457 | (400 MHz, DMSO-d$_6$) δ 8.97 (d, J = 4.2 Hz, 1H), 8.51 (dd, J = 110.4, 24.7 Hz, 3H), 8.00 (d, J = 8.5 Hz, 2H), 7.85-7.37 (m, 4H), 6.79 (d, J = 37.9 Hz, 1H), 4.65-4.18 (m, 3H), 3.54 (d, J = 147.7 Hz, 2H), 2.87 (d, J = 4.6 Hz, 3H), 2.20 (s, 3H), 1.51-1.13 (m, 6H) |
| 951 | 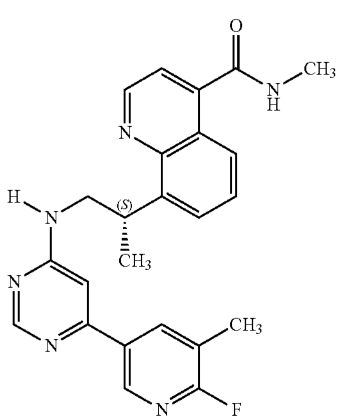 | 431 | (400 MHz, DMSO-d$_6$) δ 8.97 (d, J = 4.3 Hz, 1H), 8.84-8.24 (m, 4H), 8.00 (d, J = 8.2 Hz, 1H), 7.85-7.43 (m, 4H), 7.04 (dd, J = 145.9, 53.7 Hz, 1H), 4.52 (s, 1H), 3.92-3.34 (m, 2H), 2.87 (d, J = 4.6 Hz, 3H), 2.32 (s, 3H), 1.39 (s, 3H) |

TABLE 2-continued

| Cmpnd No. | Structure | ESMS (M + H) | ¹H NMR (300 MHz, unless indicated otherwise) NMR peaks given as δ values |
|---|---|---|---|
| 952 | 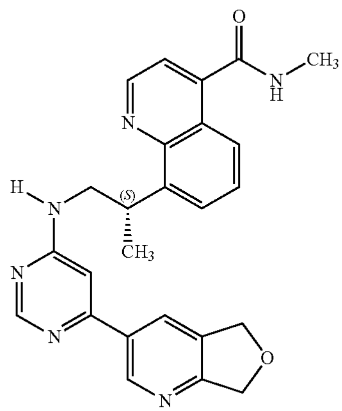 | 441 | (400 MHz, DMSO-d₆) δ 8.97 (d, J = 4.3 Hz, 2H), 8.65 (d, J = 4.5 Hz, 1H), 8.49 (s, 1H), 8.24 (s, 1H), 8.00 (d, J = 8.2 Hz, 1H), 7.87-7.44 (m, 4H), 6.91 (d, J = 34.0 Hz, 1H), 5.15 (s, 2H), 4.99 (s, 2H), 4.47 (d, J = 38.9 Hz, 1H), 3.65 (d, J = 79.1 Hz, 2H), 2.87 (d, J = 4.6 Hz, 3H), 1.39 (s, 3H) |
| 953 | 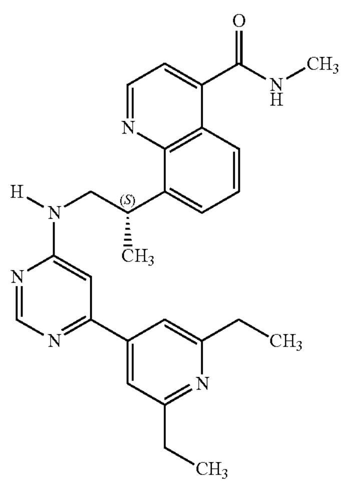 | 455 | (400 MHz, DMSO-d₆) δ 8.96 (d, J = 4.1 Hz, 1H), 8.65 (d, J = 4.7 Hz, 1H), 8.45 (d, J = 33.6 Hz, 1H), 8.00 (d, J = 7.9 Hz, 1H), 7.83-7.42 (m, 6H), 6.95 (d, J = 34.3 Hz, 1H), 4.44 (d, J = 47.6 Hz, 1H), 3.89-3.35 (m, 2H), 2.83 (dd, J = 32.8, 6.1 Hz, 7H), 1.39 (s, 3H), 1.21 (dt, J = 14.2, 7.3 Hz, 6H) |
| 954 | 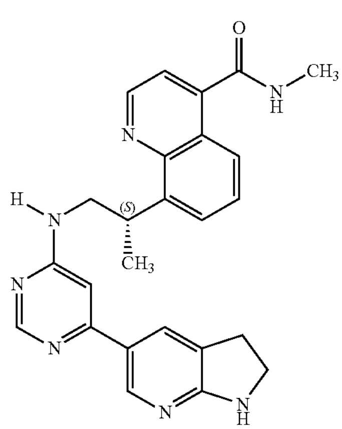 | 440 | |

TABLE 2-continued

| Cmpnd No. | Structure | ESMS (M + H) | ¹H NMR (300 MHz, unless indicated otherwise) NMR peaks given as δ values |
|---|---|---|---|
| 955 | 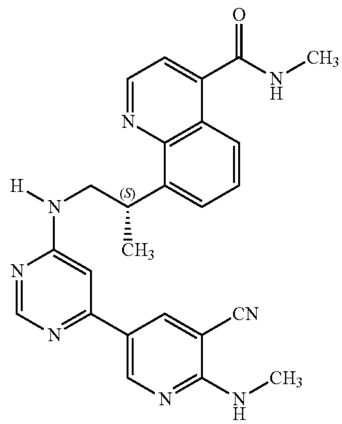 | 453 | |
| 956 | 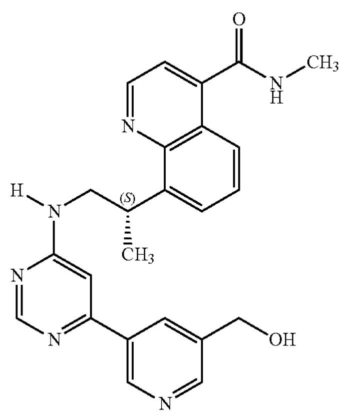 | 429 | (400 MHz, DMSO-d$_6$) δ 8.98 (s, 2H), 8.73-8.43 (m, 3H), 8.23 (s, 1H), 8.00 (d, J = 8.9 Hz, 1H), 7.86-7.47 (m, 4H), 6.93 (d, J = 26.8 Hz, 1H), 5.37 (d, J = 60.4 Hz, 1H), 4.57 (d, J = 38.2 Hz, 3H), 3.92-3.34 (m, 2H), 2.87 (d, J = 4.6 Hz, 3H), 1.40 (s, 3H) |
| 957 | 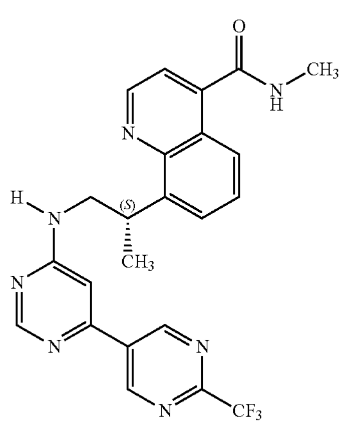 | | (400 MHz, DMSO-d$_6$) δ 9.56 (d, J = 55.4 Hz, 2H), 8.97 (d, J = 4.2 Hz, 1H), 8.72-8.39 (m, 2H), 7.99 (d, J = 8.1 Hz, 1H), 7.80 (d, J = 21.1 Hz, 2H), 7.69-6.98 (m, 3H), 4.48 (d, J = 47.7 Hz, 1H), 3.94-3.35 (m, 2H), 2.85 (t, J = 8.4 Hz, 3H), 1.39 (s, 3H) |

TABLE 2-continued

| Cmpnd No. | Structure | ESMS (M + H) | ¹H NMR (300 MHz, unless indicated otherwise) NMR peaks given as δ values |
|---|---|---|---|
| 958 | 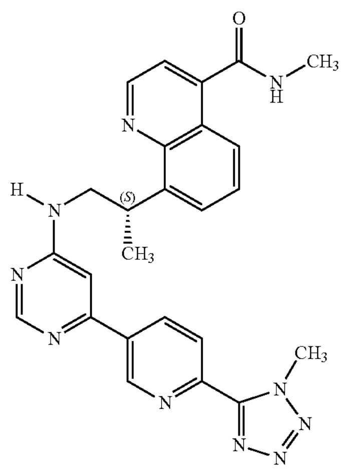 | 481 | (400 MHz, DMSO-d₆) δ 9.25 (d, J = 45.4 Hz, 1H), 8.95 (d, J = 32.7 Hz, 1H), 8.73-8.25 (m, 4H), 8.00 (d, J = 8.4 Hz, 1H), 7.83-7.04 (m, 5H), 4.44 (d, J = 17.0 Hz, 4H), 3.66 (d, J = 100.6 Hz, 2H), 2.87 (d, J = 4.6 Hz, 3H), 1.40 (s, 3H) |
| 959 | 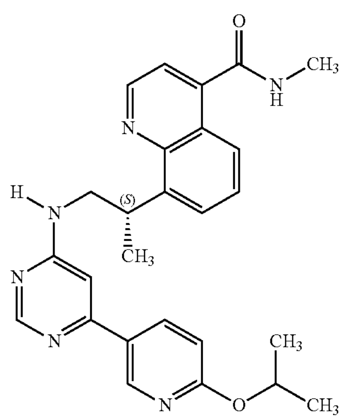 | 457 | (400 MHz, DMSO-d₆) δ 8.98 (d, J = 4.2 Hz, 1H), 8.66 (d, J = 4.6 Hz, 2H), 8.44 (s, 1H), 8.12 (d, J = 38.4 Hz, 1H), 7.99 (d, J = 8.4 Hz, 1H), 7.85-7.41 (m, 4H), 6.76 (d, J = 75.1 Hz, 2H), 5.26 (d, J = 42.7 Hz, 1H), 4.46 (d, J = 41.4 Hz, 1H), 3.71 (s, 2H), 2.87 (d, J = 4.6 Hz, 3H), 1.35 (dd, J = 23.9, 6.0 Hz, 9H) |
| 960 | 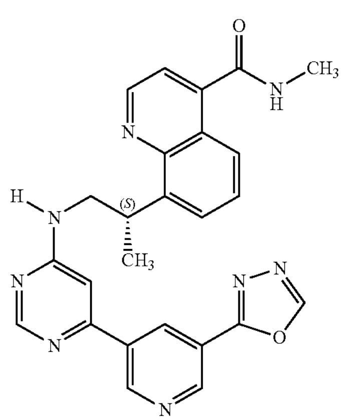 | 467 | (400 MHz, DMSO-d₆) δ 9.38 (d, J = 84.8 Hz, 3H), 9.07-8.45 (m, 4H), 8.00 (d, J = 8.2 Hz, 1H), 7.87-7.00 (m, 5H), 4.53 (s, 1H), 3.91-3.36 (m, 2H), 2.87 (d, J = 4.6 Hz, 3H), 1.40 (s, 3H) |

TABLE 2-continued

| Cmpnd No. | Structure | ESMS (M + H) | ¹H NMR (300 MHz, unless indicated otherwise) NMR peaks given as δ values |
|---|---|---|---|
| 961 | 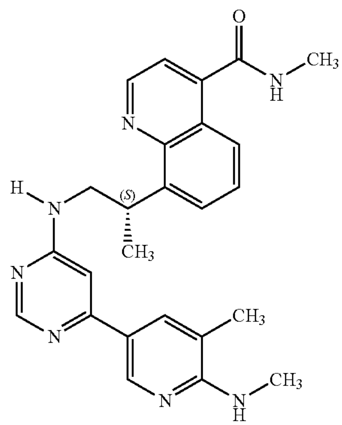 | 442 | (400 MHz, DMSO-d₆) δ 8.99 (d, J = 4.3 Hz, 1H), 8.73-8.25 (m, 3H), 7.99 (d, J = 8.0 Hz, 1H), 7.87-7.44 (m, 4H), 7.31 (s, 1H), 6.70 (d, J = 48.0 Hz, 1H), 6.36 (s, 1H), 4.44 (d, J = 44.4 Hz, 1H), 3.52 (d, J = 152.3 Hz, 2H), 2.88 (dd, J = 12.9, 4.5 Hz, 6H), 2.10 (s, 3H), 1.38 (d, J = 6.8 Hz, 3H) |
| 962 | 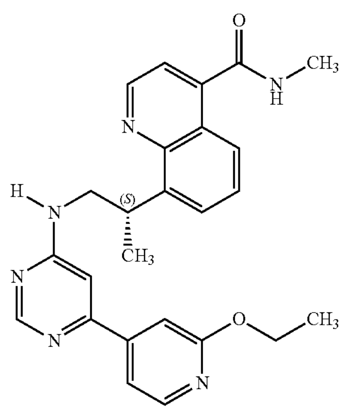 | 443 | (400 MHz, DMSO-d₆) δ 8.94 (d, J = 40.3 Hz, 1H), 8.65 (s, 1H), 8.50 (s, 1H), 8.21 (d, J = 43.5 Hz, 1H), 8.00 (d, J = 8.3 Hz, 1H), 7.48 (ddd, J = 229.7, 114.5, 76.4 Hz, 7H), 4.44 (d, J = 64.2 Hz, 3H), 3.94-3.33 (m, 2H), 2.87 (d, J = 4.6 Hz, 3H), 1.37 (s, 6H) |
| 963 | 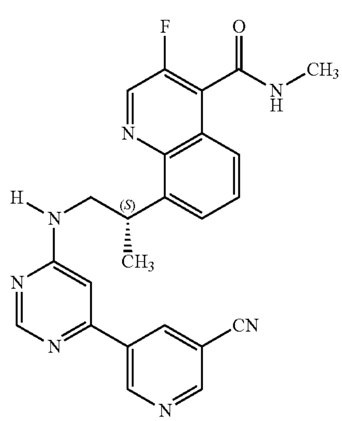 | 442 | (400 MHz, DMSO-d₆) δ 9.34 (d, J = 2.2 Hz, 1H), 8.93 (ddd, J = 52.8, 48.0, 25.2 Hz, 4H), 8.46 (d, J = 47.5 Hz, 1H), 7.72 (t, J = 8.6 Hz, 4H), 7.42-6.83 (m, 1H), 4.44 (d, J = 40.6 Hz, 1H), 3.63 (d, J = 118.0 Hz, 2H), 2.89 (t, J = 8.1 Hz, 3H), 1.38 (s, 3H) |

| Cmpnd No. | Structure | ESMS (M + H) | ¹H NMR (300 MHz, unless indicated otherwise) NMR peaks given as δ values |
|---|---|---|---|
| 964 | 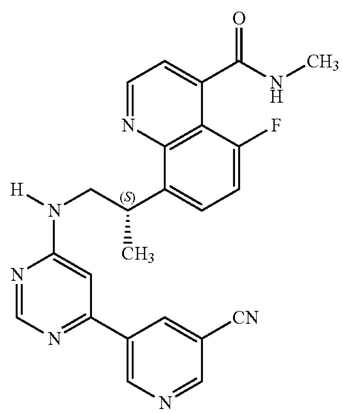 | 443 | (400 MHz, DMSO-d₆) δ 9.40 (t, J = 37.2 Hz, 1H), 9.13 (d, J = 1.8 Hz, 1H), 9.05-8.61 (m, 2H), 8.60-8.31 (m, 2H), 7.76 (s, 2H), 7.55-6.89 (m, 3H), 4.46 (s, 1H), 3.61 (d, J = 124.9 Hz, 2H), 2.81 (t, J = 7.4 Hz, 3H), 1.38 (s, 3H) |
| 965 | 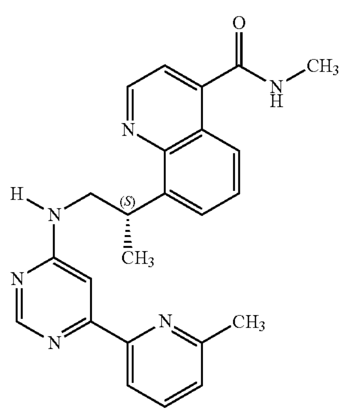 | 413 | (400 MHz, DMSO-d₆) δ 9.24-8.04 (m, 3H), 7.98 (d, J = 8.5 Hz, 1H), 7.93-7.17 (m, 6H), 4.44 (t, J = 30.0 Hz, 1H), 3.53 (d, J = 169.1 Hz, 2H), 2.87 (d, J = 4.6 Hz, 3H), 2.57-2.50 (m, 3H), 1.37 (s, 3H) |
| 966 | 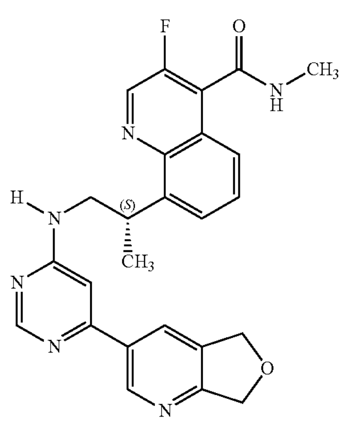 | 459 | (400 MHz, DMSO-d₆) δ 9.25-8.73 (m, 3H), 8.53-8.09 (m, 2H), 7.86-7.47 (m, 4H), 6.88 (d, J = 43.9 Hz, 1H), 5.14 (s, 2H), 4.99 (s, 2H), 4.42 (d, J = 48.3 Hz, 1H), 3.54 (d, J = 175.7 Hz, 2H), 2.90 (d, J = 4.6 Hz, 3H), 1.38 (d, J = 6.7 Hz, 3H) |

TABLE 2-continued

| Cmpnd No. | Structure | ESMS (M + H) | ¹H NMR (300 MHz, unless indicated otherwise) NMR peaks given as δ values |
|---|---|---|---|
| 967 | 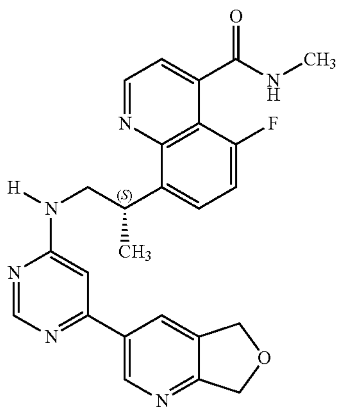 | 459 | (400 MHz, DMSO-d$_6$) δ 8.93 (t, J = 37.8 Hz, 2H), 8.56-8.11 (m, 3H), 7.86-7.34 (m, 4H), 6.89 (d, J = 44.1 Hz, 1H), 5.15 (s, 2H), 4.99 (s, 2H), 4.40 (d, J = 43.0 Hz, 1H), 3.91-3.34 (m, 2H), 2.82 (d, J = 4.6 Hz, 3H), 1.38 (s, 3H) |
| 968 | 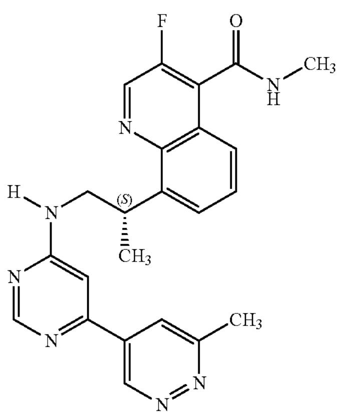 | 432 | (400 MHz, DMSO-d$_6$) δ 9.43 (d, J = 46.2 Hz, 1H), 9.02 (s, 1H), 8.81 (t, J = 19.6 Hz, 1H), 8.48 (d, J = 52.8 Hz, 1H), 7.94 (d, J = 27.6 Hz, 1H), 7.73 (d, J = 6.6 Hz, 4H), 7.49-6.90 (m, 1H), 4.43 (d, J = 32.6 Hz, 1H), 3.67 (d, J = 81.3 Hz, 2H), 2.90 (d, J = 4.6 Hz, 3H), 2.70 (s, 3H), 1.38 (s, 3H) |
| 969 | 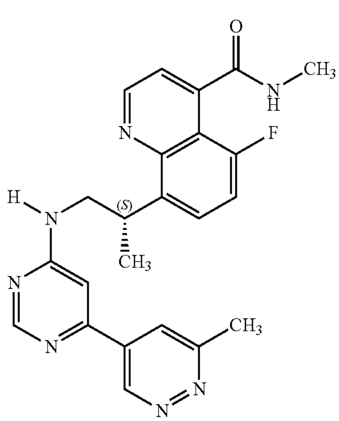 | 432 | |

TABLE 2-continued

| Cmpnd No. | Structure | ESMS (M + H) | ¹H NMR (300 MHz, unless indicated otherwise) NMR peaks given as δ values |
|---|---|---|---|
| 970 | 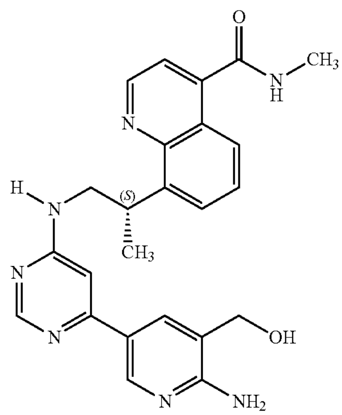 | 444 | (400 MHz, DMSO-d₆) δ 8.99 (d, J = 4.0 Hz, 1H), 8.62 (t, J = 21.0 Hz, 1H), 8.38 (s, 1H), 8.14 (d, J = 36.7 Hz, 1H), 7.99 (d, J = 7.3 Hz, 1H), 7.84-7.42 (m, 4H), 7.30 (s, 1H), 6.69 (s, 1H), 6.17 (s, 2H), 4.42 (d, J = 61.6 Hz, 1H), 3.90-3.60 (m, 4H), 2.87 (d, J = 4.6 Hz, 3H), 1.38 (d, J = 6.9 Hz, 3H) |
| 971 | 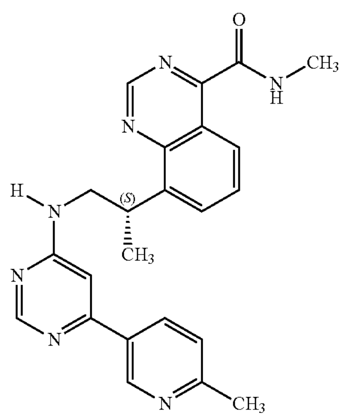 | 414.07 | (400 MHz, methanol-d₄) δ 9.29 (s, 1H), 8.86 (br. s, 1H), ? 8.80 (dd, J = 8.6, 1.3 Hz, 1H), 8.37 (d, J = 1.1 Hz, 1H), 8.14 (s, 1H), 8.04-7.87 (m, 1H), 7.71 (dd, J = 8.6, 7.2 Hz, 1H), 7.39 (d, J = 8.2 Hz, 1H), 6.71 (br. s, 1H), 4.51 (q, J = 7.1 Hz, 1H), 4.10-3.60 (m, 2H), 3.01 (s, 3H), 2.58 (s, 3H), 1.48 (d, J = 7.0 Hz, 3H) |
| 972 | 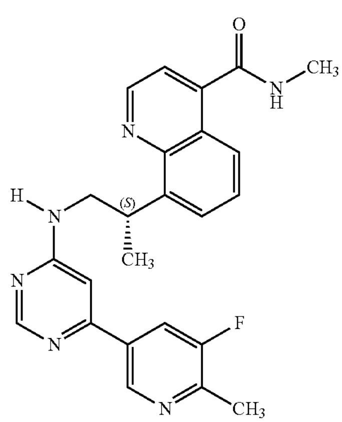 | 431 | (400 MHz, DMSO-d₆) δ 8.93 (t, J = 31.3 Hz, 2H), 8.63 (t, J = 16.2 Hz, 1H), 8.49 (s 7.97 (t, J = 18.5 Hz, 2H), 7.83-7.44 (m, 4H), 6.89 (d, J = 45.3 Hz, 1H), 4.47 (d, J = 35.2 Hz, 1H), 3.92-3.35 (m, 2H), 2.87 (d, J = 4.6 Hz, 3H), 2.49 (d, J = 1.8 Hz, 3H), 1.38 (s, 3H) |

TABLE 2-continued

| Cmpnd No. | Structure | ESMS (M + H) | ¹H NMR (300 MHz, unless indicated otherwise) NMR peaks given as δ values |
|---|---|---|---|
| 973 | 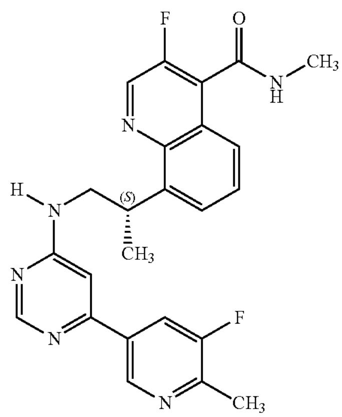 | 449 | (400 MHz, DMSO-d$_6$) δ 9.10-8.73 (m, 3H), 8.48 (s, 1H), 8.00 (d, J = 40.9 Hz, 1H), 7.69 (dd, J = 35.2, 24.2 Hz, 4H), 6.89 (d, J = 40.5 Hz, 1H), 4.41 (d, J = 43.3 Hz, 1H), 3.55 (d, J = 165.6 Hz, 2H), 2.90 (d, J = 4.6 Hz, 3H), 2.49 (d, J = 1.8 Hz, 3H), 1.37 (d, J = 6.3 Hz, 3H) |
| 974 | 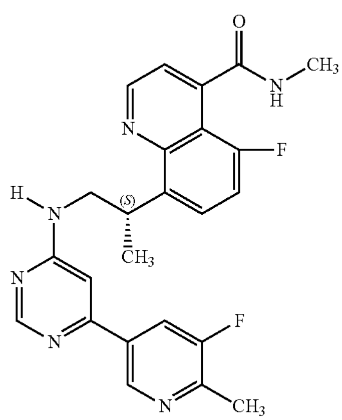 | 449 | (400 MHz, DMSO-d$_6$) δ 8.94 (t, J = 33.1 Hz, 2H), 8.55-8.37 (m, 2H), 8.00 (d, J = 48.5 Hz, 1H), 7.85-7.37 (m, 4H), 6.94 (s, 1H), 4.39 (d, J = 46.5 Hz, 1H), 3.55 (d, J = 144.1 Hz, 2H), 2.82 (d, J = 4.6 Hz, 3H), 2.49 (d, J = 1.8 Hz, 3H), 1.37 (d, J = 6.0 Hz, 3H) |
| 975 | 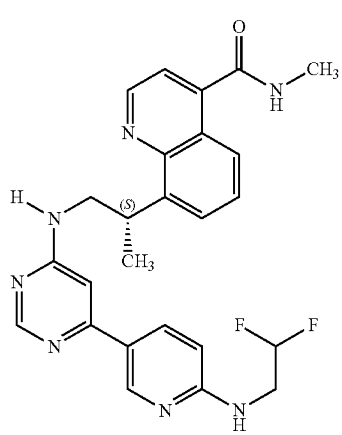 | 478.12 | |

TABLE 2-continued

| Cmpnd No. | Structure | ESMS (M + H) | ¹H NMR (300 MHz, unless indicated otherwise) NMR peaks given as δ values |
|---|---|---|---|
| 976 | 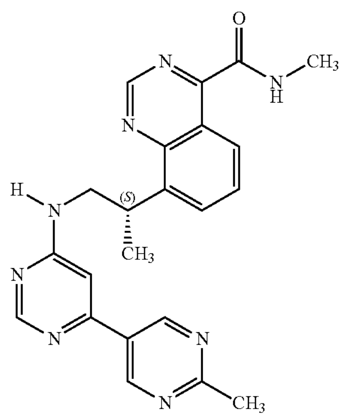 | 415.15 | (methanol-d₄) δ 9.30 (s, 1H), 9.13 (br. s, 2H), 8.80 (d, J = 8.4 Hz, 1H), 8.41 (d, J = 1.3 Hz, 1H), 8.00 (d, J = 7.3 Hz, 1H), 7.72 (dd, J = 8.6, 7.3 Hz, 1H), 6.76 (s, 1H), 4.53 (q, J = 7.1 Hz, 1H), 4.02-3.68 (m, 2H), 3.08-2.91 (m, 3H), 2.75 (s, 3H), 1.49 (d, J = 6.9 Hz, 3H) |
| 977 | 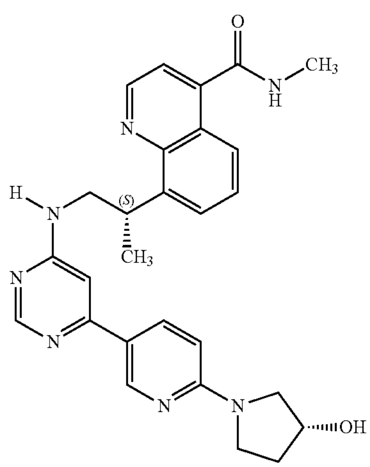 | 464.53 | (400 MHz, CDCl₃) δ 8.68 (d, J = 1.7 Hz, 1H), 8.61 (d, J = 1.8 Hz, 1H), 7.01 (d, J = 8.4 Hz, 1H), 6.94 (d, J = 2.3 Hz, 1H), 6.89 (s, 1H), 5.96 (d, J = 8.4 Hz, 1H), 4.75 (s, 1H), 4.43-4.35 (m, 2H), 4.22 (s, 1H), 4.19-4.10 (m, 2H), 3.98-3.86 (m, 4H), 3.82 (s, 1H), 3.36-3.28 (m, 4H), 2.23-2.08 (m, 2H), 1.94-1.79 (m, 6H) |
| 978 | 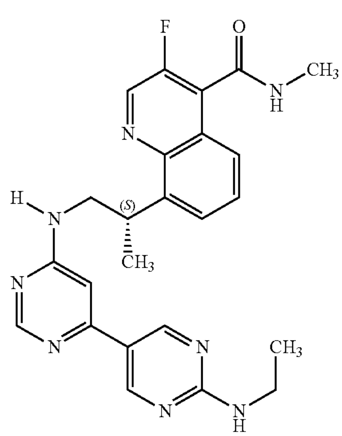 | 461.06 | |

TABLE 2-continued

| Cmpnd No. | Structure | ESMS (M + H) | ¹H NMR (300 MHz, unless indicated otherwise) NMR peaks given as δ values |
|---|---|---|---|
| 979 | 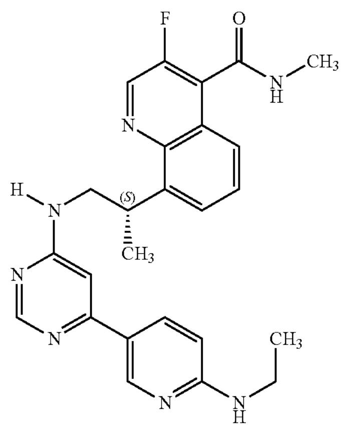 | 460.21 | |
| 980 | 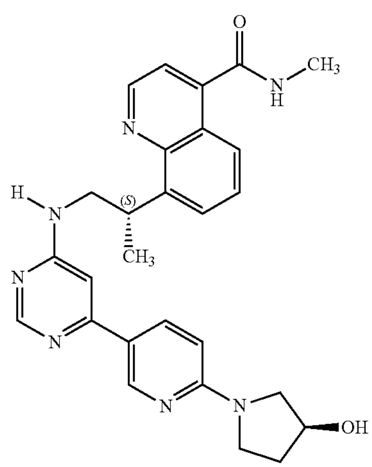 | 484.15 | |
| 981 | 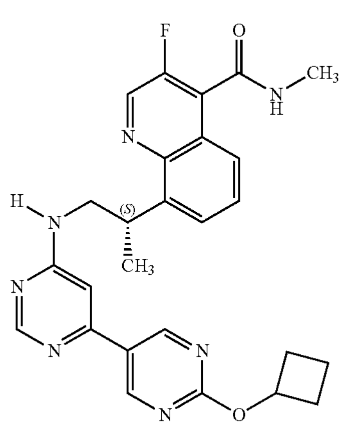 | 488 | (400 MHz, DMSO-d₆) δ 9.01 (s, 3H), 8.84 (d, J = 4.7 Hz, 1H), 8.43 (d, J = 29.7 Hz, 1H), 7.71 (t, J = 8.3 Hz, 3H), 7.60 (s, 1H), 6.82 (d, J = 32.5 Hz, 1H), 5.29-5.09 (m, 1H), 4.43 (d, J = 38.3 Hz, 1H), 3.65 (d, J = 86.1 Hz, 2H), 2.90 (d, J = 4.6 Hz, 3H), 2.42 (s, 2H), 2.12 (s, 2H), 1.81 (d, J = 10.9 Hz, 1H), 1.66 (d, J = 10.1 Hz, 1H), 1.37 (d, J = 6.3 Hz, 3H) |

TABLE 2-continued

| Cmpnd No. | Structure | ESMS (M + H) | ¹H NMR (300 MHz, unless indicated otherwise) NMR peaks given as δ values |
|---|---|---|---|
| 982 | 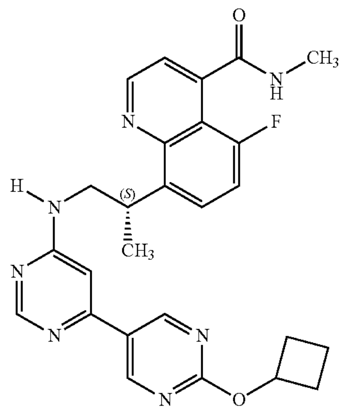 | 488 | (400 MHz, DMSO-$d_6$) δ 9.01 (t, J = 11.0 Hz, 3H), 8.45 (d, J = 4.7 Hz, 2H), 7.88-7.38 (m, 4H), 7.04 (dd, J = 55.6, 50.8 Hz, 1H), 5.18 (t, J = 17.1 Hz, 1H), 4.40 (d, J = 41.2 Hz, 1H), 3.73 (s, 2H), 2.82 (d, J = 4.6 Hz, 3H), 2.43 (s, 2H), 2.11 (d, J = 8.2 Hz, 2H), 1.81 (d, J = 9.7 Hz, 1H), 1.70-1.61 (m, 1H), 1.36 (d, J = 6.3 Hz, 3H) |
| 983 | 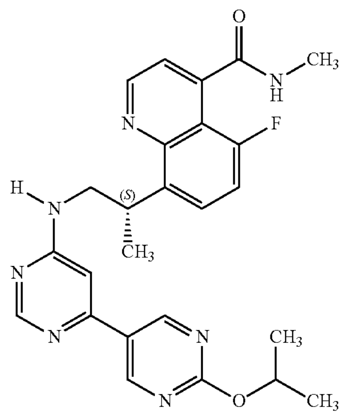 | 476 | (400 MHz, DMSO-$d_6$) δ 9.01 (t, J = 12.2 Hz, 3H), 8.45 (d, J = 4.6 Hz, 2H), 7.86-7.37 (m, 4H), 6.85 (s, 1H), 5.28 (s, 1H), 4.41 (d, J = 30.9 Hz, 1H), 3.64 (d, J = 74.6 Hz, 2H), 2.82 (d, J = 4.6 Hz, 3H), 1.35 (d, J = 6.0 Hz, 9H) |
| 984 | 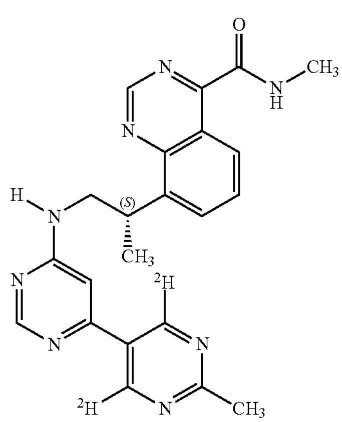 | 4117.13 | (methanol-$d_4$) δ 9.30 (s, 1H), 8.80 (dd, J = 8.5, 1.3 Hz, 1H), 8.40 (d, J = 1.2 Hz, 1H), 7.98 (d, J = 7.2 Hz, 1H), 7.71 (dd, J = 8.6, 7.3 Hz, 1H), 6.77 (s, 1H), 4.52 (q, J = 7.1 Hz, 1H), 3.95-3.76 (m, 2H), 3.01 (s, 3H), 2.74 (s, 3H), 1.49 (d, J = 7.0 Hz, 3H) |

Biological Assay of Compounds of the Invention

Example 12

DNA-PK Inhibition Assay

Compounds were screened for their ability to inhibit DNA-PK kinase using a standard radiometric assay. Briefly, in this kinase assay the transfer of the terminal $^{33}$P-phosphate in $^{33}$P-ATP to a peptide substrate is interrogated. The assay was carried out in 384-well plates to a final volume of 50 µL per well containing approximately 6 nM DNA-PK, 50 mM HEPES (pH 7.5), 10 mM MgCl$_2$, 25 mM NaCl, 0.01% BSA, 1 mM DTT, 10 µg/mL sheared double-stranded DNA (obtained from Sigma), 0.8 mg/mL DNA-PK peptide (Glu-Pro-Pro-Leu-Ser-Gln-Glu-Ala-Phe-Ala-Asp-Leu-Trp-Lys-Lys-Lys, obtained from American Peptide), and 100 µM ATP. Accordingly, compounds of the invention were dissolved in DMSO to make 10 mM initial stock solutions. Serial dilutions in DMSO were then made to obtain the final solutions for the assay. A 0.75 µL aliquot of DMSO or inhibitor in DMSO was added to each well, followed by the addition of ATP substrate solution containing $^{33}$P-ATP (obtained from Perkin Elmer). The reaction was started by the addition of DNA-PK, peptide and ds-DNA. After 45 min, the reaction was quenched with 25 µL of 5% phosphoric acid. The reaction mixture was transferred to MultiScreen HTS 384-well PH plates (obtained from Millipore), allowed to bind for one hour, and washed three times with 1% phosphoric acid. Following the addition of 50 µL of Ultima Gold™ high efficiency scintillant (obtained from Perkin Elmer), the samples were counted in a Packard TopCount NXT Microplate Scintillation and Luminescence Counter (Packard BioScience). The K$_i$ values were calculated using Microsoft Excel Solver macros to fit the data to the kinetic model for competitive tight-binding inhibition.

Each of compounds I to 983 has a K$_i$ of less than or equal to 0.30 micromolar for the inhibition of DNA-PK. Each of compounds 1, 8, 11, 16, 28, 30, 32, 34-38, 40-46, 55, 57, 60, 63, 73, 79-80, 82-87, 91-92, 94, 96-105, 107, 109-110, 114-123, 125-128, 130-142, 144-159, 165-168, 172-180, 182-183, 186, 188-189, 193-195, 197-206, 208-211, 213-215, 217-218, 220, 222-223, 225, 227-228, 232-233, 235-243, 245-250, 252-266, 268-279, 283-287, 289-290, 293-294, 296, 299, 303-304, 307-328, 331-333, 338-342, 345-349, 351, 353-370, 372, 375-378, 382, 385, 387-396, 398-402, 405-409, 412, 414, 416-420, 423-424, 429-432, 434-438, 441-445, 447, 449, 451-454, 456-460, 462, 464-467, 469, 472, 475-481, 483-486, 490, 493-495, 497, 501-505, 508-510, 513-515, 519, 522-524, 526-527, 535-538, 541, 545-546, 549-550, 553-557, 559, 561-563, 568-569, 572-597, 603-608, 612-615, 618-620, 622-625, 627-628, 630, 632-639, 641-642, 644-645, 648-652, 654-662, 666-667, 669-685, 689, 697-698, 701-724, 726-738, 740-743, 746-759, 762-772, 774-783, 785, 787, 789-795, 797-805, 807-886, 889-964, and 966-979 and 981-984 has a K$_i$ of less than 0.030 micromolar for the inhibition of DNA-PK.

Example 13

Effects on Cell Viability Following Irradiation

To evaluate the radiosensitizing effects of compounds of the invention in combination with ionizing radiation (IR), a broad panel of cell lines across multiple tumor types and genetic backgrounds were tested. Cells were incubated with DMSO or compound 578 for 30 minutes and then exposed to various doses of radiation (0, 0.5, 1, 2, 4, 6, 8, and 16 Gy). Cell viability was assessed at 6 days using CellTiter-Glo® (Promega, Inc). The EC$_{50}$ (Gy) values generated in the presence of DMSO or compound 578 in combination with IR are shown in Table 3. Compound 578 had a radiosensitizing effect on cancer cell lines sensitive to radiation, with EC$_{50}$ shifts ranging from 1.7 to 10.6-fold. The glioblastoma cell lines tested appeared generally less sensitive to radiation alone and, therefore, demonstrated less radiosensitization with compound 578 in this assay. With the exception of the normal human fibroblast cell line, HS68, only marginal radiosensitization was observed in human fibroblast cell lines (HFL1, IMR90 and MRC5) and in the normal epithelial cell line, ARPE19, normal human bronchial epithelial cells (NHBE), and smooth airway epithelial cells (SAEC). Compound 578 had minimal effect on cell viability as a single agent or in combination with radiation in the DNA-PK null SCID mouse cell line. These data suggest that DNA-PK inhibition results in broad radiosensitization across many different tumor cell types.

TABLE 3

Effect of compound 578 on EC$_{50}$ following irradiation

| | | | Compound 578 | | |
| --- | --- | --- | --- | --- | --- |
| Origin | Cell Line | DMSO EC$_{50}$ IR (Gy) | 0.7 µM EC$_{50}$ IR (Gy) | 2.1 µM EC$_{50}$ IR (Gy) | EC$_{50}$ IR shift @ 0.7 µM |
| Breast Cancer | DU4475 | 1.6 | <0.5 | <0.5 | >3 |
| | MCF7 | 8.5 | 4.9 | 3.3 | 1.7 |
| Colorectal Cancer | Colo-205 | 6.1 | 0.7 | 0.7 | 8.9 |
| (CRC) | DLD-1 | 3.3 | 0.6 | 0.7 | 5.1 |
| | HCT116 | 2 | 0.5 | <0.5 | 4 |
| | LS411N | 7.8 | 2.3 | 1.9 | 3.4 |
| Gastric-Esophageal Cancer | OE19 | 4.9 | 0.5 | <0.5 | 9.9 |
| Fibrosarcoma | HT1080 | 0.7 | 1.9 | 0.9 | 3.6 |
| Glioblastoma | A172 | >16 | 1.7 | 0.9 | >10 |
| (GBM) | DBTRG-05MG | >16 | 4.2 | 5 | >3 |
| | U87MG | >16 | >16 | >16 | * |
| Hepatocellular Carcinoma | Huh7 | 7.2 | 1.3 | 0.8 | 5.5 |
| (HCC) | SMCC7721 | 5.4 | 1.7 | 0.6 | 3.2 |
| | SNU449 | 9.6 | 3.3 | 1.8 | 2.9 |
| Head and Neck Squamous Cell Carcinoma (HNSCC) | FaDu | 10 | 2 | 1.9 | 4.9 |

TABLE 3-continued

Effect of compound 578 on $EC_{50}$ following irradiation

| | | | Compound 578 | | |
|---|---|---|---|---|---|
| Origin | Cell Line | DMSO $EC_{50}$ IR (Gy) | 0.7 µM $EC_{50}$ IR (Gy) | 2.1 µM $EC_{50}$ IR (Gy) | $EC_{50}$ IR shift @ 0.7 µM |
| Melanoma | SK-MEL-5 | 8.9 | 2.7 | 2.3 | 3.2 |
| Lung Cancer | A549 | 5.3 | 0.5 | <0.5 | 10.6 |
| | H1299 | 10 | 1.1 | 1.5 | 9 |
| | H2009 | 7.6 | 2.7 | 2.5 | 2.8 |
| | H460 | 2 | 0.9 | 0.7 | 2.2 |
| | H838 | 4.9 | 0.6 | <0.5 | 8 |
| | SW900 | 8.1 | 4.2 | 4.3 | 1.9 |
| Pancreatic Cancer | Miapaca2 | 7.1 | 2.4 | 1.9 | 3 |
| | PATU8889T | 5.2 | 1.1 | 0.9 | 4.6 |
| Prostate Cancer | PC3 | 5.2 | 0.5 | <0.5 | 10.4 |
| SCID Tumor (DNA-PK null) | SCID | 2.6 | 2.8 | 3.1 | 0.9 |

* $EC_{50}$ shifts could not be calculated for these cell lines

Example 14

In Vivo Efficacy

The efficacy of compound 578 in vivo was evaluated in the primary OD26749 NSCLC subcutaneous xenograft model. This primary NSCLC tumor was obtained from a patient with a poorly differentiated adenocarcinoma and was serially passaged in SCID mice prior to this study. Nude mice were surgically implanted with 150-mg fragments of OD26749 tumor at passage 3 (P3). Whole body ionizing radiation (IR, 2 Gy/treatment) was administered using a dual Cesium 137 source and initiated when tumors reached approximately 350 mm³. Tumor volumes were measured twice a week during the course of the study. Anti-tumor efficacy is expressed as % T/C (tumor/control) while regression is expressed as % T/Ti, the reduction in tumor volume compared to the starting tumor volume.

Compound 578 [in 16% Captisol®+HPMC/PVP] was administered orally (b.i.d. at 0 and 4 hours) at 25, 50, 100 mg/kg and (q.d.) 200 mg/kg on Day 19 post implantation. A single 2-Gy dose of whole body IR was given 15 minutes after compound administration. Control animals were given vehicle orally b.i.d. (0 and 4 hours). On Day 26 post implantation, the same regimens were repeated.

By Day 30 post implantation, 100 mg/kg b.i.d. compound 578 in combination with 2 Gy whole body IR had induced significant regression (% T/Ti of −3.1; P<0.001) compared to IR alone while the 25 and 50-mg/kg b.i.d. and the 200-mg/kg q.d. groups all demonstrated significant tumor growth inhibition (% T/C of 25.6, 11.7, and 6.5, respectively).

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:
1. A compound, wherein the compound is
(476)
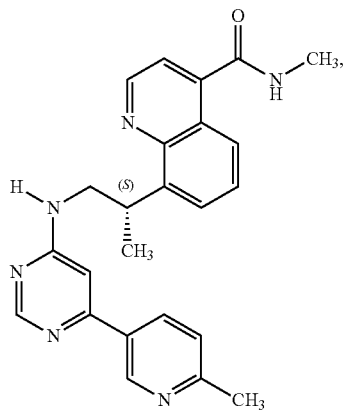
(484)
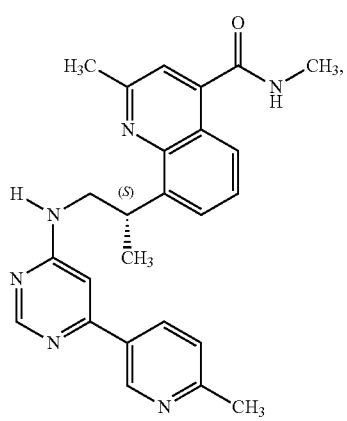
(515)
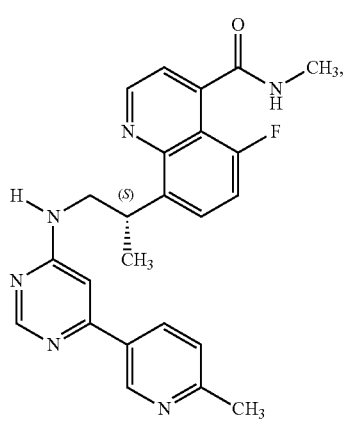
-continued
(545)
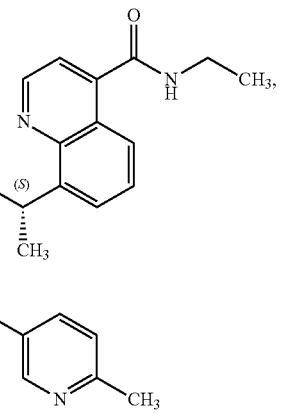
(546)
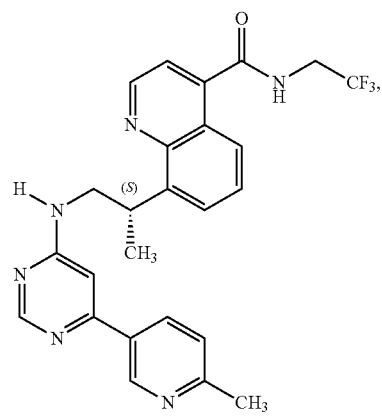
(549)
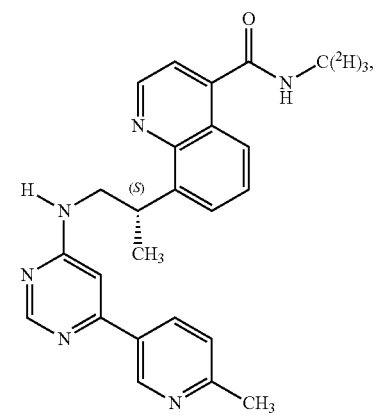
(562)
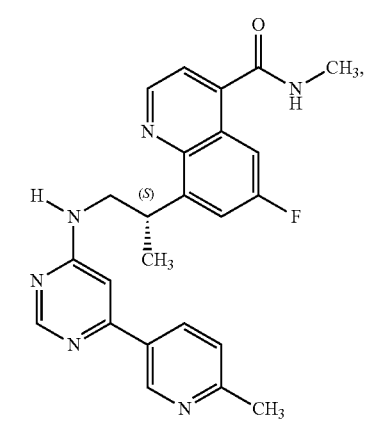

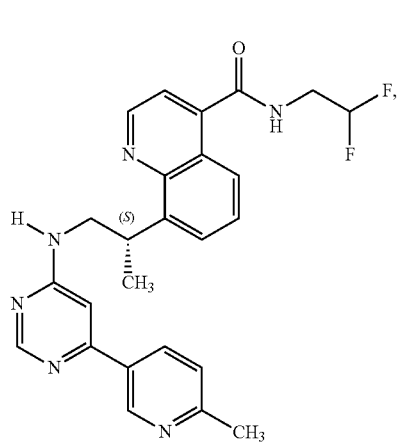
(569)
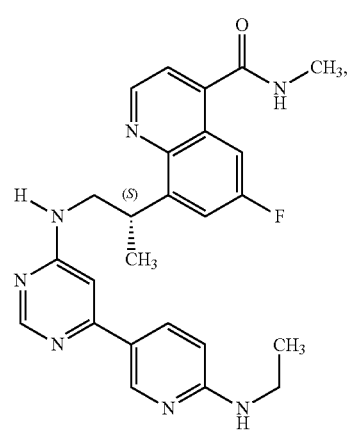
(572)
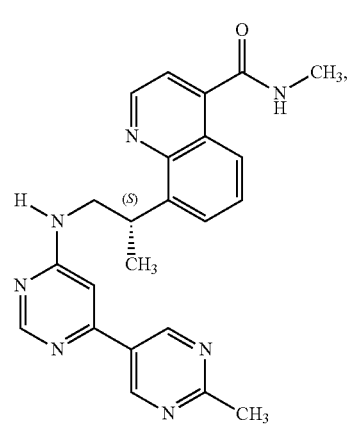
(578)
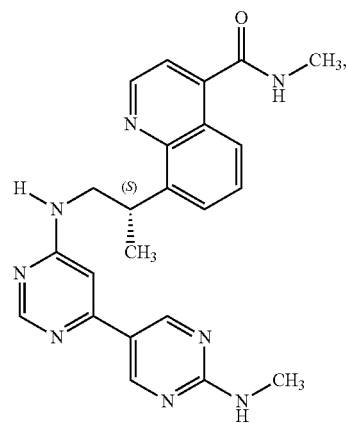
(579)
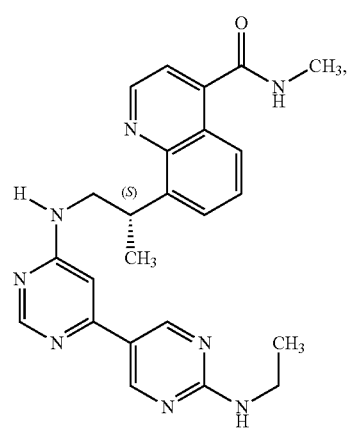
(581)
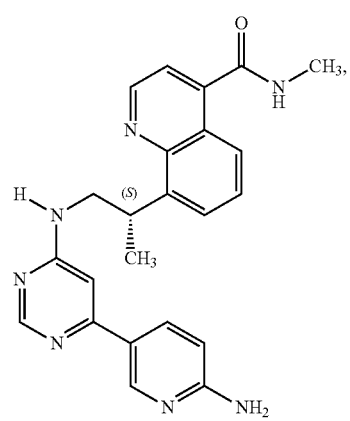
(586)

(592) 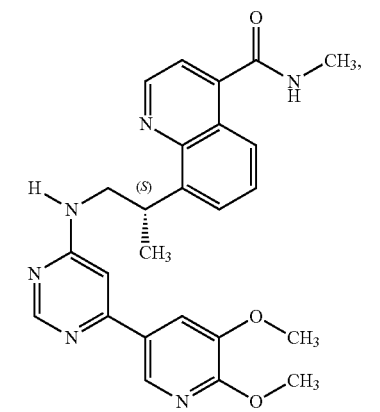
(603) 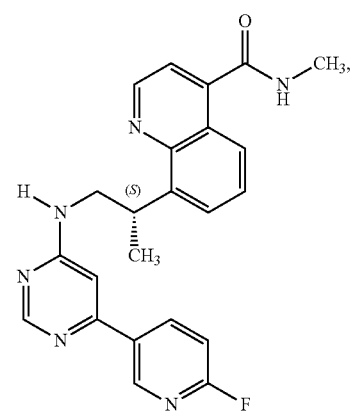
(604) 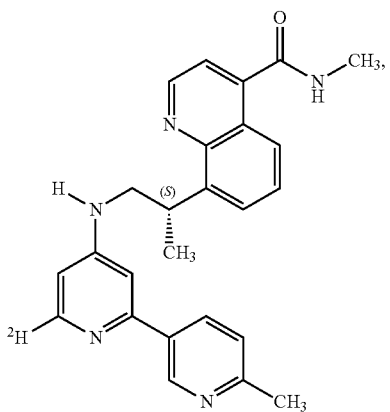
(606) 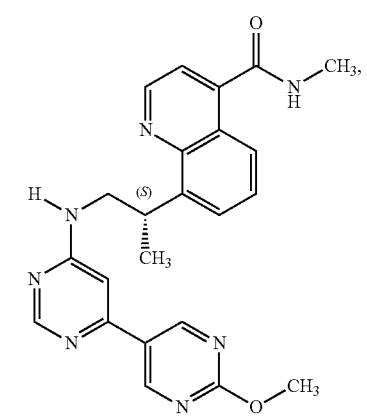
(607) 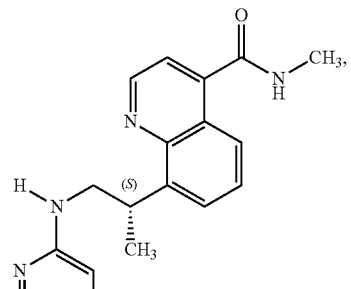
(608) 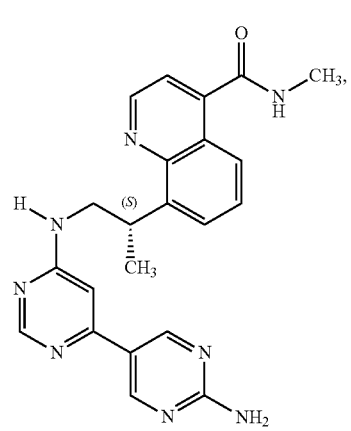
(615) 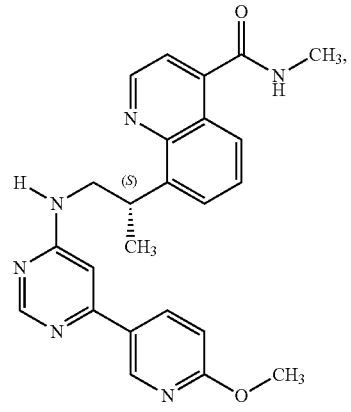
(618) 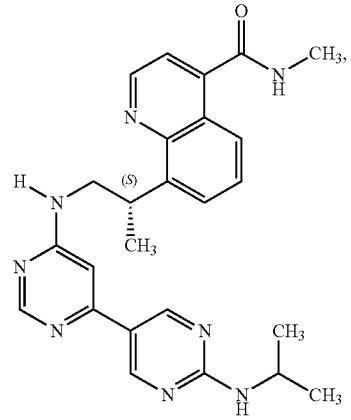

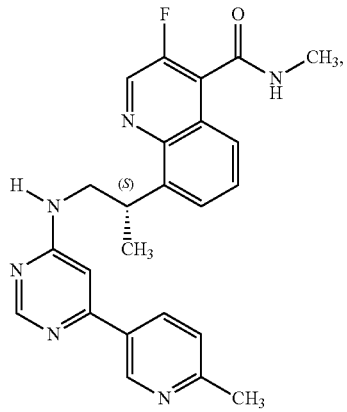 (620)
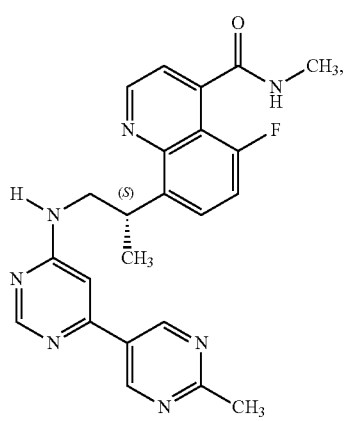 (622)
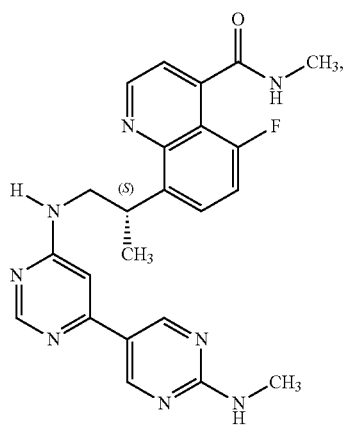 (623)
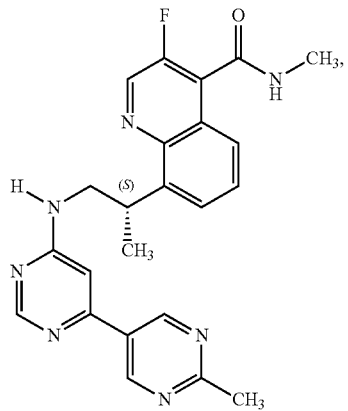 (636)
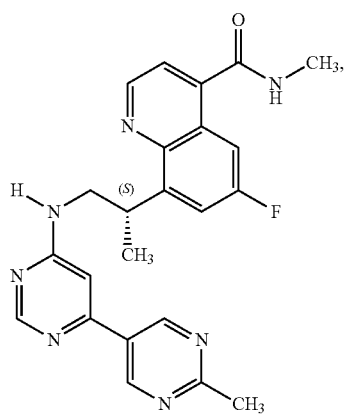 (637)
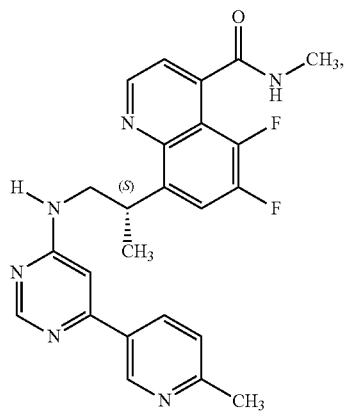 (638)
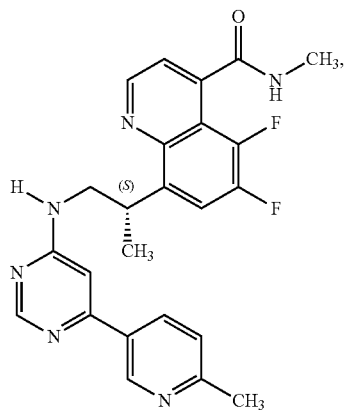 (639)

(641)
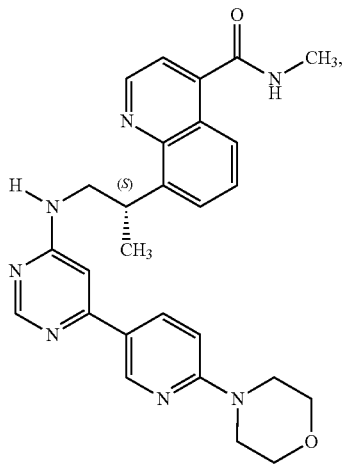
(644)
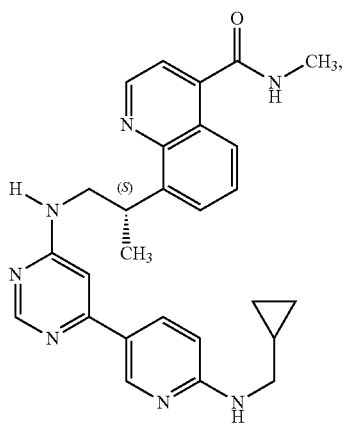
(645)
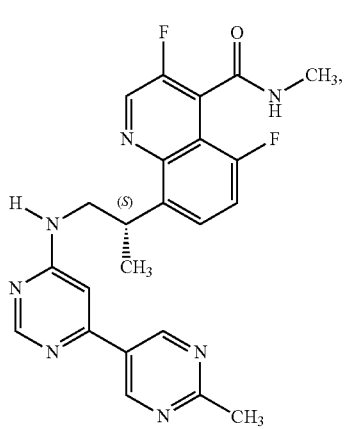
(646)
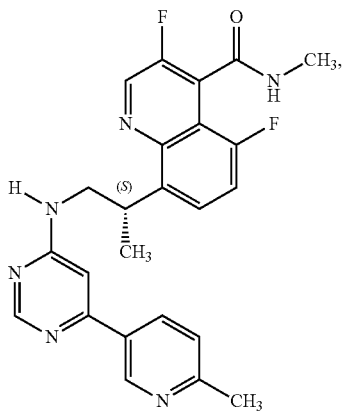
(647)
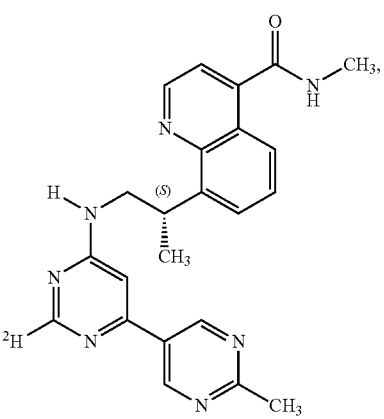
(649)
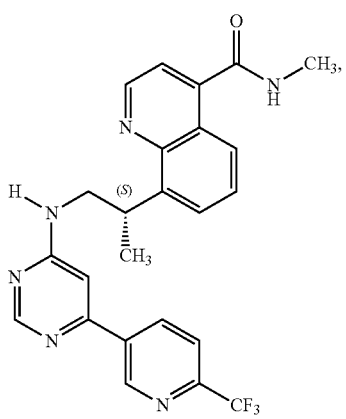

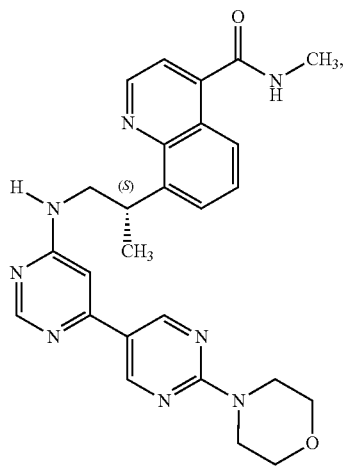
(650)
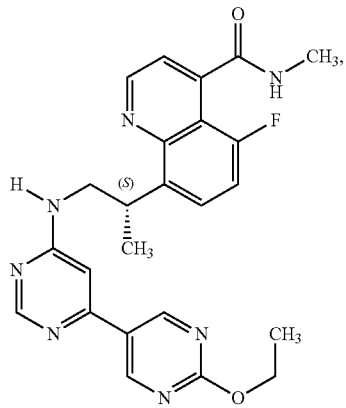
(652)
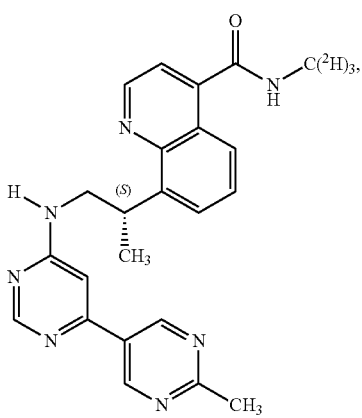
(654)
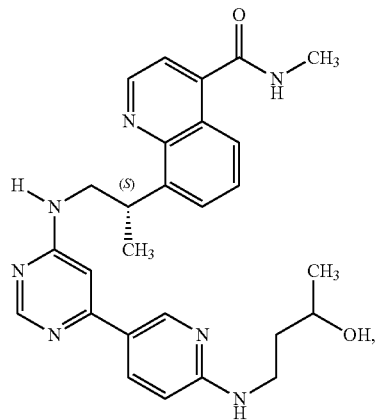
(709)
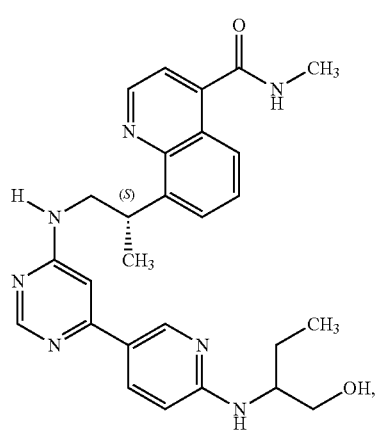
(724)
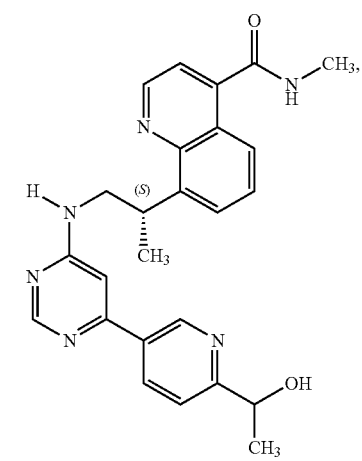
(730)

(769)
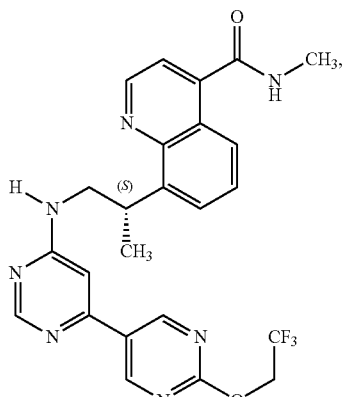
(791)
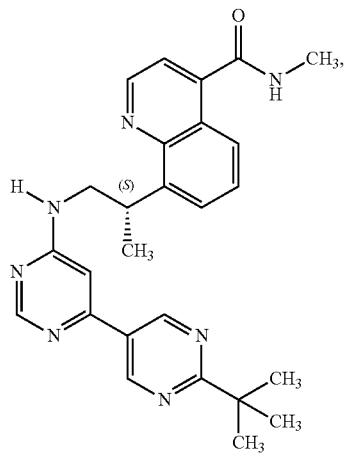
(789)
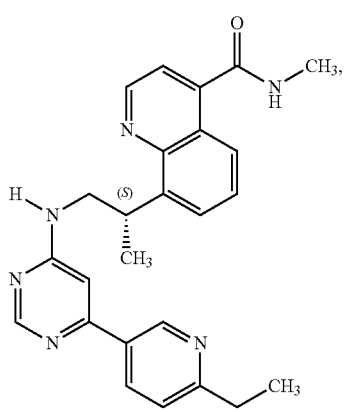
(808)
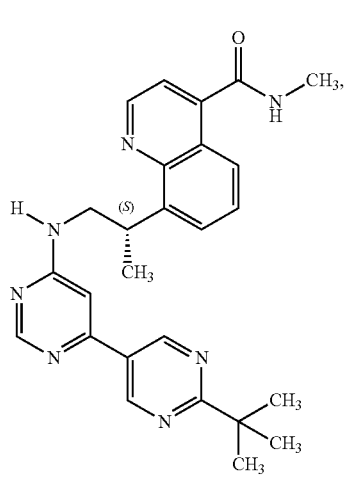
(790)
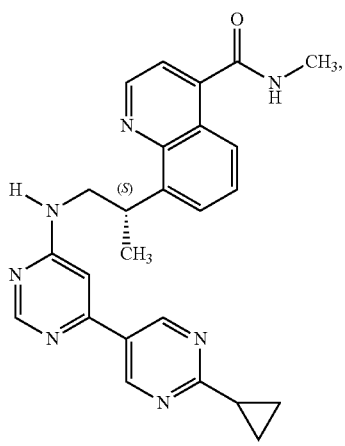
(816)
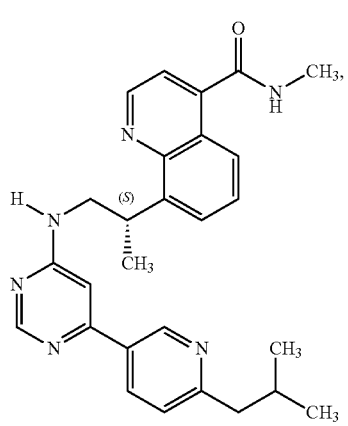

(821) 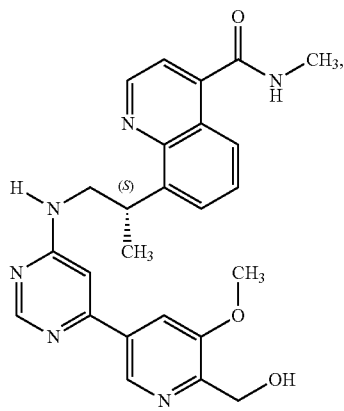
(822) 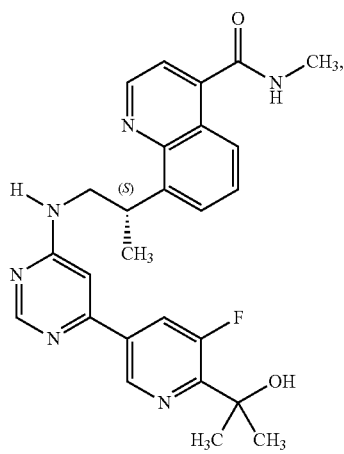
(829) 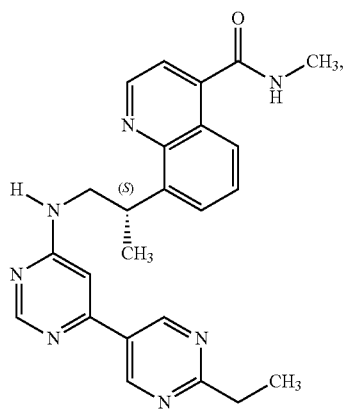
(830) 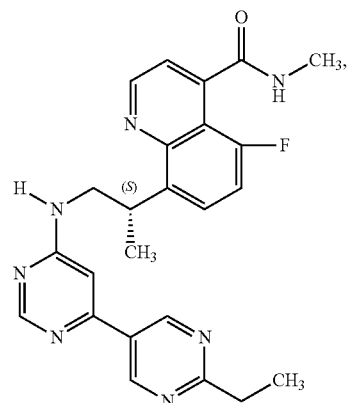
(831) 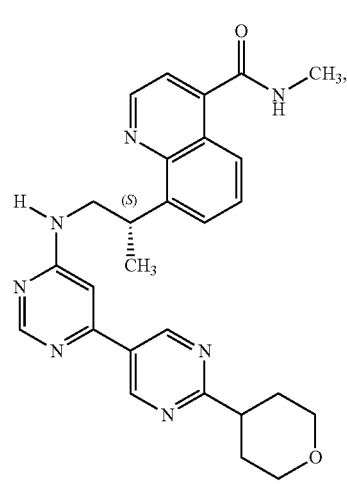
(832) 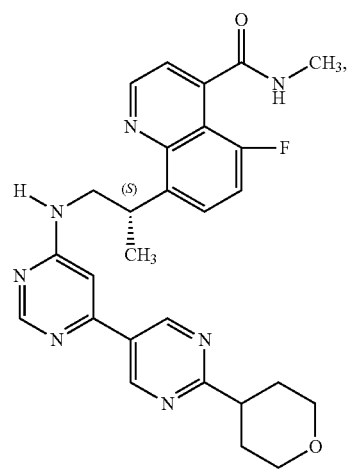

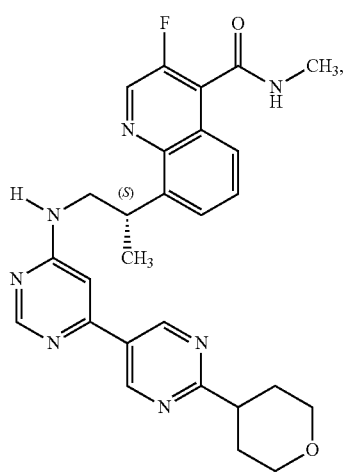
(833)
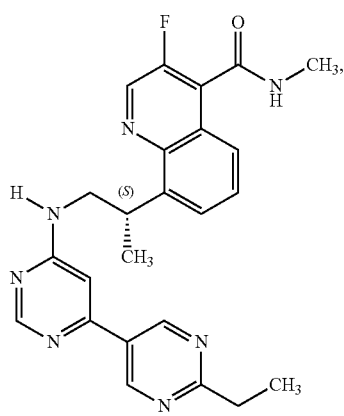
(836)
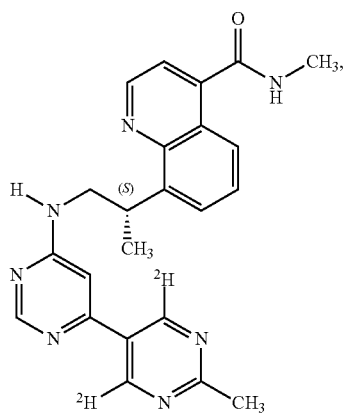
(844)
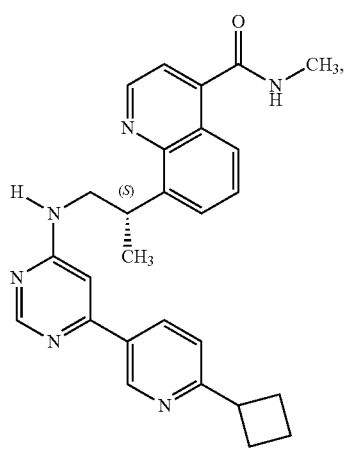
(845)
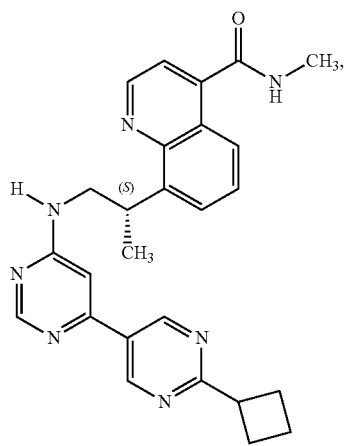
(846)
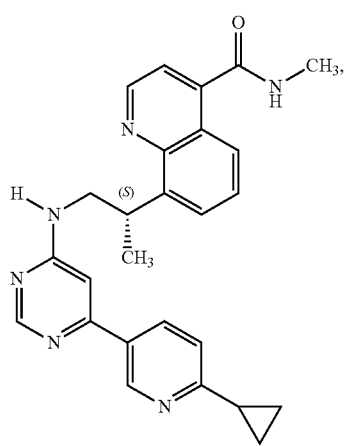
(847)

697
-continued
(848)
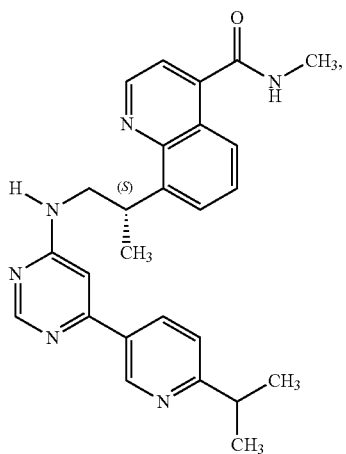
(849)
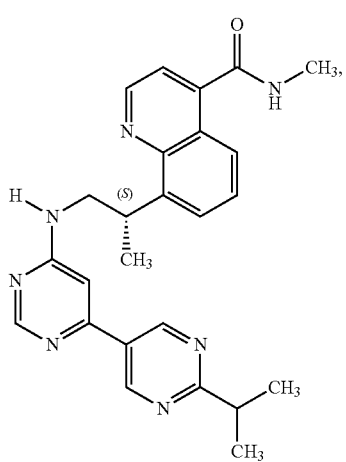
(850)
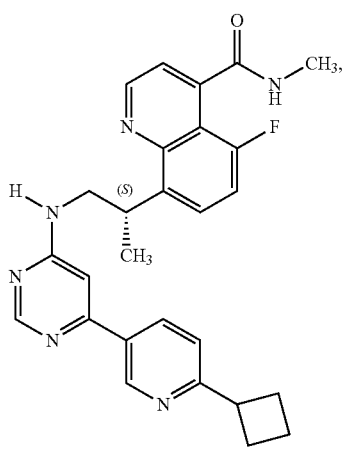
698
-continued
(851)
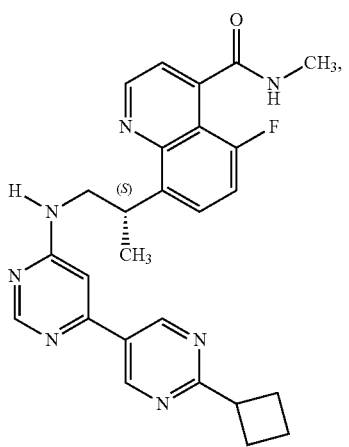
(852)
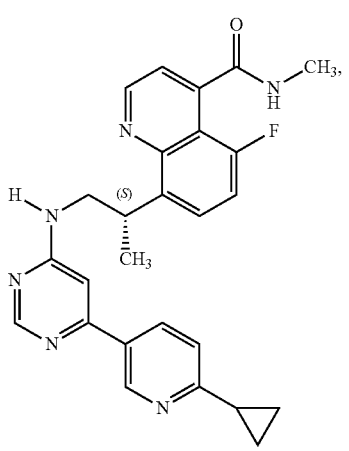
(853)
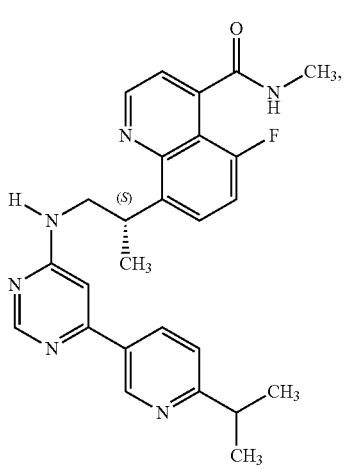

| 699 -continued | 700 -continued |
|---|---|
| 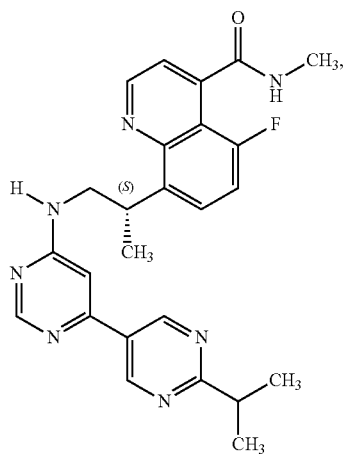 (854) | 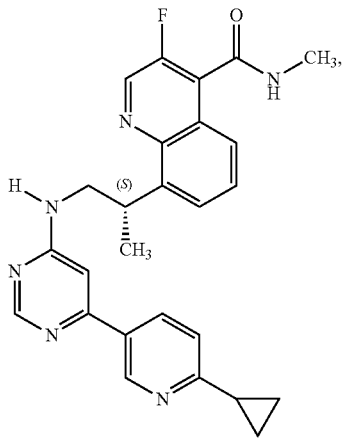 (857) |
| 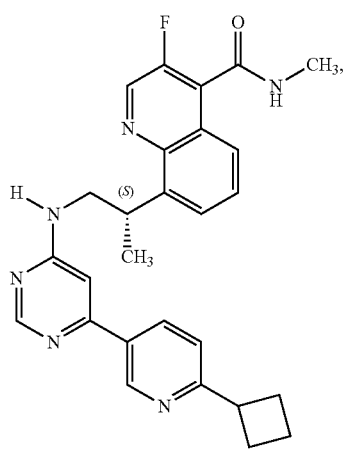 (855) | 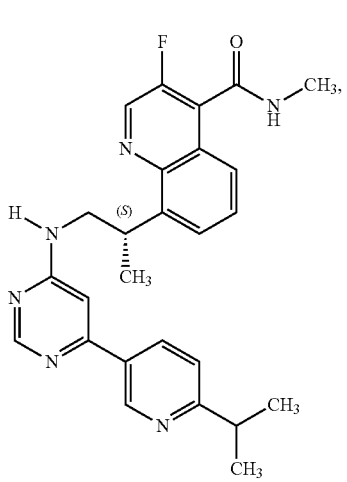 (858) |
| 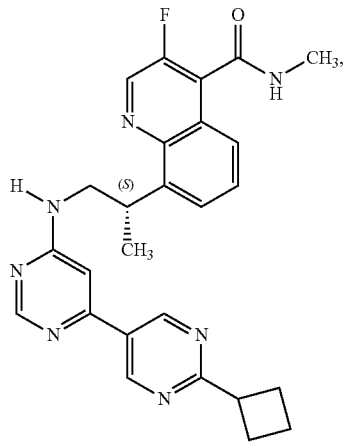 (856) | 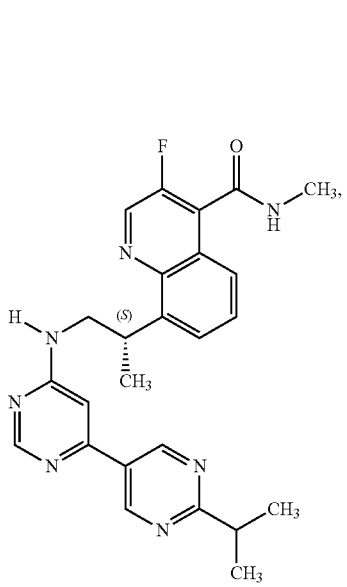 (859) |

(861)
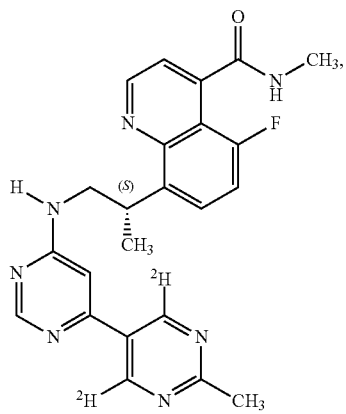
(862)
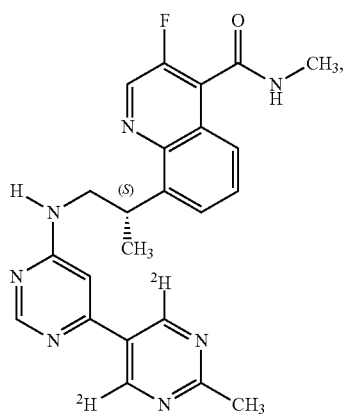
(865)
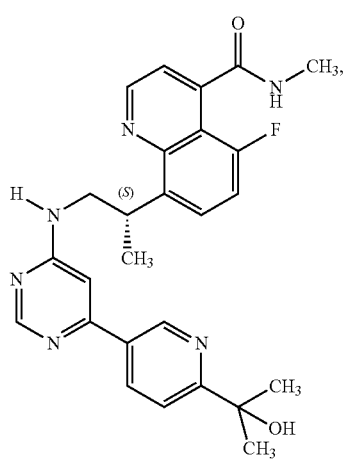
(866)
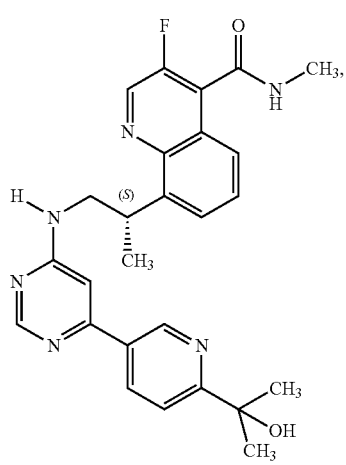
(867)
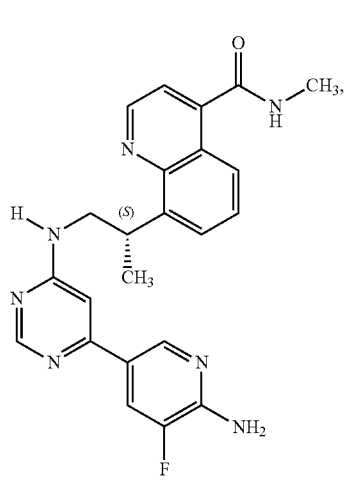
(870)
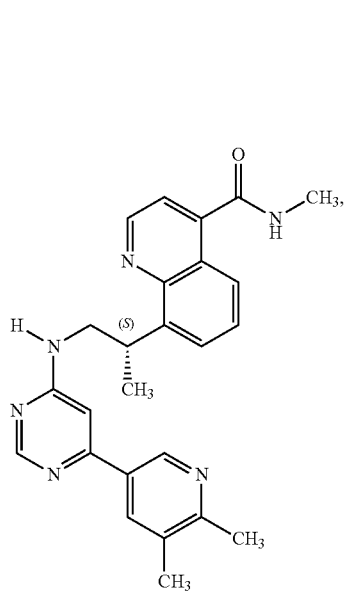

(875)
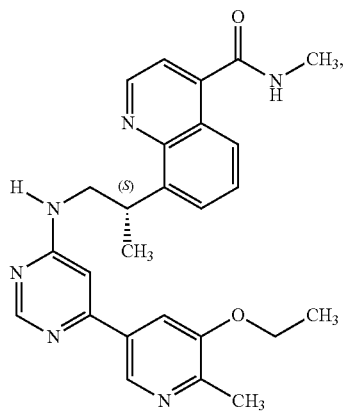

(880)
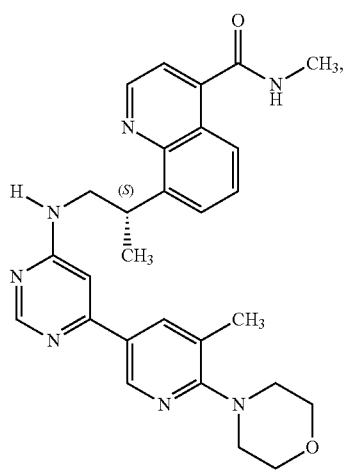

(881)
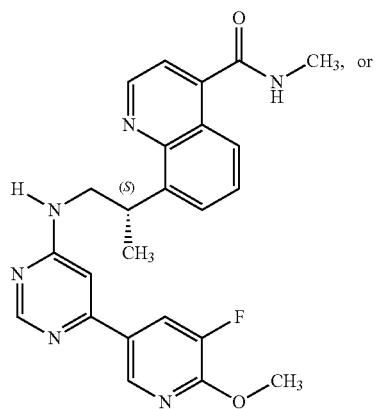

(886)
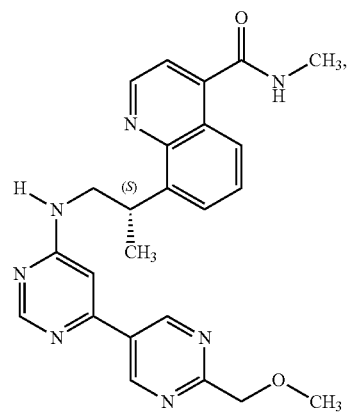

or a pharmaceutically acceptable salt thereof.

2. A pharmaceutical composition comprising a compound according to claim 1 and a pharmaceutically acceptable excipient.

3. The compound of claim 1, represented by the following formula or a pharmaceutically acceptable salt thereof:

(476)
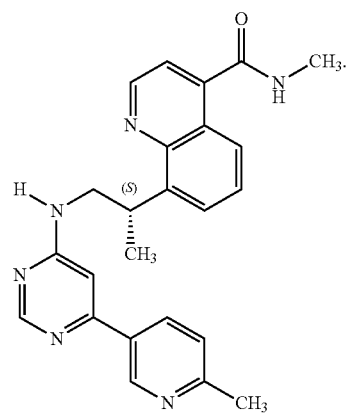

4. The compound of claim 1, represented by the following formula or a pharmaceutically acceptable salt thereof:

(549)
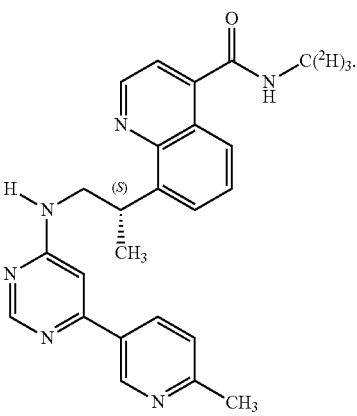

5. The compound of claim 1, represented by the following formula or a pharmaceutically acceptable salt thereof:

(578)

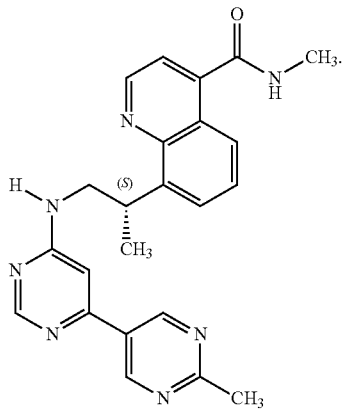

6. A compound represented by the following formula:

(578)

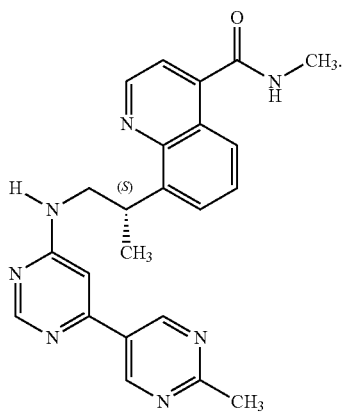

7. The compound of claim 1, represented by the following formula or a pharmaceutically acceptable salt thereof:

(604)

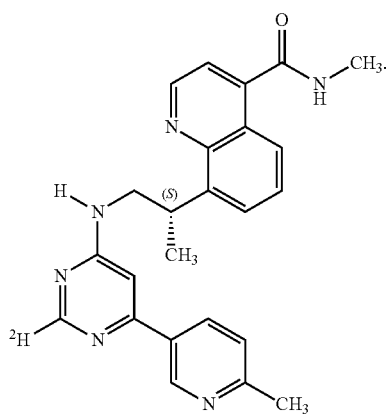

8. The compound of claim 1, represented by the following formula or a pharmaceutically acceptable salt thereof:

(647)

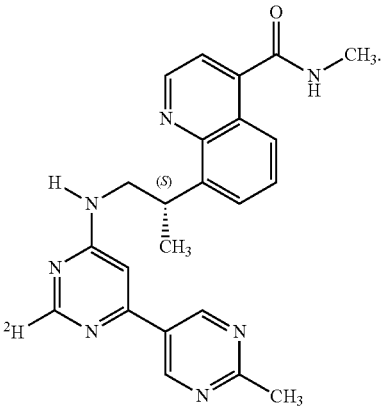

9. The compound of claim 1, represented by the following formula or a pharmaceutically acceptable salt thereof:

(654)

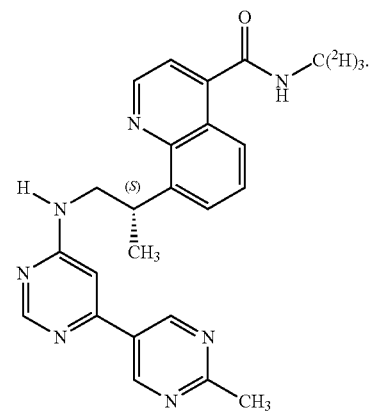

10. The compound of claim 1, represented by the following formula or a pharmaceutically acceptable salt thereof:

(844)

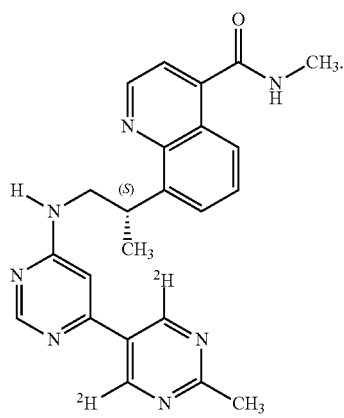

11. A compound represented by the following formula:

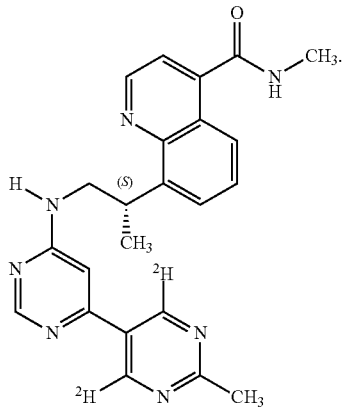

(844)

12. The compound of claim 1, represented by the following formula or a pharmaceutically acceptable salt thereof:

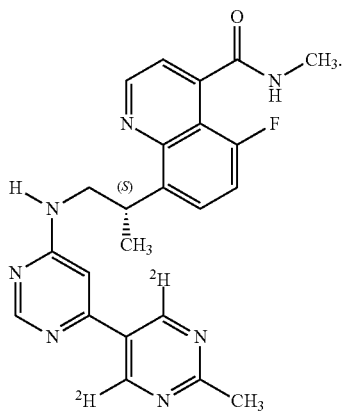

(861)

13. The compound of claim 1, represented by the following formula or a pharmaceutically acceptable salt thereof:

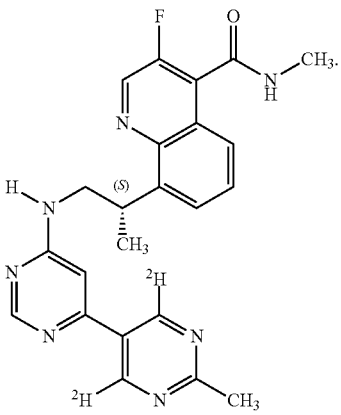

(862)

14. A pharmaceutical composition comprising a compound according to claim 5 and a pharmaceutically acceptable excipient.

15. A pharmaceutical composition comprising a compound according to claim 6 and a pharmaceutically acceptable excipient.

16. A pharmaceutical composition comprising a compound according to claim 10 and a pharmaceutically acceptable excipient.

17. A pharmaceutical composition comprising a compound according to claim 11 and a pharmaceutically acceptable excipient.

\* \* \* \* \*

SEQUENCE LISTING

<160> NUMBER OF SEQ ID NOS: 1

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Glu Pro Pro Leu Ser Gln Glu Ala Phe Ala Asp Leu Trp Lys Lys Lys
1               5                   10                  15